(12) United States Patent
Gersbach et al.

(10) Patent No.: US 10,745,714 B2
(45) Date of Patent: Aug. 18, 2020

(54) RNA-GUIDED GENE EDITING AND GENE REGULATION

(71) Applicant: Duke University, Durham, NC (US)

(72) Inventors: Charles A. Gersbach, Durham, NC (US); Isaac B. Hilton, Durham, NC (US); Pablo Perez-Pinera, Urbana, IL (US); Ami M. Kabadi, Greensboro, NC (US); Pratiksha I. Thakore, Durham, IL (US); David G. Ousterout, Raleigh, NC (US); Joshua B. Black, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/991,333

(22) Filed: May 29, 2018

(65) Prior Publication Data

US 2018/0320197 A1    Nov. 8, 2018

Related U.S. Application Data

(62) Division of application No. 14/895,316, filed as application No. PCT/US2014/041190 on Jun. 5, 2014.

(Continued)

(51) Int. Cl.
*C12N 15/85*      (2006.01)
*A61K 38/46*      (2006.01)
(Continued)

(52) U.S. Cl.
CPC ............ *C12N 15/85* (2013.01); *A61K 38/465* (2013.01); *A61K 48/0058* (2013.01);
(Continued)

(58) Field of Classification Search
None
See application file for complete search history.

(56) References Cited

U.S. PATENT DOCUMENTS 5,593,972 A    1/1997    Weiner et al.
5,773,700 A    6/1998    Van Grinsven et al.
(Continued)

FOREIGN PATENT DOCUMENTS

CA          2749305          7/2010
JP       2015-534817 A       12/2015
(Continued)

OTHER PUBLICATIONS

European Patent Office Extended Search Report for Application No. 18172956.7 dated Nov. 26, 2018 (5 pages).

(Continued)

*Primary Examiner* — Nancy A Treptow
(74) *Attorney, Agent, or Firm* — Michael Best & Friedrich LLP

(57) ABSTRACT

Disclosed herein are Clustered Regularly Interspaced Short Palindromic Repeats (CRISPR)/CRISPR-associated (Cas) 9-based system related compositions and methods of using said CRISPR/Cas9-based system related compositions for altering gene expression and genome engineering. Also disclosed herein are compositions and methods of using said compositions for altering gene expression and genome engineering in muscle, such as skeletal muscle and cardiac muscle.

17 Claims, 81 Drawing Sheets

Specification includes a Sequence Listing.

Related U.S. Application Data

(60) Provisional application No. 61/831,481, filed on Jun. 5, 2013, provisional application No. 61/839,127, filed on Jun. 25, 2013, provisional application No. 61/904,911, filed on Nov. 15, 2013, provisional application No. 61/967,466, filed on Mar. 19, 2014, provisional application No. 61/981,575, filed on Apr. 18, 2014.

(51) Int. Cl.
*A61K 48/00* (2006.01)
*C12N 9/96* (2006.01)
*C07K 14/47* (2006.01)
*C12N 9/22* (2006.01)
*C12N 15/90* (2006.01)

(52) U.S. Cl.
CPC ............ *C07K 14/4708* (2013.01); *C12N 9/22* (2013.01); *C12N 9/96* (2013.01); *C12N 15/907* (2013.01); *A61K 48/005* (2013.01); *C07K 2319/71* (2013.01); *C12N 2740/16043* (2013.01); *C12N 2800/40* (2013.01); *C12N 2840/20* (2013.01); *C12Y 301/00* (2013.01)

(56) References Cited

U.S. PATENT DOCUMENTS

| | | | |
|---|---|---|---|
| 5,962,428 | A | 10/1999 | Carrano et al. |
| 9,738,879 | B2 | 8/2017 | Gersbach et al. |
| 9,890,364 | B2 | 2/2018 | Joung et al. |
| 2004/0175727 | A1 | 9/2004 | Draghia-Akli et al. |
| 2007/0185042 | A1 | 8/2007 | Tsai et al. |
| 2011/0197290 | A1 | 8/2011 | Fahrenkrug et al. |
| 2011/0263682 | A1 | 10/2011 | De Kimpe et al. |
| 2011/0301073 | A1 | 12/2011 | Gregory et al. |
| 2013/0274129 | A1 | 10/2013 | Katzen et al. |
| 2014/0179006 | A1* | 6/2014 | Zhang ............... C12N 9/22 435/462 |
| 2014/0234975 | A1 | 8/2014 | Silva et al. |
| 2014/0356956 | A1* | 12/2014 | Church ............... C12N 15/102 435/441 |
| 2015/0045413 | A1 | 2/2015 | De Visser et al. |
| 2015/0056705 | A1* | 2/2015 | Conway ............... C12N 15/11 435/462 |
| 2015/0079064 | A1 | 3/2015 | Gersbach et al. |
| 2015/0159178 | A1 | 6/2015 | Green et al. |

FOREIGN PATENT DOCUMENTS

| | | |
|---|---|---|
| JP | 2016-521452 A | 7/2016 |
| JP | 2016-521975 A | 7/2016 |
| JP | 2016-523082 A | 8/2016 |
| WO | WO 93/024640 | 12/1993 |
| WO | WO 94/016737 | 8/1994 |
| WO | WO 01/83783 | 11/2001 |
| WO | WO 2008/006028 | 1/2008 |
| WO | WO 2011/036640 | 3/2011 |
| WO | WO 2011/154427 | 12/2011 |
| WO | WO 2013/163628 | 10/2013 |
| WO | 2014/081855 A1 | 5/2014 |
| WO | 2014/093595 A1 | 6/2014 |

OTHER PUBLICATIONS

United States Patent Office Action for U.S. Appl. No. 14/895,316 dated Oct. 22, 2018 (11 pages).
United States Patent Office Action for U.S. Appl. No. 15/789,348 dated Aug. 13, 2018 (15 pages).
Chinese Patent Office Action for Application No. 201480044748.X dated Aug. 20, 2018 (32 pages, English translation included).
Japanese Patent Office Action for Application No. 2016-518017 dated Aug. 27, 2018 (9 pages, English translation included).
Chinese Patent Office Action for Application No. 201480044748.X dated Apr. 26, 2019 (10 pages, English translation included).
Aartsma-Rus, A. et al., "Antisense-mediated exon skipping: a versatile tool with therapeutic and research applications," RNA 13, 2007, 1609-1624.
Aartsma-Rus, A. et al., "Exploring the frontiers of therapeutic exon skipping for Duchenne muscular dystrophy by double targeting within one or multiple exons," Mol Ther, 2006, 14:401-407.
Aartsma-Rus, A. et al., "Theoretic applicability of antisense-mediated exon skipping for Duchenne muscular dystrophy mutations," Human Mutat, 2009, 30:293-299.
Adler, A.F. et al., "Nonviral direct conversion of primary mouse embryonic fibroblasts to neuronal cells," Molecular therapy, 2012 Nucleic acids 1, e32.
Aiuti, A. et al., "Lentiviral hematopoietic stem cell gene therapy in patients with Wiskott-Aldrich syndrome," Science, 2013, 341(6148): p. 1233151.
Anders, S. et al., "Differential expression analysis for sequence count data," Genome biology 11, 2010, R106.
Anguela, X. M. et al., "Robust ZFN-mediated genome editing in adult hemophilic mice," Blood, 2013, 122:3283-3287.
Aoki, Y. et al., "Bodywide skipping of exons 45-55 in dystrophic mdx52 mice by systemic antisense delivery," Proc Natl Acad Sci USA, 2012, 109:13763-13768.
Bartsevich, V. V. et al., "Engineered zinc finger proteins for controlling stem cell fate," Stem Cells 21, 2003, 632-637.
Beerli, R. R. et al., "Chemically regulated zinc finger transcription factors," J Biol Chem, 2000, 275(42): p. 32617-32627.
Beerli, R.R. et al., "3rd Engineering polydactyl zinc-finger transcription factors," Nat Biotechnol 20, 2002, 135-141.
Beerli, R.R. et al., "3rd Positive and negative regulation of endogenous genes by designed transcription factors," Proc Natl Acad Sci U S A 97, 2000, 1495-1500.
Beerli, R.R. et al., "3rd Toward controlling gene expression at will: specific regulation of the erbB-2/HER-2 promoter by using polydactyl zinc finger proteins constructed from modular building blocks," Proc Natl Acad Sci U S A 95, 1998, 14628-14633.
Beltran, A. et al., "Re-activation of a dormant tumor suppressor gene maspin by designed transcription factors," Oncogene 26, 2007, 2791-2798.
Benedetti, S. et al., "Repair or Replace? Exploiting Novel Gene and Cell Therapy Strategies for Muscular Dystrophies," FEBS Journal (2013).
Berghella, L. et al., "Reversible immortalization of human myogenic cells by site-specific excision of a retrovirally transferred oncogene," Human gene therapy 10, 1999, 1607-1617.
Bhakta, M. S. et al., "Highly active zinc-finger nucleases by extended modular assembly," Genome Res, 2013, 530-538.
Bidou, L. et al., "Sense from nonsense: therapies for premature stop codon diseases," Trends in Molecular Medicine 18, 2012, 679-688.
Blancafort, P. et al., "3rd Scanning the human genome with combinatorial transcription factor libraries," Nat Biotechnol 21, 2003, 269-274.
Boch, J. et al., "Breaking the code of DNA binding specificity of TAL-type III effectors," Science 326, 2009, 1509.
Bowles, D. E. et al., "Phase 1 Gene Therapy for Duchenne Muscular Dystrophy Using a Translation Optimized AAV Vector," Molecular Therapy 20, 2012, 443-455.
Brunet, E. et al., "Chromosomal translocations induced at specific loci in human stem cells," Proc Natl Acad Sci USA, 2009, 106:10620-10625.
Buler et al. Energy-sensing factors coactivator peroxisome proliferator-activated receptor gamma coactivator 1-alpha (PGC-1 alpha) and AMP-activated protein kinase control expression of inflammatory mediators in liver. The Journal of Biological Chemistry, vol. 287, No. 3, pp. 1847-1860, Jan. 13, 2012.
Bultmann, S. et al., "Targeted transcriptional activation of silent oct4 pluripotency gene by combining designer TALEs and inhibition of epigenetic modifiers," Nucleic Acids Res 40, 2012, 5368-5377.
Cerletti, M. et al., "Highly efficient, functional engraftment of skeletal muscle stem cells in dystrophic muscles," Cell 134, 2008, 37-47.

(56) References Cited

OTHER PUBLICATIONS

Cermak, T. et al., "Efficient design and assembly of custom TALEN and other TAL effector-based constructs for DNA targeting," Nucleic Acids Res 30, 2011, e82.
Chapdelaine, P. et al., "Meganucleases can restore the reading frame of a mutual dystrophin," Gene therapy 17, 2010, 846-858.
Cheng, A. W. et al., "Multiplexed activation of endogenous genes by CRISPR-on, an RNA-guided transcriptional activator system," Cell Res, 2013, 23(10): p. 1163-1171.
Cho, S. W. et al., "Analysis of off-target effects of CRISPR/Cas-derived RNA-guided endonucleases and nickases," Genome Res, 2014, 24:132-141.
Cho, S.W. et al., "Targeted genome engineering in human cells with the Cas9 RNA-guided endonuclease," Nat Biotechnol 31, 2013, 230-232.
Christian, M. et al., "Targeting DNA double-strand breaks with TAL effector nucleases," Genetics 186, 2010, 757-761.
Cirak, S. et al., "Exon skipping and dystrophin restoration in patients with Duchenne muscular dystrophy after systemic phosphorodiamidate morpholino oligomer treatment: an open-label, phase 2, dose-escalation study," Lancet 378, 2011, 595-605.
Cong, L. et al., "Multiplex Genome Engineering Using CRISPR/Cas Systems," Science 339, 2013, 819-823.
Cornu et al., "Quantification of zinc finger nuclease-associated toxicity," Meth Mol Biol, 2010, 649:237-245.
Cornu, T. I. et al., "DNA-binding specificity is a major determinant of the activity and toxicity of zinc-finger nucleases," Mol Ther, 2008, 16:352-358.
Cradick, T. J. et al., "CRISPR/Cas9 systems targeting beta-globin and CCR5 genes have substantial off-target activity," Nucleic Acids Res, 2013, 41(20): p. 9584-9592.
Darabi, R. et al., "Human ES- and iPS-derived myogenic progenitors restore dystrophin and improve contractility upon transplantation in dystrophic mice," Cell Stem Cell 10, 2012, 610-619.
Dezawa, M. et al., "Bone marrow stromal cells generate muscle cells and repair muscle degeneration," Science Signaling 309, 2005, 314.
Ding, Q. et al., "A TALEN Genome-Editing System for Generating Human Stem Cell-Based Disease Models," 2013, Cell Stem Cell 12, 238-251.
Ding, Q. et al., "Enhanced efficiency of human pluripotent stem cell genome editing through replacing TALENs with CRISPRs," Cell Stem Cell, 2013, 12:393-394.
Doyle, E. L. et al., "TAL Effector-Nucleotide Targeter (TALE-NT) 2.0: tools for TAL effector design and target prediction," Nucleic Acids Res 40, 2012, W117-122.
Doyon, Y. et al., "Enhancing zinc-finger-nuclease activity with improved obligate heterodimeric architectures," Nat Methods 8, 2010, 74-79.
Edelstein et al. Gene therapy clinical trials worldwide 1989-2004—an overview. J. Gene Med. vol. 6, pp. 597-602, 2004.
Esvelt et al., "Orthogonal Cas9 proteins for RNA-guided gene regulation and editing," Nature Methods 2013, 10(11): p. 1116-1121.
Farinelli, G. et al., "Lentiviral vectors for the treatment of primary immunodeficiencies," J Inherit Metab Dis, 2014.
Farzadfard, F. et al., "Tunable and Multifunctional Eukaryotic Transcription Factors Based on CRISPR/Cas," ACS Synth Biol, 2013, 604-613.
Flanigan, K. M. et al., "Mutational spectrum of DMD mutations in dystrophinopathy patients: application of modern diagnostic techniques to a large cohort," Human mutation 30, 2009, 1657-1666.
Fonfara, I. et al., "Phylogeny of Cas9 determines functional exchangeability of dual-RNA and Cas9 among orthologous type II CRISPR-Cas systems," Nucleic Acids Res, 2013.
Fu, Y., et al., "High-frequency off-target mutagenesis induced by CRISPR-Cas nucleases in human cells," Nat Biotechnol, 2013, 31(9): p. 822-826.
Fu, Y., et al., "Improving CRISPR-Cas nuclease specificity using truncated guide RNAs," 2014, Nat Biotechnol 32, 279-284.
Gaj, T. et al., "Targeted gene knockout by direct delivery of zinc-finger nuclease proteins," Nature Methods, 2012.
Gaj, T. et al., "ZFN, TALEN, and CRISPR/Cas-based methods for genome engineering," Trends Biotechnol, 2013, 31:397-405.
Garg, A. et al., "Engineering synthetic TAL effectors with orthogonal target sites," Nucleic Acids Res 40, 2012, 7584-7595.
Gertz, J. et al., "Transposase mediated construction of RNA-seq libraries," Genome Res 22, 2012, 134-141.
Goemans, N. M. et al., "Systemic administration of PRO051 in Duchenne's muscular dystrophy," The New England journal of medicine 364, 2011, 1513-1522.
Gou, D. et al., "A novel approach for the construction of multiple shRNA expression vectors," J Gene Med, 2007, 9(9): p. 751-763.
Graslund, T. et al., "3rd Exploring strategies for the design of artificial transcription factors: targeting sites proximal to known regulatory regions for the induction of gamma-globin expression and the treatment of sickle cell disease," J Biol Chem 280, 2005, 3707-3714.
Gregorevic, P. et al., "Systemic delivery of genes to striated muscles using adeno-associated viral vectors," Nat Med, 2004, 10:828-834.
Guo, J. et al., "Directed evolution of an enhanced and highly efficient FokI cleavage domain for zinc finger nucleases," J Mol Biol, 2010.
Guschin, D. Y. et al., "A rapid and general assay for monitoring endogenous gene modification," Methods Mol Biol 649, 2010, 247-256.
Hockemeyer, D. et al., "Efficient targeting of expressed and silent genes in human ESCs and iPSCs using zinc-finger nucleases," Nat Biotechnol, 2009, 27(9): p. 851-857.
Hockemeyer, D. et al., "Genetic engineering of human pluripotent cells using TALE nucleases," Nat Biotechnol 29, 2011, 731-734.
Hoffman, E. P. et al., "Dystrophin: the protein product of the Duchenne muscular dystrophy locus," Cell, 1987, 51:919.
Hou, Z. et al., "Efficient genome engineering in human pluripotent stem cells using Cas9 from Neisseria meningitidis," Proc Natl Acad Sci USA, 2013, 110:15644-15649.
Hsu et al. (2012) "Dissecting Neural Function Using Targeted Genome Engineering Technologies", ACS Chem. Neurosci., pp. 603-610.
Hsu et al., "DNA targeting specificity of RNA-guided Cas9 nucleases," Nature Biotechnology 31, 2013, 827-832 doi:10.1038/nbt.2647.
Humbert et al., "Targeted gene therapies: tools, applications, optimization", Critical Reviews in Biochemistry and Molecular Biology, CRC Press, vol. 47, No. 3, Apr. 2012, pp. 264-281.
Hwang, W. Y. et al., "Efficient genome editing in zebrafish using CRISPR-Cas system," Nat Biotechnol, 2013, 31(3):p. 227-229.
Jinek, M. et al., "A programmable dual-RNA-guided DNA endonuclease in adaptive bacterial immunity," Science 337, 2012, 816-821.
Jinek, M. et al., "RNA-programmed genome editing in human cells. eLife 2," e00471, 2013.
Jinek, M. et al., "Structures of Cas9 endonucleases reveal RNA-mediated conformational activation," Science, 2014, 343(6176): p. 1247997.
Joung, J. K. et al., "TALENs: a widely applicable technology for targeted genome editing," Nature Reviews Molecular Cell Biology 14, 2013, 49-55.
Kayali et al., "Site-directed gene repair of the dystrophin gene mediated by PNA-ssODNs," Human Molecular Genetics, vol. 19, No. 16, Aug. 15, 2010, pp. 3266-3281.
Kearns, N. A. et al., "Cas9 effector-mediated regulation of transcription and differentiation in human pluripotent stem cells," Development, 2014, 141(1): p. 219-223.
Kim, H. et al., "Surrogate reporters for enrichment of cells with nuclease-induced mutations," Nat Methods, 2011, 8:941-943.
Kim, Y. et al., "TALENs and ZFNs are associated with different mutation signatures," Nat Methods, 2013.
Kimura, E. et al., "Cell-lineage regulated myogenesis for dystrophin replacement: a novel therapeutic approach for treatment of muscular dystrophy," Hum Mol Genet 17, 2008, 2507-2517.
Konermann, S. et al., "Optical control of mammalian endogenous transcription and epigenetic states," Nature, 2013, 500(7463): p. 472-476.

(56) References Cited

OTHER PUBLICATIONS

Konieczny, P. et al., "Gene and cell-mediated therapies for muscular dystrophy," Muscle Nerve, 2013, 47:649-663.
Kubokawa, I. et al., "Molecular characterization of the 5'-UTR of retinal dystrophin reveals a cryptic intron that regulates translational activity," Molecular Vision, 2010, vol. 16, pp. 2590-2597.
Kyte et al., "A Simple Method for Displaying the Hydropathic Character of a Protein," J. Mol. Biol., 1982, 157:105-132.
Langmead, B. et al., "Ultrafast and memory-efficient alignment of short DNA sequences to the human genome," Genome biology 10, 2009, R25.
Larson, M. H. et al., "CRISPR interference (CRISPRi) for sequence-editing control of gene expression," Nat Protoc, 2013, 8(11): p. 2180-2196.
Latta-Mahieu et al. Gene transfer of a chimeric trans-activator is immunogenic and results in short-lived transgene expression. Human Gene Therapy, vol. 13, No. 13, pp. 1611-1620, Sep. 2002.
Lattanzi, L. et al., "High efficiency myogenic conversion of human fibroblasts by adenoviral vector-mediated MyoD gene transfer. An alternative strategy for ex vivo gene therapy of primary myopathies," The Journal of clinical investigation 101, 1998, 2119-2128.
Lee, H. J. et al., "Targeted chromosomal deletions in human cells using zinc finger nucleases," Genome research 20, 2010, 81-89.
Li, D. et al., "Marginal level dystrophin expression improves clinical outcome in a strain of dystrophin/utrophin double knockout mice," PLoS One, 2010, 5:e15286.
Li, H. et al, "Invivo genome editing restores haemostasis in a mouse model of haemophilia," Nature 475, 2011, 217-221.
Li, T. et al., "Modularly assembled designer TAL effector nucleases for targeted gene knockout and gene replacement in eukaryotes," Nucleic Acids Research, 2011, vol. 39, No. 14, pp. 6315-6325.
Li, Y. et al., "Transcription activator-like effector hybrids for conditional control and rewiring of chromosomal transgene expression," Scientific reports 2, 2012, 897.
Liang, J.C. et al., "Engineering biological systems with synthetic RNA molecules," Mol Cell 43, 2011, 915-926.
Lohmueller, J.J. et al., "A tunable zinc finger-based framework for Boolean logic computation in mammalian cells," Nucleic Acids Res 40, 2012, 5180-5187.
Lovric, J. et al., "Terminal Differentiation of Cardiac and Skeletal Myocytes Induces Permissivity to AAV Transduction by Relieving Inhibition Imposed by DNA Damage Response Proteins," Molecular Therapy, 2012, 2087-2097.
Lu, Q. L. et al., "The status of exon skipping as a therapeutic approach to duchenne muscular dystrophy," Molecular Therapy 19, 2011, 9-15.
Lund et al. "Promoter-targeted phage display selections with preassembled synthetic zinc finger libraries for endogenous gene regulation." Journal of Molecular Biology, vol. 340, pp. 599-613, 2004.
Luo et al. Synthetic DNA delivery systems. Nature Biotechnology, vol. 18, pp. 33-37, 2000.
Maeder et al. Robust, synergistic regulation of human gene expression using TALE activators. Nature Methods, vol. 10, No. 3, pp. 243-246, Feb. 10, 2013, including pp. 1/14-14/14 of Supplementary Material.
Maeder, M. L., "Targeted DNA demethylation and activation of endogenous genes using programmable TALE-TET1 fusion proteins," Nat Biotechnol, 2013, 31(12): p. 1137-1142.
Maeder, M.L. et al., "Robust, synergistic regulation of human gene expression using TALE activators," Nat Methods 10, 2013, 243-245.
Mali, P. et al., "Cas9 as a versatile tool for engineering biology," Nat Methods, 2013, 10(10): p. 957-963.
Mali, P. et al., "CAS9 transcriptional activators for target specificity screening and paired nickases for cooperative genome engineering," Nat Biotechnol, 2013, 31(9): p. 833-838.
Mali, P. et al., "RNA-Guided Human Genome Engineering via Cas9," Science 339, 2013, 823-826.
Mamchaoui, K. et al., "Immortalized pathological human myoblasts: towards a universal tool for the study of neuromuscular disorders," Skelet Muscle 1, 2011, 1-11.
Mendell, J. R. et al., "Dystrophin immunity in Duchenne's muscular dystrophy," New England Journal of Medicine 363, 2010, 1429-1437.
Mendenhall, E. M. et al., "Locus-specific editing of histone modification at endogenous enhancers," Nat Biotechnol, 2013, 31(12): p. 1133-1136.
Mercer, A. C. et al., "Regulation of Endogenous Human Gene Expression by Ligand-Inducible TALE Transcription Factors," ACS Synth Biol, 2013.
Miller, J.C. et al., "A TALE nuclease architecture for efficient genome editing," Nat Biotechnol 29, 2011, 143-148.
Moscou, M. J. et al., "A simple cipher governs DNA recognition by TAL effectors," Science 326, 2009, 1501.
Murphy et al., "The in vitro transcription of the 7SK RNA gene by RNA polymerase III is dependable only on the presence of an upstream promoter," Cell, 1987, 51:81-87.
Mussolino, C. et al., "A novel TALE nuclease scaffold enables high genome editing activity in combination with low toxicity," Nucleic Acids Res 39, 2011, 9283-9293.
Myslinski et al., "An unusually compact external promoter for RNA polymerase III transcription of the human H1RNA gene," Nucleic Acids Res, 2001, 29:2502-2509.
Negroni, E. et al., "In Vivo Myogenic Potential of Human CD133+ Muscle-derived Stem Cells: A Quantitative Study," Molecular Therapy 17, 2009, 1771-1778.
Nishimasu, H. et al., "Crystal structure of cas9 in complex with guide RNA and target DNA Cell," 2014, 156(5): p. 935-949.
Ohshima et al., "Nucleotide sequence of mouse genomic loci including a gene or pseudogene for U6 (4.8S) nuclear RNA," Nucleic Acids Res, 1981, 9:5145-5158.
Ousterout et al., "Reading frame correction by targeted genome editing restores dystrophin expression in cells from Duchenne muscular dystrophy patients," Mol Ther, 2013, 21:1718-1726.
Palu et al. In pursuit of new developments for gene therapy of human diseases. J. Biotechnol. vol. 68, pp. 1-13, 1999.
Papayannakos, C. et al., "Understanding lentiviral vector chromatin targeting: working to reduce insertional mutagenic potential for gene therapy," Gene Ther, 2013, 20(6): p. 581-588.
Park, K.S. et al., "Phenotypic alteration of eukaryotic cells using randomized libraries of artificial transcription factors," Nat Biotechnol 21, 2003, 1208-1214.
Pattanayak, V. et al., "High-throughput profiling of off-target DNA cleavage reveals RNA-programmed Cas9 nuclease specificity," Nat Biotechnol, 2013, 31(9): p. 839-843.
Peault, B. et al., "Stem and progenitor cells in skeletal muscle development, maintenance, and therapy," Molecular Therapy 15, 2007, 867-877.
Perez, E. et al., "Establishment of HIV-1 resistance in CD4+T cells by genome editing using zinc-finger nucleases," Nature biotechnology 26, 2008, 808-816.
Perez-Pinera et al. Abstract 855. "Synergistic Transcriptional Activation by Combinations of Engineered TALEs" was publicly presented at the American Society of Gene & Cell Therapy's 15th Annual Meeting in Philadelphia, Pennsylvania during the Late Abstracts Poster Session Ill: Saturday, May 19, 2012.
Perez-Pinera et al. Synergistic and tunable human gene activation by combinations of synthetic transcription factors. Nature Methods, vol. 10, No. 3, pp. 239-244, Feb. 3, 2013, including pp. 1/12-12-12 of Supplementary Material.
Perez-Pinera et al., "Gene targeting to the ROSA26 locus directed by engineered zinc finger nucleases," Nucleic Acids Research, 2012, 40:3741-3752.
Perez-Pinera et al., "RNA-guided gene activation by CRISPR-Cas9-based transcription factors," Nat Methods, 2013, 10:973-976.
Perez-Pinera, P. et al., "Advances in targeted genome editing," Current Opinion in Chemical Biology 16, 2012, 268-277.
Perez-Pinera, P. et al., "Synergistic and tunable human gene activation by combinations of synthetic transcription factors," Nat Methods 10, 2013, 239-242.

(56) References Cited

OTHER PUBLICATIONS

Persons, D. A., "Lentiviral vector gene therapy: effective and safe?" Mol Ther, 2010, 18(5): p. 861-862.
Piacentino et al., "X-Linked Inhibitor of Apoptosis Protein-Mediated Attenuation of Apoptosis, Using a Novel Cardiac-Enhanced Adeno-Associated Viral Vector," Human Gene Therapy, 2012, 23:635-646.
Pichavant, C. et al., "Current status of pharmaceutical and genetic therapeutic approaches to treat DMD," Molecular Therapy 19, 2011, 830-840.
Polstein, L. R. and Gersbach, C. A., "Light-inducible spatiotemporal control of gene activation by customizable zinc finger transcription factors," J Am Chem Soc, 2012, 134(40): p. 16480-16483.
Popplewell, L. et al., "Gene correction of a duchenne muscular dystrophy mutation by meganuclease-enhanced exon knock-in," Hum Gene Ther, 2013, 24:692-701.
Qi, L.S. et al., "Repurposing CRISPR as an RNA-guided platform for sequence-specific control of gene expression," Cell 152, 2013, 1173-1183.
Ran, F. A. et al., "Double nicking by RNA-guided CRISPR Cas9 for enhanced genome editing specificity," Cell, 2013, 154(6): p. 1380-1389.
Rebar, E.J. et al., "Induction of angiogenesis in a mouse model using engineered transcription factors," Nat Med 8, 2002, 1427-1432.
Reyon, D. et al., "FLASH assembly of TALENs for high-throughput genome editing," Nat Biotechnol 30, 2012, 460-465.
Rousseau, J. et al., "Endonucleases: tools to correct the dystrophin gene" The Journal of Gene Medicine, 2011, vol. 13, pp. 522-537.
Saito et al., "Specific activation of microRNA-127 with downregulation of the proto-oncogene BCL6 by chromatin-modifying drugs in human cancer cells," Cancer Cell, 2006, vol. 9, pp. 435-443.
Salmon, P. and Trono, D., "Production and titration of lentiviral vectors," Curr Protoc Neurosci, 2006, Chapter 4: Unit 4 21.
Sambrook et al., Molecular Cloning and Laboratory manual, Second Ed., Cold Spring Harbor (1989).
Schmid-Burgk, J. L. et al., "A ligation-independent cloning technique for high-throughput of transcription activator-like effector genes," Nat Biotechnol 31, 2012, 76-81.
Scholze et al. TAL effectors are remote controls for gene activation. Current Opinion in Microbiology, vol. 14, pp. 47-53, Jan. 2011.
Schultz, B. R. & Chamberlain, J. S., "Recombinant adeno-associated virus transduction and integration," Molecular Therapy 16, 20088, 1189-1199.
Sebastiano, V. et al., "In Situ Genetic Correction of the Sickle Cell Anemia Mutation in Human Induced Pluripotent Stem Cells Using Engineered Zinc Finger Nucleases," Stem Cells 29, 2011, 1717-1726.
Seidel et al., "Chromatin-modify gin agents in anti-cancer therapy," Biochimie, 2012, vol. 94, pp. 2264-2279.
Seto et al., "Gene Replacement Therapies for Duchenne Muscular Dystrophy Using Adeno-Associated Viral Vectors," Current Gene Therapy, 2012, 12:139-151.
Sharma, S. et al., "Efficiency of nonhomologous DNA and joining varies among somatic tissues, despite similarity in mechanism," Cellular and Molecular Life Science 68, 2011, 661-676.
Silva, G. et al., "Meganucleases and other tools for targeted genome engineering: perspective and challenges for gene therapy," Current gene therapy, 2011, 11:11-27.
Şöllü, C. et al., "Autonomous zinc-finger nuclease pairs for targeted chromosomal deletion," Nucleic acids research 38, 2010, 8269-8276.
Song, L. et al., "Dnase-seq: a high-resolution technique for mapping active gene regulatory elements across the genome from mammalian cells," Cold Spring Harbor protocols 2010, pdb prot5384.
Song, L. et al., "Open chromatin defined by DNaseI and FAIRE identifies regulatory elements that shape cell-type identify," Genome Res 21, 2011, 1757-1767.
Sun, N. et al., "Optimized TAL effector nucleases (TALENs) for use in treatment of sickle cell disease," Molecular bioSystems 8, 2012, 1255-1263.
Szyf, M., "Epigenetics, DNA methylation, and chromatin modifying drugs," Annual Review of Pharmacology and Toxicology, 2009, vol. 49, pp. 243-263.
Taniguchi-Ikeda, M. et al., "Pathogenic exon-trapping by SVA retrotransposon and rescue in Fukuyama muscular dystrophy," Nature 478, 2011, 127-131.
Tebas, P. et al., "Gene editing of CCR5 in autologous CD4 T cells of persons infected with HIV," N Engl J Med, 2014, 370:901-910.
Tedesco, F. S. et al., "Repairing skeletal muscle: regenerative potential of skeletal muscle stem cells," J Clin Invest, 2010, 120:11-19.
Tedesco, F. S. et al., "Stem Cell-Mediated Transfer of a Human Artificial Chromosome Ameliorates Musculat Dystrophy," Science Translational Medicine 3, 96ra78-96ra78, 2011.
Tedesco, F. S. et al., "Transplantation of Genetically Corrected Human iPSC-Derived Progenitors in Mice with Limb-Girdle Muscular Dystrophy," Science Translational Medicine 4, 140ra189, 2012.
Urnov, F. et al., "Highly efficient endogenous human gene correction using designed zinc-finger nucleases," Nature 435, 2005, 646-651.
Van Putten, M. et al., "Low dystrophin levels in heart can delay heart failure in mdx mice," J Mol Cell Cardiol, 2014, 69C:17-23.
Van Putten, M. et al., "Low dystrophin levels increase survival and improve muscle pathology and function in dystrophin/utrophin double-knockout mice," FASEB J, 2013, 27:2484-2495.
Verma and Weitzman. Gene Therapy: Twenty-first century medicine. Annual Review of Biochemistry, vol. 74, pp. 711-738, 2005.
Verma et al. Gene therapy—promises, problems and prospects. Nature, vol. 389, pp. 239-242, 1997.
Vierbuchen, T. et al., "Direct conversion of fibroblasts to functional neurons by defined factors," Nature 463, 2010, 1035-1041.
Wang et al., "Adeno-associated virus vector carrying human minidystrophin genes effectively ameliorates muscular dystrophy in mdx mouse model," Proc Natl Acad Sci USA. (2000) 97(25):13714-13719.
Wang, H. et al., "One-Step Generation of Mice Carrying Mutations in Multiple Genes by CRISPR-Cas-Mediated Genome Engineering," Cell, 2013, 153(4): p. 910-918.
Wein, N. et al., "Efficient bypass of mutations in dysferlin deficient patient cells by antisense-induced exon skipping," Hum Mutat 31, 2010, 136-142.
Welch, E. M. et al., "PTC124 targets genetic disorders caused by nonsense mutations," Nature 447, 2007, 87-91.
Yan et al. Biochimica et Biophysica Acta, vol. 1835, No. 1, pp. 76-85, Jan. 2013.
Yang, L., "Optimization of scarless human stem cell genome editing," Nucleic Acids Res, 2013, 41:9049-9061.
Yusa, K. et al., "Targeted gene correction of α1-antitrypsin deficiency in induced pluripotent stem cells," Nature 478, 2011, 391-394.
Zhang, F. et al. "Efficient construction of sequence-specific TAL effectors for modulating mammalian transcription," Nat Biotechnol 29, 2011, 149-153.
Zhu, C. H. et al., "Cellular senescence in human telomerase reverse transcriptase and cyclin-dependent kinase 4: consequences in aging muscle and therapeutic strategies for muscular dystrophies," Aging cell 6, 2007, 515-523.
Zou, J. et al., "Site-specific gene correction of a point mutation in human iPS cells derived from an adult patient with sickle cell disease," Blood 118, 2011, 4599-4608.
International Search Report and Written Opinion for Application No. PCT/US14/41190 dated Dec. 17, 2014 (14 pages).
United States Patent Office Action for U.S. Appl. No. 14/220,116 dated Jul. 22, 2015 (26 pages).
United States Patent Office Final Action for U.S. Appl. No. 14/220,116 dated May 4, 2016 (29 pages).
Extended European Search Report for Application No. 13781472.9 dated Feb. 3, 2016 (11 pages).

(56) References Cited

OTHER PUBLICATIONS

United States Patent Office Action for U.S. Appl. No. 14/397,420 dated Jun. 2, 2016 (8 pages).
United States Patent Office Action for U.S. Appl. No. 14/397,420 dated Oct. 5, 2016 (10 pages).
International Search Report and Written Opinion for Application No. PCT/US13/38536 dated Nov. 29, 2013 (27 pages).
United States Patent Office Action for U.S. Appl. No. 14/220,116 dated Dec. 2, 2016 (16 pages).
United States Patent Office Action for U.S. Appl. No. 14/895,316 dated Dec. 15, 2016 (13 pages).
Extended European Search Report for Application No. 14806852.1 dated Dec. 8, 2016 (6 pages).
European Examination Report for Application No. 13781472.9 dated Mar. 2, 2017 (5 pages).
European Patent Office Action for Application No. 14806852.1 dated Sep. 15, 2017 (5 pages).
United States Patent Office Action for U.S. Appl. No. 14/220,116 dated Jul. 19, 2017 (15 pages).
United States Patent Office Notice of Allowance for U.S. Appl. No. 14/220,116 dated Sep. 19, 2017 (8 pages).
European Patent Office Action for U.S. Appl. No. 13781472.9 dated Jan. 4, 2018 (4 pages).
European Patent Office Action for Application No. 14806852.1 dated Feb. 9, 2018 (4 pages).
United States Patent Office Action for U.S. Appl. No. 14/895,316 dated Mar. 21, 2018 (8 pages).
United States Patent Office Action for U.S. Appl. No. 15/789,348 dated Feb. 22, 2018 (14 pages).
Japanese Patent Office Action for Application No. 2016-518017 dated Jul. 4, 2019 (7 pages, English translation included).
United States Patent Office Action for U.S. Appl. No. 14/895,316 dated Apr. 19, 2019 (11 pages).
Australian Patent Office Examination Report No. 1 for Application No. 2014274840 dated Mar. 13, 2019 (5 pages).
United States Patent Office Action for U.S. Appl. No. 15/789,348 dated May 22, 2019 (13 pages).
European Patent Office Extended Search Report for Application No. 19168481.0 dated Jun. 24, 2019 (5 pages).
Chinese Patent Office Action for Application No. 201480044748.X dated Dec. 16, 2019 (11 pages, English translation included).
United States Patent Office Notice of Allowance for U.S. Appl. No. 14/895,316 dated Jan. 27, 2020 (7 pages).
United States Patent Office Notice of Allowance for U.S. Appl. No. 15/634,425 dated Mar. 9, 2020 (8 pages).
Kwa et al., "Chromatin modifying agents—the cutting edge of anticancer therapy," Drug Discovery Today, 2011, 16 ($^{13}/_{14}$):543-547.
United States Patent Office Action for U.S. Appl. No. 15/789,348 dated Dec. 10, 2019 (18 pages).
United States Patent Office Action for U.S. Appl. No. 15/634,425 dated Aug. 8, 2019 (10 pages).
United States Patent Office Notice of Allowance for U.S. Appl. No. 14/895,316 dated Sep. 30, 2019 (9 pages).

* cited by examiner

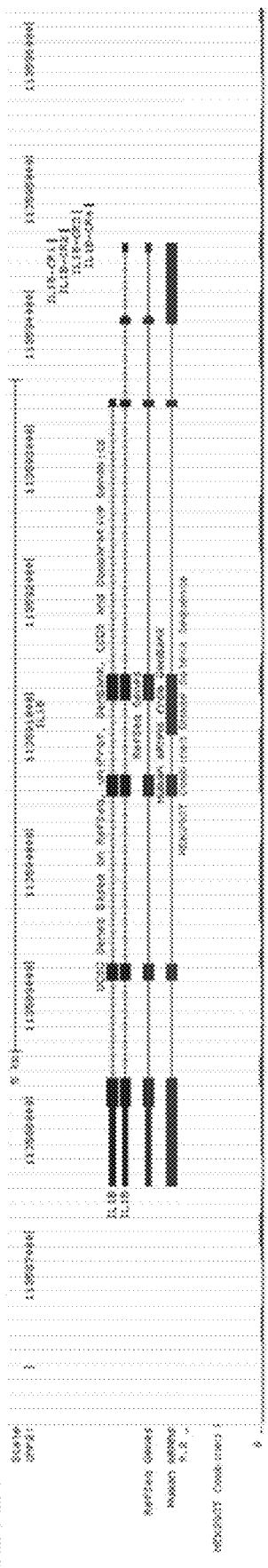
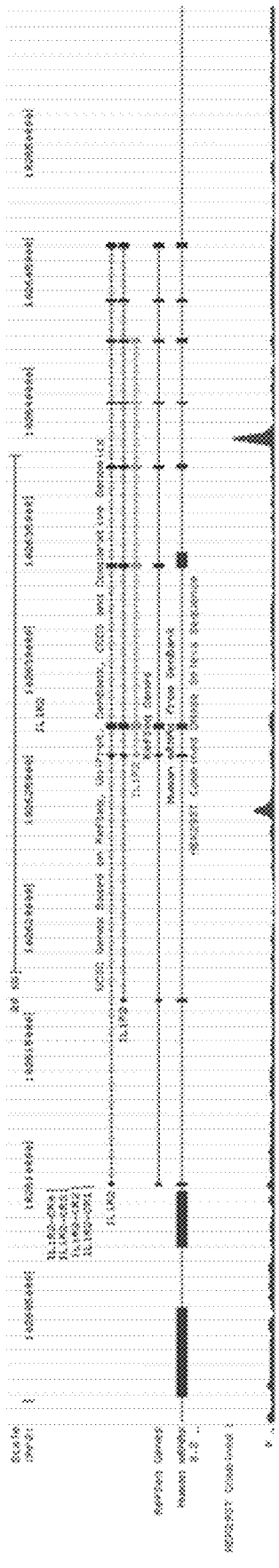
Fig. 4D

M*DYKDHDGDYKDHDIDYKDDDDK*MAPKKKRKV<u>GRGMDKKYSIGLAIGTNSVGWAVITD
EYKVPSKKFKVLGNTDRHSIKKNLIGALLFDSGETAEATRLKRTARRRYTRRKNRICYLQ
EIFSNEMAKVDDSFFHRLEESFLVEEDKKHERHPIFGNIVDEVAYHEKYPTIYHLRKKLVD
STDKADLRLIYLALAHMIKFRGHFLIEGDLNPDNSDVDKLFIQLVQTYNQLFEENPINASG
VDAKAILSARLSKSRRLENLIAQLPGEKKNGLFGNLIALSLGLTPNFKSNFDLAEDAKLQL
SKDTYDDDLDNLLAQIGDQYADLFLAAKNLSDAILLSDILRVNTEITKAPLSASMIKRYDEH
HQDLTLLKALVRQQLPEKYKEIFFDQSKNGYAGYIDGGASQEEFYKFIKPILEKMDGTEE
LLVKLNREDLLRKQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDKNLPNEKVL
PKHSLLYEYFTVYNELTKVKYVTEGMRKPAFLSGEQKKAIVDLLFKTNRKVTVKQLKEDY
FKKIECFDSVEISGVEDRFNASLGTYHDLLKIIKDKDFLDNEENEDILEDIVLTLTLFEDRE
MIEERLKTYAHLFDDKVMKQLKRRRYTGWGRLSRKLINGIRDKQSGKTILDFLKSDGFAN
RNFMQLIHDDSLTFKEDIQKAQVSGQGDSLHEHIANLAGSPAIKKGILQTVKVVDELVKV
MGRHKPENIVIEMARENQTTQKGQKNSRERMKRIEEGIKELGSQILKEHPVENTQLQNE
KLYLYYLQNGRDMYVDQELDINRLSDYDVDAIVPQSFLKDDSIDNKVLTRSDKNRGKSD
NVPSEEVVKKMKNYWRQLLNAKLITQRKFDNLTKAERGGLSELDKAGFIKRQLVETRQIT
KHVAQILDSRMNTKYDENDKLIREVKVITLKSKLVSDFRKDFQFYKVREINNYHHAHDAY
LNAVVGTALIKKYPKLESEFVYGDYKVYDVRKMIAKSEQEIGKATAKYFFYSNIMNFFKTE
ITLANGEIRKRPLIETNGETGEIVWDKGRDFATVRKVLSMPQVNIVKKTEVQTGGFSKESI
LPKRNSDKLIARKKDWDPKKYGGFDSPTVAYSVLVVAKVEKGKSKKLKSVKELLGITIME
RSSFEKNPIDFLEAKGYKEVKKDLIIKLPKYSLFELENGRKRMLASAGELQKGNELALPSK
YVNFLYLASHYEKLKGSPEDNEQKQLFVEQHKHYLDEIIEQISEFSKRVILADANLDKVLS
AYNKHRDKPIREQAENIIHLFTLTNLGAPAAFKYFDTTIDRKRYTSTKEVLDATLIHQSITG
LYETRIDLSQLGGD</u>PIAGSKASPKKKRKVGRA***DALDDFDLDMLGSDALDDFDLDMLGS
DALDDFDLDMLGSDALDDFDLDML***IN<u>*YPYDVPDYA*</u>S (SEQ ID NO: 1)

FLAG epitope tag = italicized
Nuclear localization sequence = bold
*Streptococcus pyogenes* Cas9 = underlined
VP64 (4x minimal VP16 domain) = italicized and bold
HA epitope tag = italicized and underlined

Fig. 9A

GAGGGCCTATTTCCCATGATTCCTTCATATTTGCATATACGATACAAGGCTG
TTAGAGAGATAATTGGAATTAATTTGACTGTAAACACAAAGATATTAGTACA
AAATACGTGACGTAGAAAGTAATAATTTCTTGGGTAGTTTGCAGTTTTAAAA
TTATGTTTTAAAATGGACTATCATATGCTTATCGTAACTTGAAAGTATTTCGA
TTTCTTGGCTTTATATATCTTGTGGAAAGGACGAAACACC*G*GG*TCTTC*GA*GA*
*AGA*CC*TGTTTTAGAGCTAGAAATAGCAAGTTAAAATAAGGCTAGTCCGTTATC*
*AACTTGAAAAAGTGGCACCGAGTCGGTGC*<u>TTTTTTT</u> (SEQ ID NO:2)

U6 promoter = bold
+1 transcription start site = underlined
BbsI restriction sites to clone in guide RNA = italicized and underlined
Chimeric guide RNA sequence = italicized
Poly-T terminator sequence = bold and underlined

Fig. 9B

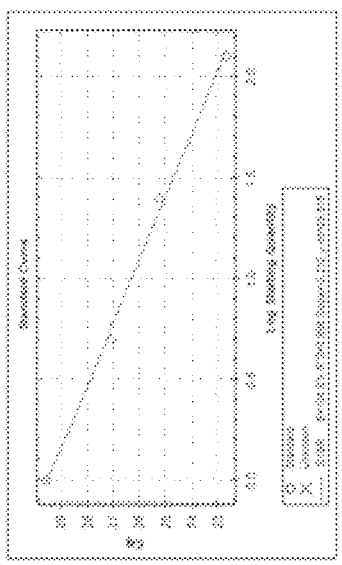
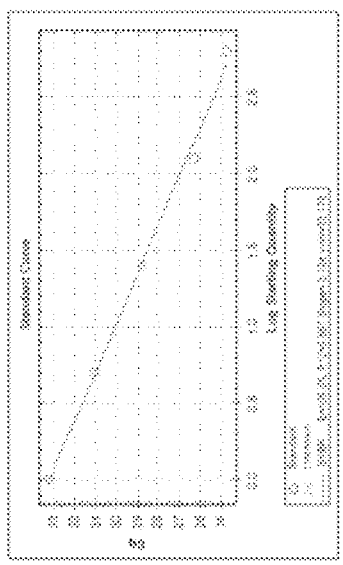
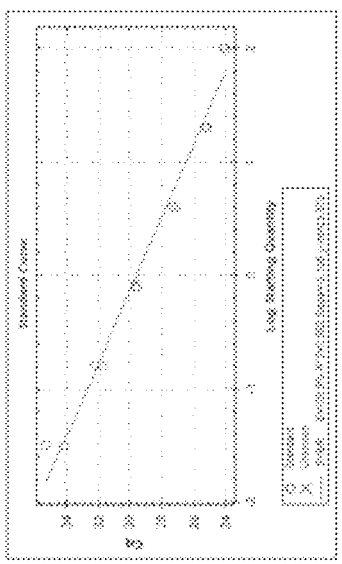
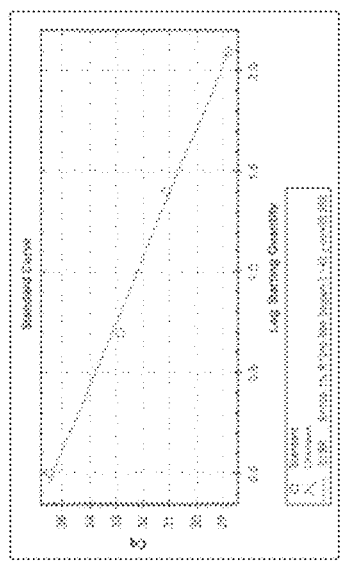
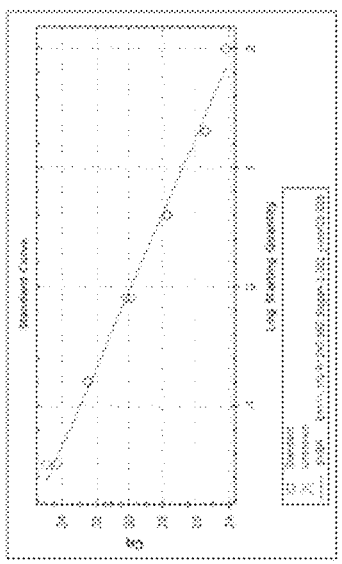
Fig. 10A

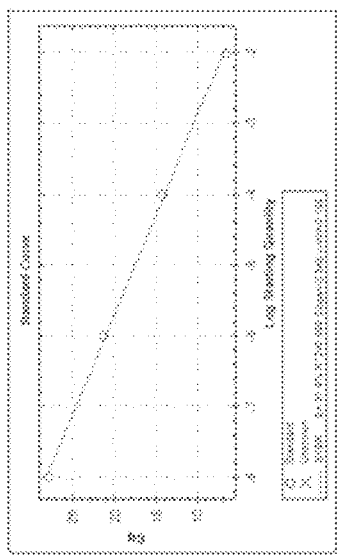
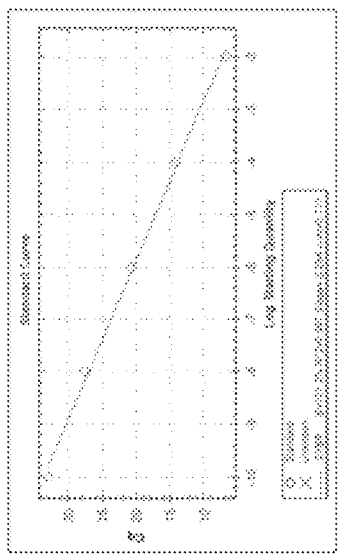
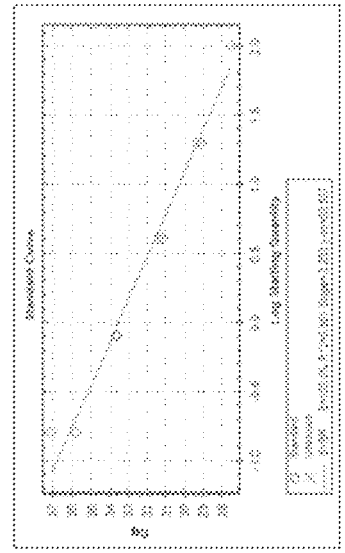
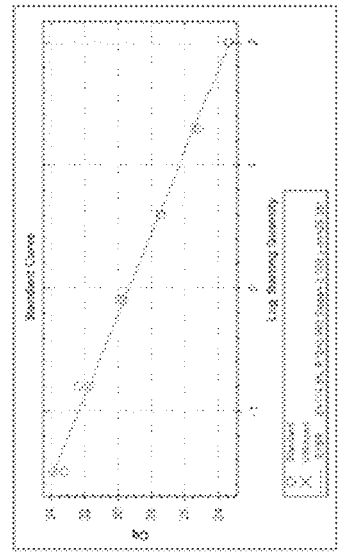
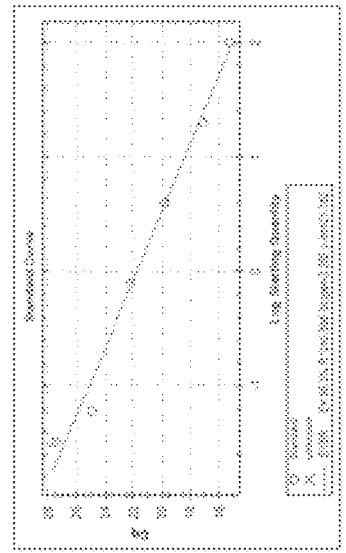
Fig. 10B

Fig. 11A
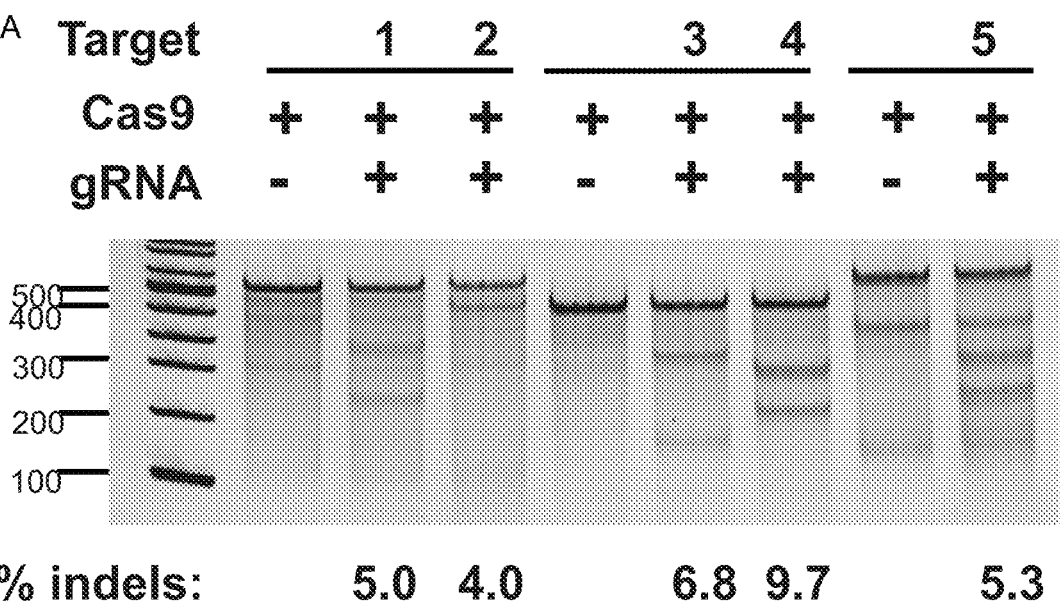
Fig. 11B
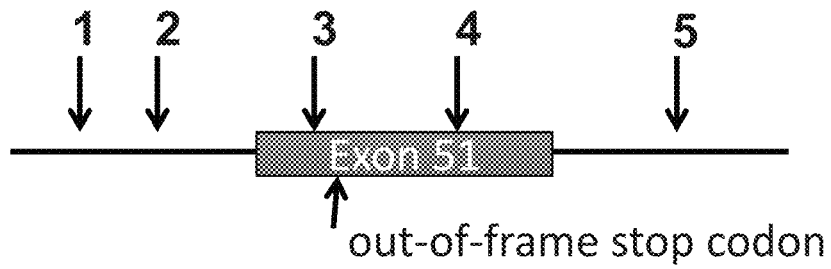
out-of-frame stop codon
Fig. 11C
Expected cleavage sizes
CR1=352/237
CR2=461/128
CR3=301/150
CR4=272/179
CR5=280/203

Fig. 20A

| SEQ ID NO: | |
|---|---|
| 405 | Intron 50  Exon 51  ▼  PAM |
| 406 | AAAATATTTAGCTCCTACTCAGACTGTTACTCTGGTGACACAA |
| | TTTATAAATCGAGGATGAGTCTGACAATGAGACCACTGTGTT |
| | ‖‖‖‖‖‖‖‖‖‖‖‖‖‖‖‖‖‖‖ |
| | sgRNA  5'-GCCUACUCAGACUGUUACUC...... |

Fig. 20B

SEQ ID NO:  Deletions

| 407 | TAGCTCCTACTCAGACTGTTACTCTGGTGACACAAC (x16) | Length | Frame |
|---|---|---|---|
| 408 | TAGCTCCTACTCAGACT--------GGTGACACAAC | -8 | +2 |
| 409 | TAGCTCCTAC--------------TCTGGTGACACAAC | -12 | +3 |
| 410 | TAGCTCCTACTCAGAC--------TGGTTACACAAC (x2) | -8 | +2 |
| 411 | TAGCTCCTACTCAGAC------------------ | -11 | +3 |
| 412 | TAGCTCCTACTCAGACTGTT----------ACACAAC | -9 | +3 |
| 413 | TAGCTCCTACTCAGACTG------TGGTGACGTGAC | -6 | +3 |
| 414 | TAGCTCCTACTCAGAC-----TCTGGTGACACAAC | -4 | +1 |
| 415 | TAGCTCCTACTCAGA------CCTCTGGTGACACAAC (x2) | -5 | +2 |
| 416 | TAGCTCCTACTCAGGCTG-----GCTGGTGACACAAC | -4 | +1 |
| 417 | TAGCTCCTACTCAGACT---ACTCTGGTGACACAAC | -3 | +3 |
| 418 | TAGCTCCTACTCAGAC--------TGTTGACACAAC | -8 | +2 |
| 419 | --------------------CTGGTGACACAAC | -26 | +2 |
| 420 | TAGCTCCTACTCAGACTGTTA------GACACAAC | -7 | +1 |
| 421 | TAGCTCCTACTCAGACT-----GTCTGGTGACACAAC | -3 | +3 |

Insertions

| 422 | CAGAC---------------TGTTACTCTGGTGAC (x16) | Length | Frame |
|---|---|---|---|
| 423 | CAGACCACTGTGTCCTA-------CTGGTGAC | +9 | +3 |

Fig. 20C

Total events: 17/33 (52%)
+1 Frame: 3/17 (18%)
+2 Frame: 7/17 (41%)
+3 Frame: 7/17 (41%)

Fig. 20D

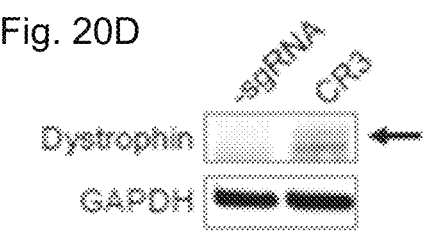

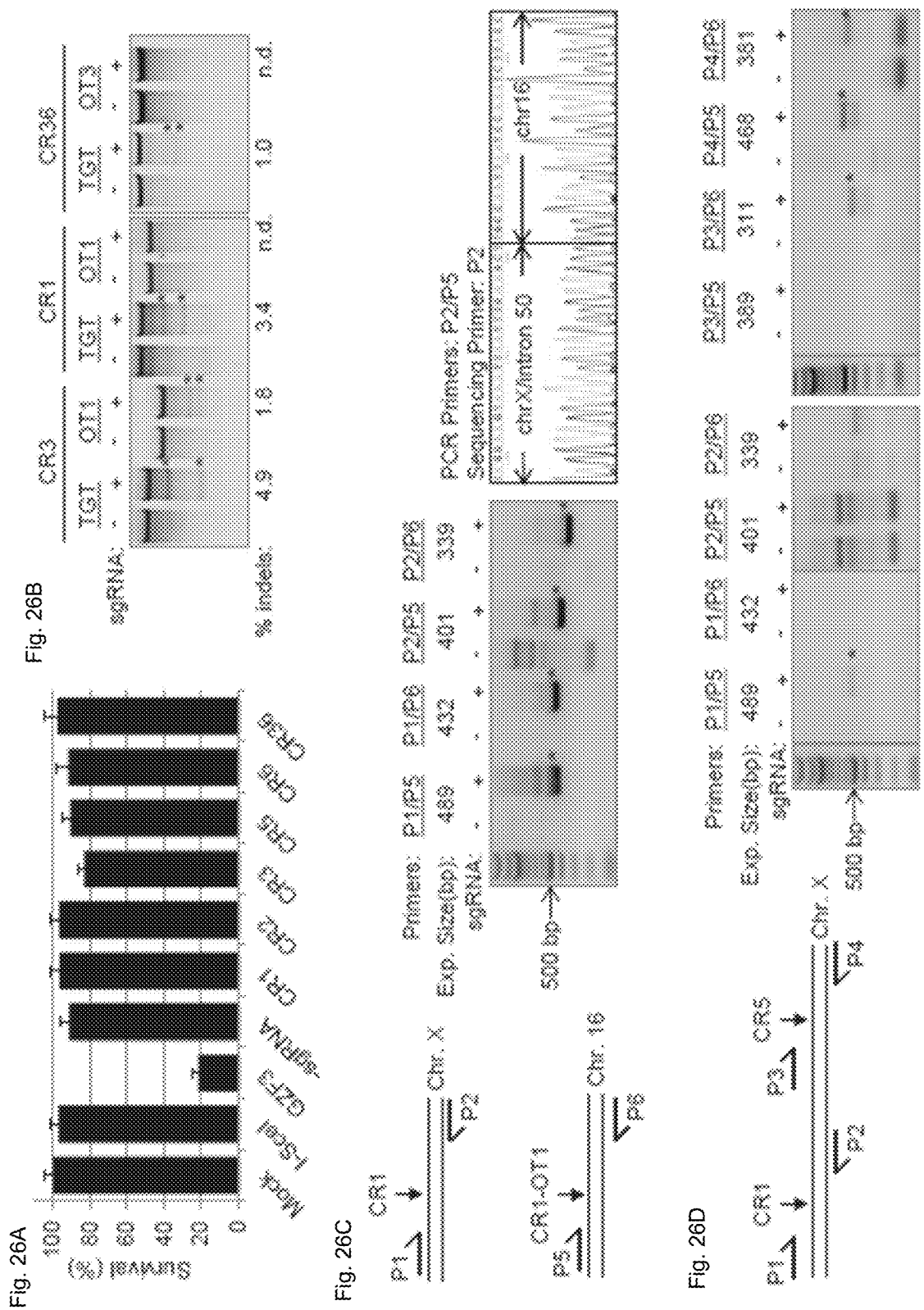

Rosa T2A opt DNA sequence (SEQ ID NO: 434)

ATGAGGTCTGACTACAAGGACCATGACGGTGATTATAAAGATCATGACATCGATTACAAGGATGACGATGACAAGAT
GGCCCCCAAGAAGAAGaggaaggtgggcctcgaGCCCCGGAGAAAAACCGTACAAGTGCCCTGAGTGCGGGAAATCAT
TCTCCGACCCTGGCGCGCTCGTCCGGCACCAAAGGACGCATACAGGGGAAAAGCCGTATAAGTGTCCCGAGTGTGGA
AAGAGCTTCTCGCAGAGAGCCCACCTTGAACGACACCAAAGAACACACACTGGTGAGAAACCCTATAAGTGTCCAGA
GTGCGGCAAATCGTTTAGCAGATCCGATGACTTGGTGCGCCACCAGCGGACACACACGGGTGAAAAGCCCTACAAAT
GCCCGGAGTGTGGGAAGTCGTTTTCAAGGTCGGATCATCTGACTACCCATAGCGGCACCCATACGGGAGCggcggcc
cgcgcctGGTGAAGAGCGAGCTGGAGGAGAAGAAGTCCGAGCTGCGGCACAAGCTGAAGTACGTGCCCCACGAGTA
CATCGAGCTGATCGAGATCGCCAGGAACCCCACCCAGGACCGCATCCTGGAGATGAAGGTGATGGAGTTCTTCATGA
AGGTGTACGGCTACAGGGGAGAGCACCTGGGCGGAAGCAGAAAGCCTGACGGCGCCATCTATACAGTGGGCAGCCCC
ATCGATTACGGCGTGATCGTGGATACAAAGGCCTACAGCGGCGGCTACAATCTGCCTATCGGCCAGGCCGACGAGAT
GCAGAGATACGTGAAGGAGAACCAGACCCGGAATAAGCACATCAACCCCAACGAGTGGTGGAAGGTGTACCCTAGCA
GCGTGACCGAGTTCAAGTTCCTGTTCGTGAGCGGCCACTTCAAGGGCAACTACAAGGCCCAGCTGACCAGGCTGAAC
CGCAAAACCAACTGCAATGGCGCCGTGCTGAGCGTGGAGGAGCTGCTGATCGGCGGCGAGATGATCAAAGCCGGCAC
CCTGACACTGGAGGAGGTGCGGCGCAAGTTCAACAACGGCGAGATCAACTTCGAGGGCAGAGGAAGTCTTCTAACAT
GCGGTGACGTGGAGGAGAATCCCGGCCCTAgatcTGACTACAAAGACCATGACGGTGATTATAAAGATCATGACATC
GATTACAAGGATGACGATGACAAGATGGCCCCCAAGAAGAAGaggaaggtgggcctcgagccGGGAGAGAAGCCGTA
CAAGTGTCCCGAATGTGGAAAGAGCTTCTCACAGTCGGGGGACTTCGGCGCCACCAGCGCACACATACTGGTGAAA
AGCCGTATAAGTGTCCAGAATGTGGCAAATCATTCTCCACATCAGGGAGCCTGGTCAGGCACCAGCGAACCCACACG
GGTGAGAAGCCTATAAGTGCCCCGAATGCGGGAAGTCCTTTTCGCAGAGAGCCCACTTGGAGAGGCACCAGAGGAC
CCATACGGGGAGAAACCTTACAAGTGCCCTGAATGCGGAAAGTCGTTCTCGACCCATCTGGATCTCATCAGACATC
AGAGAACGCACACTGGAGAGAAACCCTACAAATGCCCCGAGTGTGGGAAGTCGTTTAGCCGAAAGGACAATCTCAAA
AACCATCAACCGACACACGGGTGAAAAACCATACAAATGCCCGGAGTGCGGCAAATCGTTTCCCAACTTGCGCA
CTTGCGGGCACACCAACGCACGCATACTGGAGCGGCCGCccgcgccCTGGTGAAGAGCGAGCTGGAGGAGAAGAAGT
CCGAGCTGCGGCACAAGCTGAAGTACGTGCCCCACGAGTACATCGAGCTGATCGAGATCGCCAGGAACCCCACCCAG
GACCGCATCCTGGAGATGAAGGTGATGGAGTTCTTCATGAAGGTGTACGGCTACAGGGGAGAGCACCTGGGCGGAAG
CAGAAAGCCTGACGGCGCCATCTATACAGTGGGCAGCCCCATCGATTACGGCGTGATCGTGGACACAAAGGCCTACA
GCGGCGGCTACAATCTGCCTATCGGCCAGGCCGACGAGATGGAGAGATACGTGGAGGAGAACCAGACACGGGATAAG
CACCTCAACCCCAACGAGTGGTGGAAGGTGTACCCTAGCAGCGTGACCGAGTTCAAGTTCCTGTTCGTGAGCGGCCA
CTTCAAGGGCAACTACAAGGCCCAGCTGACCAGGCTGAACCACATCACCAACTGCAATGGCGCCGTGCTGAGCGTGG
AGGAGCTGCTGATCGGCGGCGAGATGATCAAAGCCGGCACCCTGACACTGGAGGAGGTGCGGCGCAAGTTCAACAAC
GGCGAGATCAACTTCTGA

Rosa T2A opt protein sequence (SEQ ID NO: 435)

MRSDYKDHDGDYKDHDIDYKDDDDMAPKKKRKVGLEPGEKPYKCPECGKSFSDPGALVRHQRTHTGEKPYKCPECG
KSFSQRAHLERHQRTHTGEKPYKCPECGKSFSRSDDLVRHQRTHTGEKPYKCPECGKSFSRSDNLTRHQFTHTGAAA
RALVKSELEEKKSELRHKLKYVPHEYIELIEIARNPTQDRILEMKVMEFFMKVYGYRGEHLGGSRKPDGAIYTVGSP
IDYGVIVDTKAYSGGYNLPIGQADEMQRYVKENQTRNKHINPNEWWKVYPSSVTEFKFLFVSGHFKGNYKAQLTRLN
RKTNCNGAVLSVEELLIGGEMIKAGTLTLEEVRRKFNNGEINFEGRGSLLTCGDVEENPGPRSDYKDHDGDYKDHDI
DYKDDDDKMAPKKKRKVGLEPGEKPYKCPECGKSFSQSGDLRRHQRTHTGEKPYKCPECGKSFSTSGSLVRHQRTHT
GEKPYKCPECGKSFSQRAHLERHQRTHTGEKPYKCPECGKSFSTRLDLIRHQRTHTGEKPYKCPECGKSFSRKDNLK
NHQPTHTGEKPYKCPECGKSFSQLAHLRAHQRTHTGAAARALVKSELEEKKSELRHKLKYVPHEYIELIEIARNPTQ
DRILEMKVMEFFMKVYGYRGEHLGGSRKPDGAIYTVGSPIDYGVIVDTKAYSGGYNLPIGQADEMERYVEENQTRDK
RLNPNEWWKVYPSSVTEFKFLFVSGHFKGNYKAQLTRLNRITNCNGAVLSVEELLIGGEMIKAGTLTLEEVRRKFNN
GEINF

Fig. 33

SASTG capsid sequence (SEQ ID NO: 436)

tggcaactcctctatgcgcactcgctcgctcgtgggcctggcgacaaaggtcgccagacggacgtgctttgca
cgtccggcccaccgagcgagcgagtgcgcatagagggagtggccaactccatcactagagtatggcagtgacgta
acgcgaagcgcgcgaagcgagaccacgcctaccagctgcgtcagcagtcaggtgaccttttgcgacagtttgcgac
accacgtggccgctgagggtatatattctcgagtgagcgaaccaggagctccattttgaccgcgaaatttgaacgag
cagcagccatgccggggttctacgagattgtcctgaaggtcccgagtgacctggacgagcacctgccgggcatttct
aactcgtttgttaactgggtggccgagaaggaatgggagctgccgccggattctgacatggatccgaatctgattga
gcaggcaccctgaccgtgccgaaaagcttcagcgcgagttcctggtggagtggcgccgcgtgagtaaggccccgg
aggccctctttttgtccagttcgaaaaggggggagacctacttccacctgcacgtgctgattgagaccatcggggtc
aaatccatggtggtcggccgctacgtgagccagattaaagagaagctggtgaccgcatctaccggggtcgagcc
gcagcttccgaactggttcgcggtgaccaaaacgcgaaatggcgccggggcgggaacaaggtggtggacgactgct
acatccccaactacctgctccccaagaccagcccgagctccagtgggcgtggactaacatggaccagtatttaagc
gctgtttgaatctcgcggagcgtaaacggctggtggcgcagcatctgacgcacgtgtcgcagacgcaggagcagaa
caaagagaatcagaaccccaattctgacgcgccggtcatcaggtcaaaaacctcagccaggtacatggagctggtcg
ggtggctggtggaccgcgggatcacgtcagaaaagcaatggattcaggaggaccaggcctcgtacatctccttcaac
gccgctccaactcgcggtcccagatcaaggccgcgctggacaatgcctccaagatcatgagcctgacaaagacggc
tccggactacctggtgggcagcaaccgcggaggacattaccaaaaatcgtatctaccaaatcctggagctgaacg
ggtacgatccgcagtacgcggcctccgtcttcctgggctgggcgcaaaagaagttcgggaagaggaacaccatctgg
ctctttgggccggccacgacgggtaaaaaccaacatcgcggaagccatcgcccacgccgtgcccttctacggctgcgt
aaactggaccaatgagaactttccctccaacgattgcgtcgacaagatggtgatctggtgtcgaggagggcaagatga
cggccaaggtcgtggagagcgccaaggccattctgggcggaagcaaggtgcgcgtggaccaaaagtgcaagtcatcg
gcccagatcgaacccactcccgtgatcgtcacctccaacaccaacatgtgcgccgtgattgacggaacagcaccac
cttcgagcatcagcagccgctgcaggaccggatgtttaaatttgaacttacccgccgtttggaccatgactttggga
aggtcaccaaacaggaagtaaaggactttttccggtgggcttccgatcacgtgactgacgtggctcatgagttctac
gtcagaaaggtggagctaagaaacgcccgcctccaatgacgcggatgtaagcgagccaaaacggcagtgcacgtc
acttgcgcagccgacaacgtcagacgcggaagcaccggcggactacgggacaggtaccaaaacaaatgttctcgtc
acgtgggcatgaatctgatgcttttccctgtaaaacatgcgagagaatgaatcaaattccaatgtctgttttacg
catggtcaaagagactgtgggaatgcttcctggaatgtcagaatctcaaccgtttctgtcgtcaaaagaagac
ttatcagaaactgtgtccaattcatcatatcctgggaagggcacccgagattgcctgttcggcctgcgatttggcca
atgtggacttggatgactgtgtttctgagcaataaatgacttaaaccaggtatggctgctgacggttatcttccaga
ttggctcgaggacaacctttctgaaggcattcgtgagtggtggctctgaaacctggagtccctcaacccaaagcga
accaacaacaccaggacaaccgtcggggtcttgtcttccgggttacaaataccctggaccgggtaacggactcgac
aaaggagagccggtcaacgaggcggacgcggcagccctcgaacacgacaaagcttacgaccagcagctcaaggccgg
tgacaacccgtacctcaagtacaaccacgtcgacgccagtttcaggagcgtcttcaagaagtacgtcttttgggg
gcaaccttggcagagcagtcttccaggccaaaaagaggatccttgagcctcttggtctggtgaggaagcagctaaa
acggctcctggaaagaagaggcctgtagatcagtctcctcaggaaccggactcatcatctggtgttggcaaatcggg
caaacagcctgccagaaaaagactaaatttcggtcagactggcgactcagagtcagtcccagaccctcaacctctcg
gagaaccaccagcagccccacaagtttgggatctaatacaatggcttcaggcggtggcgcaccaatggcagacaat
aacgagggtgccgatggagtgggtaattcctcaggaaattggcattgcgattcccaatggctggcgacagagtcat
caccaccagcaccagaacctggccctgccacttacaacaaccatctctacaagcaaatctccagcGTtcaACGg
gagcttcaaacgacaaccactactttggctacagcacccctgggggtatttgactttaacagattccactgccac
ttctcaccacgtgactggcagcgactcattaacaacaactgggattccgccaagaaactcagcttcaagctctt
caacatccaagttaaagaggtcacgcagaacgatggcacgacgactattgccaataaccttaccagcacggttcaag
tgttttacgactcggagtatcagctcccgtacgtgctcggtcggcgcaccaaggctgtctccgccgtttccagcg
gacgtcttcatggtccctcagtatggataccctcaccctgaacaacggaagtcaagggtggagctcatcctttta
ctgctggagtacttccttcgcagtgctaaggactggaaataacttccaattcagctatacctcgaggatgtac
cttttcacagcagctacgtcaagccagagtttggatcgcttgatgaatcctcttattgatcagtatctgtactac
ctgaacagaacgcaaggaacaacctctggaacaaccaaccaatcacggctgcttttagccaggctgggcctcagtc
tatgtctttgcaggccagaaattggctacctgggcctgctaccggcaacagagactttcaaagactgctaacgaca
acaacaacagtaactttccttggacagcggccagcaaatatcatctcaatggccgcgactcgctggtgaatccagga
ccagctatggccagtcacaaggacgatgaagaaaaattttttcctatgcacggcaatctaatattggcaaagaagg
gacaacggcaagtaacgcagaattagataatgtaatgattacggatgaagaagagattcgtaccaccaatcctgtgg
caacagagcagtatggaactgtggcaaataacttgcagagctcaaatacagctcccacgactagaactgtcaatgat
cagggggccttacctggatggtgtggcaagatcgtgacgtgtaccttcaaggaccatctgggcaaagattcctca
cacggatggacactttcatcctttctcctgatgggaggctttggactgaaacatccgcctcctcaaatcatgatca
aaaatactccggtaccggcaaatcctccgacgactttcagcccggccaagttgcttcattatcactcagtactcc

Fig. 34A

```
actggacaggtcagcgtggaaattgagtgggagctacagaaagaaaacagcaaacgttggaatccagagattcagta
cacttccaactacaacaagtctgttaatgtggactttactgtagacactaatggtgtttatagtgaacctgcccta
ttggaacccgtatctcacacgaaacttgtaatcctggttaatcaataaaccgtttaattcgtttcagttgaacttt
ggctcttgtgcacttcttatcttatcttgtttccatggctactgcgtagataagcagcggcctgcggcgcttgcgt
tcgcggtttacaactgtggttaatatttaactctcgccataccctagtgatggagttggccactcctctatgcg
cactcgctcgtcggtggcggacgtgaaagcacgtccgtctcgcgacctttggtcgccaggcccaccgagcg
agcagtgcgcatagaggcagtggccaa
```

SASTG capsid peptide sequence (SEQ ID NO: 437)

MAADGYLPDWLEDNLSEGIREWWALKPGVPQPKANQQHQDNRRGLVLPGYKYLGPGNGLDKGEPVNEADAAALEHDK
AYDQQLKAGDNPYLKYNHADAEFQERLQEDTSFGGNLGRAVFQAKKRILEPLGLVEEAAKTAPGKKRPVDQSPQEPD
SSSGVGKSGKQPARKRLNFGQTGDSESVPDPQPLGEPPAAPTSLGSNTMASGGGAPMADNNEGADGVGNSSGNNECD
SQWLGDRVITTSTRTWALPTYNNHLYKQISSASTGASMDNHYFGYSTPWGYFDFNRFHCHFSPRDWQRLINNNWGFR
PKKLSFKLFNIQVKEVTQNDGTTTIAMNLTSTVQVFTDSEYQLPYVLGSAHQGCLPPFPADVFMVPQYGYLTLNNGS
QAVGRSSFYCLEYFPSQMLRTGNNFQFSYTFEDVPFHSSYAHSQSLDRLMNPLIDQYLYYLNRTQSTTSGTTNQSRL
LFSQAGPQSMSLQARNWLPGPCYRQQRLSKTANDNNNSNFPWTAASKYHLNGRDSLVNPGPAMASHKDDEEKFFPMH
GNLIFGKEGTTASNAELDNVMITSEEEIRTTNPVATEQYGTVANNLQSSNTAPTTRTVNDQGALPGMVWQDRDVYLQ
GPIWAKIPHTGSHFHPSFLMGGFGLKHPPPQIMIKNTPVPANPPTTFSPAKFASFITQYSTGQVSVEIEWELQKENS
KRWNPEIQYTSNYNKSVNVDFTVDTNGVYSEPRPIGTRYLTRNL
```

Fig. 34B

DZF16 ZFN target site (SEQ ID NO:442):

5'-CAAACTAGAAATGCCATCTTCCTTGATGTTGGAGGTACCTGC-3'

3'-GTTTGATCTTTACGGTAGAAGGAACTACAACCTCCATGGACG-5'

DZF16-L6 left full amino acid sequence (SEQ ID NO:443)

MDYKDHDGDYKDHDIDYKDDDDKMAPKKKRKVGRLEPGEKPYKCPECGKSFSRKDALEGHQRTHTGEKPY
KCPECGKSFSHRTTLTNHQRTHTGEKPYKCPECGKSFSQRNALAGHQRTHTGEKPYKCPECGKSFSHKNA
LQNHQRTHTGEKPYKCPECGKSFSDPGHLVRHQRTHTGEKPYKCPECGKSFSTSGNLVRHQRTHTGAAAR
ALVKSELEEKKSELRHKLKYVPHEYIELIEIARNPTQDRILEMKVMEFFMKVYGYRGEHLGGSRKPDGAI
YTVGSPIDYGVIVDTKAYSGGYNLPIGQADEMERYVEENQTRDKHLNPNEWWKVYPSSVTEFKFLFVSGH
FKGNYKAQLTRLNHITNCNGAVLSVEELLIGGEMIKAGTLTLEEVRRKFNNGEINF*

DZF16-R6 right full amino acid sequence (SEQ ID NO:444)

MDYKDHDGDYKDHDIDYKDDDDKMAPKKKRKVGRLEPGEKPYKCPECGKSFSQQRSLVGHQRTHTGEKPY
KCPECGKSFSDKKDLTRHQPTHTGEKPYKCPECGKSFSTSGHLVRHQRTHTGEKPYKCPECGKSFSQRAH
LERHQRTHTGEKPYKCPECGKSFSTSGSLVRHQRTHTGEKPYKCPECGKSFSTSGNLVRHQRTHTGAAAR
ALVKSELEEKKSELRHKLKYVPHEYIELIEIARNPTQDRILEMKVMEFFMKVYGYRGEHLGGSRKPDGAI
YTVGSPIDYGVIVDTKAYSGGYNLPIGQADEMQRYVKENQTRNKHINPNEWWKVYPSSVTEFKFLFVSGH
FKGNYKAQLTRLNRKTNCNGAVLSVEELLIGGEMIKAGTLTLEEVRRKFNNGEINF*

Fig. 35

E51C3 target site (SEQ ID NO:445):

5'-(t)ATCTGCCCATGACTGGCGCAGGG(a)-3'

3'-(a)TAGACGGGTACTGACCGCGTCCC(t)-5'

E51C-3L left full amino acid sequence (SEQ ID NO:446)

MDYKDHDGDYKDHDIDYKDDDDKMAPKKKRKVGRLEPGERPFQCRICMRNFSSKQALAVHTRTHTGEKPF
QCRICMRNFSQSTTLKRHLRTHTGEKPFQCRICMRNFSRSDHLSLHLKTHLRGSQLVKSELEEKKSELRH
KLKYVPHEYIELIEIARNPTQDRILEMKVMEFFMKVYGYRGEHLGGSRKPDGAIYTVGSPIDYGVIVDTK
AYSGGYNLPIGQADEMQRYVKENQTRNKHINPNEWWKVYPSSVTEFKFLFVSGHFKGNYKAQLTRLNRKT
NCNGAVLSVEELLIGGEMIKAGTLTLEEVRRKFNNGEINF*

E51C-3R right full amino acid sequence (SEQ ID NO:447)

MDYKDHDGDYKDHDIDYKDDDDKMAPKKKRKVGRLEPGERPFQCRICMRNFSRRAHLQNHTRTHTGEKPF
QCRICMRNFSQSTTLKRHLRTHTGEKPFQCRICMRNFSDGGHLTRHLKTHLRGSQLVKSELEEKKSELRH
KLKYVPHEYIELIEIARNPTQDRILEMKVMEFFMKVYGYRGEHLGGSRKPDGAIYTVGSPIDYGVIVDTK
AYSGGYNLPIGQADEMERYVEENQTRDKHLNPNEWWKVYPSSVTEFKFLFVSGHFKGNYKAQLTRLNHIT
NCNGAVLSVEELLIGGEMIKAGTLTLEEVRRKFNNGEINF*

Fig. 36

DZF15 target site (SEQ ID NO:448):

5'-ACTAGAAATGCCATCTTCCTTGATGTTGGAGGTACCTGCTCT-3'
3'-TGATCTTTACGGTAGAAGGAACTACAACCTCCATGGACGAGA-5'

DZF15-L6 left full amino acid sequence (SEQ ID NO:449)

MDYKDHDGDYKDHDIDYKDDDDKMAPKKKRKVGRLEPGEKPYKCPECGKSFSRRFTLTNHQRTHTGEKPY
KCPECGKSFSQRNALAGHQRTHTGEKPYKCPECGKSFSHRNALQNHQRTHTGEKPYKCPECGKSFSDPGH
LVRHQRTHTGEKPYKCPECGKSFSTSGNLVRHQRTHTGEKPYKCPECGKSFSQSSNLVRHQRTHTGAAAR
ALVKSELEEKSELRHKLKYVPHEYIELIEIARNPTQDRILEMKVMEFFMKVYGYRGEHLGGSRKPDGAI
YTVGSPIDYGVIVDTKAYSGGYNLPIGQADEMERYVEENQTRQKHLNPNEWWKVYPSSVTEFKFLFVSGH
FKGNYKAQLTRLNHITNCNGAVLSVEELLIGGEMIKAGTLTLEEVRRKFNNGEINF*

DZF15-R6 right full amino acid sequence (SEQ ID NO:450)

MDYKDHDGDYKDHDIDYKDDDDKMAPKKKRKVGRLEPGEKPYKCPECGKSFSQRNALAGHQRTHTGEKPY
KCPECGKSFSQQRSLVGHQRTHTGEKPYKCPECGKSFSDKKDLTRHQRTHTGEKPYKCPECGKSFSTSGH
LVRHQRTHTGEKPYKCPECGKSFSQRAHLERHQRTHTGEKPYKCPECGKSFSTSGSLVRHQRTHTGAAAR
ALVKSELEEKSELRHKLKYVPHEYIELIEIARNPTQDRILEMKVMEFFMKVYGYRGEHLGGSRKPDGAI
YTVGSPIDYGVIVDTKAYSGGYNLPIGQADEMQRYVKENQTRNKHINPNEWWKVYPSSVTEFKFLFVSGH
FKGNYKAQLTRLNRKTNCNGAVLSVEELLIGGEMIKAGTLTLEEVRRKFNNGEINF*

DZF15-L5 left full amino acid sequence (SEQ ID NO:451)

MDYKDHDGDYKDHDIDYKDDDDKMAPKKKRKVGRLEPGEKPYKCPECGKSFSQRNALAGHQRTHTGEKPY
KCPECGKSFSHRNALQNHQRTHTGEKPYKCPECGKSFSDPGHLVRHQRTHTGEKPYKCPECGKSFSTSGN
LVRHQRTHTGEKPYKCPECGKSFSQSSNLVRHQRTHTGAAARALVKSELEEKSELRHKLKYVPHEYIEL
IEIARNPTQDRILEMKVMEFFMKVYGYRGEHLGGSRKPDGAIYTVGSPIDYGVIVDTKAYSGGYNLPIGQ
ADEMERYVEENQTRQKHLNPNEWWKVYPSSVTEFKFLFVSGHFKGNYKAQLTRLNHITNCNGAVLSVEEL
LIGGEMIKAGTLTLEEVRRKFNNGEINF*

DZF15-R5 right full amino acid sequence (SEQ ID NO:452)

MDYKDHDGDYKDHDIDYKDDDDKMAPKKKRKVGRLEPGEKPYKCPECGKSFSQQRSLVGHQRTHTGEKPY
KCPECGKSFSDKKDLTRHQRTHTGEKPYKCPECGKSFSTSGHLVRHQRTHTGEKPYKCPECGKSFSQRAH
LERHQRTHTGEKPYKCPECGKSFSTSGSLVRHQRTHTGAAARALVKSELEEKSELRHKLKYVPHEYIEL
IEIARNPTQDRILEMKVMEFFMKVYGYRGEHLGGSRKPDGAIYTVGSPIDYGVIVDTKAYSGGYNLPIGQ
ADEMQRYVKENQTRNKHINPNEWWKVYPSSVTEFKFLFVSGHFKGNYKAQLTRLNRKTNCNGAVLSVEEL
LIGGEMIKAGTLTLEEVRRKFNNGEINF*

Fig. 37

E51C4 target site (SEQ ID NO:453):

5'-(t)GCCATCTTCCTTGATGTTGGAGGT(a)-3'
3'-(a)CGGTAGAAGGAACTACAACCTCCA(t)-5'

E51C-4L left full amino acid sequence (SEQ ID NO:454)

MDYKDHDGDYKDHDIDYKDDDDKMAPKKKRKVGRLEPGERPFQCRICMRNFSSPSKLARHTRTHTGEKPF
QCRICMRNFSVRHNLTRHLRTHTGEKPFQCRICMRNFSQRNNLGRHLKTHTGAAARALVKSELEEKKSEL
RHKLKYVPHEYIELIEIARNPTQDRILEMKVMEFFMKVYGYRGEHLGGSRKPDGAIYTVGSPIDYGVIVD
TKAYSGGYNLPIGQADEMQRYVKENQTRNKHINPNEWWKVYPSSVTEFKFLFVSGHFKGNYKAQLTRLNR
KTNCNGAVLSVEELLIGGEMIKAGTLTLEEVRRKFNNGEINF*

E51C-4R right full amino acid sequence (SEQ ID NO:455)

MDYKDHDGDYKDHDIDYKDDDDKMAPKKKRKVGRLEPGERPFQCRICMRNFSIPNHLARHTRTHTGEKPF
QCRICMRNFSQSAHLKRHLRTHTGEKPFQCRICMRNFSHRNSLTRHLKTHTGAAARALVKSELEEKKSEL
RHKLKYVPHEYIELIEIARNPTQDRILEMKVMEFFMKVYGYRGEHLGGSRKPDGAIYTVGSPIDYGVIVD
TKAYSGGYNLPIGQADEMERYVEENQTRDKHLNPNEWWKVYPSSVTEFKFLFVSGHFKGNYKAQLTRLNH
ITNCNGAVLSVEELLIGGEMIKAGTLTLEEVRRKFNNGEINF*

Fig. 38

"Single vector, multiplex CRISPR system"
"Dual vector, multiplex CRISPR system"
"Single vector, single gRNA system"
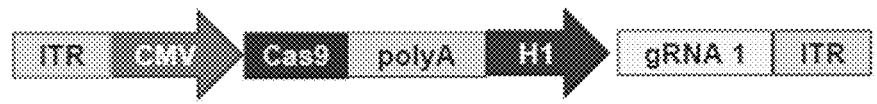
Fig. 39

SaCas9-NLS (NLS underlined) (SEQ ID NO: 459)

atgaaaaggaactacattctggggctggacatcggattacaagcgtgggtatggattattgactatgaaacaag
ggacgtgatcgacgcaggcgtcagactgttcaaggaggccaacgtggaaaacaatgagggacggagaagcaagaggg
gagccaggcgcctgaaacgacgagaaggcacagaatccagagggtgaagaaactgctgttcgattacaacctgctg
accgaccattctgagctgagtggaattaatcctatgaagccagggtgaaggcctgagtcagaagctgtcagagga
agagtttttcgcagctctgctgcacctggctaagcgcgaggagtgcataacgtcaatgaggtggaagaggacaccg
gcaacgagctgtctacaaggaacagatctcacgcaatagcaaagctctggaagagaagtatgtcgcagagctgcag
ctggaacggctgaagaaagatggcgaggtgagaggtcaattaataggttcaagcaagcgactacgtcaagaagc
caagcagctgctgaaagtgcagaaggcttaccaccagctggatcagagcttcatcgatacttatatcgacctgctgg
agactcgggagaacctactatgagggaccaggagaagggagccccttcggatggaagaacatcaaggaatggtacgag
atgctgatggacattgcacctatttccagaagagctgagaagcgtcaagtacgcttataacgcagatctgtacaa
cgccctgaatgacctgaacaacctggtcatcaccagggatgaaaacgagaaactggaatactatgagaagttccaga
tcatcgaaaacgtgtttaagcagaagaaaagcctacactgaaacagattgctaaggagatcctggtcaacgaagag
gacatcaagggctaccggtgacaagcactggaaaaccagagttcaccaatctgaaagtgtatcacgatattaagga
catcacagcacggaaagaaatcattgagaacgccgaactgctggatcagattgctaagatcctgactatctaccaga
gctccgaggacatccaggaagagctgactaacctgaacagcgagctgacccaggaagagatcgaacagattagtaat
ctgaagggctacaccggaacacacaacctgtccctgaaagctatcgatctgattctggatgagctgtggcatacaaa
cgacaatcagattgcaatctttaaccggctgaagctggtcccaaaaaaggtggacctgagtcagcagaaagagatcc
aaccacactggtggacgatttcattctgtcacccgtggtcaagcggagcttcatccagagcatcaaagtgatcaac
gccatcatcaagaagtacggcctgcccaatgatatcattatcgagctggctagggagaagaacagcaaggacgcaca
gaagatgatcaatgagatgcagaaacgaaaccggcagaccaatgaacgcattgaagagattatccgaactaccggga
aagagaacgcaaagtacctgattgaaaaaatcaagctgcacgatatgcaggaggggaagtgtctgtattctctggag
gccatccctggagacctgctgaacaatccattcaactacgaggtcgatcatattatcccagagagcgtgtccttt
cgacaattctttaacaacaaggtgctgtcaagcaggaagagaatctaaaagcgcaataggactctttccagt
acctgtctagttcagattccaagatctcttacgaaacctttaaaagcacattctgaatctggccaaaggaaaggc
cgcatcagcaagaccaaaaggagtacctgctggaagagcgggacatcaacagattctccgtccagaaggatttat
taacggaatctggtggacacaagatacgctactcgcggcctgatgaatctgctgcgatcctatttccgggtgaaca
atctgatgtgaaagtcaagtccatcaacgrgggttcacatctttctgaggcgcaaatggaagttaaaaaggag
cgcaacaaggtacaagcaccatgcgaagatgctctgattatcgcaaatgccgacttcatctttaaggagtggaa
aaagctggacaaagccaagaaagtgatggagaaccagatgttcgaagaagcaggcgcaatctatgccgaatcg
agacagaacaggagtacaaggagatttcatcactcctaccagatcaagatatcaaggatttcaaggactacaag
tactctcacggggtgataaaaagccaacagagagctgatcaatgacacctgtatagtacaagaaaagacgataa
gggaatacctgattgtgaacaatctgaacggactgtacgacaaagataatacaagctgaaaagctgatcaaca
aaagtccgagaagctgtgatgtgccaccatgatcctcagatatatcagaaactgaagctgattatggagcagtac
ggcgacgagaagaacccactgtataagtactatgaagagactgggaactacctgaccaagtatagcaaaaaggataa
tggccccgtgatcaagaagatcaagtactatgggaacaagctgaatgcccatctggacatcacagacgattaccta
acagtcgcaacaaggtggtcaagctgtcactgaagccatacagattcgatgtctatctggacaacggcgtgtataaa
ttcgtgactgtcaagaatctggatgtcatcaaaaaggagaactactatgaagtgaatagcaagtgctacgaagaggc
taaaaagctgaaaaagattagcaaccaggcagagttcatcgcctcctttttacaacaacgacctgattaagatcaatg
gcgaactgtataggtcatcgggctgaacaatgatctgctgaaccgcattgaagtgaatatgattgacatcacttac
cgagagtatctggaaaacatgaatgataagcgcccccctcgaattatcaaaacaattgcctctaagactcagagtat
caaaaagtactcaaccgacattctggggaaacctgtatgaggtgaagagcaaaagcaccctcagattataaaagg
gcagcggagcaagcgcctgctgctactaagaaagctggtcaagctaagaaaaagaaa**ggatcctacccatacgat
gttccagattacgcttaa**

SaCas9 gRNA (SEQ ID NO: 460)

[protospacer]gttttagtactctggaaacagaatctactaaaacaaggcaaaatgccgtgtttatctcgtcaac
ttgttggcgagatttttt

Fig. 40

NmCas9 (NLS 1 underlined NLS 2 underlined/bold, HA tag bold)(SEQ ID NO: 461)

atggtgcctaagaagaagagaaaggtggctgccttcaaacctaattcaatcaactacatcctcggcctcgatatcgg
catcgcatccgtcggctgggcatggtagaaattgacgaagaagaaaacccatccgcctgattgatttgggcgtgc
gcgtatttgagcgtgccgaagtaccgaaaacaggcgactccttgccatggcaaggcgttggcgcgcagtgttcgc
cgcctgacccgccgtcgcgccacgctgcttcggacccgccgcctattgaaacgcgaaggcgtattacaagccgc
caattttgacgaaacggcttgattaaatccttaccgaatacaccatggcaacttcgcgcagccgcattagaccgca
aactgacgcctttagagtggtcggcagtcttgttgcatttaatcaaacatcgcggctatttatcgcaacggaaaaac
gagggcgaaactgccgataaggagcttggcgctttgcttaaaggcgtagccggcaatgcccatgccttacagacagg
cgatttccgcacaccggccgaattggctttaaataaatttgagaaagaaagcggccatatccgcaatcagcgcagcg
attattcgcatacgttcagccgcaaagatttacaggcggagctgatttttgctgtttgaaaaacaaaaagaatttggc
aatccgcatgtttcaggcggccttaaagaaggtattgaaaccctacgatgacgcaacgccctgccctgtccggcga
tgccgttcaaaaatgtgggcgcattgcaccttcgaaccggcagagccgaaagccgctaaaaacacctacacagccg
aacgtttcatctggctgaccaagctgaacaacctgcgtattttagagcaagcagcgagcggccattgaccgatacc
gaacgcgccacgcttatggacgagccatacagaaaatccaaactgacttacgacaagcccgtaagctgctggttt
agaagataccgccttttcaaaggcttgcgctatggtaaagacaatgccgaagcctcaacattgatggaaatgaagg
cctaccatgccatcagccgtgcactggaaaagaaggattgaaagacaaaaatccccattaaaccttctcccgaa
ttacaagacgaaatccggcacggcattctcccgttcaaaaccgatgaagacattacaggccgtctgaaagaccgtat
acagccgaaatcttagaagcgctgttgaaacacatcagcttcgataagttcgtccaaatttccttgaaagcattgc
gccgaattgtgcctctaatggaacaaggcaaacgttacgatgaagcctgcgccgaaatctacggagaccattacgg
aagaagaatacggaagaaaagatttatctgcgccgattccgccgacgaaatccgcaacccgtcgtcttcgcgc
gttatctcaagcacgtaaggtcattaacggcgtggtacgccgttacggctcccagctcgtatccatattgaaactg
caagggaagtaggtaaatcgtttaaagaccgcaaagaaattgagaaacgccaagaagaaaaccgcaaagaccggaa
aaagccgccgccaaattccgagagtatttcccaattttgtcgagaacccaaatccaaagatattctgaaactgcg
cctgtacgagcaacaacacggcaaatgcctgtattcggcaaagaaatcaacttagccgtctgaacgaaaaaggct
atgtcgaaatcgaccatgcctgccgttctcgcgcacatgggacgacagttcaacaataaagtactggtattgggc
agcgaaaaccaaacaaaggcaatcaaacccttacgaatacttcaacggcaaagacaacagccgcgaatggcagga
atttaaagcgcgtgtcgaaaccagccgttttccgcgcagtaaaaaacaacggattctgctgcaaaattcgatgaag
acggctttaaagaacgcaatctgaacgacacgcgctacgtcaaccgtttcctgtgtcaatttgttgccgaccgtatg
cggctgacaggtaaaggcaagaaacgtgtcttgcatccaacggacaaattaccaatctgttgcgcggcttttgggg
attgcgcaaagtgcgtgcggaaaacgaccgccatcacgccttggacgccgtcgtcgttcctgctcgaccgttgcca
tgcagcagaaaattaccgtttttgtacgctataaagagatgaacgcgtttgacgtaaaaccatagacaaagaaaca
ggagaagtgctgcatcaaaaaacacacttcccacaaccttgggaattttcgcacaagaagtcatgattcgcgtctt
cggcaaaccggacggcaaacccgaattcgaagaagccgatacctagaaaaactgcgcacgttgcttgccgaaaaat
tatcatctcgcccgaagcgtacacgaatacgttacgccactgtttgtttcagcgcgcccaatcggaagatgagc
gggcaagggcatatggagaccgtcaaatccgccaaacgactggacgaaggcgtcagcgtgttgcgcgtaccgctgac
acagttaaaactgaaagacttggaaaaaatggtcaatcgggagcgcgaacctagctatacgaagcactgaaagcac
ggctggaagcacataaaacgatcctgccaaagcctttgcgagccgttttacaaatacgataaagcaggcaaccgc
acccaacaggtaaaagccgtacgcgtagagcaagtacagaaaaccggcgtatgggtgcgcaaccataacggtattgc
cgacaacgcaaccatggtgcgcgtagatgtgtttgagaaaggcgacaagtattatctggtaccgatttacagttggc
aggtagcgaaagggatttgccggatagggctgttgtacaaggaaaagatgaagaagattggcaacttattgatgat
agtttcaactttaaattctcattacaccctaatgatttagtcgaggttataacaaaaaagctagaatgtttggtta
ctttgccagctgccatcgaggcacaggtaatatcaatatacgcattcatgatcttgatcataaaattggcaaaaatg
gaatactggaagtatcggcgtcaaaaccgcccttcattccaaaaataccaaattgacgaactgggaaagaaatc
agaccatgccgtctgaaaaaacgccggcctgtccgttacccatacgatgttccagattacgctgcagct<u>**ccagcagc
gaagaaaaagaagctgga**</u>ttaa

NmCas9 short hairpin from Thomson PNAS 2013 (SEQ ID NO: 462)

[protospacer]GTTGTAGCTCCCTTTCTCATTTCGGAAACGAAATGAGAACCGTTGCTACAATAAGGCCGTCTGA
AAAGATGTGCCGCAACGCTCTGCCCCTTAAAGCTTCTGCTTTAAGGGGCTTTTTT

NmCas9 long hairpin from Church Nature Biotech 2013 (SEQ ID NO: 463)

[protospacer]GTTGTAGCTCCCTTTCTCATTTCGCAGTGCTACAATGAAAATTGTCGCACTGCGAAATGAGAACC
GTTGCTACAATAAGGCCGTCTGAAAAGATGTGCCGCAACGCTCTGCCCCTTAAAGCTTCTGCTTTAAGGGGCTTTT
TT

Fig. 41

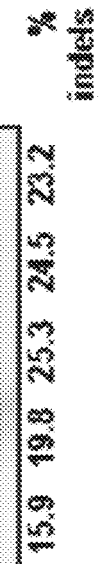
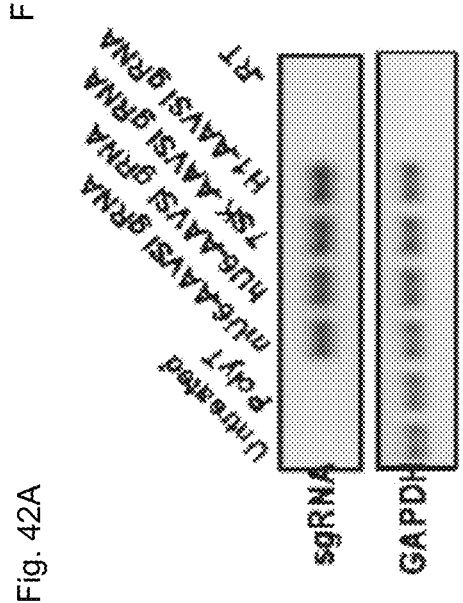
Fig. 42A
Fig. 42B
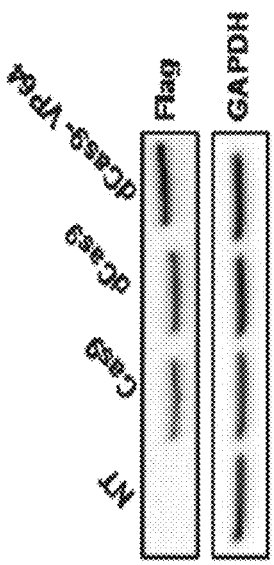
Fig. 42C

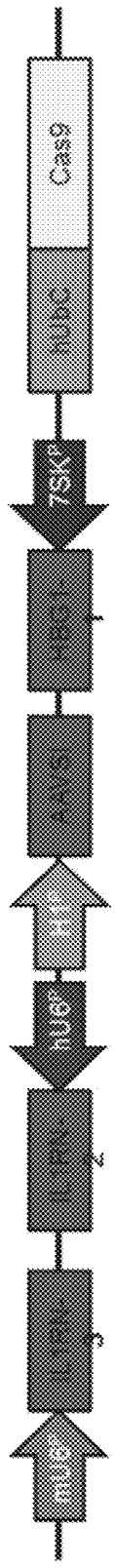
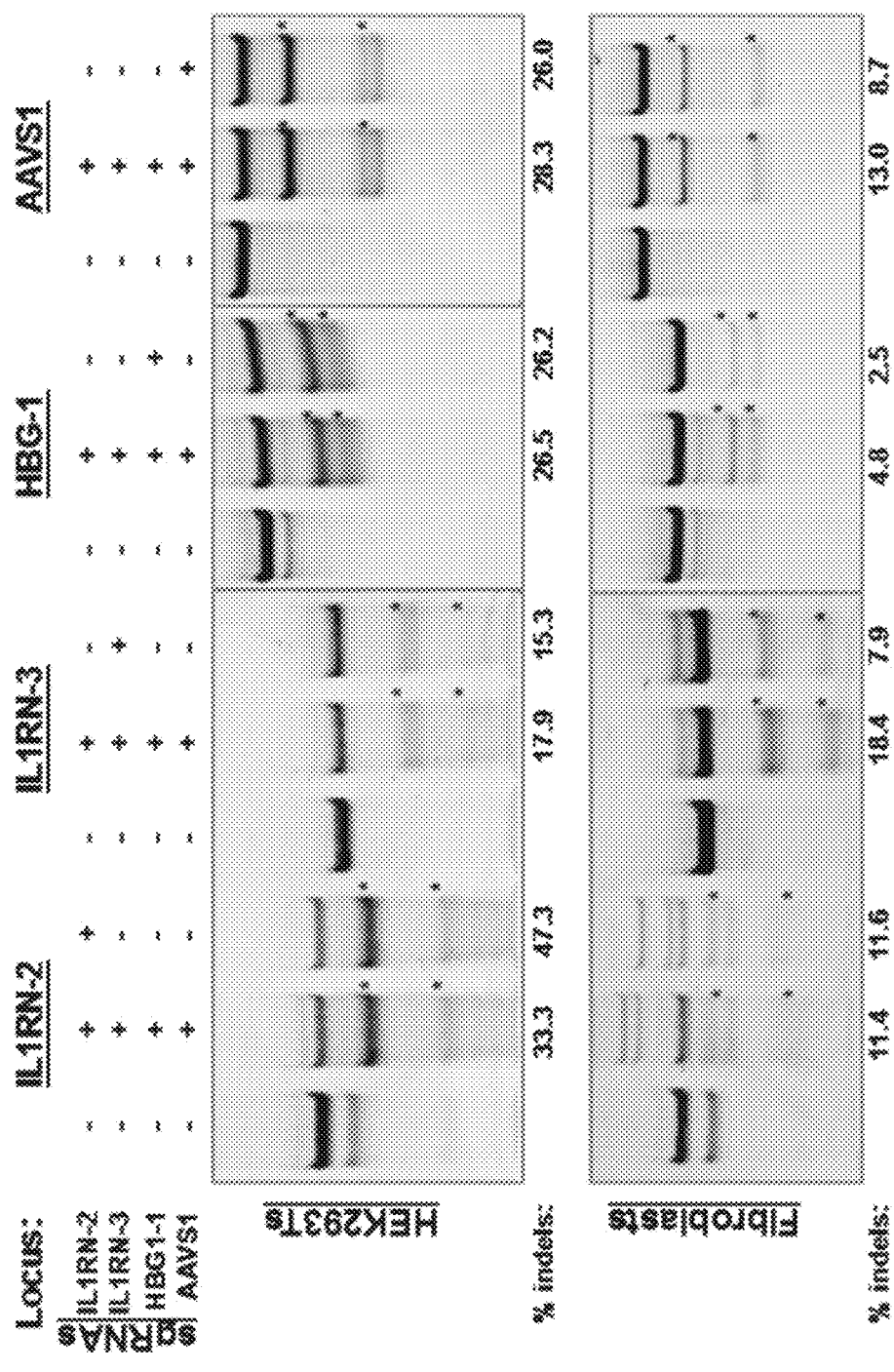
Fig. 44A
Fig. 44B

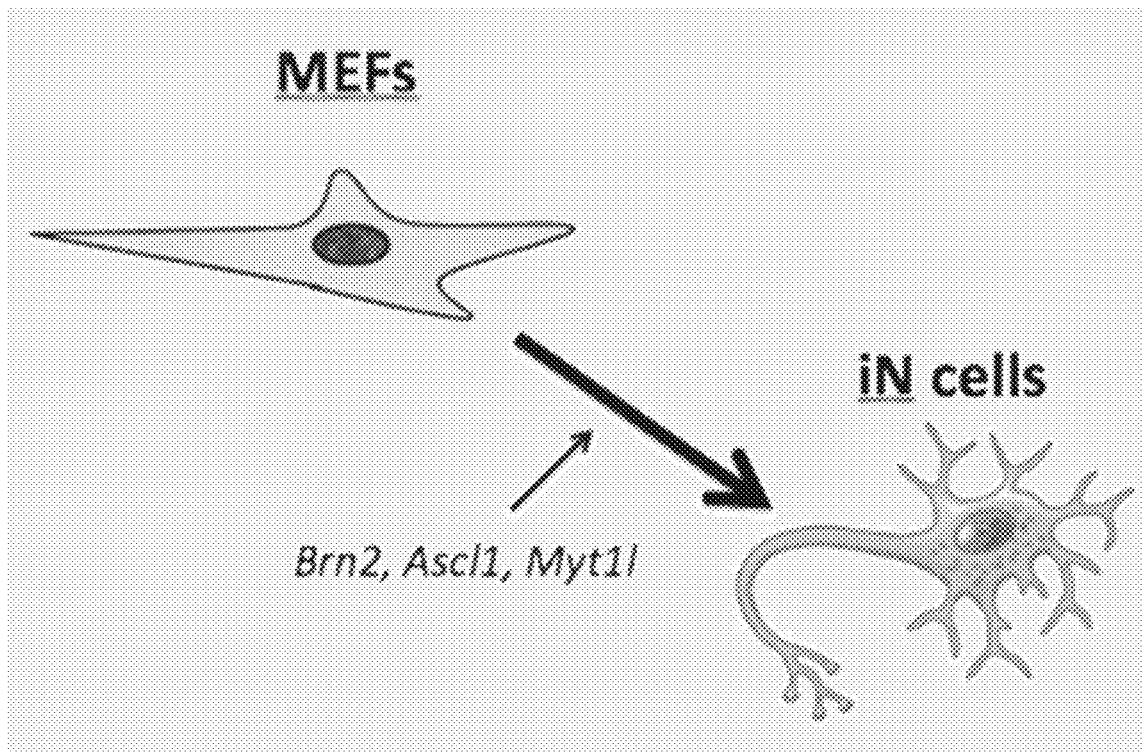
Fig. 48
Fig. 49A
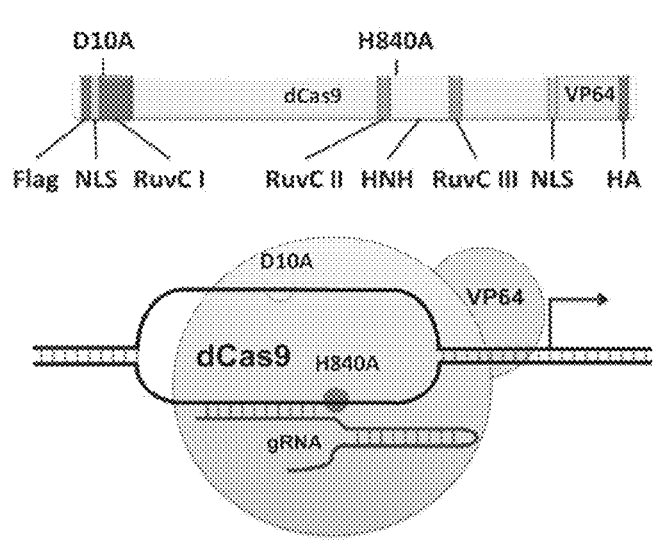
Fig. 49B
Fig. 49C
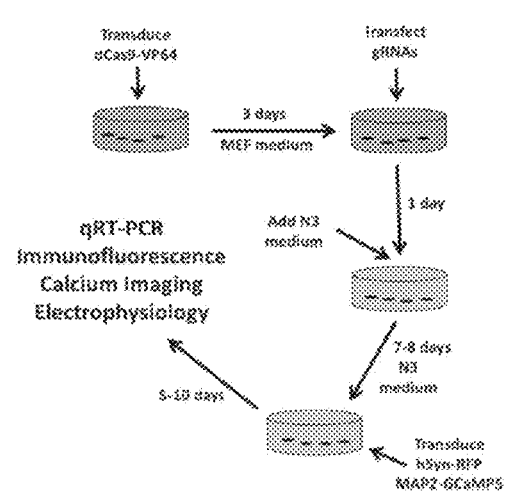

Fig. 51A
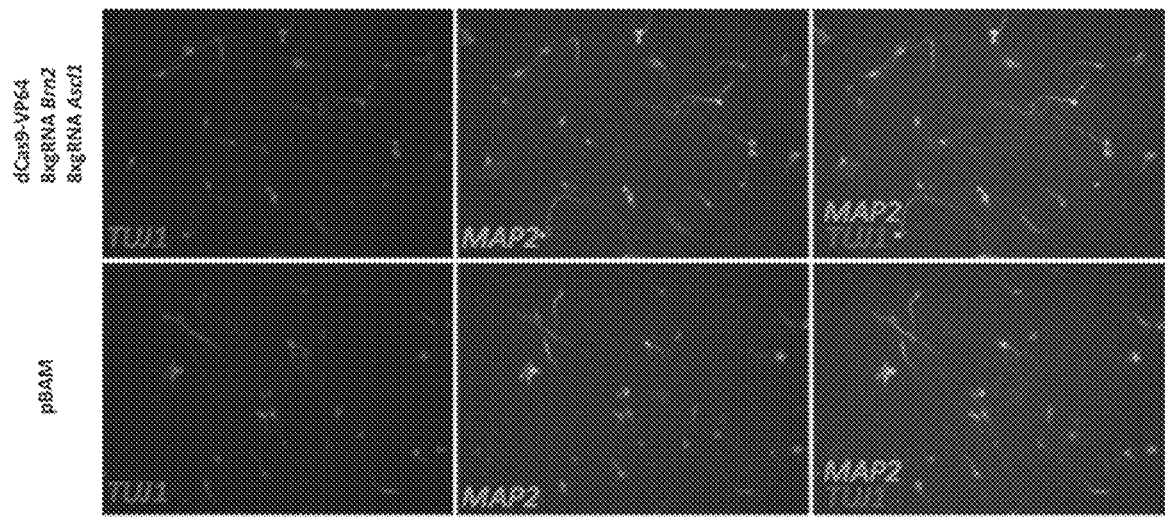
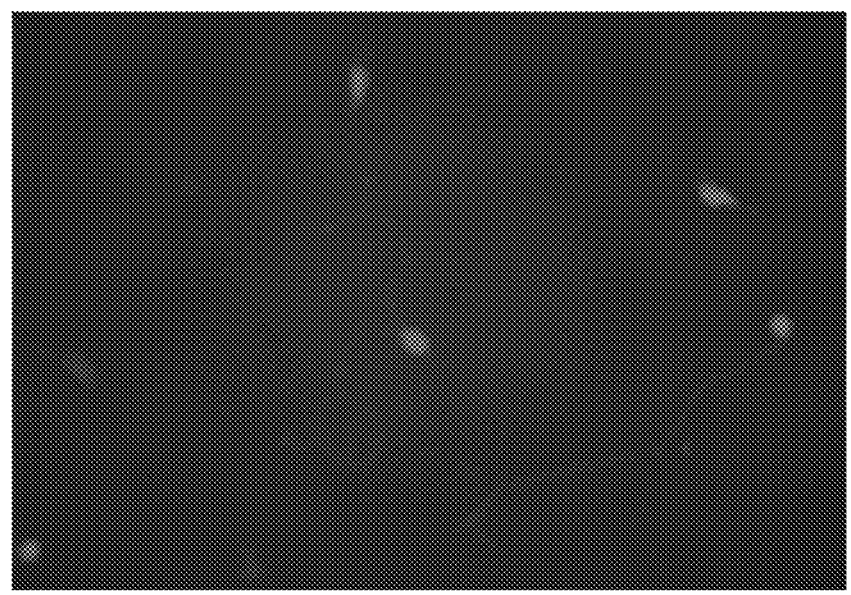
Fig. 51B

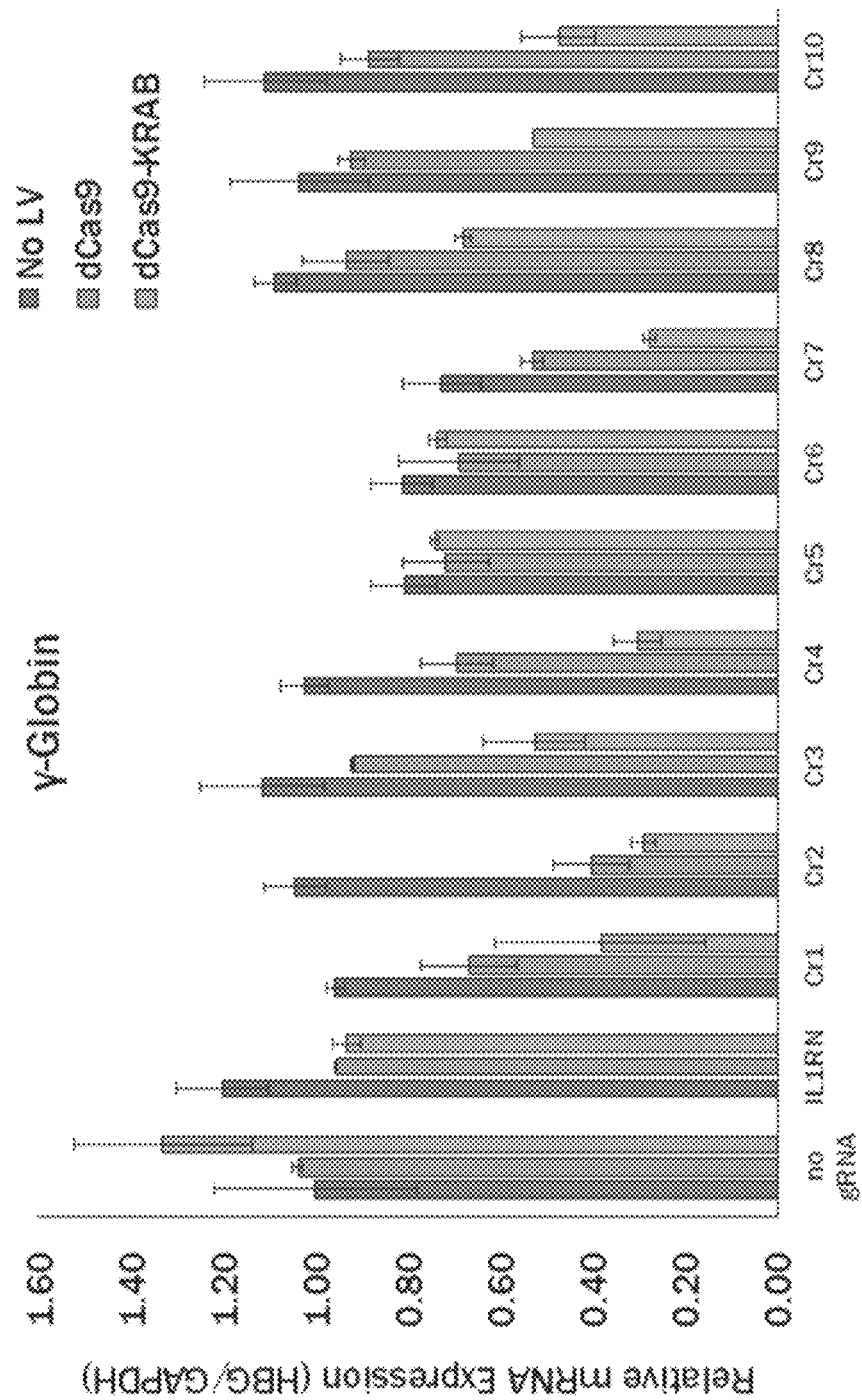

i. dCas9

MDYKDHDGDYKDHDIDYKDDDDKMAPKKKRKVGRGMDKKYSIGLAIGTNSVGWAVITDEY
KVPSKKFKVLGNTDRHSIKKNLIGALLFDSGETAEATRLKRTARRRYTRRKNRICYLQEI
FSNEMAKVDDSFFHRLEESFLVEEDKKHERHPIFGNIVDEVAYHEKYPTIYHLRKKLVDS
TDKADLRLIYLALAHMIKFRGHFLIEGDLNPDNSDVDKLFIQLVQTYNQLFEENPINASG
VDAKAILSARLSKSRRLENLIAQLPGEKRNGLFGNLIALSLGLTPNFKSNFDLAEDAKLQ
LSKDTYDDDLDNLLAQIGDQYADLFLAAKNLSDAILLSDILRVNTEITKAPLSASMIKRY
DEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILT
FRIPYYVGPLARGNSRFAWMTRKSEETITPWNFEEVVDKGASAQSFIERMTNFDKNLPNE
KVLPKHSLLYEYFTVYNELTKVKYVTEGMRKPAFLSGEQKKAIVDLLFKTNRKVTVKQLK
EDYFKKIECFDSVEISGVEDRFNASLGTYHDLLKIIKDKDFLDNEENEDILEDIVLTLTL
FEDREMIEERLKTYAHLFDDKVMKQLKRRRYTGWGRLSRKLINGIRDKQSGKTILDFLKS
DGFANRNFMQLIHDDSLTFKEDIQKAQVSGQGDSLHEHIANLAGSPAIKKGILQTVKVVD
ELVKVMGRHKPENIVIEMARENQTTQKGQKNSRERMKRIEEGIKELGSQILKEHPVENTQ
LQNEKLYLYYLQNGRDMYVDQELDINRLSDYDVDHIVPQSFLKDDSIDNKVLTRSDKNRG
KSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAH
DAYLNAVVGTALIKKYPKLESEFVYGDYKVYDVRKMIAKSEQEIGKATAKYFFYSNIMNF
FKTEITLANGEIRKRPLIETNGETGEIVWDKGRDFATVRKVLSMPQVNIVKKTEVQTGGF
SKESILPKRNSDKLIARKKDWDPKKYGGFDSPTVAYSVLVVAKVEKGKSKKLKSVKELLG
ITIMERSSFEKNPIDFLEAKGYKEVKKDLIIKLPKYSLFELENGRKRMLASAGELQKGNE
LALPSKYVNFLYLASHYEKLKGSPEDNEQKQLFVEQHKHYLDEIIEQISEFSKRVILADA
NLDKVLSAYNKHRDKPIREQAENIIHLFTLTNLGAPAAFKYFDTTIDRKRYTSTKEVLDA
TLIHQSITGLYETRIDLSQLGGDPKKKRKVG

Amino Acid Legend:

"Flag" Epitope
Nuclear Localization Sequence
Streptococcus pyogenes Cas9 (D10A, H840A)
VP64 Effector
p300 Core Effector
"HA" Epitope

Fig. 61A ii. dCas9^{VP64}

MDYKDHDGDYKDHDIDYKDDDDKMAPKKKRKVGRGMDKKYSIGLAIGTNSVGWAVITDEY
KVPSKKFKVLGNTDRHSIKKNLIGALLFDSGETAEATRLKRTARRRYTRRKNRICYLQEI
FSNEMAKVDDSFFHRLEESFLVEEDKKHERHPIFGNIVDEVAYHEKYPTIYHLRKKLVDS
TDKADLRLIYLALAHMIKFRGHFLIEGDLNPDNSDVDKLFIQLVQTYNQLFEENPINASG
VDAKAILSARLSKSRRLENLIAQLPGEKKNGLFGNLIALSLGLTPNFKSNFDLAEDAKLQ
LSKDTYDDDLDNLLAQIGDQYADLFLAAKNLSDAILLSDILRVNTEITKAPLSASMIKRY
DEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILT
FRIPYYVGPLARGNSRFAWMTRKSEETITPWNFEEVVDKGASAQSFIERMTNFDKNLPNE
KVLPKHSLLYEYFTVYNELTKVKYVTEGMRKPAFLSGEQKKAIVDLLFKTNRKVTVKQLK
EDYFKKIECFDSVEISGVEDRFNASLGTYHDLLKIIKDKDFLDNEENEDILEDIVLTLTL
FEDREMIEERLKTYAHLFDDKVMKQLKRRRYTGWGRLSRKLINGIRDKQSGKTILDFLKS
DGFANRNFMQLIHDDSLTFKEDIQKAQVSGQGDSLHEHIANLAGSPAIKKGILQTVKVVD
ELVKVMGRHKPENIVIEMARENQTTQKGQKNSREERMKRIEEGIKELGSQILKEHPVENTQ
LQNEKLYLYYLQNGRDMYVDQELDINRLSDYDVDAIVPQSFLKDDSIDNKVLTRSDKNRG
KSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAH
DAYLNAVVGTALIKKYPKLESEFVYGDYKVYDVRKMIAKSEQEIGKATAKYFFYSNIMNF
FKTEITLANGEIRKRPLIETNGETGEIVWDKGRDFATVRKVLSMPQVNIVKKTEVQTGGF
SKESILPKRNSDKLIARKKDWDPKKYGGFDSPTVAYSVLVVAKVEKGKSKKLKSVKELLG
ITIMERSSFEKNPIDFLEAKGYKEVKKDLIIKLPKYSLFELENGRKRMLASAGELQKGNE
LALPSKYVNFLYLASHYEKLKGSPEDNEQKQLFVEQHKHYLDEIIEQISEFSKRVILADA
NLDKVLSAYNKHRDKPIREQAENIIHLFTLTNLGAPAAFKYFDTTIDRKRYTSTKEVLDA
TLIHQSITGLYETRIDLSQLGGDPIAGSKASPKKKRKVGRADALDDFDLDMLGSDALDDF
DLDMLGSDALDDFDLDMLGSDALDDFDLDMLINYPYDVPDYAS

Fig. 61B iii.  dCas9^sp300 Core

MDYKDHDGDYKDHDIDYKDDDDKMAPKKKRKVGRGMDKKYSIGLAIGTNSVGWAVITDEY
KVPSKKFKVLGNTDRHSIKKNLIGALLFDSGETAEATRLKRTARRRYTRRKNRICYLQEI
FSNEMAKVDDSFFHRLEESFLVEEDKKHERHPIFGNIVDEVAYHEKYPTIYHLRKKLVDS
TDKADLRLIYLALAHMIKFRGHFLIEGDLNPDNSDVDKLFIQLVQTYNQLFEENPINASG
VDAKAILSARLSKSRRLENLIAQLPGEKKNGLFGNLIALSLGLTPNFKSNFDLAEDAKLQ
LSKDTYDDDLDNLLAQIGDQYADLFLAAKNLSDAILLSDILRVNTEITKAPLSASMIKRY
DEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILT
FRIPYYVGPLARGNSRFAWMTRKSEETITPWNFEEVVDKGASAQSFIERMTNFDKNLPNE
KVLPKHSLLYEYFTVYNELTKVKYVTEGMRKPAFLSGEQKKAIVDLLFKTNRKVTVKQLK
EDYFKKIECFDSVEISGVEDRFNASLGTYHDLLKIIKDKDFLDNEENEDILEDIVLTLTL
FEDREMIEERLKTYAHLFDDKVMKQLKRRRYTGWGRLSRKLINGIRDKQSGKTILDFLKS
DGFANRNFMQLIHDDSLTFKEDIQKAQVSGQGDSLHEHIANLAGSPAIRKGILQTVKVVD
ELVKVMGRHKPENIVIEMARENQTTQKGQKNSRERMKRIEEGIKELGSQILKEHPVENTQ
LQNEKLYLYYLQNGRDMYVDQELDINRLSDYDVDAIVPQSFLKDDSIDNKVLTRSDKNRG
KSDNVPSEEVVKKMKNYWRQLLNAKLITQRKFDNLTKAERGGLSELDKAGFIKRQLVETR
QITKHVAQILDSRMNTKYDENDKLIREVKVITLKSKLVSDFRKDFQFYKVREINNYHHAH
DAYLNAVVGTALIKKYPKLESEFVYGDYKVYDVRKMIAKSEQEIGKATAKYFFYSNIMNF
FKTEITLANGEIRKRPLIETNGETGEIVWDKGRDFATVRKVLSMPQVNIVKKTEVQTGGF
SKESILPKRNSDKLIARKKDWDPKKYGGFDSPTVAYSVLVVAKVEKGKSKKLKSVKELLG
ITIMERSSFEKNPIDFLEAKGYKEVKKDLIIKLPKYSLFELENGRKRMLASAGELQKGNE
LALPSKYVNFLYLASHYEKLKGSPEDNEQKQLFVEQHKHYLDEIIEQISEFSKRVILADA
NLDKVLSAYNKHRDKPIREQAENIIHLFTLTNLGAPAAFKYFDTTIDRKRYTSTKEVLDA
TLIHQSITGLYETRIDLSQLGGDPIAGSKASPKKKRKVGRAIFKPEELRQAIMPTLEALY
RODPESLPFROPVDPQLLGIPDYFDIVKSPMDLSTIKRKLDTGQYQEPWQYVDDIWLMFN
NAWLYNRKTSRVYKYCSKLSEVFEQEIDPVMQSLGYCCGRKLEFSPQTLCCYGKQLCTIP
RDATYYSYQNRYHFCEKCFNEIQGESVSLGDDPSQPQTTINKEQFSKRKNDTLDPELFVE
CTECGRKMHQICVLHHEIIWPAGFVCDGCLKKSARTRKENKFSAKRLPSTRLGTFLENRV
NDFLRRQNHPESGEVTVRVVHASDKTVEVKPGMKARFVDSGEMAESFPYRTKALFAFEEI
DGVDLCFFGMHVQEYGSDCPPPNQRRVYISYLDSVHFFRPKCLRTAVYHEILIGYLEYVK
KLGYTTGHIWACPPSEGDDYIFHCHPPDQKIPKPKRLQEWYKKMLDKAVSERIVHDYKDI
FKQATEDRLTSAKELPYFEGDFWPNVLEESIKELEQEEERKREENTSNESTDVPKGDSK
NAKKKNNKKTSKNKSSLSRGNKKKPGMPNVSNDLSQKLYATMEKHKEVFFVIRLIAGPAA
NSLPPIVDPDPLIPCDLMDGRDAFLTLARDKHLEFSSLRRAQWSTMCMLVELHTQSQDYP
YDVPDYAS

Fig. 61C

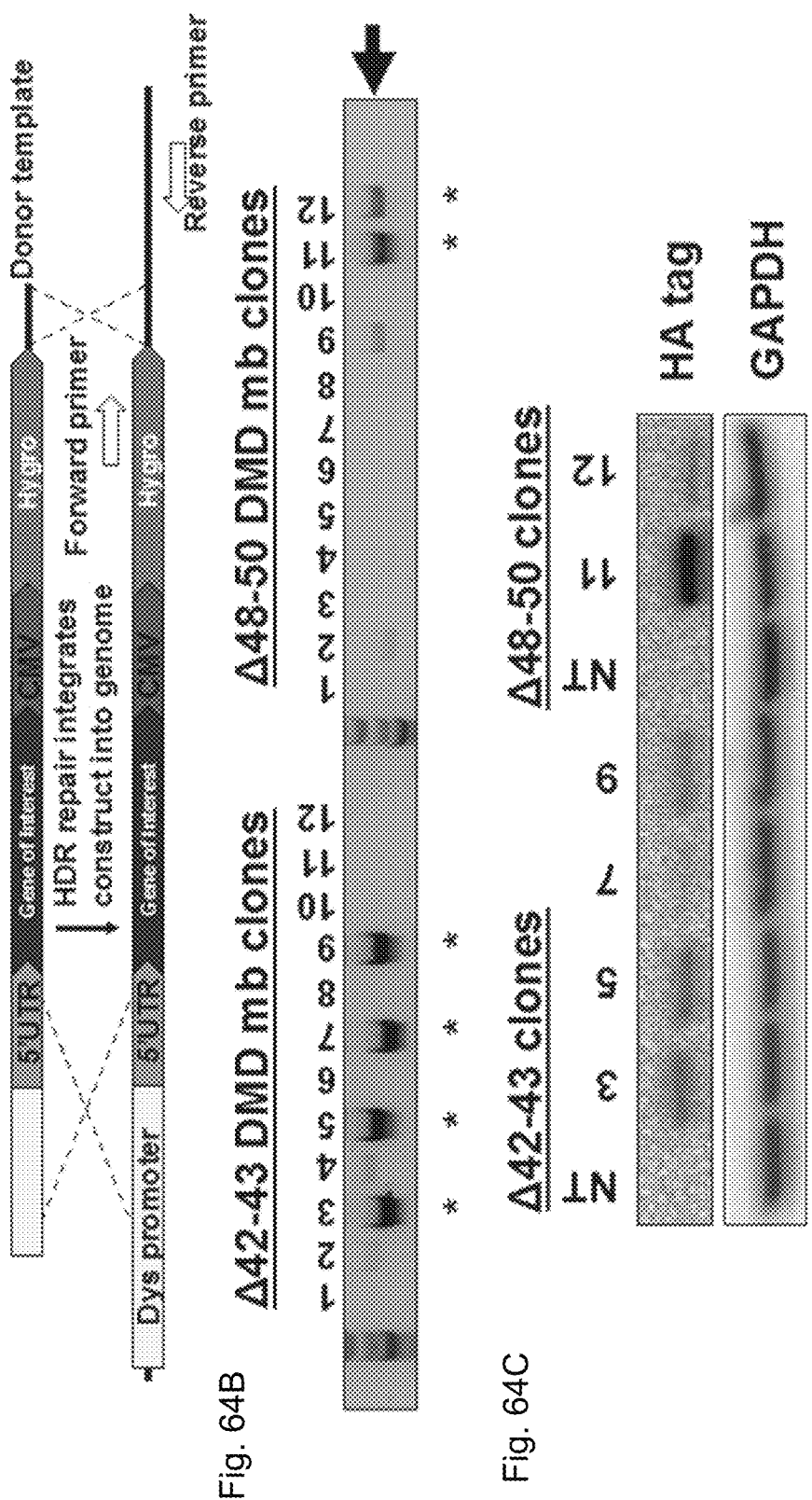

RNA-GUIDED GENE EDITING AND GENE REGULATION

CROSS REFERENCE TO RELATED APPLICATIONS

This application is a divisional of U.S. patent application Ser. No. 14/895,316 filed Dec. 2, 2015, which is a national stage filing under 35 U.S.C. 371 of International Patent Application No. PCT/US2014/041190, filed Jun. 5, 2014, which claims the benefit of priority to U.S. Provisional Application No. 61/831,481, filed Jun. 5, 2013, U.S. Provisional Application No. 61/839,127, filed Jun. 25, 2013, U.S. Provisional Application No. 61/904,911, filed Nov. 15, 2013, U.S. Provisional Application No. 61/967,466, filed Mar. 19, 2014, and U.S. Provisional Application No. 61/981,575, filed Apr. 18, 2014, all of which are incorporated herein by reference in their entirety.

STATEMENT OF GOVERNMENT INTEREST

This invention was made with government support under federal grant numbers DP2-OD008586 and R01DA036865 awarded by NIH and CBET-1151035 awarded by the National Science Foundation. The U.S. Government has certain rights to this invention.

SEQUENCE LISTING

The instant application contains a Sequence Listing which has been submitted electronically in ASCII format and is hereby incorporated by reference in its entirety. Said ASCII copy, created on Jul. 6, 2018, is named "028193-9164-US04_As_Filed_Subst_Sequence_Listing" and is 331,443 bytes in size.

TECHNICAL FIELD

The present disclosure relates to the field of gene expression alteration, genome engineering and genomic alteration of genes using Clustered Regularly Interspaced Short Palindromic Repeats (CRISPR)/CRISPR-associated (Cas) 9-based systems and viral delivery systems. The present disclosure also relates to the field of genome engineering and genomic alteration of genes in muscle, such as skeletal muscle and cardiac muscle.

BACKGROUND

Synthetic transcription factors have been engineered to control gene expression for many different medical and scientific applications in mammalian systems, including stimulating tissue regeneration, drug screening, compensating for genetic defects, activating silenced tumor suppressors, controlling stem cell differentiation, performing genetic screens, and creating synthetic gene circuits. These transcription factors can target promoters or enhancers of endogenous genes, or be purposefully designed to recognize sequences orthogonal to mammalian genomes for transgene regulation. The most common strategies for engineering novel transcription factors targeted to user-defined sequences have been based on the programmable DNA-binding domains of zinc finger proteins and transcription-activator like effectors (TALEs). Both of these approaches involve applying the principles of protein-DNA interactions of these domains to engineer new proteins with unique DNA-binding specificity. Although these methods have been widely successful for many applications, the protein engineering necessary for manipulating protein-DNA interactions can be laborious and require specialized expertise.

Additionally, these new proteins are not always effective. The reasons for this are not yet known but may be related to the effects of epigenetic modifications and chromatin state on protein binding to the genomic target site. In addition, there are challenges in ensuring that these new proteins, as well as other components, are delivered to each cell. Existing methods for delivering these new proteins and their multiple components include delivery to cells on separate plasmids or vectors which leads to highly variable expression levels in each cell due to differences in copy number. Additionally, gene activation following transfection is transient due to dilution of plasmid DNA, and temporary gene expression may not be sufficient for inducing therapeutic effects. Furthermore, this approach is not amenable to cell types that are not easily transfected. Thus another limitation of these new proteins is the potency of transcriptional activation.

Site-specific nucleases can be used to introduce site-specific double strand breaks at targeted genomic loci. This DNA cleavage stimulates the natural DNA-repair machinery, leading to one of two possible repair pathways. In the absence of a donor template, the break will be repaired by non-homologous end joining (NHEJ), an error-prone repair pathway that leads to small insertions or deletions of DNA. This method can be used to intentionally disrupt, delete, or alter the reading frame of targeted gene sequences. However, if a donor template is provided along with the nucleases, then the cellular machinery will repair the break by homologous recombination, which is enhanced several orders of magnitude in the presence of DNA cleavage. This method can be used to introduce specific changes in the DNA sequence at target sites. Engineered nucleases have been used for gene editing in a variety of human stem cells and cell lines, and for gene editing in the mouse liver. However, the major hurdle for implementation of these technologies is delivery to particular tissues in vivo in a way that is effective, efficient, and facilitates successful genome modification.

Hereditary genetic diseases have devastating effects on children in the United States. These diseases currently have no cure and can only be managed by attempts to alleviate the symptoms. For decades, the field of gene therapy has promised a cure to these diseases. However technical hurdles regarding the safe and efficient delivery of therapeutic genes to cells and patients have limited this approach. Duchenne Muscular Dystrophy (DMD) is the most common hereditary monogenic disease and occurs in 1 in 3500 males. DMD is the result of inherited or spontaneous mutations in the dystrophin gene. Dystrophin is a key component of a protein complex that is responsible for regulating muscle cell integrity and function. DMD patients typically lose the ability to physically support themselves during childhood, become progressively weaker during the teenage years, and die in their twenties. Current experimental gene therapy strategies for DMD require repeated administration of transient gene delivery vehicles or rely on permanent integration of foreign genetic material into the genomic DNA. Both of these methods have serious safety concerns. Furthermore, these strategies have been limited by an inability to deliver the large and complex dystrophin gene sequence.

SUMMARY

The present invention is directed to a fusion protein comprising two heterologous polypeptide domains. The first polypeptide domain comprises a Clustered Regularly Interspaced Short Palindromic Repeats associated (Cas) protein and the second polypeptide domain has an activity selected from the group consisting of transcription activation activity, transcription repression activity, transcription release factor activity, histone modification activity, nuclease activity, nucleic acid association activity, methylase activity, and demethylase activity. The Cas protein may comprise Cas9. The Cas9 may comprise at least one amino acid mutation which knocks out nuclease activity of Cas9. The at least one amino acid mutation may be at least one of D10A and H840A. The Cas protein may comprise iCas9 (amino acids 36-1403 of SEQ ID NO: 1). The second polypeptide domain may have transcription activation activity. The second polypeptide domain may comprise at least one VP16 transcription activation domain repeat. The second polypeptide domain may comprise a VP16 tetramer ("VP64") or a p65 activation domain. The fusion protein may further comprise a linker connecting the first polypeptide domain to the second polypeptide domain. The fusion protein may comprise iCas9-VP64.

The present invention is directed to a DNA targeting system comprising said fusion protein and at least one guide RNA (gRNA). The at least one gRNA may comprise a 12-22 base pair complementary polynucleotide sequence of the target DNA sequence followed by a protospacer-adjacent motif. The at least one gRNA may target a promoter region of a gene, an enhancer region of a gene, or a transcribed region of a gene. The at least one gRNA may target an intron of a gene. The at least one gRNA may target an exon of a gene. The at least one gRNA may target a the promoter region of a gene selected from the group consisting of ASCL1, BRN2, MYT1L, NANOG, VEGFA, TERT, IL1B, IL1R2, IL1RN, HBG1, HBG2, and MYOD1. The at least one gRNA may comprise at least one of SEQ ID NOs: 5-40, 65-144, 492-515, 540-563, and 585-625.

The present invention is directed to a DNA targeting system that binds to a dystrophin gene comprising Cas9 and at least one guide RNA (gRNA). The at least one gRNA may target an intron of the dystrophin gene. The at least one gRNA may target an exon of the dystrophin gene. The at least one guide RNA may comprise at least one of SEQ ID NOs: 5-40, 65-144, 492-515, 540-563, and 585-625. The DNA targeting system may comprise between one and ten different gRNAs.

The present invention is directed to an isolated polynucleotide encoding said fusion protein or said DNA targeting system.

The present invention is directed to a vector comprising said isolated polynucleotide.

The present invention is directed to a cell comprising said isolated polynucleotide or said vector.

The present invention is directed to a method of modulating mammalian gene expression in a cell. The method comprises contacting the cell with said fusion protein, said DNA targeting system, said isolated polynucleotide, or said vector. The gene expression may be induced.

The present invention is directed to a method of transdifferentiating or inducing differentiation of a cell. The method comprises contacting the cell with said fusion protein, said DNA targeting system, said isolated polynucleotide, or said vector. The cell may be a fibroblast cell or an induced pluripotent stem cells. The fibroblast cell may be trandifferentiated into a neuronal cell or a myogenic cell. The DNA targeting system may be contacted with the cell and at least one gRNA targets a promoter region of at least one gene selected from the group consisting of ASCL1, BRN2, MYOD1, and MYT1L. The DNA targeting system may comprise at least one gRNA that targets the promoter region of the ASCL1 gene and at least one gRNA that targets the promoter region of the BRN2 gene. The DNA targeting system may comprise between one and twenty different gRNAs. The DNA targeting system may comprise 8 or 16 different gRNAs. The DNA targeting system may comprise dCas9-VP64. The DNA targeting system may be delivered to the cell virally or non-virally.

The present invention is directed to a method of correcting a mutant gene in a cell. The method comprises administering to a cell containing said DNA targeting system, said isolated polynucleotide, or said vector. The correction of the mutant gene may comprise homology-directed repair. The method may further comprise administering to the cell a donor DNA. The mutant gene may comprise a frameshift mutation which causes a premature stop codon and a truncated gene product. The correction of the mutant gene may comprise nuclease mediated non-homologous end joining. The correction of the mutant gene may comprise a deletion of a premature stop codon, a disruption of a splice acceptor site, a deletion of one or more exons, or disruption of a splice donor sequence. The deletion of one or more exons may result in the correction of the reading frame.

The present invention is directed to a method of treating a subject in need thereof having a mutant dystrophin gene. The method comprises administering to the subject said DNA targeting system, said isolated polynucleotide, or said vector. The subject may be suffering from Duchenne muscular dystrophy.

The present invention is directed to a method of correcting a mutant dystrophin gene in a cell. The method comprises administering to a cell containing a mutant dystrophin gene said DNA targeting system, said isolated polynucleotide, said vector, or said cell. The mutant dystrophin gene may comprise a premature stop codon, disrupted reading frame via gene deletion, an aberrant splice acceptor site, or an aberrant splice donor site, and wherein the target region is upstream or downstream of the premature stop codon, disrupted reading frame, aberrant splice acceptor site, or the aberrant splice donor site. The correction of the mutant dystrophin gene may comprise homology-directed repair. The method may further comprise administering to the cell a donor DNA. The mutant dystrophin gene may comprise a frameshift mutation which causes a premature stop codon and a truncated gene product. The correction of the mutant dystrophin gene may comprise nuclease mediated non-homologous end joining. The correction of the mutant dystrophin gene may comprise a deletion of a premature stop codon, correction of a disrupted reading frame, or modulation of splicing by disruption of a splice acceptor site or disruption of a splice donor sequence. The correction of the mutant dystrophin gene may comprise a deletion of exons 45-55 or exon 51.

The present invention is directed to a kit comprising said fusion protein, said DNA targeting system, said isolated polynucleotide, said vector, or said cell.

The present invention is directed to a method of modulating mammalian gene expression in a cell. The method comprises contacting the cell with a polynucleotide encoding a DNA targeting system. The DNA targeting system comprises said fusion protein and at least one guide RNA (gRNA). The DNA targeting system may comprise between one and ten different gRNAs. The different gRNAs may bind to different target regions within the target gene. The target regions may be separated by at least one nucleotide. The target regions may be separated by about 15 to about 700 base pairs. Each of the different gRNAs may bind to at least one different target genes. The different target genes may be located on same chromosome. The different target genes may be located on different chromosomes. The at least one target region may be within a non-open chromatin region, an open chromatin region, a promoter region of the target gene, an enhancer region of the target gene, a transcribed region of the target gene, or a region upstream of a transcription start site of the target gene. The at least one target region may be located between about 1 to about 1000 base pairs upstream of a transcription start site of a target gene. The at least one target region may be located between about 1 to about 600 base pairs upstream of a transcription start site of a target gene. The gene expression may be induced. The DNA targeting system may comprise two different gRNAs, three different gRNAs, four different gRNAs, five different gRNAs, six different gRNAs, seven different gRNAs, eight different gRNAs, nine different gRNAs, or ten different gRNAs. The at least one guide RNA may target a promoter region of a gene selected from the group consisting of ASCL1, BRN2, MYT1L, NANOG, VEGFA, TERT, IL1B, IL1R2, IL1RN, HBG1, HBG2, and MY0D1. The at least one guide RNA may comprise at least one of SEQ ID NOs: 5-40, 65-144, 492-515, 540-563, and 585-625. The at least one target region may be within an intron or an exon of a target gene.

The present invention is directed to a composition for inducing mammalian gene expression in a cell. The composition comprises said fusion protein and at least one guide RNA (gRNA).

The present invention is directed to a composition for inducing mammalian gene expression in a cell. The composition comprises an isolated polynucleotide sequence encoding said fusion protein and at least one guide RNA (gRNA). The at least one guide RNA may target a promoter region of a gene selected from the group consisting of ASCL1, BRN2, MYT1L, NANOG, VEGFA, TERT, IL1B, IL1R2, IL1RN, HBG1, HBG2, and MYOD1. The at least one guide RNA may comprise at least one of SEQ ID NOs 5-40, 65-144, 492-515, 540-563, and 585-625.

The present invention is directed to a cell comprising said composition for inducing mammalian gene expression in a cell.

The present invention is directed to a kit comprising said composition for inducing mammalian gene expression in a cell or said cell comprising said composition for inducing mammalian gene expression in a cell.

The present invention is directed to a kit for inducing mammalian gene expression in a cell. The kit comprises said composition for inducing mammalian gene expression in a cell or said cell comprising said composition for inducing mammalian gene expression in a cell.

The present invention is directed to a composition for genome editing in a muscle of a subject. The composition comprises a modified adeno-associated virus (AAV) vector and a nucleotide sequence encoding a site-specific nuclease. The muscle is skeletal muscle or cardiac muscle. The modified AAV vector may have enhanced cardiac and skeletal muscle tissue tropism. The site-specific nuclease may comprise a zinc finger nuclease, a TAL effector nuclease, or a CRISPR/Cas9 system. The site-specific nuclease may bind a gene or locus in the cell of the muscle. The gene or locus may be dystrophin gene. The composition may further comprise a donor DNA or transgene.

The present invention is directed to a kit comprising said composition for genome editing in a muscle of a subject.

The present invention is directed to a method of genome editing in a muscle of a subject. The method comprises administering to the muscle said composition for genome editing in a muscle of a subject, wherein the muscle is skeletal muscle or cardiac muscle. The genome editing may comprise correcting a mutant gene or inserting a transgene. Correcting a mutant gene may comprise deleting, rearranging, or replacing the mutant gene. Correcting the mutant gene may comprise nuclease-mediated non-homologous end joining or homology-directed repair.

The present invention is directed to a method of treating a subject. The method comprises administering said composition for genome editing in a muscle of a subject to a muscle of the subject, wherein the muscle is skeletal muscle or cardiac muscle. The subject may be suffering from a skeletal muscle condition or a genetic disease. The subject may be suffering from Duchenne muscular dystrophy.

The present invention is directed to a method of correcting a mutant gene in a subject, the method comprises administering said composition for genome editing in a muscle of a subject. The muscle is skeletal muscle or cardiac muscle. The composition may be injected into the skeletal muscle of the subject. The composition may be injected systemically to the subject. The skeletal muscle may be tibialis anterior muscle.

The present invention is directed to a modified lentiviral vector for genome editing in a subject comprising a first polynucleotide sequence encoding said fusion protein and a second polynucleotide sequence encoding at least one sgRNA. The first polynucleotide sequence may be operably linked to a first promoter. The first promoter may be a constitutive promoter, an inducible promoter, a repressible promoter, or a regulatable promoter. The second polynucleotide sequence may encode between one and ten different sgRNAs. The second polynucleotide sequence may encode two different sgRNAs, three different sgRNAs, four different sgRNAs, five different sgRNAs, six different sgRNAs, seven different sgRNAs, eight different sgRNAs, nine different sgRNAs, or ten different sgRNAs. Each of the polynucleotide sequences encoding the different sgRNAs may be operably linked to a promoter. Each of the promoters operably linked to the different sgRNAs may be the same promoter. Each of the promoters operably linked to the different sgRNAs may be different promoters. The promoter may be a constitutive promoter, an inducible promoter, a repressible promoter, or a regulatable promoter. The sgRNA may bind to a target gene. Each of the sgRNA may bind to a different target region within one target loci. Each of the sgRNA may bind to a different target region within different gene loci. The fusion protein may comprise Cas9 protein or iCas9-VP64 protein. The fusion protein may comprise a VP64 domain, a p300 domain, or a KRAB domain. The two or more endogenous genes may be transcriptionally activated. The two or more endogenous genes may be repressed.

The present invention is directed to a method of activating an endogenous gene in a cell. The method comprises contacting a cell with said modified lentiviral vector. The endogenous gene may be transiently activated. The endogenous gene may be stably activated. The endogenous gene may be transiently repressed. The endogenous gene may be stably repressed. The fusion protein may be expressed at similar levels to the sgRNAs. The fusion protein may be expressed at different levels to the sgRNAs. The cell may be a primary human cell.

The present invention is directed to a method of multiplex gene editing in a cell. The method comprises contacting a cell with said modified lentiviral vector. The multiplex gene editing may comprise correcting at least one mutant gene or inserting a transgene. Correcting a mutant gene may comprise deleting, rearranging, or replacing the at least one mutant gene. Correcting the at least one mutant gene may comprise nuclease-mediated non-homologous end joining or homology-directed repair. The multiplex gene editing may comprise deleting at least one gene, wherein the gene is an endogenous normal gene or a mutant gene. The multiplex gene editing may comprise deleting at least two genes. The multiplex gene editing may comprise deleting between two and ten genes.

The present invention is directed to a method of modulating gene expression of at least one target gene in a cell. The method comprises contacting a cell with said modified lentiviral vector. The gene expression of at least two genes may be modulated. The gene expression of between two genes and ten genes may be modulated. The gene expression of the at least one target gene may be modulated when gene expression levels of the at least one target gene are increased or decreased compared to normal gene expression levels for the at least one target gene.

BRIEF DESCRIPTION OF THE DRAWINGS

FIG. 1A and FIG. 1B show an RNA-guided transcriptional activator was created by fusing the inactivated Cas9 (iCas9, D10A/H840A) to the VP64 transactivation domain. iCas9-VP64 recognizes genomic target sites through the hybridization of a guide RNA (gRNA) to a 20 bp target sequence. FIG. 1C shows expression plasmids for four gRNAs or crRNA/tracrRNAs targeted to sequences in the IL1RN promoter were co-transfected with the iCas9-VP64 expression plasmid into HEK293T cells. Activation of IL1RN expression was assessed by qRT-PCR. FIG. 1D shows four gRNA expression plasmids were co-transfected with iCas9-VP64 individually or in combination. Robust gene activation was observed by qRT-PCR only in response to the combination of gRNAs. FIG. 1E shows activation of IL1RN expression was confirmed by assessing secretion of the IL-1ra gene product into the media by ELISA. IL-1ra was only detected in three of the six samples treated with the combination of gRNAs. For FIG. 1C and FIG. 1E, data are shown as the mean±s.e.m. (n=3 independent experiments). Treatment with the combination of gRNAs was statistically different than all other treatments (*P≤0.02) by Tukey's test. FIG. 1F shows RNA-seq was performed on samples treated with empty expression vector (n=2) or co-transfected with the expression plasmids for iCas9-VP64 and the four gRNAs targeting IL1RN (n=2). The only statistically significant changes in gene expression between these treatments were an increase in the four IL1RN isoforms (false discovery rate≤3×10$^{-4}$) and a decrease in IL32 (false discovery rate=0.03).

FIGS. 4A-4D show positions of gRNA target sites and DNAse hypersensitivity of human target genes. The four gRNA target sites for each locus are designated as custom tracks above each gene and DNase-seq data indicating DNAse-hypersensitive open chromatin regions is shown below each gene. DNase-seq was performed in HEK293T cells to identify DNase hypersensitive regions, as previously described (Song et al., Cold Spring Harbor protocols 2010, pdb prot5384 (2010); Song et al. Genome Res 21, 1757-1767 (2011)). The results show that open chromatin was not a requirement for gene activation by combinations of gRNAs with iCas9-VP64.

FIG. 8A shows gRNA target sites in the human ASCL1 promoter (SEQ ID NO: 3) are conserved in the mouse ASCL1 promoter (SEQ ID NO: 4). Target sites are indicated by solid lines and the transcribed region is indicated by dashed line. FIG. 8B shows ASCL1 expression in MEFs increased at two days after iCas9-VP64/gRNA treatment as determined by qRT-PCR. FIGS. 8C-8H show that after 10 days in neural induction media, cells were stained for Ascl1 and Tuj 1, an early marker of neuronal differentiation (FIGS. 8C-8D), or for Tuj 1 and MAP2, a marker of more mature neuronal differentiation (FIGS. 8E-8F). FIGS. 8F-8G show that some Tuj1-positive cells adopted neuronal morphologies. FIG. 8G shows that a single cell was found to be positive for Tuj 1 and MAP2. FIG. 8H shows Tuj1-positive cells were readily identified in the iCas9-VP64/gRNA-treated cultures (~0.05%) but were absent in controls. n=3 independent samples and data are represented as mean±standard error of the mean. gRNA 75/25 is significantly different than gRNA 50/50 and control (*P<0.01, Tukey's test).

FIG. 9A shows the iCas9-VP64 protein sequence (SEQ ID NO: 1) and FIG. 9B shows the sequence of the gRNA expression cassette with U6 promoter (SEQ ID NO: 2).

FIGS. 10A-10B show the standard curves for qRT-PCR. For each gene, the experimental sample with the highest expression level was diluted to create a standard curve that was assayed by qRT-PCR to ensure efficient amplification over an appropriate dynamic range. The efficiencies of all amplification reactions were within 90-115%.

FIG. 11A and FIG. 11B show the validation of RNA-guided repair. FIG. 11A shows the Surveyor assay results of genomic DNA harvested from HEK 293T cells two days after Cas9 was co-transfected into the cells with empty vector (negative control) or gRNA. FIG. 11B shows the location of the gRNA target. FIG. 11C shows the expected cleavage sizes for each gRNA.

FIG. 16A shows sgRNA sequences were designed to bind sequences in the exon 45-55 mutational hotspot region of the dystrophin gene, such that gene editing could restore dystrophin expression from a wide variety of patient-specific mutations. Arrows within introns indicate sgRNA targets designed to delete entire exons from the genome. Arrows within exons indicate sgRNA targets designed to create targeted frameshifts in the dystrophin gene. FIG. 16B shows an example of frame correction following introduction of small insertions or deletions by NHEJ DNA repair in exon 51 using the CR3 sgRNA. FIG. 16B discloses SEQ ID NOS: 633-636, respectively, in order of appearance. FIG. 16C shows a schematic of multiplex sgRNA targets designed to delete exon 51 and restore the dystrophin reading frame in a patient mutation with the deletion of exons 48-50. FIG. 16D shows a schematic of multiplex sgRNA targets designed to delete the entire exon 45-55 region to address a variety of DMD patient mutations.

FIG. 19A shows a plasmid expressing a human-codon optimized SpCas9 protein linked to a GFP marker using a T2A ribosomal skipping peptide sequence was co-electroporated into human DMD myoblasts with one or two plasmids carrying sgRNA expression cassettes. FIG. 19B shows the indicated sgRNA expression cassettes were independently co-transfected into HEK293Ts with a separate plasmid expressing SpCas9 with (bottom) or without (top) a GFP marker linked to SpCas9 by a T2A ribosomal skipping peptide sequence. Gene modification frequencies were assessed at 3 days post-transfection by the Surveyor assay. FIG. 19C shows DMD myoblasts with deletions of exons 48-50 in the dystrophin gene were treated with sgRNAs that correct the dystrophin reading frame in these patient cells. Gene modification was assessed at 20 days post-electroporation in unsorted (bulk) or GFP+ sorted cells. FIG. 19D shows GFP expression in DMD myoblasts 3 days after electroporation with indicated expression plasmids. Transfection efficiencies and sorted cell populations are indicated by the gated region.

FIGS. 20A-20D show targeted frameshifts to restore the dystrophin reading frame using CRISPR/Cas9. FIG. 20A shows the 5' region of exon 51 was targeted using a sgRNA (SEQ ID NO: 637), CR3, that binds immediately upstream of the first out-of-frame stop codon. PAM: protospacer-adjacent motif. FIG. 20B shows the exon 51 locus was PCR amplified from HEK293T cells treated with SpCas9 and CR3 expression cassettes. Sequences of individual clones were determined by Sanger sequencing. The top sequence (bolded, exon in red) is the native, unmodified sequence. The number of clones for each sequence is indicated in parentheses. FIG. 20C shows summary of total gene editing efficiency and reading frame conversions resulting from gene modification shown in FIG. 20B. FIG. 20D shows western blot for dystrophin expression in human DMD myoblasts treated with SpCas9 and the CR3 sgRNA expression cassette (FIG. 19C) to create targeted frameshifts to restore the dystrophin reading frame. Dystrophin expression was probed using an antibody against the rod-domain of the dystrophin protein after 6 days of differentiation.

FIG. 21A shows end-point genomic PCR across the exon 51 locus in human DMD myoblasts with a deletion of exons 48-50. The top arrow indicates the expected position of full-length PCR amplicons and the two lower arrows indicate the expected position of PCR amplicons with deletions caused by the indicated sgRNA combinations. FIG. 21B shows PCR products from FIG. 21A were cloned and individual clones were sequenced to determine insertions and deletions present at the targeted locus (SEQ ID NOS: 424, 638, 425-428, 639 and 429-431, respectively, in order of appearance). The top row shows the wild-type unmodified sequence and the triangles indicate SpCas9 cleavage sites. At the right are representative chromatograms showing the sequences of the expected deletion junctions (SEQ ID NOS: 640-642, respectively, in order of appearance). FIG. 21C shows end-point RT-PCR analysis of dystrophin mRNA transcripts in CRISPR/Cas9-modified human 448-50 DMD myoblasts treated with the indicated sgRNAs. A representative chromatogram of the expected deletion PCR product is shown at the right. Asterisk: band resulting from hybridization of the deletion product strand to the unmodified strand. FIG. 21D shows rescue of dystrophin protein expression by CRISPR/Cas9 genome editing was assessed by western blot for the dystrophin protein with GAPDH as a loading control. The arrow indicates the expected restored dystrophin protein band.

FIG. 22A shows end-point genomic PCR of genomic DNA to detect deletion of the region between intron 44 and intron 55 after treating HEK293Ts or DMD myoblasts with the indicated sgRNAs. FIG. 22B shows individual clones of PCR products (SEQ ID NOS: 432, 643 and 433, respectively, in order of appearance) of the expected size for the deletions from DMD myoblasts in FIG. 22A were analyzed by Sanger sequencing to determine the sequences of genomic deletions present at the targeted locus. Below is a representative chromatograms showing the sequence of the expected deletion junctions (SEQ ID NO: 644). FIG. 22C shows end-point RT-PCR analysis of dystrophin mRNA transcripts in CRISPR/Cas9-modified human 448-50 DMD myoblasts treated with the indicated sgRNAs. A representative chromatogram of the expected deletion PCR product is shown at the right (SEQ ID NO: 645). FIG. 22D shows analysis of restored dystrophin protein expression by western blot following electroporation of DMD myoblasts with sgRNAs targeted to intron 44 and/or intron 55.

FIGS. 25A-25C show sections from muscles injected with untreated human DMD myoblasts. FIGS. 25D-25F show sections from muscles injected with CR1/5 treated human DMD myoblasts enriched by flow cytometry. White arrows indicate dystrophin positive fibers.

FIGS. 26A-26D show evaluation of CRISPR/Cas9 toxicity and off-target effects for CR1/CR5-mediated deletion of exon 51 in human cells. FIG. 26A shows results of a cytotoxicity assay in HEK293T cells treated with human-optimized SpCas9 and the indicated sgRNA constructs. Cytotoxicity is based on survival of GFP-positive cells that are co-transfected with the indicated nuclease. I-SceI is a well-characterized non-toxic meganuclease and GZF3 is a known toxic zinc finger nuclease. FIG. 26B shows surveyor analysis at off-target sites in sorted hDMD cells treated with expression cassettes encoding Cas9 and the indicated sgRNAs. These three off-target sites tested in hDMD cells were identified from a panel of 50 predicted sites tested in HEK293T cells (FIG. 27 and Table 4). TGT: on-target locus for indicated sgRNA. OT:off-target locus. FIGS. 26C-26D show end-point nested PCR to detect chromosomal translocations in HEK293T cells treated with Cas9 and CR1 (FIG. 26C) or sorted hDMD cells treated with Cas9, CR1, and CR5 (FIG. 26D). The schematic depicts the relative location of nested primer pairs customized for each translocation event. The expected size of each band was estimated based on the primer size and the location of the predicted sgRNA cut site at each locus. Asterisks indicate bands detected at the expected size. The identities of the bands in FIG. 26C were verified by Sanger sequencing from each end (FIG. 30). A representative chromatogram for the P2/P5 translocation in HEK293T cells is shown (SEQ ID NO: 646).

FIG. 32A shows proliferating C2C12s were transduced with the indicated amount of virus and harvested at 4 days post-infection. Arrows indicate expected bands sizes resulting from Surveyor cleavage. FIG. 32B shows C2C12s were incubated in differentiation medium for 5 days and then transduced with the indicated amount of AAV-SASTG-ROSA virus in 24 well plates. Samples were collected at 10 days post-transduction. FIG. 32C shows the indicated amount of AAV-SASTG-ROSA was injected directly into the tibialis anterior of C57BL/6J mice and muscles were harvested 4 weeks post-infection. The harvested TA muscles were partitioned into 8 separate pieces for genomic DNA analysis, each shown in a separate lane.

FIG. 33 shows Rosa T2A opt DNA sequence (SEQ ID NO: 434) and Rosa T2A opt protein sequence (SEQ ID NO: 435).

FIGS. 34A and 34B show SASTG capsid DNA sequence (SEQ ID NO: 436) and SASTG capsid peptide sequence (SEQ ID NO: 437).

FIG. 35 shows DZF16 ZFN target site sequence (SEQ ID NO: 442), DZF16-L6 left full amino acid sequence (SEQ ID NO: 443) and DZF16-R6 right full amino acid sequence (SEQ ID NO: 444).

FIG. 36 shows E51C3 ZFN target site sequence (SEQ ID NO: 445), E51C3-3L left full amino acid sequence (SEQ ID NO: 446) and E51C3-3R right full amino acid sequence (SEQ ID NO: 447).

FIG. 37 shows DZF15 ZFN target site sequence (SEQ ID NO: 448), DZF15-L6 left full amino acid sequence (SEQ ID NO: 449), DZF15-R6 right full amino acid sequence (SEQ ID NO: 450), DZF15-L5 left full amino acid sequence (SEQ ID NO: 451), DZF15-R5 right full amino acid sequence (SEQ ID NO: 452).

FIG. 38 shows E51C4 ZFN target site sequence (SEQ ID NO: 453), E51C4-4L left full amino acid sequence (SEQ ID NO: 454) and E51C4-4R right full amino acid sequence (SEQ ID NO: 455).

FIG. 39 shows schematic diagrams of a "Single vector, multiplex CRISPR system," Dual vector, multiplex CRISPR system," and "Single vector, single gRNA system."

FIG. 40 shows the nucleotide sequences of SaCas9-NLS (with the NLS underlined) (SEQ ID NO: 459) and SaCas9 gRNA (SEQ ID NO: 460).

FIG. 41 shows the nucleotide sequences of NmCas9 (with the NLS 1 underlined, the NLS 2 underlined and bolded, and the HA tag bolded; SEQ ID NO: 461), NmCas9 short hairpin from Thomson PNAS 2013 (SEQ ID NO: 462), and NmCas9 long hairpin from Church Nature Biotech 2013 (SEQ ID NO: 463).

FIGS. 42A-42C show validation of sgRNA and lentiviral Cas9 expression constructs. FIG. 42A shows constructs encoding unique Pol III promoters expressing sgRNAs targeting the AAVS1 locus or a construct containing the hU6 promoter immediately followed by poly-thymidine to terminate expression ("PolyT") were transfected into HEK293T cells. End-point RT-PCR was used to probe for expression of each indicated promoter/sgRNA construct two days post-transfection. RT: no reverse transcriptase control. FIG. 42B shows HEK293Ts were transfected with expression vectors encoding the AAVS1 zinc-finger nuclease or Cas9-T2A-GFP and the indicated promoter/sgRNA expression cassettes and assessed for gene modification levels 3 days post-transfection using the Surveyor assay. FIG. 42C shows HEK293T cells were transduced with lentiviral constructs encoding the indicated Cas9-T2A-GFP constructs without sgRNAs and assessed for Cas9 expression by western blot 7 days post-transduction by probing for a FLAG epitope tag on the N-terminus of the Cas9 protein.

FIG. 43 discloses SEQ ID NOS: 661-672, respectively, in order of appearance.

FIGS. 44A-44B show single lentiviral delivery of a multiplex CRISPR/Cas9 system. FIG. 44A shows four sgRNAs targeting distinct genomic loci were cloned into a lentiviral vector expressing the active Cas9 nuclease. FIG. 44B shows HEK293Ts and primary human dermal fibroblasts were transduced with lentivirus expressing the indicated sgRNAs and assayed for cleavage events using the Surveyor assay. HEK293Ts were assayed 7 days post transduction. The human fibroblasts were assayed 10 days post transduction.

FIG. 48 shows a schematic representing the direct conversion of fibroblasts to neurons through ectopic expression of the BAM neuronal transcription factors.

FIG. 49A shows a schematic of the dCas9-VP64 construct. dCas9-VP64 is a catalytically inactive form of the Cas9 protein fused to a tetramer of the VP16 transcriptional activation domain. FIG. 49B is a schematic showing the mechanism of RNA-guided recruitment of dCas9-VP64 to a genomic target. FIG. 49C is a schematic of the experimental protocol to generate iNs with CRISPR/Cas9 transcription factors.

FIG. 51A shows TUB and MAP2-postive cells generated by ectopic BAM factors or by dCas9-VP64 and gRNAs targeted to the BRN2 and ASCU promoters. FIG. 51B shows cells with neuronal morphology expressing a hSyn-RFP reporter at day 11 in N3 medium.

FIGS. 52A-52B show activation of downstream targets of Ascl1 and Brn2, i.e., master regulatory genes, in iCas9-VP64-treated murine embryonic fibroblasts using dCas9-VP64 transcription factors to convert the fibroblasts to neurons. Mouse embryonic fibroblasts (MEFs) were transfected with a control GFP expression plasmid or the iCas9-VP64 expression plasmid and a combination of eight gRNA expression plasmids targeting ASCL1 and BRN2. The dCas9 transcription factors were delivered virally. After 10 days in neural induction media, cells were stained for Tuj 1, an early marker of neuronal differentiation and MAP2, a marker of more mature neuronal differentiation. The conversion to neurons was efficient.

FIG. 53A shows Cas9-based effectors bind genomic sequences in the presence of a chimeric gRNA molecule consisting of a constant region that complexes with Cas9 preceded by an exchangeable 20 bp protospacer that confers target site specificity. FIG. 53A discloses SEQ ID NO: 673. FIG. 53B shows Cas9-based synthetic transcription factors repress transcription of a target gene by interfering with RNA polymerase activity or by binding within the promoter and blocking the binding sites of endogenous transcription factors. FIG. 53C shows targeting regulatory elements such as enhancers could also potentially block the expression of multiple distal genes.

FIGS. 55A-55E that single gRNAs targeting the HS2 enhancer effect potent transcriptional repression of globin genes. FIG. 55A shows dCas9 and dCas9-KRAB repressors were delivered on a lentiviral vector. Single gRNAs were transiently transfected for screening. When assayed by quantitative RT-PCR at 3 days post-transfection, K562s expressing dCas9-KRAB achieve up to 80% repression of γ-globin (FIG. 55B), ε-globin (FIG. 55C), and β-globin (FIG. 55D) genes, as compared to control cells that received no gRNA treatment. FIG. 55E shows protein expression in cells expressing dCas9 or dCas9-KRAB and treated with Cr4 or Cr8 show mild repression of γ-globin expression at day 3, compared to β-actin controls.

FIG. 57A shows dCas9 and dCas9-KRAB repressors were co-expressed on a lentiviral vector with single gRNAs. When assayed by quantitative RT-PCR at 7 days post-transduction, K562s expressing dCas9-KRAB achieve up to 95% repression of γ-globin (FIG. 57B), ε-globin (FIG. 57C), and β-globin genes (FIG. 57D), as compared to control cells that received no lentiviral treatment.

FIGS. 61A-61C show the amino acid sequences of the dCas9 constructs. The legend for all FIGS. 61A-61C is shown in FIG. 61A. FIGS. 61A-61C disclose SEQ ID NOS: 674-676, respectively, in order of appearance.

FIGS. 64A-64C show TALEN mediated integration of minidystrophin at the 5'UTR of the Dp427m skeletal muscle isoform of dystrophin in skeletal myoblast cell lines derived from human DMD patients carrying different deletions in the dystrophin gene. DMD patient cells were electroporated with constructs encoding a TALEN pair active at the 5'UTR locus and a donor template carrying the minidystrophin gene. FIG. 64A is a schematic showing how minidystrophin is integrated into the 5'UTR. FIG. 64B shows hygromycin-resistant clonal cell lines were isolated and screened by PCR for successful site-specific integrations at the 5'UTR using the primers shown in FIG. 64A. Asterisks indicate clones selected for further analysis in FIG. 64C. FIG. 64C shows clonally isolated DMD myoblasts with detected integration events were differentiated for 6 days and assessed for expression of an HA tag fused to the C terminus of minidystrophin.

DETAILED DESCRIPTION

Figure 1A:
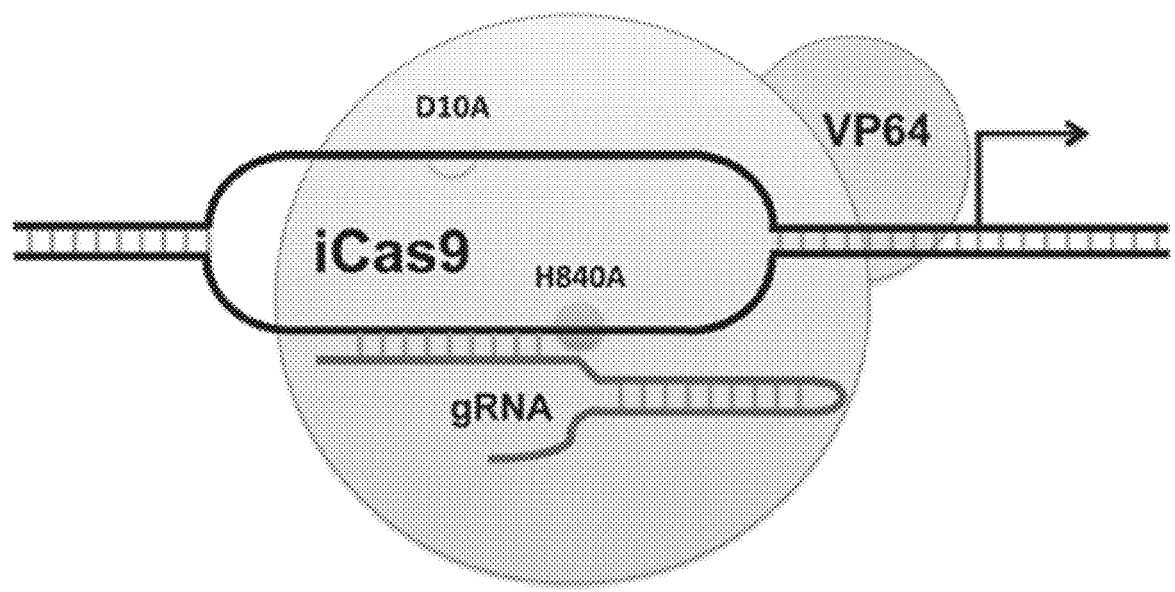
FIGS. 1A-1F show RNA-guided activation of the human IL1RN gene by iCas9-VP64.

As described herein, certain methods and engineered CRISPR/CRISPR-associated (Cas) 9-based system compositions have been discovered to be useful for altering the expression of genes, genome engineering, and correcting or reducing the effects of mutations in genes involved in genetic diseases. The CRISPR/Cas9-based system involves a Cas9 protein and at least one guide RNA, which provide the DNA targeting specificity for the system. In particular, the present disclosure describes a Cas9 fusion protein that combines the DNA sequence targeting function of the CRISPR/Cas9-based system with an additional activity, thus allowing changes in gene expression and/or epigenetic status. The system may also be used in genome engineering and correcting or reducing the effects of gene mutations.

The present disclosure also provides certain compositions and methods for delivering CRISPR/CRISPR-associated (Cas) 9-based system and multiple gRNAs to target one or more endogenous genes. Co-transfection of multiple sgRNAs targeted to a single promoter allow for synergistic activation, however, co-transfection of multiple plasmids leads to variable expression levels in each cell due to differences in copy number. Additionally, gene activation following transfection is transient due to dilution of plasmid DNA over time. Moreover, many cell types are not easily transfected and transient gene expression may not be sufficient for inducing a therapeutic effect. To address these limitations, a single lentiviral system was developed to express Cas9 and up to four sgRNAs from independent promoters. A platform is disclosed that expresses Cas9 or dCas9 fusion proteins and up to four gRNAs from a single lentiviral vector. The lentiviral vector expresses a constitutive or inducible Cas9 or dCas9-VP64 in addition to one, two, three, or four gRNAs expressed from independent promoters. This system enables control of both the magnitude and timing of CRISPR/Cas9-based gene regulation. Furthermore, the lentiviral platform provides the potent and sustained levels of gene expression that will facilitate therapeutic applications of the CRISPR/Cas9 system in primary cells. Finally, this system may be used for editing multiple genes simultaneously, such as the concurrent knockout of several oncogenes.

The present disclosure also provides certain compositions and methods for delivering site-specific nucleases to skeletal muscle and cardiac muscle using modified adeno-associated virus (AAV) vectors. The site-specific nucleases, which may be engineered, are useful for altering the expression of genes, genome engineering, correcting or reducing the effects of mutations in genes involved in genetic diseases, or manipulating genes involved in other conditions affecting skeletal muscle or cardiac muscle or muscle regeneration. The engineered site-specific nucleases may include a zinc finger nuclease (ZFN), a TAL effector nuclease (TALEN), and/or a CRISPR/Cas9 system for genome editing. As described herein, genes in skeletal muscle tissue were successfully edited in vivo using this unique delivery system. The disclosed invention provides a means to rewrite the human genome for therapeutic applications and target model species for basic science applications.

Gene editing is highly dependent on cell cycle and complex DNA repair pathways that vary from tissue to tissue. Skeletal muscle is a very complex environment, consisting of large myofibers with more than 100 nuclei per cell. Gene therapy and biologics in general have been limited for decades by in vivo delivery hurdles. These challenges include stability of the carrier in vivo, targeting the right tissue, getting sufficient gene expression and active gene product, and avoiding toxicity that might overcome activity, which is common with gene editing tools. Other delivery vehicles, such as direct injection of plasmid DNA, work to express genes in skeletal muscle and cardiac muscle in other contexts, but do not work well with these site-specific nucleases for achieving detectable levels of genome editing.

While many gene sequences are unstable in AAV vectors and therefore undeliverable, these site-specific nucleases are surprisingly stable in the AAV vectors. When these site-specific nucleases are delivered and expressed, they remained active in the skeletal muscle tissue. The protein stability and activity of the site-specific nucleases are highly tissue type- and cell type-dependent. These active and stable nucleases are able to modify gene sequences in the complex environment of skeletal muscle. The current invention describes a way to deliver active forms of this class of therapeutics to skeletal muscle or cardiac muscle that is effective, efficient and facilitates successful genome modification.

The present disclosure also provides certain fusion epigenetic effector molecules, a dCas9-p300 fusion protein, which provides a robust and potentially more widely applicable tool for synthetic transcriptional modulation compared to the dCas9-VP64 fusion. The activated target genes to a substantially greater extent than the dCas9-VP64 fusion protein at all loci tested. In addition, the p300 has intrinsic endogenous activity at enhancers within the human genome. The dCas9-p300 fusion protein may be able to activate endogenous target gene promoters and enhancer regions.

The dCas9-p300 fusion protein can be used in human tissue culture cell lines to activate gene expression. This fusion protein may be used to direct the epigenetic state of target loci within human cells with precision and predictability in order to control differentiation, modulate cellular regulation, and apply innovative potential therapies. Current technologies are limited in the strength of activation and the extent and sustainability of epigenetic modulation; obstacles which may be obviated via utilization of this new fusion protein.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Adeno-associated virus" or "AAV" as used interchangeably herein refers to a small virus belonging to the genus Dependovirus of the Parvoviridae family that infects humans and some other primate species. AAV is not currently known to cause disease and consequently the virus causes a very mild immune response.

"Binding region" as used herein refers to the region within a nuclease target region that is recognized and bound by the nuclease.

"Cardiac muscle" or "heart muscle" as used interchangeably herein means a type of involuntary striated muscle found in the walls and histological foundation of the heart, the myocardium. Cardiac muscle is made of cardiomyocytes or myocardiocytes. Myocardiocytes show striations similar to those on skeletal muscle cells but contain only one, unique nucleus, unlike the multinucleated skeletal cells.

"Cardiac muscle condition" as used herein refers to a condition related to the cardiac muscle, such as cardiomyopathy, heart failure, arrhythmia, and inflammatory heart disease.

"Coding sequence" or "encoding nucleic acid" as used herein means the nucleic acids (RNA or DNA molecule) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered. The coding sequence may be codon optimize.

"Complement" or "complementary" as used herein means a nucleic acid can mean Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

"Correcting", "genome editing" and "restoring" as used herein refers to changing a mutant gene that encodes a truncated protein or no protein at all, such that a full-length functional or partially full-length functional protein expression is obtained. Correcting or restoring a mutant gene may include replacing the region of the gene that has the mutation or replacing the entire mutant gene with a copy of the gene that does not have the mutation with a repair mechanism such as homology-directed repair (HDR). Correcting or restoring a mutant gene may also include repairing a frameshift mutation that causes a premature stop codon, an aberrant splice acceptor site or an aberrant splice donor site, by generating a double stranded break in the gene that is then repaired using non-homologous end joining (NHEJ). NHEJ may add or delete at least one base pair during repair which may restore the proper reading frame and eliminate the premature stop codon. Correcting or restoring a mutant gene may also include disrupting an aberrant splice acceptor site or splice donor sequence. Correcting or restoring a mutant gene may also include deleting a non-essential gene segment by the simultaneous action of two nucleases on the same DNA strand in order to restore the proper reading frame by removing the DNA between the two nuclease target sites and repairing the DNA break by NHEJ.

"Donor DNA", "donor template" and "repair template" as used interchangeably herein refers to a double-stranded DNA fragment or molecule that includes at least a portion of the gene of interest. The donor DNA may encode a full-functional protein or a partially-functional protein.

"Duchenne Muscular Dystrophy" or "DMD" as used interchangeably herein refers to a recessive, fatal, X-linked disorder that results in muscle degeneration and eventual death. DMD is a common hereditary monogenic disease and occurs in 1 in 3500 males. DMD is the result of inherited or spontaneous mutations that cause nonsense or frame shift mutations in the dystrophin gene. The majority of dystrophin mutations that cause DMD are deletions of exons that disrupt the reading frame and cause premature translation termination in the dystrophin gene. DMD patients typically lose the ability to physically support themselves during childhood, become progressively weaker during the teenage years, and die in their twenties.

"Dystrophin" as used herein refers to a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids.

"Exon 51" as used herein refers to the $51^{st}$ exon of the dystrophin gene. Exon 51 is frequently adjacent to frame-disrupting deletions in DMD patients and has been targeted in clinical trials for oligonucleotide-based exon skipping. A clinical trial for the exon 51 skipping compound eteplirsen recently reported a significant functional benefit across 48 weeks, with an average of 47% dystrophin positive fibers compared to baseline. Mutations in exon 51 are ideally suited for permanent correction by NHEJ-based genome editing.

"Frameshift" or "frameshift mutation" as used interchangeably herein refers to a type of gene mutation wherein the addition or deletion of one or more nucleotides causes a shift in the reading frame of the codons in the mRNA. The shift in reading frame may lead to the alteration in the amino acid sequence at protein translation, such as a missense mutation or a premature stop codon.

"Functional" and "full-functional" as used herein describes protein that has biological activity. A "functional gene" refers to a gene transcribed to mRNA, which is translated to a functional protein.

"Fusion protein" as used herein refers to a chimeric protein created through the joining of two or more genes that originally coded for separate proteins. The translation of the fusion gene results in a single polypeptide with functional properties derived from each of the original proteins.

"Genetic construct" as used herein refers to the DNA or RNA molecules that comprise a nucleotide sequence that encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Genetic disease" as used herein refers to a disease, partially or completely, directly or indirectly, caused by one or more abnormalities in the genome, especially a condition that is present from birth. The abnormality may be a mutation, an insertion or a deletion. The abnormality may affect the coding sequence of the gene or its regulatory sequence. The genetic disease may be, but not limited to DMD, hemophilia, cystic fibrosis, Huntington's chorea, familial hypercholesterolemia (LDL receptor defect), hepatoblastoma, Wilson's disease, congenital hepatic porphyria, inherited disorders of hepatic metabolism, Lesch Nyhan syndrome, sickle cell anemia, thalassaemias, xeroderma pigmentosum, Fanconi's anemia, retinitis pigmentosa, ataxia telangiectasia, Bloom's syndrome, retinoblastoma, and Tay-Sachs disease.

"Homology-directed repair" or "HDR" as used interchangeably herein refers to a mechanism in cells to repair double strand DNA lesions when a homologous piece of DNA is present in the nucleus, mostly in G2 and S phase of the cell cycle. HDR uses a donor DNA template to guide repair and may be used to create specific sequence changes to the genome, including the targeted addition of whole genes. If a donor template is provided along with the site specific nuclease, such as with a CRISPR/Cas9-based systems, then the cellular machinery will repair the break by homologous recombination, which is enhanced several orders of magnitude in the presence of DNA cleavage. When the homologous DNA piece is absent, non-homologous end joining may take place instead.

"Genome editing" as used herein refers to changing a gene. Genome editing may include correcting or restoring a mutant gene. Genome editing may include knocking out a gene, such as a mutant gene or a normal gene. Genome editing may be used to treat disease or enhance muscle repair by changing the gene of interest.

"Identical" or "identity" as used herein in the context of two or more nucleic acids or polypeptide sequences means that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Mutant gene" or "mutated gene" as used interchangeably herein refers to a gene that has undergone a detectable mutation. A mutant gene has undergone a change, such as the loss, gain, or exchange of genetic material, which affects the normal transmission and expression of the gene. A "disrupted gene" as used herein refers to a mutant gene that has a mutation that causes a premature stop codon. The disrupted gene product is truncated relative to a full-length undisrupted gene product.

"Non-homologous end joining (NHEJ) pathway" as used herein refers to a pathway that repairs double-strand breaks in DNA by directly ligating the break ends without the need for a homologous template. The template-independent re-ligation of DNA ends by NHEJ is a stochastic, error-prone repair process that introduces random micro-insertions and micro-deletions (indels) at the DNA breakpoint. This method may be used to intentionally disrupt, delete, or alter the reading frame of targeted gene sequences. NHEJ typically uses short homologous DNA sequences called micro-homologies to guide repair. These microhomologies are often present in single-stranded overhangs on the end of double-strand breaks. When the overhangs are perfectly compatible, NHEJ usually repairs the break accurately, yet imprecise repair leading to loss of nucleotides may also occur, but is much more common when the overhangs are not compatible.

"Normal gene" as used herein refers to a gene that has not undergone a change, such as a loss, gain, or exchange of genetic material. The normal gene undergoes normal gene transmission and gene expression.

"Nuclease mediated NHEJ" as used herein refers to NHEJ that is initiated after a nuclease, such as a cas9, cuts double stranded DNA.

"Nucleic acid" or "oligonucleotide" or "polynucleotide" as used herein means at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Partially-functional" as used herein describes a protein that is encoded by a mutant gene and has less biological activity than a functional protein but more than a non-functional protein.

"Premature stop codon" or "out-of-frame stop codon" as used interchangeably herein refers to nonsense mutation in a sequence of DNA, which results in a stop codon at location not normally found in the wild-type gene. A premature stop codon may cause a protein to be truncated or shorter compared to the full-length version of the protein.

"Promoter" as used herein means a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

"Repeat variable diresidue" or "RVD" as used interchangeably herein refers to a pair of adjacent amino acid residues within a DNA recognition motif (also known as "RVD module"), which includes 33-35 amino acids, of a TALE DNA-binding domain. The RVD determines the nucleotide specificity of the RVD module. RVD modules may be combined to produce an RVD array. The "RVD array length" as used herein refers to the number of RVD modules that corresponds to the length of the nucleotide sequence within the TALEN target region that is recognized by a TALEN, i.e., the binding region.

"Site-specific nuclease" as used herein refers to an enzyme capable of specifically recognizing and cleaving DNA sequences. The site-specific nuclease may be engineered. Examples of engineered site-specific nucleases include zinc finger nucleases (ZFNs), TAL effector nucleases (TALENs), and CRISPR/Cas9-based systems.

"Skeletal muscle" as used herein refers to a type of striated muscle, which is under the control of the somatic nervous system and attached to bones by bundles of collagen fibers known as tendons. Skeletal muscle is made up of individual components known as myocytes, or "muscle cells", sometimes colloquially called "muscle fibers." Myocytes are formed from the fusion of developmental myoblasts (a type of embryonic progenitor cell that gives rise to a muscle cell) in a process known as myogenesis. These long, cylindrical, multinucleated cells are also called myofibers.

"Skeletal muscle condition" as used herein refers to a condition related to the skeletal muscle, such as muscular dystrophies, aging, muscle degeneration, wound healing, and muscle weakness or atrophy.

"Spacers" and "spacer region" as used interchangeably herein refers to the region within a TALEN or ZFN target region that is between, but not a part of, the binding regions for two TALENs or ZFNs.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc.) and a human). In some embodiments, the subject may be a human or a non-human. The subject or patient may be undergoing other forms of treatment.

"Target gene" as used herein refers to any nucleotide sequence encoding a known or putative gene product. The target gene may be a mutated gene involved in a genetic disease.

"Target region" as used herein refers to the region of the target gene to which the site-specific nuclease is designed to bind and cleave.

"Transcription activator-like effector" or "TALE" as used herein refers to a protein structure that recognizes and binds to a particular DNA sequence. The "TALE DNA-binding domain" refers to a DNA-binding domain that includes an array of tandem 33-35 amino acid repeats, also known as RVD modules, each of which specifically recognizes a single base pair of DNA. RVD modules may be arranged in any order to assemble an array that recognizes a defined sequence.

A binding specificity of a TALE DNA-binding domain is determined by the RVD array followed by a single truncated repeat of 20 amino acids. A TALE DNA-binding domain may have 12 to 27 RVD modules, each of which contains an RVD and recognizes a single base pair of DNA. Specific RVDs have been identified that recognize each of the four possible DNA nucleotides (A, T, C, and G). Because the TALE DNA-binding domains are modular, repeats that recognize the four different DNA nucleotides may be linked together to recognize any particular DNA sequence. These targeted DNA-binding domains may then be combined with catalytic domains to create functional enzymes, including artificial transcription factors, methyltransferases, integrases, nucleases, and recombinases.

"Transcription activator-like effector nucleases" or "TALENs" as used interchangeably herein refers to engineered fusion proteins of the catalytic domain of a nuclease, such as endonuclease FokI, and a designed TALE DNA-binding domain that may be targeted to a custom DNA sequence. A "TALEN monomer" refers to an engineered fusion protein with a catalytic nuclease domain and a designed TALE DNA-binding domain. Two TALEN monomers may be designed to target and cleave a TALEN target region.

"Transgene" as used herein refers to a gene or genetic material containing a gene sequence that has been isolated from one organism and is introduced into a different organism. This non-native segment of DNA may retain the ability to produce RNA or protein in the transgenic organism, or it may alter the normal function of the transgenic organism's genetic code. The introduction of a transgene has the potential to change the phenotype of an organism.

"Variant" used herein with respect to a nucleic acid means (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes may be identified, in part, by considering the hydropathic index of amino acids, as understood in the art. Kyte et al., *J. Mol. Biol.* 157:105-132 (1982). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may encode an iCas9-VP64 fusion protein comprising the amino acid sequence of SEQ ID NO: 1 or at least one gRNA nucleotide sequence of any one of SEQ ID NOs: 5-40, 65-144, 492-515, 540-563, and 585-625. Alternatively, the vector may encode Cas9 and at least one gRNA nucleotide sequence of any one of SEQ ID NOs: 5-40, 65-144, 492-515, 540-563, and 585-625.

"Zinc finger" as used herein refers to a protein structure that recognizes and binds to DNA sequences. The zinc finger domain is the most common DNA-binding motif in the human proteome. A single zinc finger contains approximately 30 amino acids and the domain typically functions by binding 3 consecutive base pairs of DNA via interactions of a single amino acid side chain per base pair.

"Zinc finger nuclease" or "ZFN" as used interchangeably herein refers to a chimeric protein molecule comprising at least one zinc finger DNA binding domain effectively linked to at least one nuclease or part of a nuclease capable of cleaving DNA when fully assembled.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

2. COMPOSITIONS FOR GENOME EDITING

The present invention is directed to compositions for genome editing, genomic alteration or altering gene expression of a target gene. The compositions may include a may include viral vector and fusion protein such as a site-specific nuclease or CRISPR/Cas9-system with at least one gRNA.

a. Compositions for Genome Editing in Muscle

The present invention is directed to a composition for genome editing a target gene in skeletal muscle or cardiac muscle of a subject. The composition includes a modified AAV vector and a nucleotide sequence encoding a site-specific nuclease. The composition delivers active forms of site-specific nucleases to skeletal muscle or cardiac muscle. The composition may further comprise a donor DNA or a transgene. These compositions may be used in genome editing, genome engineering, and correcting or reducing the effects of mutations in genes involved in genetic diseases and/or other skeletal or cardiac muscle conditions.

The target gene may be involved in differentiation of a cell or any other process in which activation, repression, or disruption of a gene may be desired, or may have a mutation such as a deletion, frameshift mutation, or a nonsense mutation. If the target gene has a mutation that causes a premature stop codon, an aberrant splice acceptor site or an aberrant splice donor site, the site-specific nucleases may be designed to recognize and bind a nucleotide sequence upstream or downstream from the premature stop codon, the aberrant splice acceptor site or the aberrant splice donor site. The site-specific nucleases may also be used to disrupt normal gene splicing by targeting splice acceptors and donors to induce skipping of premature stop codons or restore a disrupted reading frame. The site-specific nucleases may or may not mediate off-target changes to protein-coding regions of the genome.

3. CRISPR SYSTEM

"Clustered Regularly Interspaced Short Palindromic Repeats" and "CRISPRs", as used interchangeably herein refers to loci containing multiple short direct repeats that are found in the genomes of approximately 40% of sequenced bacteria and 90% of sequenced archaea. The CRISPR system is a microbial nuclease system involved in defense against invading phages and plasmids that provides a form of acquired immunity. The CRISPR loci in microbial hosts contain a combination of CRISPR-associated (Cas) genes as well as non-coding RNA elements capable of programming the specificity of the CRISPR-mediated nucleic acid cleavage. Short segments of foreign DNA, called spacers, are incorporated into the genome between CRISPR repeats, and serve as a 'memory' of past exposures. Cas9 forms a complex with the 3' end of the sgRNA, and the protein-RNA pair recognizes its genomic target by complementary base pairing between the 5' end of the sgRNA sequence and a predefined 20 bp DNA sequence, known as the protospacer. This complex is directed to homologous loci of pathogen DNA via regions encoded within the crRNA, i.e., the protospacers, and protospacer-adjacent motifs (PAMs) within the pathogen genome. The non-coding CRISPR array is transcribed and cleaved within direct repeats into short crRNAs containing individual spacer sequences, which direct Cas nucleases to the target site (protospacer). By simply exchanging the 20 bp recognition sequence of the expressed sgRNA, the Cas9 nuclease can be directed to new genomic targets. CRISPR spacers are used to recognize and silence exogenous genetic elements in a manner analogous to RNAi in eukaryotic organisms.

Three classes of CRISPR systems (Types I, II and III effector systems) are known. The Type II effector system carries out targeted DNA double-strand break in four sequential steps, using a single effector enzyme, Cas9, to cleave dsDNA. Compared to the Type I and Type III effector systems, which require multiple distinct effectors acting as a complex, the Type II effector system may function in alternative contexts such as eukaryotic cells. The Type II effector system consists of a long pre-crRNA, which is transcribed from the spacer-containing CRISPR locus, the Cas9 protein, and a tracrRNA, which is involved in pre-crRNA processing. The tracrRNAs hybridize to the repeat regions separating the spacers of the pre-crRNA, thus initiating dsRNA cleavage by endogenous RNase III. This cleavage is followed by a second cleavage event within each spacer by Cas9, producing mature crRNAs that remain associated with the tracrRNA and Cas9, forming a Cas9:crRNA-tracrRNA complex.

The Cas9:crRNA-tracrRNA complex unwinds the DNA duplex and searches for sequences matching the crRNA to cleave. Target recognition occurs upon detection of complementarity between a "protospacer" sequence in the target DNA and the remaining spacer sequence in the crRNA. Cas9 mediates cleavage of target DNA if a correct protospacer-adjacent motif (PAM) is also present at the 3' end of the protospacer. For protospacer targeting, the sequence must be immediately followed by the protospacer-adjacent motif (PAM), a short sequence recognized by the Cas9 nuclease that is required for DNA cleavage. Different Type II systems have differing PAM requirements. The S. pyogenes CRISPR system may have the PAM sequence for this Cas9 (SpCas9) as 5'-NRG-3', where R is either A or G, and characterized the specificity of this system in human cells. A unique capability of the CRISPR/Cas9 system is the straightforward ability to simultaneously target multiple distinct genomic loci by co-expressing a single Cas9 protein with two or more sgRNAs. For example, the Streptococcus pyogenes Type II system naturally prefers to use an "NGG" sequence, where "N" can be any nucleotide, but also accepts other PAM sequences, such as "NAG" in engineered systems (Hsu et al., Nature Biotechnology (2013) doi:10.1038/nbt.2647). Similarly, the Cas9 derived from Neisseria meningitidis (NmCas9) normally has a native PAM of NNNNGATT, but has activity across a variety of PAMs, including a highly degenerate NNNNGNNN PAM (Esvelt et al. Nature Methods (2013) doi:10.1038/nmeth.2681).

4. CRISPR/Cas9-BASED SYSTEM

Figure 53A:
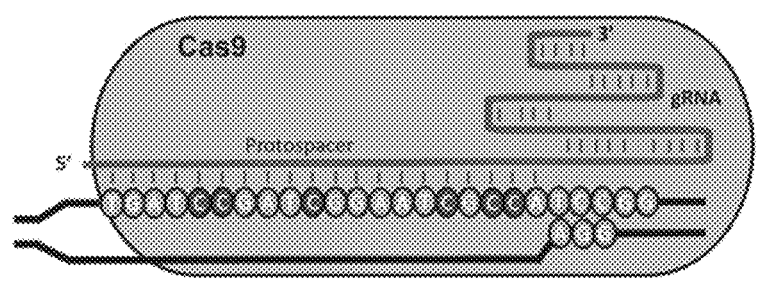
FIGS. 53A-53C show the CRISPR/Cas9 platform for control of mammalian gene regulation.

An engineered form of the Type II effector system of Streptococcus pyogenes was shown to function in human cells for genome engineering. In this system, the Cas9 protein was directed to genomic target sites by a synthetically reconstituted "guide RNA" ("gRNA", also used interchangeably herein as a chimeric single guide RNA ("sgRNA")), which is a crRNA-tracrRNA fusion that obviates the need for RNase III and crRNA processing in general (see FIG. 53A). Provided herein are CRISPR/Cas9-based engineered systems for use in genome editing and treating genetic diseases. The CRISPR/Cas9-based engineered systems may be designed to target any gene, including genes involved in a genetic disease, aging, tissue regeneration, or wound healing. The CRISPR/Cas9-based systems may include a Cas9 protein or Cas9 fusion protein and at least one gRNA. The Cas9 fusion protein may, for example, include a domain that has a different activity that what is endogenous to Cas9, such as a transactivation domain.

The target gene may be involved in differentiation of a cell or any other process in which activation of a gene may be desired, or may have a mutation such as a frameshift mutation or a nonsense mutation. If the target gene has a mutation that causes a premature stop codon, an aberrant splice acceptor site or an aberrant splice donor site, the CRISPR/Cas9-based system may be designed to recognize and bind a nucleotide sequence upstream or downstream from the premature stop codon, the aberrant splice acceptor site or the aberrant splice donor site. The CRISPR-Cas9-based system may also be used to disrupt normal gene splicing by targeting splice acceptors and donors to induce skipping of premature stop codons or restore a disrupted reading frame. The CRISPR/Cas9-based system may or may not mediate off-target changes to protein-coding regions of the genome.

a. Cas9

The CRISPR/Cas9-based system may include a Cas9 protein or a Cas9 fusion protein. Cas9 protein is an endonuclease that cleaves nucleic acid and is encoded by the CRISPR loci and is involved in the Type II CRISPR system. The Cas9 protein may be from any bacterial or archaea species, such as Streptococcus pyogenes. The Cas9 protein may be mutated so that the nuclease activity is inactivated. An inactivated Cas9 protein from Streptococcus pyogenes (iCas9, also referred to as "dCas9") with no endonuclease activity has been recently targeted to genes in bacteria, yeast, and human cells by gRNAs to silence gene expression through steric hindrance. As used herein, "iCas9" and "dCas9" both refer to a Cas9 protein that has the amino acid substitutions D10A and H840A and has its nuclease activity inactivated. For example, the CRISPR/Cas9-based system may include a Cas9 of SEQ ID NO: 459 or 461.

b. Cas9 Fusion Protein

The CRISPR/Cas9-based system may include a fusion protein. The fusion protein may comprise two heterologous polypeptide domains, wherein the first polypeptide domain comprises a Cas protein and the second polypeptide domain has an activity such as transcription activation activity, transcription repression activity, transcription release factor activity, histone modification activity, nuclease activity, nucleic acid association activity, methylase activity, or demethylase activity. The fusion protein may include a Cas9 protein or a mutated Cas9 protein, as described above, fused to a second polypeptide domain that has an activity such as transcription activation activity, transcription repression activity, transcription release factor activity, histone modification activity, nuclease activity, nucleic acid association activity, methylase activity, or demethylase activity.

(1) Transcription Activation Activity

The second polypeptide domain may have transcription activation activity, i.e., a transactivation domain. For example, gene expression of endogenous mammalian genes, such as human genes, may be achieved by targeting a fusion protein of iCas9 and a transactivation domain to mammalian promoters via combinations of gRNAs. The transactivation domain may include a VP16 protein, multiple VP16 proteins, such as a VP48 domain or VP64 domain, or p65 domain of NF kappa B transcription activator activity. For example, the fusion protein may be iCas9-VP64.

(2) Transcription Repression Activity

The second polypeptide domain may have transcription repression activity. The second polypeptide domain may have a Kruppel associated box activity, such as a KRAB domain, ERF repressor domain activity, Mxil repressor domain activity, SID4X repressor domain activity, Mad-SID repressor domain activity or TATA box binding protein activity. For example, the fusion protein may be dCas9-KRAB.

(3) Transcription Release Factor Activity

The second polypeptide domain may have transcription release factor activity. The second polypeptide domain may have eukaryotic release factor 1 (ERF1) activity or eukaryotic release factor 3 (ERF3) activity.

(4) Histone Modification Activity

The second polypeptide domain may have histone modification activity. The second polypeptide domain may have histone deacetylase, histone acetyltransferase, histone demethylase, or histone methyltransferase activity. The histone acetyltransferase may be p300 or CREB-binding protein (CBP) protein, or fragments thereof. For example, the fusion protein may be dCas9-p300.

(5) Nuclease Activity

The second polypeptide domain may have nuclease activity that is different from the nuclease activity of the Cas9 protein. A nuclease, or a protein having nuclease activity, is an enzyme capable of cleaving the phosphodiester bonds between the nucleotide subunits of nucleic acids. Nucleases are usually further divided into endonucleases and exonucleases, although some of the enzymes may fall in both categories. Well known nucleases are deoxyribonuclease and ribonuclease.

(6) Nucleic Acid Association Activity

The second polypeptide domain may have nucleic acid association activity or nucleic acid binding protein-DNA-binding domain (DBD) is an independently folded protein domain that contains at least one motif that recognizes double- or single-stranded DNA. A DBD can recognize a specific DNA sequence (a recognition sequence) or have a general affinity to DNA. nucleic acid association region selected from the group consisting of helix-turn-helix region, leucine zipper region, winged helix region, winged helix-turn-helix region, helix-loop-helix region, immunoglobulin fold, B3 domain, Zinc finger, HMG-box, Wor3 domain, TAL effector DNA-binding domain.

(7) Methylase Activity

The second polypeptide domain may have methylase activity, which involves transferring a methyl group to DNA, RNA, protein, small molecule, cytosine or adenine. The second polypeptide domain may include a DNA methyltransferase.

(8) Demethylase Activity

The second polypeptide domain may have demethylase activity. The second polypeptide domain may include an enzyme that remove methyl (CH3-) groups from nucleic acids, proteins (in particular histones), and other molecules. Alternatively, the second polypeptide may covert the methyl group to hydroxymethylcytosine in a mechanism for demethylating DNA. The second polypeptide may catalyze this reaction. For example, the second polypeptide that catalyzes this reaction may be Tet1.

c. gRNA

The gRNA provides the targeting of the CRISPR/Cas9-based system. The gRNA is a fusion of two noncoding RNAs: a crRNA and a tracrRNA. The sgRNA may target any desired DNA sequence by exchanging the sequence encoding a 20 bp protospacer which confers targeting specificity through complementary base pairing with the desired DNA target. gRNA mimics the naturally occurring crRNA:tracrRNA duplex involved in the Type II Effector system. This duplex, which may include, for example, a 42-nucleotide crRNA and a 75-nucleotide tracrRNA, acts as a guide for the Cas9 to cleave the target nucleic acid. The "target region", "target sequence" or "protospacer" as used interchangeably herein refers to the region of the target gene to which the CRISPR/Cas9-based system targets. The CRISPR/Cas9-based system may include at least one gRNA, wherein the gRNAs target different DNA sequences. The target DNA sequences may be overlapping. The target sequence or protospacer is followed by a PAM sequence at the 3' end of the protospacer. Different Type II systems have differing PAM requirements. For example, the *Streptococcus pyogenes* Type II system uses an "NGG" sequence, where "N" can be any nucleotide.

The number of gRNA administered to the cell may be at least 1 gRNA, at least 2 different gRNA, at least 3 different gRNA at least 4 different gRNA, at least 5 different gRNA, at least 6 different gRNA, at least 7 different gRNA, at least 8 different gRNA, at least 9 different gRNA, at least 10 different gRNAs, at least 11 different gRNAs, at least 12 different gRNAs, at least 13 different gRNAs, at least 14 different gRNAs, at least 15 different gRNAs, at least 16 different gRNAs, at least 17 different gRNAs, at least 18 different gRNAs, at least 18 different gRNAs, at least 20 different gRNAs, at least 25 different gRNAs, at least 30 different gRNAs, at least 35 different gRNAs, at least 40 different gRNAs, at least 45 different gRNAs, or at least 50 different gRNAs. The number of gRNA administered to the cell may be between at least 1 gRNA to at least 50 different gRNAs, at least 1 gRNA to at least 45 different gRNAs, at least 1 gRNA to at least 40 different gRNAs, at least 1 gRNA to at least 35 different gRNAs, at least 1 gRNA to at least 30 different gRNAs, at least 1 gRNA to at least 25 different gRNAs, at least 1 gRNA to at least 20 different gRNAs, at least 1 gRNA to at least 16 different gRNAs, at least 1 gRNA to at least 12 different gRNAs, at least 1 gRNA to at least 8 different gRNAs, at least 1 gRNA to at least 4 different gRNAs, at least 4 gRNAs to at least 50 different gRNAs, at least 4 different gRNAs to at least 45 different gRNAs, at least 4 different gRNAs to at least 40 different gRNAs, at least 4 different gRNAs to at least 35 different gRNAs, at least 4 different gRNAs to at least 30 different gRNAs, at least 4 different gRNAs to at least 25 different gRNAs, at least 4 different gRNAs to at least 20 different gRNAs, at least 4 different gRNAs to at least 16 different gRNAs, at least 4 different gRNAs to at least 12 different gRNAs, at least 4 different gRNAs to at least 8 different gRNAs, at least 8 different gRNAs to at least 50 different gRNAs, at least 8 different gRNAs to at least 45 different gRNAs, at least 8 different gRNAs to at least 40 different gRNAs, at least 8 different gRNAs to at least 35 different gRNAs, 8 different gRNAs to at least 30 different gRNAs, at least 8 different gRNAs to at least 25 different gRNAs, 8 different gRNAs to at least 20 different gRNAs, at least 8 different gRNAs to at least 16 different gRNAs, or 8 different gRNAs to at least 12 different gRNAs.

The gRNA may comprise a complementary polynucleotide sequence of the target DNA sequence followed by a PAM sequence. The gRNA may comprise a "G" at the 5' end of the complementary polynucleotide sequence. The gRNA may comprise at least a 10 base pair, at least a 11 base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair complementary polynucleotide sequence of the target DNA sequence followed by a PAM sequence. The PAM sequence may be "NGG", where "N" can be any nucleotide. The gRNA may target at least one of the promoter region, the enhancer region or the transcribed region of the target gene. The gRNA may bind and target a nucleic acid sequence of corresponding to at least one of SEQ ID NOs: 5-40, 65-144, 492-515, 540-563, 585-625, 462 (FIG. 40), 464 (FIG. 41), and 465 (FIG. 41).

The gRNA may target any nucleic acid sequence. The nucleic acid sequence target may be DNA. The DNA may be any gene. For example, the gRNA may target a gene, such as BRN2, MYT1L, ASCL1, NANOG, VEGFA, TERT, IL1B, IL1R2, IL1RN, HBG1, HBG2, MYOD1, OCT4, and DMD.

(1) Dystrophin

Dystrophin is a rod-shaped cytoplasmic protein which is a part of a protein complex that connects the cytoskeleton of a muscle fiber to the surrounding extracellular matrix through the cell membrane. Dystrophin provides structural stability to the dystroglycan complex of the cell membrane. The dystrophin gene is 2.2 megabases at locus Xp21. The primary transcription measures about 2,400 kb with the mature mRNA being about 14 kb. 79 exons code for the protein which is over 3500 amino acids. Normal skeleton muscle tissue contains only small amounts of dystrophin but its absence of abnormal expression leads to the development of severe and incurable symptoms. Some mutations in the dystrophin gene lead to the production of defective dystrophin and severe dystrophic phenotype in affected patients. Some mutations in the dystrophin gene lead to partially-functional dystrophin protein and a much milder dystrophic phenotype in affected patients.

DMD is the result of inherited or spontaneous mutations that cause nonsense or frame shift mutations in the dystrophin gene. Naturally occurring mutations and their consequences are relatively well understood for DMD. It is known that in-frame deletions that occur in the exon 45-55 region contained within the rod domain can produce highly functional dystrophin proteins, and many carriers are asymptomatic or display mild symptoms. Furthermore, more than 60% of patients may theoretically be treated by targeting exons in this region of the dystrophin gene. Efforts have been made to restore the disrupted dystrophin reading frame in DMD patients by skipping non-essential exons during mRNA splicing to produce internally deleted but functional dystrophin proteins. The deletion of internal dystrophin exons retain the proper reading frame but cause the less severe Becker muscular dystrophy.

(2) CRISPR/Cas9-Based System for Targeting Dystrophin

A CRISPR/Cas9-based system specific for dystrophin gene are disclosed herein. The CRISPR/Cas9-based system may include Cas9 and at least one gRNA to target the dystrophin gene. The CRISPR/Cas9-based system may bind and recognize a target region. The target regions may be chosen immediately upstream of possible out-of-frame stop codons such that insertions or deletions during the repair process restore the dystrophin reading frame by frame conversion. Target regions may also be splice acceptor sites or splice donor sites, such that insertions or deletions during the repair process disrupt splicing and restore the dystrophin reading frame by splice site disruption and exon exclusion. Target regions may also be aberrant stop codons such that insertions or deletions during the repair process restore the dystrophin reading frame by eliminating or disrupting the stop codon.

Single or multiplexed sgRNAs may be designed to restore the dystrophin reading frame by targeting the mutational hotspot at exons 45-55 and introducing either intraexonic small insertions and deletions, or large deletions of one or more exons. Following treatment with Cas9 and one or more sgRNAs, dystrophin expression may be restored in Duchenne patient muscle cells in vitro. Human dystrophin was detected in vivo following transplantation of genetically corrected patient cells into immunodeficient mice. Significantly, the unique multiplex gene editing capabilities of the CRISPR/Cas9 system enable efficiently generating large deletions of this mutational hotspot region that can correct up to 62% of patient mutations by universal or patient-specific gene editing approaches.

The CRISPR/Cas9-based system may use gRNA of varying sequences and lengths. Examples of gRNAs may be found in Table 6. The CRISPR/Cas9-based system may target a nucleic acid sequence of SEQ ID NOs: 65-144, or a complement thereof. The gRNA may include a nucleotide sequence selected from the group consisting of SEQ ID NO: 65-144, or a complement thereof. For example, the disclosed CRISPR/Cas9-based systems were engineered to mediate highly efficient gene editing at exon 51 of the dystrophin gene. These CRISPR/Cas9-based systems restored dystrophin protein expression in cells from DMD patients.

(a) Exons 51 and 45-55

Exon 51 is frequently adjacent to frame-disrupting deletions in DMD. Elimination of exon 51 from the dystrophin transcript by exon skipping can be used to treat approximately 15% of all DMD patients. This class of DMD mutations is ideally suited for permanent correction by NHEJ-based genome editing and HDR. The CRISPR/Cas9-based systems described herein have been developed for targeted modification of exon 51 in the human dystrophin gene. These CRISPR/Cas9-based systems were transfected into human DMD cells and mediated efficient gene modification and conversion to the correct reading frame. Protein restoration was concomitant with frame restoration and detected in a bulk population of CRISPR/Cas9-based system-treated cells. Similarly, the elimination of exons 45-55 of the dystrophin transcript can be used to treat approximately 62% of all DMD patients.

(3) AAV/CRISPR Constructs

AAV may be used to deliver CRISPRs using various construct configurations (see FIG. 39). For example, AAV may deliver Cas9 and gRNA expression cassettes on separate vectors. Alternatively, if the small Cas9 proteins, derived from species such as Staphylococcus aureus or Neisseria meningitidis, are used then both the Cas9 and up to two gRNA expression cassettes may be combined in a single AAV vector within the 4.7 kb packaging limit (see FIG. 39).

5. MULTIPLEX CRISPR/Cas9-BASED SYSTEM

The present disclosure is directed to a multiplex CRISPR/Cas9-Based System which includes a CRISPR/CRISPR-associated (Cas) 9-based system, such as Cas9 or dCas9, and multiple gRNAs to target one or more endogenous genes. This platform utilizes a convenient Golden Gate cloning method to rapidly incorporate up to four independent sgRNA expression cassettes into a single lentiviral vector. Each sgRNA was efficiently expressed and could mediate multiplex gene editing at diverse loci in immortalized and primary human cell lines. Transient transcriptional activation in cell lines stably expressing dCas9-VP64 was demonstrated to be tunable by synergistic activation with one to four sgRNAs. Furthermore, the single lentiviral vector can induce sustained and long-term endogenous gene expression in immortalized and primary human cells. This system allows for rapid assembly of a single lentiviral vector that enables efficient multiplex gene editing or activation in model and primary cell lines.

The multiplex CRISPR/Cas9-Based System provides potency of transcriptional activation and tunable induction of transcriptional activation. Readily generated by Golden Gate assembly, the final vector expresses a constitutive Cas9 or dCas9-VP64 in addition to one, two, three, or four sgRNAs expressed from independent promoters. Each promoter is capable of efficiently expressing sgRNAs that direct similar levels of Cas9 nuclease activity. Furthermore, lentiviral delivery of a single vector expressing Cas9 and four sgRNAs targeting independent loci resulted in simultaneous multiplex gene editing of all four loci. Tunable transcriptional activation at two endogenous genes in both transient and stable contexts was achieved using lentiviral delivery of Cas9 with or without sgRNAs. Highly efficient and long-term gene activation in primary human cells is accomplished. This system is therefore an attractive and efficient method to generate multiplex gene editing and long-term transcriptional activation in human cells.

The multiplex CRISPR/Cas9-Based System allows efficient multiplex gene editing for simultaneously inactivating multiple genes. The CRISPR/Cas9 system can simultaneously target multiple distinct genomic loci by co-expressing a single Cas9 protein with two or more sgRNAs, making this system uniquely suited for multiplex gene editing or synergistic activation applications. The CRISPR/Cas9 system greatly expedites the process of molecular targeting to new sites by simply modifying the expressed sgRNA molecule. The single lentiviral vector may be combined with methods for achieving inducible control of these components, either by chemical or optogenetic regulation, to facilitate investigation of the dynamics of gene regulation in both time and space.

The multiplex CRISPR/Cas9-based systems may transcriptionally activate two or more endogenous genes. The multiplex CRISPR/Cas9-based systems may transcriptionally repress two or more endogenous genes. For example, at least two endogenous genes, at least three endogenous genes, at least four endogenous genes, at least five endogenous genes, or at least ten endogenous genes may be activated or repressed by the multiplex CRISPR/Cas9-based system. Between two and fifteen genes, between two and ten genes, between two and five genes, between five and fifteen genes, or between five and ten genes may be activated or repressed by the multiplex CRISPR/Cas9-based system.

(1) Modified Lentiviral Vector

The multiplex CRISPR/Cas9-based system includes a modified lentiviral vector. The modified lentiviral vector includes a first polynucleotide sequence encoding a fusion protein and a second polynucleotide sequence encoding at least one sgRNA. The fusion protein may be the fusion protein of the CRISPR/Cas9-based system, as described above. The first polynucleotide sequence may be operably linked to a promoter. The promoter may be a constitutive promoter, an inducible promoter, a repressible promoter, or a regulatable promoter.

The second polynucleotide sequence encodes at least 1 sgRNA. For example, the second polynucleotide sequence may encode at least 1 sgRNA, at least 2 sgRNAs, at least 3 sgRNAs, at least 4 sgRNAs, at least 5 sgRNAs, at least 6 sgRNAs, at least 7 sgRNAs, at least 8 sgRNAs, at least 9 sgRNAs, at least 10 sgRNAs, at least 11 sgRNA, at least 12 sgRNAs, at least 13 sgRNAs, at least 14 sgRNAs, at least 15 sgRNAs, at least 16 sgRNAs, at least 17 sgRNAs, at least 18 sgRNAs, at least 19 sgRNAs, at least 20 sgRNAs, at least 25 sgRNA, at least 30 sgRNAs, at least 35 sgRNAs, at least 40 sgRNAs, at least 45 sgRNAs, or at least 50 sgRNAs.

The second polynucleotide sequence may encode between 1 sgRNA and 50 sgRNAs, between 1 sgRNA and 45 sgRNAs, between 1 sgRNA and 40 sgRNAs, between 1 sgRNA and 35 sgRNAs, between 1 sgRNA and 30 sgRNAs, between 1 sgRNA and 25 different sgRNAs, between 1 sgRNA and 20 sgRNAs, between 1 sgRNA and 16 sgRNAs, between 1 sgRNA and 8 different sgRNAs, between 4 different sgRNAs and 50 different sgRNAs, between 4 different sgRNAs and 45 different sgRNAs, between 4 different sgRNAs and 40 different sgRNAs, between 4 different sgRNAs and 35 different sgRNAs, between 4 different sgRNAs and 30 different sgRNAs, between 4 different sgRNAs and 25 different sgRNAs, between 4 different sgRNAs and 20 different sgRNAs, between 4 different sgRNAs and 16 different sgRNAs, between 4 different sgRNAs and 8 different sgRNAs, between 8 different sgRNAs and 50 different sgRNAs, between 8 different sgRNAs and 45 different sgRNAs, between 8 different sgRNAs and 40 different sgRNAs, between 8 different sgRNAs and 35 different sgRNAs, between 8 different sgRNAs and 30 different sgRNAs, between 8 different sgRNAs and 25 different sgRNAs, between 8 different sgRNAs and 20 different sgRNAs, between 8 different sgRNAs and 16 different sgRNAs, between 16 different sgRNAs and 50 different sgRNAs, between 16 different sgRNAs and 45 different sgRNAs, between 16 different sgRNAs and 40 different sgRNAs, between 16 different sgRNAs and 35 different sgRNAs, between 16 different sgRNAs and 30 different sgRNAs, between 16 different sgRNAs and 25 different sgRNAs, or between 16 different sgRNAs and 20 different sgRNAs. Each of the polynucleotide sequences encoding the different sgRNAs may be operably linked to a promoter. The promoters that are operably linked to the different sgRNAs may be the same promoter. The promoters that are operably linked to the different sgRNAs may be different promoters. The promoter may be a constitutive promoter, an inducible promoter, a repressible promoter, or a regulatable promoter.

The at least one sgRNA may bind to a target gene or loci. If more than one sgRNA is included, each of the sgRNAs binds to a different target region within one target loci or each of the sgRNA binds to a different target region within different gene loci. The fusion protein may include Cas9 protein or iCas9-VP64 protein. The fusion protein may include a VP64 domain, a p300 domain, or a KRAB domain.

6. SITE-SPECIFIC NUCLEASES

The composition, as described above, includes a nucleotide sequence encoding a site-specific nuclease that binds and cleaves a target region. The site-specific nuclease may be engineered. For example, an engineered site-specific nuclease may be a CRISPR/Cas9-based system, a ZFN, or a TALEN. The site-specific nuclease may bind and cleave a gene or locus in the genome of a cell in the skeletal muscle or cardiac muscle. For example, the gene or locus may be the Rosa26 locus or the dystrophin gene.

a. CRISPR/Cas9-Based System

The CRISPR/Cas9-based system, as described above, may be used to introduce site-specific double strand breaks at targeted genomic loci.

b. Zinc Finger Nucleases (ZFN)

The site-specific nuclease may be a ZFN. A single zinc finger contains approximately 30 amino acids and the domain functions by binding 3 consecutive base pairs of DNA via interactions of a single amino acid side chain per base pair. The modular structure of the zinc finger motif permits the conjunction of several domains in series, allowing for the recognition and targeting of extended sequences in multiples of 3 nucleotides. These targeted DNA-binding domains can be combined with a nuclease domain, such as FokI, to generate a site-specific nuclease, called a "zinc finger nuclease" (ZFNs) that can be used to introduce site-specific double strand breaks at targeted genomic loci. This DNA cleavage stimulates the natural DNA-repair machinery, leading to one of two possible repair pathways, NHEJ and HDR. For example, the ZFN may target the Rosa26 locus (Perez-Pinera et al. Nucleic Acids Research (2012) 40:3741-3752) or a dystrophin gene. Examples of ZFNs are shown in Table 1 and FIGS. 35-38. In Table 1, the DNA recognition helices are underlined and "Fok ELD-S" and "Fok KKR-S" refers to the FokI nuclease domain that is fused to the zinc finger protein DNA-binding domains. In FIGS. 35-38, the target DNA sequence in the target sites (i.e., in SEQ ID NOs: 442, 445, 448, and 453) and the DNA recognition helices in the ZFN amino acid sequences (i.e., in SEQ ID NOs: 443, 444, 446, 447, 449-452, 454, and 455) are underlined, respectively.

TABLE 1

Full amino acid sequences of identified ZFNs.

ZFN B left Fok ELD-S full amino acid sequence
(SEQ ID NO: 438)
MDYKDHDGDYKDHDIDYKDDDDKMAPKKKRKVGRLEPGEKPYKCPECGKS
FSRKDALRGHQRTHTGEKPYKCPECGKSFSHRTTLTNHQRTHTGEKPYKC
PECGKFSQRNALAGHQRTHTGEKPYKCPECGKSFSHKNALQNHQRTHTG
EKPYKCPECGKSFSDPGHLVRHQRTHTGEKPYKCPECGKSFSTSGNLVRH
QRTHTGAAARALVKSELEEKKSELRHKLKYVPHEYIELIEIARNPTQDRI
LEMKVMEFFMKVYGYRGEHLGGSRKPDGAIYTVGSPIDYGVIVDTKAYSG
GYNLPIGQADEMERYVEENQTRDKHLNPNEWWKVYPSSVTEFKFLEVSGH
FKGNYKAQLTRLNHITNCNGAVLSVEELLIGGEMIKAGTLTLEEVRRKFN
NGEINF*

ZFN B right Fok KKR-S full amino acid sequence
(SEQ ID NO: 439)
MDYKDHDGDYKDHDIDYKDDDDKMAPKKKRKVGRLEPGEKPYKCPECGKS
FSQQRSLVGHQRTHTGEKPYKCPECGKSFSDKKDLTRHQRTHTGEKPYKC
PECGKFSTSGHLVRHQRTHTGEKPYKCPECGKSFSQRAHLERHQRTHTG
EKPYKCPECGKSFSTSGSLVRHQRTHTGEKPYKCPECGKSFSTSGNLVRH
QRTHTGAAARALVKSELEEKKSELRHKLKYVPHEYIELIEIARNPTQDRI
LEMKVMEFFMKVYGYRGEHLGGSRKPDGAIYTVGSPIDYGVIVDTKAYSG
GYNLPIGQADEMQRYVKENQTRNKHINPNEWWKVYPSSVTEFKFLEVSGH
FKGNYKAQLTRLNRKTNCNGAVLSVEELLIGGEMIKAGTLTLEEVRRKFN
NGEINF*

ZFN J left Fok KKR-S full amino acid sequence
(SEQ ID NO: 440)
MDYKDHDGDYKDHDIDYKDDDDKMAPKKKRKVGRLEPGERPFQCRICMRN
FSSKQALAVHTRTHTGEKPFQCRICMRNESQSTTLKRHLRTHTGEKPFQC
RICMRNFSRSDHLSLHLKTHLRGSQLVKSELEEKKSELRHKLKYVPHEYI
ELIEIARNPTQDRILEMKVMEFFMKVYGYRGEHLGGSRKPDGAIYTVGSP
IDYGVIVDTKAYSGGYNLPIGQADEMQRYVKENQTRNKHINPNEWWKVYP
SSVTEFKFLEVSGHFKGNYKAQLTRLNRKTNCNGAVLSVEELLIGGEMIK
AGTLTLEEVRRKFNNGEINF*

ZFN J right Fok ELD-S full amino acid sequence
(SEQ ID NO: 441)
MDYKDHDGDYKDHDIDYKDDDDKMAPKKKRKVGRLEPGERPFQCRICMRN
FSRRAHLQNHTRTHTGEKPFQCRICMRNESQSTTLKRHLRTHTGEKPFQC
RICMRNFSDGGHLTRHLKTHLRGSQLVKSELEEKKSELRHKLKYVPHEYI
ELIEIARNPTQDRILEMKVMEFFMKVYGYRGEHLGGSRKPDGAIYTVGSP
IDYGVIVDTKAYSGGYNLPIGQADEMERYVEENQTRDKHLNPNEWWKVYP
SSVTEFKFLEVSGHFKGNYKAQLTRLNHITNCNGAVLSVEELLIGGEMIK
AGTLTLEEVRRKFNNGEINF* c. TAL Effector Nucleases (TALENs)

TALENs may be used to introduce site-specific double strand breaks at targeted genomic loci. Site-specific double-strand breaks are created when two independent TALENs bind to nearby DNA sequences, thereby permitting dimerization of FokI and cleavage of the target DNA. TALENs have advanced genome editing due to their high rate of successful and efficient genetic modification. This DNA cleavage may stimulate the natural DNA-repair machinery, leading to one of two possible repair pathways: homology-directed repair (HDR) or the non-homologous end joining (NHEJ) pathway. The TALENs may be designed to target any gene involved in a genetic disease.

The TALENs may include a nuclease and a TALE DNA-binding domain that binds to the target gene in a TALEN target region. The target gene may have a mutation such as a frameshift mutation or a nonsense mutation. If the target gene has a mutation that causes a premature stop codon, the TALEN may be designed to recognize and bind a nucleotide sequence upstream or downstream from the premature stop codon. A "TALEN target region" includes the binding regions for two TALENs and the spacer region, which occurs between the binding regions. The two TALENs bind to different binding regions within the TALEN target region, after which the TALEN target region is cleaved. Examples of TALENs are described in International Patent Application No. PCT/US2013/038536, which is incorporated by reference in its entirety.

7. TRANSCRIPTIONAL ACTIVATORS

The composition, as described above, includes a nucleotide sequence encoding a transcriptional activator that activates a target gene. The transcriptional activator may be engineered. For example, an engineered transcriptional activator may be a CRISPR/Cas9-based system, a zinc finger fusion protein, or a TALE fusion protein.

a. CRISPR/Cas9-Based System

The CRISPR/Cas9-based system, as described above, may be used to activate transcription of a target gene with RNA. The CRISPR/Cas9-based system may include a fusion protein, as described above, wherein the second polypeptide domain has transcription activation activity or histone modification activity. For example, the second polypeptide domain may include VP64 or p300.

b. Zinc Finger Fusion Proteins

The transcriptional activator may be a zinc finger fusion protein. The zinc finger targeted DNA-binding domains, as described above, can be combined with a domain that has transcription activation activity or histone modification activity. For example, the domain may include VP64 or p300.

c. TALE Fusion Proteins

TALE fusion proteins may be used to activate transcription of a target gene. The TALE fusion protein may include a TALE DNA-binding domain and a domain that has transcription activation activity or histone modification activity. For example, the domain may include VP64 or p300.

8. COMPOSITIONS

The present invention is directed to a composition for altering gene expression and engineering or altering genomic DNA in a cell or subject. The composition may also include a viral delivery system.

a. Compositions for Genome Editing in Muscle

The present invention is directed to a composition for genome editing a target gene in skeletal muscle or cardiac muscle of a subject. The composition includes a modified AAV vector and a nucleotide sequence encoding a site-specific nuclease. The composition delivers active forms of site-specific nucleases to skeletal muscle or cardiac muscle. The composition may further comprise a donor DNA or a transgene. These compositions may be used in genome editing, genome engineering, and correcting or reducing the effects of mutations in genes involved in genetic diseases and/or other skeletal or cardiac muscle conditions.

The target gene may be involved in differentiation of a cell or any other process in which activation, repression, or disruption of a gene may be desired, or may have a mutation such as a deletion, frameshift mutation, or a nonsense mutation. If the target gene has a mutation that causes a premature stop codon, an aberrant splice acceptor site or an aberrant splice donor site, the site-specific nucleases may be designed to recognize and bind a nucleotide sequence upstream or downstream from the premature stop codon, the aberrant splice acceptor site or the aberrant splice donor site. The site-specific nucleases may also be used to disrupt normal gene splicing by targeting splice acceptors and donors to induce skipping of premature stop codons or restore a disrupted reading frame. The site-specific nucleases may or may not mediate off-target changes to protein-coding regions of the genome.

b. Adeno-Associated Virus Vectors

The composition, as described above, includes a modified adeno-associated virus (AAV) vector. The modified AAV vector may have enhanced cardiac and skeletal muscle tissue tropism. The modified AAV vector may be capable of delivering and expressing the site-specific nuclease in the cell of a mammal. For example, the modified AAV vector may be an AAV-SASTG vector (Piacentino et al. (2012) Human Gene Therapy 23:635-646). The modified AAV vector may deliver nucleases to skeletal and cardiac muscle in vivo. The modified AAV vector may be based on one or more of several capsid types, including AAV1, AAV2, AAV5, AAV6, AAV8, and AAV9. The modified AAV vector may be based on AAV2 pseudotype with alternative muscle-tropic AAV capsids, such as AAV2/1, AAV2/6, AAV2/7, AAV2/8, AAV2/9, AAV2.5 and AAV/SASTG vectors that efficiently transduce skeletal muscle or cardiac muscle by systemic and local delivery (Seto et al. Current Gene Therapy (2012) 12:139-151).

c. CRISPR/Cas9-Based System

The present disclosure also provides DNA targeting systems or compositions of at least one CRISPR/Cas9-based system, as described above. These compositions may be used in genome editing, genome engineering, and correcting or reducing the effects of mutations in genes involved in genetic diseases. The composition includes a CRISPR/Cas9-based system that includes a Cas9 protein or Cas9 fusion protein, as described above. The CRISPR/Cas9-based system may also include at least one gRNA, as described above.

d. Multiplex CRISPR/Cas9-Based System

The present disclosure also provides multiplex CRISPR/Cas9-based systems, as described above. These compositions may be used in genome editing, genome engineering, and correcting or reducing the effects of mutations in genes involved in genetic diseases. These compositions may be used to target more than one gene. The composition includes a modified lentiviral vector comprising a CRISPR/Cas9-based system that includes a Cas9 protein or Cas9 fusion protein, as described above and more than one gRNA, as described above.

9. METHODS OF USES

Potential applications of the compositions are diverse across many areas of science and biotechnology. The disclosed compositions may be used to repair genetic mutations that cause disease. The disclosed compositions may be used to disrupt genes such that gene disruption leads to increases in muscle regeneration or muscle strength, or decreases in muscle aging. The disclosed compositions may be used to introduce therapeutic genes to be expressed systemically from skeletal muscle or cardiac muscle, such as clotting factors or monoclonal antibodies. The disclosed compositions may be used to modulate mammalian gene expression. The disclosed compositions may be used to transdifferentiate or induce the differentiation of a cell or correct a mutant gene in a cell. Examples of activation of genes related to cell and gene therapy, genetic reprogramming, and regenerative medicine are provided. RNA-guided transcriptional activators may be used to reprogram cell lineage specification. Activation of endogenous genes encoding the key regulators of cell fate, rather than forced overexpression of these factors, may potentially lead to more rapid, efficient, stable, or specific methods for genetic reprogramming, transdifferentiation, and/or induced differentiation.

10. METHODS OF GENOME EDITING IN MUSCLE

The present disclosure is directed to a method of genome editing in a skeletal muscle or cardiac muscle of a subject. The method comprises administering to the skeletal muscle or cardiac muscle of the subject the composition for genome editing in skeletal muscle or cardiac muscle, as described above. The genome editing may include correcting a mutant gene or inserting a transgene. Correcting the mutant gene may include deleting, rearranging, or replacing the mutant gene. Correcting the mutant gene may include nuclease-mediated NHEJ or HDR.

11. METHODS OF USING CRISPR/Cas9-BASED SYSTEM

Potential applications of the CRISPR/Cas9-based system are diverse across many areas of science and biotechnology. The disclosed CRISPR/Cas9-based systems may be used to modulate mammalian gene expression. The disclosed CRISPR/Cas9-based systems may be used to transdifferentiate or induce differentiation of a cell or correct a mutant gene in a cell. Examples of activation of genes related to cell and gene therapy, genetic reprogramming, and regenerative medicine are provided. RNA-guided transcriptional activators may be used to reprogram cell lineage specification. Although reprogramming was incomplete and inefficient in these experiments, there are many ways by which this method could be improved, including repeated transfections of iCas9-VP64/gRNA combinations, stable expression of these factors, and targeting multiple genes, such as Brn2 and Mytl1 in addition to Ascl1 for transdifferentiation into a neuronal phenotype. Activation of endogenous genes encoding the key regulators of cell fate, rather than forced overexpression of these factors, may potentially lead to more rapid, efficient, stable, or specific methods for genetic reprogramming and transdifferentiation or induced differentiation of a cell. Finally, Cas9 fusions to other domains, including repressive and epigenetic-modifying domains, could provide a greater diversity of RNA-guided transcriptional regulators to complement other RNA-based tools for mammalian cell engineering.

a. Methods of Activating Gene Expression

The present disclosure provides a mechanism for activating the expression of endogenous genes, such as mammalian genes, based on targeting a transcriptional activator to promoters via RNA using a CRISPR/Cas9 based system, as described above. This is fundamentally different from previously described methods based on engineering sequence-specific DNA-binding proteins and may provide opportunities for targeted gene regulation. Because the generation of gRNA expression plasmids simply involves synthesizing two short custom oligonucleotides and one cloning step, it is possible to generate many new gene activators quickly and economically. The gRNAs can also be transfected directly to cells following in vitro transcription. Multiple gRNAs targeted to single promoters were shown, but simultaneous targeting of multiple promoters could also be possible. Recognition of genomic target sites with RNAs, rather than proteins, may also circumvent limitations of targeting epigenetically modified sites, such as methylated DNA.

In contrast to current methods based on engineering DNA-binding proteins, Cas9 fused to a transcriptional activation domain can be targeted by combinations of guide RNA molecules to induce the expression of endogenous human genes. This straightforward and versatile approach for targeted gene activation circumvents the need for engineering new proteins and allows for widespread synthetic gene regulation.

The method may include administering to a cell or subject a CRISPR/Cas9-based system, a polynucleotide or vector encoding said CRISPR/Cas9-based system, or DNA targeting systems or compositions of at least one CRISPR/Cas9-based system, as described above. The method may include administering a CRISPR/Cas9-based system, such as administering a Cas9 fusion protein containing transcription activation domain or a nucleotide sequence encoding said Cas9 fusion protein. The Cas9 fusion protein may include a transcription activation domain such as aVP16 protein or a transcription co-activator such as a p300 protein.

(1) dCas9-VP16

The Cas9 fusion protein may include a transcription activation domain such as aVP16 protein. The transcription activation domain may contain at least 1 VP16 protein, at least 2 VP16 proteins, at least 3 VP16 proteins, at least 4 VP16 proteins (i.e., a VP64 activator domain), at least 5 VP16 proteins, at least 6 VP16 proteins, at least 6 VP16 proteins, or at least 10 VP16 proteins. The Cas9 protein may be a Cas9 protein in which the nuclease activity is inactivated. For example, the Cas9 protein in the fusion protein may be iCas9 (amino acids 36-1403 of SEQ ID NO: 1), which includes the amino acid substitutions of D10A and H840A. The Cas9 fusion protein may be iCas9-VP64.

(2) dCas9-p300

The Cas9 fusion protein may include a transcription co-activation domain such as a p300 protein. The p300 protein (also known as EP300 or E1A binding protein p300) is encoded by the EP300 gene and regulates the activity of many genes in tissues throughout the body. The p300 protein plays a role in regulating cell growth and division, prompting cells to mature and assume specialized functions (differentiate) and preventing the growth of cancerous tumors. The p300 protein activates transcription by connecting transcription factors with a complex of proteins that carry out transcription in the cell's nucleus. The p300 interaction with transcription factors is managed by one or more of p300 domains: the nuclear receptor interaction domain (RID), the CREB and MYB interaction domain (KIX), the cysteine/histidine regions (TAZ1/CH1 and TAZ2/CH3) and the interferon response binding domain (IBiD). The last four domains, KIX, TAZ1, TAZ2 and IBiD of p300, each bind tightly to a sequence spanning both transactivation domains 9aaTADs of transcription factor p53. The protein functions as histone acetyltransferase that regulates transcription via chromatin remodeling, and is important in the processes of cell proliferation and differentiation. It mediates cAMP-gene regulation by binding specifically to phosphorylated CREB protein.

Figure 58:
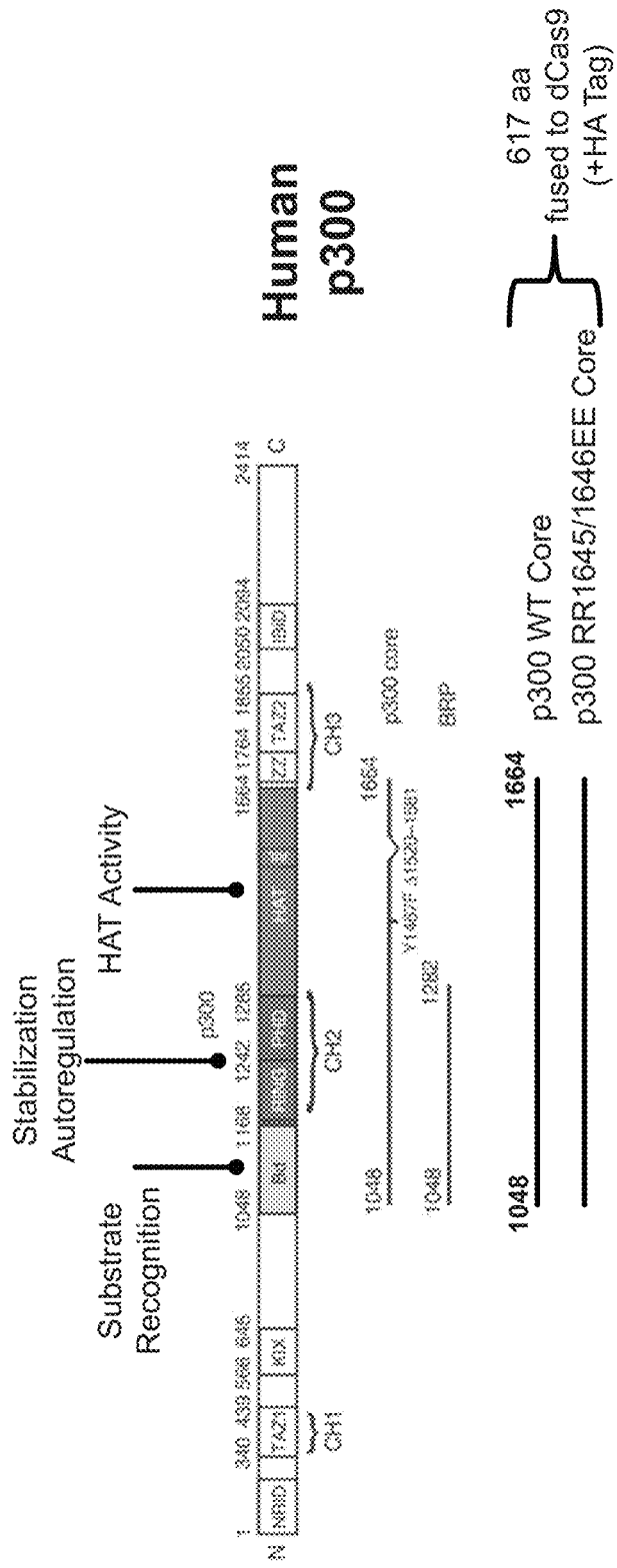
FIG. 58 shows that isolating the p300 HAT "Core" for targeted epigenetic modification of histones only via dCas9 fusion.

The p300 protein may activate Mothers against decapentaplegic homolog 7, MAF, TSG101, Peroxisome proliferator-activated receptor alpha, NPAS2, PAX6, DDX5, MYBL2, Mothers against decapentaplegic homolog 1, Mothers against decapentaplegic homolog 2, Lymphoid enhancer-binding factor 1, SNIP1, TRERF1, STAT3, EID1, RAR-related orphan receptor alpha, ELK1, HIF1A, ING5, Peroxisome proliferator-activated receptor gamma, SS18, TCF3, Zif268, Estrogen receptor alpha, GPS2, MyoD, YY1, ING4, PROX1, CITED1, HNF1A, MEF2C, MEF2D, MAML1, Twist transcription factor, PTMA, IRF2, DTX1, Flap structure-specific endonuclease 1, Myocyte-specific enhancer factor 2A, CDX2, BRCA1, HNRPU, STATE, CITED2, RELA, TGS1, CEBPB, Mdm2, NCOA6, NFATC2, Thyroid hormone receptor alpha, BCL3, TFAP2A, PCNA, P53 and TALL The transcription co-activation domain may include a human p300 protein or a fragment thereof. The transcription co-activation domain may include a wild-type human p300 protein or a mutant human p300 protein, or fragments thereof. The transcription co-activation domain may include the core lysine-acetyltranserase domain of the human p300 protein, i.e., the p300 HATCore (also known as "p300 WTCore"; see FIG. 58). The Cas9 protein may be a Cas9 protein in which the nuclease activity is inactivated. For example, the Cas9 protein in the fusion protein may be iCas9 (amino acids 36-1403 of SEQ ID NO: 1), which includes the amino acid substitutions of D10A and H840A. The Cas9 fusion protein may be iCas9-p300 WTCore.

(3) gRNA

The method may also include administering to a cell or subject a CRISPR/Cas9-based system at least one gRNA, wherein the gRNAs target different DNA sequences. The target DNA sequences may be overlapping. The number of gRNA administered to the cell may be at least 1 gRNA, at least 2 different gRNAs, at least 3 different gRNAs at least 4 different gRNAs, at least 5 different gRNAs, at least 6 different gRNAs, at least 7 different gRNAs, at least 8 different gRNAs, at least 9 different gRNAs, at least 10 different gRNAs, at least 11 different gRNAs, at least 12 different gRNAs, at least 13 different gRNAs, at least 14 different gRNAs, at least 15 different gRNAs, at least 16 different gRNAs, at least 17 different gRNAs, at least 18 different gRNAs, at least 18 different gRNAs, at least 20 different gRNAs, at least 25 different gRNAs, at least 30 different gRNAs, at least 35 different gRNAs, at least 40 different gRNAs, at least 45 different gRNAs, or at least 50 different gRNAs. The number of gRNA administered to the cell may be between at least 1 gRNA to at least 50 different gRNAs, at least 1 gRNA to at least 45 different gRNAs, at least 1 gRNA to at least 40 different gRNAs, at least 1 gRNA to at least 35 different gRNAs, at least 1 gRNA to at least 30 different gRNAs, at least 1 gRNA to at least 25 different gRNAs, at least 1 gRNA to at least 20 different gRNAs, at least 1 gRNA to at least 16 different gRNAs, at least 1 gRNA to at least 12 different gRNAs, at least 1 gRNA to at least 8 different gRNAs, at least 1 gRNA to at least 4 different gRNAs, at least 4 gRNAs to at least 50 different gRNAs, at least 4 different gRNAs to at least 45 different gRNAs, at least 4 different gRNAs to at least 40 different gRNAs, at least 4 different gRNAs to at least 35 different gRNAs, at least 4 different gRNAs to at least 30 different gRNAs, at least 4 different gRNAs to at least 25 different gRNAs, at least 4 different gRNAs to at least 20 different gRNAs, at least 4 different gRNAs to at least 16 different gRNAs, at least 4 different gRNAs to at least 12 different gRNAs, at least 4 different gRNAs to at least 8 different gRNAs, at least 8 different gRNAs to at least 50 different gRNAs, at least 8 different gRNAs to at least 45 different gRNAs, at least 8 different gRNAs to at least 40 different gRNAs, at least 8 different gRNAs to at least 35 different gRNAs, 8 different gRNAs to at least 30 different gRNAs, at least 8 different gRNAs to at least 25 different gRNAs, 8 different gRNAs to at least 20 different gRNAs, at least 8 different gRNAs to at least 16 different gRNAs, 8 different gRNAs to at least 12 different gRNAs, at least 8 different gRNAs to at least 8 different gRNAs, The gRNA may comprise a complementary polynucleotide sequence of the target DNA sequence followed by NGG. The gRNA may comprise a "G" at the 5' end of the complementary polynucleotide sequence. The gRNA may comprise at least a 10 base pair, at least a 11 base pair, at least a 12 base pair, at least a 13 base pair, at least a 14 base pair, at least a 15 base pair, at least a 16 base pair, at least a 17 base pair, at least a 18 base pair, at least a 19 base pair, at least a 20 base pair, at least a 21 base pair, at least a 22 base pair, at least a 23 base pair, at least a 24 base pair, at least a 25 base pair, at least a 30 base pair, or at least a 35 base pair complementary polynucleotide sequence of the target DNA sequence followed by NGG. The gRNA may target at least one of the promoter region, the enhancer region or the transcribed region of the target gene. The gRNA may include a nucleic acid sequence of at least one of SEQ ID NOs: 5-40, 65-144, 492-515, 540-563, and 585-625.

b. Methods of Repressing Gene Expression

Figure 53B:
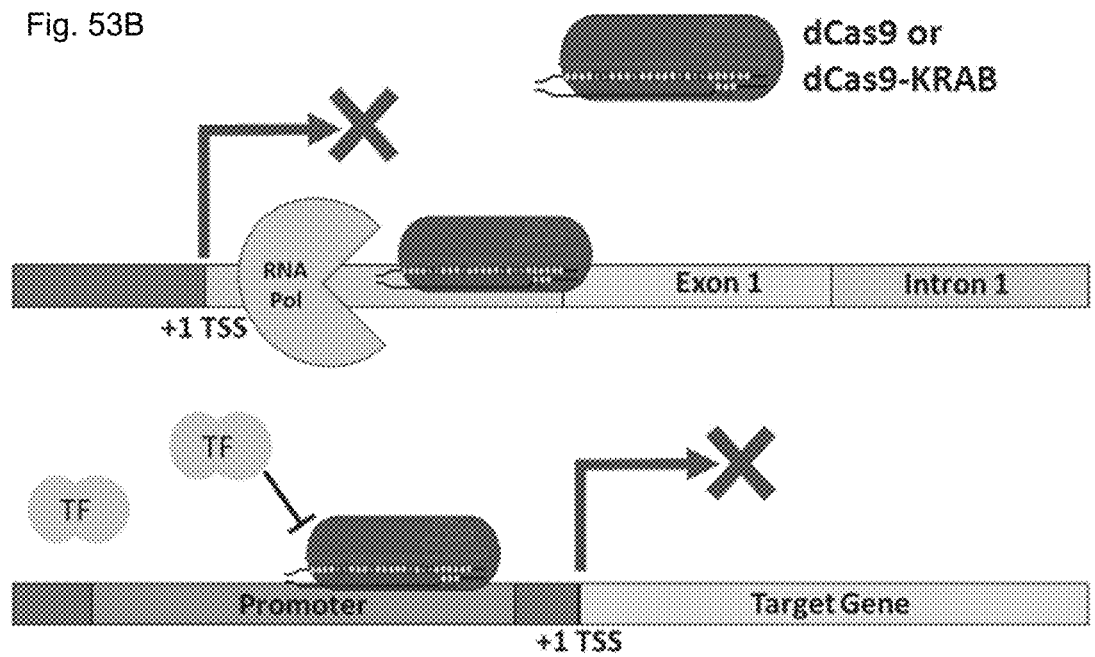
Figure 53C:
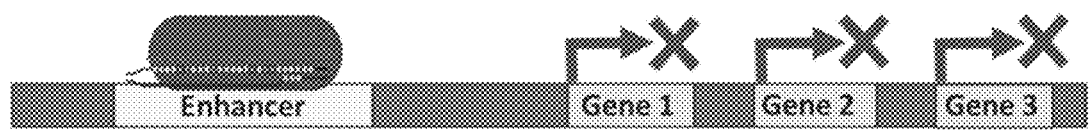

The present disclosure provides a mechanism for repressing the expression of endogenous genes, such as mammalian genes, based on targeting genomic regulatory elements, such as distal enhancers, via RNA using a CRISPR/Cas9 based system, as described above. The Cas9 fusion protein may include a transcriptional repressor, such as the KRAB repressor. The Cas9 fusion protein may be dCas9-KRAB. The dCas9-KRAB may additionally affect epigenetic gene regulation by recruiting heterochromatin-forming factors to the targeted locus. The CRISPR/dCas9-KRAB system may be used to repress the transcription of genes, but can also be used to target genomic regulatory elements which were previously inaccessible by traditional repression methods such as RNA interference (FIG. 53B). Delivering dCas9-KRAB with gRNAs targeted to a distal enhancer may disrupt expression of multiple genes regulated by the targeted enhancer (see FIG. 53C). The targeted enhancer may be any enhancer for a gene such as the HS2 enhancer.

a. Methods of Transdifferentiation or Induced Differentiation

The present disclosure provides a mechanism for transdifferentiating or inducing differentiation of cells by activating endogenous genes via RNA using a CRISPR/Cas9-based system, as described above.

(1) Transdifferentiation

The CRISPR/Cas9-based system may be used to transdifferentiate cells. Transdifferentiation, also known as lineage reprogramming or direct conversion, is a process where cells convert from one differentiated cell type to another without undergoing an intermediate pluripotent state or progenitor cell type. It is a type of metaplasia, which includes all cell fate switches, including the interconversion of stem cells. Transdifferentiation of cells has potential uses for disease modeling, drug discovery, gene therapy and regenerative medicine. Activation of endogenous genes, such as BRN2, MYT1L, ASCLJ, NANOG, and/or MYOD1, using the CRISPR/Cas9 based system described above may lead to transdifferentiation of several cell types, such as fibroblasts, cardiomyocytes, hepatocytes, chondrocytes, mesenchymal progenitor cells, hematopoetic stem cells, or smooth muscle cells, into neuronal and myogenic phenotypes, respectively.

(2) Inducing Differentiation

The CRISPR/Cas9-based system may be used to induce differentiation of cells, such as stem cells, cardiomyocytes, hepatocytes, chondrocytes, mesenchymal progenitor cells, hematopoetic stem cells, or smooth muscle cells. For example, stem cells, such as embryonic stem cells or pluripotent stem cells, may be induced to differentiate into muscle cells or vascular endothelial cell, i.e., induce neuronal or myogenic differentiation.

12. USES OF MULTIPLEX CRISPR/Cas9-BASED SYSTEM

Figure 47:
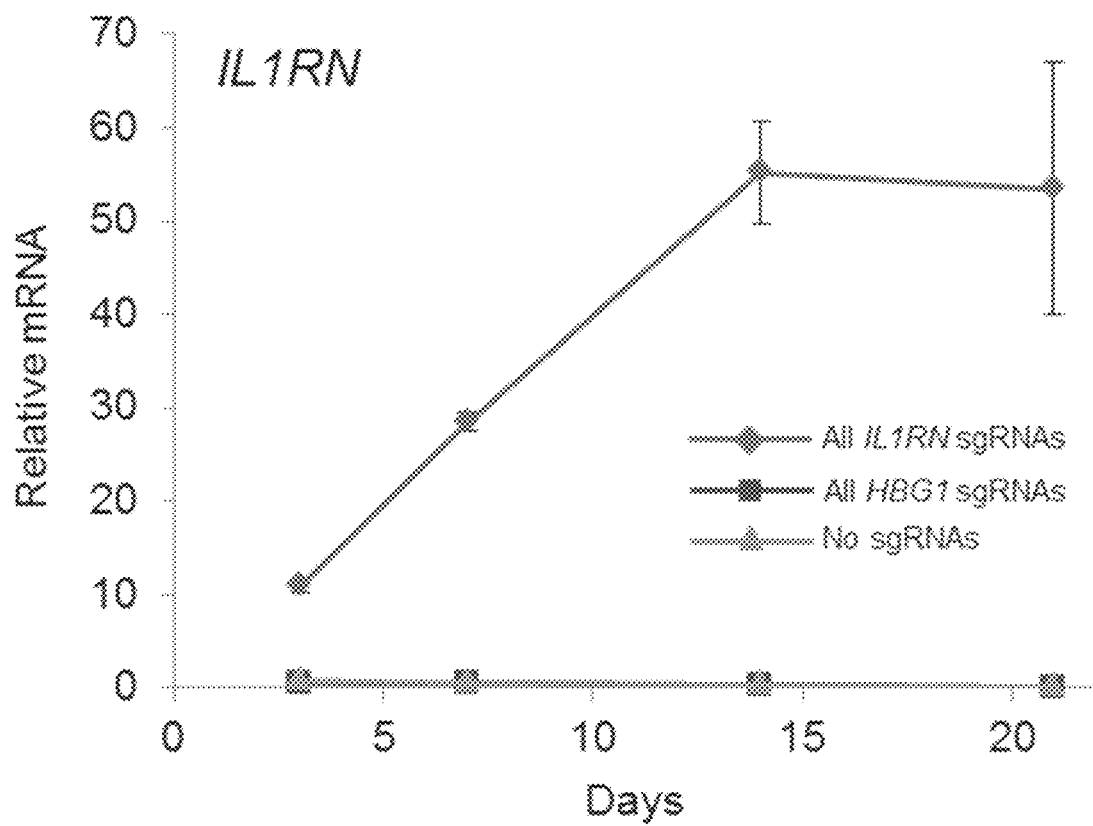
FIG. 47 shows IL1RN mRNA expression levels.

The multiplex CRISPR/Cas9-Based System takes advantage of the simplicity and low cost of sgRNA design and may be helpful in exploiting advances in high-throughput genomic research using CRISPR/Cas9 technology. For example, the single lentiviral vectors described here are useful in expressing Cas9 and numerous sgRNAs in difficult cell lines, such as primary fibroblasts described here (FIG. 47). The multiplex CRISPR/Cas9-Based System may be used in the same ways as the CRISPR/Cas9-Based System described above.

In addition to the described transcriptional activation and nuclease functionality, this system will be useful for expressing other novel Cas9-based effectors that control epigenetic modifications for diverse purposes, including interrogation of genome architecture and pathways of endogenous gene regulation. As endogenous gene regulation is a delicate balance between multiple enzymes, multiplexing Cas9 systems with different functionalities will allow for examining the complex interplay among different regulatory signals. The vector described here should be compatible with aptamer-modified sgRNAs and orthogonal Cas9s to enable independent genetic manipulations using a single set of sgRNAs.

The multiplex CRISPR/Cas9-Based System may be used to activate at least one endogenous gene in a cell. The method includes contacting a cell with the modified lentiviral vector. The endogenous gene may be transiently activated or stably activated. The endogenous gene may be transiently repressed or stably repressed. The fusion protein may be expressed at similar levels to the sgRNAs. The fusion protein may be expressed at different levels compared to the sgRNAs. The cell may be a primary human cell.

The multiplex CRISPR/Cas9-Based System may be used in a method of multiplex gene editing in a cell. The method includes contacting a cell with the modified lentiviral vector. The multiplex gene editing may include correcting a mutant gene or inserting a transgene. Correcting a mutant gene may include deleting, rearranging or replacing the mutant gene. Correcting the mutant gene may include nuclease-mediated non-homologous end joining or homology-directed repair. The multiplex gene editing may include deleting or correcting at least one gene, wherein the gene is an endogenous normal gene or a mutant gene. The multiplex gene editing may include deleting or correcting at least two genes. For example, at least two genes, at least three genes, at least four genes, at least five genes, at least six genes, at least seven genes, at least eight genes, at least nine genes, or at least ten genes may be deleted or corrected.

The multiplex CRISPR/Cas9-Based System may be used in a method of multiplex modulation of gene expression in a cell. The method includes contacting a cell with the modified lentiviral vector. The method may include modulating the gene expression levels of at least one gene. The gene expression of the at least one target gene is modulated when gene expression levels of the at least one target gene are increased or decreased compared to normal gene expression levels for the at least one target gene. The gene expression levels may be RNA or protein levels.

13. METHODS OF CORRECTING A MUTANT GENE AND TREATING A SUBJECT

The present disclosure is also directed to a method of correcting a mutant gene in a subject. The method comprises administering to the skeletal muscle or cardiac muscle of the subject the composition for genome editing in skeletal muscle or cardiac muscle, as described above. Use of the composition to deliver the site-specific nuclease to the skeletal muscle or cardiac muscle may restore the expression of a full-functional or partially-functional protein with a repair template or donor DNA, which can replace the entire gene or the region containing the mutation. The site-specific nuclease may be used to introduce site-specific double strand breaks at targeted genomic loci. Site-specific double-strand breaks are created when the site-specific nuclease binds to a target DNA sequences, thereby permitting cleavage of the target DNA. This DNA cleavage may stimulate the natural DNA-repair machinery, leading to one of two possible repair pathways: homology-directed repair (HDR) or the non-homologous end joining (NHEJ) pathway.

The present disclosure is directed to genome editing with a site-specific nuclease without a repair template, which can efficiently correct the reading frame and restore the expression of a functional protein involved in a genetic disease. The disclosed site-specific nucleases may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active site-specific nucleases with an efficient gene editing method for the treatment of genetic diseases caused by mutations in nonessential coding regions that cause frameshifts, premature stop codons, aberrant splice donor sites or aberrant splice acceptor sites.

a. Nuclease Mediated Non-Homologous End Joining

Restoration of protein expression from an endogenous mutated gene may be through template-free NHEJ-mediated DNA repair. In contrast to a transient method targeting the target gene RNA, the correction of the target gene reading frame in the genome by a transiently expressed site-specific nuclease may lead to permanently restored target gene expression by each modified cell and all of its progeny.

Nuclease mediated NHEJ gene correction may correct the mutated target gene and offers several potential advantages over the HDR pathway. For example, NHEJ does not require a donor template, which may cause nonspecific insertional mutagenesis. In contrast to HDR, NHEJ operates efficiently in all stages of the cell cycle and therefore may be effectively exploited in both cycling and post-mitotic cells, such as muscle fibers. This provides a robust, permanent gene restoration alternative to oligonucleotide-based exon skipping or pharmacologic forced read-through of stop codons and could theoretically require as few as one drug treatment. NHEJ-based gene correction using a CRISPR/Cas9-based system, as well as other engineered nucleases including meganucleases and zinc finger nucleases, may be combined with other existing ex vivo and in vivo platforms for cell- and gene-based therapies, in addition to the plasmid electroporation approach described here. For example, delivery of a CRISPR/Cas9-based system by mRNA-based gene transfer or as purified cell permeable proteins could enable a DNA-free genome editing approach that would circumvent any possibility of insertional mutagenesis.

b. Homology-Directed Repair

Restoration of protein expression from an endogenous mutated gene may involve homology-directed repair. The method as described above further includes administrating a donor template to the cell. The donor template may include a nucleotide sequence encoding a full-functional protein or a partially-functional protein. For example, the donor template may include a miniaturized dystrophin construct, termed minidystrophin ("minidys"), a full-functional dystrophin construct for restoring a mutant dystrophin gene, or a fragment of the dystrophin gene that after homology-directed repair leads to restoration of the mutant dystrophin gene.

c. Methods of Correcting a Mutant Gene and Treating a Subject Using CRISPR/Cas9

The present disclosure is also directed to genome editing with the CRISPR/Cas9-based system to restore the expression of a full-functional or partially-functional protein with a repair template or donor DNA, which can replace the entire gene or the region containing the mutation. The CRISPR/Cas9-based system may be used to introduce site-specific double strand breaks at targeted genomic loci. Site-specific double-strand breaks are created when the CRISPR/Cas9-based system binds to a target DNA sequences using the gRNA, thereby permitting cleavage of the target DNA. The CRISPR/Cas9-based system has the advantage of advanced genome editing due to their high rate of successful and efficient genetic modification. This DNA cleavage may stimulate the natural DNA-repair machinery, leading to one of two possible repair pathways: homology-directed repair (HDR) or the non-homologous end joining (NHEJ) pathway. For example, a CRISPR/Cas9-based system directed towards the dystrophin gene may include a gRNA having a nucleic acid sequence of any one of SEQ ID NOs: 65-115.

The present disclosure is directed to genome editing with CRISPR/Cas9-based system without a repair template, which can efficiently correct the reading frame and restore the expression of a functional protein involved in a genetic disease. The disclosed CRISPR/Cas9-based system and methods may involve using homology-directed repair or nuclease-mediated non-homologous end joining (NHEJ)-based correction approaches, which enable efficient correction in proliferation-limited primary cell lines that may not be amenable to homologous recombination or selection-based gene correction. This strategy integrates the rapid and robust assembly of active CRISPR/Cas9-based system with an efficient gene editing method for the treatment of genetic diseases caused by mutations in nonessential coding regions that cause frameshifts, premature stop codons, aberrant splice donor sites or aberrant splice acceptor sites.

The present disclosure provides methods of correcting a mutant gene in a cell and treating a subject suffering from a genetic disease, such as DMD. The method may include administering to a cell or subject a CRISPR/Cas9-based system, a polynucleotide or vector encoding said CRISPR/Cas9-based system, or composition of said CRISPR/Cas9-based system as described above. The method may include administering a CRISPR/Cas9-based system, such as administering a Cas9 protein or Cas9 fusion protein containing a second domain having nuclease activity, a nucleotide sequence encoding said Cas9 protein or Cas9 fusion protein, and/or at least one gRNA, wherein the gRNAs target different DNA sequences. The target DNA sequences may be overlapping. The number of gRNA administered to the cell may be at least 1 gRNA, at least 2 different gRNA, at least 3 different gRNA at least 4 different gRNA, at least 5 different gRNA, at least 6 different gRNA, at least 7 different gRNA, at least 8 different gRNA, at least 9 different gRNA, at least 10 different gRNA, at least 15 different gRNA, at least 20 different gRNA, at least 30 different gRNA, or at least 50 different gRNA, as described above. The gRNA may include a nucleic acid sequence of at least one of SEQ ID NOs: 65-115. The method may involve homology-directed repair or non-homologous end joining.

14. METHODS OF TREATING A DISEASE

The present disclosure is directed to a method of treating a subject in need thereof. The method comprises administering to a tissue of a subject the composition for altering gene expression and engineering or altering genomic DNA in a cell or subject genome editing, as described above. The method may comprises administering to the skeletal muscle or cardiac muscle of the subject the composition for genome editing in skeletal muscle or cardiac muscle, as described above. The subject may be suffering from a skeletal muscle or cardiac muscle condition causing degeneration or weakness or a genetic disease. For example, the subject may be suffering from Duchenne muscular dystrophy, as described above.

a. Duchenne Muscular Dystrophy

The method, as described above, may be used for correcting the dystrophin gene and recovering full-functional or partially-functional protein expression of said mutated dystrophin gene. In some aspects and embodiments the disclosure provides a method for reducing the effects (e.g., clinical symptoms/indications) of DMD in a patient. In some aspects and embodiments the disclosure provides a method for treating DMD in a patient. In some aspects and embodiments the disclosure provides a method for preventing DMD in a patient. In some aspects and embodiments the disclosure provides a method for preventing further progression of DMD in a patient.

15. CONSTRUCTS AND PLASMIDS

The compositions, as described above, may comprise genetic constructs that encodes the CRISPR/Cas9-based system, as disclosed herein. The genetic construct, such as a plasmid, may comprise a nucleic acid that encodes the CRISPR/Cas9-based system, such as the Cas9 protein and Cas9 fusion proteins and/or at least one of the gRNAs. The compositions, as described above, may comprise genetic constructs that encodes the modified AAV vector and a nucleic acid sequence that encodes the site-specific nuclease, as disclosed herein. The genetic construct, such as a plasmid, may comprise a nucleic acid that encodes the site-specific nuclease. The compositions, as described above, may comprise genetic constructs that encodes the modified lentiviral vector, as disclosed herein. The genetic construct, such as a plasmid, may comprise a nucleic acid that encodes the Cas9-fusion protein and at least one sgRNA. The genetic construct may be present in the cell as a functioning extrachromosomal molecule. The genetic construct may be a linear minichromosome including centromere, telomeres or plasmids or cosmids.

The genetic construct may also be part of a genome of a recombinant viral vector, including recombinant lentivirus, recombinant adenovirus, and recombinant adenovirus associated virus. The genetic construct may be part of the genetic material in attenuated live microorganisms or recombinant microbial vectors which live in cells. The genetic constructs may comprise regulatory elements for gene expression of the coding sequences of the nucleic acid. The regulatory elements may be a promoter, an enhancer, an initiation codon, a stop codon, or a polyadenylation signal.

The nucleic acid sequences may make up a genetic construct that may be a vector. The vector may be capable of expressing the fusion protein, such as the Cas9-fusion protein or site-specific nuclease, in the cell of a mammal. The vector may be recombinant. The vector may comprise heterologous nucleic acid encoding the fusion protein, such as the Cas9-fusion protein or site-specific nuclease. The vector may be a plasmid. The vector may be useful for transfecting cells with nucleic acid encoding the Cas9-fusion protein or site-specific nuclease, which the transformed host cell is cultured and maintained under conditions wherein expression of the Cas9-fusion protein or the site-specific nuclease system takes place.

Coding sequences may be optimized for stability and high levels of expression. In some instances, codons are selected to reduce secondary structure formation of the RNA such as that formed due to intramolecular bonding.

The vector may comprise heterologous nucleic acid encoding the CRISPR/Cas9-based system or the site-specific nuclease and may further comprise an initiation codon, which may be upstream of the CRISPR/Cas9-based system or the site-specific nuclease coding sequence, and a stop codon, which may be downstream of the CRISPR/Cas9-based system or the site-specific nuclease coding sequence. The initiation and termination codon may be in frame with the CRISPR/Cas9-based system or the site-specific nuclease coding sequence. The vector may also comprise a promoter that is operably linked to the CRISPR/Cas9-based system or the site-specific nuclease coding sequence. The promoter operably linked to the CRISPR/Cas9-based system or the site-specific nuclease coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human ubiquitin C (hUbC), human actin, human myosin, human hemoglobin, human muscle creatine, or human metalothionein. The promoter may also be a tissue specific promoter, such as a muscle or skin specific promoter, natural or synthetic. Examples of such promoters are described in US Patent Application Publication No. US20040175727, the contents of which are incorporated herein in its entirety.

The vector may also comprise a polyadenylation signal, which may be downstream of the CRISPR/Cas9-based system or the site-specific nuclease. The polyadenylation signal may be a SV40 polyadenylation signal, LTR polyadenylation signal, bovine growth hormone (bGH) polyadenylation signal, human growth hormone (hGH) polyadenylation signal, or human f3-globin polyadenylation signal. The SV40 polyadenylation signal may be a polyadenylation signal from a pCEP4 vector (Invitrogen, San Diego, Calif.).

The vector may also comprise an enhancer upstream of the CRISPR/Cas9-based system, i.e., the Cas9 protein or Cas9 fusion protein coding sequence or sgRNAs, or the site-specific nuclease. The enhancer may be necessary for DNA expression. The enhancer may be human actin, human myosin, human hemoglobin, human muscle creatine or a viral enhancer such as one from CMV, HA, RSV or EBV. Polynucleotide function enhancers are described in U.S. Pat. Nos. 5,593,972, 5,962,428, and WO94/016737, the contents of each are fully incorporated by reference. The vector may also comprise a mammalian origin of replication in order to maintain the vector extrachromosomally and produce multiple copies of the vector in a cell. The vector may also comprise a regulatory sequence, which may be well suited for gene expression in a mammalian or human cell into which the vector is administered. The vector may also comprise a reporter gene, such as green fluorescent protein ("GFP") and/or a selectable marker, such as hygromycin ("Hygro").

The vector may be expression vectors or systems to produce protein by routine techniques and readily available starting materials including Sambrook et al., Molecular Cloning and Laboratory Manual, Second Ed., Cold Spring Harbor (1989), which is incorporated fully by reference. In some embodiments the vector may comprise the nucleic acid sequence encoding the CRISPR/Cas9-based system, including the nucleic acid sequence encoding the Cas9 protein or Cas9 fusion protein and the nucleic acid sequence encoding the at least one gRNA comprising the nucleic acid sequence of at least one of SEQ ID NOs: 5-40, 65-144, 492-515, 540-563, and 585-625.

16. PHARMACEUTICAL COMPOSITIONS

The composition may be in a pharmaceutical composition. The pharmaceutical composition may comprise about 1 ng to about 10 mg of DNA encoding the CRISPR/Cas9-based system or CRISPR/Cas9-based system protein component, i.e., the Cas9 protein or Cas9 fusion protein. The pharmaceutical composition may comprise about 1 ng to about 10 mg of the DNA of the modified AAV vector and nucleotide sequence encoding the site-specific nuclease. The pharmaceutical composition may comprise about 1 ng to about 10 mg of the DNA of the modified lentiviral vector. The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity may include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The composition may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the composition for genome editing in skeletal muscle or cardiac muscle at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA vector encoding the composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

17. METHODS OF DELIVERY

Provided herein is a method for delivering the pharmaceutical formulations, preferably compositions described above, for providing genetic constructs. The delivery of the compositions may be the transfection or electroporation of the composition as a nucleic acid molecule that is expressed in the cell and delivered to the surface of the cell. The nucleic acid molecules may be electroporated using BioRad Gene Pulser Xcell or Amaxa Nucleofector IIb devices. Several different buffers may be used, including BioRad electroporation solution, Sigma phosphate-buffered saline product # D8537 (PBS), Invitrogen OptiMEM I (OM), or Amaxa Nucleofector solution V (N. V.). Transfections may include a transfection reagent, such as Lipofectamine 2000.

Upon delivery of the composition to the tissue, and thereupon the vector into the cells of the mammal, the transfected cells will express the fusion protein, such as a CRISPR/Cas9-based system and/or a site-specific nuclease. The composition may be administered to a mammal to alter gene expression or to re-engineer or alter the genome. For example, the composition may be administered to a mammal to correct the dystrophin gene in a mammal. The mammal may be human, non-human primate, cow, pig, sheep, goat, antelope, bison, water buffalo, bovids, deer, hedgehogs, elephants, llama, alpaca, mice, rats, or chicken, and preferably human, cow, pig, or chicken.

a. CRISPR/Cas9-Based System

The vector encoding a CRISPR/Cas9-based system protein component, i.e., the Cas9 protein or Cas9 fusion protein, may be delivered to the mammal by DNA injection (also referred to as DNA vaccination) with and without in vivo electroporation, liposome mediated, nanoparticle facilitated, and/or recombinant vectors. The recombinant vector may be delivered by any viral mode. The viral mode may be recombinant lentivirus, recombinant adenovirus, and/or recombinant adeno-associated virus.

The nucleotide encoding a CRISPR/Cas9-based system protein component, i.e., the Cas9 protein or Cas9 fusion protein, may be introduced into a cell to genetically correct the target gene or alter gene expression of a gene, such as activate or repress endogenous genes. For example, a nucleotide encoding a CRISPR/Cas9-based system protein component, i.e., the Cas9 protein or Cas9 fusion protein, directed towards a mutant dystrophin gene by the gRNA may be introduced into a myoblast cell from a DMD patient. Alternatively, they may be introduced into a fibroblast cell from a DMD patient, and the genetically corrected fibroblast cell may be treated with MyoD to induce differentiation into myoblasts, which may be implanted into subjects, such as the damaged muscles of a subject to verify that the corrected dystrophin protein was functional and/or to treat the subject. The modified cells may also be stem cells, such as induced pluripotent stem cells, bone marrow-derived progenitors, skeletal muscle progenitors, human skeletal myoblasts from DMD patients, CD133+ cells, mesoangioblasts, and MyoD- or Pax7-transduced cells, or other myogenic progenitor cells. For example, the CRISPR/Cas9-based system may cause neuronal or myogenic differentiation of an induced pluripotent stem cell.

18. ROUTES OF ADMINISTRATION

The compositions may be administered to a subject by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian may readily determine the dosing regimen and route of administration that is most appropriate for a particular animal. The compositions may be administered by traditional syringes, needleless injection devices, "microprojectile bombardment gone guns", or other physical methods such as electroporation ("EP"), "hydrodynamic method", or ultrasound.

The composition may be delivered to the mammal by several technologies including DNA injection (also referred to as DNA vaccination) with and without in vivo electroporation, liposome mediated, nanoparticle facilitated, recombinant vectors such as recombinant lentivirus, recombinant adenovirus, and recombinant adenovirus associated virus. The composition may be injected into the skeletal muscle or cardiac muscle. For example, the composition may be injected into the tibialis anterior muscle.

19. CELL TYPES

Any of these delivery methods and/or routes of administration could be utilized with a myriad of cell types, for example, those cell types currently under investigation for cell-based therapies. Cell types may be fibroblasts, pluripotent stem cells, cardiomyocytes, hepatocytes, chondrocytes, mesenchymal progenitor cells, hematopoetic stem cells, smooth muscle cells, or K562 human erythroid leukemia cell line.

a. DMD

Cell types currently under investigation for cell-based therapies of DMD include immortalized myoblast cells, such as wild-type and DMD patient derived lines, for example 448-50 DMD, DMD 8036 (de148-50), C25C14 and DMD-7796 cell lines, primal DMD dermal fibroblasts, induced pluripotent stem cells, bone marrow-derived progenitors, skeletal muscle progenitors, human skeletal myoblasts from DMD patients, CD133+ cells, mesoangioblasts, cardiomyocytes, hepatocytes, chondrocytes, mesenchymal progenitor cells, hematopoetic stem cells, smooth muscle cells, and MyoD- or Pax7-transduced cells, or other myogenic progenitor cells. Immortalization of human myogenic cells may be used for clonal derivation of genetically corrected myogenic cells. Cells may be modified ex vivo to isolate and expand clonal populations of immortalized DMD myoblasts that contain a genetically corrected dystrophin gene and are free of other nuclease-introduced mutations in protein coding regions of the genome. Alternatively, transient in vivo delivery of nucleases by non-viral or non-integrating viral gene transfer, or by direct delivery of purified proteins and gRNAs containing cell-penetrating motifs may enable highly specific correction in situ with minimal or no risk of exogenous DNA integration.

20. KITS

Provided herein is a kit, which may be used to edit a genome in skeletal muscle or cardiac muscle, such as correcting a mutant gene. The kit comprises a composition for genome editing in skeletal muscle or cardiac muscle, as described above, and instructions for using said composition. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

The composition for genome editing in skeletal muscle or cardiac muscle may include a modified AAV vector and a nucleotide sequence encoding a site-specific nuclease, as described above. The site-specific nuclease may include a ZFN, a TALEN, or CRISPR/Cas9-based system, as described above, that specifically binds and cleaves a mutated gene. The site-specific nuclease, as described above, may be included in the kit to specifically bind and target a particular region in the mutated gene. The site-specific nuclease may be specific for a mutated dystrophin gene, as described above. The kit may further include donor DNA, a gRNA, or a transgene, as described above.

a. CRISPR/Cas9-Based System

Provided herein is a kit, which may be used to correct a mutated gene. The kit comprises at least one component for correcting a mutated gene and instructions for using the CRISPR/Cas9-based system. Instructions included in kits may be affixed to packaging material or may be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

At least one component may include at least one CRISPR/Cas9-based system, as described above, which specifically targets a gene. The kit may include a Cas9 protein or Cas9 fusion protein, a nucleotide sequence encoding said Cas9 protein or Cas9 fusion protein, and/or at least one gRNA. The CRISPR/Cas9-based system, as described above, may be included in the kit to specifically bind and target a particular target region upstream, within or downstream of the coding region of the target gene. For example, a CRISPR/Cas9-based system may be specific for a promoter region of a target gene or a CRISPR/Cas9-based system may be specific for a mutated gene, for example a mutated dystrophin gene, as described above. The kit may include donor DNA, as described above.

21. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present invention has multiple aspects, illustrated by the following non-limiting examples.

Example 1

Materials and Methods

Cell culture and transfection. HEK293T cells were obtained from the American Tissue Collection Center (ATCC) through the Duke University Cancer Center Facilities and were maintained in DMEM supplemented with 10% fetal bovine serum and 1% penicillin/streptomycin at 37° C. with 5% $CO_2$. HEK293T cells were transfected with Lipofectamine 2000 (Invitrogen) according to manufacturer's instructions. Transfection efficiencies were routinely higher than 80% as determined by fluorescence microscopy following delivery of a control eGFP expression plasmid. Cas9 expression plasmid was transfected at a mass ratio of 3:1 to either the individual gRNA expression plasmids or the identical amount of gRNA expression plasmid consisting of a mixture of equal amounts of the four gRNAs.

Primary mouse embryonic fibroblasts (PMEF-HL, Millipore, Billerica, MASS.A) were seeded (75,000 per well) in 24-well TCPS plates (BD, Franklin Lakes, N.J.) and maintained at 37° C. and 5% $CO_2$ in complete MEF medium consisting of high glucose DMEM supplemented with 10% Premium Select FBS (Atlanta Biologicals, Lawrenceville, Ga.), 25 µg $mL^{-1}$ genmtamicin (Invitrogen), 1× GlutaMAX, non-essential amino acids, sodium pyruvate, and β-mercaptoethanol (Invitrogen). MEF transfections were performed with a single 1 µg $cm^{-2}$ dose of total plasmid DNA, delivered as cationic nanocomplexes following electrostatic condensation with poly(CBA-ABOL) in serum- and antibiotic-free OptiMEM, as described previously (Adler et al. *Molecular therapy. Nucleic acids* 1, e32 (2012)). OptiMEM was replaced with complete MEF medium 4 hrs after transfection. 48 hrs after transfection, MEFs were processed for qRT-PCR, or the complete MEF medium was replaced with N3 neural induction medium containing: DMEM/F-12 (Invitrogen), 1× N-2 Supplement (Invitrogen), 10 ng $mL^{-1}$ human bFGF2 (Stemgent, Cambridge, Mass.), and 25 µg $mL^{-1}$ gentamicin (Invitrogen). A GFP reporter vector (pmax-GFP, 3486 bp, Amaxa, Cologne, Germany) was used to optimize transfection conditions. Cas9 expression plasmid was transfected at a mass ratio of 3:1 or 1:1 to an equal mixture of four gRNA expression plasmids.

Plasmids. The plasmids encoding wild-type and H840A Cas9 were obtained from Addgene (Plasmid #39312 and Plasmid #39316; Jinek, et al. *Science* 337, 816-821 (2012)). H840A Cas9 was cloned into the vector pcDNA3.1 in frame with a FLAG epitope tag and a nuclear localization sequence (NLS) at the N-terminus with a primer pair that introduced the D10A mutation. The VP64 domain, an NLS, and an HA epitope tag were cloned in frame with the Cas9 ORF at the C-terminus (FIG. 1A, FIG. 9A). The tracrRNA and crRNA expression cassettes (Cong et al. *Science* 339, 819-823 (2013)) were ordered as gBlocks (Integrated DNA Technologies (IDT)) and cloned into a pZDonor plasmid (Sigma) with KpnI and SacII sites. A chimeric guide RNA expression cassette (Mali et al. *Science* 339, 823-826 (2013)) was also ordered as gBlocks with modifications to include a BbsI restriction site to facilitate rapid cloning of new guide RNA spacer sequences (FIG. 9B). The oligonucleotides containing the target sequences were obtained from IDT, hybridized, phosphorylated, and cloned in the appropriate plasmids using BbsI sites. The target sequences are provided in Table 2.

TABLE 2

Target sequences of gRNAs

| Target | Name | Sequence | SEQ ID NO |
|---|---|---|---|
| ASCL1 | CR1 | GCTGGGTGTCCCATTGAAA | 5 |
|  | CR2 | CAGCCGCTCGCTGCAGCAG | 6 |
|  | CR3 | TGGAGAGTTTGCAAGGAGC | 7 |
|  | CR4 | GTTTATTCAGCCGGGAGTC | 8 |
| NANOG | CR1 | CGCCAGGAGGGGTGGGTCTA | 9 |
|  | CR2 | CCTTGGTGAGACTGGTAGA | 10 |
|  | CR3 | GTCTTCAGGTTCTGTTGCT | 11 |
|  | CR4 | ATATTCCTGATTTAAAAGT | 12 |
| VEGFA | CR1 | TTAAAAGTCGGCTGGTAGC | 13 |
|  | CR2 | CGGGCCGGGGGCGGGGTCC | 14 |
|  | CR3 | GCCCGAGCCGCGTGTGGAA | 15 |
|  | CR4 | CCTTCATTGCGGCGGGCTG | 16 |
| TERT | CR1 | CCGACCCCTCCCGGGTCCC | 17 |
|  | CR2 | CAGGACCGCGCTTCCCACG | 18 |
|  | CR3 | TGCACCCTGGGAGCGCGAG | 19 |
|  | CR4 | CCGCACGCACCTGTTCCCA | 20 |
| IL1B | CR1 | AAAACAGCGAGGGAGAAAC | 21 |
|  | CR2 | TTAACTTGATTGTGAAATC | 22 |
|  | CR3 | AAAACAATGCATATTTGCA | 23 |
|  | CR4 | AAAATCCAGTATTTTAATG | 24 |
| IL1R2 | CR1 | ACCCAGCACTGCAGCCTGG | 25 |
|  | CR2 | AACTTATGCGGCGTTTCCT | 26 |
|  | CR3 | TCACTTTAAAACCACCTCT | 27 |
|  | CR4 | GCATCTTTTTCTCTTTAAT | 28 |
| IL1RN | CR1 | TGTACTCTCTGAGGTGCTC | 29 |
|  | CR2 | ACGCAGATAAGAACCAGTT | 30 |
|  | CR3 | CATCAAGTCAGCCATCAGC | 31 |
|  | CR4 | GAGTCACCCTCCTGGAAAC | 32 |
| HBG1/2 | CR1 | GCTAGGGATGAAGAATAAA | 33 |
|  | CR2 | TTGACCAATAGCCTTGACA | 34 |
|  | CR3 | TGCAAATATCTGTCTGAAA | 35 |
|  | CR4 | AAATTAGCAGTATCCTCTT | 36 |
| MYOD1 | CR1 | CCTGGGCTCCGGGCGTTT | 37 |
|  | CR2 | GGCCCCTGCGGCCACCCCG | 38 |
|  | CR3 | CTCCCTCCCTGCCCGGTAG | 39 |
|  | CR4 | AGGTTTGGAAAGGGCGTGC | 40 |

Western blot. Cells were lysed in 50 mM Tris-Cl (pH 7.4), 150 mM NaCl, 0.5% Triton X-100, and 0.1% SDS. Lysates were mixed with loading buffer, boiled for 5 min, and equal volumes of protein were run in NuPAGE® Novex 4-12% or 10% Bis-Tris Gel polyacrylamide gels and transferred to nitrocellulose membranes. Non-specific antibody binding was blocked with 50 mM Tris/150 mM NaCl/0.1% Tween-20 (TB S-T) with 5% nonfat milk for 30 min. The membranes were incubated with primary antibodies (HRP-conjugated anti-Flag (Cell Signaling, Cat #2044) in 5% BSA in TBS-T diluted 1:1000 overnight; anti-GAPDH (Cell Signaling, clone 14C10) in 5% milk in TB S-T diluted 1:5000 for 30 min; anti-ASCL1 (Santa Cruz, clone sc-48449) in 5% BSA diluted 1:500; or anti-g-globin (Santa Cruz, clone 51-7) in 5% milk diluted 1:500 and the membranes were washed with TB S-T for 30 min. Membranes labeled with primary antibodies were incubated with anti-rabbit HRP-conjugated antibody (Sigma-Aldrich) diluted 1:5000 for 30 min, antigoat (1:3000) or anti-mouse (1:5000) and washed with TBS-T for 30 min. Membranes were visualized using the Immun-Star WesternC™ Chemiluminescence Kit (Bio-Rad) and images were captured using a ChemiDoc™ XRS+ System and processed using ImageLab software (Bio-Rad).

ELISA. Serum-free culture media (OPTI-MEM) was collected and frozen at −80° C. Human IL-1ra secretion into culture media was quantified via enzyme-linked immunosorbent assay (ELISA), according to the manufacturer's protocols (R&D Systems, Cat. No. DY280).

The standard curve was prepared by diluting recombinant human IL-1ra in OPTI-MEM and the IL-1ra in culture media was measured undiluted. The samples were concentrated about 8 fold via centrifugation through 3 kDa MWCO filters for 20 min (Amicon Ultra, Cat # UFC500396). Reported values were corrected by the concentration factor for each sample.

Optical density was measured at 450 nm, with a wavelength correction at 540 nm. Each standard and sample was assayed in duplicate. The duplicate readings were averaged and normalized by subtracting the average zero standard optical density. A standard curve was generated by log-transforming the data and performing a linear regression of the IL-1ra concentration versus the optical density. Reported values are the mean and standard error of the mean from three independent experiments (n=3) that were performed on different days with technical duplicates that were averaged for each experiment.

qRT-PCR. Total RNA was isolated using the RNeasy Plus RNA isolation kit (Qiagen). cDNA synthesis was performed using the SuperScript® VILO™ cDNA Synthesis Kit (Invitrogen). Real-time PCR using PerfeCTa® SYBR® Green FastMix was performed with the CFX96 Real-Time PCR Detection System (Bio-Rad) with oligonucleotide primers reported in Table 3 that were designed using Primer3Plus software and purchased from IDT.

TABLE 3

Sequences of primers used for qRT-PCR.

| Target | Forward Primer | SEQ ID NO | Reverse Primer | SEQ ID NO |
|---|---|---|---|---|
| hASCL1 | GGAGCTTCTCGACTTCACCA | 41 | AACGCCACTGACAAGAAAGC | 53 |
| NANOG | GATTTGTGGGCCTGAAGAAA | 42 | CAGATCCATGGAGGAAGGAA | 54 |
| VEGF4 | AAGGAGGAGGGCAGAATCAT | 43 | GGGTACTCCTGGAAGATGTCC | 55 |
| TERT | AAACCTTCCTCAGCTATGCCC | 44 | GTTTGCGACGCATGTTCCTC | 56 |
| IL1B | AGCTGATGGCCCTAAACAGA | 45 | AAGCCCTTGCTGTAGTGGTG | 57 |
| IL1R2 | CAGGAGGACTCTGGCACCTA | 46 | CGGCAGGAAAGCATCTGTAT | 58 |
| IL1RN | GGAATCCATGGAGGGAAGAT | 47 | TGTTCTCGCTCAGGTCAGTG | 59 |
| HBG1/2 | GCTGAGTGAACTGCACTGTGA | 48 | GAATTCTTTGCCGAAATGGA | 60 |
| MYOD1 | CTCTCTGCTCCTTTGCCACA | 49 | GTGCTCTTCGGGTTTCAGGA | 61 |

TABLE 3-continued

Sequences of primers used for qRT-PCR.

| Target | Forward Primer | SEQ ID NO | Reverse Primer | SEQ ID NO |
|---|---|---|---|---|
| GAPDH | CAATGACCCCTTCATTGACC | 50 | TTGATTTTGGAGGGATCTCG | 62 |
| mASCL1 | GGAACAAGAGCTGCTGGACT | 51 | GTTTTTCTGCCTCCCCATTT | 63 |
| mGAPDH | AACTTTGGCATTGTGGAAGG | 52 | GGATGCAGGGATGATGITCT | 64 |

Primer specificity was confirmed by agarose gel electrophoresis and melting curve analysis. Reaction efficiencies over the appropriate dynamic range were calculated to ensure linearity of the standard curve (FIG. 10). The results are expressed as fold-increase mRNA expression of the gene of interest normalized to GAPDH expression by the $\Delta\Delta C_T$ method. Reported values are the mean and standard error of the mean from three independent experiments performed on different days (n=3) with technical duplicates that were averaged for each experiment.

RNA-Seq. RNA seq libraries were constructed. Briefly, first strand cDNA was synthesized from oligo dT Dynabead® (Invitrogen) captured mRNA using SuperScript® VILO™ cDNA Synthesis Kit (Invitrogen). Second strand cDNA was synthesized using DNA Polymerase I (New England Biolabs). cDNA was purified using Agencourt AMPure XP beads (Beckman Coulter) and Nextera transposase (Illumina; 5 min at 55° C.) was used to simultaneously fragment and insert sequencing primers into the double-stranded cDNA. Transposition reactions were halted using QG buffer (Qiagen) and fragmented cDNA was purified on AMPure XP beads. Indexed sequencing libraries were generated by 6 cycles of PCR.

Libraries were sequenced using 50-bp single end reads on two lanes of an Illumina HiSeq 2000 instrument, generating between 29 million and 74 million reads per library. Reads were aligned to human RefSeq transcripts using Bowtie (Langmead et al. *Genome biology* 10, R25 (2009)). The statistical significance of differential expression, including correction for multiple hypothesis testing, was calculated using DESeq (Anders et al. *Genome biology* 11, R106 (2010)). Raw RNA-seq reads and the number of reads aligned to each RefSeq transcript have been deposited for public access in the Gene Expression Omnibus (GEO), with accession number currently pending.

Immunofluorescence staining. For detection of Tuj 1 and MAP2 expression, transfected MEFs were fixed at day 10 of culture in N3 medium with 4% PFA (EMS, Hatfield, Pa.) at room temperature (RT) for 20 min. Cells were then incubated in blocking buffer containing 0.2% Triton X-100, 3% w/v BSA, and 10% goat serum (Sigma-Aldrich, Saint Louis, Mo.) for two hrs at room temperature with rabbit anti-Tuj 1 (Covance, Princeton, N.J., clone TUJ1 1-15-79, 1:500) and mouse anti-MAP2 (BD, clone Ap20, 1:500), or for an additional 24 hrs at 4° C. with mouse anti-Ascl1 (BD clone 24B72D11.1, 1:100). The cells were then washed three times with PBS, incubated for 1 hr at room temperature in blocking buffer with Alexa Fluor 488 goat anti-mouse IgG and Alexa Fluor 594 goat anti-rabbit IgG (Invitrogen, 1:200), and washed three times with PBS. Stained MEFs were then scanned with a Nikon Eclipse TE2000-U inverted fluorescence microscope with a ProScanII motorized stage (Prior Scientific, Rockland, Mass.) to produce large mosaic images of each complete culture area. These mosaics were processed with a FIJI macro to automatically and uniformly threshold each image according to local contrast, exclude small debris, and to count the number of Tuj1+ cells in each well.

Statistics. Statistical analysis was performed by Tukey's test with alpha equal to 0.05 in JMP 10 Pro.

Example 2

Results

Figure 1B:
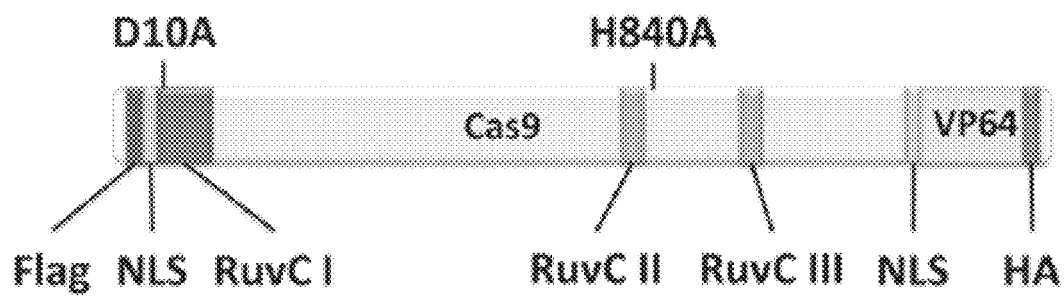
Figure 1C:
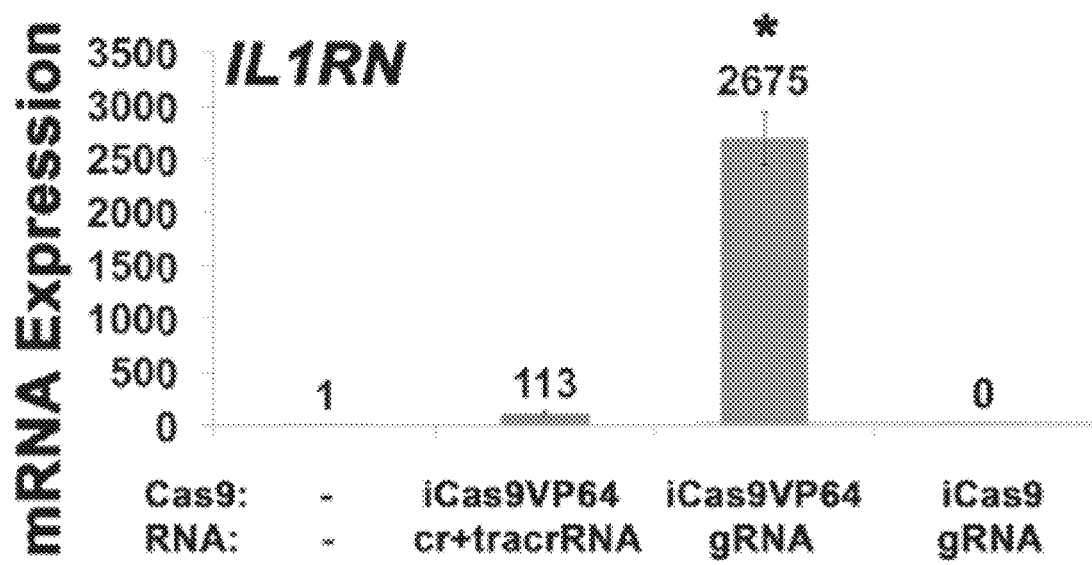
Figure 1D:
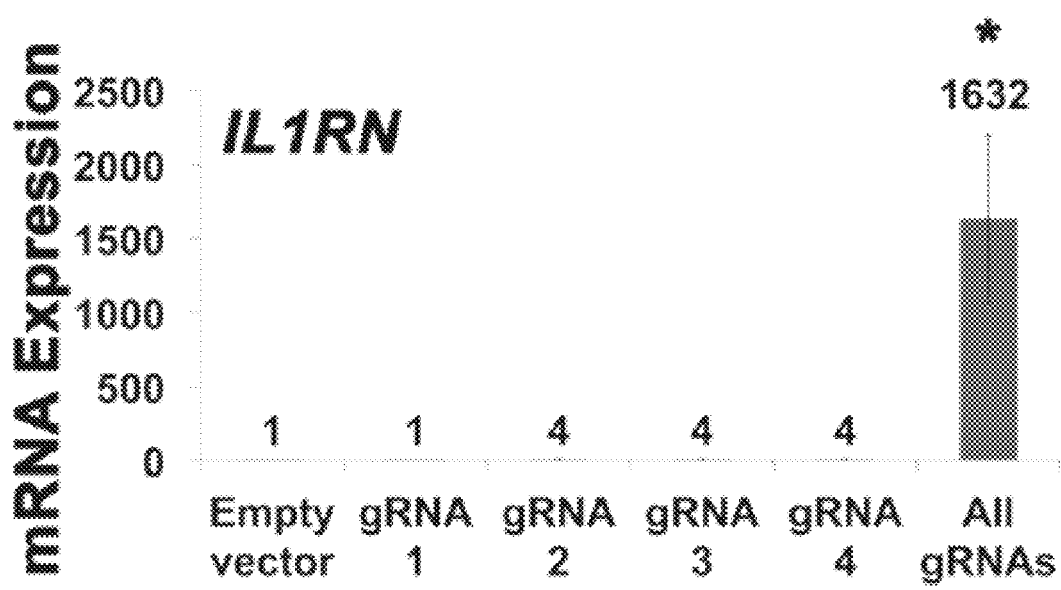
Figure 1E:
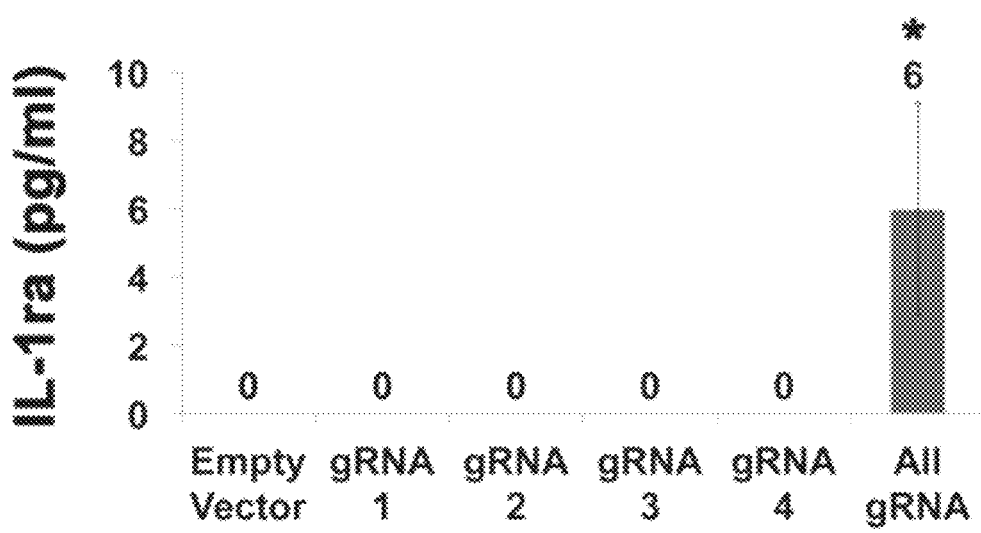
Figure 1F:
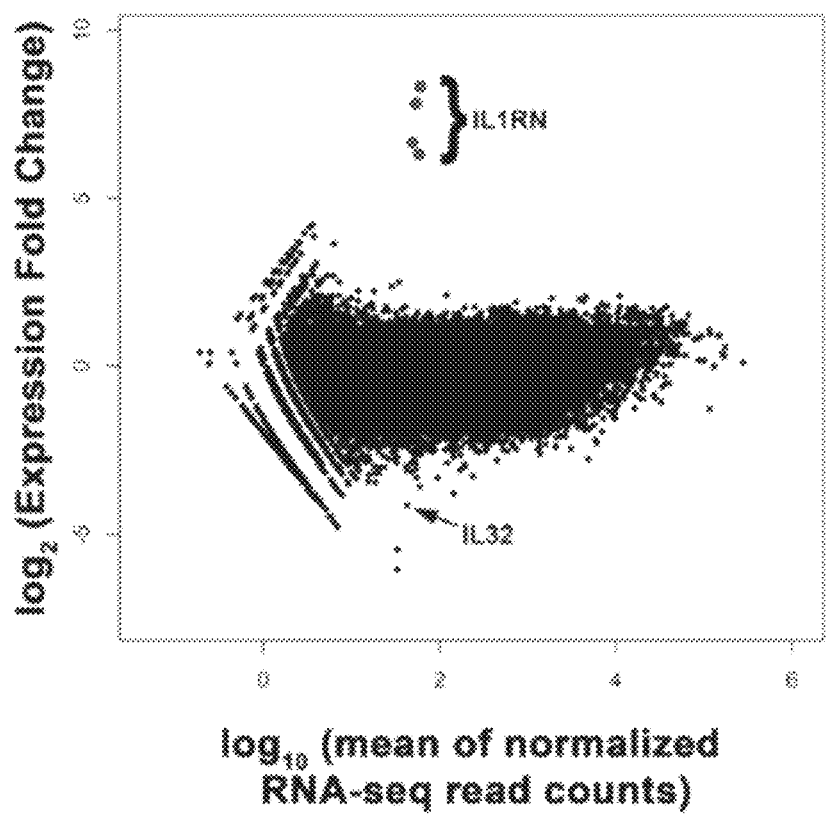
Figure 2A:
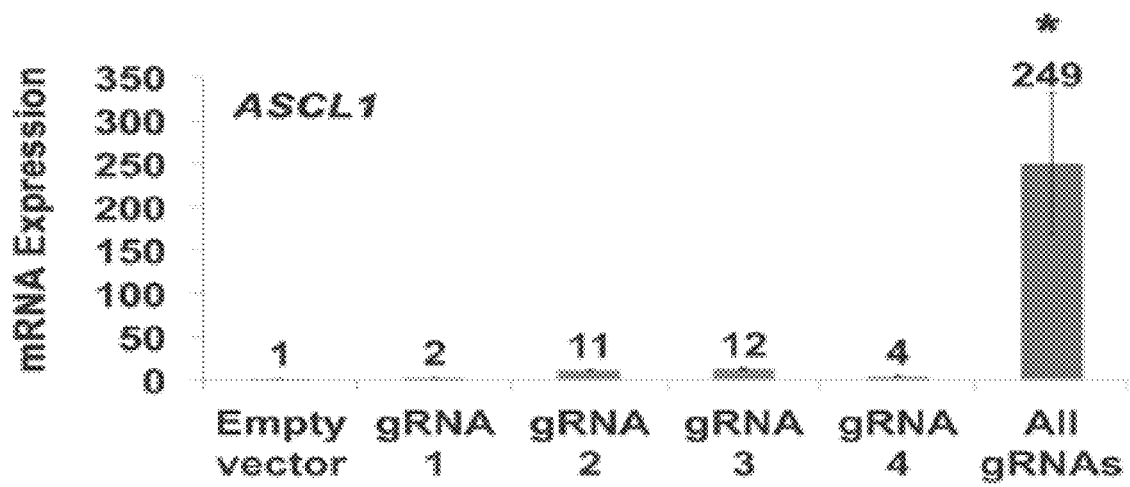
FIGS. 2A-2H show RNA-guided activation of human genes relevant to cell and gene therapy, genetic reprogramming, and regenerative medicine. HEK293T cells were transfected with the iCas9-VP64 expression plasmid and four gRNAs individually or in combination. Target gene expression was measured by qRT-PCR and normalized to GAPDH mRNA levels. Data are shown as the mean±s.e.m. (n=3 independent experiments). Treatment with the combination of gRNAs was statistically different than all other treatments (*P<0.05) by Tukey's test.
Figure 2B:
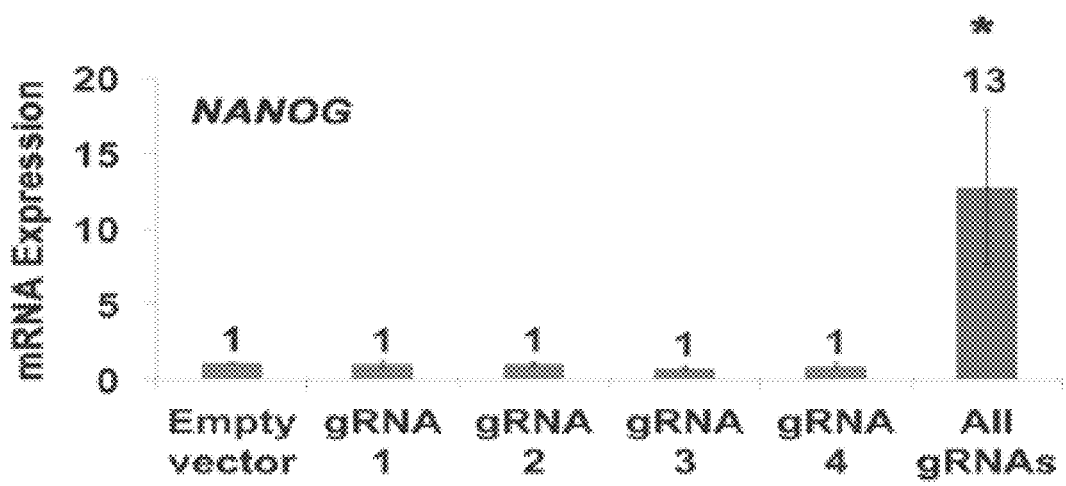
Figure 2C:
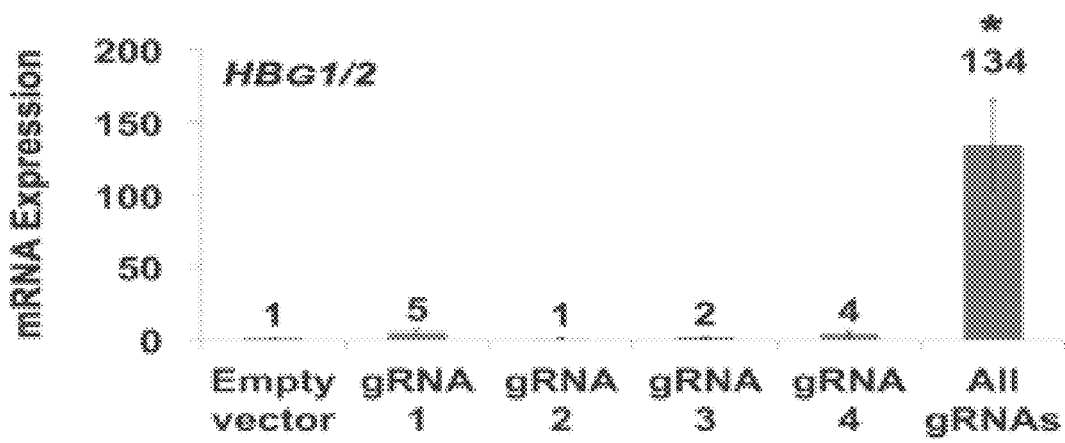
Figure 2D:
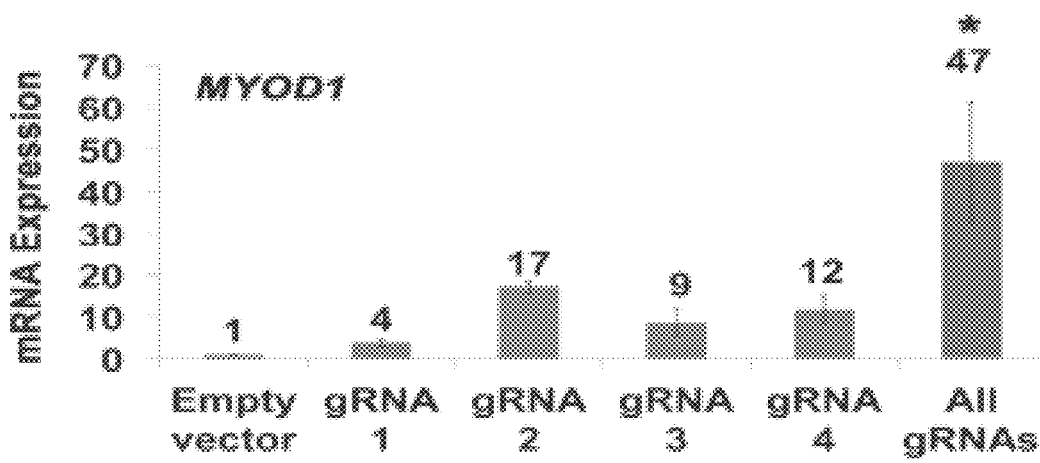
Figure 2E:
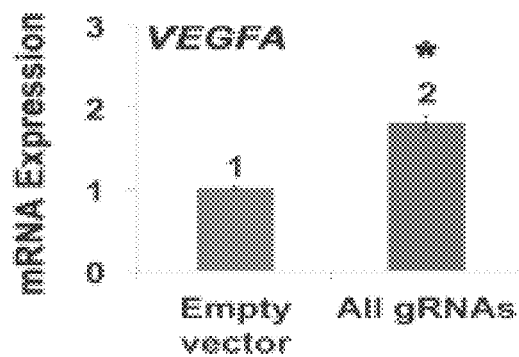
Figure 2F:
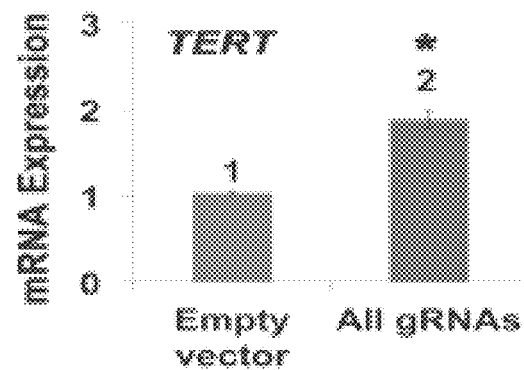
Figure 2G:
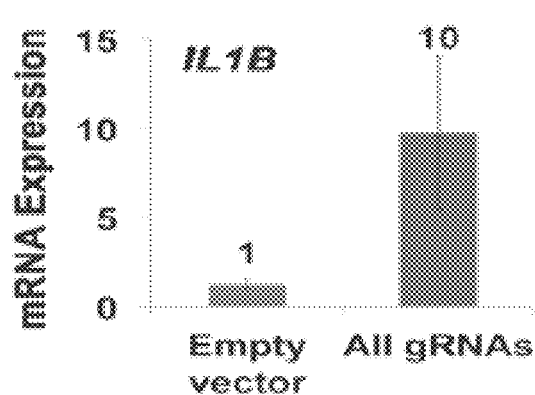
Figure 2H:
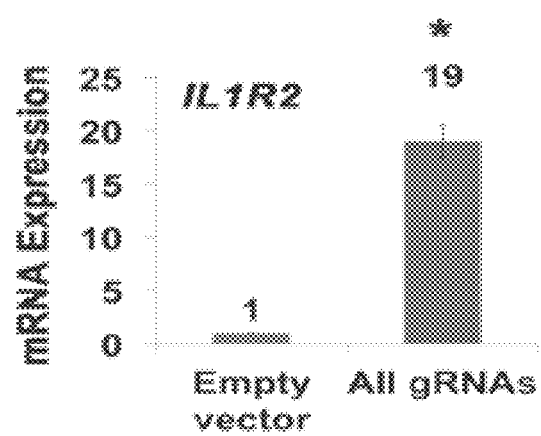
Figure 3:
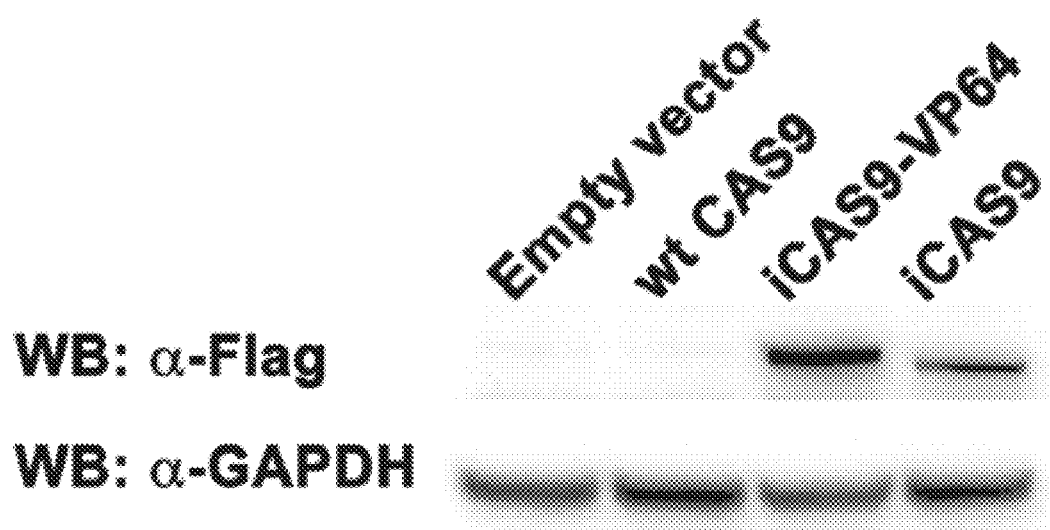
FIG. 3 shows expression of iCas9-VP64. Expression of iCas9-VP64 in transfected HEK293 cells was confirmed by western blot for the N-terminal Flag epitope tag. The wt Cas9 expression plasmid does not contain the epitope tag.
Figure 4A:
Figure 4B:
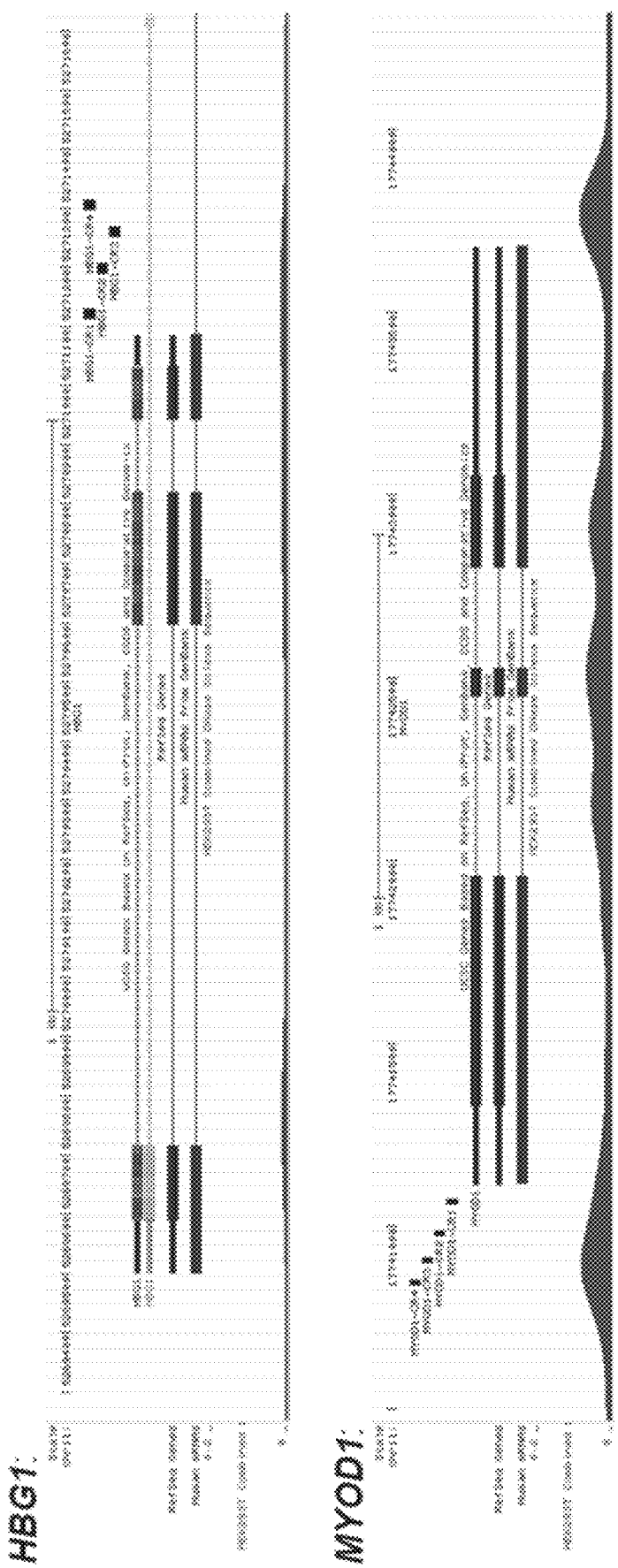
Figure 4C:
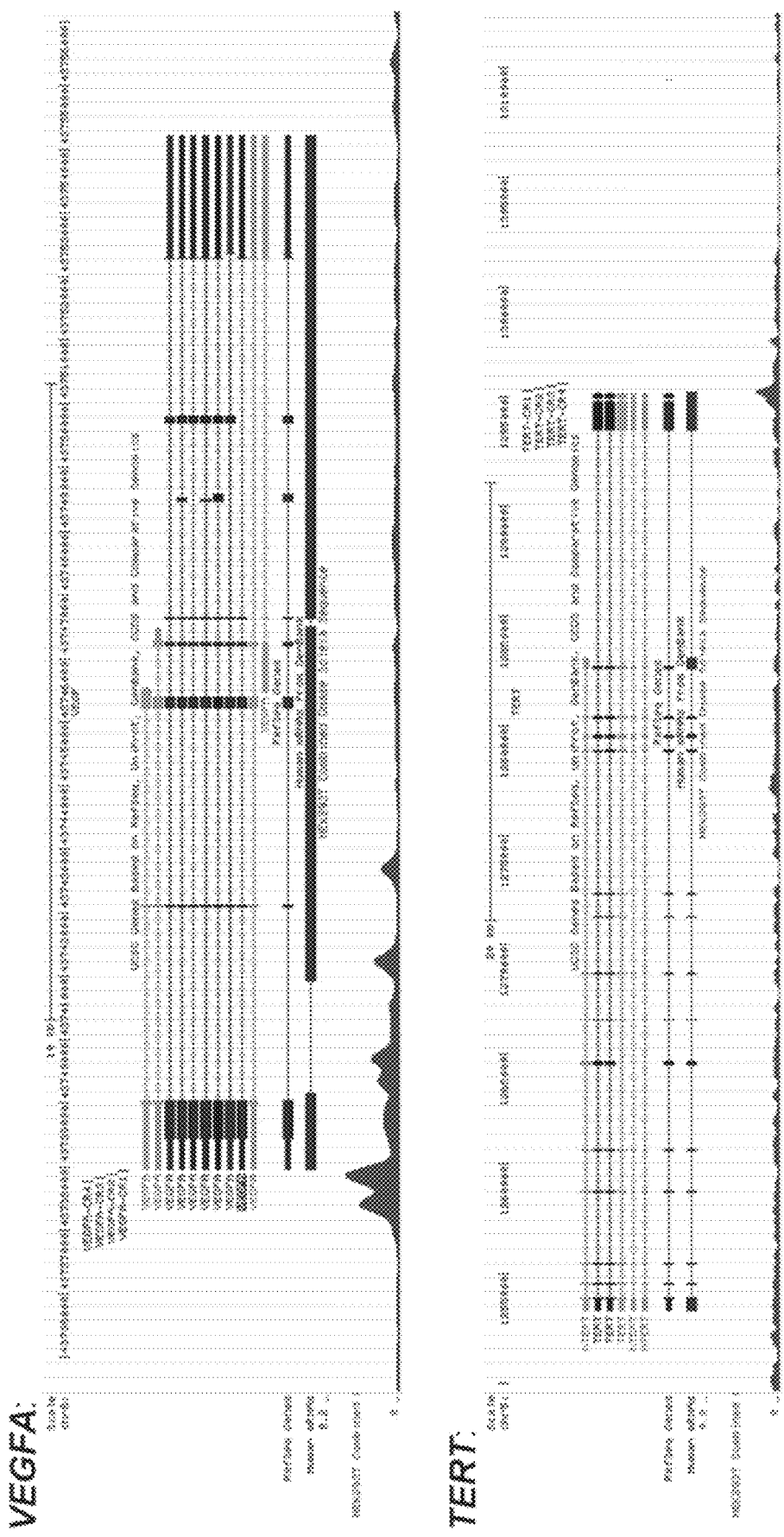
Figure 5:
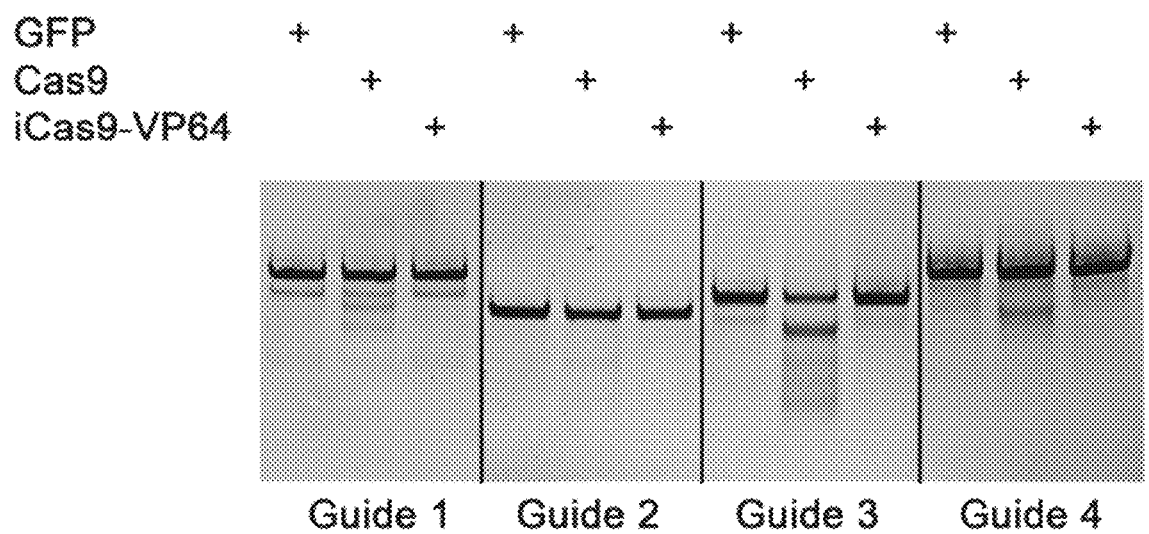
FIG. 5 shows the absence of nuclease activity by iCas9-VP64. Wild-type Cas9 or inactivated (D10A, H840A) iCas9-VP64 expression plasmids were co-transfected with expression plasmids for four different guide RNAs targeting the IL1RN promoter. Nuclease activity was determined by the Surveyor assay (Guschin et al., Methods Mol Biol 649, 247-256 (2010)). The lower molecular weight bands indicative of nuclease activity and DNA repair by non-homologous end joining are only present following treatment with wild-type Cas9, supporting abrogation of nuclease activity by iCas9-VP64.

To create a CRISPR/Cas9-based transcriptional activation system, catalytic residues of Cas9 (D10A, H840A) were mutated to create iCas9 and genetically fused with a C-terminal VP64 acidic transactivation domain (FIGS. 1A and 1B). Robust expression of iCas9-VP64 was observed from the transfected plasmid in human embryonic kidney (HEK) 293T cells by western blot of the N-terminal Flag epitope tag (FIG. 3). The CRISPR system recognizes its target through base pairing of a 20 bp sequence in the gRNA to a complementary DNA target, which is followed by the NGG protospacer-adjacent motif (PAM) sequence, where N is any base pair. Combinations of synthetic transcription factors targeted to endogenous human promoters result in synergistic and robust activation of gene expression. Therefore four gRNA target sites followed by the NGG PAM sequence were identified in the promoter of the IL1RN gene within 500 bp of the transcriptional start site (FIG. 4, Table 2). To compare crRNA- and gRNA-based targeting strategies, the four target site sequences were introduced into crRNA and gRNA expression plasmids[17] and co-transfected with the iCas9-VP64 expression plasmid into HEK293T cells. Although substantial induction of IL1RN expression was observed by qRT-PCR in samples treated with the combination of crRNAs, much higher levels were achieved with the combination of gRNAs (FIG. 1C). No changes to gene expression were observed in cells treated with gRNAs and an expression plasmid for iCas9 without VP64, demonstrating the critical role of the activation domain in modulating gene expression (FIG. 1C). Nuclease activity at these target sites was confirmed to have been abrogated in the iCas9-VP64 system by performing the Surveyor assay to detect DNA repair events in samples treated with iCas9-VP64 and wild-type Cas9 (FIG. 5). By transfecting each of the four gRNAs individually or in combination, targeting multiple sites in the promoter with combinations of gRNAs showed robust increases in gene expression (FIG. 1D). High levels of IL1RN expression were observed only when the gRNA combinations were co-transfected with iCas9-VP64 (FIG. 1D), as seen with other classes of engineered transcription factors. Similarly, production of the IL-1 receptor antagonist (IL-1ra) protein, encoded by the IL1RN gene, was only observed in three of the six samples treated with the combination of gRNAs across three different experiments, whereas it was never detected in samples treated with single gRNAs or control plasmid (FIG. 1E). To examine the specificity of gene activation by iCas9-VP64, global gene expression of HEK293T cells treated with the combination of four gRNAs by RNA-seq was assessed (FIG. 1F). Notably, the only genes with significantly increased expression relative to control (false discovery rate$\leq 3 \times 10^{-4}$) were the four isoforms expressed from the IL1RN locus (FIG. 4), indicating a high level of specificity of gene activation.

Figure 6:
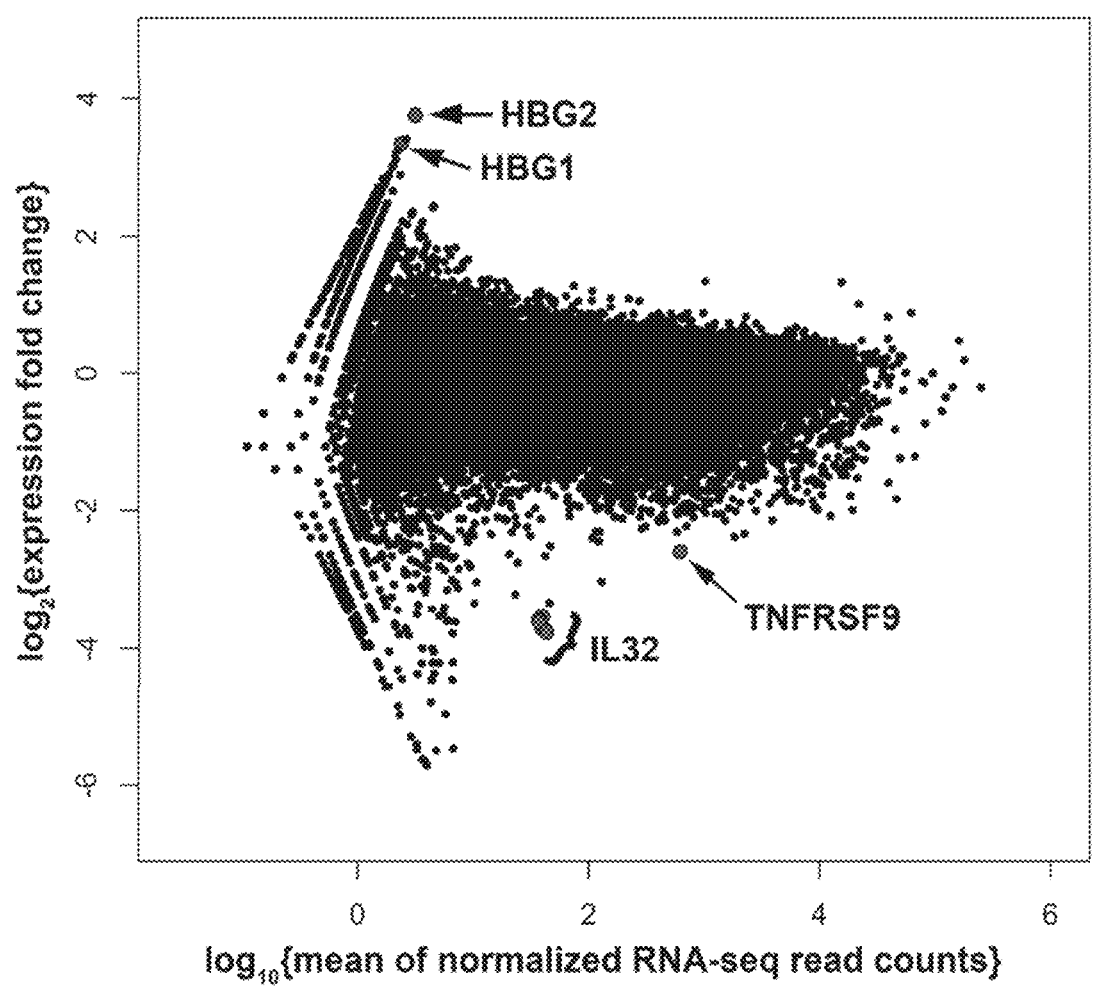
FIG. 6 shows RNA-seq for samples treated with gRNAs targeting HBG1 and HBG2. RNA-seq was performed on samples treated with a control empty expression vector (n=3) or cotransfected with the expression plasmids for iCas9-VP64 and the four gRNAs targeting HBG1 (n=2). Three of these gRNAs also target HBG2. Increases in both HBG1 and HBG2 relative to control were observed but were not statistically significant due to low expression levels. The only statistically significant changes in gene expression between these treatments were decreases in IL32 (false discovery rate=0.0007) and TNFRS9 (false discovery rate=0.002).
Figure 7:
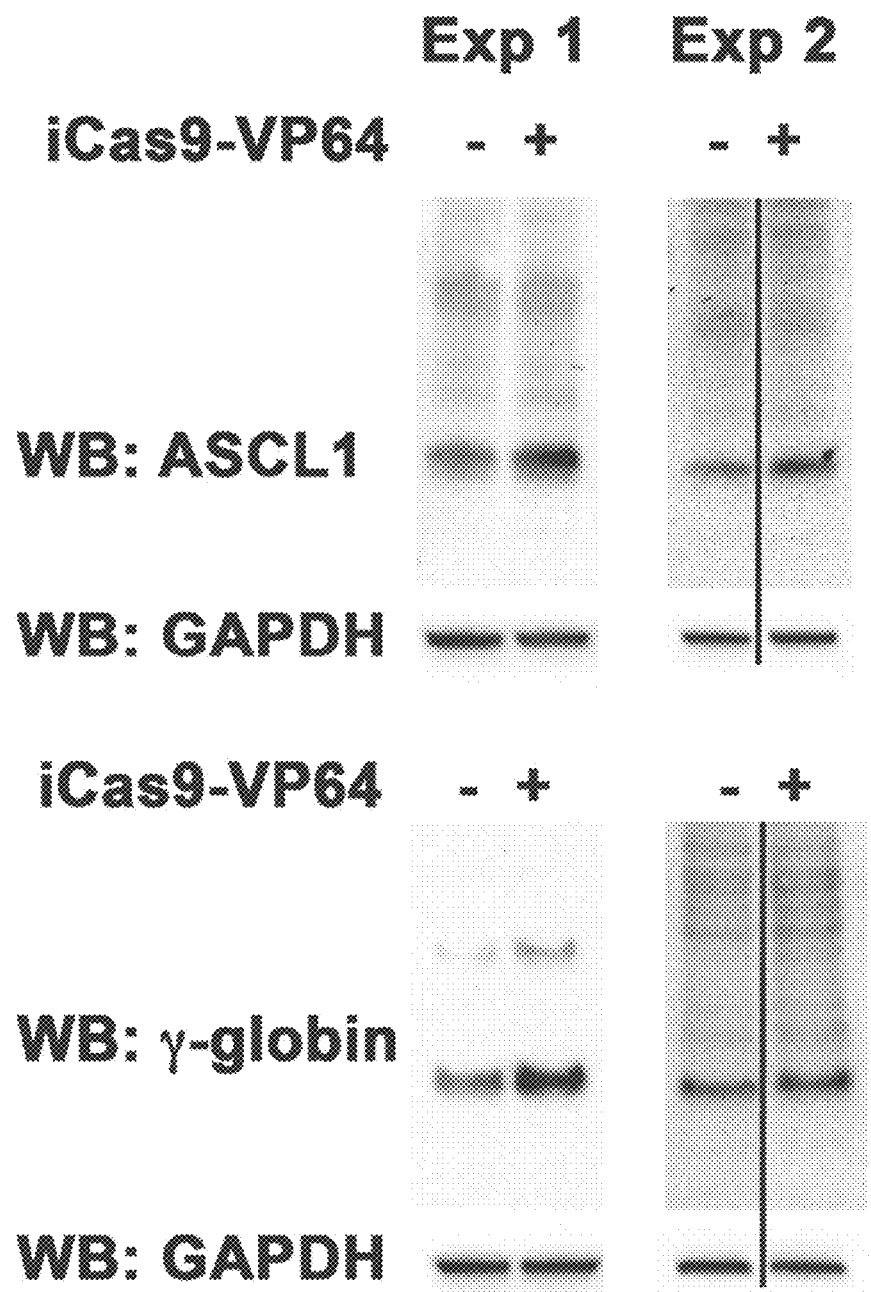
FIG. 7 shows upregulation of Ascl1 and γ-globin by iCas9-VP64. HEK293T cells were transfected with iCas9-VP64 and four gRNAs targeting the ASCU or HBG1 promoter. Levels of corresponding Ascl1 and γ-globin protein production were assessed by western blot. Low levels of these proteins were detectable in HEK293T cells and increases in expression were detectable following iCas9-VP64 treatment in two independent experiments.
Figure 8A:
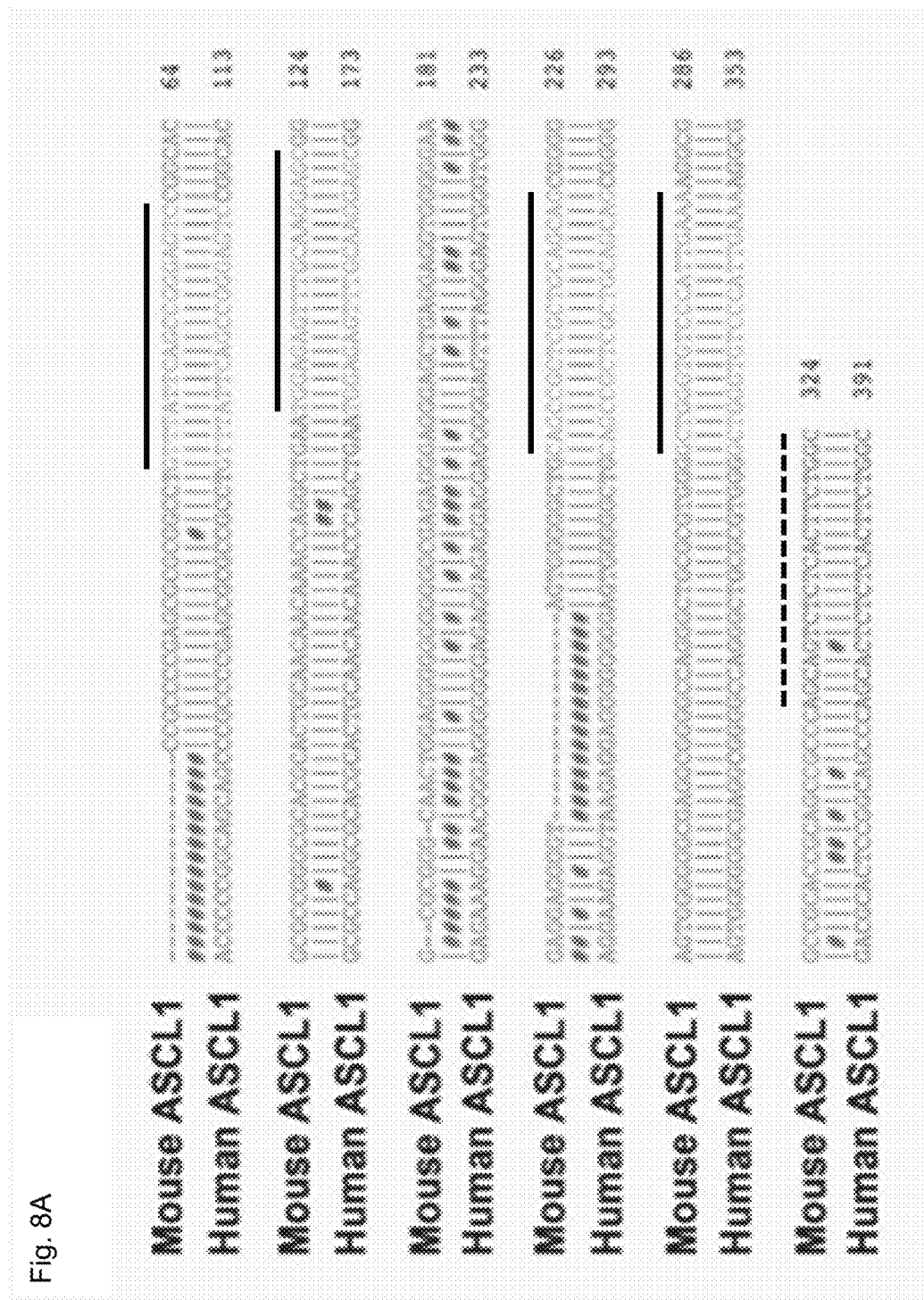
FIGS. 8A-8H show activation of downstream targets of Ascl1 in iCas9-VP64-treated murine embryonic fibroblasts. Mouse embryonic fibroblasts (MEFs) were transfected with a control GFP expression plasmid or the iCas9-VP64 expression plasmid and a combination of four gRNA expression plasmids targeting ASCL1 at a ratio of 50:50 or 75:25.
Figure 8B:
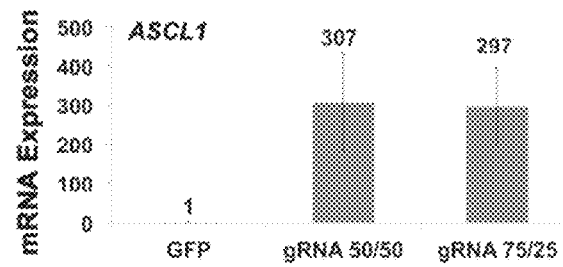
Figure 8C:
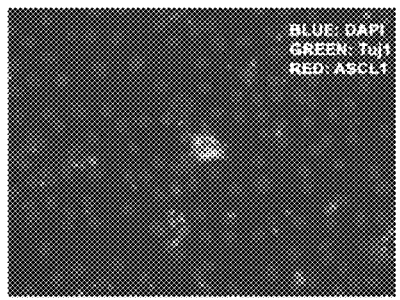
Figure 8D:
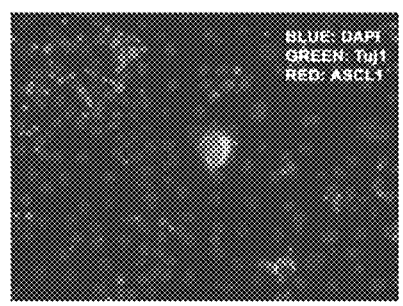
Figure 8E:
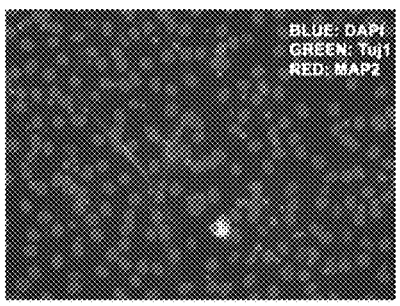
Figure 8F:
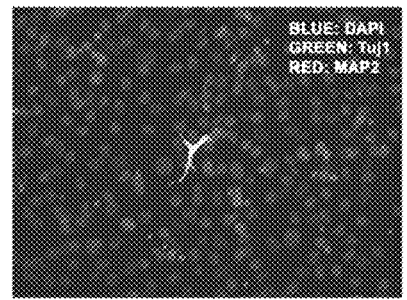
Figure 8G:
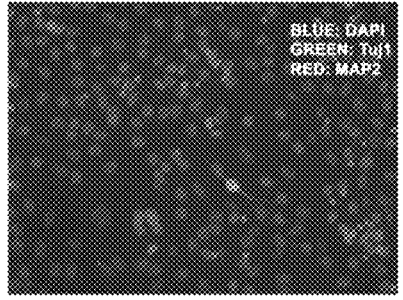
Figure 8H:
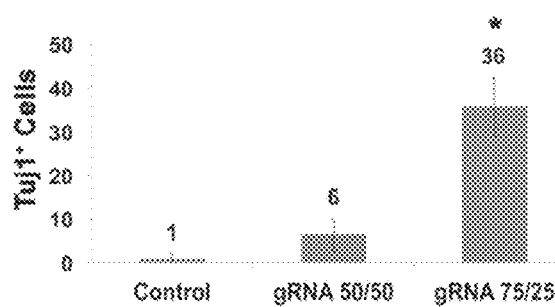

To demonstrate the general applicability of this system, four gRNAs were designed to target each of the promoters of eight other genes relevant to medicine and biotechnology, including ASCL1, NANOG, HBG1/2, MYOD1, VEGFA, TERT, IL1B, and IL1R2 (FIG. 4, Table 2). Forced expression of ASCL1 and MYOD1 leads to transdifferentiation of several cell types into neuronal and myogenic phenotypes, respectively. NANOG is a marker of pluripotency and that is also used in genetic reprogramming strategies. Activation of the homologs HBG1 and HBG2, which encode γ-globin during fetal development, can be used as a therapeutic strategy to compensate for β-globin mutations in sickle cell disease. Up-regulation of VEGFA by synthetic transcription factors has been explored as a strategy to enhance tissue regeneration and wound healing. The forced expression of telomerase, encoded by the TERT gene, can be used to immortalize cell lines. IL1B encodes the IL-1β cytokine that mediates inflammation and autoimmunity. IL-1β signaling can be blocked by expression of IL-1ra or the decoy receptor encoded by IL1R2. Expression of each of these genes was enhanced by co-transfection of expression plasmids for iCas9-VP64 and the four gRNAs into HEK293T cells, as determined by qRT-PCR (FIGS. 2A-2H). In some cases expression of a single gRNA was sufficient to induce gene expression, but in all cases co-transfection of the four gRNAs led to synergistic effects (FIGS. 2A-2D). Notably, chromatin accessibility, as determined by DNase-seq, was not a predictor of successful gene activation (FIG. 4). RNA-seq was performed on cells transfected with iCas9-VP64 and the four gRNAs targeting HBG1, three of which also target HBG2. This revealed specific and reproducible increases in expression of both HBG1 and HBG2, which cannot be distinguished by RNA-seq, although statistical significance was not achieved due to low total expression levels (FIG. 6). Increases in protein expression of Ascl1 and γ-globin following treatment with iCas9-VP64 and the four gRNAs were detected by western blot (FIG. 7), corroborating higher mRNA levels observed by qRT-PCR (FIGS. 2A-2H). Low baseline levels of Ascl1 and γ-globin protein expression were detectable in empty vector controls. As preliminary evidence that the activation of gene targets by iCas9-VP64 can lead to secondary changes in gene networks and cell phenotypes, expression plasmids for iCas9-VP64 and the four gRNAs targeting ASCL1 were co-transfected into murine embryonic fibroblasts (MEFs) (FIGS. 8A-8H). Forced expression of Ascl1 in MEFs has been shown to partially activate the neuronal gene network, including the downstream target Tuj 1. Because the gRNA target sites are conserved in the human and mouse ASCL1 promoters (FIG. 8A), activation of ASCL1 expression was also observed in MEFs treated with plasmids encoding iCas9-VP64 and the four gRNAs (FIG. 8B). Furthermore, cells expressing Ascl1 and the neuronal marker Tuj 1 were readily detected by immunofluorescence staining 12 days after transfection in the iCas9-VP64/gRNA-treated samples (FIGS. 8C-8H). No Tuj1-positive cells were observed in the cells treated with the control plasmid.

Thus far there has not been any comprehensive survey of the specificity of Cas9/CRISPR activity in mammalian cells. Using RNA-seq, targeted gene activation was shown to be exquisitely specific with no detectable off-target gene activation (FIG. 1F, FIG. 6). IL1RN and HBG1/2 were chosen for this specificity analysis as the gene products, IL-1ra and γ-globin, may not generate secondary effects on gene expression in HEK293T cells. Exploiting the synergistic activity of multiple weak transcriptional activators, in contrast to using a single strong activator, may increase specific gene regulation since it is unlikely that multiple adjacent off-target sites would exist at another locus. Interestingly, the IL32 gene was moderately downregulated (false discovery rate <0.03) in both the samples treated with iCas9-VP64 and either the IL1RN- or HBG1/2-targeted gRNAs compared to control samples treated with only an empty expression plasmid (FIG. 1F, FIG. 6). Because both the IL1RN and HBG1/2-targeted samples were similarly affected, it is unlikely that this is the result of off-target iCas9-VP64 activity related to the identity of the target sequences.

Figure 15:
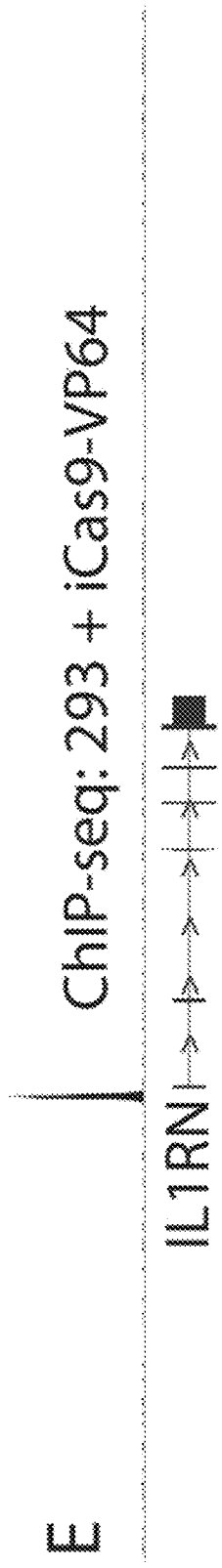
FIG. 15 shows ChIP sequencing data illustrating the specific binding of iCas9-VP64 targeting the IL1RN promoter. HEK 293T cells were transfected with iCas9-VP64 targeting the IL1RN promoter.

To evaluate the specificity with which iCas9-VP64 binds the genome, ChIP sequencing was performed using an anti-HA antibody on cells treated with iCas9-VP64 and four gRNAs targeting the IL1RN promoter. The experiment revealed that iCas9 targets the IL1RN promoter (FIG. 15). Moreover, the experiment revealed an extremely high level of specificity. The iCas9 had only 10 potential off-target binding sites (FDR<5%). To further query the specificity, RNA sequencing experiments were performed with iCas9 EGEMs and found that only IL1RN gene isoforms increased in expression relative to control (FDR≤3×10.4).

Example 3

CRISPRs Targeting the Dystrophin Gene—Methods and Materials

Plasmid constructs. The expression cassettes for the *S. pyogenes* sgRNA and human codon optimized Cas9 (hCas9) nuclease were used, as previously described (Perez-Pinera et al., Nat Methods 10:973-976 (2013)). In order to create a fluorescent reporter system to enrich CRISPR/Cas9-modified cells, a GeneBlock (IDT) was synthesized containing a portion of the 3' end of the Cas9 coding sequence fused to a T2A skipping peptide immediately upstream of a multiple cloning site and subsequently cloned into the hCas9 expression vector. An eGFP reporter gene was then cloned into the T2A vector to allow co-translation of Cas9 and eGFP proteins from the same expression vector (hCas9-T2A-GFP, SEQ ID NO: 116).

Cell culture and transfection. HEK293T cells were obtained from the American Tissue Collection Center (ATCC) through the Duke Cell Culture Facility and were maintained in DMEM supplemented with 10% bovine calf serum and 1% penicillin/streptomycin. Immortalized myoblasts (Mamchaoui, K. et al. *Skelet Muscle* 1, 1-11 (2011)) (one from a wild-type donor, and two Δ48-50 DMD patient derived lines) were maintained in skeletal muscle media (PromoCell) supplemented with 20% bovine calf serum (Sigma), 50 µg/ml fetuin, 10 ng/ml human epidermal growth factor (Sigma), 1 ng/ml human basic fibroblast growth factor (Sigma), 10 µg/ml human insulin (Sigma), 1% GlutaMAX (Invitrogen), and 1% penicillin/streptomycin (Invitrogen). Primary DMD dermal fibroblasts were obtained from the Coriell Cell repository (GM05162A, Δ46-50) and maintained in DMEM supplemented with 10% fetal bovine serum, 1 ng/mL human basic fibroblast growth factor, and 1% penicillin/streptomycin. All cell lines were maintained at 37° C. and 5% $CO_2$.

HEK293T cells were transfected with Lipofectamine 2000 (Invitrogen) with 400 ng of each expression vector according to the manufacturer's protocol in 24 well plates. Immortalized myoblasts and primary fibroblasts were transfected with 5 µg of each expression vector by electroporation using the Gene Pulser XCell (BioRad) with PBS as an electroporation buffer using optimized conditions for each line (FIGS. 1A-1F) (Ousterout et al. Mol Ther 21:1718-1726 (2013)). Transfection efficiencies were measured by delivering an eGFP expression plasmid (pmaxGFP, Clontech) and using flow cytometry. These efficiencies were routinely≥95% for HEK293T and >70% for the primary fibroblasts and immortalized myoblasts. For all experiments, the indicated mass of electroporated plasmid corresponds to the amount used for each CRISPR/Cas9-based system.

Cel-I quantification of endogenous gene modification (Surveyor Assay). CRISPR/Cas9-based system-induced lesions at the endogenous target site were quantified using the Surveyor nuclease assay (Guschin, D. Y. et al. *Meth Mol Biol* 649, 247-256 (2010)), which can detect mutations characteristic of nuclease-mediated NHEJ. After transfection, cells were incubated for 3 or 10 days at 37° C. and genomic DNA was extracted using the DNeasy Blood and Tissue kit (QIAGEN). The target locus was amplified by 35 cycles of PCR with the AccuPrime High Fidelity PCR kit (Invitrogen) using primers specific to each locus (see Table 4), such as 5'-GAGTTTGGCTCAAATTGTTACTCTT-3' (SEQ ID NO: 626) and 5'-GGGAAATGGTCTAGGAGAG-TAAAGT-3' (SEQ ID NO: 627).

TABLE 4

Summary of top 10 off target sites predicted in silico and activity at each site as detected by the Surveyor assay in HEK293T cells transfected with Cas9 and the indicated sgRNA expression cassettes. n.d.: not detected.

| SEQ ID NO. | GuideTarget | Sequence | PAM | Score | Chr | Gene | Intron/Exon | # MMS | % indels |
|---|---|---|---|---|---|---|---|---|---|
| 67 | CR3 | Guide | GCCTACTCAGACTGTTACTC | — | — | — | — | — | — | — |
| 150 | | Target | tCCTACTCAGACTGTTACTC | TGG | — | X | DMD | Exon | 1 | 13.0 |
| 151 | | OT1 | tCCTACTCAcACTGTTACTC | AGG | 7.4 | 1 | STRIP1 | Intron | 2 | 9.3 |
| 152 | | OT2 | aCCTgCTCAcACTGTTACTC | CAG | 2.5 | 2 | ARHGAP25 | Intron | 3 | n.d. |
| 153 | | OT3 | GCaTtCTCAaACTGTTACTC | AGG | 2.4 | 13 | None | None | 3 | n.d. |
| 154 | | OT4 | GgaTtCTCAcACTGTTACTC | GGG | 1.3 | 14 | PGPEP1 | Exon | 4 | n.d. |
| 155 | | OT5 | aCaTACTtAtACTGTTACTC | TAG | 1.3 | 19 | MDGA2 | Intron | 4 | n.d. |
| 156 | | OT6 | tatTcCTaAGACTGTTACTC | AAG | 0.9 | 8 | LPPR1 | Intron | 5 | n.d. |

TABLE 4-continued

Summary of top 10 off target sites predicted in silico and activity at each site as detected by the Surveyor assay in HEK293T cells transfected with Cas9 and the indicated sgRNA expression cassettes.
n.d.: not detected.

| SEQ ID NO. | Guide | Target | Sequence | PAM | Score | Chr | Gene | Intron/Exon | # MMS | % indels |
|---|---|---|---|---|---|---|---|---|---|---|
| 157 | | OT7 | aaggACTaAGACTGTTACTC | GGG | 0.9 | 9 | RNF122 | Intron | 5 | n.d. |
| 158 | | OT8 | GagctCTCAtACTGTTACTC | TAG | 0.8 | 3 | DNMBP | Exon | 5 | n.d. |
| 159 | | OT9 | GCaaAaTgAGACTGTTACTC | CAG | 0.8 | 5 | SLC12A2 | Intron | 4 | n.d. |
| 160 | | OT10 | cCtcAtTCAGACTGTTACTC | AAG | 0.8 | 4 | KCNIP4 | Intron | 4 | n.d. |
| 65 | CR1 | Guide | GATTGGCTTTGATTTCCCTA | — | — | — | — | — | — | — |
| 161 | | Target | cATTGGCTTTGATTTCCCTA | GGG | — | X | DMD | Intron | 1 | 8.3 |
| 162 | | OT1 | aATTGGCATTGATTTCCCTA | GAG | 7.1 | 16 | None | None | 2 | 0.8 |
| 163 | | OT2 | cATTGGCTTTaATTTCCCTA | TAG | 4.8 | 4 | None | None | 2 | n.d. |
| 164 | | OT3 | GATaGGCTgTGATTTCCCTA | GAG | 3.9 | 9 | None | None | 2 | n.d. |
| 165 | | OT4 | GAaTaGcCTTGATTTCCCTA | AAG | 2.4 | 1 | None | None | 3 | n.d. |
| 166 | | OT5 | aATTtGCTTTGATTTCCCTg | AGG | 1.5 | 1 | TIMM17A | Intron | 3 | n.d. |
| 167 | | OT6 | GATgtGCTTTGATTTCCCTt | GGG | 1.4 | 17 | MYO1D | Intron | 3 | n.d. |
| 168 | | OT7 | aATTGGtTTTaATTTCCCTA | AAG | 1.1 | 8 | PIK1A | Intron | 3 | n.d. |
| 169 | | OT8 | aATTGGgTTTGATTTCCCTt | TGG | 1.1 | 11 | MS4A1 | Intron | 3 | n.d. |
| 170 | | OT9 | GATgGGtTTTtATTTCCCTA | GAG | 1.0 | 11 | None | None | 3 | n.d. |
| 171 | | OT10 | GAaTGGtTTTGATTTCCCTg | GAG | 1.0 | 11 | None | None | 3 | n.d. |
| 69 | CR5 | Guide | GCAGTTGCCTAAGAACTGGT | — | — | — | — | — | — | — |
| 172 | | Target | aCAGTTGCCTAAGAACTGGT | GGG | — | X | DMD | Intron | 1 | 14.0 |
| 173 | | OT1 | cCAGTTGtCTAAGAACTGGg | GAG | 1.5 | 5 | NRG1 | Intron | 3 | n.d. |
| 174 | | OT2 | GCAGTTGCCTgtGAACTGGT | AGG | 1.4 | X | None | None | 2 | n.d. |
| 175 | | OT3 | GCAGaTGCagAAGAACTGGT | GAG | 1.4 | 19 | SMIM7 | Intron | 3 | n.d. |
| 176 | | OT4 | GCAGTTcCagAAGAACTGGT | GAG | 0.9 | 11 | GLB1L2 | Intron | 3 | n.d. |
| 177 | | OT5 | caAcTTGCCTAtGAACTGGT | AGG | 0.7 | 8 | ASAP1 | Intron | 4 | n.d. |
| 178 | | OT6 | aCAccTGCCTAAGAACTGGa | GGG | 0.7 | 11 | None | None | 4 | n.d. |
| 179 | | OT7 | tCAGgTGgCTAAGAACTGGg | TGG | 0.7 | 14 | NIN | Intron | 4 | n.d. |
| 180 | | OT8 | GaAGTTGgCcAAGAACTGGa | GAG | 0.6 | 7 | None | None | 4 | n.d. |
| 181 | | OT9 | GCtGcTGCCcAAGAACTGGc | AGG | 0.6 | 11 | AMOTL1 | Intron | 4 | n.d. |
| 182 | | OT10 | tCAGcTGgCTAAGAACgGGT | AAG | 0.6 | 7 | ACTR3C | Intron | 4 | n.d. |
| 70 | CR6 | Guide | GGGGCTCCACCCTCACGAGT | — | — | — | — | — | — | — |
| 183 | | Target | aGGGCTCCACCCTCACGAGT | GGG | — | X | DMD | Intron | 1 | 19.9 |
| 184 | | OT1 | GcaGCTCagCCCTCACGAGT | CAG | 0.8 | 3 | None | None | 4 | n.d. |
| 185 | | OT2 | GGGGCTtCAgCaTCACGAGT | GAG | 0.8 | 8 | None | None | 3 | n.d. |
| 186 | | OT3 | GGGGCTCtcCCCTCACtAGT | GAG | 0.6 | 8 | None | None | 3 | n.d. |
| 187 | | OT4 | GGGGaTCCACCtTCACcAGT | CAG | 0.6 | 2 | None | None | 3 | n.d. |
| 188 | | OT5 | aGGGCTggACCCTCACaAGT | AAG | 0.4 | 16 | AXIN1 | Intron | 4 | n.d. |
| 189 | | OT6 | tGGtCTCCtCCCcCACGAGT | GGG | 0.4 | 2 | None | None | 4 | n.d. |

TABLE 4-continued

Summary of top 10 off target sites predicted in silico and activity
at each site as detected by the Surveyor assay in HEK293T cells
transfected with Cas9 and the indicated sgRNA expression cassettes.
n.d.: not detected.

| SEQ ID NO. | GuideTarget | Sequence | PAM | Score | Chr | Gene | Intron/ Exon | # MMS | % indels |
|---|---|---|---|---|---|---|---|---|---|
| 190 | OT7 | aGGGCTCCcaCCcCACGAGT | GAG | 0.3 | 5 | None | None | 4 | n.d. |
| 191 | OT8 | GaGGCTCCAtaCTCACcAGT | GAG | 0.3 | 11 | None | None | 4 | n.d. |
| 192 | OT9 | GGaGCTgCcCCtTCACGAGT | GGG | 0.3 | 3 | None | None | 4 | n.d. |
| 193 | OT10 | atGaCTCCACCCTCAaGAGT | AAG | 0.3 | 8 | AGPAT5 | None | 4 | n.d. |
| 100 | CR36 Guide | GCCTTCTTTATCCCCTATCG | — | — | — | — | — | — | — |
| 194 | Target | GCCTTCTTTATCCCCTATCG | AGG | — | X | DMD | Intron | 0 | 20.6 |
| 195 | OT1 | GtCTgCTgTgTCCCCTATCG | GGG | 1.3 | 21 | None | None | 4 | n.d. |
| 196 | OT2 | cCCTTCTcTATCCCCTgTCG | TGG | 1.3 | 8 | None | None | 3 | n.d. |
| 197 | OT3 | GCCTTCTTTATCCCCTcTCt | TGG | 0.9 | 10 | None | None | 2 | 0.5 |
| 198 | OT4 | GCgcTCTTTtTCCCCTATCt | TAG | 0.6 | 16 | None | None | 4 | n.d. |
| 199 | OT5 | GCCcTCTgTcTCCCCTgTCG | CAG | 0.5 | 1 | NFASC | None | 4 | n.d. |
| 200 | OT6 | tCCATCTtTgTCCCCTATtG | AGG | 0.5 | 10 | None | None | 4 | n.d. |
| 201 | OT7 | aCCtTCTCTcTCCCCTATaG | AGG | 0.5 | 5 | LOC100996485 | Intron | 4 | n.d. |
| 202 | OT8 | GttTTCTTTtTCCCCTATgG | GAG | 0.5 | 3 | None | None | 4 | n.d. |
| 203 | OT9 | tgCTTCTTaATCCCCTATCa | AAG | 0.4 | 7 | None | None | 4 | n.d. |
| 204 | OT10 | aCCTTCTTacTCCCCTATCc | GGG | 0.4 | 10 | ADARB2 | None | 4 | n.d. |

The resulting PCR products were randomly melted and reannealed in a thermal cycler with the program: 95° C. for 240 s, followed by 85° C. for 60 s, 75° C. for 60 s, 65° C. for 60 s, 55° C. for 60 s, 45° C. for 60 s, 35° C. for 60 s, and 25° C. for 60 s with a −0.3° C./s rate between steps. Following reannealing, 8 µL of PCR product was mixed with 1 µL of Surveyor Nuclease S and 1 µL of Enhancer S (Transgenomic) and incubated at 42° C. for 1 hr. After incubation, 6 µL of digestion product was loaded onto a 10% TBE polyacrylamide gel and run at 200V for 30 min. The gels were stained with ethidium bromide and quantified using ImageLab (Bio-Rad) by densitometry as previously described (Guschin, et al. Meth Mol Biol 649, 247-256 (2010)).

Fluorescence-activated cell sorting of myoblasts. DMD myoblasts were electroporated with 5 micrograms each of hCas9-T2A-GFP and sgRNA expression vectors and incubated at 37° C. and 5% $CO_2$. Three days after electroporation, cells were trypsinized and collected for FACS sorting using a FACSvantage II sorting machine. GFP-positive cells were collected and grown for analysis.

PCR-based assay to detect genomic deletions. The exon 51 or exon 45-55 loci were amplified from genomic DNA by PCR (Invitrogen AccuPrime High Fidelity PCR kit) using primers flanking each locus. The flanking primers were CelI-CR1/2-F and CelI-CRS-R for exon 51 or CelI-CR6-F and CelI-CR36-R for exon 45-55 analysis (Table 4). PCR products were separated on TAE-agarose gels and stained with ethidium bromide for analysis.

PCR-based detection of translocations. Loci with predicted possible translocations were amplified by a two-step nested PCR (Invitrogen AccuPrime High Fidelity PCR kit for each step) of genomic DNA from cells transfected with Cas9 alone (control) or Cas9 with sgRNA. In the first step, translocations that may occur at each on-target and off-target sgRNA target site were amplified by 35 cycles of PCR using combinations of Surveyor primers for each locus that were modified to include restriction sites to facilitate cloning and sequencing analysis (Table 4). One microliter of each PCR reaction was subjected to a second round of amplification by 35 rounds of PCR using nested primer sets custom designed for each individual predicted translocation (Table 4). Each second nested PCR primer binds within the same approximate region within the primary amplicon; however, each pair was optimized using Primer3 online bioinformatics software to ensure specific detection of each translocation. PCR amplicons corresponding to the expected length of predicted translocations and only present in cells treated with sgRNA were purified (QIAGEN Gel Extraction kit) and analyzed by Sanger sequencing.

mRNA analysis. Immortalized myoblasts were differentiated into myofibers by replacing the growth medium with DMEM supplemented with 1% insulin-transferrin-selenium (Invitrogen #51500056) and 1% penicillin/streptomycin (Invitrogen #15140) for 5 days before the cells were trypsinized and collected. Total RNA was isolated from these cells using the RNeasy Plus Mini Kit (QIAGEN) according to the manufacturer's instructions. RNA was reverse transcribed to cDNA using the VILO cDNA synthesis kit (Life Technologies #11754) and 1.5 micrograms of RNA for 2 hrs at 42° C. according to the manufacturer's instructions. The target loci were amplified by 35 cycles of PCR with the AccuPrime High Fidelity PCR kit (Invitrogen) using primers annealing to exons 44 and 52 to detect exon 51 deletion by CR1/5 or CR2/5 or primers annealing to exons 44 and 60 to detect exon 45-55 deletion by CR6/36 (Table 4). PCR products were run on TAE-agarose gels and stained with ethidium bromide for analysis. The resolved PCR bands were cloned and analyzed by Sanger sequencing to verify the expected exon junctions. Table 5 lists the sequences of primers used in Example 4.

TABLE 5

| SEQ ID NO. | Primer name | Primer sequence | Notes |
| --- | --- | --- | --- |
| 205 | CelI-CR1/2-F | GAGAGGTTATGTGGCTTTACCA | Forward Surveyor primer for CR1/2 |
| 206 | CelI-CR1-R | AAAAATGCTTCCCACTTTGC | Reverse Surveyor primer for CR1 |
| 207 | CelI-CR2-R | CTCATTCTCATGCCTGGACA | Reverse Surveyor primer for CR2 |
| 208 | CelI-CR3-F | GAGTTTGGCTCAAATTGTTACTCTT | Forward Surveyor primer for CR3 |
| 209 | CelI-CR3-R | GGGAAATGGTCTAGGAGAGTAAAGT | Reverse Surveyor primer for CR3 |
| 210 | CelI-CR4/31-F | GTTTGGCTCAAATTGTTACTCTTCA | Forward Surveyor primer for CR4 or CR31 |
| 211 | CelI-CR4/31-R | GTGAGAGTAATGTGTTTGCTGAGAG | Reverse Surveyor primer for CR4 or CR31 |
| 212 | CelI-CR5-F | CGGGCTTGGACAGAACTTAC | Forward Surveyor primer for CR5 |
| 213 | CelI-CR5-R | CTGCGTAGTGCCAAAACAAA | Reverse Surveyor primer for CR5 |
| 214 | CelI-CR6-F | TAATTTCATTGAAGAGTGGCTGAA | Forward Surveyor primer for CR6 |
| 215 | CelI-CR6-R | AAGCCCTGTGTGGTAGTAGTCAGT | Reverse Surveyor primer for CR6 |
| 216 | CelI-CR7-F | TGAGTCATGTTGGATAACCAGTCT | Forward Surveyor primer for CR7 |
| 217 | CelI-CR7-R | GAAGGTCAGGAACATACAATTCAA | Reverse Surveyor primer for CR7 |
| 218 | CelI-CR10/11-F | GATATGGGCATGTCAGTTTCATAG | Forward Surveyor primer for CR10 or CR11 |
| 219 | CelI-CR10/11-R | TGCTGTTGATTAATGGTTGATAGG | Reverse Surveyor primer for CR10 or CR11 |
| 220 | CelI-CR12/13-F | TTTTAAATTGCCATGTTTGTGTC | Forward Surveyor primer for CR12 or CR13 |
| 221 | CelI-CR12/13-R | ATGAATAACCTAATGGGCAGAAAA | Reverse Surveyor primer for CR12 or CR13 |
| 222 | CelI-CR14/15-F | TCAAGTCGCTTCATTTTGATAGAC | Forward Surveyor primer for CR14 or CR15 |
| 223 | CelI-CR14/15-R | CACAACAAAACATATAGCCAAAGC | Reverse Surveyor primer for CR14 or CR15 |
| 224 | CelI-CR16/17-F | TGCTGCTAAAATAACACAAATCAGT | Forward Surveyor primer for CR16 or CR17 |
| 225 | CelI-CR16/17-R | CTGTGCCTATTGTGGTTATCCTG | Reverse Surveyor primer for CR16 or CR17 |
| 226 | CelI-CR18/19-F | ATTGATCTGCAATACATGTGGAGT | Forward Surveyor primer for CR18 or CR19 |
| 227 | CelI-CR18/19-R | TTTGCCTCTGCTATTACAGTATGG | Reverse Surveyor primer for CR18 or CR19 |
| 228 | CelI-CR20/21-F | TGTAGGGTGGTTGGCTAAAATAAT | Forward Surveyor primer for CR20 or CR21 |
| 229 | CelI-CR20/21-R | TTTTTGCACAGTCAATAACACAAA | Reverse Surveyor primer for CR20 or CR21 |
| 230 | CelI-CR22/23-F | GGCTGGTCTCACAATTGTACTTTA | Forward Surveyor primer for CR22 or CR23 |

TABLE 5-continued

| SEQ ID NO. | Primer name | Primer sequence | Notes |
|---|---|---|---|
| 231 | CelI-CR22/23-R | CATTATGGACTGAAAATCTCAGCA | Reverse Surveyor primer for CR22 or CR23 |
| 232 | CelI-CR24/25-F | ATCATCCTAGCCATAACACAATGA | Forward Surveyor primer for CR24 or CR25 |
| 233 | CelI-CR24/25-R | TTCAGCTTTAACGTGATTTTCTGT | Reverse Surveyor primer for CR24 or CR25 |
| 234 | CelI-CR26/27-F | GGATTCAGAAGCTGTTTACGAAGT | Forward Surveyor primer for CR26 or CR27 |
| 235 | CelI-CR26/27-R | TTTAGCTGGATTGGAAAAACAAAT | Reverse Surveyor primer for CR26 or CR27 |
| 236 | CelI-CR28/29-F | AACTCACCCCATTGTTGGTATATT | Forward Surveyor primer for CR28 or CR29 |
| 237 | CelI-CR28/29-R | CCTTGTCCAAATACCGAAATACAT | Reverse Surveyor primer for CR28 or CR29 |
| 238 | CelI-CR33-F | CACATAATTCATGAACTTGGCTTC | Forward Surveyor primer for CR33 |
| 239 | CelI-CR33-R | TAGTAGCTGGGGAGGAAGATACAG | Reverse Surveyor primer for CR33 |
| 240 | CelI-CR34-F | TTTTTGTTTTAATTGCGACTGTGT | Forward Surveyor primer for CR34 |
| 241 | CelI-CR34-R | AGAAAAGGGGTTTTCTTTTGACTT | Reverse Surveyor primer for CR34 |
| 242 | CelI-CR35-F | CATTGTGACTGGATGAGAAGAAAC | Forward Surveyor primer for CR35 |
| 243 | CelI-CR35-R | AACGGCTGTTATTAAAGTCCTCAG | Reverse Surveyor primer for CR35 |
| 244 | CelI-CR36-F | CAAGTCAGAAGTCACTTGCTTTGT | Forward Surveyor primer for CR36 |
| 245 | CelI-CR36-R | TTTTATGTGCAGGAATCAGTCTGT | Reverse Surveyor primer for CR36 |
| 246 | Dys-E44-F | TGGCGGCGTTTTCATTAT | Forward RT-PCR primer binding in exon 44 |
| 247 | Dys-E52-R | TTCGATCCGTAATGATTGTTCTAGCC | Reverse RT-PCR primer binding in exon 52 |
| 248 | Dys-E60-R | GGTCTTCCAGAGTGCTGAGG | Reverse RT-PCR primer binding in exon 60 |
| 249 | CR3-CelI-OT1-F | TGTGTGCTTCTGTACACATCATCT | Forward Surveyor primer for CR3 off-target 1 |
| 250 | CR3-CelI-OT1-R | AGATTTCAACCCTCAAAAACTGAG | Reverse Surveyor primer for CR3 off-target 1 |
| 251 | CR3-CelI-OT2-F | TAAACTCTTTCTTTTCCGCAATTC | Forward Surveyor primer for CR3 off-target 2 |
| 252 | CR3-CelI-OT2-R | CAAGGTGACCTGCTACCTAAAAAT | Reverse Surveyor primer for CR3 off-target 2 |
| 253 | CR3-CelI-OT3-F | TATGACCAAGGCTATGTGTTCACT | Forward Surveyor primer for CR3 off-target 3 |
| 254 | CR3-CelI-OT3-R | ACAGCCTCTCTCCAGTAACATTCT | Reverse Surveyor primer for CR3 off-target 3 |
| 255 | CR3-CelI-OT4-F | TATTCTTGCAGTGGTTTCACATTT | Forward Surveyor primer for CR3 off-target 4 |
| 256 | CR3-CelI-OT4-R | ATATTTTAAGCCAAGACCCAACAA | Reverse Surveyor primer for CR3 off-target 4 |
| 257 | CR3-CelI-OT5-F | CTTTCAACTGTCTGTCTGATTGCT | Forward Surveyor primer for CR3 off-target 5 |
| 258 | CR3-CelI-OT5-R | AACAGCCTCTCTTCATTGTTCTCT | Reverse Surveyor primer for CR3 off-target 5 |

TABLE 5-continued

| SEQ ID NO. | Primer name | Primer sequence | Notes |
|---|---|---|---|
| 259 | CR3-CelI-OT6-F | CTCTGGAACTTGTCTCTGTCTTGA | Forward Surveyor primer for CR3 off-target 6 |
| 260 | CR3-CelI-OT6-R | CTTTCCTGCGTTCTCATGTTACTA | Reverse Surveyor primer for CR3 off-target 6 |
| 261 | CR3-CelI-OT7-F | CCTTATATCCGTATCGCTCACTCT | Forward Surveyor primer for CR3 off-target 7 |
| 262 | CR3-CelI-OT7-R | CATATCTGTCTAACTTCCGCACAC | Reverse Surveyor primer for CR3 off-target 7 |
| 263 | CR3-CelI-OT8-F | ACAGGTGTTATGTTGTCTGCATCT | Forward Surveyor primer for CR3 off-target 8 |
| 264 | CR3-CelI-OT8-R | ACTCCATTCCCAGATTAGTTATGC | Reverse Surveyor primer for CR3 off-target 8 |
| 265 | CR3-CelI-OT9-F | CTGTTTTCTTTGTGAGAGTGGAGA | Forward Surveyor primer for CR3 off-target 9 |
| 266 | CR3-CelI-OT9-R | TGTAAGGTGGTCAAACTTGCTCTA | Reverse Surveyor primer for CR3 toff-arget 9 |
| 267 | CR3-CelI-OT10-F | TTTTTTCCTAGTACCCACAGATTTTT | Forward Surveyor primer for CR3 off-target 10 |
| 268 | CR3-CelI-OT10-R | TCCCTGATTCTCTCATTTGTGTTA | Reverse Surveyor primer for CR3 off-target 10 |
| 269 | CR1-CelI-OT1-F | TTGGGAACATCAGAGAAAGTATGA | Forward Surveyor primer for CR1 off-target 1 |
| 270 | CR1-CelI-OT1-R | ACAAATTACAGTCTCCTGGGAAAG | Reverse Surveyor primer for CR1 off-target 1 |
| 271 | CR1-CelI-OT2-F | AGTAGCTTACCTTGGCAGAGAAAA | Forward Surveyor primer for CR1 off-target 2 |
| 272 | CR1-CelI-OT2-R | TGACATACTGTTACCCTTTGCAGT | Reverse Surveyor primer for CR1 off-target 2 |
| 273 | CR1-CelI-OT3-F | GAAAGGCTCAGTGAATGTTTGTT | Forward Surveyor primer for CR1 off-target 3 |
| 274 | CR1-CelI-OT3-R | CACTGCATCATCTCATTAAATCAA | Reverse Surveyor primer for CR1 off-target 3 |
| 275 | CR1-CelI-OT4-F | CCCATATATTCATGATTACCCACA | Forward Surveyor primer for CR1 off-target 4 |
| 276 | CR1-CelI-OT4-R | TATCAGAACGAGCACTAAAAGCAC | Reverse Surveyor primer for CR1 off-target 4 |
| 277 | CR1-CelI-OT5-F | TTGGGAGGCTGAGGTACAAG | Forward Surveyor primer for CR1 off-target 5 |
| 278 | CR1-CelI-OT5-R | GAATGAAAAACAAACAGAAGGTGA | Reverse Surveyor primer for CR1 off-target 5 |
| 279 | CR1-CelI-OT6-F | CTCCTCATCTGTACCCTTCAATCT | Forward Surveyor primer for CR1 off-target 6 |
| 280 | CR1-CelI-OT6-R | AGAGTGGCATCTAGTGTCAGTGAG | Reverse Surveyor primer for CR1 off-target 6 |
| 281 | CR1-CelI-OT7-F | TACCAAAAGCTTCTCCTGTTTACC | Forward Surveyor primer for CR1 off-target 7 |
| 282 | CR1-CelI-OT7-R | GTAAGTTGGATGGCCTATTCTTTG | Reverse Surveyor primer for CR1 off-target 7 |
| 283 | CR1-CelI-OT8-F | GAAGGAAATGCAAGGATACAAGAT | Forward Surveyor primer for CR1 off-target 8 |

TABLE 5-continued

| SEQ ID NO. | Primer name | Primer sequence | Notes |
|---|---|---|---|
| 284 | CR1-CelI-OT8-R | TGATTGAAAGAATCATTCCAGAAA | Reverse Surveyor primer for CR1 off-target 8 |
| 285 | CR1-CelI-OT9-F | TCAGAAGGAAAATTGAAATTGGTT | Forward Surveyor primer for CR1 off-target 9 |
| 286 | CR1-CelI-OT9-R | CAGATGTGTTCTTCATCATTCCTC | Reverse Surveyor primer for CR1 off-target 9 |
| 287 | CR1-CelI-OT10-F | TTCTCTTTAGGGAAAGCTCTCAAA | Forward Surveyor primer for CR1 off-target 10 |
| 288 | CR1-CelI-OT10-R | GGGTATAGATCATATGGAGGGAAG | Reverse Surveyor primer for CR1 off-target 10 |
| 289 | CR5-CelI-OT1-F | AGATGATCTGCCCACCTCAG | Forward Surveyor primer for CR5 off-target 1 |
| 290 | CR5-CelI-OT1-R | CTTTCTTCCTCATTTAGTGGCAAT | Reverse Surveyor primer for CR5 off-target 1 |
| 291 | CR5-CelI-OT2-F | ATGAATTGCAGATTGATGGTACTG | Forward Surveyor primer for CR5 off-target 2 |
| 292 | CR5-CelI-OT2-R | TCTCACCAAGAACCAAATTGTCTA | Reverse Surveyor primer for CR5 off-target 2 |
| 293 | CR5-CelI-OT3-F | GTAGGATACCTTGGCAACAGTCTT | Forward Surveyor primer for CR5 off-target 3 |
| 294 | CR5-CelI-OT3-R | TTAACGAATTGTGAGATTTGCTGT | Reverse Surveyor primer for CR5 off-target 3 |
| 295 | CR5-CelI-OT4-F | TCAGAAAGTCAAGTAGCACACACA | Forward Surveyor primer for CR5 off-target 4 |
| 296 | CR5-CelI-OT4-R | AGAAGCACACACTCAGGTAAAGC | Reverse Surveyor primer for CR5 off-target 4 |
| 297 | CR5-CelI-OT5-F | TCTTTGGGGAATAATGACTAAAA | Forward Surveyor primer for CR5 off-target 5 |
| 298 | CR5-CelI-OT5-R | TTTGGCATTTATGGGAATAAAACT | Reverse Surveyor primer for CR5 off-target 5 |
| 299 | CR5-CelI-OT6-F | ACTAATTCTGGTCAAGCCCATCA | Forward Surveyor primer for CR5 off-target 6 |
| 300 | CR5-CelI-OT6-R | TTAAGACATCGGATGAACAGAAAG | Reverse Surveyor primer for CR5 off-target 6 |
| 301 | CR5-CelI-OT7-F | AGAAGCTTTCTGACATGATCTGC | Forward Surveyor primer for CR5 off-target 7 |
| 302 | CR5-CelI-OT7-R | TCAATTGCATTAGGACTTAGACCA | Reverse Surveyor primer for CR5 off-target 7 |
| 303 | CR5-CelI-OT8-F | GTTAAATTACCTGTGAAGCCCTTG | Forward Surveyor primer for CR5 off-target 8 |
| 304 | CR5-CelI-OT8-R | CGGAAAACAGATCCACTTTATGAT | Reverse Surveyor primer for CR5 off-target 8 |
| 305 | CR5-CelI-OT9-F | AAATCCACTGGAAACATCTTGAGT | Forward Surveyor primer for CR5 off-target 9 |
| 306 | CR5-CelI-OT9-R | AGTCTCTTCAGAATCATGCCCTAT | Reverse Surveyor primer for CR5 off-target 9 |
| 307 | CR5-CelI-OT10-F | GCTTGGTGGCACATACCTGTAG | Forward Surveyor primer for CR5 off-target 10 |
| 308 | CR5-CelI-OT10-R | GGTAGGTAGATTTGCTTGCTTGTT | Reverse Surveyor primer for CR5 off-target 10 |

TABLE 5-continued

| SEQ ID NO. | Primer name | Primer sequence | Notes |
|---|---|---|---|
| 309 | CR6-CelI-OT1-F | AGCTCTCAGCAGAGTAGGGATTTA | Forward Surveyor primer for CR6 off-target 1 |
| 310 | CR6-CelI-OT1-R | GTGAGTCTACTGCACCCCATC | Reverse Surveyor primer for CR6 off-target 1 |
| 311 | CR6-CelI-OT2-F | TGACACTGTGAAGTCAATTCTGTC | Forward Surveyor primer for CR6 toff-arget 2 |
| 312 | CR6-CelI-OT2-R | TCAAGAACTTGACAATGAGCAAAT | Reverse Surveyor primer for CR6 off-target 2 |
| 313 | CR6-CelI-OT3-F | TATCCGATCCACTGTTGTGTGT | Forward Surveyor primer for CR6 off-target 3 |
| 314 | CR6-CelI-OT3-R | CAGGAGACCCAAAACCACTCTAC | Reverse Surveyor primer for CR6 off-target 3 |
| 315 | CR6-CelI-OT4-F | TTGTTCTACAAATAGGGCTTCCTT | Forward Surveyor primer for CR6 off-target 4 |
| 316 | CR6-CelI-OT4-R | TGTTAAGTTTGGGCTTATGTTCCT | Reverse Surveyor primer for CR6 off-target 4 |
| 317 | CR6-CelI-OT5-F | CACAAGTCTCACTGCACAAACAT | Forward Surveyor primer for CR6 off-target 5 |
| 318 | CR6-CelI-OT5-R | TGACCCATGATTATCTCTCTTTGA | Reverse Surveyor primer for CR6 off-target 5 |
| 319 | CR6-CelI-OT6-F | TTCAGCTTCTGATTGGTTTTAATG | Forward Surveyor primer for CR6 off-target 6 |
| 320 | CR6-CelI-OT6-R | CCAATTCCTTAATTTTCCCTACAG | Reverse Surveyor primer for CR6 off-target 6 |
| 321 | CR6-CelI-OT7-F | ATCTCAGACCAGGAGGGAGAC | Forward Surveyor primer for CR6 off-target 7 |
| 322 | CR6-CelI-OT7-R | CCTCAGGGTCAGTACATTTTCAG | Reverse Surveyor primer for CR6 off-target 7 |
| 323 | CR6-CelI-OT8-F | TTCTTAGGACATTGCTCCACATAC | Forward Surveyor primer for CR6 off-target 8 |
| 324 | CR6-CelI-OT8-R | GCAAACATAATGCAACTCGTAATC | Reverse Surveyor primer for CR6 off-target 8 |
| 325 | CR6-CelI-OT9-F | GCAAGGGAGTCTGTGTCTTTG | Forward Surveyor primer for CR6 off-target 9 |
| 326 | CR6-CelI-OT9-R | TCATTTAAGTGGCTGTTCTGTGTT | Reverse Surveyor primer for CR6 off-target 9 |
| 327 | CR6-CelI-OT10-F | ACAAAACAGAGAGAAAAGGCAGAG | Forward Surveyor primer for CR6 off-target 10 |
| 328 | CR6-CelI-OT10-R | GTTTTGATTTCTGGTGCCTACAG | Reverse Surveyor primer for CR6 off-target 10 |
| 329 | CR36-CelI-OT1-F | ACTGAAGCTGAAGCCCAGTC | Forward Surveyor primer for CR36 off-target 1 |
| 330 | CR36-CelI-OT1-R | ACATGAGCTCTCAGGTTTCTGAC | Reverse Surveyor primer for CR36 off-target 1 |
| 331 | CR36-CelI-OT2-F | TCAAACTTAGATGGTTCCCTATGTT | Forward Surveyor primer for CR36 off-target 2 |
| 332 | CR36-CelI-OT2-R | GTACCCTGAAAATGTAGGGTGACT | Reverse Surveyor primer for CR36 off-target 2 |
| 333 | CR36-CelI-OT3-F | CACTTCCCAAGTGAGGCAAT | Forward Surveyor primer for CR36 off-target 3 |

TABLE 5-continued

| SEQ ID NO. | Primer name | Primer sequence | Notes |
|---|---|---|---|
| 334 | CR36-CeII-OT3-R | CTATACTTGGGGCTGACTTGCTAC | Reverse Surveyor primer for CR36 off-target 3 |
| 335 | CR36-CeII-OT4-F | TCGTATAGGTTACTTTGGCTCACA | Forward Surveyor primer for CR36 off-target 4 |
| 336 | CR36-CeII-OT4-R | AGGGATCTTTACTCCTCAGTGTGT | Reverse Surveyor primer for CR36 off-target 4 |
| 337 | CR36-CeII-OT5-F | TGTAGAAGTTGGAATATCCTGCTG | Forward Surveyor primer for CR36 off-target 5 |
| 338 | CR36-CeII-OT5-R | GTCAACAATTTGATCTCAGGCTTC | Reverse Surveyor primer for CR36 off-target 5 |
| 339 | CR36-CeII-OT6-F | CTCAGTACTAAAGATGGACGCTTG | Forward Surveyor primer for CR36 off-target 6 |
| 340 | CR36-CeII-OT6-R | AATCATTTCAGTCTTCCCAACAAT | Reverse Surveyor primer for CR36 off-target 6 |
| 341 | CR36-CeII-OT7-F | GGGAATCACAGTAGATGTTTGTCA | Forward Surveyor primer for CR36 off-target 7 |
| 342 | CR36-CeII-OT7-R | AGACCAGGAGGTAAGAACATTTTG | Reverse Surveyor primer for CR36 off-target 7 |
| 343 | CR36-CeII-OT8-F | CCACATAGAAAGAGACTTGCAGAA | Forward Surveyor primer for CR36 off-target 8 |
| 344 | CR36-CeII-OT8-R | AGAGATGCCAAAAGAACAGTCAAT | Reverse Surveyor primer for CR36 off-target 8 |
| 345 | CR36-CeII-OT9-F | TGTGCCTTAGGCTATGTAAACTGT | Forward Surveyor primer for CR36 off-target 9 |
| 346 | CR36-CeII-OT9-R | AAACCCTTGTAACCAAAATTACCA | Reverse Surveyor primer for CR36 off-target 9 |
| 347 | CR36-CeII-OT10-F | TAACTGCATCAGAAGTCCTTGCTA | Forward Surveyor primer for CR36 off-target 10 |
| 348 | CR36-CeII-OT10-R | GGAGACCAAGCTGCTAAAGTCA | Reverse Surveyor primer for CR36 off-target 10 |
| 349 | CeII-CR3-F-nested | GTGGTGccgcggGAGTTTGGCTCAAATTGTTACTCTT | Nested PCR first round primers |
| 350 | CeII-CR3-R-nested | GTGGTGccgcggGGGAAATGGTCTAGGAGAGTAAAGT | Nested PCR first round primers |
| 351 | CeII-CR1-F-nested | GTGGTGccgcggGAGAGGTTATGTGGCTTTACCA | Nested PCR first round primers |
| 352 | CeII-CR1-R-nested | GTGGTGccgcggCTCATTCTCATGCCTGGACA | Nested PCR first round primers |
| 353 | CeII-CR5-F-nested | GTGGTGccgcggCGGGCTTGGACAGAACTTAC | Nested PCR first round primers |
| 354 | CeII-CR5-R-nested | GTGGTGccgcggCTGCGTAGTGCCAAAACAAA | Nested PCR first round primers |
| 355 | CeII-CR6-F-nested | GTGGTGccgcggTAATTTCATTGAAGAGTGGCTGAA | Nested PCR first round primers |
| 356 | CeII-CR6-R-nested | GTGGTGccgcggAAGCCCTGTGTGGTAGTAGTCAGT | Nested PCR first round primers |
| 357 | CeII-CR36-F-nested | GTGGTGccgcggCAAGTCAGAAGTCACTTGCTTTGT | Nested PCR first round primers |
| 358 | CeII-CR36-R-nested | GTGGTGccgcggTTTTATGTGCAGGAATCAGTCTGT | Nested PCR first round primers |

TABLE 5-continued

| SEQ ID NO. | Primer name | Primer sequence | Notes |
|---|---|---|---|
| 359 | CR3-Ce1I-OT1-F-nested | GTGGTGccgcggTGTGTGCTTCTGTACACATCATCT | Nested PCR first round primers |
| 360 | CR3-Ce1I-OT1-R-nested | GTGGTGccgcggAGATTTCAACCCTCAAAAACTGAG | Nested PCR first round primers |
| 361 | CR1-Ce1I-OT1-F-nested | GTGGTGccgcggTTGGGAACATCAGAGAAAGTATGA | Nested PCR first round primers |
| 362 | CR1-Ce1I-OT1-R-nested | GTGGTGccgcggACAAATTACAGTCTCCTGGGAAAG | Nested PCR first round primers |
| 363 | CR36-Ce1I-OT3-F-nested | GTGGTGccgcggCACTTCCCAAGTGAGGCAAT | Nested PCR first round primers |
| 364 | CR36-Ce1I-OT3-R-nested | GTGGTGccgcggCTATACTTGGGGCTGACTTGCTAC | Nested PCR first round primers |
| 365 | CR3-P1/P3-F | GTGGTGccgcggTTGGCTCTTTAGCTTGTGTTTC | Nested PCR second round primers |
| 366 | CR3-P1/P3-R | GTGGTGccgcggTGAGACTCCCAAAGGCAATC | Nested PCR second round primers |
| 367 | CR3-P1/P4-F | GTGGTGccgcggTTGGCTCTTTAGCTTGTGTTTC | Nested PCR second round primers |
| 368 | CR3-P1/P4-R | GTGGTGccgcggACTGAGGGGTGATCTTGGTG | Nested PCR second round primers |
| 369 | CR3-P2/P3-F | GTGGTGccgcggGCAGAGAAAGCCAGTCGGTA | Nested PCR second round primers |
| 370 | CR3-P2/P3-R | GTGGTGccgcggTGAGACTCCCAAAGGCAATC | Nested PCR second round primers |
| 371 | CR3-P2/P4-F | GTGGTGccgcggGCAGAGAAAGCCAGTCGGTA | Nested PCR second round primers |
| 372 | CR3-P2/P4-R | GTGGTGccgcggACTGAGGGGTGATCTTGGTG | Nested PCR second round primers |
| 373 | CR1-P1/P5-F | GTGGTGccgcggCCAGAGTTCCTAGGGCAGAG | Nested PCR second round primers |
| 374 | CR1-P1/P5-R | GTGGTGccgcggAGCTAGTCCCCACATTCCAC | Nested PCR second round primers |
| 375 | CR1-P1/P6-F | GTGGTGccgcggCCAGAGTTCCTAGGGCAGAG | Nested PCR second round primers |
| 376 | CR1-P1/P6-R | GTGGTGccgcggGGTGGAGGGAAACTTTAGGC | Nested PCR second round primers |
| 377 | CR1-P2/P5-F | GTGGTGccgcggCTCATTCTCATGCCTGGACA | Nested PCR second round primers |
| 378 | CR1-P2/P5-R | GTGGTGccgcggAGCTAGTCCCCACATTCCAC | Nested PCR second round primers |
| 379 | CR1-P2/P6-F | GTGGTGccgcggTCTCATGCCTGGACAAGTAACT | Nested PCR second round primers |
| 380 | CR1-P2/P6-R | GTGGTGccgcggGGTGGAGGGAAACTTTAGGC | Nested PCR second round primers |
| 381 | CR5-P3/P5-F | GTGGTGccgcggGGCTTGGACAGAACTTACCG | Nested PCR second round primers |
| 382 | CR5-P3/P5-R | GTGGTGccgcggCACCACTGTCTGCCTAAGGA | Nested PCR second round primers |
| 383 | CR5-P4/P6-F | GTGGTGccgcggGGCTTGGACAGAACTTACCG | Nested PCR second round primers |

TABLE 5-continued

| SEQ ID NO. | Primer name | Primer sequence | Notes |
|---|---|---|---|
| 384 | CR5-P4/P6-R | GTGGTGccgcggGGTGGAGGGAAACTTTAGGC | Nested PCR second round primers |
| 385 | CR5-P3/P5-F | GTGGTGccgcggCGTAGTGCCAAAACAAACAGT | Nested PCR second round primers |
| 386 | CR5-P3/P5-R | GTGGTGccgcggCACCACTGTCTGCCTAAGGA | Nested PCR second round primers |
| 387 | CR5-P4/P6-F | GTGGTGccgcggCGTAGTGCCAAAACAAACAGT | Nested PCR second round primers |
| 388 | CR5-P4/P6-R | GTGGTGccgcggGGTGGAGGGAAACTTTAGGC | Nested PCR second round primers |
| 389 | CR6-P1/P5-F | GTGGTGccgcggGCGAGGGCCTACTTGATATG | Nested PCR second round primers |
| 390 | CR6-P1/P5-R | GTGGTGccgcggCTTCCCAAGTGAGGCAATGC | Nested PCR second round primers |
| 391 | CR6-P1/P6-F | GTGGTGccgcggACGTTTTGTGCTGCTGTAACA | Nested PCR second round primers |
| 392 | CR6-P1/P6-R | GTGGTGccgcggCTGCAGGCACATTCTCTTCC | Nested PCR second round primers |
| 393 | CR6-P2/P5-F | GTGGTGccgcggGCCCTGTGTGGTAGTAGTCA | Nested PCR second round primers |
| 394 | CR6-P2/P5-R | GTGGTGccgcggCTTCCCAAGTGAGGCAATGC | Nested PCR second round primers |
| 395 | CR6-P2/P6-F | GTGGTGccgcggCAGTATTAAGGGGTGGGAGCT | Nested PCR second round primers |
| 396 | CR6-P2/P6-R | GTGGTGccgcggTCTCTTCCTCACACAGCTGA | Nested PCR second round primers |
| 397 | CR36-P3/P5-F | GTGGTGccgcggGGAGCTTGGAGGGAAGAGAA | Nested PCR second round primers |
| 398 | CR36-P3/P5-R | GTGGTGccgcggCTTCCCAAGTGAGGCAATGC | Nested PCR second round primers |
| 399 | CR36-P4/P6-F | GTGGTGccgcggATGGATGGGGAAGACACTGG | Nested PCR second round primers |
| 400 | CR36-P4/P6-R | GTGGTGccgcggCTGCAGGCACATTCTCTTCC | Nested PCR second round primers |
| 401 | CR36-P3/P5-F | GTGGTGccgcggGGATGAAACAGGGCAGGAAC | Nested PCR second round primers |
| 402 | CR36-P3/P5-R | GTGGTGccgcggTTCCCAAGTGAGGCAATGC | Nested PCR second round primers |
| 403 | CR36-P4/P6-F | GTGGTGccgcggTTTGCAGAGCCATGATGAGG | Nested PCR second round primers |
| 404 | CR36-P4/P6-R | GTGGTGccgcggCGACAGCCAAAACAGCCG | Nested PCR second round primers |

Western blot analysis. To assess dystrophin protein expression, immortalized myoblasts were differentiated into myofibers by replacing the growth medium with DMEM supplemented with 1% insulin-transferrin-selenium (Invitrogen) and 1% antibiotic/antimycotic (Invitrogen) for 4-7 days, such as 6 or 7 days. Fibroblasts were transdifferentiated into myoblasts by inducing MyoD overexpression and incubating the cells in DMEM supplemented with 1% insulin-transferrin-selenium (Invitrogen), 1% antibiotic/antimycotic (Invitrogen) and 3 µg/mL doxycycline for 15 days. Dystrophin expression was assessed at 3 days after transfecting HEK293T cells. Cells were trypsinized, collected and lysed in RIPA buffer (Sigma) supplemented with a protease inhibitor cocktail (Sigma) and the total protein amount was quantified using the bicinchoninic acid assay according to the manufacturer's instructions (Pierce). Samples were then mixed with NuPAGE loading buffer (Invitrogen) and 5% β-mercaptoethanol and heated to 85° C.

for 10 minutes. Twenty-five micrograms of protein were separated on 4-12% NuPAGE Bis-Tris gels (Invitrogen) with MES buffer (Invitrogen). Proteins were transferred to nitrocellulose membranes for 1-2 hrs in transfer buffer containing 10-20% methanol, such as 10% methanol, and 0.01% SDS. The blot was then blocked for 1 hr with 5% milk-TBST at room temperature. Blots were probed with the following primary antibodies: MANDYS8 to detect dystrophin (1:100, Sigma D8168) and rabbit anti-GAPDH (1:5000, Cell Signaling 2118S). Blots were then incubated with mouse or rabbit horseradish peroxidase-conjugated secondary antibodies (Santa Cruz) and visualized using the ChemiDoc chemilumescent system (BioRad) and Western-C ECL substrate (BioRad).

Transplantation into immunodeficient mice. All animal experiments were conducted under protocols approved by the Duke Institutional Animal Care & Use Committee. Cells were trypsinized, collected and washed in 1× Hank's Balanced Salt Solution (HBSS, Sigma). Two million cells were pelleted and resuspended in five μL 1× HB SS (Sigma) supplemented with cardiotoxin (Sigma # C9759) immediately prior to injection. These cells were transplanted into the hind limb tibialis anterior (TA) muscle of NOD.SCID-.gamma (NSG) mice (Duke CCIF Breeding Core) by intramuscular injection. Four weeks after injection, mice were euthanized and the TA muscles were harvested.

Immunofluorescence staining. Harvested TA muscles were incubated in 30% glycerol overnight at 4° C. before mounting and freezing in Optimal Cutting Temperature compound. Serial 10 micron sections were obtained by cryosectioning of the embedded muscle tissue at −20° C. Cryosections were then washed in PBS to remove the OCT compound and subsequently blocked for 30-60 minutes at room temperature in PBS containing 10% heat-inactivated fetal bovine serum for spectrin detection or 5% heat-inactivated fetal bovine serum for dystrophin detection. Cryosections were incubated overnight at 4° C. with the following primary antibodies that are specific to human epitopes only: anti-spectrin (1:20, Leica NCL-SPEC1) or anti-dystrophin (1:2, Leica NCL-DYS3). After primary staining, spectrin or dystrophin expression was detected using a tyramide-based immunofluorescence signal amplification detection kit (Life Technologies, TSA Kit #22, catalog # T-20932,). Briefly, cryosections were incubated with 1:200 goat anti-mouse biotin-XX secondary (Life Technologies # B2763) in blocking buffer for 1 hr at room temperature. The signal was then amplified using streptavidin-HRP conjugates (1:100, from TSA Kit) in blocking buffer for 1 hr at room temperature. Finally, cryosections were incubated with tyramide-AlexaFluor488 conjugates (1:100, TSA kit) in manufacturer-provided amplification buffer for 10 minutes at room temperature. Stained cryosections were then mounted in ProLong AntiFade (Life Technologies # P36934) and visualized with conventional fluorescence microscopy.

Cytotoxicity assay. To quantitatively assess potential sgRNA or SpCas9 nuclease-associated cytotoxicity, HEK293T cells were transfected with 10 ng of a GFP reporter and 100 ng SpCas9 expression vector and 100 ng sgRNA expression vector using Lipofectamine 2000 according to the manufacturer's instructions (Invitrogen). The percentage of GFP positive cells was assessed at 2 and 5 days by flow cytometry. The survival rate was calculated as the decrease in GFP positive cells from days 2 to 5 and normalized to cells transfected with an empty nuclease expression vector as described (Cornu et al., Meth Mol Biol 649:237-245 (2010)).

Example 4

CRISPRs Targeting the Dystrophin Gene—Results

The CRISPR/Cas9-based system was designed to target the dystrophin gene. Various gRNAs were chosen to target different regions of the human and mouse dystrophin gene based on NNNNN NNNNN NNNNN NNNNN NGG (SEQ ID NO: 677) and GNNNN NNNNN NNNNN NNNNN NGG (SEQ ID NO: 678) (see Tables 6, 7 and 8).

TABLE 6

| Name (SEQ ID NO) | Species | Gene | Target | Strand | 19 bp for chimeric (add G on 5' end) | PAM |
|---|---|---|---|---|---|---|
| DCR1 (628) | Human | DMD | Intron 50 | + | attggctttgatttccta (SEQ ID NO: 65) | GGG |
| DCR2 (66) | Human | DMD | Intron 50 | − | tgtagagtaagtcagccta (SEQ ID NO: 679) | TGG |
| DCR3 (629) | Human | DMD | Exon 51-55' | + | cctactcagactgttactc (SEQ ID NO: 67) | TGG |
| DCR4 (68) | Human | DMD | Exon 51-53' | + | ttggacagaacttaccgac (SEQ ID NO: 680) | TGG |
| DCR5 (630) | Human | DMD | Intron 51 | − | cagttgcctaagaactggt (SEQ ID NO: 69) | GGG |
| DCR6 (631) | Human | DMD | Intron 44 | − | GGGCTCCACCCTCACGAGT (SEQ ID NO: 70) | GGG |
| DCR7 (71) | Human | DMD | Intron 55 | + | TTTGCTTCGCTATAAAACG (SEQ ID NO: 681) | AGG |
| DCR8 (72) | Human | DMD | Exon 41 | + | TCTGAGGATGGGGCCGCAA (SEQ ID NO: 682) | TGG |
| DCR9 (73) | Human | DMD | Exon 44 | − | GATCTGTCAAATCGCCTGC (SEQ ID NO: 683) | AGG |

TABLE 6-continued

| Name (SEQ ID NO) | Species | Gene | Target | Strand | 19 bp for chimeric (add G on 5' end) | PAM |
|---|---|---|---|---|---|---|
| DCR10 (74) | Human | DMD | Exon 45 | + | CCAGGATGGCATTGGGCAG (SEQ ID NO: 684) | CGG |
| DCR11 (75) | Human | DMD | Exon 45 | + | CTGAATCTGCGGTGGCAGG (SEQ ID NO: 685) | AGG |
| DCR12 (76) | Human | DMD | Exon 46 | − | TTCTTTTGTTCTTCTAGCc (SEQ ID NO: 686) | TGG |
| DCR13 (77) | Human | DMD | Exon 46 | + | GAAAAGCTTGAGCAAGTCA (SEQ ID NO: 687) | AGG |
| DCR14 (78) | Human | DMD | Exon 47 | + | GAAGAGTTGCCCCTGCGCC (SEQ ID NO: 688) | AGG |
| DCR15 (79) | Human | DMD | Exon 47 | + | ACAAATCTCCAGTGGATAA (SEQ ID NO: 689) | AGG |
| DCR16 (80) | Human | DMD | Exon 48 | − | TGTTTCTCAGGTAAAGCTC (SEQ ID NO: 690) | TGG |
| DCR17 (81) | Human | DMD | Exon 48 | + | GAAGGACCATTTGACGTTa (SEQ ID NO: 691) | AGG |
| DCR18 (82) | Human | DMD | Exon 49 | − | AACTGCTATTTCAGTTTCc (SEQ ID NO: 692) | TGG |
| DCR19 (83) | Human | DMD | Exon 49 | + | CCAGCCACTCAGCCAGTGA (SEQ ID NO: 693) | AGG |
| DCR20 (84) | Human | DMD | Exon 50 | + | gtatgcttttctgttaaag (SEQ ID NO: 694) | AGG |
| DCR21 (85) | Human | DMD | Exon 50 | + | CTCCTGGACTGACCACTAT (SEQ ID NO: 695) | TGG |
| DCR22 (86) | Human | DMD | Exon 52 | + | GAACAGAGGCGTCCCCAGT (SEQ ID NO: 696) | TGG |
| DCR23 (87) | Human | DMD | Exon 52 | + | GAGGCTAGAACAATCATTA (SEQ ID NO: 697) | CGG |
| DCR24 (88) | Human | DMD | Exon 53 | + | ACAAGAACACCTTCAGAAC (SEQ ID NO: 698) | CGG |
| DCR25 (89) | Human | DMD | Exon 53 | − | GGTTTCTGTGATTTTCTTT (SEQ ID NO: 699) | TGG |
| DCR26 (90) | Human | DMD | Exon 54 | + | GGCCAAAGACCTCCGCCAG (SEQ ID NO: 700) | TGG |
| DCR27 (91) | Human | DMD | Exon 54 | + | TTGGAGAAGCATTCATAAA (SEQ ID NO: 701) | AGG |
| DCR28 (92) | Human | DMD | Exon 55 | − | TCGCTCACTCACCctgcaa (SEQ ID NO: 702) | AGG |
| DCR29 (93) | Human | DMD | Exon 55 | + | AAAAGAGCTGATGAAACAA (SEQ ID NO: 703) | TGG |
| DCR30 (94) | Human | DMD | 5'UTR/ Exon 1 | + | TAcACTTTTCaAAATGCTT (SEQ ID NO: 704) | TGG |
| DCR31 (95) | Human | DMD | Exon 51 | + | gagatgatcatcaagcaga (SEQ ID NO: 705) | AGG |
| DCR32 (96) | Mouse | DMD | mdx mutation | + | ctttgaaagagcaaTaaaa (SEQ ID NO: 706) | TGG |
| DCR33 (97) | Human | DMD | Intron 44 | − | CACAAAAGTCAAATCGGAA (SEQ ID NO: 707) | TGG |
| DCR34 (98) | Human | DMD | Intron 44 | − | ATTTCAATATAAGATTCGG (SEQ ID NO: 708) | AGG |

TABLE 6-continued

| Name (SEQ ID NO) | Species | Gene | Target | Strand | 19 bp for chimeric (add G on 5' end) | PAM |
|---|---|---|---|---|---|---|
| DCR35 (99) | Human | DMD | Intron 55 | − | CTTAAGCAATCCCGAACTC (SEQ ID NO: 709) | TGG |
| DCR36 (632) | Human | DMD | Intron 55 | − | CCTTCTTTATCCCCTATCG (SEQ ID NO: 100) | AGG |
| DCR40 (104) | Mouse | DMD | Exon 23 | − | aggccaaacctcggcttac (SEQ ID NO: 710) | NNGRR |
| DCR41 (105) | Mouse | DMD | Exon 23 | + | TTCGAAAATTTCAGgtaag (SEQ ID NO: 711) | NNGRR |
| DCR42 (106) | Mouse | DMD | Exon 23 | + | gcagaacaggagataacag (SEQ ID NO: 712) | NNGRRT |
| DCR43 (107) | Mouse | ACVR2B | Exon 1 | + | gcggccctcgcccttctct (SEQ ID NO: 713) | ggggat |
| DCR48 (108) | Human | DMD | Intron 45 | − | TAGTGATCGTGGATACGAG (SEQ ID NO: 714) | AGG |
| DCR49 (109) | Human | DMD | Intron 45 | − | TACAGCCCTCGGTGTATAT (SEQ ID NO: 715) | TGG |
| DCR50 (110) | Human | DMD | Intron 52 | − | GGAAGGAATTAAGCCCGAA (SEQ ID NO: 716) | TGG |
| DCR51 (111) | Human | DMD | Intron 53 | − | GGAACAGCTTTCGTAGTTG (SEQ ID NO: 718) | AGG |
| DCR52 (112) | Human | DMD | Intron 54 | + | ATAAAGTCCAGTGTCGATC (SEQ ID NO: 719) | AGG |
| DCR53 (113) | | | Intron 54 | + | AAAACCAGAGCTTCGGTCA (SEQ ID NO: 720) | AGG |
| DCR54 (114) | Mouse | Rosa26 | ZFN region | + | GAGTCTTCTGGGCAGGCTTAA AGGCTAACC (SEQ ID NO: 720) | TGG |
| DCR55 (115) | Mouse | Rosa26 | mRNA | − | TCGGGTGAGCATGTCTTTAAT CTACCTCGA (SEQ ID NO: 721) | TGG |
| DCR49 (116) | Human | DMD | Ex 51 | − | gtgtcaccagagtaacagt (SEQ ID NO: 722) | ctgagt |
| DCR50 (117) | Human | DMD | Ex 51 | + | tgatcatcaagcagaaggt (SEQ ID NO: 723) | atgag |
| DCR60 (118) | Mouse | DMD | Exon 23 | + | AACTTCGAAAATTTCAGgta (SEQ ID NO: 724) | agccgagg |
| DCR61 (119) | Mouse | DMD | Intron 22 | + | gaaactcatcaaatatgcgt (SEQ ID NO: 725) | gttagtgt |
| DCR62 (120) | Mouse | DMD | Intron 22 | − | tcatttacactaacacgcat (SEQ ID NO: 726) | atttgatg |
| DCR63 (121) | Mouse | DMD | Intron 22 | + | gaatgaaactcatcaaatat (SEQ ID NO: 727) | gcgtgtta |
| DCR64 (122) | Mouse | DMD | Intron 23 | − | tcatcaatatctttgaagga (SEQ ID NO: 728) | ctctgggt |
| DCR65 (123) | Mouse | DMD | Intron 23 | − | tgttttcataggaaaaatag (SEQ ID NO: 729) | gcaagttg |
| DCR66 (124) | Mouse | DMD | Intron 23 | + | aattggaaaatgtgatggga (SEQ ID NO: 730) | aacagata |
| DCR67 (125) | Human | DMD | Exon 51 | + | atgatcatcaagcagaaggt (SEQ ID NO: 731) | atgagaaa |

TABLE 6-continued

| Name (SEQ ID NO) | Species | Gene | Target | Strand | 19 bp for chimeric (add G on 5' end) | PAM |
|---|---|---|---|---|---|---|
| DCR68 (126) | Human | DMD | Exon 51 | + | agatgatcatcaagcagaag (SEQ ID NO: 732) | gtatgaga |
| DCR69 (127) | Human | DMD | Exon 51 | − | cattttttctcataccttct (SEQ ID NO: 733) | gcttgatg |
| DCR70 (128) | Human | DMD | Exon 51 | + | tcctactcagactgttactc (SEQ ID NO: 734) | tggtgaca |
| DCR71 (129) | Human | DMD | Exon 51 | − | acaggttgtgtcaccagagt (SEQ ID NO: 735) | aacagtct |
| DCR72 (130) | Human | DMD | Exon 51 | − | ttatcattttttctctacc (SEQ ID NO: 736) | ttctgctt |
| DCR73 (131) | Human | DMD | Intron 51 | − | ttgcctaagaactggtggga (SEQ ID NO: 737) | aatggtct |
| DCR74 (132) | Human | DMD | Intron 51 | − | aaacagttgcctaagaactg (SEQ ID NO: 738) | gtgggaaa |
| DCR75 (133) | Human | DMD | Intron 51 | + | tttcccaccagttcttaggc (SEQ ID NO: 739) | aactgttt |
| DCR76 (134) | Human | DMD | Intron 50 | + | tggctttgatttccctaggg (SEQ ID NO: 740) | tccagctt |
| DCR77 (135) | Human | DMD | Intron 50 | − | tagggaaatcaaagccaatg (SEQ ID NO: 741) | aaacgttc |
| DCR78 (136) | Human | DMD | Intron 50 | − | gaccctagggaaatcaaagc (SEQ ID NO: 742) | caatgaaa |
| DCR79 (137) | Human | DMD | Intron 44 | − | TGAGGGCTCCACCCTCACGA (SEQ ID NO: 743) | GTGGGTTT |
| DCR80 (138) | Human | DMD | Intron 44 | − | AAGGATTGAGGGCTCCACCC (SEQ ID NO: 744) | TCACGAGT |
| DCR81 (139) | Human | DMD | Intron 44 | − | GCTCCACCCTCACGAGTGGG (SEQ ID NO: 745) | TTTGGTTC |
| DCR82 (140) | Human | DMD | Intron 55 | − | TATCCCCTATCGAGGAAACC (SEQ ID NO: 746) | ACGAGTTT |
| DCR83 (141) | Human | DMD | Intron 55 | + | GATAAAGAAGGCCTATTTCA (SEQ ID NO: 747) | TAGAGTTG |
| DCR84 (142) | Human | DMD | Intron 55 | − | AGGCCTTCTTTATCCCCTAT (SEQ ID NO: 748) | CGAGGAAA |
| DCR85 (143) | Human | DMD | Intron 44 | − | TGAGGGCTCCACCCTCACGA (SEQ ID NO: 749) | GTGGGT |
| DCR86 (144) | Human | DMD | Intron 55 | + | GATAAAGAAGGCCTATTTCA (SEQ ID NO: 750) | TAGAGT |

TABLE 7

| Name | Notes | % Mod |
|---|---|---|
| DCR1 | Delete exon 51 | 6.6 |
| DCR2 | Delete exon 51 | 10.3 |
| DCR3 | Frameshift | 13 |
| DCR4 | Delete exon 51 | 11.9 |
| DCR5 | Delete exon 51 | 12.4 |
| DCR6 | As close to exon 44 as possible in intron 44 (in case of patient deletions) | 16.1 |
| DCR7 | As close to exon 56 as possible in intron 55 (in case of patient deletions) | 6.8 |
| DCR8 | Can correct exon 42-43 deletion (−1/+2) only, (−2/+1) is not correctable by this | 17.3 |

TABLE 7-continued

| Name | Notes | % Mod |
|---|---|---|
| DCR9 | Skip exon 44 (5') | 14.4 |
| DCR10 | Frameshift | 14.9 |
| DCR11 | Correct downstream of exon 45 | <1 |
| DCR12 | 5' splice acceptor/frameshift | <1 |
| DCR13 | Correct downstream of exon 46 | 16.9 |
| DCR14 | Frameshift | 17.2 |
| DCR15 | Correct downstream of exon 47 | 15.4 |
| DCR16 | Frameshift | 11.5 |
| DCR17 | Correct downstream of exon 48 | <1 |
| DCR18 | 5' splice acceptor/frameshift | 1.8 |
| DCR19 | Correct downstream of exon 49 | 33.7 |
| DCR20 | 5' splice acceptor | 14.9 |
| DCR21 | Correct downstream of exon 50 | 24.1 |
| DCR22 | Frameshift | 25.9 |
| DCR23 | Correct downstream of exon 52 | 25.2 |
| DCR24 | Frameshift (can only correct +1 frame) | 24.8 |
| DCR25 | Correct downstream of exon 53 | 2.6 |
| DCR26 | Frameshift | 24.5 |
| DCR27 | Correct downstream of exon 54 | 13.4 |
| DCR28 | 5' splice acceptor | 21.6 |
| DCR29 | Correct downstream of exon 55 | 19.2 |
| DCR30 | Integrate minidys in exon 1 | not tested |
| DCR31 | Correct downstream of exon 51 | 18.9 |
| DCR32 | Delete stop codon | not tested |
| DCR33 | Alternative to CR6 | 1.3 |
| DCR34 | Alternative to CR6 | 13.2 |
| DCR35 | Alternative to CR7 | 22.5 |
| DCR36 | Alternative to CR7 | 26.4 |
| DCR40 | Disrupt exon 23 5' splice donor (correct mdx mutation) | |
| DCR41 | Disrupt exon 23 5' splice donor (correct mdx mutation) | |
| DCR42 | Delete exon 53 mdx4cv mutation | |
| DCR43 | Disrupt myostatin receptor | |

TABLE 8

| Name | Cas9 | | Notes | Cas9 used |
|---|---|---|---|---|
| DCR49 | S. Aureus | | Frameshift in exon 51 | SaCas9 (from Zhang pX441) (NNGRRT PAM) |
| DCR50 | S. Aureus | | Disrupt 5' end of exon 51 | SaCas9 (from Zhang pX441) (NNGRR PAM) |
| DCR60 | N. Meningitidis | NNNNGANN | Target 3' splice donor of exon 23 to bypass mdx mutation | NmCas9 (NNNNGANN PAM) |
| DCR61 | N. Meningitidis | NNNNGNNT | Delete exon 23 and bypass mdx mutation | NmCas9 (NNNNGNNT PAM) |
| DCR62 | N. Meningitidis | NNNNGANN | Delete exon 23 and bypass mdx mutation | NmCas9 (NNNNGANN PAM) |
| DCR63 | N. Meningitidis | NNNNGTTN | Delete exon 23 and bypass mdx mutation | NmCas9 (NNNNGTTN PAM) |
| DCR64 | N. Meningitidis | NNNNGNNT | Delete exon 23 and bypass mdx mutation | NmCas9 (NNNNGNNT PAM) |
| DCR65 | N. Meningitidis | NNNNGTTN | Delete exon 23 and bypass mdx mutation | NmCas9 (NNNNGTTN PAM) |
| DCR66 | N. Meningitidis | NNNNGANN | Delete exon 23 and bypass mdx mutation | NmCas9 (NNNNGANN PAM) |
| DCR67 | N. Meningitidis | NNNNGANN | Target 3' splice donor of exon 51 to skip exon | NmCas9 (NNNNGANN PAM) |
| DCR68 | N. Meningitidis | NNNNGANN | Target 3' splice donor of exon 51 to skip exon | NmCas9 (NNNNGANN PAM) |
| DCR69 | N. Meningitidis | NNNNGANN | Target 3' splice donor of exon 51 to skip exon | NmCas9 (NNNNGANN PAM) |
| DCR70 | N. Meningitidis | NNNNGANN | Frameshift in exon 51 | NmCas9 (NNNNGANN PAM) |
| DCR71 | N. Meningitidis | NNNNGNNT | Frameshift in exon 51 | NmCas9 (NNNNGNNT PAM) |
| DCR72 | N. Meningitidis | NNNNGNNT | Target 3' splice donor of exon 51 to skip exon | NmCas9 (NNNNGNNT PAM) |
| DCR73 | N. Meningitidis | NNNNGNNT | Delete exon 51 (bind as close to DCR5 as possible) | NmCas9 (NNNNGNNT PAM) |
| DCR74 | N. Meningitidis | NNNNGANN | Delete exon 51 (bind as close to DCR5 as possible) | NmCas9 (NNNNGANN PAM) |
| DCR75 | N. Meningitidis | NNNNGTTN | Delete exon 51 (bind as close to DCR5 as possible) | NmCas9 (NNNNGTTN PAM) |

TABLE 8-continued

| Name | Cas9 | | Notes | Cas9 used |
|---|---|---|---|---|
| DCR76 | N. Meningitidis | NNNNGNNT | Delete exon 51 (bind as close to DCR1/2 as possible) | NmCas9 (NNNNGNNT PAM) |
| DCR77 | N. Meningitidis | NNNNGTTN | Delete exon 51 (bind as close to DCR1/2 as possible) | NmCas9 (NNNNGTTN PAM) |
| DCR78 | N. Meningitidis | NNNNGANN | Delete exon 51 (bind as close to DCR1/2 as possible) | NmCas9 (NNNNGANN PAM) |
| DCR79 | N. Meningitidis | NNNNGNNT | Delete exons 45-55-overlaps NNNNGTTN PAM, bind as close to DCR6 as possible | NmCas9 (NNNNGNNT PAM) |
| DCR80 | N. Meningitidis | NNNNGANN | Delete exons 45-55, bind as close to DCR6 as possible | NmCas9 (NNNNGANN PAM) |
| DCR81 | N. Meningitidis | NNNNGTTN | Delete exons 45-55, bind as close to DCR6 as possible | NmCas9 (NNNNGTTN PAM) |
| DCR82 | N. Meningitidis | NNNNGNNT | Delete exons 45-55, bind as close to DCR36 as possible-overlaps NNNNGTTN | NmCas9 (NNNNGNNT PAM) PAM |
| DCR83 | N. Meningitidis | NNNNGTTN | Delete exons 45-55, bind as close to DCR36 as possible | NmCas9 (NNNNGTTN PAM) |
| DCR84 | N. Meningitidis | NNNNGANN | Delete exons 45-55, bind as close to DCR36 as possible | NmCas9 (NNNNGANN PAM) |
| DCR85 | S. Aureus | NNGRRT | Delete exons 45-55, bind as close to DCR6 as possible | SaCas9 (from Zhang pX441) (NNGRRT PAM) |
| DCR86 | S. Aureus | NNGRRT | Delete exons 45-55, bind as close to DCR36 as possible | SaCas9 (from Zhang pX441) (NNGRRT PAM) |

In particular, 400 ng of Cas9 was co-transfected into HEK 293T cells with either 400 ng of empty vector or gRNA that targets the region encompassing Exon 51, i.e., CR1, CR2, CR3, CR4, and CR5 (see FIG. 11B). Genomic DNA was harvested at 2 days post-transfection and analyzed using the Surveyor assay (see FIGS. 11A and 11C).

Figure 12:
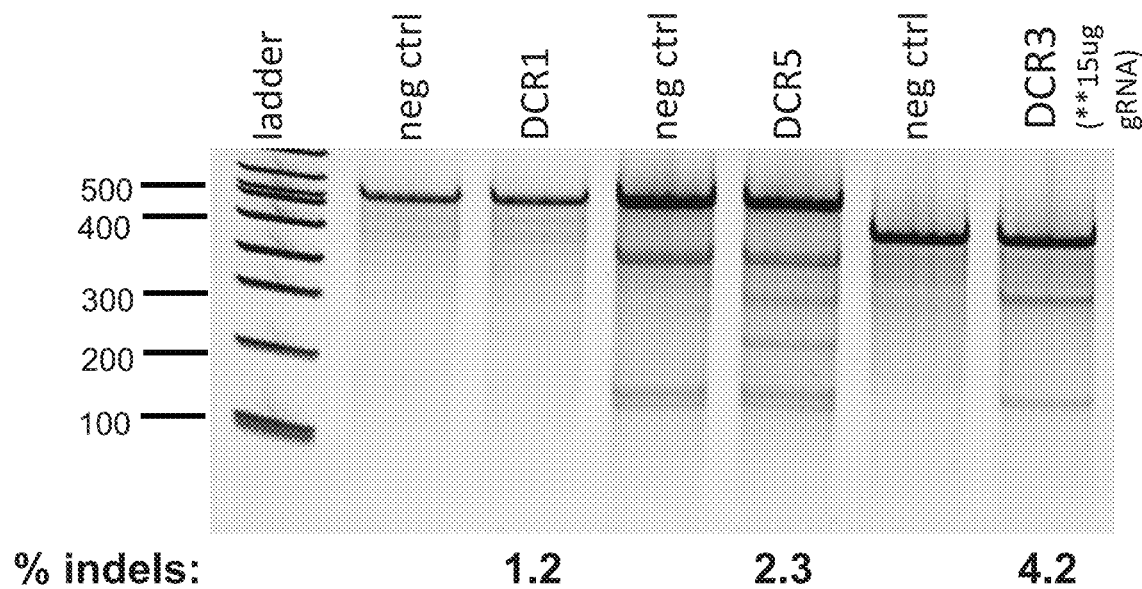
FIG. 12 shows RNA-guided repair in DMD 8036 (de148-50) cells as shown by Surveyor assay.
Figure 13:
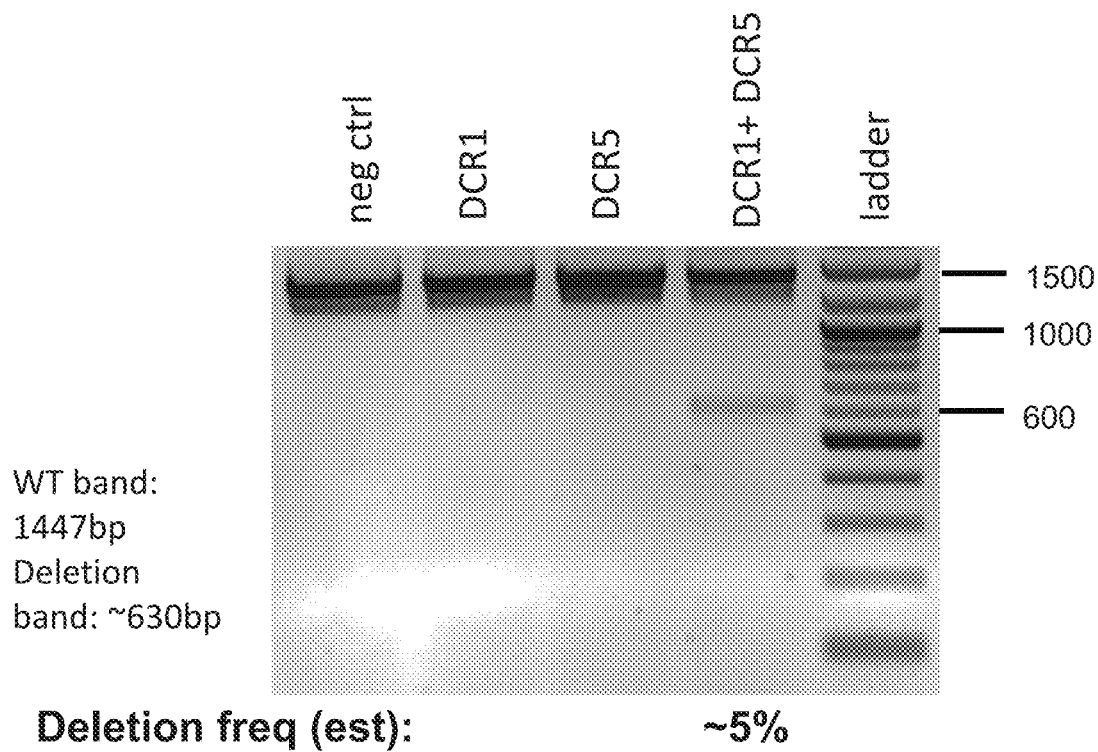
FIG. 13 shows RNA-guided repair in DMD 8036 (de148-50) cells as shown by PCR across the entire locus. The PCR of a wild-type dystrophin gene generates a fragment of 1447 bp in size, whereas PCR of the mutant gene in the DMD 8036 cell line shows a deletion of approximately 817 bp. The deletion band after introduction of the CRISPR/Cas9-based system was approximately 630 bp.
Figure 14:
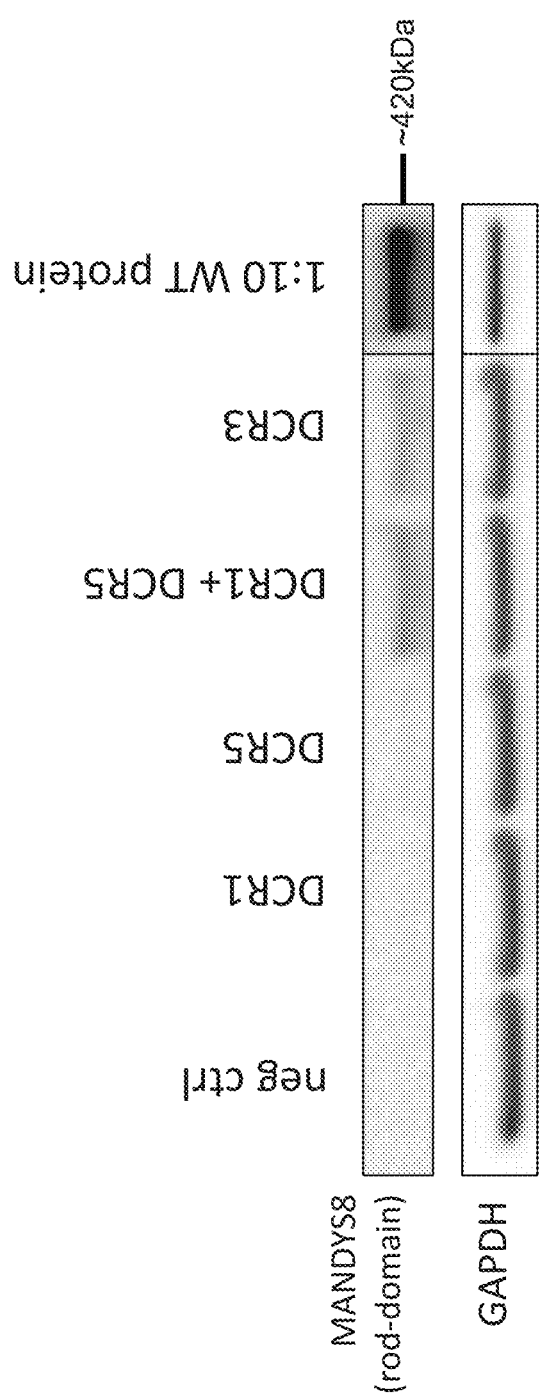
FIG. 14 shows RNA-guided repair in DMD 8036 (de148-50) cells as shown by Western blot with MANDYS8 (anti-dystrophin antibody) and GAPDH antibody (positive control).

The CRISPR/Cas9-based system was used in DMD 8036 (del48-50) cells to determine if the system could repair a mutant dystrophin gene. 5 µg of Cas9 was co-transfected into DMD 8036 (del48-50) cells with either 7.5 µg of empty vector or gRNA. In particular, 7.5 µg of CR1 ("DCR1"), 7.5 µg of CR5 ("DCR5"), 15 µg of CR3 ("DCR3") or 7.5 µg of a combination of CR1 and CR5 (DCR1+DCR5) were used. Genomic DNA was harvested at 3 days post-transfection and analyzed using the Surveyor assay (FIG. 12) or PCR analysis across the entire locus (FIG. 13). This locus was amplified by PCR using primers flanking the region containing the genomic targets for CR1 and CR5 (the forward primer: 5'-gagaggttatgtggctttacca (SEQ ID NO:457), the reverse primer: 5'-ctgcgtagtgccaaaacaaa (SEQ ID NO:458)), resulting in a 1447 bp band for the wild-type locus or an expected size of approximately 630 bp for the deleted locus. After 7 days of differentiation, western blot of the treated cells shows expression of dystrophin protein (see FIG. 14).

Example 5

Targeting CRISPR/Cas9 to Hotspot Mutations in the Human Dystrophin Gene

Figure 16A:
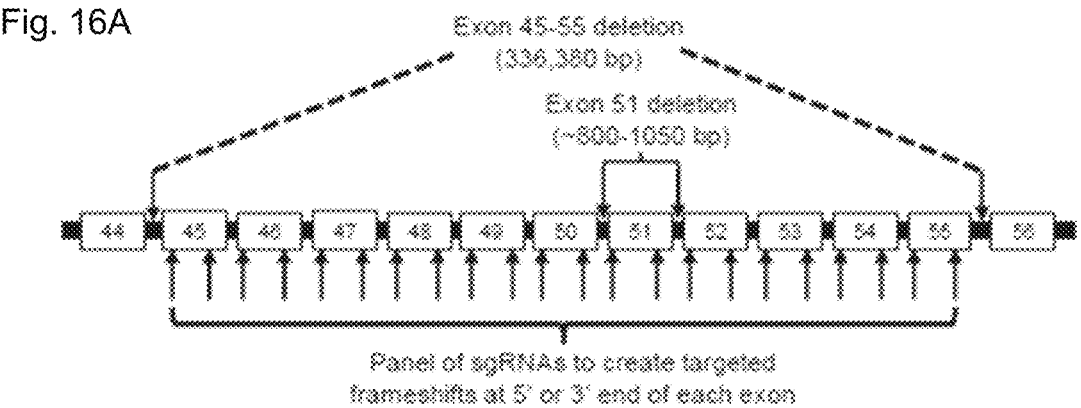
FIGS. 16A-16D show CRISPR/Cas9 targeting of the dystrophin gene.
Figure 16B:
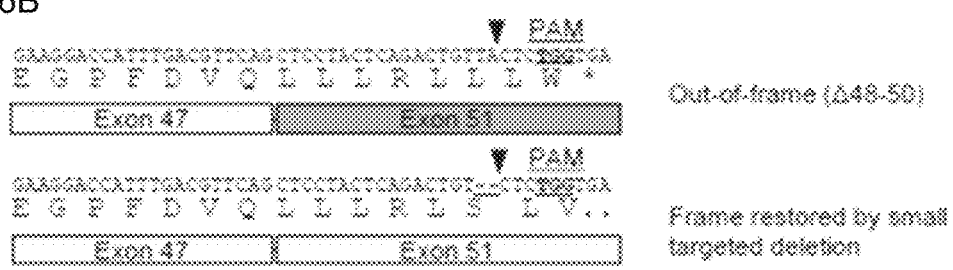
Figure 16C:
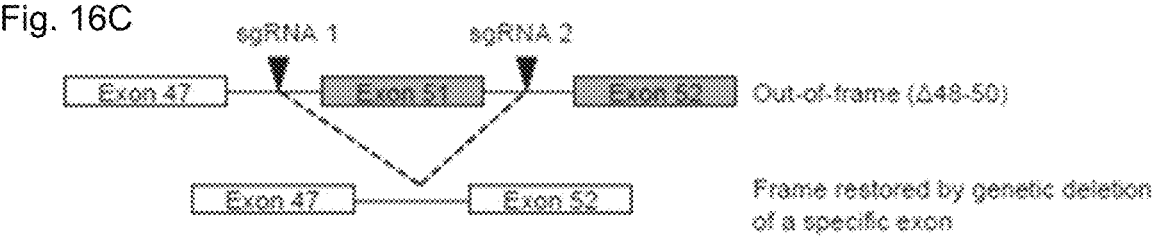
Figure 16D:
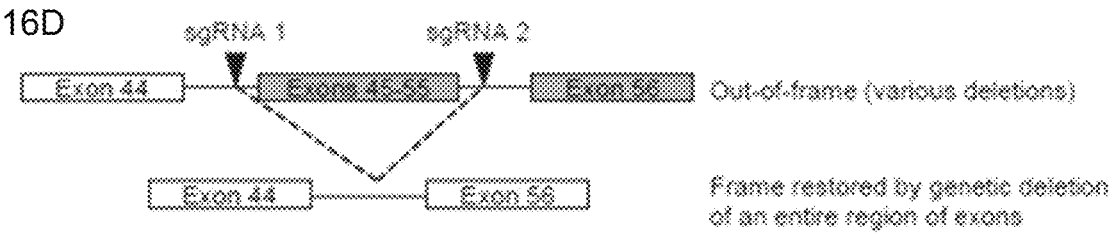

To utilize the CRISPR/Cas9 gene editing platform for correcting a wide range of dystrophin mutations, dozens of sgRNAs targeted to the hotspot mutation region between exons 45-55 were created (FIGS. 16A-16D). The *S. pyogenes* system that utilizes a human-codon optimized SpCas9 nuclease and a chimeric single-guide RNA (sgRNA) expression vector to guide efficient site-specific gene editing was used. Similar to Example 4 targeting exon 51 with TALENs, protospacers were selected to target the 5' and 3' ends of exons 45 through 55 which meet the 5'-NRG-3' PAM requirement of SpCas9. Small insertions or deletions created by NHEJ-based DNA repair within these exons can generate targeted frameshift mutations that address various dystrophin mutations surrounding each exon (FIGS. 16A-16B). For example, CR3 was designed to correct dystrophin mutations or deletions surrounding exon 51 by introducing small insertions or deletions in the 5' end of exon 51 to restore the downstream dystrophin reading frame (FIG. 16B). Additionally, sgRNAs were designed to employ the multiplex capability of the CRISPR/Cas9 system and specifically delete individual exons or a series of exons to restore the dystrophin reading frame, similar to the methods of oligonucleotide-based exon skipping. For this purpose, sgRNAs were targeted to the intronic regions surrounding exon 51 (FIG. 16C) or exons 45-55 (FIG. 16D). These sgRNAs were intentionally targeted to sites nearest to the downstream or upstream exon intended to be included in the resulting transcript to minimize the likelihood that the background patient deletion would include the intronic sgRNA target sites.

Example 6

Screening of sgRNAs Targeted to the Dystrophin Gene in Human Cells

Figure 17:
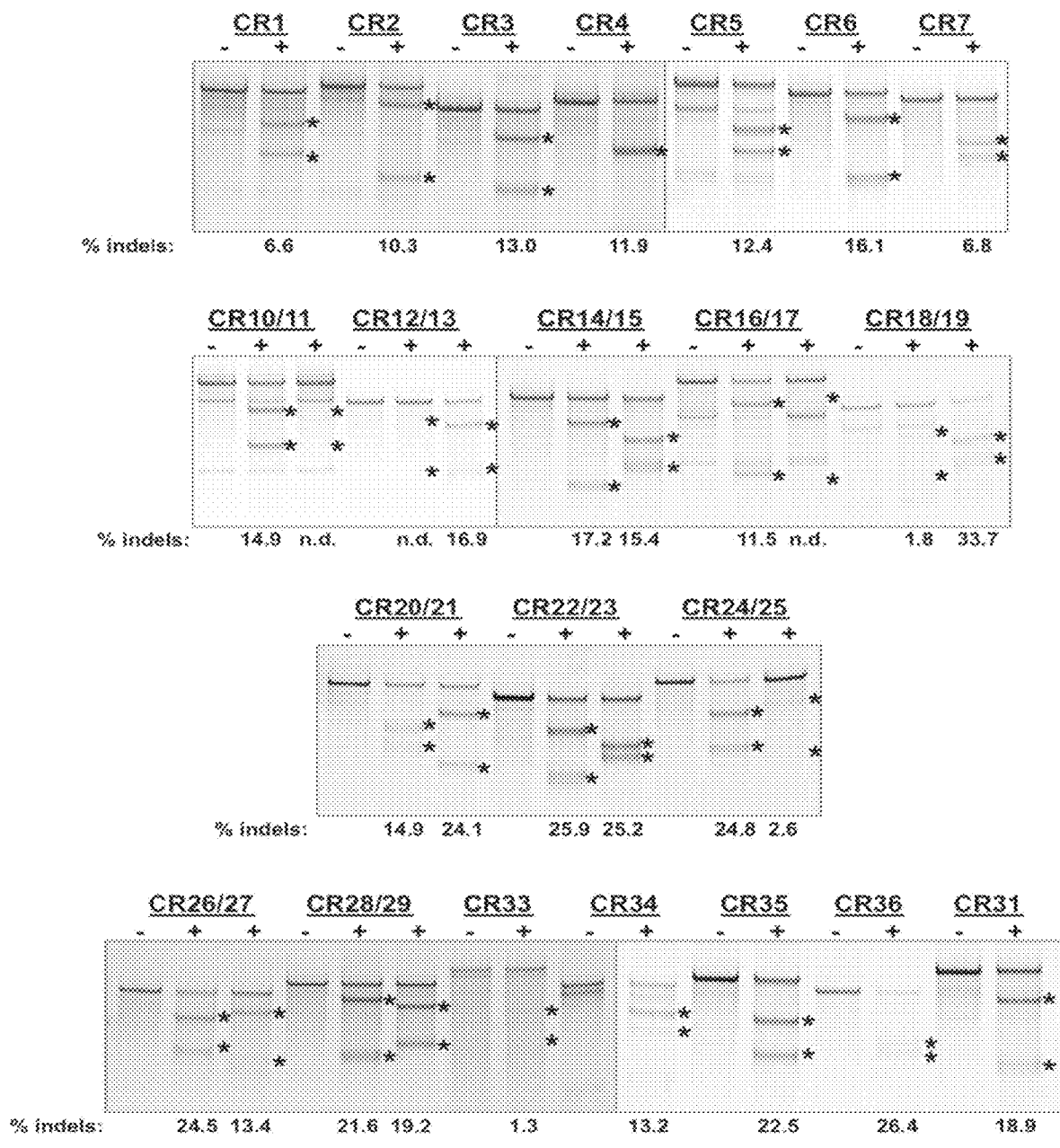
FIG. 17 shows images of TBE-PAGE gels used to quantify Surveyor assay results to measure day 3 gene modification in Table 7. Asterisks mark expected sizes of bands indicative of nuclease activity.
Figure 18:
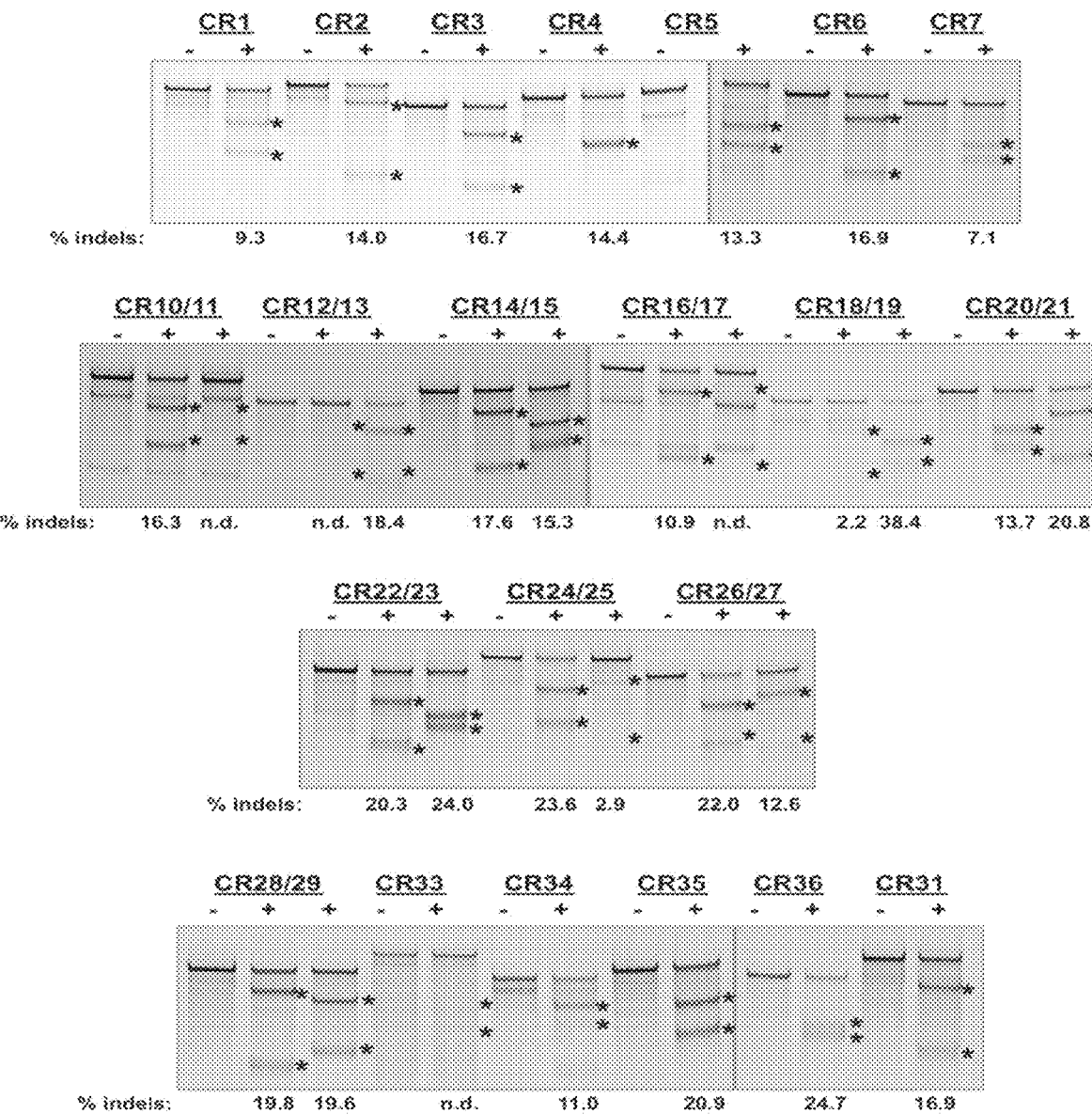
FIG. 18 shows images of TBE-PAGE gels used to quantify Surveyor assay results to measure day 10 gene modification in Table 7. Asterisks mark expected sizes of bands indicative of nuclease activity.

Gene editing frequency in the human HEK293T cell line was assessed to rapidly determine different sgRNA targeting efficiencies. HEK293Ts were transfected with constructs encoding human codon-optimized SpCas9 and the indicated sgRNA. Each sgRNA was designed to modify the dystrophin gene as indicated. The frequency of gene modification at day 3 or day 10 post-transfection was determined by the Surveyor assay. The ratio of measured Surveyor signal at day 3 and day 10 was calculated to quantify the stability of gene editing frequencies for each sgRNA in human cells. As quantified by the Surveyor assay 3 days post-transfection, 29/32 (~90%) of the sgRNAs tested were able to mediate highly efficient gene modification at the intended locus (Table 9, FIG. 17). The gene editing frequencies were stable for almost all of the sgRNAs (<25% signal change from day 3 to day 10, Table 9, FIG. 18), indicating that gene editing mediated by each individual sgRNA was well-tolerated. A notable exception is CR33, which had no detectable activity at day 10, although activity may be below the sensitivity of the Surveyor assay (est. ~1%).

TABLE 9

Measured activity of sgRNAs in human cells

| Target | sgRNA # | % modified alleles at day 3 | % modified alleles at day 10 | % change day 10/day 3 |
|---|---|---|---|---|
| Multiplex deletion of exon 51 | | | | |
| Int 50 | CR1 | 6.6 | 9.3 | 41.8 |
| Int 50 | CR2 | 10.3 | 14.0 | 36.2 |
| Ex 51 | CR4 | 11.9 | 14.4 | 21.3 |
| Int 51 | CR5 | 12.4 | 13.3 | 7.8 |
| Multiplex deletion of exons 45-55 | | | | |
| Int 44 | CR6 | 16.1 | 16.9 | 4.3 |
| Int 44 | CR33 | 1.3 | <1 | n.d. |
| Int 44 | CR34 | 13.2 | 11.0 | −16.6 |
| Int 55 | CR7 | 6.8 | 7.1 | 5.3 |
| Int 55 | CR35 | 22.5 | 20.9 | −7.1 |
| Int 55 | CR36 | 26.4 | 24.7 | −6.4 |
| Targeted frameshifts | | | | |
| Ex 45 | CR10 | 14.9 | 16.3 | 9.3 |
| Ex 45 | CR11 | <1 | <1 | n.d. |
| Ex 46 | CR12 | <1 | <1 | n.d. |
| Ex 46 | CR13 | 16.9 | 18.4 | 9.2 |
| Ex 47 | CR14 | 17.2 | 17.6 | 2.9 |
| Ex 47 | CR15 | 15.4 | 15.3 | −0.9 |
| Ex 48 | CR16 | 11.5 | 10.9 | −5.0 |
| Ex 48 | CR17 | <1 | <1 | n.d. |
| Ex 49 | CR18 | 1.8 | 2.2 | 20.1 |
| Ex 49 | CR19 | 33.7 | 38.4 | 13.9 |
| Ex 50 | CR20 | 14.9 | 13.7 | −7.6 |
| Ex 50 | CR21 | 24.1 | 20.8 | −13.5 |
| Ex 51 | CR3 | 13.0 | 16.7 | 28.0 |
| Ex 51 | CR31 | 18.9 | 16.9 | −10.2 |
| Ex 52 | CR22 | 25.9 | 20.3 | −21.6 |
| Ex 52 | CR23 | 25.2 | 24.0 | −4.8 |
| Ex 53 | CR24 | 24.8 | 23.6 | −4.6 |
| Ex 53 | CR25 | 2.6 | 2.9 | 9.5 |
| Ex 54 | CR26 | 24.5 | 22.0 | −10.1 |
| Ex 54 | CR27 | 13.4 | 12.6 | −5.9 |
| Ex 55 | CR28 | 21.6 | 19.8 | −8.4 |
| Ex 55 | CR29 | 19.2 | 19.6 | 2.2 |

Example 7

Figure 19A:
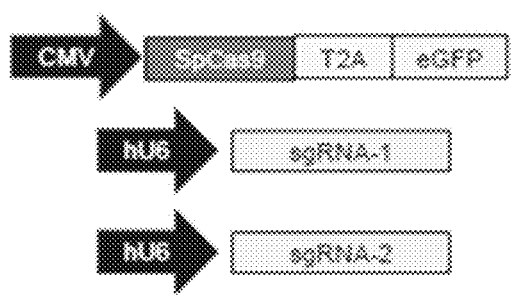
FIGS. 19A-19D show fluorescence-activated flow sorting to enrich genetically modified DMD myoblasts.
Figure 19B:
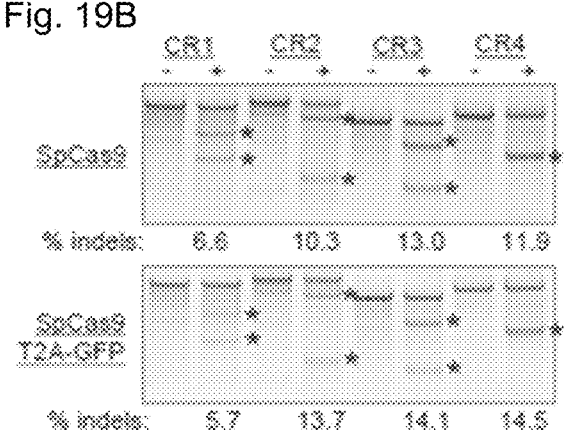
Figure 19C:
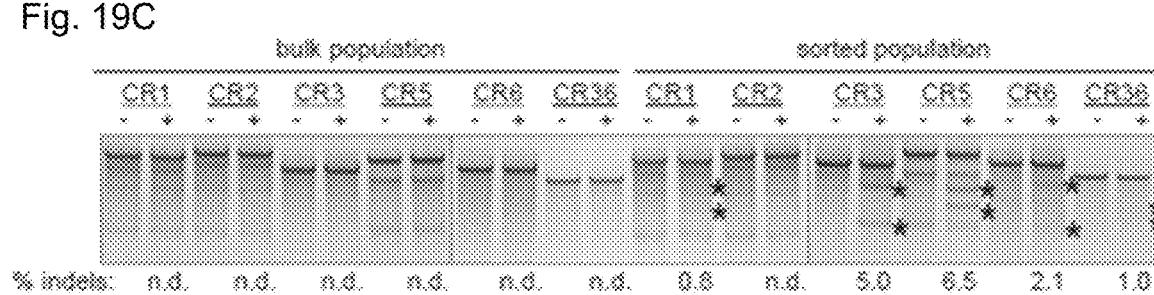
Figure 19D:
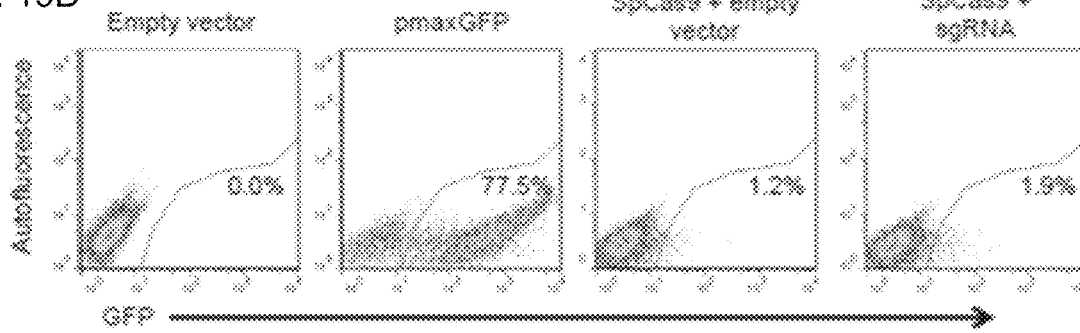

Enrichment of Gene-Edited Cells Using a Fluorescence-Based Reporter System sgRNAs were selected to correct specific mutations in DMD patient myoblast cell lines. After transfection into DMD myoblasts, unexpectedly low or undetectable gene modification activity was observed as measured by the Surveyor assay (FIG. 19C, bulk population). Flow cytometry was used to select for transfected cells co-expressing GFP through a 2A ribosomal skipping peptide linked to the SpCas9 protein (FIG. 19A). The addition of this fluorescent reporter to the SpCas9 expression vector did not seem to significantly impact gene editing activity in HEK293T cells (FIG. 19B). A low percentage of transfected myoblasts (~0.5-2%) expressed the fluorescent reporter at 3 days after electroporation, despite high transfection efficiencies of control GFP expression plasmids (typically >70%, FIG. 19D, pmaxGFP). Given the high levels of CRISPR/Cas9 activity in the easily transfected HEK293T line, inefficient transgene expression after electroporation of SpCas9-T2A-GFP and sgRNA constructs into the DMD cells may explain the low observed gene editing efficiencies in unsorted cells. After sorting the GFP-positive DMD myoblasts, a substantial increase was observed in detectable activity at most sgRNA target loci (FIG. 19C). Therefore, all subsequent experiments used cells sorted for SpCas9 expression by expression of this fluorescent reporter.

Example 8

Restoration of Dystrophin Expression by Targeted Frameshifts

Small insertions and deletions created by NHEJ DNA repair may be used to create targeted frameshifts to correct aberrant reading frames. A sgRNA, CR3, was designed to restore the dystrophin reading frame by introducing small insertions and deletions within exon 51 (FIGS. 16B, 20A). The types of insertions and deletions generated by CRISPR/Cas9 at this locus were assessed by Sanger sequencing of alleles from the genomic DNA of HEK293T cells co-transfected with expression plasmids for SpCas9 and the CR3 sgRNA (FIG. 20B). Notably, the insertions and deletions resulted in conversion to all three reading frames (FIGS. 20B, 20C). To demonstrate genetic correction in a relevant patient cell line, expression plasmids for SpCas9 and the CR3 sgRNA were electroporated into a DMD myoblast line with a deletion of exons 48-50 that is correctable by creating frameshifts in exon 51. The treated cells were sorted, verified to have gene modification activity by the Surveyor assay (CR3, FIG. 19C sorted population), and differentiated into myotubes to test for restored dystrophin expression. Expression of dystrophin protein was observed concomitant with the detectable nuclease activity (FIG. 20D). The *S. pyogenes* CRISPR/Cas9 system presents a powerful method to quickly generate targeted frameshifts to address a variety of patient mutations and restore expression of the human dystrophin gene.

Example 9

Figure 21A:
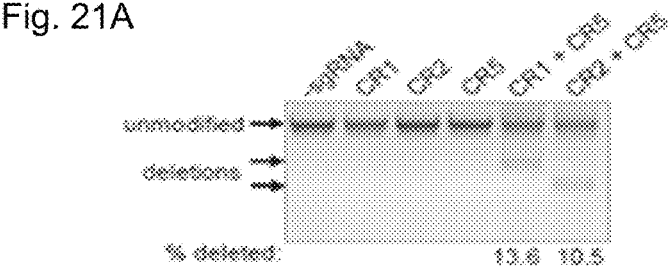
FIGS. 21A-21D show deletion of exon 51 from the human genome using multiplex CRISPR/Cas9 gene editing.
Figure 21B:
Figure 21C:
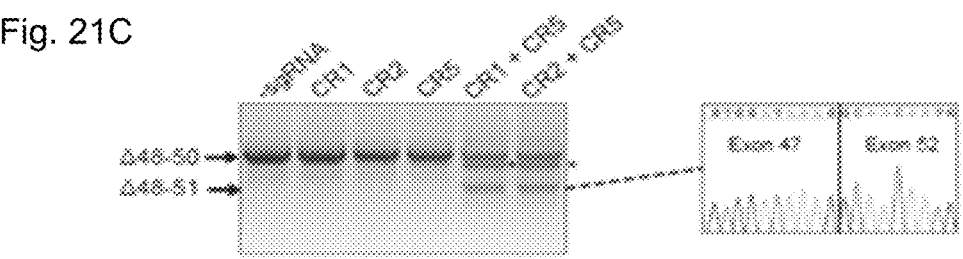
Figure 21D:

Multiplex CRISPR/Cas9 Gene Editing Mediates Genomic Deletion of Exon 51 and Rescues Dystrophin Protein Expression The multiplexing capability of the CRISPR/Cas9 system presents a novel method to efficiently generate genomic deletions of specific exons for targeted gene correction. DMD patient myoblasts with background deletions correctable by exon 51 skipping were treated with two combinations of sgRNAs flanking exon 51 (CR1/CR5 or CR2/CR5) and sorted to enrich for gene-edited cells as in FIGS. 19A-19D. As detected by end-point PCR of the genomic DNA from these treated cells, the expected genomic deletions were only present when both sgRNAs were electroporated into the cells with SpCas9 (FIG. 21A). Sanger sequencing confirmed the expected junction of the distal chromosomal segments (FIG. 21B) for both deletions. After differentiating the sorted myoblasts, a deletion of exon 51 from the mRNA transcript was detected only in the cells treated with both sgRNAs (FIG. 21C). Finally, restored dystrophin protein expression was detected in the treated cells concomitant with observed genome- and mRNA-level deletions of exon 51 (FIG. 21D).

Example 10

Dystrophin Rescue by a Multi-Exon Large Genomic Deletion

Figure 22A:
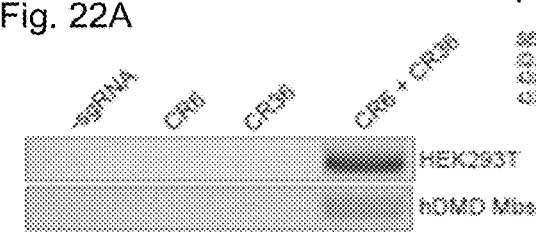
FIGS. 22A-22D show deletion of the entire exon 45-55 region in human DMD myoblasts by multiplex CRISPR/Cas9 gene editing.
Figure 22B:
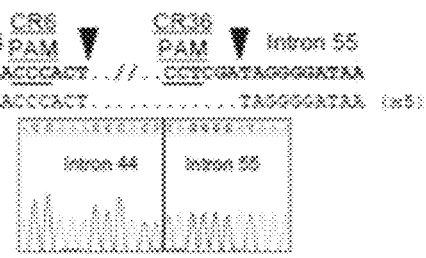
Figure 22C:
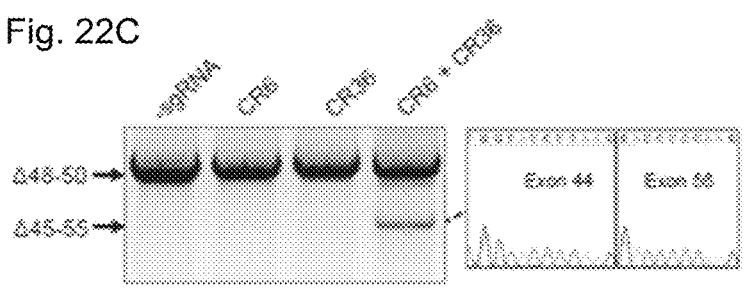
Figure 22D:
Figure 23:
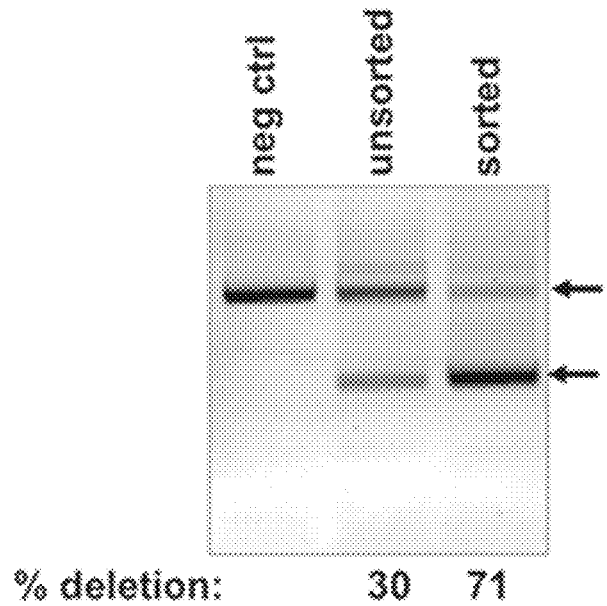
FIG. 23 shows verification of flow cytometry-based enrichment of gene-modified DMD myoblasts used for in vivo cell transplantation experiment. DMD myoblasts were treated with Cas9 with or without sgRNA expression vectors for CR1 and CR5 and sorted for GFP+ cells by flow cytometry. Deletions at the exon 51 locus were detected by end-point PCR using primers flanking the locus. Neg ctrl: DMD myoblasts treated with Cas9 only and sorted for GFP+ cells.

Although addressing patient-specific mutations is a powerful use of the CRISPR/Cas9 system, it would be advantageous to develop a single method that can address a myriad of common patient deletions. For example, a promising strategy is to exclude the entire exon 45-55 region as a method to correct up to 62% of known patient deletions. Multiplex CRISPR/Cas9-based gene editing was tested to determine if it may be able to generate efficient deletion of the exon 45-55 locus in human cells. After transfection into HEK293T cells, the expected deletion of 336,000 bp was detected by PCR of the genomic DNA (FIG. 22A). Similarly, this deletion was detected by PCR of the genomic DNA from SpCas9/sgRNA-treated DMD patient cells harboring a background deletion of exons 48-50 of unknown length (FIG. 22A). Sanger sequencing of this deletion band from the genomic DNA of treated DMD cells revealed the expected junctions of intron 44 and intron 55 immediately adjacent to the sgRNA target sites (FIG. 22B). After differentiation of treated DMD cells, the expected deletion of exons 45-55 was detected in the dystrophin mRNA transcript and verified to be a fusion of exons 44 and 56 by Sanger sequencing (FIG. 22C). Restored protein expression was observed by western blot in the sorted cell populations containing the CRISPR/Cas9-induced deletion of exons 45-55 from the genome and resulting mRNA transcripts (FIG. 22D). These data demonstrate that multiplex CRISPR/Cas9 editing presents a single universal method to restore the dystrophin reading frame in more than 60% of DMD patient mutations.

Example 11

Transplantation of Corrected Myoblasts into Immunodeficient Mice

Figure 24:
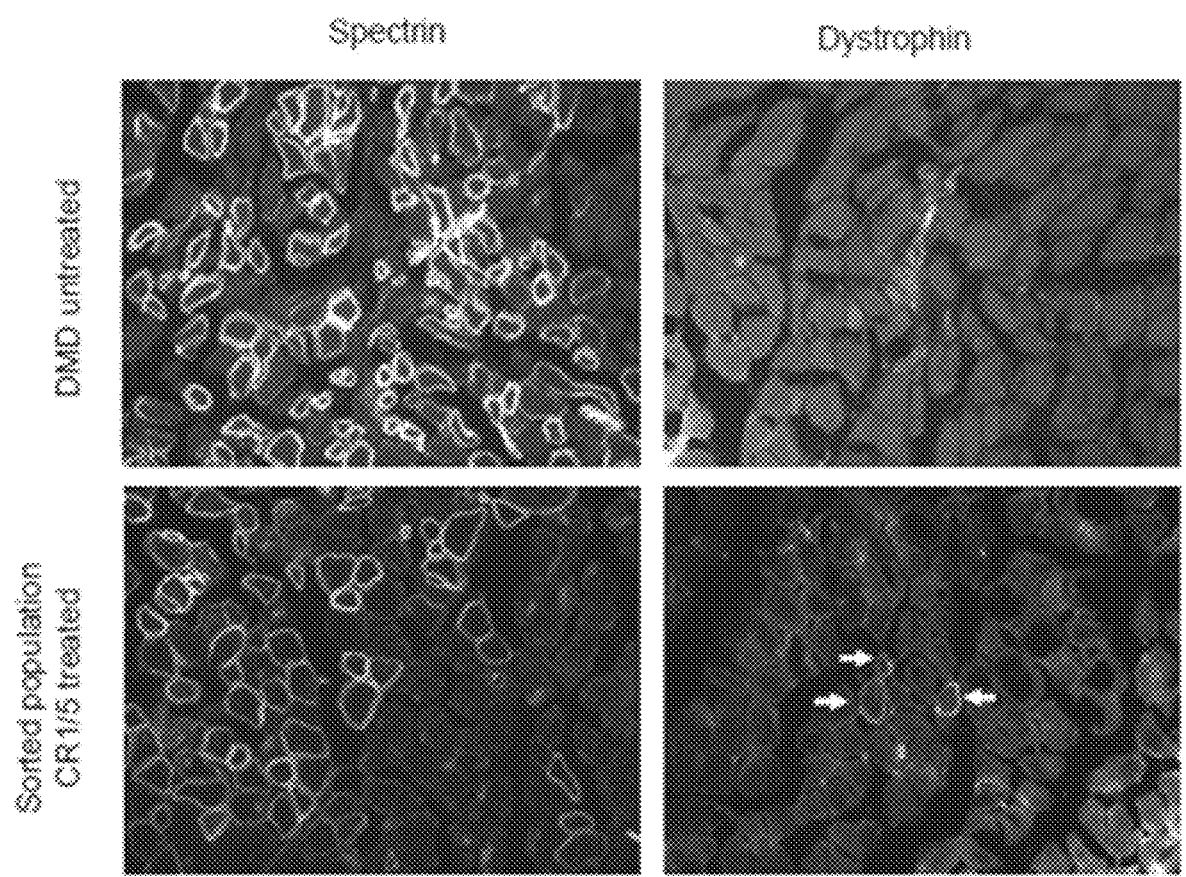
FIG. 24 shows expression of restored human dystrophin in vivo following transplantation of CRISPR/Cas9-treated human DMD myoblasts into immunodeficient mice. Human 448-50 DMD myoblasts were treated with SpCas9, CR1, and CR5 to delete exon 51 and sorted for GFP expression as shown in FIG. 19. These sorted cells and untreated control cells were injected into the hind limbs of immunodeficient mice and assessed for human-specific protein expression in muscle fibers after 4 weeks post-transplantation. Cryosections were stained with anti-human spectrin, which is expressed by both uncorrected and corrected myoblasts that have fused into mouse myofibers, or anti-human dystrophin antibodies as indicated. White arrows indicate muscle fibers positive for human dystrophin.
Figure 25A:
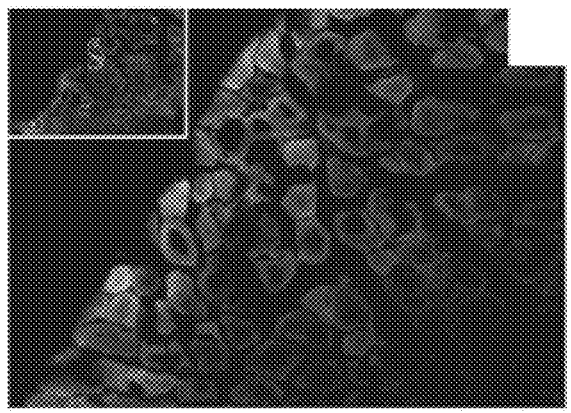
FIGS. 25A-25F show additional immunofluorescence images probing human dystrophin expression. Serial sections from regions stained with anti-human spectrin are shown inset in top left.
Figure 25B:
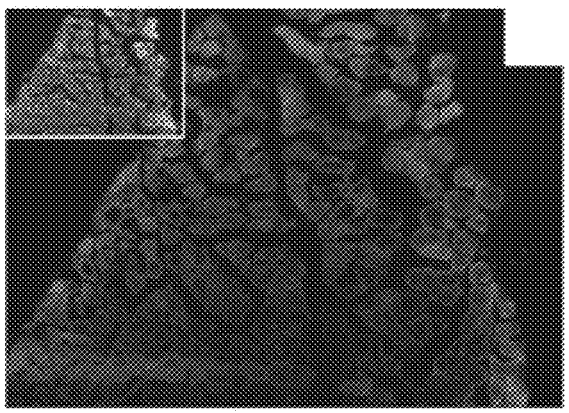
Figure 25C:
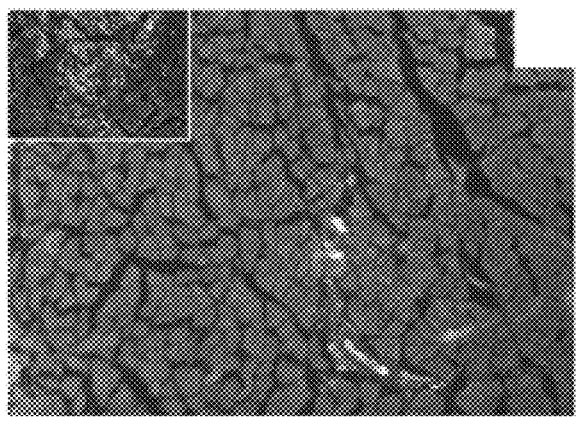
Figure 25D:
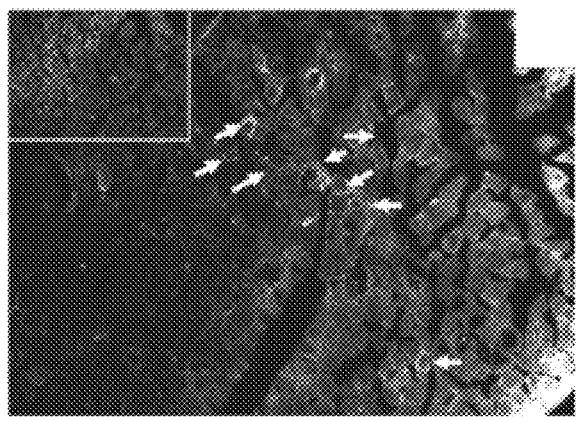
Figure 25E:
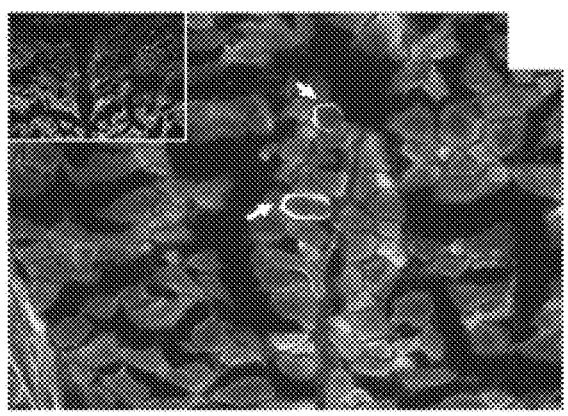
Figure 25F:
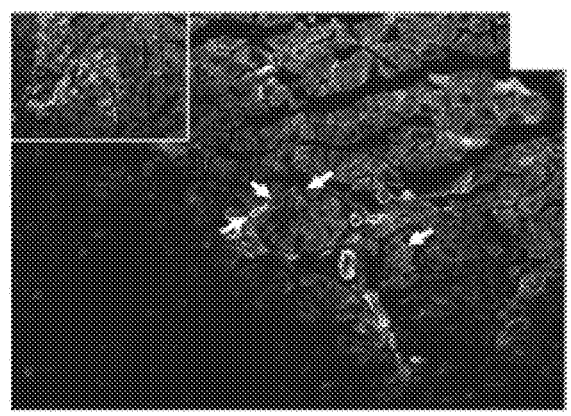

A promising method for DMD therapy is to correct a population of autologous patient muscle progenitor cells that can be engrafted into the patient's skeletal muscle tissue to rescue dystrophin expression. To demonstrate the ability of the corrected cells to express human dystrophin in vivo, a population of DMD myoblasts that were treated with sgRNAs CR1 and CR5, which flank exon 51, was transplanted and sorted for expression of GFP as before (FIGS. 19A-19D, FIG. 23). After 4 weeks, muscle fibers positive for human spectrin, which is expressed by both corrected and uncorrected cells, were detected in cryosections of injected muscle tissue (FIG. 24). A number of these fibers were also positive for human dystrophin with expression localized to the sarcolemma, demonstrating functional gene correction in these cells (FIG. 24, FIGS. 25A-25F). No fibers positive for human dystrophin were observed in sections from mice injected with the untreated DMD myoblasts (FIG. 24, FIGS. 25A-25F), indicating that the CRISPR/Cas9-modified cells were the source of human dystrophin expression.

Example 12

Off-target and Cytotoxicity Analysis

Figure 27:
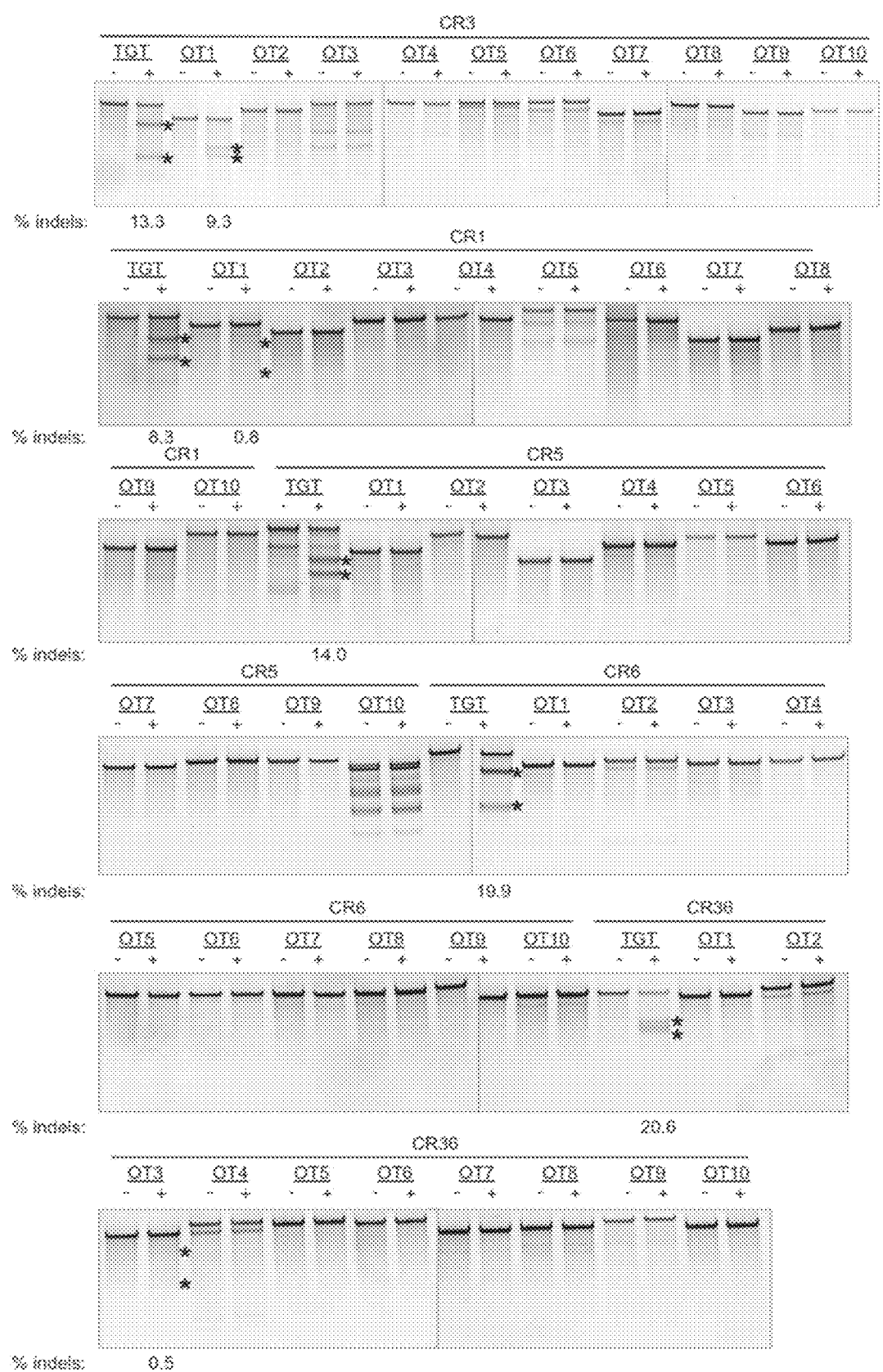
FIG. 27 shows images of TBE-PAGE gels used to quantify Surveyor assay results to measure on-target and off-target gene modification in Table 4. Asterisks mark expected sizes of bands indicative of nuclease activity.

The relative cytotoxicity of the CRISPR/Cas9 system was assessed in human cells for select sgRNAs by adapting a flow cytometry-based GFP retention assay as previously described (Ousterout et al., Mol Ther 21:1718-1726 (2013)). Minimal cytotoxicity was observed for SpCas9 co-expressed with or without sgRNAs after transfection into human cells (FIG. 26A). Publicly available tools are available to assess and prioritize potential CRISPR/Cas9 activity at off-target loci based on predicted positional bias of a given mismatch in the sgRNA protospacer sequence and the total number of mismatches to the intended target site (Hsu et al., Nat Biotechnol 31:827-826 (2013)). This public webserver was used to predict the most likely off-target sites for the sgRNAs used to correct the dystrophin gene in this study (Table 4). The top ten potential off-target sites were assessed by the Surveyor assay in HEK293T cells treated with SpCas9 and individual sgRNA expression cassettes for CR1, CR3, CR5, CR6, or CR36. CR1, CR3 and CR36 each had one of these ten predicted off-target loci demonstrate significant levels of gene modification (Table 4 and FIG. 27). Interestingly, the CR3 off-target sequence had substantial homology and similar modification frequencies to the intended on-target (9.3% at OT-1 vs. 13.3% at intended site (Table 4 and FIG. 27). Notably, CR3-OT1 was the only one of these three off-target sites to show significant levels of activity in the sorted hDMD cells by the Surveyor assay (FIG. 26B).

Figure 28A:
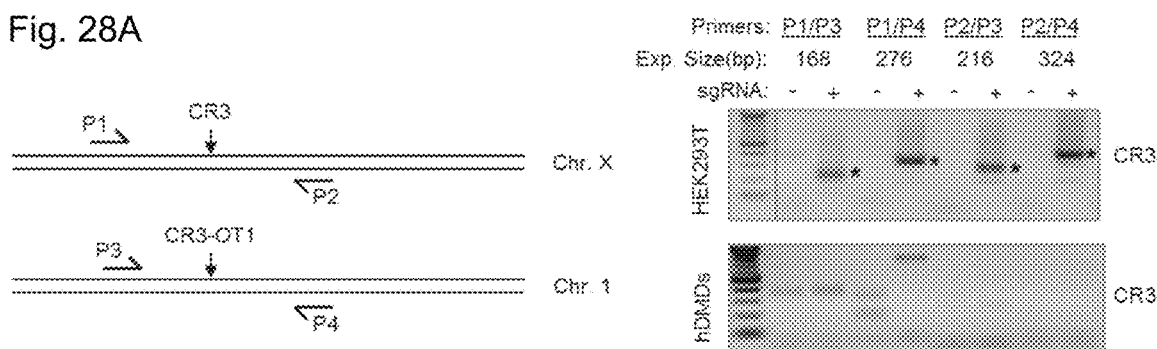
FIGS. 28A-28C show end-point nested PCR to detect chromosomal translocations caused by CRISPR/Cas9 off-target activity for CR3 and CR6/CR36 in human cells. Nested end-point PCR analysis was used to detect translocations in HEK293T or sorted hDMD cells treated with Cas9 and CR3 as indicated (FIG. 28A), HEK293T cells treated with Cas9 and CR36 alone (FIG. 28B), or sorted hDMD cells treated with Cas9, CR6, and CR36 expression cassettes (FIG. 28C). The second nested PCR reaction for translocation was amplified using custom primers for each predicted translocation locus to maximize specificity (See Table 4). The schematic depicts the relative location of nested primer pairs used to probe for the presence of translocations. Each possible translocation event was first amplified from genomic DNA isolated from cells treated with or without the indicated sgRNA(s). A second nested PCR reaction was performed using primers within the predicted PCR amplicons that would result from translocations. Expected size was estimated based on the indicated primer binding site and the predicted sgRNA cut site at each locus. *indicates bands detected at the expected size and verified by Sanger sequencing from each end. # indicates amplicons in which Sanger sequencing showed sequences other than the predicted translocation, likely a result of mispriming during the nested PCR.
Figure 28B:
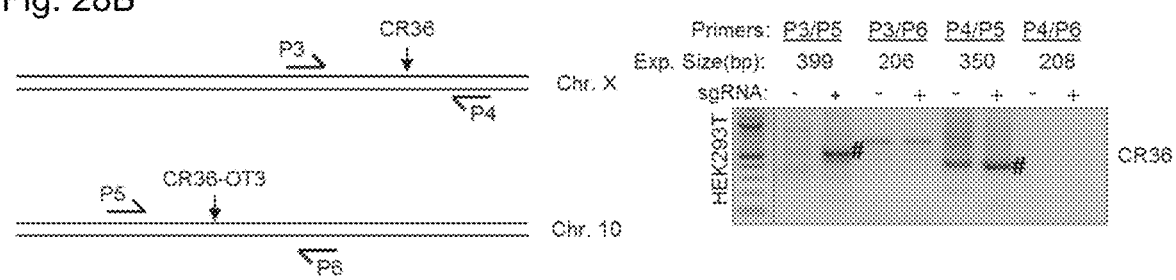
Figure 28C:
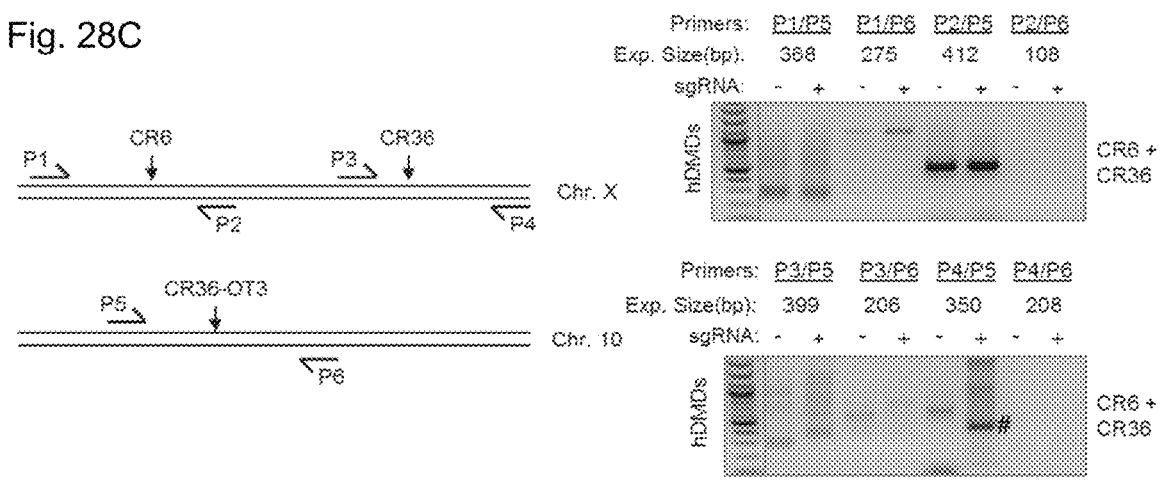
Figure 29:
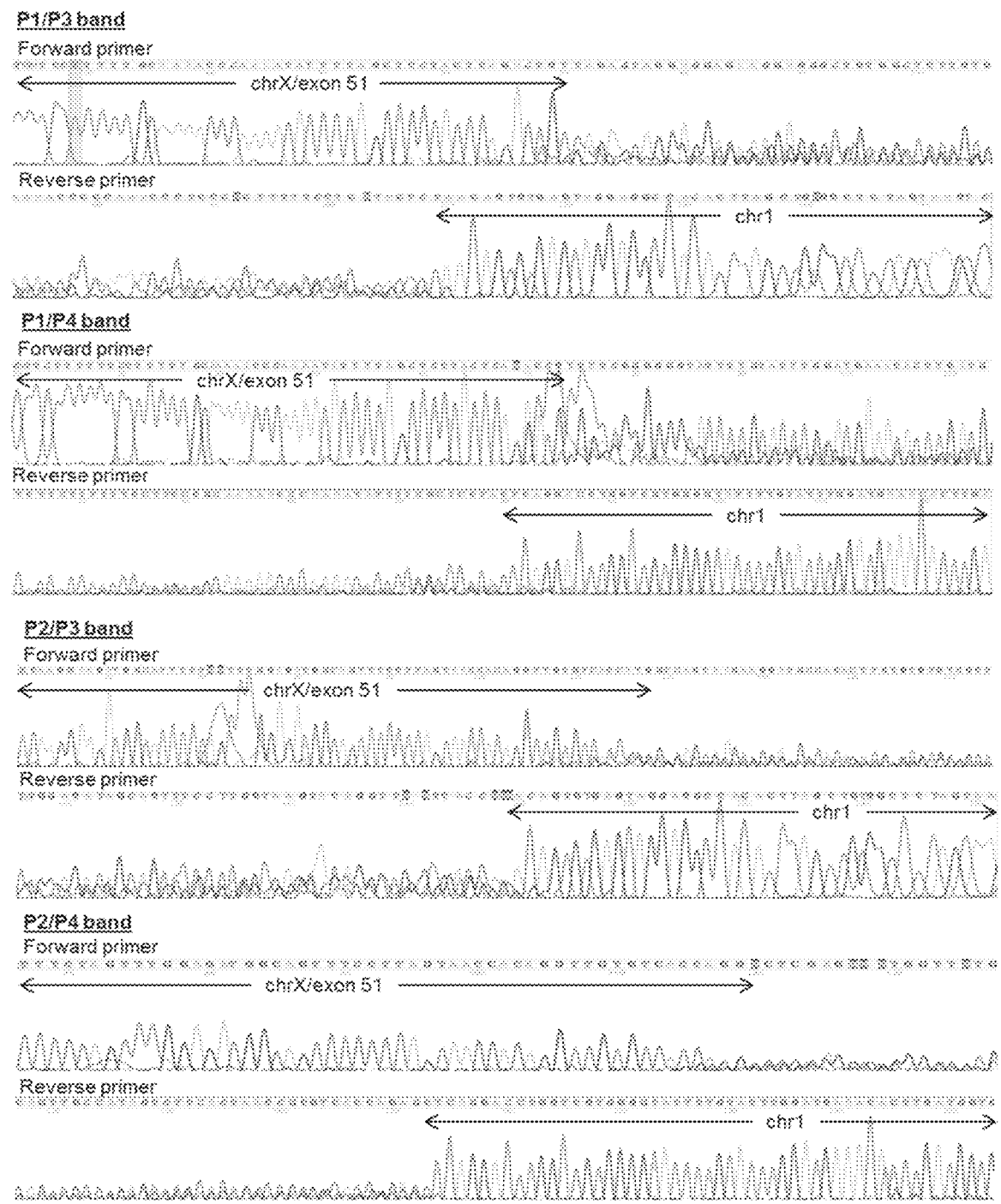
FIG. 29 shows Sanger sequencing chromatograms (SEQ ID NOS: 647-654, respectively, in order of appearance) for bands detected in FIGS. 28A-28C resulting from translocations between CR3 and CR3-OT1, on chromosomes X and 1, respectively, in HEK293T cells treated with Cas9 and CR3 gene cassettes. Arrows show regions of homology to the indicated chromosome nearby the expected break points caused by the appropriate sgRNAs. Note that sequencing reads become out of phase near the break point due to the error-prone nature of DNA repair by non-homologous end-joining.
Figure 30:
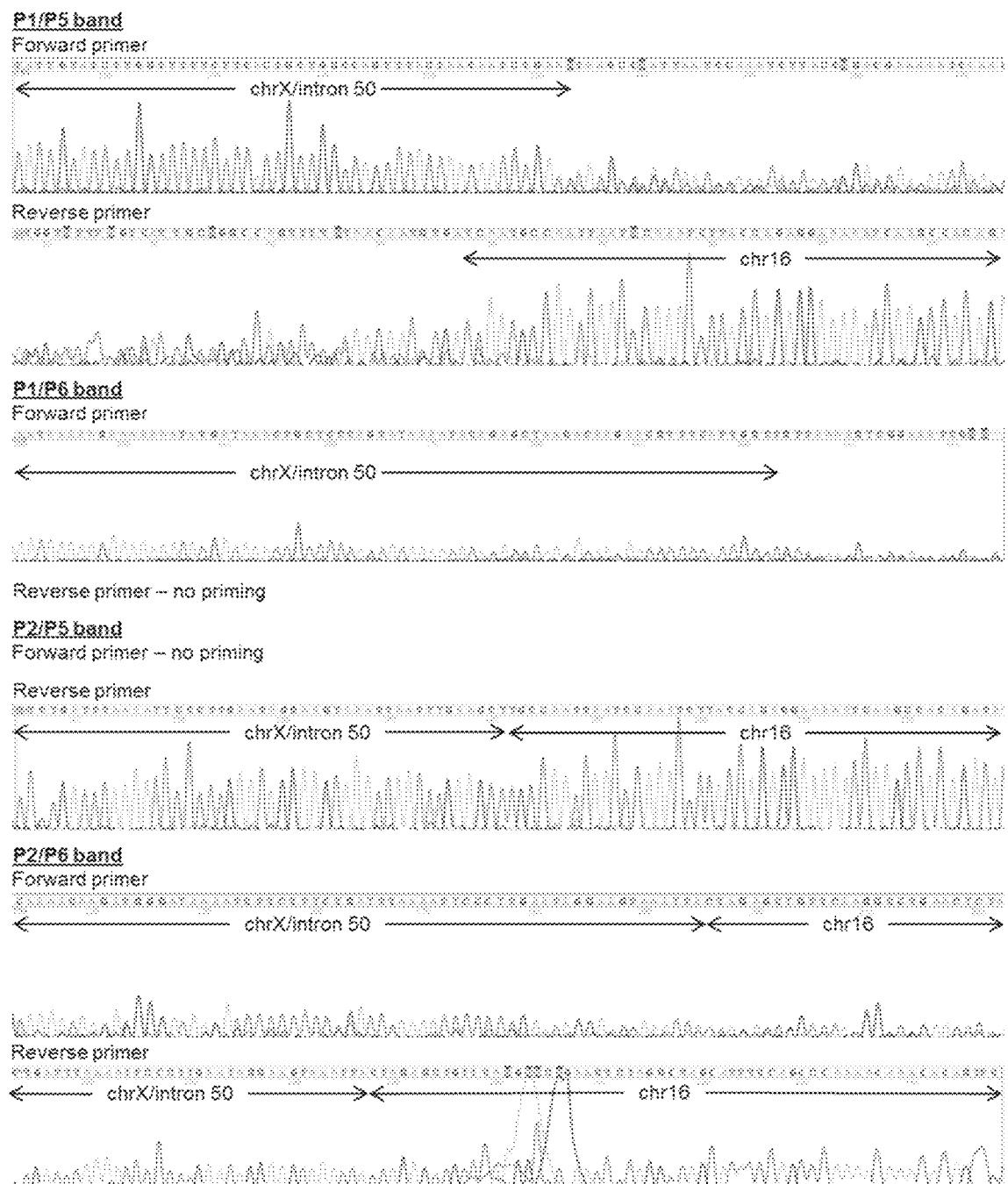
FIG. 30 shows Sanger sequencing chromatograms (SEQ ID NOS: 655-660, respectively, in order of appearance) for bands detected in FIG. 26C resulting from translocations between CR1 and CR1-OT1, on chromosomes X and 16, respectively, in HEK293T cells treated with Cas9 and CR1 gene cassettes. Arrows show regions of homology to the indicated chromosome nearby the expected break points caused by the appropriate sgRNAs. Note that sequencing reads become out of phase near the break point due to the error-prone nature of DNA repair by non-homologous end-joining.

Nuclease activity at off-target sites may cause unintended chromosomal rearrangements by distal re-ligation between cleaved target and off-target loci on distinct chromosomes. This presents a significant concern for deletion-based gene correction strategies due to the increased potential for off-target activity by using two or more nucleases, such as in multiplex CRISPR/Cas9 gene editing. Potential translocations were probed for using a highly sensitive nested genomic PCR assay to detect translocations at the validated off-target loci (Table 4) during both single and multiplex CRISPR/Cas9 editing strategies. Using this assay, translocations were readily detected between on-target and off-target sites in the model HEK293T cell line that also shows high levels of off-target activity (FIG. 26C and FIG. 28A, 28B). Sanger sequencing of the PCR amplicons confirmed the identity of the predicted translocation event for each primer pair (FIGS. 29-30). A subset of the translocations detected in the HEK293T cells were also detectable by nested PCR in the sorted hDMD myoblasts, although the signal was considerably weaker and the sequence identity was not confirmed due to low yield of product (FIG. 26D and FIGS. 28A, 28C). Translocations were not detected using this assay in HEK293T or sorted hDMD cells treated with CR6 or CR6/CR36, respectively, (FIGS. 28A-28C) that had low levels of off-target activity at CR6-OT3 only in HEK293T cells (Table 4). These results underscore the importance of selecting highly specific sgRNAs, particularly for multiplex editing applications, and show that this approach can benefit from ongoing efforts to improve the specificity of the CRISPR/Cas9 system. These data suggest that the selected sgRNAs are able to correct the dystrophin gene without significant toxicity and with only a single strongly predicted off-target site with detectable levels of activity.

Example 13

Discussion

Genome editing is a powerful tool for correcting genetic disease and the recent development of the CRISPR/Cas9 system is dramatically accelerating progress in this area. The correction of DMD, the most common genetic disease that also currently has no approved therapeutic options, was demonstrated. Many gene- and cell-based therapies for DMD are in preclinical development and clinical trials, and genome editing methods are compatible with many of these approaches. For example, genome editing may be combined with patient-specific cell-based therapies for DMD. The CRISPR/Cas9 system may function in human pluripotent stem cells and other human cell lines, as well as human skeletal myoblasts, as shown. Importantly, gene editing with CRISPR/Cas9 did not abolish the myogenic capacity of these cells, as demonstrated by efficient dystrophin expression in vitro and in vivo after transplantation into immunodeficient mice. Thus, this strategy should be compatible with cell-based therapies for DMD.

Additionally, an enriched pool of gene-corrected cells demonstrated expression of human dystrophin in vivo following engraftment into immunodeficient mice. CRISPR/Cas9 gene editing did not have significant toxic effects in human myoblasts as observed by stable gene editing frequencies and minimal cytotoxicity of several sgRNAs. However, gene editing activity was confirmed at three out of 50 predicted off-target sites across five sgRNAs and CRISPR/Cas9-induced chromosomal translocations between on-target and off-target sites were detectable. The CRISPR/Cas9 technology is an efficient and versatile method for correcting a significant fraction of dystrophin mutations and can serve as a general platform for treating genetic disease.

Additionally, direct transfection of the sgRNA and Cas9 mRNA, in contrast to the plasmid-based delivery method used here, may be used to increase specificity and safety by reducing the duration of Cas9 expression and eliminating the possibility of random plasmid integration. Alternatively, delivery of the CRISPR/Cas9 system directly to skeletal and/or cardiac muscle by viral, plasmid, or RNA delivery vectors may be used for in vivo genome editing and translation of this approach. The large size of S. pyogenes Cas9 gene (~4.2 kilobases) presents a challenge to its use in size-restricted adeno-associated viral vectors. However, Cas9 genes from other species, such as N. meningitidis and S. thermophilus, are short enough to efficiently package both Cas9 and sgRNA expression cassettes into single AAV vectors for in vivo gene editing applications.

The CRISPR/Cas9 system enabled efficient modification of nearly 90% of tested targets, consistent with other reports of robust activity of this system at diverse loci. The robustness and versatility of this technology is a significant advancement towards at-will creation of patient-specific gene editing. Low levels of dystrophin, including as little as 4% of wild-type expression, may be sufficient to improve survival, motor function, and cardiac function in a mouse model. The levels of CRISPR/Cas9 activity may be sufficient for therapeutic benefit.

The use of multiplexing with CRISPR/Cas9 to delete exons also presents a unique set of opportunities and challenges. The deletion of complete exons from the genome to restore dystrophin expression was performed, in contrast to restoring the reading frame of the dystrophin gene with small indels generated by NHEJ-based DNA repair following the action of a single nuclease. The protein product of the edited gene is predictable and already characterized in Becker muscular dystrophy patients with the naturally occurring deletion, in contrast to the random indels created by intraexonic action of a single nuclease that will lead to the creation of novel epitopes from each DNA repair event. Furthermore, the product resulting from the exon deletions will lead to restored dystrophin for every successful gene editing event, whereas modifying the gene with random indels within exons will only restore the reading frame in the one-third of editing events that leads to the correct reading frame.

All of the sgRNAs tested were not associated with significant cytotoxic effects in human cells. Three potential off-target sites out of 50 total tested sites for the five sgRNAs used were identified to restore dystrophin expression. Furthermore, chromosomal translocations between the intended on-target sites and these off-target sites were detectable by highly sensitive nested PCR assays in HEK293T cells expressing high levels of Cas9 and sgRNAs. Notably, the off-target activity and translocations identified in HEK293T cells, which is an immortalized and aneuploid cell line that expresses very high levels of Cas9 and sgRNA, did not occur at as high a level and in some cases were undetectable in the hDMD myoblasts. Importantly, this level of specificity may be tolerable given the severity of DMD, the lack of an apparent cytotoxic effect in human cells Example 14

An engineered AAV capsid, termed SASTG (FIG. 34; SEQ ID NOs: 436 and 437), was developed for enhanced cardiac and skeletal muscle tissue tropism (Piacentino et al. (2012) Human Gene Therapy 23:635-646). A ZFN targeting the Rosa26 locus ("Rosa26 ZFN"; FIG. 33; SEQ ID NO: 434 and 435) was shown to be highly active in mouse cells (Perez-Pinera et al. Nucleic Acids Research (2012) 40:3741-3752). AAV-SASTG vectors encoding the Rosa26 ZFN protein were designed and subsequently generated and purified by the UNC Viral Vector Core. The Surveyor assay (Guschin et al., *Methods Mol Biol* 649, 247-256 (2010)) was used to demonstrate NHEJ mutagenesis at the Rosa26 locus following delivery of AAV-SASTG Rosa26 ZFNs in cultured C2C12 myoblasts that were actively cycling or forced into differentiation by serum removal (not shown).

Figure 31:
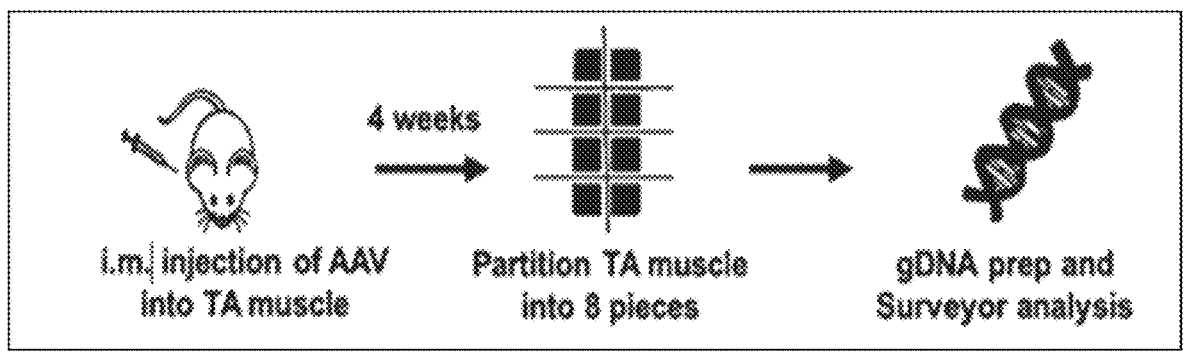
FIG. 31 shows an overview of in vivo AAV injections and tissue harvest.
Figure 32A:
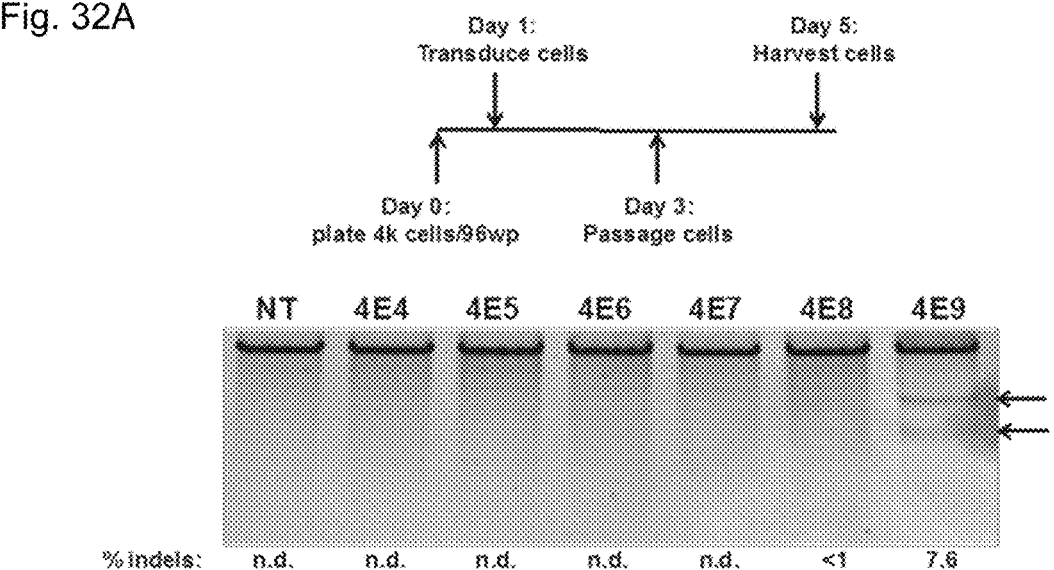
FIGS. 32A-32C show Surveyor analysis of Rosa26 ZFN activities in skeletal muscle in vitro and in vivo following delivery of AAV-SASTG-ROSA. Arrows indicate expected bands resulting from Surveyor cleavage. n.d.: not detected.
Figure 32B:
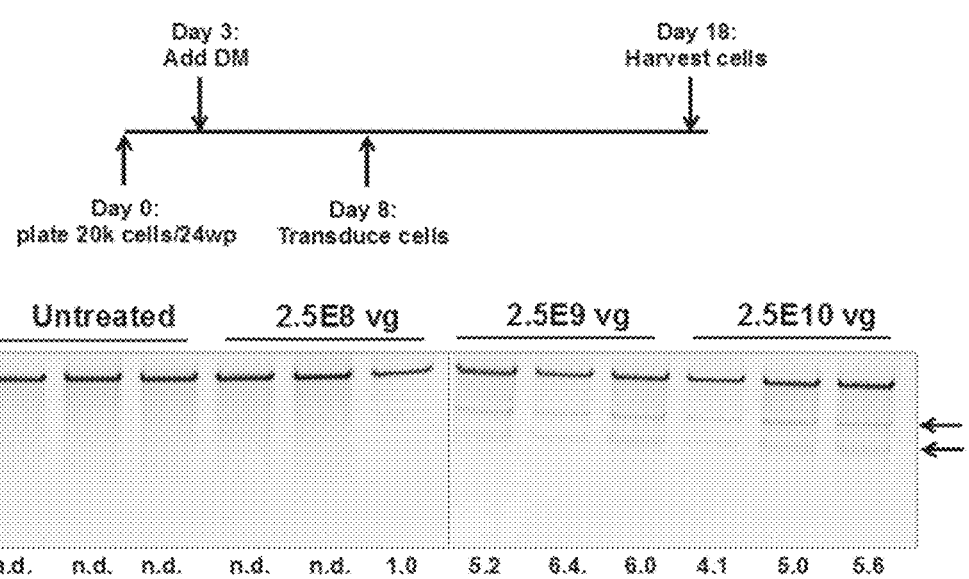
Figure 32C:
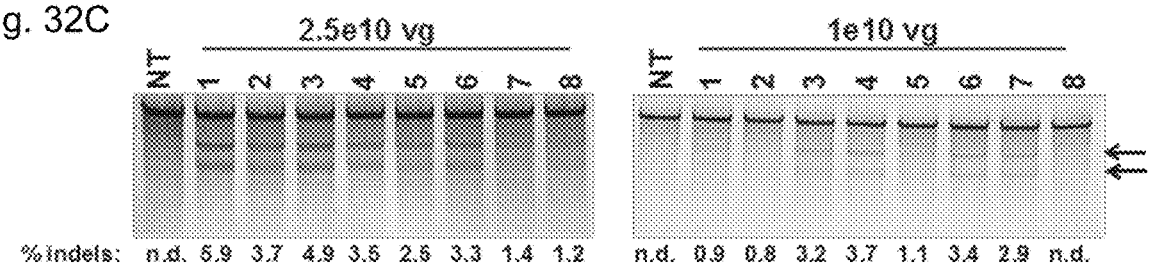

To verify that adult post-mitotic skeletal muscle were efficiently targeted by the Rosa26 ZFN following AAV transfer, AAV-SASTG vectors encoding the Rosa26 ZFN were injected directly into the tibialis anterior (TA) muscle of 6 week old C57BL6/J mice at titers of 1e10 vector genomes (vg) or 2.5e10 vg per muscle. Mice were sacrificed 4 weeks after injection and the TA muscles were harvested and partitioned into several fragments for genomic DNA extraction and analysis (FIG. 31). Genomic DNA was PCR amplified and subjected to the Surveyor assay to detect NHEJ mutations characteristic of ZFN mutagenesis at the Rosa26 target site (FIGS. 32A-32C). FIGS. 32A-32C show Surveyor analysis of Rosa26 ZFN activities in skeletal muscle in vitro and in vivo following delivery of AAV-SASTG-ROSA. Proliferating C2C12s were transduced with the indicated amount of virus and harvested at 4 days post-infection (FIG. 32A). C2C12s were incubated in differentiation medium for 5 days and then transduced with the indicated amount of AAV-SASTG-ROSA virus in 24 well plates (FIG. 32B). Samples were collected at 10 days post-transduction. The indicated amount of AAV-SASTG-ROSA was injected directly into the tibialis anterior of C57BL/6J mice and muscles were harvested 4 weeks post-infection. The harvested TA muscles were partitioned into 8 separate pieces for genomic DNA analysis, each shown in a separate lane (FIG. 32C). Notably, high levels of gene modification were detected in all fragments at the highest dose (2.5e10 vg).

Example 15

AAV-CRISPR Constructs for Targeting Mutant Dystrophin Genes

AAV constructs are designed to therapeutically correct mutations of the dystrophin gene that cause Duchenne muscular dystrophy and skeletal and cardiac muscle degeneration. CRISPR/Cas9 systems can be delivered using the AAV to restore the dystrophin reading frame by deleting exon 51, deleting exons 45-55, disrupting splice donor or acceptor sites, or creating frameshifts within exon 51 (Ousterout et al., Molecular Therapy 2013) to restore the dystrophin reading frame and protein expression. The CRISPR/Cas9 system will include a Cas9 having a sequence of SEQ ID NO: 64 or 114 (See FIGS. 40 and 41). gRNAs that could be combined with these Cas9s, targeting their respective PAM sequences, are provided (see FIGS. 40 and 41; see also Tables 2 and 3).

Example 16

Generation of Induced Neurons (iNs)

The generation of induced neurons (iNs) from other cell lineages has potential applications in regenerative medicine and the study of neurological diseases. The direct conversion of mouse embryonic fibroblasts (MEFs) to functional neuronal cells may occur through the delivery of a cocktail of three neuronal transcription factors—BRN2, ASCL1, and MYT1L (BAM factors, FIG. 48). Other methods may include additional factors to induce various neuronal subtypes. These experiments require transcription factors to be delivered ectopically, and the activation of the corresponding endogenous loci to sustain the neuronal phenotype. The CRISPR/Cas9 system was engineered as a versatile transcription factor to activate endogenous genes in mammalian cells with the capacity to target any promoter in the genome through an RNA-guided mechanism (FIGS. 49A,49B).

Materials & Methods. The CRISPR/Cas9-transcription factor was used to activate the endogenous genes encoding ASCL1 and BRN2 to directly reprogram MEFs to functional induced neurons.

Cell Culture: MEFs were seeded in either 24-well TCPS plates or on poly-D-lysine/laminin-coated coverslips. Following transduction of dCas9-VP64 and transfection of the gRNAs (see Tables 10 and 11 for sequences of gRNAs), the cells were cultured in MEF medium (Adler et al. Mol Ther Nucleic Acids 1:e32 (2012)) for 24 hrs and then transferred to N3 neural induction medium (Vierbuchen et al. *Nature* 463:1035-1041 (2010)) for the duration of the experiment (FIG. 49B).

TABLE 10 gRNAs for mouse ASCL1 (CR13):

| Oligo (5' to 3') | 5' overhang | | ASCL1 Target Sequence | SEQ ID NO |
|---|---|---|---|---|
| CR13-1_S: | cacc | G | CAGCCGCTCGCTGCAGCAG (SEQ ID NO: 468) | 492 |
| CR13-1_AS: | AAAC | | CTGCTGCAGCGAGCGGCTG C (SEQ ID NO: 469) | 493 |
| CR13-2_S: | cacc | G | GCTGGGTGTCCCATTGAAA (SEQ ID NO: 470) | 494 |
| CR13-2_AS: | AAAC | | TTTCAATGGGACACCCAGC C (SEQ ID NO: 471) | 495 |
| CR13-3_S: | cacc | G | GTTTATTCAGCCGGGAGTC (SEQ ID NO: 472) | 496 |
| CR13-3_AS: | AAAC | | GACTCCCGGCTGAATAAAC C (SEQ ID NO: 473) | 497 |

TABLE 10-continued gRNAs for mouse ASCL1 (CR13):

| Oligo (5' to 3') | 5' overhang | | ASCL1 Target Sequence | SEQ ID NO |
|---|---|---|---|---|
| CR13-4_S: | cacc | G | TGGAGAGTTTGCAAGGAGC (SEQ ID NO: 474) | 498 |
| CR13-4_AS: | AAAC | | GCTCCTTGCAAACTCTCCA C (SEQ ID NO: 475) | 499 |
| CR13-5_S: | cacc | G | CCCTCCAGACTTTCCACCT (SEQ ID NO: 476) | 500 |
| CR13-5_AS: | AAAC | | AGGTGGAAAGTCTGGAGGG C (SEQ ID NO: 477) | 501 |
| CR13-6_S: | cacc | G | AATTTTCTTCCAAGTTCTC (SEQ ID NO: 478) | 502 |
| CR13-6_AS: | AAAC | | GAGAACTTGGAAGAAAATT C (SEQ ID NO: 479) | 503 |
| CR13-7_S: | cacc | G | CTGCGGAGAGAAGAAAGGG (SEQ ID NO: 480) | 504 |
| CR13-7_AS: | AAAC | | CCCTTTCTTCTCTCCGCAG C (SEQ ID NO: 481) | 505 |
| CR13-8_S: | cacc | G | AGAGCCACCCCTGGCTCC (SEQ ID NO: 482) | 506 |
| CR13-8_AS: | AAAC | | GGAGCCAGGGGTGGCTCT C (SEQ ID NO: 483) | 507 |
| CR13-9_S: | cacc | G | cgaagccaaccgcggcggg (SEQ ID NO: 484) | 508 |
| CR13-9_AS: | AAAC | | cccgccgcggttggcttcg C (SEQ ID NO: 485) | 509 |
| CR13-10_S: | cacc | G | agagggaagacgatcgccc (SEQ ID NO: 486) | 510 |
| CR13-10_AS: | AAAC | | gggcgatcgtcttccctct C (SEQ ID NO: 487) | 511 |
| CR13-11_S: | cacc | G | ccccttttaactttcctccg (SEQ ID NO: 488) | 512 |
| CR13-11_AS: | AAAC | | cggaggaaagttaaagggg C (SEQ ID NO: 489) | 513 |
| CR13-12_S: | cacc | G | gcagccccgcttccttcaa (SEQ ID NO: 490) | 514 |
| CR13-12_AS: | AAAC | | ttgaaggaagcggggctgc C (SEQ ID NO: 491) | 515 |

TABLE 11 gRNAs for mouse BRN2 (CR16):

| Oligo (5' to 3') | 5' overhang | | BRN2 Target Sequence | SEQ ID NO |
|---|---|---|---|---|
| CR16-1_S: | cacc | G | CGAGAGCGAGAGGAGGGAG (SEQ ID NO: 516) | 540 |
| CR16-1_AS: | AAAC | | CTCCCTCCTCTCGCTCTCG C (SEQ ID NO: 517) | 541 |
| CR16-2_S: | cacc | G | GAGAGAGCTTGAGAGCGCG (SEQ ID NO: 518) | 542 |

TABLE 11-continued gRNAs for mouse BRN2 (CR16):

| Oligo (5' to 3') | 5' overhang | BRN2 Target Sequence | SEQ ID NO |
|---|---|---|---|
| CR16-2_AS: | AAAC | CGCGCTCTCAAGCTCTCTC C (SEQ ID NO: 519) | 543 |
| CR16-3_S: | cacc G | GGTGGAGGGGCGGGGCCC (SEQ ID NO: 520) | 544 |
| CR16-3_AS: | AAAC | GGGCCCCGCCCCCTCCACC C (SEQ ID NO: 521) | 545 |
| CR16-4_S: | cacc G | GGTATCCACGTAAATCAAA (SEQ ID NO: 522) | 546 |
| CR16-4_AS: | AAAC | TTTGATTTACGTGGATACC C (SEQ ID NO: 523) | 547 |
| CR16-5_S: | cacc G | CCAATCACTGGCTCCGGTC (SEQ ID NO: 524) | 548 |
| CR16-5_AS: | AAAC | GACCGGAGCCAGTGATTGG C (SEQ ID NO: 525) | 549 |
| CR16-6_S: | cacc G | GGCGCCCGAGGGAAGAAGA (SEQ ID NO: 526) | 550 |
| CR16-6_AS: | AAAC | TCTTCTTCCCTCGGCGCC C (SEQ ID NO: 527) | 551 |
| CR16-7_S: | cacc G | GGGTGGGGTACCAGAGGA (SEQ ID NO: 528) | 552 |
| CR16-7_AS: | AAAC | TCCTCTGGTACCCCCACCC C (SEQ ID NO: 529) | 553 |
| CR16-8_S: | cacc G | CCGGGGACAGAAGAGAGGG (SEQ ID NO: 530) | 554 |
| CR16-8_AS: | AAAC | CCCTCTCTTCTGTCCCCGG C (SEQ ID NO: 531) | 555 |
| CR16-9_S: | cacc G | gagagagagtgggagaagc (SEQ ID NO: 532) | 556 |
| CR16-9_AS: | AAAC | gcttctcccactctctctc C (SEQ ID NO: 533) | 557 |
| CR16-10_S: | cacc G | aaagtaactgtcaaatgcg (SEQ ID NO: 534) | 558 |
| CR16-10_AS: | AAAC | cgcatttgacagttactttt C (SEQ ID NO: 535) | 559 |
| CR16-11_S: | cacc G | ttaaccagagcgcccagtc (SEQ ID NO: 536) | 560 |
| CR16-11_AS: | AAAC | gactgggcgctctggttaa C (SEQ ID NO: 537) | 561 |
| CR16-12_S: | cacc G | cgtcggagctgcccgctag (SEQ ID NO: 538) | 562 |
| CR16-12_AS: | AAAC | ctagcgggcagctccgacg C (SEQ ID NO: 539) | 563 | qRT-PCR & IF: Activation of endogenous ASCL1 was assessed by qRT-PCR and immunofluorescence in MEFs on day 3 following delivery of either dCas9-VP64 and gRNAs, ASCL1 cDNA, or a negative control vector encoding luciferase. The generation of iNs was evaluated by TUJ1 and MAP2 co-staining and identification of cells with neuronal morphology and extended processes.

Live Cell Reporters: After 7-8 days in N3 medium, MEFs cultured on poly-D-lysine/laminin-coated coverslips were transduced with viruses carrying hSyn-RFP and MAP2-GCamP5 reporters to identify the most mature iNs for functional characterization via calcium imaging and electrophysiology (FIG. 49B).

Figure 50A:
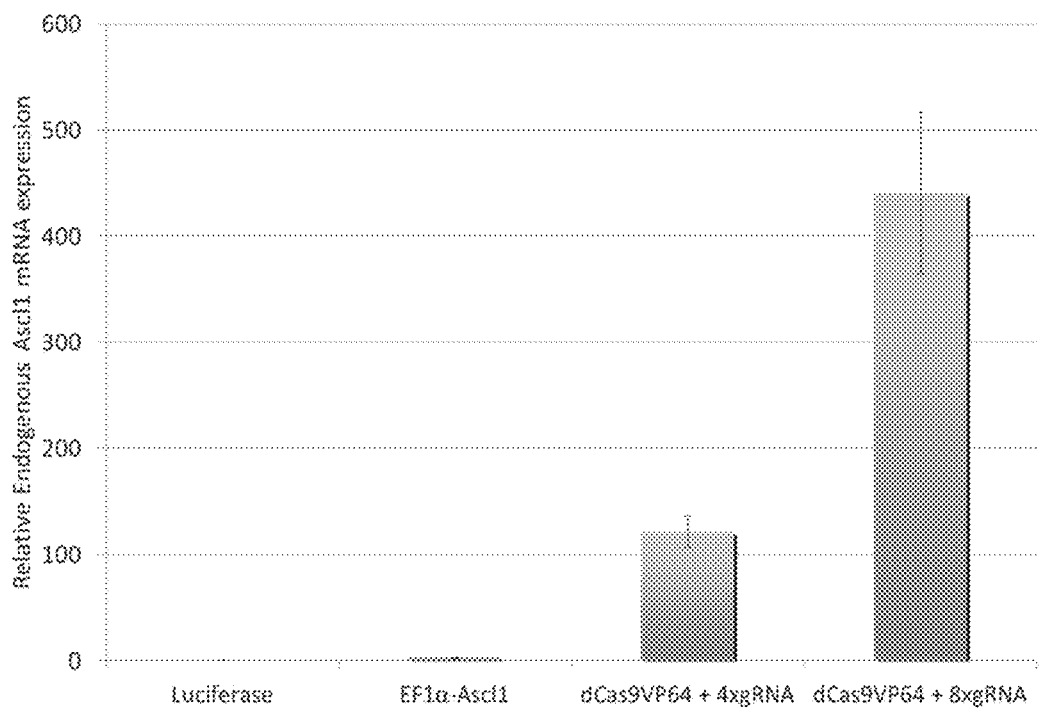
FIGS. 50A-50B shows endogenous ASCU expression at day 3 determined by qRT-PCR (FIG. 50A) or total ASCU protein detected by immunofluorescence in MEFs transduced with dCas9-VP64 and transfected with either gRNAs targeted to the ASCU promoter, ASCU cDNA, or luciferase (FIG. 50B). Asterisk (*) indicates significant ($p<0.05$) increase in ASCL1 expression with the co-delivery of 8 gRNAs compared to 4 gRNAs. Ectopic expression of ASCU produced more protein than induced by dCas9-VP64 and 8 gRNAs targeted to the Ascl1 promoter, but did not activate the endogenous locus by day 3 in culture.
Figure 50B:
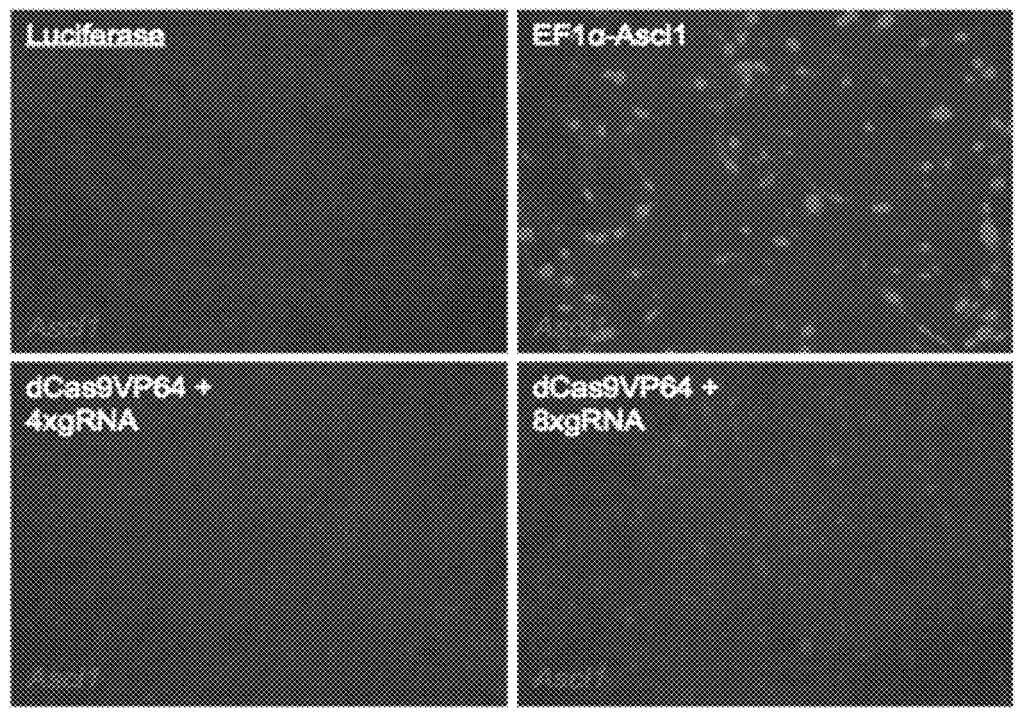
Figure 52A:
FIG. 52A shows a cell with neuronal morphology positive for the GCaMPS calcium indicator in the presence (bottom) or absence (top) of KC1 in the culture medium.
Figure 52B:
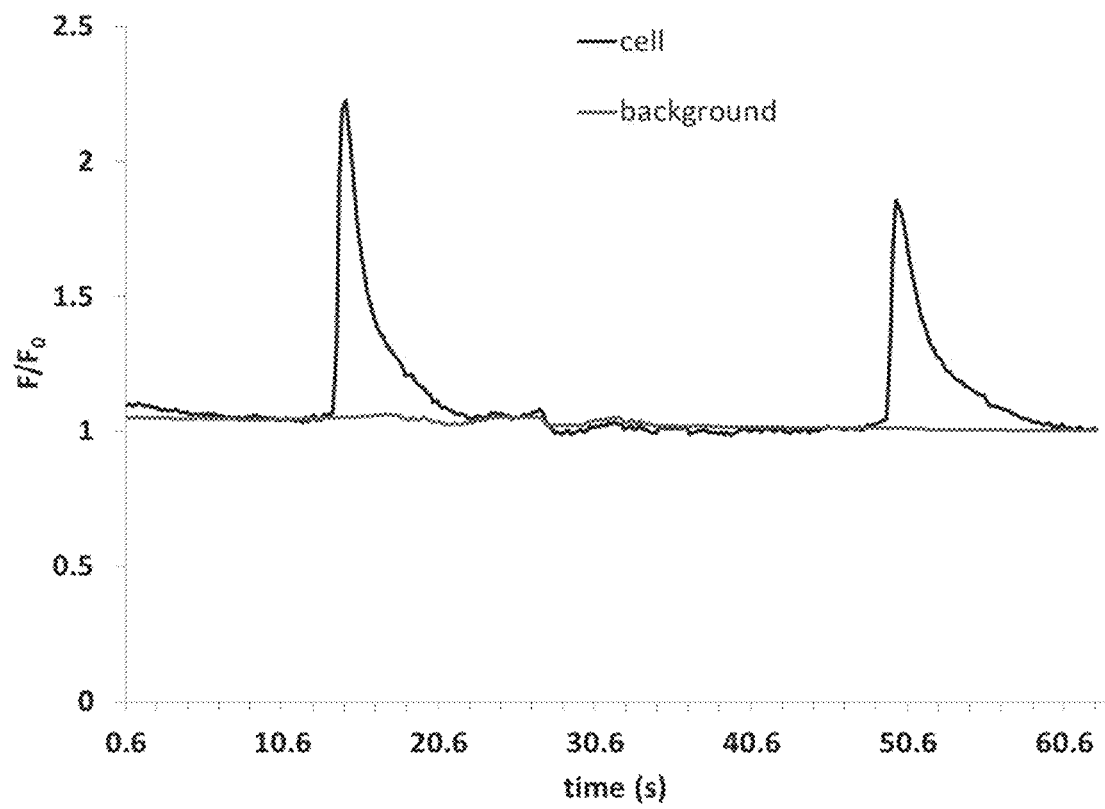
FIG. 52B shows a trace of normalized fluorescent intensity over time showing depolarization of the cell in response to KC1 addition.

Results. dCas9-VP64 and gRNAs targeted to the ASCL1 promoter activated the endogenous gene in MEFs. Co-delivery of 8 gRNAs activated the endogenous gene 400-fold, a significant increase ($p<0.05$) over the 100-fold activation induced by the co-delivery of 4 gRNAs (FIG. 50A). Nuclear-localized Ascl1 protein was detected by immunofluorescence in MEFs. Ectopic Ascl1 expression produced more Ascl1 protein than dCas9-VP64 with either gRNA cocktail, but did not activate the endogenous locus by day 3 (FIG. 50A,50B). TUB and MAP2 co-positive cells with extended processes were identified by immunofluorescence after 13 days in neurogenic medium following delivery of dCas9-VP64 and gRNAs targeting the ASCL1 and BRN2 promoters (FIG. 51A first row). A similar number of TUB and MAP2 co-positive cells were identified with ectopic expression of the BAM factors (FIG. 51A second row). Cells with a neuronal morphology expressing the hSyn-RFP reporter were visible in culture as early as day 11 in neurogenic medium (FIG. 51B). A cell expressing the MAP2-GCaMP5 calcium indicator exhibited KC1-induced depolarization detected with a fluorescent microscope (FIG. 52A,52B).

The direct conversion of mouse embryonic fibroblasts to TUB and MAP2 co-positive cells with a neuronal morphology was accomplished through activation of endogenous BRN2 and ASCL1 by CRISPR/Cas9-based transcription factors. Though dCas9-VP64 produces less protein than ectopic expression of ASCL1 (FIG. 50B), the generation of neuronal-like cells is similar. The activation of the endogenous loci may induce a reprogramming cascade of events that is not mechanistically identical to that generated with ectopic expression.

dCas9-VP64 was able to penetrate heterochromatin and activated stably silenced endogenous genes, a characteristic of only a subset of "pioneer" transcription factors. As a result, converting cell lineage with CRISPR/Cas9-transcription factors may better overcome epigenetic barriers to reprogramming than ectopic expression of transcription factors, particularly in hard-to-reprogram cell-types, such as adult human cells. This may have clinical importance in the field of regenerative medicine, as it is often desired to use autologous sources in cell replacement therapies.

Example 17

Multiplex CRISPR/Cas9-Based Genome Engineering—Materials and Methods

Plasmid constructs. The expression cassettes for the S. pyogenes sgRNA and human codon optimized Cas9 (hCas9) nuclease were used, as described above. Additional promoters for mU6 (Ohshima et al., Nucleic Acids Res 9:5145-5158 (1981)), H1 (Myslinski et al., Nucleic Acids Res 29:2502-2509 (2001)), and 7SK (Murphy et al., Cell 51:81-87 (1987)) pol-III promoters were synthesized using GeneBlocks (IDT) and cloned in place of the hU6 sgRNA expression cassette. A GeneBlock (IDT) was cloned onto the 3' end of the Cas9 coding sequence to fuse a T2A skipping peptide and eGFP gene immediately after Cas9 to monitor vector expression. The coding region for hCas9-T2A-GFP (SEQ ID NO: 145) was then transferred into a lentiviral expression vector containing the human ubiquitin C (hUbC) promoter to drive expression of hCas9-T2A-GFP, as well as restriction sites to facilitate Golden Gate cloning of sgRNA expression cassettes immediately upstream of the hUbC promoter (FIG. 42A).

Protocol for assembly of custom lentiviral vectors. Assembly of custom lentiviral vectors expressing up to four sgRNAs of choice and active Cas9, dCas9, or dCas9-VP64 was accomplished in less than five days. The cloning method used the Golden Gate cloning and type IIS restriction enzymes that cleave outside their recognition sequence to create unique overhangs. Golden Gate assembly expedited cloning as all four expression cassettes were ligated into the final lentiviral vector in one step. The lentiviral vector expressed active Cas9, cCas9, or dCas9-VP64 in addition to one, two, three, or four sgRNAs expressed from independent promoters.

Step 1: Single stranded oligos containing each 20 bp protospacer were annealed in such a fashion to create sticky ends and were ligated into the desired pZDonor-promoter vector. Order two single stranded oligos for each desired genomic target. To anneal the complimentary oligos, mix 8 µL sense oligo+8 µL antisense oligo (both at 10 mM)+2 µL 10× ligase buffer. The oligos are melted and reannealed in a PCR machine with the program: 96° C. for 300 seconds, followed by 85° C. for 20 seconds, 75° C. for 20 seconds, 65° C. for 20 seconds, 55° C. for 20 seconds, 45° C. for 20 seconds, 35° C. for 20 seconds, and 25° C. for 20 seconds with a −0.3° C./second rate between steps. To phosphorylate the sticky ends, add 1 µL 25 mM ATP+1 microliter T4 Polynucleotide Kinase (NEB) and incubate at 37° C. for 60 minutes followed by 65° C. for 20 minutes to heat inactivate the enzyme. Each protospacer was ligated into the desired expression vector using T4 DNA ligase (NEB) incubated at 16° C. for 60 minutes using 50ng of vector and 1 µL, of annealed oligonucleotides in a 10 pt. reaction volume according to manufacturer's instructions. Five microliters of each ligation was transformed into XL1 blue chemically competent bacteria (Agilent) following the manufacturer's instructions. Plate transformation onto LB agar plates containing 50 µg/mL, kanamycin (Sigma) and incubate overnight at 37° C. In our experience, >90% of the colonies will contain the desired ligation product. Sequencing using the M13 reverse standard sequencing primer was performed to validate each final sgRNA construct prior to moving onto step 2.

Step 2: Construct the four promoter-gRNA cassettes into a lentiviral destination vector using Golden Gate assembly. After completion of step 1, there are four independent plasmids each expressing a different sgRNA from a different promoter. To assemble the four different promoter-sgRNA constructs into the desired destination vector, combine 200 ng of each sgRNA expression plasmid and desired lentiviral destination vector with 1L of T4 DNA ligase (NEB), 1 µL BsmBI FastDigest (Fisher Scientific), and 2 µL 10× T4 ligase buffer (NEB) in a 20 pt reaction volume. Incubate the reaction as follows: 37° C. for 10 minutes, 16° C. for 15 minutes, 37° C. for 30 minutes, 80° C. for 5 minutes. Transform 5 µL of ligation reaction into SURE 2 chemically competent cells (Agilent) following the manufacturer's instructions. Plate transformations onto LB agar plates containing 100 µg/mL ampicillin and incubate overnight at 37° C. Optionally, colonies can be screened by lacZ-based blue/white screening using IPTG and X-gal; however, in our experience, >90% of the transformants contain the proper ligation product. Due to the inverted repeats formed by the opposing sgRNA expression cassettes, the final constructs may be unstable and thus we recommend maintaining these plasmids in the SURE 2 cell line and screening the final plasmid with a test PCR using the sense primer 5'-TCGGGTTTATTACAGGGACAGCAG-3' (SEQ ID NO:464) and antisense primer 5'-TCTAAGGCCGAGTCT-TATGAGCAG-3' (SEQ ID NO:465). These primers amplify across the four promoter-gRNA region. Due to the repetitive nature, a distinct banding pattern should be observed with the largest product approximately 1800 bp in size.

Cell culture and transfection. HEK293T cells were obtained from the American Tissue Collection Center (ATCC, Manassas, Va.) through the Duke University Cancer Center Facilities and were maintained in DMEM supplemented with 10% FBS and 1% penicillin streptomycin. Primary human dermal fibroblasts (Catalog ID: GM03348) were obtained from Coriell Institute (Camden, N.J.) and were maintained in DMEM supplemented with 10% FBS and 1% penicillin streptomycin. All cells were cultured at 37° C. with 5% $CO_2$. HEK293T cells were transfected with Lipofectamine 2000 (Life Technologies) with 200 ng of each sgRNA expression vector (800 ng total pDNA) according to the manufacturer's protocol in 24 well plates.

Viral production and transduction. All lentiviral vectors used is this study are second generation and were produced using standard viral production methods. Briefly, 3.5 million HEK293Ts were plated per 10 cm dish. The following day, cells were transfected by the calcium phosphate transfection method with 20 µg of transfer vector, 6 µg of pMD2G, and 10 µg psPAX2. The media was changed 12-14 hrs post transfection. The viral supernatant was collected 24 and 48 hrs after this media change, passed through a 0.45 micron filter and pooled. For transduction, the cell medium was replaced with viral supernatant supplemented with 4 µg/mL polybrene. The viral supernatant was exchanged for fresh medium 12-24 hrs later.

Reverse Transcription PCR. RNA was isolated using the miRNeasy Mini RNA isolation kit (Qiagen). DNAse digestion was performed using the DNA-free Kit (Applied Biosystems). cDNA synthesis was performed using the SuperScript VILO cDNA Synthesis Kit (Invitrogen). cDNA was PCR amplified using Taq DNA polymerase (NEB) and the resulting product was run on TAE agarose gels. Images were captured using a ChemiDoc XRS+ System and processed using ImageLab software (Bio-Rad).

Quantitative Real Time PCR. RNA was isolated using the RNeasy Plus RNA isolation kit (Qiagen). cDNA synthesis was performed using the SuperScript VILO cDNA Synthesis Kit (Invitrogen). Real-time PCR using PerfeCTa SYBR Green FastMix (Quanta Biosciences) was performed with the CFX96 Real-Time PCR Detection System (Bio-Rad). Primer specificity was confirmed by agarose gel electrophoresis and melting curve analysis. Reaction efficiencies over the appropriate dynamic range were calculated to ensure linearity of the standard curve. The results are expressed as fold-increase mRNA expression of the gene of interest normalized to β-Actin expression using the ΔΔCt method. Reported values are the mean and S.E.M. from two independent experiments (n=2) where technical replicates were averaged for each experiment.

Western Blot. Cells were lysed in RIPA Buffer (Sigma) supplemented with protease inhibitor cocktail (Sigma). Protein concentration was measured using BCA protein assay reagent (Thermo Scientific) and BioTek Synergy 2 Multi-Mode Microplate Reader. Lysates were mixed with loading buffer and boiled for 5 min; 25 µg of protein were run in NuPage 10% Bis-Tris Gel polyacrylamide gels (Bio-Rad) and transferred to nitrocellulose membranes. Nonspecific antibody binding was blocked with TBST (50 mM Tris, 150 mM NaCl and 0.1% Tween-20) with 5% nonfat milk for 1 hr at room temperature. The membranes were incubated with primary antibodies: (anti-MyoD (1:250, Santa Cruz Sc-32758) in 5% BSA in TBST overnight at 4° C.; anti-Myogenin (1:250, Santa Cruz Sc-12732) in 5% BSA overnight at 4° C.; anti-FLAG-HRP (1:1000, Cell Signaling 2044) in 5% milk in TB ST for 60 min at room temperature; anti-GAPDH (1:5000, Cell Signaling, clone 14C10) in 5% milk in TBST for 30 min at room temperature. Membranes were then washed three times with TB ST for 15 minutes total. Membranes were incubated with anti-rabbit HRP-conjugated antibody (Sigma, A 6154) or anti-mouse HRP-conjugated antibody (Santa Cruz, S.C.-2005) diluted 1:5,000 for 30 min and washed with TBST three times for 15 min each. Membranes were visualized using the ImmunStar WesternC Chemiluminescence Kit (Bio-Rad) and images were captured using a ChemiDoc XRS+ System and processed using ImageLab software (Bio-Rad).

CeI-I quantification of endogenous gene modification. CRISPR/Cas9 nuclease lesions at the endogenous target site were quantified using the Surveyor nuclease assay, which can detect mutations characteristic of nuclease-mediated NHEJ. After transfection or transduction, cells were incubated for 3-10 days at 37° C. and genomic DNA was extracted using the DNeasy Blood and Tissue kit (Qiagen). The target locus was amplified by 35 cycles of PCR with the AccuPrime High Fidelity PCR kit (Invitrogen). The resulting PCR products were randomly melted and reannealed in a PCR machine with the program: 95° C. for 240 seconds, followed by 85° C. for 60 seconds, 75° C. for 60 seconds, 65° C. for 60 seconds, 55° C. for 60 seconds, 45° C. for 60 seconds, 35° C. for 60 seconds, and 25° C. for 60 seconds with a −0.3° C./second rate between steps. Following re-annealing, 8 µL of PCR product was mixed with 1 µL of Surveyor Nuclease S and 1 µL of Enhancer S (Transgenomic, Omaha, Nebr.) and incubated at 42° C. for 1 hr. After incubation, 6 µL of digestion product was loaded onto a 10% TBE polyacrylamide gel and run at 200 V for 30 minutes. The gels were stained with ethidium bromide and quantified using ImageLab (Bio-Rad) by densitometry (Perez-Pinera et al., Nucleic Acids Res 40:3741-3751 (2012)).

Statistical Analysis. At least two independent experiments were compiled as means and standard errors of the mean. Effects were evaluated with multivariate ANOVA and Dunnett's post hoc test using JMP 10 Pro.

Example 18

Development of a Single Lentiviral Vector for Multiplex CRISPR/Cas9 Applications A limitation of current CRISPR/Cas9 gene editing systems, particularly transactivator systems, is the simultaneous and efficient delivery of multiple sgRNAs and Cas9 protein for multiplex gene editing and synergistic gene activation applications, especially in difficult to transfect cell types. To overcome this limitation, we developed a single lentiviral vector that efficiently expresses Cas9 and up to four sgRNAs. In order to maximize the expression efficiency of each sgRNA, this vector expresses four sgRNAs from four independent pol III promoters (human U6 promoter, mouse U6 promoter, 7SK, and H1). We validated sgRNA expression from each promoter using end-point RT-PCR to detect a sgRNA targeting the AAVS1 locus (FIG. 42A). To test the activity of each sgRNA expression construct, we co-transfected each promoter construct expressing an sgRNA targeting AAVS1 independently with an active Cas9 expression construct into human HEK293T cells. Notably, we detected consistent and high levels of gene modification at the target locus for each sgRNA that are comparable to a well-characterized zinc-finger nuclease with high activity at the AAVS1 locus (FIG. 42B). Furthermore, lentiviral delivery of different Cas9-based constructs, including an active Cas9 nuclease, dead Cas9, and dead Cas9 fused to the VP64 transactivator domain, resulted in expression of full-length Cas9 protein in HEK293T cells as determined by western blot (FIG. 42C).

Figure 43:
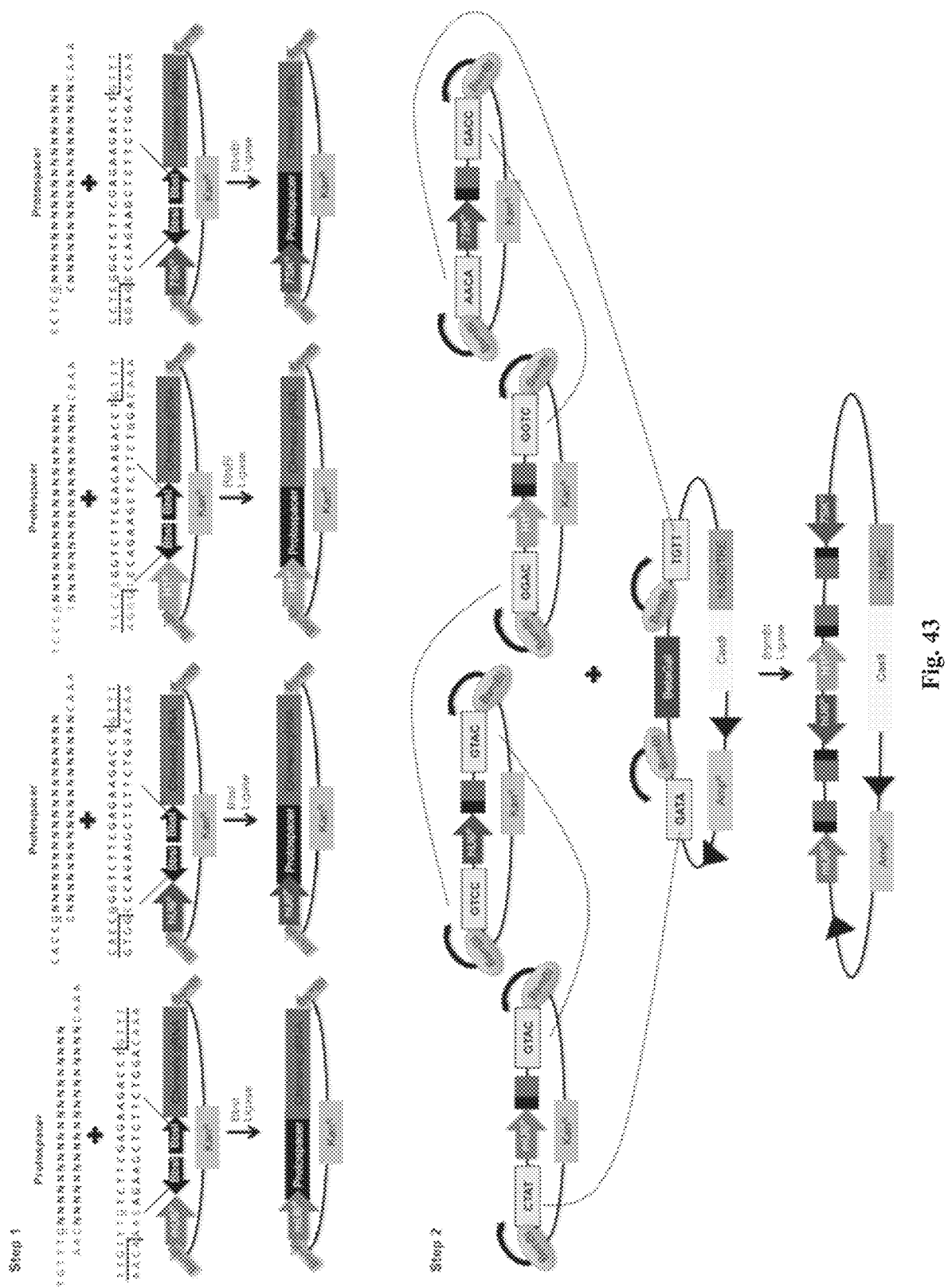
FIG. 43 shows Golden Gate assembly of single lentiviral CRISPR/Cas9 expression cassettes.

Using these components, we developed a Golden Gate cloning method to facilitate rapid and efficient cloning of multiple sgRNA expression cassettes into a single lentiviral vector expressing the desired Cas9 effector (FIG. 43). In the first step, oligonucleotides encoding sgRNA protospacer sequences are cloned independently into different expression vectors, each with a distinct promoter driving sgRNA expression. In the second step, each sgRNA expression construct is subcloned into a lentiviral Cas9 expression vector of choice by Golden Gate assembly. This strategy allows for robust and rapid cloning of up to four sgRNAs into a single lentiviral vector for gene editing or activation applications. To express less than four sgRNAs, a PolyT terminator sequence is cloned down-stream of unused promoters to prevent transcription from the unused promoters. Each vector co-expresses the choice Cas9 with eGFP via a 2A skipping peptide to enable fluorescence-activated flow sorting and enrichment of cells with a high multiplicity of infection. Finally, the entire region containing the sgRNA and Cas9 expression cassettes is flanked by loxP sites to mediate removal by Cre-lox excision.

Example 19

Validation of a Single Lentiviral sgRNA/Cas9 Expression Vector for Multiplex Genome Engineering To validate the independent activity of each sgRNA, we assembled a single lentiviral vector expressing active Cas9 and four sgRNAs, each targeting an independent loci (FIG. 44A). As control vectors, we assembled constructs expressing only one sgRNA along with polyT protospacers in the other three positions. We transduced HEK293Ts and primary fibroblasts with lentiviral vectors expressing the indicated sgRNAs and monitored gene modification frequencies at 7 or 10 days post-transduction, respectively (FIG. 44B). In both cell types, the single lentiviral vector mediated highly efficient multiplex editing at all four loci (FIG. 44B). Interestingly, expression of all four sgRNAs together resulted in higher modification frequencies than a single sgRNA alone at 3 out of 4 loci in fibroblasts (FIG. 44B). We observed efficient multiplex gene editing in fibroblasts, which are conventionally a difficult to transfect cell type. These data demonstrate that a single lentivirus can express four active sgRNAs efficiently and that this lentiviral platform can be used to target four distinct loci for multiplex CRISPR/Cas9 gene editing.

Example 20

Figure 45A:
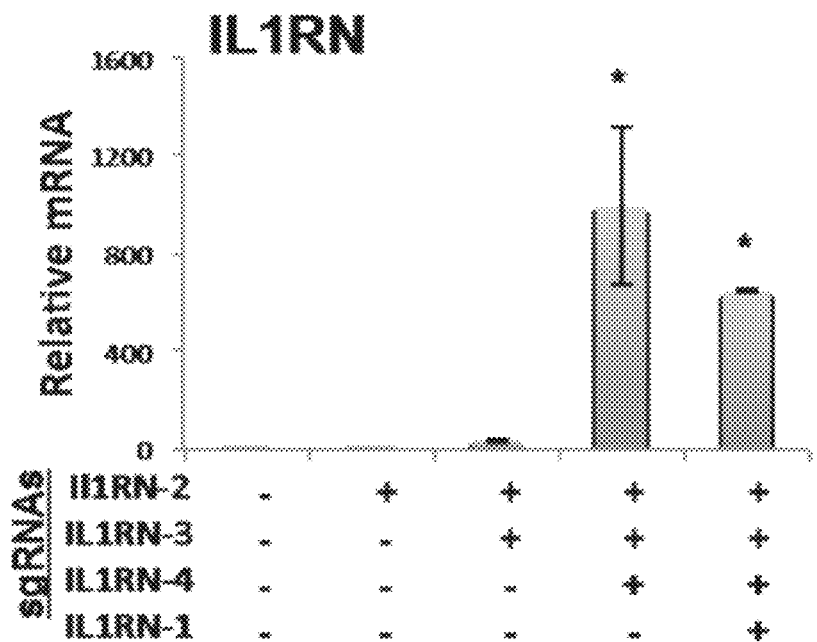
FIGS. 45A-45D show transient gene activation in HEK293Ts stably expressing dCas9-VP64. HEK293Ts were transduced with lentivirus to stably express dCas9-VP64 and were subsequently transfected with plasmid expressing the indicated sgRNA combinations. By varying the number of sgRNAs delivered, tunable endogenous gene activation of the endogenous IL1RN (FIG. 45A) and HBG1 (FIG. 45B) loci was achieved 3 days post transfection. Peak levels of endogenous IL1RN (FIG. 45C) and HBG1 (FIG. 45D) were observed 3-6 days post transfection and the level of activation returned to background levels between days 15-20. Importantly, the cell lines were able to reactive following a second transfection on day 20 albeit at a lower level than previously observed.
Figure 45B:
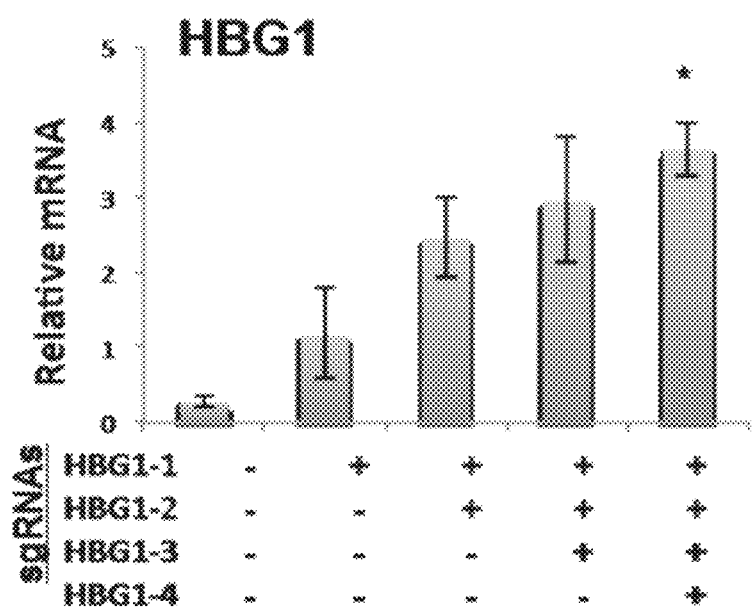
Figure 45C:
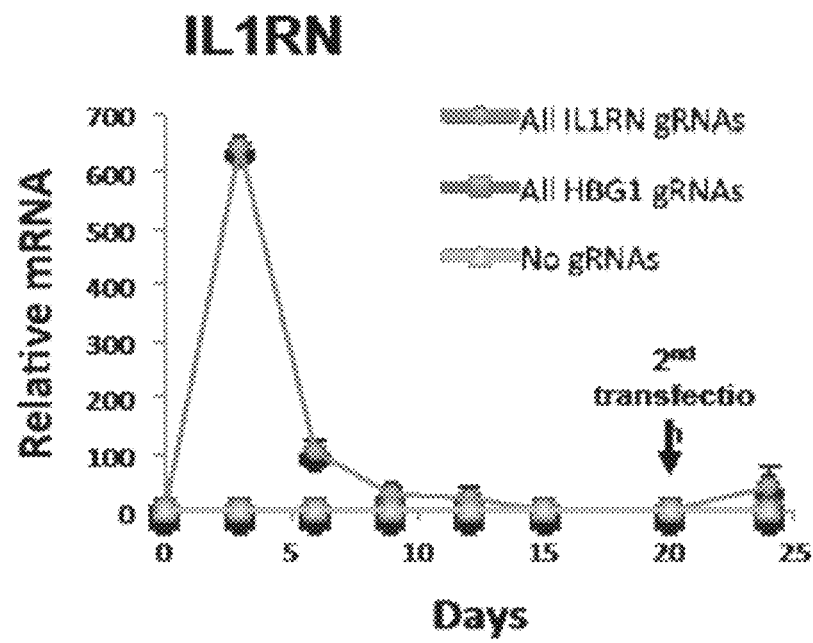
Figure 45D:
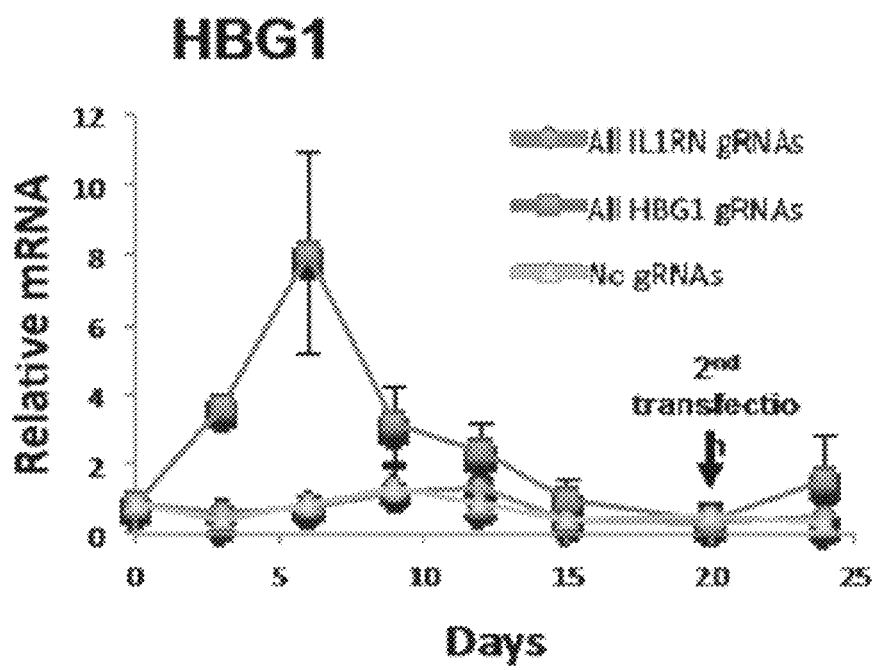

Transient RNA-Guided Gene Activation in Cell Lines Stably Expressing a Lentiviral Cas9-Based Transactivator Next, we were interested in developing a system that enables transient gene activation by transfecting sgRNAs into model cell lines stably expressing Cas9. HEK293Ts were transduced with different Cas9-T2A-GFP and GFP expression was monitored using flow cytometry. Following normal passaging every 2-3 days, each cell line exhibited stable GFP expression for up to 35 days post transduction. Transduced HEK293Ts were then transfected with one to four separate sgRNA expression constructs targeting either the IL1RN or HBG1 promoter. Transient transfection of these sgRNA constructs in stable dCas9-VP64 expressing cells lines resulted in tunable endogenous gene activation (FIGS. 45A,45B). Gene activation following transient transfection of sgRNA constructs in cells expressing dCas9-VP64 reached a maximum level of activation approximately 3-6 post-transfection and fell to undetectable levels by 20 days post-transfection (FIGS. 45C,45D). Furthermore, we were able to re-activate each gene by a second transfection of all four sgRNA constructs targeting each promoter, although activation levels were significantly lower than observed from the first transfection (FIGS. 45C, 45D). This reduction in activity after the second transfection may be due to reduced vector expression or competitive growth of untransduced cells. Despite this, these data demonstrate that lentiviral Cas9 combined with transient sgRNA delivery can be used as a versatile system to tunably and transiently activate and re-activate target genes in a Cas9 stably tranduced cell line.

Example 21

Figure 46A:
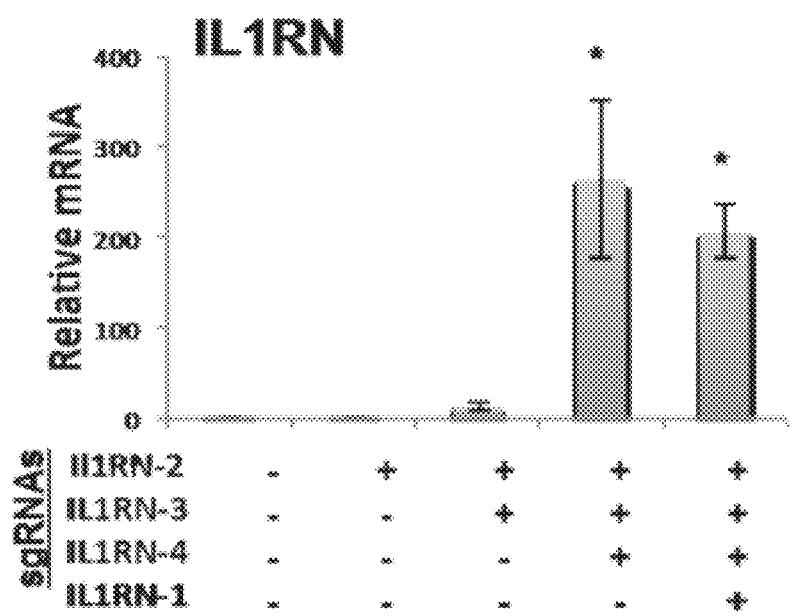
FIGS. 46A-46D show stable gene activation in HEK293Ts using a single lentiviral multiplex dCas9-VP64 vector. HEK293Ts were transduced with lentivirus to stably express dCas9-VP64 and the indicated combinations of gRNAs. By varying the number of sgRNAs delivered, tunable endogenous gene activation of the endogenous IL1RN (FIG. 46A) and HBG1 (FIG. 46B) loci was achieved 7 days post transduction. Peak levels of endogenous IL1RN (FIG. 46C) and HBG1 (FIG. 46D) were observed 6 days post transduction and the level of activation was sustained out to day 21.
Figure 46B:
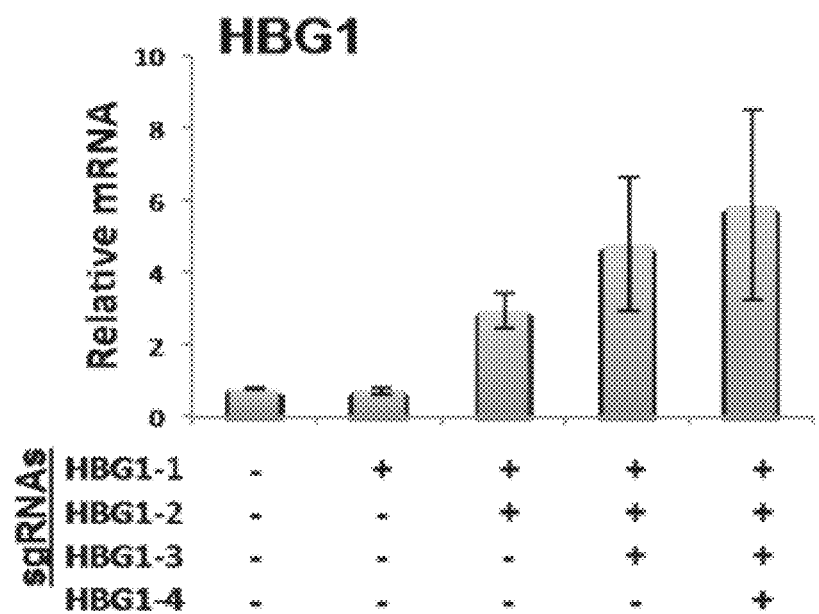
Figure 46C:
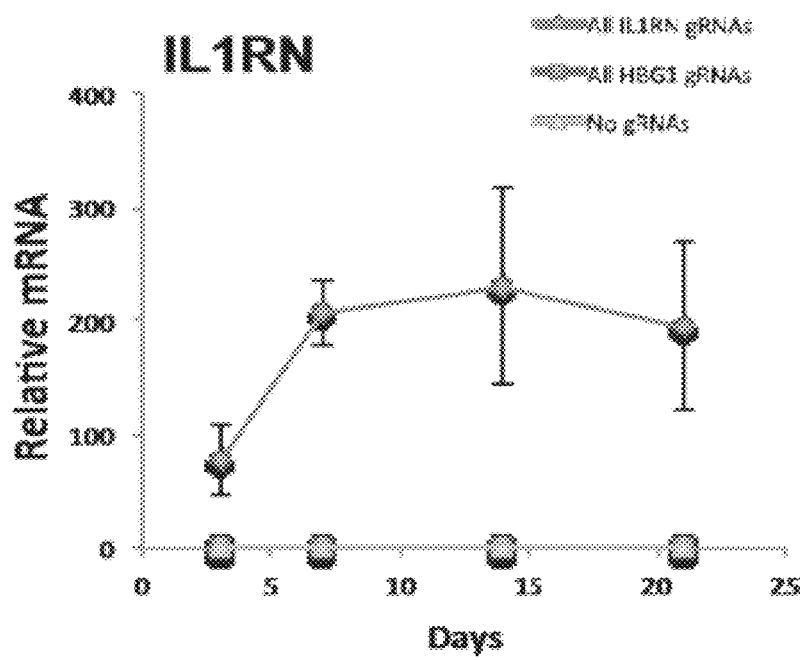
Figure 46D:
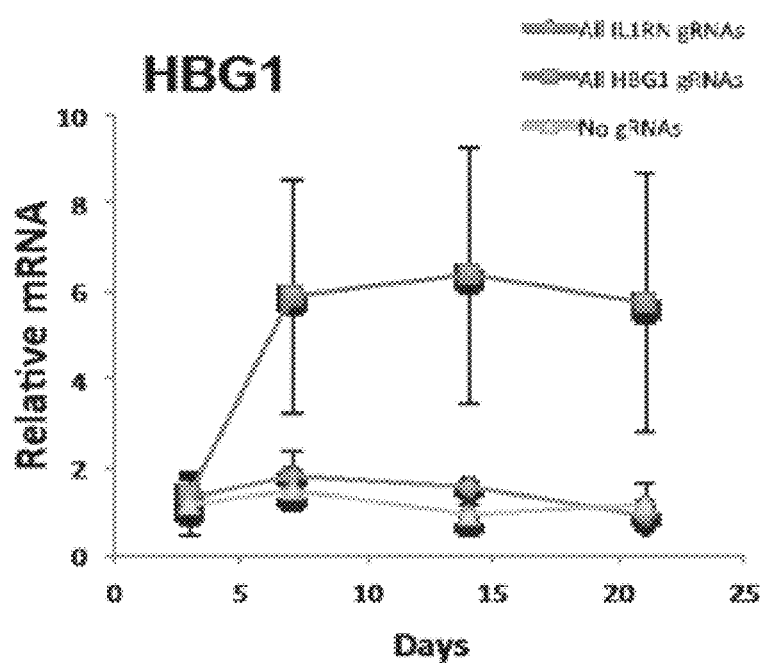

Stable Gene Activation in HEK293TCells Using a Single Lintiviral sgRNA/Cas9 Transactivator Expression Vector Lentiviral delivery may enable stable, long-term gene activation by CRISPR/Cas9 transactivation. To test this, HEK293Ts were transduced using a single lentiviral vector encoding dCas9-VP64 and one to four sgRNA expression cassettes. Similar to our transient transfection results (FIGS. 45A-45D), we were able to tunably and robustly activate expression of endogenous IL1RN and HBG1 genes (FIGS. 46A,46B). Gene activation induced by co-transfection of HEK293T cells with dCas9-VP64 and four sgRNAs targeted to the IL1RN and HBG1 promoters peaked three-five days post-transfection and gene expression returned to background levels 15-20 days post-transfection FIGS. 45C and 45D. In contrast, lentiviral delivery of dCas9-VP64 and the same four IL1RN or HBG1-targeted sgRNAs induced sustained gene activation for more than 20 days post-transduction (FIGS. 46C,46D). Thus, single lentiviral delivery of multiplex dCas9-VP64 transactivators is a useful platform to efficiently and stably upregulate target endogenous genes.

Example 22 dCas9-KRAB—Targeting the HS2 Enhancer

Figure 54:
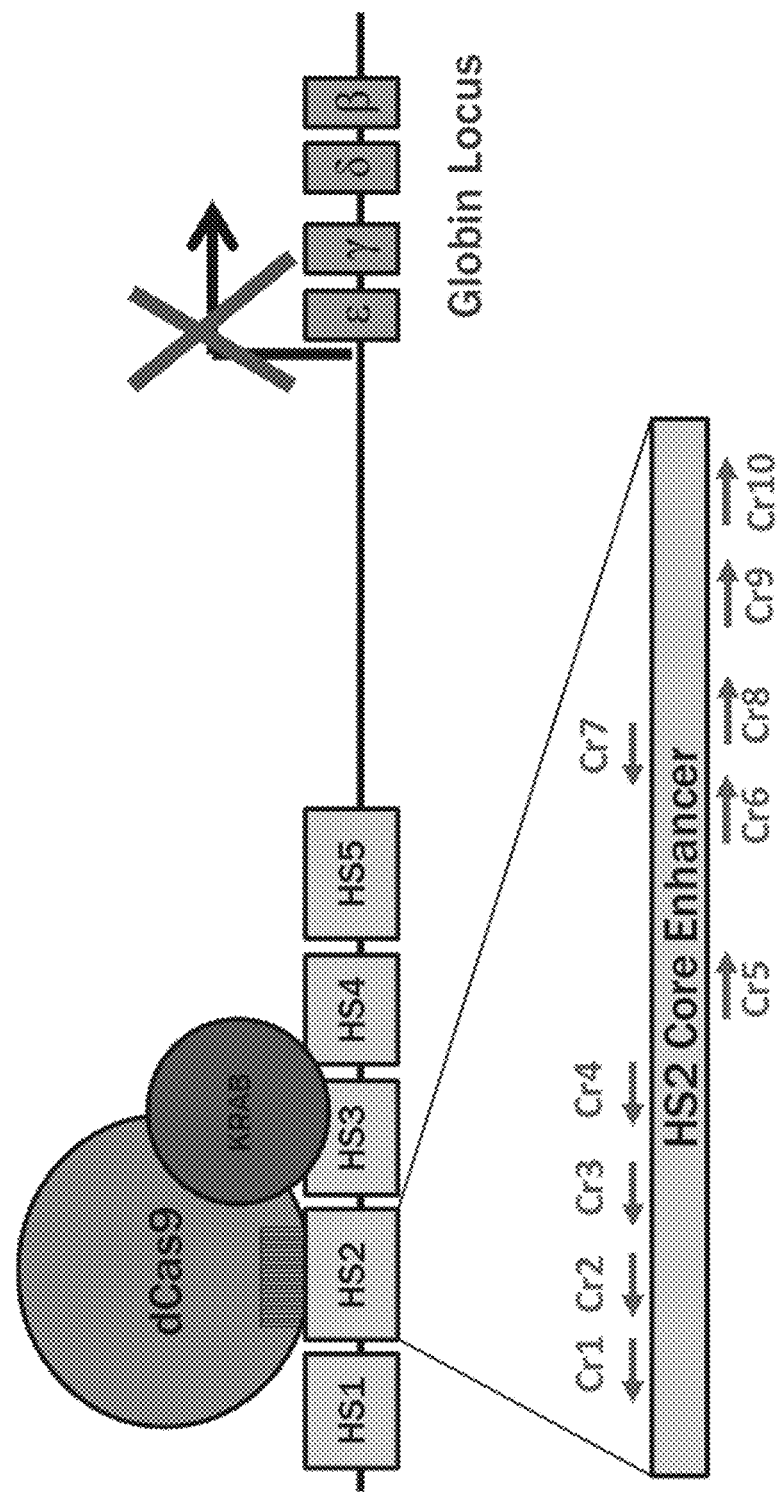
FIG. 54 shows targeting the HS2 enhancer using CRISPR/dCas9-KRAB. The HS2 region is a potent enhancer that distally regulates the expression of globin genes >10kb downstream. A panel of single gRNAs was designed to target sites along the enhancer region.

The HS2 enhancer is a well-characterized distal regulatory element necessary for activation of the globin gene locus. dCas9-KRAB with gRNAs targeted to the HS2 enhancer were delivered to determine if this system would repress γ-, ε-, and β-globin expression in the K562 human erythroid leukemia cell line (FIG. 54). A panel of gRNAs was created targeting different sites along the core region of the HS2 enhancer (SEQ ID NO: 467). See Table 12.

TABLE 12

HS2 gRNA Target Sequences

| Cr# | Protospacer | Complete gRNA Sequence |
|---|---|---|
| 1 | gagacacacagaaatgtaac (SEQ ID NO: 564) | gagacacacagaaatgtaacgtttTAGAGCTAGAAATAGCAAGTTAAAATA AGGCTAGTCCGTTATCAACTTGAAAAAGTGGCACCGAGTCGG TGCTTTTTTTCC (SEQ ID NO: 585) |
| 2 | ggtggggcactgaccccgac (SEQ ID NO: 565) | ggtggggcactgaccccgacgtttTAGAGCTAGAAATAGCAAGTTAAAATA AGGCTAGTCCGTTATCAACTTGAAAAAGTGGCACCGAGTCGG TGCTTTTTTTCC (SEQ ID NO: 586) |
| 3 | ctagagtgatgactcctatc (SEQ ID NO: 566) | ctagagtgatgactcctatcgtttTAGAGCTAGAAATAGCAAGTTAAAATAA GGCTAGTCCGTTATCAACTTGAAAAAGTGGCACCGAGTCGGT GCTTTTTTCC (SEQ ID NO: 587) |
| 4 | gactaaaactccacctcaaa (SEQ ID NO: 567) | gactaaaactccacctcaaagtttTAGAGCTAGAAATAGCAAGTTAAAATAA GGCTAGTCCGTTATCAACTTGAAAAAGTGGCACCGAGTCGGT GCTTTTTTCC (SEQ ID NO: 588) |
| 5 | aatatgtcacattctgtctc (SEQ ID NO: 568) | aatatgtcacattctgtctcgtttTAGAGCTAGAAATAGCAAGTTAAAATAAG GCTAGTCCGTTATCAACTTGAAAAAGTGGCACCGAGTCGGTG CTTTTTTCC (SEQ ID NO: 589) |
| 6 | ggactatgggaggtcactaa (SEQ ID NO: 569) | ggactatgggaggtcactaagtttTAGAGCTAGAAATAGCAAGTTAAAATA AGGCTAGTCCGTTATCAACTTGAAAAAGTGGCACCGAGTCGG TGCTTTTTTTCC (SEQ ID NO: 590) |
| 7 | gctcatgcttggactatggg (SEQ ID NO: 570) | gctcatgcttggactatggggtttTAGAGCTAGAAATAGCAAGTTAAAATAA GGCTAGTCCGTTATCAACTTGAAAAAGTGGCACCGAGTCGGT GCTTTTTTCC (SEQ ID NO: 591) |
| 8 | gttctggccaggccctgtc (SEQ ID NO: 571) | gttctggccaggccctgtcgtttTAGAGCTAGAAATAGCAAGTTAAAATAA GGCTAGTCCGTTATCAACTTGAAAAAGTGGCACCGAGTCGGT GCTTTTTTCC (SEQ ID NO: 592) |

TABLE 12-continued

HS2 gRNA Target Sequences

| Cr# | Protospacer | Complete gRNA Sequence |
|---|---|---|
| 9 | agtgccccaccccgccttc (SEQ ID NO: 572) | agtgccccaccccgccttcgttttTAGAGCTAGAAATAGCAAGTTAAAATAAGGCTAGTCCGTTATCAACTTGAAAAAGTGGCACCGAGTCGGTGCTTTTTTTCC (SEQ ID NO: 593) |
| 10 | gtggggcactgaccccgaca (SEQ ID NO: 573) | gtggggcactgaccccgacagttttTAGAGCTAGAAATAGCAAGTTAAAATAAGGCTAGTCCGTTATCAACTTGAAAAAGTGGCACCGAGTCGGTGCTTTTTTTCC (SEQ ID NO: 594) |
| 11 | aaccttctaagcaaaccttc (SEQ ID NO: 574) | aaccttctaagcaaaccttcgttttTAGAGCTAGAAATAGCAAGTTAAAATAAGGCTAGTCCGTTATCAACTTGAAAAAGTGGCACCGAGTCGGTGCTTTTTTTCC (SEQ ID NO: 595) |
| 12 | gttacacagaaccagaaggc (SEQ ID NO: 575) | gttacacagaaccagaaggcgttttTAGAGCTAGAAATAGCAAGTTAAAATAAGGCTAGTCCGTTATCAACTTGAAAAAGTGGCACCGAGTCGGTGCTTTTTTTCC (SEQ ID NO: 596) |
| 13 | gaaggttacacagaaccaga (SEQ ID NO: 576) | gaaggttacacagaaccagagttttTAGAGCTAGAAATAGCAAGTTAAAATAAGGCTAGTCCGTTATCAACTTGAAAAAGTGGCACCGAGTCGGTGCTTTTTTTCC (SEQ ID NO: 597) |
| 14 | agtcatgatgagtcatgctg (SEQ ID NO: 577) | agtcatgatgagtcatgctggttttTAGAGCTAGAAATAGCAAGTTAAAATAAGGCTAGTCCGTTATCAACTTGAAAAAGTGGCACCGAGTCGGTGCTTTTTTTCC (SEQ ID NO: 598) |
| 15 | gatgagtcatgctgaggctt (SEQ ID NO: 578) | gatgagtcatgctgaggcttgttttTAGAGCTAGAAATAGCAAGTTAAAATAAGGCTAGTCCGTTATCAACTTGAAAAAGTGGCACCGAGTCGGTGCTTTTTTTCC (SEQ ID NO: 599) |
| 16 | actctaggctgagaacatct (SEQ ID NO: 579) | actctaggctgagaacatctgttttTAGAGCTAGAAATAGCAAGTTAAAATAAGGCTAGTCCGTTATCAACTTGAAAAAGTGGCACCGAGTCGGTGCTTTTTTTCC (SEQ ID NO: 600) |
| 17 | gtccccagcaggatgcttac (SEQ ID NO: 580) | gtccccagcaggatgcttacgttttTAGAGCTAGAAATAGCAAGTTAAAATAAGGCTAGTCCGTTATCAACTTGAAAAAGTGGCACCGAGTCGGTGCTTTTTTTCC (SEQ ID NO: 601) |
| 18 | gccctgtaagcatcctgctg (SEQ ID NO: 581) | gccctgtaagcatcctgctggttttTAGAGCTAGAAATAGCAAGTTAAAATAAGGCTAGTCCGTTATCAACTTGAAAAAGTGGCACCGAGTCGGTGCTTTTTTTCC (SEQ ID NO: 602) |
| 19 | cagggcagatggcaaaaaaa (SEQ ID NO: 582) | cagggcagatggcaaaaaaagttttTAGAGCTAGAAATAGCAAGTTAAAATAAGGCTAGTCCGTTATCAACTTGAAAAAGTGGCACCGAGTCGGTGCTTTTTTTCC (SEQ ID NO: 603) |
| 20 | gaggtggagttttagtcagg (SEQ ID NO: 583) | gaggtggagttttagtcagggttttTAGAGCTAGAAATAGCAAGTTAAAATAAGGCTAGTCCGTTATCAACTTGAAAAAGTGGCACCGAGTCGGTGCTTTTTTTCC (SEQ ID NO: 604) |
| 21 | aaacggcatcataaagaaaa (SEQ ID NO: 584) | aaacggcatcataaagaaaagttttTAGAGCTAGAAATAGCAAGTTAAAATAAGGCTAGTCCGTTATCAACTTGAAAAAGTGGCACCGAGTCGGTGCTTTTTTTCC (SEQ ID NO: 605) |

Figure 55A:
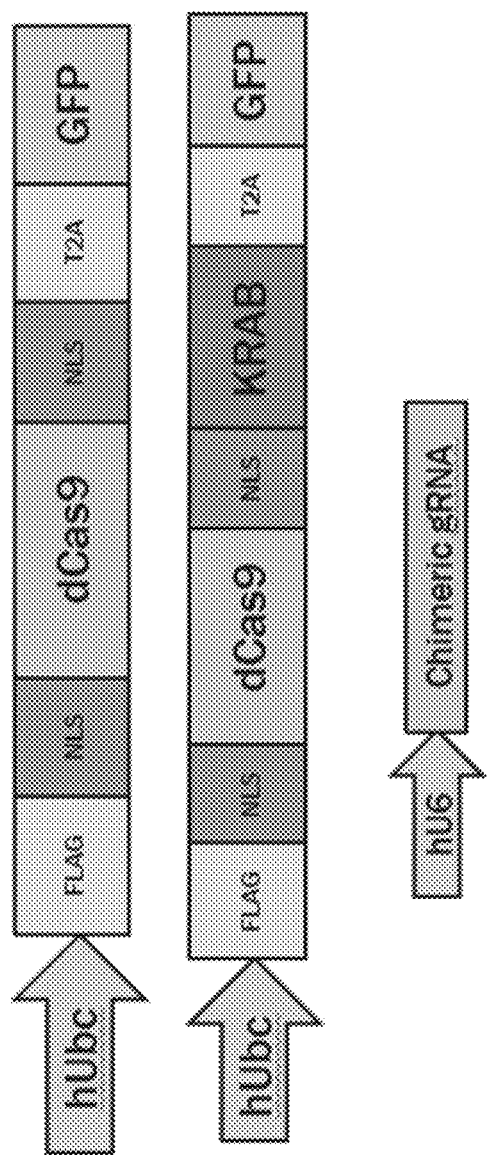
Figure 55C:
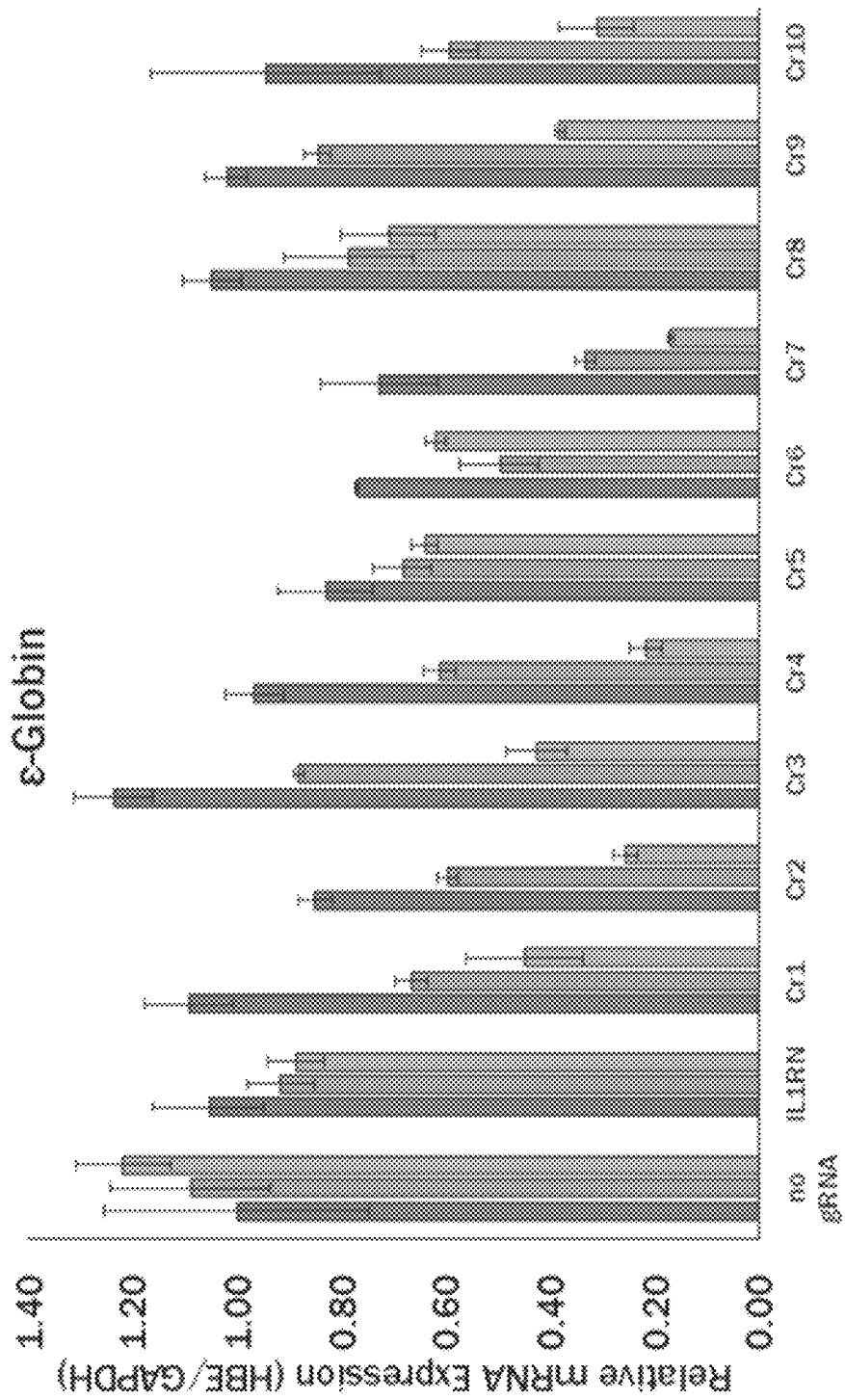
Figure 55D:
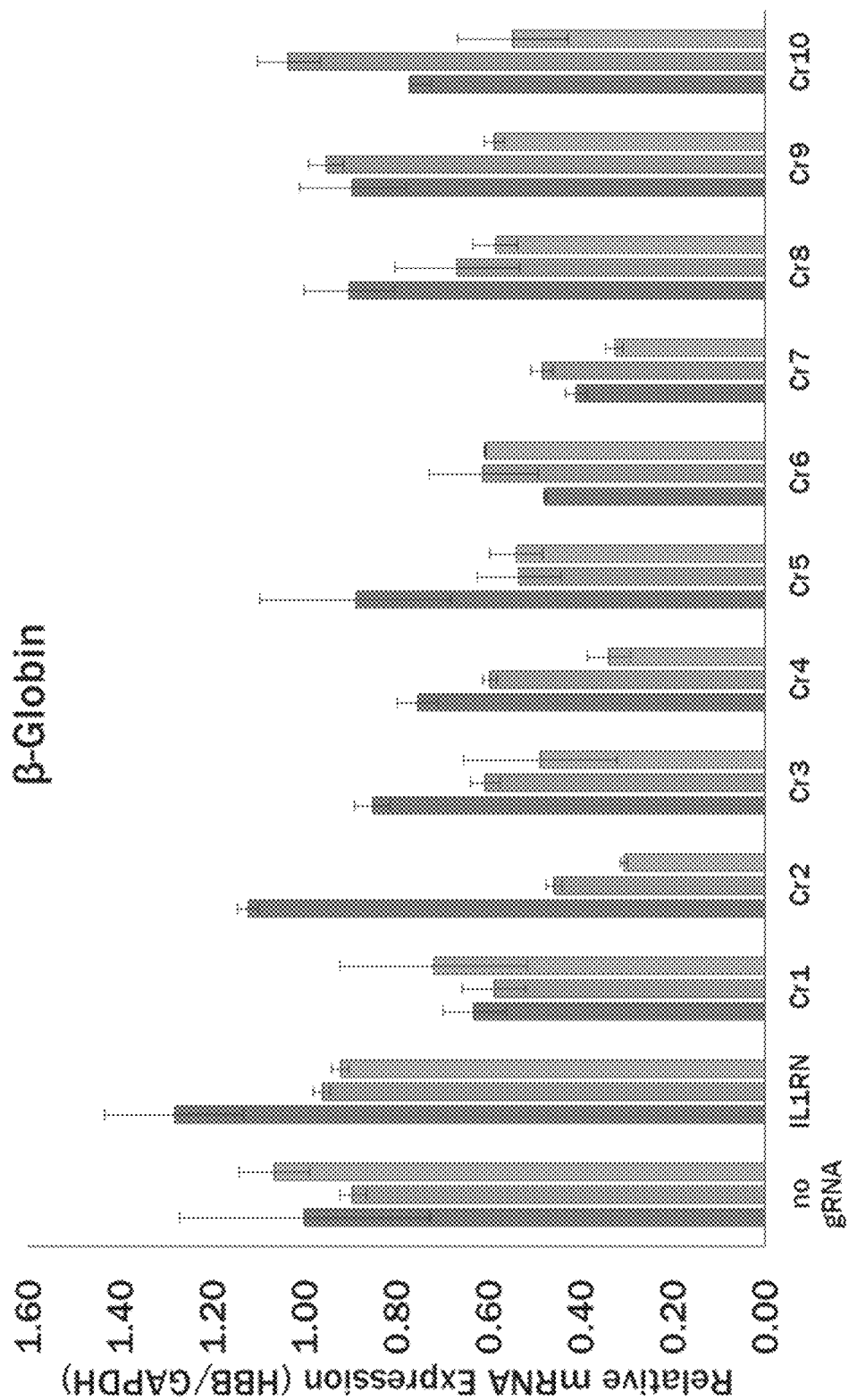
Figure 55E:
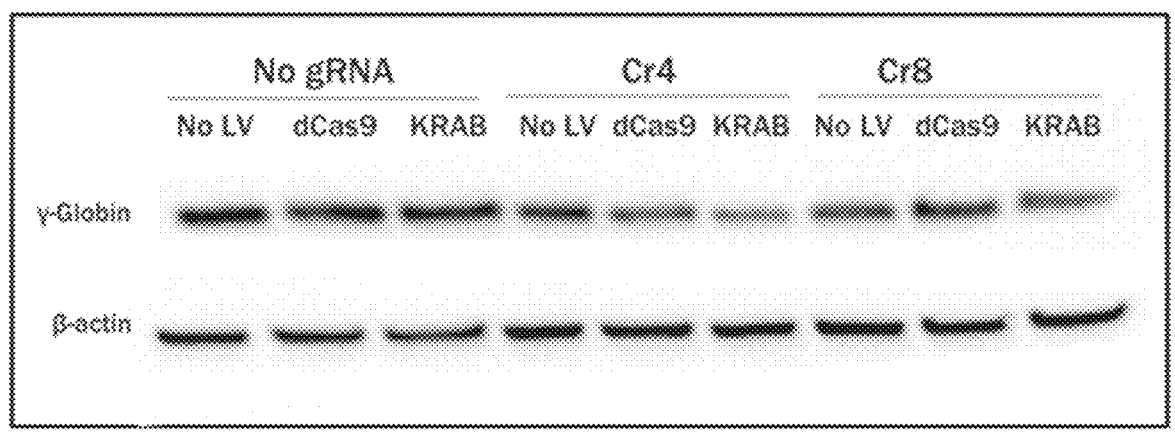
Figure 56A:
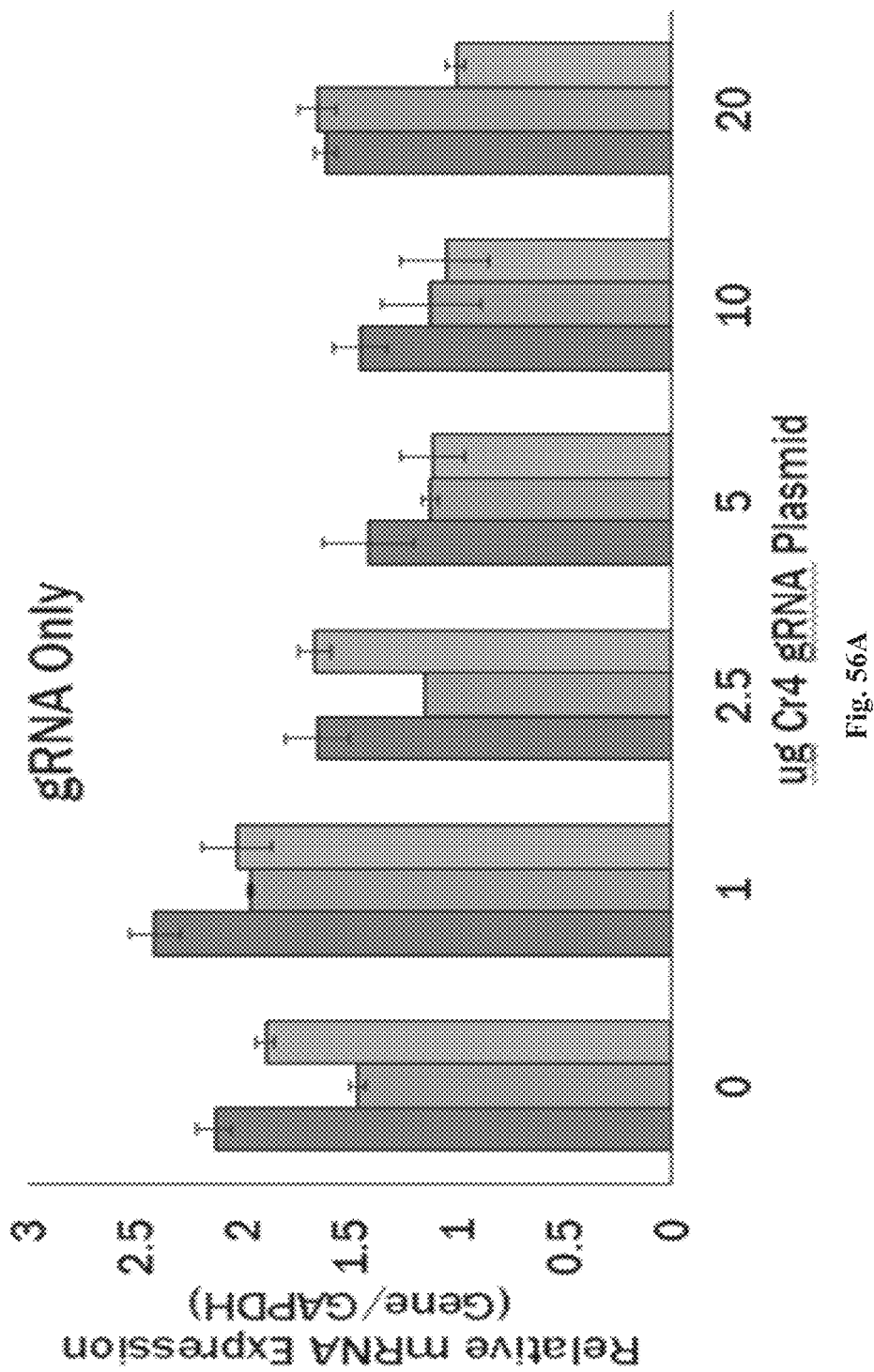
FIGS. 56A-56C expression of globin locus genes with varying doses of gRNA plasmid delivered to cells treated with no lentivirus (FIG. 56A), dCas9 lentivirus (FIG. 56B), or dCas9-KRAB lentivirus (FIG. 56C). Increasing the dose of Cr4 gRNA plasmid delivered enhanced repression in dCas9-KRAB treated cells, indicating that both the dCas9-KRAB effector and targeted gRNA play a role in achieving repression.
Figure 56B:
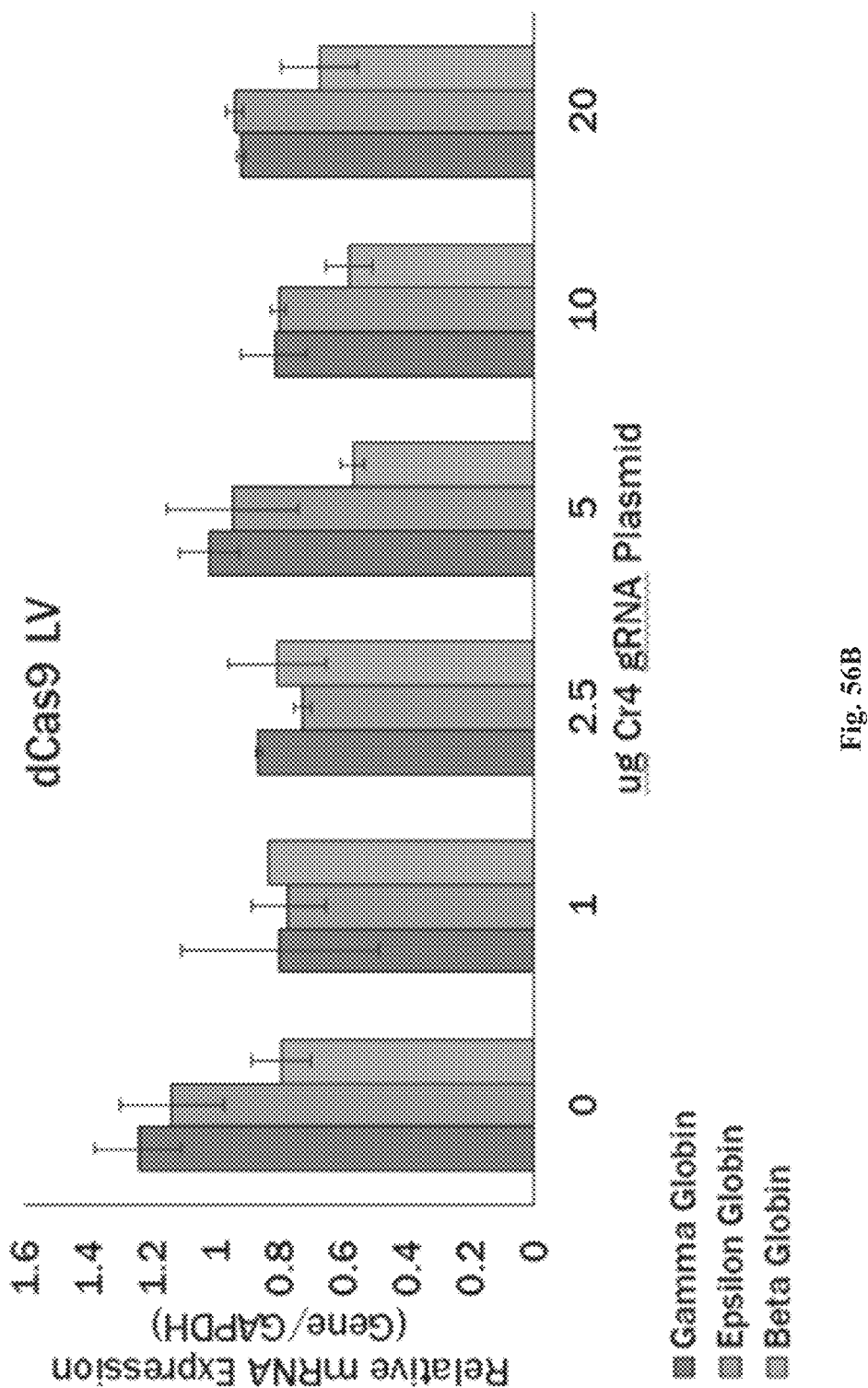
Figure 56C:
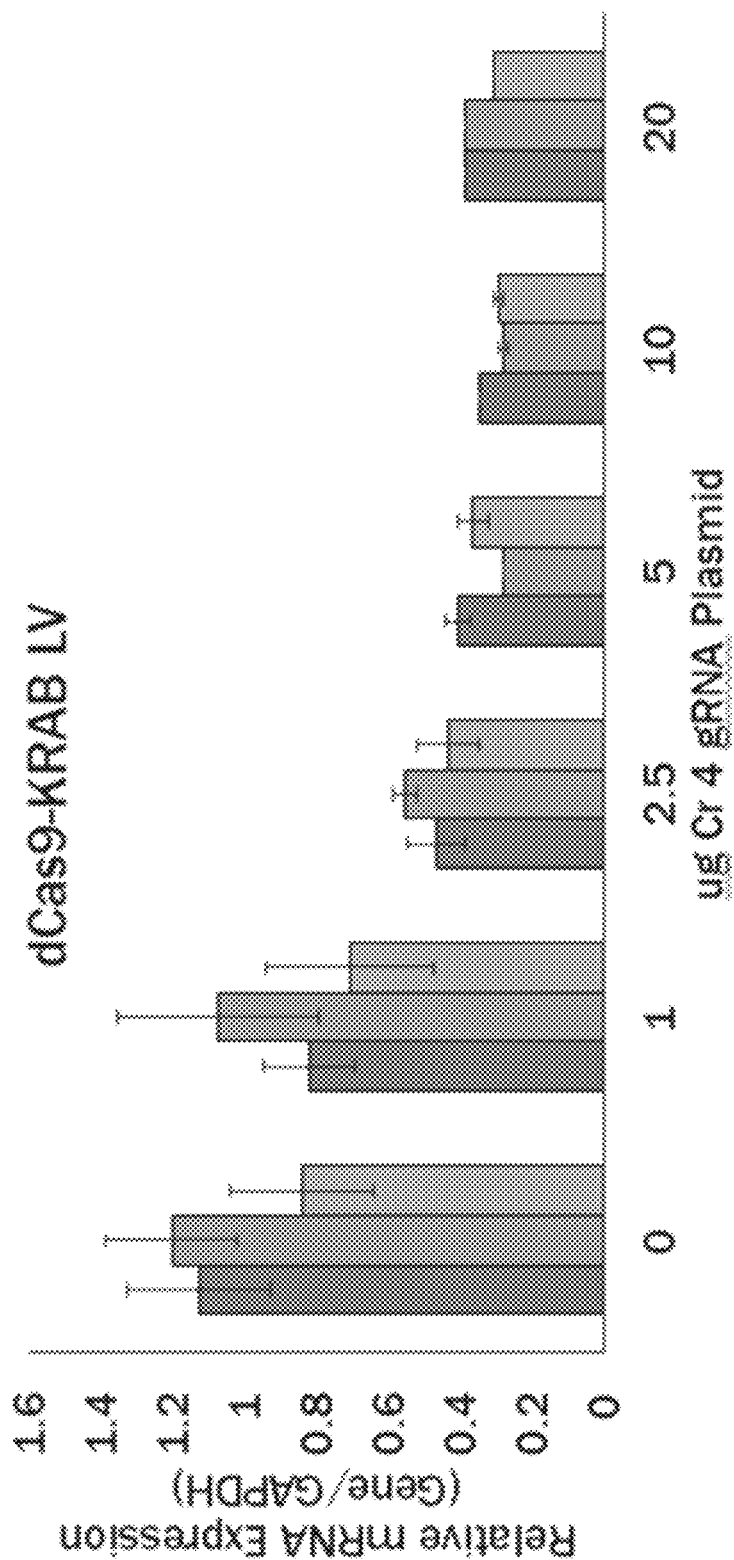

Screening single gRNAs at the globin locus by CRISPR/dCas9. dCas9 and dCas9-KRAB effectors were delivered lentivirally 5-8 days prior to electroporation with 5 µg of a plasmid encoding the U6-sgRNA expression (FIG. 55A). Cells that were not electroporated with gRNA (no gRNA) and cells treated with a gRNA targeting a different locus (IL1RN) were included as controls. Multiple gRNAs effected potent repression of ε-, γ-, and β-globin genes when assayed 3 days post-transfection, with up to 80% knockdown achieved (FIGS. 55B, 55C, 55D). Expressing a gRNA with either dCas9 or dCas9-KRAB inhibited gene expression at the globin locus. Generally, treatment with dCas9-KRAB resulted in stronger repression for a given gRNA compared to dCas9 alone, suggesting an important role for the KRAB domain in recruiting heterochromatin factors that enhance repression. The repression levels achieved are dependent on the amount of gRNA plasmid delivered by transfection only in the dCas9-KRAB treated cells (FIGS. 56A, 56B, 56C). Increasing the dose of Cr4 gRNA plasmid up to 10 increases silencing levels of the globin genes in dCas9-KRAB-treated cells.

Figure 57A:
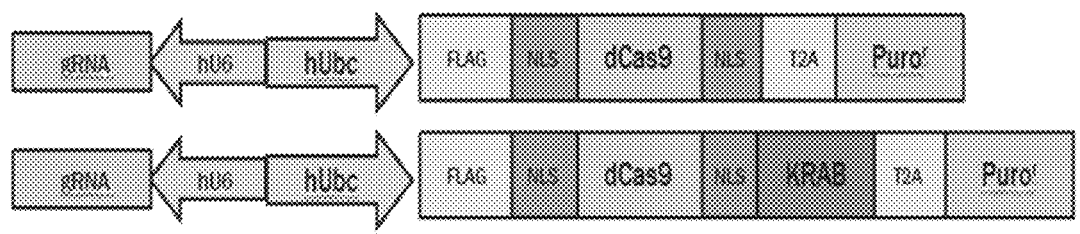
FIGS. 57A-57D show that stably delivering single gRNAs with dCas9-KRAB silences expression of the globin genes.
Figure 57B:
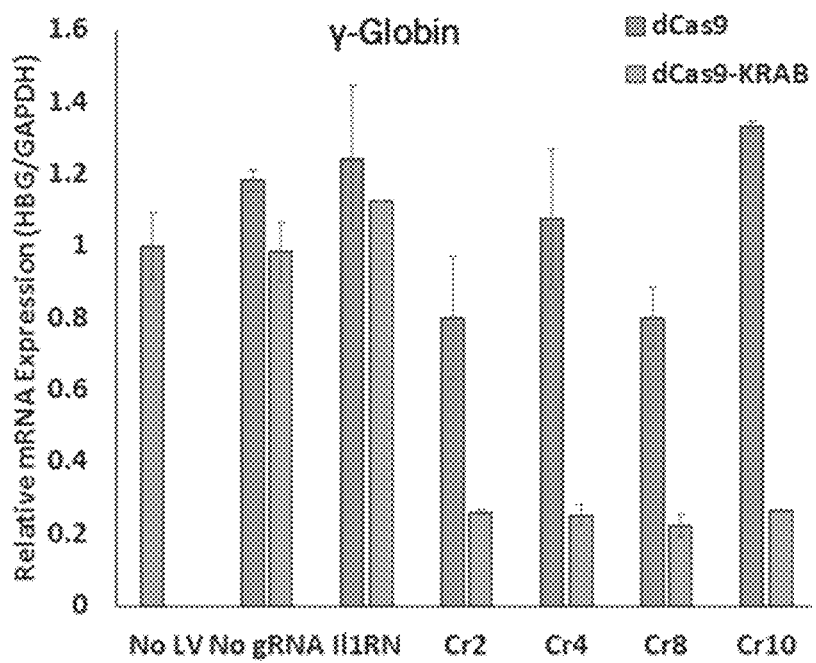
Figure 57C:
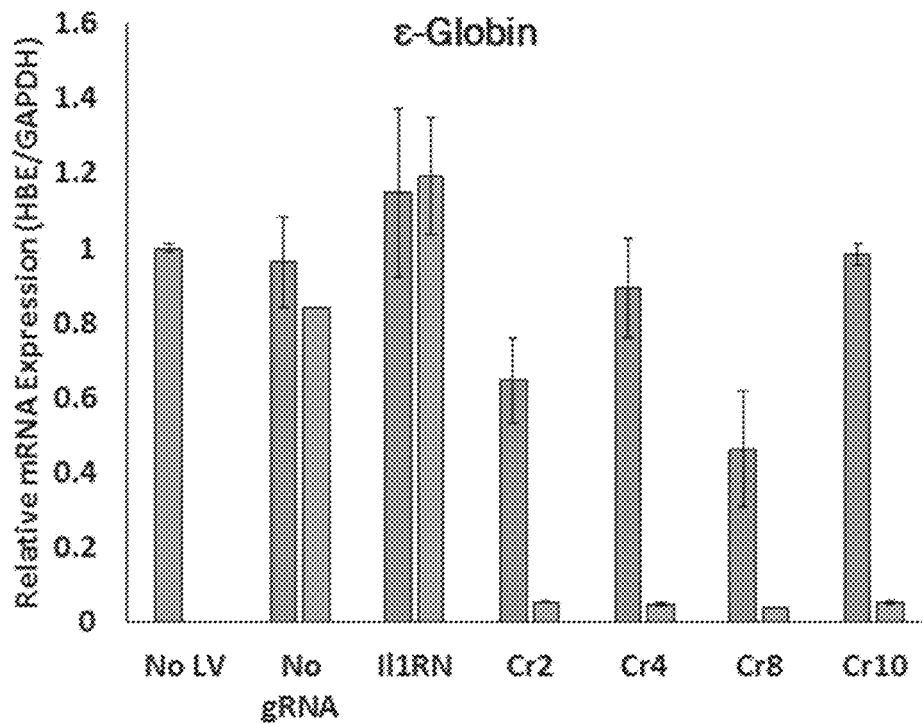
Figure 57D:
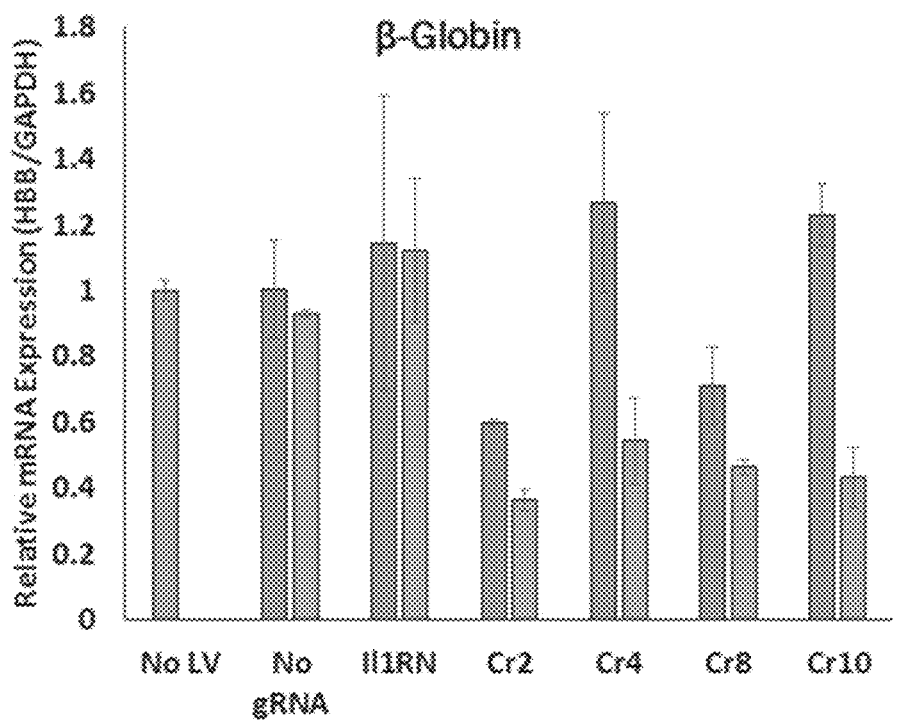

Stable silencing of globin genes by dCas9-KRAB. dCas9/dCas9-KRAB were co-expressed with single gRNAs lentivirally in K562s (FIG. 57A). Cells that were not treated with lentivirus (NT), treated with dCas9/dCas9-KRAB without a gRNA (no gRNA), and with dCas9/dCas9-KRAB and gRNA targeting a different locus (IL1RN) were included as controls. Cells treated with lentivirus were selected from days 4 to 7. Multiple gRNAs effected potent transcriptional repression of ε-, γ-, and β-globin genes when assayed 7 days after transduction, with up to 95% knockdown achieved (FIGS. 57B, 57C, 57D). Expression of ε-globin was silenced the most in response gRNAs targeted to the HS2 enhancer. Treatment with dCas9-KRAB with a gRNA resulted in dramatically more repression than treatment with dCas9 and gRNA.

These findings demonstrate that dCas9-KRAB targeted to the HS2 enhancer by gRNAs effects potent repression of the distal globin genes. This is the first example of targeted epigenetic control of distal regulatory elements in mammalian cells by the CRISPR/Cas9 system. Enhancers regulate development and disease, and this disclosure provides a method to probe and control enhancer function and may be used to determine the effects of dCas9-KRAB on local chromatin accessibility and genome-wide expression.

Example 23 dCas9-p300

Figure 59:
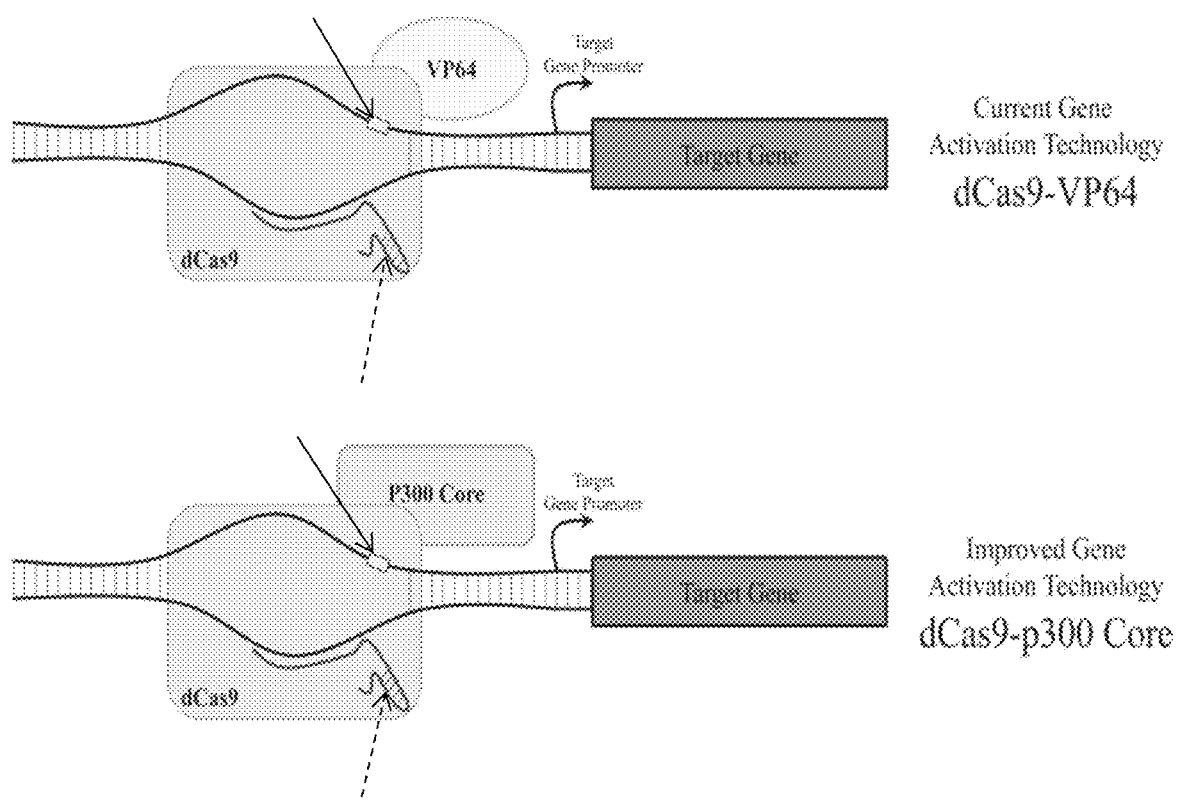
FIG. 59 shows a simplified schematic of S. pyogenes dCas9-VP64 fusion (top) and dCas9-p300 core fusion (bottom). The Protospacer Adjacent Motifs (PAM) are shown with arrows at target gene loci and synthetic guide RNA (gRNA) is shown with hatched arrows.

A dCas9-p300 fusion protein was designed and compared to dCas9-VP64 fusion protein (see FIG. 59). The amino acid constructs of dCas9 constructions are shown in FIG. 61A-61C. Cells from the Human Embryonic Kidney tissue culture line HEK293T (ATCC; CRL-11268) were seeded at a density of 1.5e5 cells per well in 24-well tissue culture dishes one day prior to transfection with Lipofectamine 2000 transfection reagent (Life Technologies). 24 hrs later cells were transfected with 1 µL Lipofectamine 2000, 375 ng dCas9 expression construct (dCas9, dCas9VP64, or dCas9p300 respectively), and 125 ng of pooled gRNA expression plasmids (4 each at equimolar ratios). Table 13 shows the gRNA information.

TABLE 13 gRNA information

| Target Location | Protospacer Sequence (5'-3') | Genomic Location (GRCh38 Primary Assembly) | Reference |
|---|---|---|---|
| IL1RN Promoter | TGTACTCTCTGAGGTGCTC (SEQ ID NO: 606) | Chr2: 113117865-113117883 | Perez-Pinera et al., Nat Methods, 2013 |
| IL1RN Promoter | ACGCAGATAAGAACCAGTT (SEQ ID NO: 607) | Chr2: 113117714-113117732 | Perez-Pinera et al., Nat Methods, 2013 |
| IL1RN Promoter | CATCAAGTCAGCCATCAGC (SEQ ID NO: 608) | Chr2: 113117781-113117799 | Perez-Pinera et al., Nat Methods, 2013 |
| IL1RN Promoter | GAGTCACCCTCCTGGAAAC (SEQ ID NO: 609) | Chr2: 113117749-113117767 | Perez-Pinera et al., Nat Methods, 2013 |
| MyoD Promoter | CCTGGGCTCCGGGGCGTTT (SEQ ID NO: 610) | Chr11: 17719509-17719527 | Perez-Pinera et al., Nat Methods, 2013 |
| MyoD Promoter | GGCCCCTGCGGCCACCCCG (SEQ ID NO: 611) | Chr11: 17719422-17719440 | Perez-Pinera et al., Nat Methods, 2013 |
| MyoD Promoter | CTCCCTCCCTGCCCGGTAG (SEQ ID NO: 612) | Chr11: 17719350-17719368 | Perez-Pinera et al., Nat Methods, 2013 |
| MyoD Promoter | AGGTTTGGAAAGGGCGTGC (SEQ ID NO: 613) | Chr11: 17719290-17719308 | Perez-Pinera et al., Nat Methods, 2013 |
| Oct4 Promoter | ACTCCACTGCACTCCAGTCT (SEQ ID NO: 614) | Chr6: 31170953-31170934 | Hu et al., Nucleic Acids Res, 2014 |
| Oct4 Promoter | TCTGTGGGGGACCTGCACTG (SEQ ID NO: 615) | Chr6: 31170885-31170866 | Hu et al., Nucleic Acids Res, 2014 |
| Oct4 Promoter | GGGGCGCCAGTTGTGTCTCC (SEQ ID NO: 616) | Chr6: 31170855-31170836 | Hu et al., Nucleic Acids Res, 2014 |
| Oct4 Promoter | ACACCATTGCCACCACCATT (SEQ ID NO: 617) | Chr6: 31170816-31170797 | Hu et al., Nucleic Acids Res, 2014 |

The 3 days post-transfection cells were harvested and assayed by RT-QPCR for mRNA expression. The RT-QPCR primer sequences are listed in Table 14.

TABLE 14

RT-QPCR Primers

| Primer Target | Primer Sequence (5'-3') | Reference |
|---|---|---|
| GAPDH Forward | CAATGACCCCTTCATTGACC (SEQ ID NO: 618) | Perez-Pinera et al., Nat Methods, 2013 |
| GAPDH Reverse | TTGATTTTGGAGGGATCTCG (SEQ ID NO: 619) | Perez-Pinera et al., Nat Methods, 2013 |
| IL1RN Forward | GGAATCCATGGAGGGAAGAT (SEQ ID NO: 620) | Perez-Pinera et al., Nat Methods, 2013 |
| IL1RN Reverse | TGTTCTCGCTCAGGTCAGTG (SEQ ID NO: 621) | Perez-Pinera et al., Nat Methods, 2013 |
| MyoD Forward | CTCTCTGCTCCTTTGCCACA (SEQ ID NO: 622) | Perez-Pinera et al., Nat Methods, 2013 |

TABLE 14-continued

RT-QPCR Primers

| Primer Target | Primer Sequence (5'-3') | Reference |
|---|---|---|
| MyoD Reverse | GTGCTCTTCGGGTTTCAGGA (SEQ ID NO: 623) | Perez-Pinera et al., Nat Methods, 2013 |
| Oct4 Forward | CGAAAGAGAAAGCGAACCAGTATCGAGAAC (SEQ ID NO: 624) | Hu et al., Nucleic Acids Res, 2014 |
| Oct4 Reverse | CGTTGTGCATAGTCGCTGCTTGATCGC (SEQ ID NO: 625) | Hu et al., Nucleic Acids Res, 2014 |

Figure 60A:
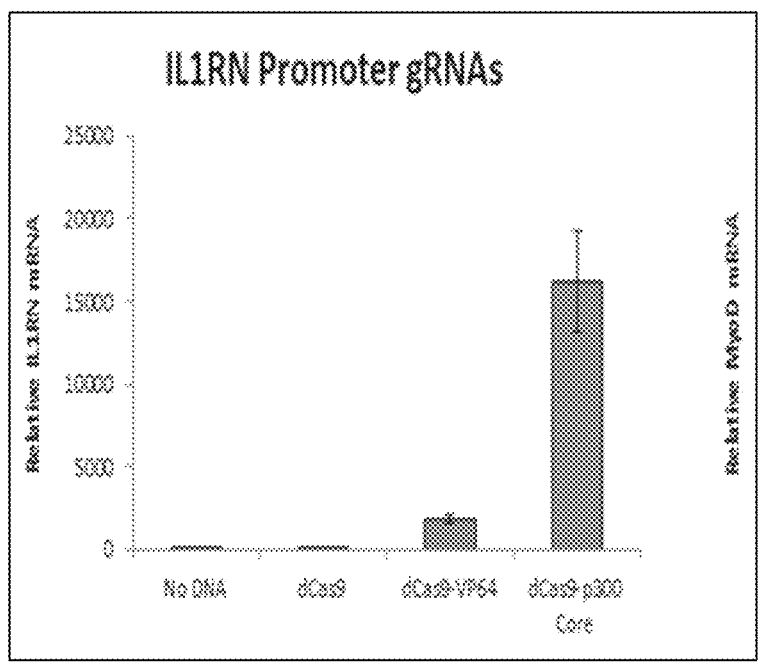
FIGS. 60A-60C show representative data at three human loci demonstrating the efficacy of activation using dCas9-p300 in relation to dCas9-VP64 and dCas9 without any fused effector domain in the human 293T cell culture line.
Figure 60B:
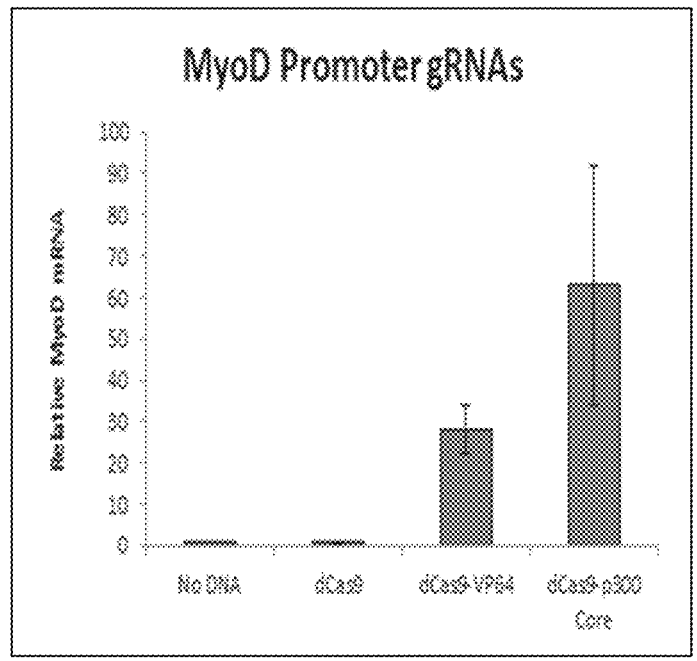
Figure 60C:
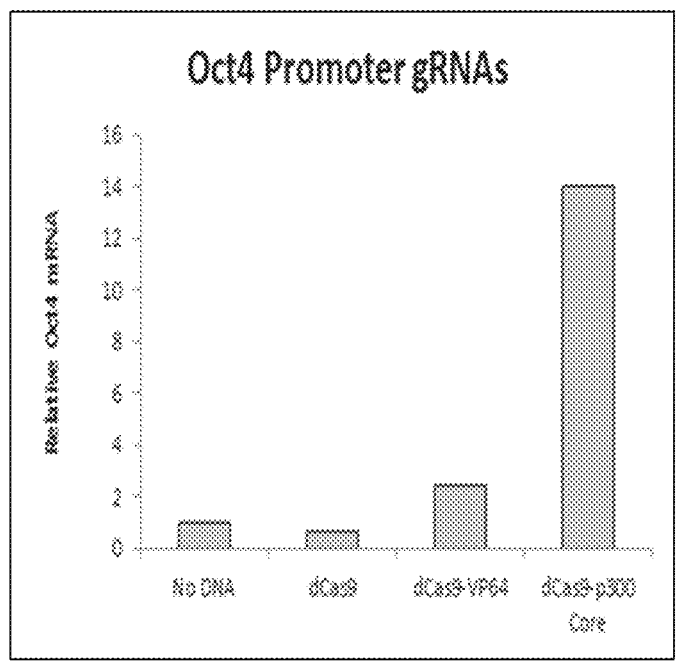

RT-QPCR was normalized to GAPDH expression using the $\Delta\Delta C_t$ method. Results are expressed as fold-increase expression of the gene of interest relative to cells treated with Lipofectamine only without DNA transfected ("No DNA") (See FIGS. 60A-60C).

Figure 62:
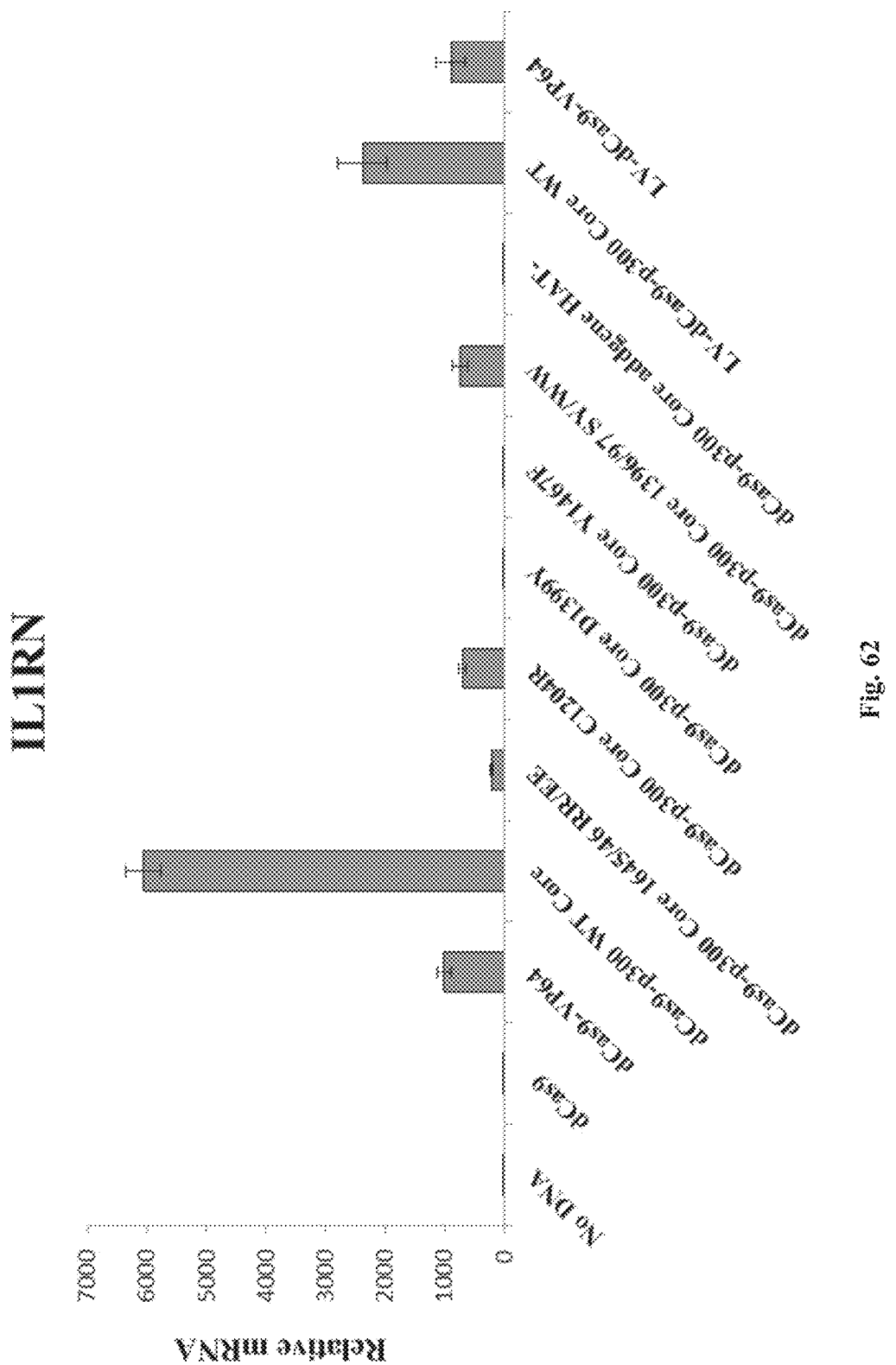
FIG. 62 shows that HAT-dCase9-p300 fusion proteins fail to activate gene expression.
Figure 63A:
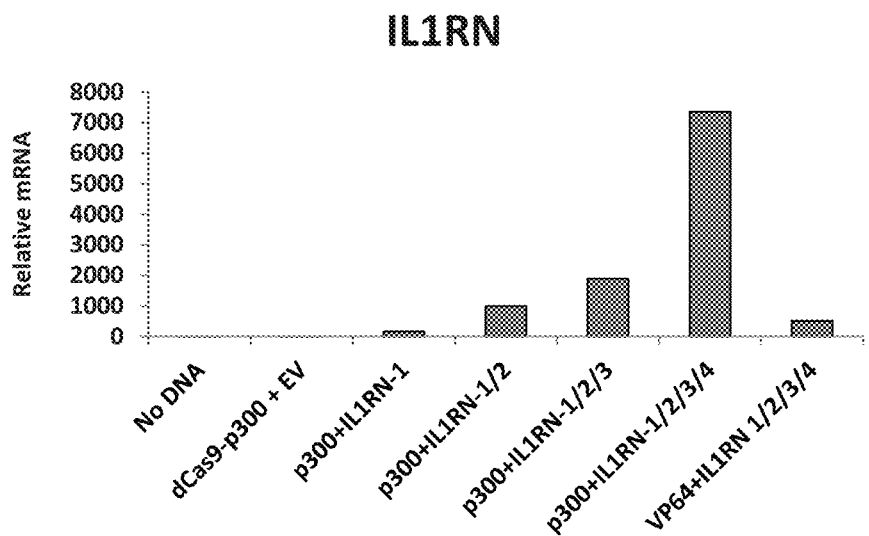
FIGS. 63A-63B show that gRNA's also act synergistically with dCas9-p300 Core.
Figure 63B:
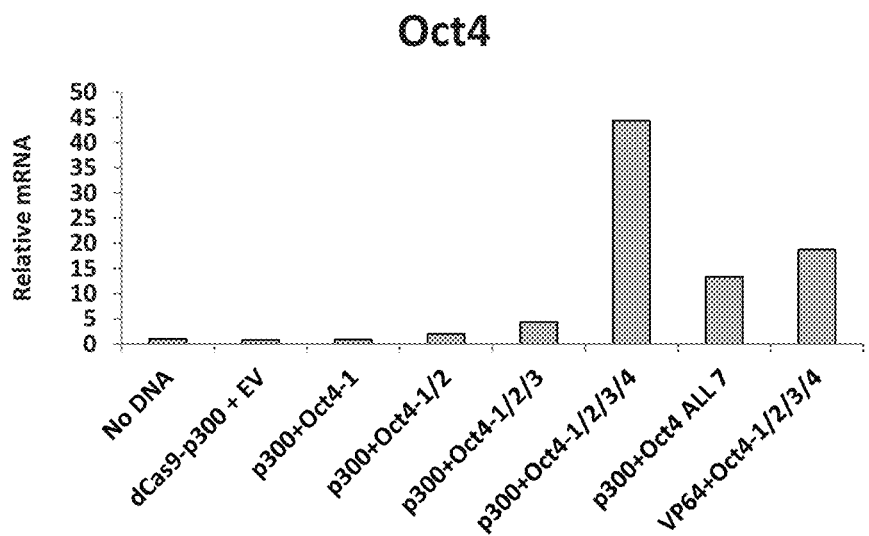

FIG. 62 shows that mutating residues in the p300 HAT domain causes a loss of its ability to activate gene expression. FIGS. 63A-63B show that multiple gRNAs work synergistically with dCas-9-p300, as showed with dCas-9-VP64.

Example 24

FIGS. 64A-64C show TALEN mediated integration of minidystrophin at the 5'UTR of the Dp427m skeletal muscle isoform of dystrophin in skeletal myoblast cell lines derived from human DMD patients carrying different deletions in the dystrophin gene. DMD patient cells were electroporated with constructs encoding a TALEN pair active at the 5'UTR locus and a donor template carrying the minidystrophin gene. FIG. 64A shows a schematic of how minidystrophin was integrated into the 5'UTR. FIG. 64B shows that hygromycin-resistant clonal cell lines were isolated and screened by PCR for successful site-specific integrations at the 5'UTR using the primers shown in FIG. 64A. Asterisks indicate clones selected for further analysis in FIG. 64C. FIG. 64C shows that clonally isolated DMD myoblasts with detected integration events were differentiated for 6 days and assessed for expression of an HA tag fused to the C terminus of minidystrophin.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

Appendix hCas9-T2A-GFP DNA sequence: SEQ ID NO: 145 (SpCas9 human optimized sequence, HA tag, T2A peptide, eGFP sequence)

```
gccaccATGGACAAGAAGTACTCCATTGGGCTCGATATCGGCACAAACAG
CGTCGGCTGGGCCGTCATTACGGACGAGTACAAGGTGCCGAGCAAAAAAT
TCAAAGTTCTGGGCAATACCGATCGCCACAGCATAAAGAAGAACCTCATT
GGCGCCCTCCTGTTCGACTCCGGGGAGACGGCCGAAGCCACGCGGCTCAA
AAGAACAGCACGGCGCAGATATACCCGCAGAAAGAATCGGATCTGCTACC
TGCAGGAGATCTTTAGTAATGAGATGGCTAAGGTGGATGACTCTTTCTTC
CATAGGCTGGAGGAGTCCTTTTTGGTGGAGGAGGATAAAAAGCACGAGCG
CCACCCAATCTTTGGCAATATCGTGGACGAGGTGGCGTACCATGAAAAGT
ACCCAACCATATATCATCTGAGGAAGAAGCTTGTAGACAGTACTGATAAG
GCTGACTTGCGGTTGATCTATCTCGCGCTGGCGCATATGATCAAATTTCG
GGGACACTTCCTCATCGAGGGGGACCTGAACCCAGACAACAGCGATGTCG
ACAAACTCTTTTATCCAACTGGTTCAGACTTACAATCAGCTTTTCGAAGAG
AACCCGATCAACGCATCCGGAGTTGACGCCAAAGCAATCCTGAGCGCTAG
GCTGTCCAAATCCCGGCGGCTCGAAAACCTCATCGCACAGCTCCCTGGGG
AGAAGAAGAACGGCCTGTTTGGTAATCTTATCGCCCTGTCACTCGGGCTG
ACCCCCAACTTTAAATCTAACTTCGACCTGGCCGAAGATGCCAAGCTTCA
ACTGAGCAAAGACACCTACGATGATGATCTCGACAATCTGCTGGCCCAGA
TCGGCGACCAGTACGCAGACCTTTTTTGGCGGCAAAGAACCTGTCAGAC
GCCATTCTGCTGAGTGATATTCTGCGAGTGAACACGGAGATCACCAAAGC
TCCGCTGAGCGCTAGTATGATCAAGCGCTATGATGAGCACCACCAAGACT
TGACTTTGCTGAAGGCCCTTGTCAGACAGCAACTGCCTGAGAAGTACAAG
GAAATTTTCTTCGATCAGTCTAAAAATGGCTACGCCGGATACATTGACGG
CGGAGCAAGCCAGGAGGAATTTTACAAATTTATTAAGCCCATCTTGGAAA
AAATGGACGGCACCGAGGAGCTGCTGGTAAAGCTTAACAGAGAAGATCTG
TTGCGCAAACAGCGCACTTTCGACAATGGAAGCATCCCCCACCAGATTCA
CCTGGGCGAACTGCACGCTATCCTCAGGCGGCAAGAGGATTTCTACCCCT
TTTTGAAAGATAACAGGGAAAAAGATTGAGAAAATCCTCACATTTCGGATA
CCCTACTATGTAGGCCCCCTCGCCCGGGGAAATTCCAGATTCGCGTGGAT
GACTCGCAAATCAGAAGAGACCATCACTCCCTGGAACTTCGAGGAAGTCG
TGGATAAGGGGGCCTCTGCCCAGTCCTTCATCGAAAGGATGACTAACTTT
GATAAAAATCTGCCTAACGAAAAGGTGCTTCCTAAACACTCTCTGCTGTA
CGAGTACTTCACAGTTTATAACGAGCTCACCAAGGTCAAATACGTCACAG
AAGGGATGAGAAAGCCAGCATTCCTGTCTGGAGAGCAGAAGAAAGCTATC
GTGGACCTCCTCTTCAAGACGAACCGGAAAGTTACCGTGAAACAGCTCAA
AGAAGACTATTTCAAAAAGATTGAATGTTTCGACTCTGTTGAAATCAGCG
GAGTGGAGGATCGCTTCAACGCATCCCTGGGAACGTATCACGATCTCCTG
AAAATCATTAAAGACAAGGACTTCCTGGACAATGAGGAGAACGAGGACAT
TCTTGAGGACATTGTCCTCACCCTTACGTTGTTTGAAGATAGGGAGATGA
TTGAAGAACGCTTGAAAACTTACGCTCATCTCTTCGACGACAAAGTCATG
AAACAGCTCAAGAGGCGCCGATATACAGGATGGGGGCGGCTGTCAAGAAA
ACTGATCAATGGGATCCGAGACAAGCAGAGTGGAAAGACAATCCTGGATT
TTCTTAAGTCCGATGGATTTGCCAACCGGAACTTCATGCAGTTGATCCAT
GATGACTCTCTCACCTTTAAGGAGGACATCCAGAAAGCACAAGTTTCTGG
CCAGGGGACAGTCTTCACGAGCACATCGCTAATCTTGCAGGTAGCCCAG
CTATCAAAAAGGGAATACTGCAGACCGTTAAGGTCGTGGATGAACTCGTC
AAAGTAATGGGAAGGCATAAGCCCGAGAATATCGTTATCGAGATGGCCCG
AGAGAACCAAACTACCCAGAGGGACAGAAGAACAGTAGGGAAAGGATGA
AGAGGATTGAAGAGGGTATAAAAGAACTGGGGTCCCAAATCCTTAAGGAA
CACCCAGTTGAAAACACCCAGCTTCAGAATGAGAAGCTCTACCTGTACTA
CCTGCAGAACGGCAGGGACATGTACGTGGATCAGGAACTGGACATCAATC
GGCTCTCCGACTACGACGTGGATCATATCGTGCCCCAGTCTTTTCTCAAA
GATGATTCTATTGATAATAAAGTGTTGACAAGATCCGATAAAAATAGAGG
GAAGAGTGATAACGTCCCCTCAGAAGAAGTTGTCAAGAAAATGAAAAATT
ATTGGCGGCAGCTGCTGAACGCCAAACTGATCACACAACGGAAGTTCGAT
AATCTGACTAAGGCTGAACGAGGTGGCCTGTCTGAGTTGGATAAAGCCGG
CTTCATCAAAAGGCAGCTTGTTGAGACACGCCAGATCACCAAGCACGTGG
CCCAAATTCTCGATTCACGCATGAACACCAAGTACGATGAAAATGACAAA
CTGATTCGAGAGGTGAAAGTTATTACTCTGAAGTCTAAGCTGGTCTCAGA
TTTCAGAAAGGACTTTCAGTTTTATAAGGTGAGAGAGATCAACAATTACC
ACCATGCGCATGATGCCTACCTGAATGCAGTGGTAGGCACTGCACTTATC
AAAAAATATCCCAAGCTTGAATCTGAATTTGTTTACGGAGACTATAAAGT
GTACGATGTTAGGAAAATGATCGCAAAGTCTGAGCAGGAAATAGGCAAGG
CCACCGCTAAGTACTTCTTTTACAGCAATATTATGAATTTTTTCAAGACC
GAGATTACACTGGCCAATGGAGAGATTCGGAAGCGACCCACTTATCGAAAC
AAACGGAGAAACAGGAGAAATCGTGTGGGACAAGGGTAGGGATTTCGCGA
CAGTCCGGAAGGTCCTGTCCATGCCGCAGGTGAACATCGTTAAAAAGACC
GAAGTACAGACCGGAGGCTTCTCCAAGGAAAGTATCCTCCCGAAAAGGAA
CAGCGACAAGCTGATCGCACGCAAAAAGATTGGGACCCCAAGAAATACG
GCGGATTCGATTCTCCTACAGTCGCTTACAGTGTACTGGTTGTGGCCAAA
GTGGAGAAAGGGAAGTCTAAAAAACTCAAAAGCGTCAAGGAACTGCTGGG
CATCACAATCATGGAGCGATCAAGCTTCGAAAAAAAACCCCATCGACTTTC
TCGAGGCGAAAGGATATAAAGAGGTCAAAAAAGACCTCATCATTAAGCTT
CCCAAGTACTCTCTCTTTGAGCTTGAAAACGGCCGGAAACGAATGCTCGC
TAGTGCGGGCGAGCTGCAGAAAGGTAACGAGCTGGCACTGCCCTCTAAAT
ACGTTAATTTCTTGTATCTGGCCAGCCACTATGAAAAGCTCAAAGGGTCT
CCCGAAGATAATGAGCAGAAGCAGCTGTTCGTGGAACAACACAAACACTA
CCTTGATGAGATCATCGAGCAAATAAGCGAATTCTCCAAAAGAGTGATCC
```

Appendix-continued

TCGCCGACGCTAACCTCGATAAGGTGCTTTCTGCTTACAATAAGCACAGG
GATAAGCCCATCAGGGAGCAGGCAGAAAACATTATCCACTTGTTTACTCT
GACCAACTTGGGCGCGCCTGCAGCCTTCAAGTACTTCGACACCACCATAG
ACAGAAAGCGGTACACCTCTACAAAGGAGGTCCTGGACGCCCACACTGATT
CATCCAGTCAATTACGGGGCTCTATGAAACAAGAATCGACCTCTCTCAGCT
CGGTGGAGACAGCAGGGCTGACCCCAAGAAGAAGAGGAAGGTGGCTAGCG
AGGGCAAGAGGAAGTCTTCTAACATGCGGTGACGTGGAGGAGAATCCCGG
CCCTGgtacCgtgagcaagggcgaggagctgttcaccgggg
tggtgcccatcctggtcgagctggacggcgacgtga
acggccacaagttcagcgtgtccggcgagggcgagggcgatgcc
acctacggcaagctgaccctgaagttcatctgcacc
accggcaagctgcccgtgccctggcccaccctcgtgaccaccct
gacctacggcgtgcagtgcttcagccgctaccccga
ccacatgaagcagcacgacttcttcaagtccgccatgcccgaag
gctacgtccaggagcgcaccatcttcttcaaggacga
cggcaactacaagacccgcgccgaggtgaaqcccctggtgaaccgcatc
gagctgaagggcatcgacttcaaggaggacggcaaca
tcctggggcacaagctggagtacaaqttcgagggcgac
ctacaacagccacaacgtctatatcatggccgacaagcagaaga
acggcatcaaggtgaacttcaagatccgccacaaca
tcgaggacggcagcgtgcagctcgccgaccactacc
agcagaacacccccatcggcgacggccccgtgctgctgcccgac
aaccactacctgagcacccagtccgccctgagcaaa
gaccccaacgagaagcgcgatcacatggtcctgctggagttcgt
gaccgccgcgggatcactctcggcatggacgagctgtacaag
AccggTTAG AAV/Rosa26 construct (SEQ ID NO: 456)
gggggggggggggggggtcggccactccctctctgcgcgctcgctcgct
cactgaggccgggcgaccaaaggtcgcccgacgcccgggcttgcccggg
cggcctcagtgagcgagcgagcgcgcagagagggagtggccaactccatc
actaggggttcctagatctgaattcggtacccgttacataacttacggta
aatggcccgcctggctgaccgcccaacgaccccgcccattgacgtcaat
aatgacgtatgttcccatagtaacgccaatagggactttccattgacgtc
aatgggtggagtatttacggtaaactgcccacttggcagtacatcaagtg
tatcatatgccaagtacgccccctattgacgtcaatgacggtaaatggcc
cgcctggcattatgcccagtacatgaccttatgggactttcctacttggc
agtacatctacgtattagtcatcgctattaccatggtgatgcggttttgg
cagtacatcaatgggcgtggatagcggtttgactcacggggatttccaag
tctccaccccattgacgtcaatgggagtttgttttggcaccaaaatcaac
gggactttccaaaatgtcgtaacaactccgccccattgacgcaaatgggc
ggtaggcgtgtacggtggaggtctatataagcagagctctctggttagtgaa
ccgtcagatcgcctggagacgccatccacgctgttttgacctccatagaa
gacaccgggaccgatccagcctccggactctagaggatccggtactcgag
gaactgaaaaaccagaaagttaactggtaagtttagtcttttgtctttt
atttcaggtcccggatcggtggtggtgcaaatcaagaaactgctcctca
gtggatgttgcctttacttctaggcctgtacggaagtgttacttctgctc
taaaagctgcggaattgtaccgcgggcccgggatccaccggTGGTAGCg
tctataggcccaccccTTGGTGGAATTCGCCATGAGGTCTGACTACAAA
GACCATGACGGTGATTATAAAGATCATGACATCGATTACAAGGATGACGA
TGACAAGATGGCCCCCAAGAAGAAGAggaaggtgggcctcgaGCCCGGAG
AAAAACCGTACAAGTGCCCTGAGTGCGGGAAATCATTCTCCGACCCTGGG
GCGCTCGTCCGGCACCAAAGGACGCATACAGGGGAAAAGCCGTATAAGTG
CCCCGAGTGTGGAAAGAGCTTCTCGCAGAGAGCCCACCTTGAACGACACC
AAAGAACACACACTGGTGAGAAACCCTATAAGTGTCCAGAGTGCGGCAAA
TCGTTTAGCAGATCCGATGACTTGGTGCGCCACCAGCGGACACACACGGG
TGAAAAGCCCTACAAATGCCCGGAGTGTGGGAAGTCGTTTTCAAGGTCGG
ATCATCTGACTACCCATCAGCGCACCCATACGGGAGCggccgcccgcgcc
ctGGTGAAGAGCGAGCTGGAGGAGAAGAAGTCCGAGCTGCGGCACAAGCT
GAAGTACGTGCCCCACGAGTACATCGAGCTGATCGAGATCGCCAGGAACC
CCACCCAGGACCGCATCCTGGAGATGAAGGTGATGGAGTTCTTCATGAAG
GTGTACGGCTACAGGGGAGAGCACCTGGGCGGAAGCAGAAAGCCTGACGG
CGCCATCTATACAGTGGGCAGCCCCATCGATTACGGCGTGATCGTGGACA
CAAAGGCCTACAGCGGCGGCTACAATCTGCCTATCGGCCAGGCCGACAAG
ATGCAGAGATACGTGAAGGAGAACCAGACCCGGAATAAGCACATCAACCC
CAACGAGTGGTGGAAGGTGTACCCTAGCAGCGTGACCGAGTTCAAGTTCC
TGTTCGTGAGCGGCCACTTCAAGGGCAACTACAAGGCCCAGCTGACCAGG
CTGAACCGCAAAACCAACTGCAATGGCGCCGTGCTGAGCGTGGAGGAGCT
GCTGATCGGCGGCGAGATGATCAAAGCCGGCACCCTGACACTGGAGGAGG
TGCGGCGCAAGTTCAACAACGGCGAGATCAACTTCGAGGGCAGAGGAAGT
CTTCTAACATGCGGTGACGTGGAGGAGAATCCCGGCCCTAgatcTGACTA
CAAAGACCATGACGGTGATTATAAAGATCATGACATCGATTACAAGGATG
ACGATGACAAGATGGCCCCCAAGAAGAAGAggaaggtgggcctcgaGCC
GGAGAGAAGCCGTACAAGTGTCCCGAATGTGGAAAGAGCTTCTCACAGTC
GGGGGACCTTCGGCGCCACCAGCGACACACATCGGTGAAAAGCCGTATA
AGTGTCCAGAATGGCAAATCATTCTCCACATCAGGGAGCCTGGTCAGG
CACCAGCGAACCCACGGGTGAGAAGCCCTATAAGTGCCCCGAATGCGGG
GAAGTCCTTTTCGCAGAGAGCCCACTTGGAGAGGCACCAGAGGACCCATA
CGGGGGAGAAACCTTACAAGTGCCCTGAATGCGGGAAAGTCGTTCTCGACC
CATCTGGATCTCATCAGACATCAGAGAACGCACACTGGAGAGAAACCCTA Appendix-continued CAAATGTCCCGAGTGTGGGAAGTCGTTTAGCCGAAAGGACAATCTCAAAA
ACCATCAACGGACACACACGGGTGAAAAACCATACAAATGCCCGGAGTGC
GGCAAATCGTTTTCCCAACTTGCGCACTTGCGGGCACACCAACGCACGCA
TACTGGAGCGGCCGCccgcgccCTGGTGAAGAGCGAGCTGGAGGAGAAGA
AGTCCGAGCTGCGGCACAAGCTGAAGTACGTGCCCCACGAGTACATCGAG
CTGATCGAGATCGCCAGGAACCCCACCCAGGACCGCATCCTGGAGATGAA
GGTGATGGAGTTCTTCATGAAGGTGTACGGCTACAGGGGAGAGCACCTGG
GCGGAAGCAGAAAGCCTGACGGCGCCATCTATACAGTGGGCAGCCCCATC
GATTACGGCGTGATCGTGGACACAAAGGCCTACAGCGGCGGCTACAATCT
GCCTATCGGCCAGGCCGACGAGATGGAGAGATACGTGGAGGAGAACCAGA
CACGGGATAAGCACCTCAACCCCAACGAGTGGTGGAAGGTGTACCCTAGC
AGCGTGACCGAGTTCAAGTTCCTGTTCGTGAGCGGCCACTTCAAGGGCAA
CTACAAGGCCCAGCTGACCAGGCTGAACCATCACCAACTGCAATGGCG
CCGTGCTGAGCGTGGAGGAGCTGCTGATCGGCGGCGAGATGATCAAAGCC
GGCACCCTGACACTGGAGGAGGTGCGGCGCAAGTTCAACAACGGCGAGAT
CAACTTCTGATTAATTAACTAATCTAGAGTcgactagagctcgctgatca
gcctcgactgtgccttctagttgccagccatctgttgtttgcccctcccc
cgtgccttccttgaccctggaaggtgccactcccactgtcctttcctaat
aaaatgaggaaattgcatcgcattgtctgagtaggtgtcattctattctg
gggggtgggtggggcaggacagcaaggggaggattgggaagacaatag
caggcatgctggggatgcggtgggctctatggcttctgaggcggaaagaa
ccagctggggctcgactcagggcatgctggggagatctgccacaacatga
cccccaccctgcgcgctcgctcgctcactgaggccgcccgggcaaagcccg
ggcgtcgggcgacctttggtcgcccggcctcagtgagcgagcgagcgcgc
agagagggagtggccaacccccccccccccccctgcagcccagctgca
ttaatgaatcggccaacgcgcggggagaggcggtttgcgtattgggcgct
cttccgcttcctcgctcactgactcgctgcgctcggtcgttcggctgcgg
cgagcggtatcagctcactcaaaggcggtaatacggttatccacagaatc
aggggataacgcaggaaagaacatgtgagcaaaaggccagcaaaaggcca
ggaaccgtaaaaaggccgcgttgctggcgtttttccataggctccgcccc
cctgacgagcatcacaaaatcgacgctcaagtcagaggtggcgaaaccc
gacaggactataaagataccaggcgtttccccctggaagctccctcgtgc
gctctcctgttccgaccctgccgcttaccggatacctgtccgcctttctc
ccttcgggaagcgtggcgctttctcaatgctcacgctgtaggtatctcag
ttcggtgtaggtcgttcgctccaagctgggctgtgtgcacgaaccccccg
ttcagcccgaccgctgcgccttatccggtaactatcgtcttgagtccaac
ccggtaagacacgacttatcgccactggcagcagccactggtaacaggat
tagcagagcgaggtatgtaggcggtgctacagagttcttgaagtggtggc
ctaactacggctacactagaagaacagtatttggtatctgcgctctgctg
aagccagttaccttcggaaaaagagttggtagctcttgatccggcaaaca
aaccaccgctggtagcggtggtttttttgtttgcaagcagcagattacgc
gcagaaaaaaaggatctcaagaagatcctttgatcttttctacggggtct
gacgctcagtggaacgaaaactcacgttaagggattttggtcatgagatt
atcaaaaaggatcttcacctagatcctttaaattaaaaatgaagttttta
aatcaatctaaagtatatatgagtaaacttggtctgacagttaccaatgc
ttaatcagtgaggcacctatctcagcgatctgtctatttcgttcatccat
agttgcctgactccccgtcgtgtagataactacgatacgggagggcttac
catctggccccagtgctgcaatgataccgcgagacccacgctcaccggct
ccagatttatcagcaataaaccagccagccggaagggccgagcgcagaag
tggtcctgcaactttatccgcctccatccagtctattaattgttgccggg
aagctagagtaagtagttcgccagttaatagtttgcgcaacgttgttgcc
attgctacaggcatcgtggtgtcacgctcgtcgtttggtatggcttcatt
cagctccggttcccaacgatcaaggcgagttacatgatccccccatgttgt
gcaaaaaagcggttagctccttcggtcctccgatcgttgtcagaagtaag
ttggccgcagtgttatcactcatggttatggcagcactgcataattctct
tactgtcatgccatccgtaagatgcttttctgtgactggtgagtactcaa
ccaagtcattctgagaatagtgtatgcggcgaccgagttgctcttgcccg
gcgtcaatacggataaccgcgccacatagcagaactttaaaagtgct
catcattggaaaacgttcttcggggcgaaaactctcaaggatcttaccgc
tgttgagatccagttcgatgtaacccactcgtgcacccaactgatcttca
gcatcttttactttcaccagcgtttctgggtgagcaaaaacaggaaggca
aaatgccgcaaaaaagggaataagggcgacacggaaatgttgaatactca
tactcttcctttttcaatattattgaagcatttatcagggttattgtctc
atgagcggatacatatttgaatgtatttagaaaaataaacaaatagggtt
ccgcgcacatttccccgaaaagtgccacctgacgtctaagaaaccatta
ttatcatgacattaacctataaaaataggcgtatcacgaggccctttcgt
ctcgcgcgtttcggtgatgacggtgaaaacctctgacacatgcagctccc
ggagacggtcacagcttgtctgtaagcggatgccgggagcagacaagccc
gtcagggcgcgtcagcgggtgttggcgggtgtcggggctggcttaactat
gcggcatcagagcagattgtactgagagtgcaccatatgcggtgtgaaat
accgcacagatgcgtaaggagaaaataccgcatcaggaaattgtaaacgt
taatattttgttaaaattcgcgttaaattttttgttaaatcagctcatttt
ttaaccaataggccgaaatcggcaaaatcccttataaatcaaaagaatag
accgagatagggttgagtgttgttccagtttggaacaagagtccactat
aaagaacgtggactccaacgtcaaagggcgaaaaaccgtctatcagggcg
atggcccactacgtgaaccatcacctaatcaagttttttggggtcgagg
tgccgtaaagcactaaatcggaaccctaaagggagcccccgatttagagc
ttgacggggaaagccggcgaacgtggcgagaaaggaagggaagaaagcga
aaggagcgggcgctagggcgctggcaagtgtagcggtcacgctgcgcgta Appendix-continued accaccacacccgccgcgcttaatgcgccgctacagggcgcgtcgcgcca
ttcgccattcaggctacgcaactgttgggaagggcgatcggtgcgggcc
tcttcgctattacgccagctggctgca HS2 Enhancer Target Sequence (SEQ ID NO: 467)
taagcttcagttttttccttagttcctgttacatttctgtgtgtctccatt
agtgacctcccatagtccaagcatgagcagttctggccaggccctgtcg
gggtcagtgccccaccccgccttctggttctgtgtaaccttctaagcaa
acctctggctcaagcacagcaatgctgagtcatgatgagtcatgctgag
gcttagggtgtgtgcccagatgttctcagcctagagtgatgactcctatc
tgggtccccagcaggatgcttacagggcagatggcaaaaaaaaggagaag
ctgaccacctgactaaaactccacctcaaacggcatcataaagaaaatgg
atgcctgagacagaatgtgacatattctagaatatatt dSpCas9-KRAB Sequence (SEQ ID NO: 466)
ATGGACTACAAAGACCATGACGGTGATTATAAAGATCATGACATCGATTA
CAAGGATGACGATGACAAGatggcccccaagaagaagaggaaggtgggcc
gcggaATGGACAAGAAGTACTCCATTGGGCTCGCCATCGGCACAAACAGC
GTCGGCTGGGCCGTCATTACGGACGAGTACAAGGTGCCGAGCAAAAATT
CAAAGTTCTGGGCAATACCGATCGCCACAGCATAAAGAAGAACCTCATTG
GCGCCCTCCTGTTCGACTCTGGGGAAACCGCCGAAGCCACGCGGCTCAAA
AGAACAGCACGGCGCAGATATACCCGCAGAAGAATCGGATCTGCTACCt
gcaGGAGATCTTTAGTAATGAGATGGCTAAGGTGGATGACTCTTTCTTCC
ATAGGCTGGAGGAGTCCTTTTTGGTGGAGGAGGATAAAAAGCACGAGCGC
CACCCAATCTTTGGCAATATCGTGGACGAGGTGGCGTACCATGAAAGTA
CCCAACCATATATCATCTGAGGAAGAAGCTTGTAGACAGTACTGATAAGG
CTGACTTGCGGTTGATCTATCTCGCGCTGGCGCATATGATCAAATTTCGG
GGACACTTCCTCATCGAGGGGGACCTGAACCCAGACAACAGCGATGTCGA
CAAACTCTTTATCCAACTGGTTCAGACTTACAATCAGCTTTTCGAAGAGA
ACCCGATCAACGCATCCGGAGTTGACGCCAAAGCAATCCTGAGCGCTAGG
CTGTCCAAATCCCGGCGGCTCGAAAACCTCATCGCACAGCTCCCTGGGGA
GAAGAAGAACGGCCTGTTTGGTAATCTTATCGCCCTGTCACTCGGGCTGA
CCCCAACTTTAAATCTAACTTCGACTCGGCCGAAGATGCCAAGCTTCAA
CTGAGCAAAGACACCTACGATGATGATCTCGACAATCTGCTGGCCCAGAT
CGGCGACCAGTACGCAGACCTTTTTTGGCGGCAAAGAACCTGTCAGACG
CCATTCTGCTGAGTGATATTCTGCGAGTGAACACGGAGATCACCAAAGCT
CCGCTGAGCGCTAGTATGATCAAGCGCTATGATGAGCACCACCAAGACTT
GACTTTGCTGAAGGCCCTTGTCAGACAGCAACTGCCTGAGAAGTACAAGG
AAATTTTCTTCGATCAGTCTAAAAATGGCTACGCCGGATACATTGACGGC
GGAGCAAGCCAGGAGGAATTTTACAAATTTATTAAGCCCATCTTGGAAAA
AATGGACGGCACCGAGGAGCTGCTGGTAAAGCTTAACAGAGAAGATCTGT
TGCGCAAACAGCGCACTTTCGACAATGGAAGCATCCCCCACCAGATTCAC
CTGGGCGAACTGCACGCTATCCTCAGGCGGCAAGAGGATTTCTACCCCTT
TTTGAAGATAACAGGGAAAGATTGAGAAAATCCTCACATTTCGGATAC
CCTACTATGTAGGCCCCCTCGCCCGGGGAAATTCCAGATTCGCGTGGATG
ACTCGCAAATCAGAAGGACCATCACTTCCCTGGAACTTCAGGAAGTCGT
GGATAAGGGGGCCTCTGCCCAGTCCTTCATCGAAAGGATGACTAACTTTG
ATAAAAATCTGCCTAACGAAAAGGTGCTTCCTAAACACTCTCTGCTGTAC
GAGTACTTCACAGTTTATAACGAGCTCACCAAGGTCAAATACGTCACAGA
AGGGATGAGAAAGCCAGCATTCCTGTCTGAAGATCAGAAGAAGCTATCG
TGGACCTCCTCTTCAAGACGAACCGGAAAGTTACCGTGAAACAGCTCAAA
GAAGACTATTTCAAAAAGATTGAATGTTTCGACTCTGTTGAAATCAGCGG
AGTGGAGGATCGCTTCAACGCATCCCTGGGAACGTATCACGATCTCCTGA
AAATCATTAAAGACAAGGACTTCCTGGACAATGAGGAGAACGAGGACATT Appendix-continued CTTGAGGACATTGTCCTCACCCTTACGTTGTTTGAAGATAGGGAGATGAT
TGAAGAACGCTTGAAAACTTACGCTCATCTCTTCGACGACAAAGTCATGA
AACAGCTCAAGAGGCGCCGATATACAGGATGGGGGCGGCTGTCAAGAAAA
CTGATCAATGGgatcCGAGACAAGCAGAGTGGAAAGACAATCCTGGATTT
TCTTAAGTCCGATGGATTTGCCAACCGGAACTTCATGCAGTTGATCCATG
ATGACTCTCTCACCTTTAAGGAGGACATCCAGAAAGCACAAGTTTCTGGC
CAGGGGGACAGTCTTCACGAGCACATCGCTAATCTTGCAGGTAGCCCAGC
TATCAAAAAGGGAATACTGCAGACCGTTAAGGTCGTGGATGAACTCGTCA
AAGTAATGGGAAGGCATAAGCCCGAGAATATCGTTATCGAGATGGCCCGA
GAGAACCAAACTACCCAGAAGGGACAGAAGAACAGTAGGGAAAGGATGAA
GAGGATTGAAGAGGGTATAAAAGAACTGGGGTCCCAAATCCTTAAGGAAC
ACCCAGTTGAAAACACCCAGCTTCAGAATGAGAAGCTCTACCTGTACTAC
CTGCAGAACGGCAGGGACATGTACGTGGATCAGGAACTGGACATCAATCG
GCTCTCCGACTACGACGTGGATGCCATCGTGCCCCAGTCTTTTCTCAAAG
ATGATTCTATTGATAATAAAGTGTTGACAAGATCCGATAAAAATAGAGGG
AAGAGTGATAACGTCCCCTCAGAAGAAGTTGTCAAGAAAATGAAAAATTA
TTGGCGGCAGCTGCTGAACGCCAAACTGATCACACAACGGAAGTTCGATA
ATCTGACTAAGGCTGAACGAGGTGGCCTGTCTGAGTTGGATAAAGCCGGC
TTCATCAAAAGGCAGCTTGTTGAGACACGCCAGATCACCAAgcacGTGGC
CCAAATTCTCGATTCACGCATGAACACCAAGTACGATGAAAATGACAAAC
TGATTCGAGAGGTGAAAGTTATTACTCTGAAGTCTAAGCTGGTCTCAGAT
TTCAGAAAGGACTTTCAGTTTTATAAGGTGAGAGAGATCAACAATTACCA
CCATGCGCATGATGCCTACCTGAATGCAGTGGTAGGCACTGCACTTATCA
AAAAATATCCCAAGCTTGAATCTGAATTTGTTTACGGAGACTATAAAGTG
TACGATGTTAGGAAAATGATCGCAAAGTCTGAGCAGGAAATAGGCAAGGC
CACCGCTAAGTACTTCTTTTACAGCAATATTATGAATTTTTTCAAGACCG
AGATTACACTGGCCAATGGAGAGATTCGGAAGCGACCACTTATCGAAACA
AACGGAGAAACAGGAGAAATCGTGTGGGACAAGGGTAGGGATTTCGCGAC
AGTCCGGAAGGTCCTGTCCATGCCGCAGGTGAACATCGTTAAAAAGACCG
AAGTACAGACCGGAGGCTTCTCCAAGGAAAGTATCCTCCCGAAAAGGAAC
AGCGACAAGCTGATCGCACGCAAAAAAGATTGGGACCCCAAGAAATACGG
CGGATTCGATTCTCCTACAGTCGCTTACAGTGTACTGGTTGTGGCCAAAG
TGGAGAAGGGAAAGTCTAAAAAACTCAAAAGCGTCAAGGAACTGCTGGGC
ATCACAATCATGGAGCGATCAAGCTTCGAAAAAAACCCCATCGACTTTCT
CGAGGCGAAAGGATATAAAGAGGTCAAAAAGACCTCATCATTAAGCTTC
CCAAGTACTCTCTCTTTGAGCTTGAAAACGGCCGGAAACGAATGCTCGCT
AGTGCGGGCGAGCTGCAGAAAGGTAACGAGCTGGCACTGCCCCTCTAAATA
CGTTAATTTCTTGTATCTGGCCAGCCACTATGAAAAGCTCAAGGGTCTC
CCGAAGATAATGACAGAAGCAGCTGTTCGTGGAACAACACAAACACTAC
CTTGATGAGATCATCGAGCAAATAAGCGAATTCTCCAAAAGAGTGATCCT
CGCCGACGCTAACCTCGATAAGGTGCTTTCTGCTTACAATAAGCACAGGG
ATAAGCCCATCAGGGAGCAGGCAGAAACATTATCCACTTGTTTACTCTG
ACCAACTTGGGCGCGCCTGCAGCCTTCAAGTACTTCGACACCACCATAGA
CAGAAAGCGGTACACCTCTACAAAGGAGGTCCTGGACGCCACACTGATTC
ATCAGTCAATTACGGGGCTCTATGAAACAAGAATCGACCTCTCTCAGCTC
GGTGGAGACAGCAGGGCTGACCTGAGCAAGAAGAAGAAGGTGGCTCAGA
TGCTAAGTCACTGACTGCCTGGTCCCGGACACTGGTGACCTTCAAGGATG
TGTTTGTGGACTTCACCAGGGAGGAGTGGAAGCTGCTGGACACTGCTCAG
CAGATCCTGTACAGAAATGTGATGCTGGAGAACTATAAGAACCTGGTTTC
CTTGGGTTATCAGCTTACTAAGCCAGATGTGATCCTCCGGTTGGAGAAGG
GAGAAGAGCCCTGGCTGGTGGAGAGAAATTCACCAAGAGACCCATCCT
GATTCAGAGACTGCATTTGAAATCAAATCATCAGTTCCGAAAAAGAAACG
CAAAGttGctagCG

SEQUENCE LISTING

<160> NUMBER OF SEQ ID NOS: 750

<210> SEQ ID NO 1
<211> LENGTH: 1483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Met Asp Lys Lys Tyr Ser Ile Gly Leu Ala Ile Gly Thr

```
                35                  40                  45
Asn Ser Val Gly Trp Ala Val Ile Thr Asp Glu Tyr Lys Val Pro Ser
 50                  55                  60

Lys Lys Phe Lys Val Leu Gly Asn Thr Asp Arg His Ser Ile Lys Lys
 65                  70                  75                  80

Asn Leu Ile Gly Ala Leu Leu Phe Asp Ser Gly Glu Thr Ala Glu Ala
                 85                  90                  95

Thr Arg Leu Lys Arg Thr Ala Arg Arg Tyr Thr Arg Arg Lys Asn
                100                 105                 110

Arg Ile Cys Tyr Leu Gln Glu Ile Phe Ser Asn Glu Met Ala Lys Val
                115                 120                 125

Asp Asp Ser Phe Phe His Arg Leu Glu Glu Ser Phe Leu Val Glu Glu
130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
                180                 185                 190

Leu Ala His Met Ile Lys Phe Arg Gly His Phe Leu Ile Glu Gly Asp
                195                 200                 205

Leu Asn Pro Asp Asn Ser Asp Val Asp Lys Leu Phe Ile Gln Leu Val
210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
                260                 265                 270

Phe Gly Asn Leu Ile Ala Leu Ser Leu Gly Leu Thr Pro Asn Phe Lys
                275                 280                 285

Ser Asn Phe Asp Leu Ala Glu Asp Ala Lys Leu Gln Leu Ser Lys Asp
290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
                340                 345                 350

Ser Ala Ser Met Ile Lys Arg Tyr Asp Glu His His Gln Asp Leu Thr
                355                 360                 365

Leu Leu Lys Ala Leu Val Arg Gln Gln Leu Pro Glu Lys Tyr Lys Glu
                370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
                420                 425                 430

Leu Leu Arg Lys Gln Arg Thr Phe Asp Asn Gly Ser Ile Pro His Gln
                435                 440                 445

Ile His Leu Gly Glu Leu His Ala Ile Leu Arg Arg Gln Glu Asp Phe
                450                 455                 460
```

```
Tyr Pro Phe Leu Lys Asp Asn Arg Glu Lys Ile Glu Lys Ile Leu Thr
465                 470                 475                 480

Phe Arg Ile Pro Tyr Val Gly Pro Leu Ala Arg Gly Asn Ser Arg
            485                 490                 495

Phe Ala Trp Met Thr Arg Lys Ser Glu Glu Thr Ile Thr Pro Trp Asn
                500                 505                 510

Phe Glu Glu Val Val Asp Lys Gly Ala Ser Ala Gln Ser Phe Ile Glu
                515                 520                 525

Arg Met Thr Asn Phe Asp Lys Asn Leu Pro Asn Glu Lys Val Leu Pro
        530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
                580                 585                 590

Lys Val Thr Val Lys Gln Leu Lys Glu Asp Tyr Phe Lys Lys Ile Glu
            595                 600                 605

Cys Phe Asp Ser Val Glu Ile Ser Gly Val Glu Asp Arg Phe Asn Ala
610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
            660                 665                 670

Thr Tyr Ala His Leu Phe Asp Asp Lys Val Met Lys Gln Leu Lys Arg
            675                 680                 685

Arg Arg Tyr Thr Gly Trp Gly Arg Leu Ser Arg Lys Leu Ile Asn Gly
690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
                740                 745                 750

Asp Ser Leu His Glu His Ile Ala Asn Leu Ala Gly Ser Pro Ala Ile
            755                 760                 765

Lys Lys Gly Ile Leu Gln Thr Val Lys Val Val Asp Glu Leu Val Lys
            770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
            835                 840                 845

Tyr Tyr Leu Gln Asn Gly Arg Asp Met Tyr Val Asp Gln Glu Leu Asp
            850                 855                 860

Ile Asn Arg Leu Ser Asp Tyr Asp Val Asp Ala Ile Val Pro Gln Ser
865                 870                 875                 880
```

-continued

```
Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
        900                 905                 910

Lys Met Lys Asn Tyr Trp Arg Gln Leu Leu Asn Ala Lys Leu Ile Thr
        915                 920                 925

Gln Arg Lys Phe Asp Asn Leu Thr Lys Ala Glu Arg Gly Gly Leu Ser
    930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
            980                 985                 990

Leu Lys Ser Lys Leu Val Ser Asp Phe Arg Lys Asp Phe Gln Phe Tyr
                995                 1000                1005

Lys Val Arg Glu Ile Asn Asn Tyr His His Ala His Asp Ala Tyr
    1010                1015                1020

Leu Asn Ala Val Val Gly Thr Ala Leu Ile Lys Lys Tyr Pro Lys
    1025                1030                1035

Leu Glu Ser Glu Phe Val Tyr Gly Asp Tyr Lys Val Tyr Asp Val
    1040                1045                1050

Arg Lys Met Ile Ala Lys Ser Glu Gln Glu Ile Gly Lys Ala Thr
    1055                1060                1065

Ala Lys Tyr Phe Phe Tyr Ser Asn Ile Met Asn Phe Phe Lys Thr
    1070                1075                1080

Glu Ile Thr Leu Ala Asn Gly Glu Ile Arg Lys Arg Pro Leu Ile
    1085                1090                1095

Glu Thr Asn Gly Glu Thr Gly Glu Ile Val Trp Asp Lys Gly Arg
    1100                1105                1110

Asp Phe Ala Thr Val Arg Lys Val Leu Ser Met Pro Gln Val Asn
    1115                1120                1125

Ile Val Lys Lys Thr Glu Val Gln Thr Gly Gly Phe Ser Lys Glu
    1130                1135                1140

Ser Ile Leu Pro Lys Arg Asn Ser Asp Lys Leu Ile Ala Arg Lys
    1145                1150                1155

Lys Asp Trp Asp Pro Lys Lys Tyr Gly Gly Phe Asp Ser Pro Thr
    1160                1165                1170

Val Ala Tyr Ser Val Leu Val Ala Lys Val Glu Lys Gly Lys
    1175                1180                1185

Ser Lys Lys Leu Lys Ser Val Lys Glu Leu Leu Gly Ile Thr Ile
    1190                1195                1200

Met Glu Arg Ser Ser Phe Glu Lys Asn Pro Ile Asp Phe Leu Glu
    1205                1210                1215

Ala Lys Gly Tyr Lys Glu Val Lys Lys Asp Leu Ile Ile Lys Leu
    1220                1225                1230

Pro Lys Tyr Ser Leu Phe Glu Leu Glu Asn Gly Arg Lys Arg Met
    1235                1240                1245

Leu Ala Ser Ala Gly Glu Leu Gln Lys Gly Asn Glu Leu Ala Leu
    1250                1255                1260

Pro Ser Lys Tyr Val Asn Phe Leu Tyr Leu Ala Ser His Tyr Glu
    1265                1270                1275

Lys Leu Lys Gly Ser Pro Glu Asp Asn Glu Gln Lys Gln Leu Phe
```

| | | | | | | | | | |
|---|---|---|---|---|---|---|---|---|---|
| | | 1280 | | | 1285 | | | 1290 | |
| Val | Glu | Gln | His | Lys | His | Tyr | Leu | Asp | Glu | Ile | Ile | Glu | Gln | Ile |
| | 1295 | | | | 1300 | | | | 1305 | |
| Ser | Glu | Phe | Ser | Lys | Arg | Val | Ile | Leu | Ala | Asp | Ala | Asn | Leu | Asp |
| | 1310 | | | | 1315 | | | | 1320 | |
| Lys | Val | Leu | Ser | Ala | Tyr | Asn | Lys | His | Arg | Asp | Lys | Pro | Ile | Arg |
| | 1325 | | | | 1330 | | | | 1335 | |
| Glu | Gln | Ala | Glu | Asn | Ile | Ile | His | Leu | Phe | Thr | Leu | Thr | Asn | Leu |
| | 1340 | | | | 1345 | | | | 1350 | |
| Gly | Ala | Pro | Ala | Ala | Phe | Lys | Tyr | Phe | Asp | Thr | Thr | Ile | Asp | Arg |
| | 1355 | | | | 1360 | | | | 1365 | |
| Lys | Arg | Tyr | Thr | Ser | Thr | Lys | Glu | Val | Leu | Asp | Ala | Thr | Leu | Ile |
| | 1370 | | | | 1375 | | | | 1380 | |
| His | Gln | Ser | Ile | Thr | Gly | Leu | Tyr | Glu | Thr | Arg | Ile | Asp | Leu | Ser |
| | 1385 | | | | 1390 | | | | 1395 | |
| Gln | Leu | Gly | Gly | Asp | Pro | Ile | Ala | Gly | Ser | Lys | Ala | Ser | Pro | Lys |
| | 1400 | | | | 1405 | | | | 1410 | |
| Lys | Lys | Arg | Lys | Val | Gly | Arg | Ala | Asp | Ala | Leu | Asp | Asp | Phe | Asp |
| | 1415 | | | | 1420 | | | | 1425 | |
| Leu | Asp | Met | Leu | Gly | Ser | Asp | Ala | Leu | Asp | Asp | Phe | Asp | Leu | Asp |
| | 1430 | | | | 1435 | | | | 1440 | |
| Met | Leu | Gly | Ser | Asp | Ala | Leu | Asp | Asp | Phe | Asp | Leu | Asp | Met | Leu |
| | 1445 | | | | 1450 | | | | 1455 | |
| Gly | Ser | Asp | Ala | Leu | Asp | Asp | Phe | Asp | Leu | Asp | Met | Leu | Ile | Asn |
| | 1460 | | | | 1465 | | | | 1470 | |
| Tyr | Pro | Tyr | Asp | Val | Pro | Asp | Tyr | Ala | Ser |
| | 1475 | | | | 1480 |

<210> SEQ ID NO 2
<211> LENGTH: 350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gagggcctat ttcccatgat tccttcatat ttgcatatac gatacaaggc tgttagagag    60
ataattggaa ttaatttgac tgtaaacaca agatattag tacaaaatac gtgacgtaga   120
aagtaataat ttcttgggta gtttgcagtt ttaaaattat gttttaaaat ggactatcat   180
atgcttatcg taacttgaaa gtatttcgat ttcttggctt tatatatctt gtggaaagga   240
cgaaacaccg ggtcttcgag aagacctgtt ttagagctag aaatagcaag ttaaaataag   300
gctagtccgt tatcaacttg aaaaagtggc accgagtcgg tgctttttt             350

<210> SEQ ID NO 3
<211> LENGTH: 338
<212> TYPE: DNA
<213> ORGANISM: Homo sapiens

<400> SEQUENCE: 3 accccggca gcagcccgcc ccgagcgcgc cgcctgttta ttcagccggg agtccggcac    60
gcgccaggcg cacgcactgc aacaacaaac ccagctgaat ggagagtttg caaggagcgg   120
gagaaaggaa cgggaggggg ggagaggaga ggaggagggg gagtttaggg agtgggtggg   180
aggaagaggt aagaggaggg gggggagtgg gggctgcagc cgctcgctgc agcagcgggg   240

-continued

```
agtgggggc gaggcgggc cagggctgcg cgtgggctg ggtgtcccat tgaaaggcg      300 gacgcactcc ggcagcccag cactctctca cttctggc                         338
```

<210> SEQ ID NO 4
<211> LENGTH: 305
<212> TYPE: DNA
<213> ORGANISM: Mus musculus

<400> SEQUENCE: 4

```
ccgccccgag cgcgcggcct gtttattcag ccgggagtcc ggcacgcgcc gggcgcacgc   60
actgcaacaa caaaccaggc tgaatggaga gtttgcaagg agcgggcgcg ggcaactgga  120
gggggggggg gcgagaggga gggagctgag gaggtggggg aagaggaggg gtagtggggg  180
ctgcagccgc tcgctgcagc agcggggagt ggggggcgag gcggggccag ggctgcgcgt  240
ggggctgggt gtcccattga aaaggcggcc gcaccgcagc cgcccagcag tctctcactt  300
ctggc                                                             305
```

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
gctgggtgtc ccattgaaa                                               19
```

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
cagccgctcg ctgcagcag                                               19
```

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
tggagagttt gcaaggagc                                               19
```

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
gtttattcag ccgggagtc                                               19
```

<210> SEQ ID NO 9

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgccaggagg ggtgggtcta                                                 20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccttggtgag actggtaga                                                  19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtcttcaggt tctgttgct                                                  19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
atattcctga tttaaaagt                                                  19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttaaaagtcg gctggtagc                                                  19

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cgggccgggg gcggggtcc                                                  19

<210> SEQ ID NO 15
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gcccgagccg cgtgtggaa                                                  19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ccttcattgc ggcgggctg                                                  19

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ccgacccctc ccgggtccc                                                  19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
caggaccgcg cttcccacg                                                  19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tgcaccctgg gagcgcgag                                                  19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccgcacgcac ctgttccca                                                  19

<210> SEQ ID NO 21
<211> LENGTH: 19
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 21
aaaacagcga gggagaaac                                            19

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ttaacttgat tgtgaaatc                                            19

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aaaacaatgc atatttgca                                            19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
aaaatccagt attttaatg                                            19

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
acccagcact gcagcctgg                                            19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aacttatgcg gcgtttcct                                            19

<210> SEQ ID NO 27
<211> LENGTH: 19
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 27
tcactttaaa accacctct                                                      19

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28 gcatctttt ctctttaat                                                       19

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tgtactctct gaggtgctc                                                      19

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
acgcagataa gaaccagtt                                                      19

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
catcaagtca gccatcagc                                                      19

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gagtcaccct cctggaaac                                                      19

<210> SEQ ID NO 33
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 33
gctagggatg aagaataaa                                                    19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ttgaccaata gccttgaca                                                    19

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tgcaaatatc tgtctgaaa                                                    19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aaattagcag tatcctctt                                                    19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
cctgggctcc ggggcgttt                                                    19

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38 ggccctgcg gccaccccg                                                     19

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 39
ctccctccct gcccggtag                                                        19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aggtttggaa agggcgtgc                                                        19

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggagcttctc gacttcacca                                                       20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gatttgtggg cctgaagaaa                                                       20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aaggaggagg gcagaatcat                                                       20

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
aaaccttcct cagctatgcc c                                                     21

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agctgatggc cctaaacaga					20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
caggaggact ctggcaccta					20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggaatccatg gagggaagat					20

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gctgagtgaa ctgcactgtg a					21

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctctctgctc ctttgccaca					20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
caatgacccc ttcattgacc					20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 51
ggaacaagag ctgctggact                                              20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
aactttggca ttgtggaagg                                              20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
aacgccactg acaagaaagc                                              20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cagatccatg gaggaaggaa                                              20

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gggtactcct ggaagatgtc c                                            21

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gtttgcgacg catgttcctc                                              20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
```
aagcccttgc tgtagtggtg                                               20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cggcaggaaa gcatctgtat                                               20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgttctcgct caggtcagtg                                               20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gaattctttg ccgaaatgga                                               20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtgctcttcg ggtttcagga                                               20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ttgattttgg agggatctcg                                               20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gtttttctgc ctccccattt                                               20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggatgcaggg atgatgttct                                               20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gattggcttt gatttcccta                                               20

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gtgtagagta agtcagccta tgg                                           23

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gcctactcag actgttactc                                               20

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gttggacaga acttaccgac tgg                                           23

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gcagttgcct aagaactggt                                               20

```
<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ggggctccac cctcacgagt                                           20

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gtttgcttcg ctataaaacg agg                                       23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gtctgaggat ggggccgcaa tgg                                       23

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ggatctgtca aatcgcctgc agg                                       23

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gccaggatgg cattgggcag cgg                                       23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gctgaatctg cggtggcagg agg                                       23
```

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gttcttttgt tcttctagcc tgg                                            23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
ggaaaagctt gagcaagtca agg                                            23

<210> SEQ ID NO 78
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
ggaagagttg cccctgcgcc agg                                            23

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gacaaatctc cagtggataa agg                                            23

<210> SEQ ID NO 80
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gtgtttctca ggtaaagctc tgg                                            23

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
ggaaggacca tttgacgtta agg                                            23

<210> SEQ ID NO 82
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
gaactgctat ttcagtttcc tgg                                              23

<210> SEQ ID NO 83
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gccagccact cagccagtga agg                                              23

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
ggtatgcttt tctgttaaag agg                                              23

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
gctcctggac tgaccactat tgg                                              23

<210> SEQ ID NO 86
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
ggaacagagg cgtccccagt tgg                                              23

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
ggaggctaga acaatcatta cgg                                              23

<210> SEQ ID NO 88

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
gacaagaaca ccttcagaac cgg                                           23

<210> SEQ ID NO 89
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89
gggtttctgt gattttcttt tgg                                           23

<210> SEQ ID NO 90
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
gggccaaaga cctccgccag tgg                                           23

<210> SEQ ID NO 91
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
gttggagaag cattcataaa agg                                           23

<210> SEQ ID NO 92
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
gtcgctcact caccctgcaa agg                                           23

<210> SEQ ID NO 93
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
gaaaagagct gatgaaacaa tgg                                           23

<210> SEQ ID NO 94
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gtacactttt caaaatgctt tgg                                              23

<210> SEQ ID NO 95
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ggagatgatc atcaagcaga agg                                              23

<210> SEQ ID NO 96
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
gctttgaaag agcaataaaa tgg                                              23

<210> SEQ ID NO 97
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
gcacaaaagt caaatcggaa tgg                                              23

<210> SEQ ID NO 98
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
gatttcaata taagattcgg agg                                              23

<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
gcttaagcaa tcccgaactc tgg                                              23

<210> SEQ ID NO 100
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 100 gccttctttta tccctatcg                                          20

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(22)
<223> OTHER INFORMATION: a, c, t, g, unknown or other

<400> SEQUENCE: 104
gaggccaaac ctcggcttac nngrr                                    25

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(22)
<223> OTHER INFORMATION: a, c, t, g, unknown or other

<400> SEQUENCE: 105
gttcgaaaat ttcaggtaag nngrr                                    25

<210> SEQ ID NO 106
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(22)
<223> OTHER INFORMATION: a, c, t, g, unknown or other

<400> SEQUENCE: 106
```
ggcagaacag gagataacag nngrrt                                           26

<210> SEQ ID NO 107
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
ggcggccctc gcccttctct ggggat                                           26

<210> SEQ ID NO 108
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gtagtgatcg tggatacgag agg                                              23

<210> SEQ ID NO 109
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gtacagccct cggtgtatat tgg                                              23

<210> SEQ ID NO 110
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gggaaggaat taagcccgaa tgg                                              23

<210> SEQ ID NO 111
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gggaacagct ttcgtagttg agg                                              23

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gataaagtcc agtgtcgatc agg                                              23

<210> SEQ ID NO 113
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gaaaaccaga gcttcggtca agg                                              23

<210> SEQ ID NO 114
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ggagtcttct gggcaggctt aaaggctaac ctgg                                  34

<210> SEQ ID NO 115
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gtcgggtgag catgtcttta atctacctcg atgg                                  34

<210> SEQ ID NO 116
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ggtgtcacca gagtaacagt ctgagt                                           26

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
gtgatcatca agcagaaggt atgag                                            25

<210> SEQ ID NO 118
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
gaacttcgaa aatttcaggt aagccgagg                                        29

<210> SEQ ID NO 119
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
ggaaactcat caaatatgcg tgttagtgt                                    29

<210> SEQ ID NO 120
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gtcatttaca ctaacacgca tatttgatg                                    29

<210> SEQ ID NO 121
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ggaatgaaac tcatcaaata tgcgtgtta                                    29

<210> SEQ ID NO 122
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
gtcatcaata tctttgaagg actctgggt                                    29

<210> SEQ ID NO 123
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
gtgttttcat aggaaaaata ggcaagttg                                    29

<210> SEQ ID NO 124
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gaattggaaa atgtgatggg aaacagata                                    29

```
<210> SEQ ID NO 125
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
gatgatcatc aagcagaagg tatgagaaa                                    29

<210> SEQ ID NO 126
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
gagatgatca tcaagcagaa ggtatgaga                                    29

<210> SEQ ID NO 127
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127 gcatttttc tcataccttc tgcttgatg                                     29

<210> SEQ ID NO 128
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gtcctactca gactgttact ctggtgaca                                    29

<210> SEQ ID NO 129
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
gacaggttgt gtcaccagag taacagtct                                    29

<210> SEQ ID NO 130
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gttatcattt tttctcatac cttctgctt                                    29

<210> SEQ ID NO 131
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gttgcctaag aactggtggg aaatggtct                                           29

<210> SEQ ID NO 132
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
gaaacagttg cctaagaact ggtgggaaa                                           29

<210> SEQ ID NO 133
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
gtttcccacc agttcttagg caactgttt                                           29

<210> SEQ ID NO 134
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gtggctttga tttccctagg gtccagctt                                           29

<210> SEQ ID NO 135
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gtagggaaat caaagccaat gaaacgttc                                           29

<210> SEQ ID NO 136
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
ggaccctagg gaaatcaaag ccaatgaaa                                           29

<210> SEQ ID NO 137
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
gtgagggctc caccctcacg agtgggttt                                          29

<210> SEQ ID NO 138
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gaaggattga gggctccacc ctcacgagt                                          29

<210> SEQ ID NO 139
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ggctccaccc tcacgagtgg gtttggttc                                          29

<210> SEQ ID NO 140
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140 gtatcccta tcgaggaaac cacgagttt                                           29

<210> SEQ ID NO 141
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ggataaagaa ggcctatttc atagagttg                                          29

<210> SEQ ID NO 142
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gaggccttct ttatcccta tcgaggaaa                                           29

<210> SEQ ID NO 143
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 143
gtgagggctc caccctcacg agtgggt                                        27

<210> SEQ ID NO 144
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
ggataaagaa ggcctatttc atagagt                                        27

<210> SEQ ID NO 145
<211> LENGTH: 4932
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
gccaccatgg acaagaagta ctccattggg ctcgatatcg gcacaaacag cgtcggctgg     60
gccgtcatta cggacgagta caaggtgccg agcaaaaaat tcaaagttct gggcaatacc    120
gatcgccaca gcataaagaa gaacctcatt ggcgccctcc tgttcgactc cggggagacg    180
gccgaagcca cgcggctcaa agaacagcca cggcgcagat atacccgcag aaagaatcgg    240
atctgctacc tgcaggagat ctttagtaat gagatggcta aggtggatga ctcttttctt    300
cataggctgg aggagtcctt tttggtggag gaggataaaa agcacgagcg ccacccaatc    360
tttggcaata tcgtggacga ggtggcgtac catgaaaagt acccaaccat atatcatctg    420
aggaagaagc ttgtagacag tactgataag gctgacttgc ggttgatcta tctcgcgctg    480
gcgcatatga tcaaatttcg gggacacttc ctcatcgagg gggacctgaa cccagacaac    540
agcgatgtcg acaaactctt tatccaactg gttcagactt acaatcagct tttcgaagag    600
aacccgatca cgcatccgg agttgacgcc aaagcaatcc tgagcgctag gctgtccaaa    660
tcccggcggc tcgaaaaacct catcgcacag ctccctgggg agaagaagaa cggcctgttt    720
ggtaatctta tcgccctgtc actcgggctg accccccaact taaatctaa cttcgacctg    780 gccgaagatg ccaagcttca actgagcaaa gacacctacg atgatgatct cgacaatctg    840
ctggcccaga tcgcgacca gtacgcagac ctttttttgg cggcaaagaa cctgtcagac    900
gccattctgc tgagtgatat tctgcgagtg aacacggaga tcaccaaagc tccgctgagc    960
gctagtatga tcaagcgcta tgatgagcac caccagact tgactttgct gaaggccctt   1020
gtcagacagc aactgcctga aagtacaag gaaattttct tcgatcagtc taaaaatggc   1080
tacgccggat acattgacgg cggagcaagc caggaggaat tttacaaatt tattaagccc   1140
atcttggaaa aaatgacgg caccgaggag ctgctggtaa agcttaacag agaagatctg   1200
ttgcgcaaac agcgcacttt cgacaatgga agcatccccc accagattca cctgggcgaa   1260
ctgcacgcta tcctcaggcg gcaagaggat ttctaccccct ttttgaaaga taacagggaa   1320
aagattgaga aaatcctcac atttcggata ccctactatg taggccccct cgcccgggga   1380
```

```
aattccagat tcgcgtggat gactcgcaaa tcagaagaga ccatcactcc ctggaacttc    1440
gaggaagtcg tggataaggg ggcctctgcc cagtccttca tcgaaaggat gactaacttt    1500
gataaaaatc tgcctaacga aaaggtgctt cctaaacact ctctgctgta cgagtacttc    1560 acagttttata cgagctcac caaggtcaaa tacgtcacag aagggatgag aaagccagca    1620
ttcctgtctg gagagcagaa gaaagctatc gtggacctcc tcttcaagac gaaccggaaa    1680
gttaccgtga acagctcaa agaagactat ttcaaaaaga ttgaatgttt cgactctgtt    1740
gaaatcagcg gagtggagga tcgcttcaac gcatccctgg gaacgtatca cgatctcctg    1800
aaaatcatta agacaagga cttcctggac aatgaggaga cgaggacat tcttgaggac     1860 attgtcctca cccttacgtt gtttgaagat agggagatga ttgaagaacg cttgaaaact    1920
tacgctcatc tcttcgacga caaagtcatg aaacagctca agaggcgccg atatacagga    1980
tgggggcggc tgtcaagaaa actgatcaat gggatccgag acaagcagag tggaaagaca    2040
atcctggatt ttcttaagtc cgatggattt gccaaccgga acttcatgca gttgatccat    2100
gatgactctc tcacctttaa ggaggacatc cagaaagcac aagtttctgg ccaggggac    2160 agtcttcacg agcacatcgc taatcttgca ggtagcccag ctatcaaaaa gggaatactg    2220
cagaccgtta aggtcgtgga tgaactcgtc aaagtaatgg gaaggcataa gcccgagaat    2280
atcgttatcg agatggcccg agagaaccaa actacccaga agggacagaa gaacagtagg    2340
gaaaggatga gaggattga gagggtata aagaactgg ggtcccaaat ccttaaggaa      2400
cacccagttg aaaacaccca gcttcagaat gagaagctct acctgtacta cctgcagaac    2460
ggcagggaca tgtacgtgga tcaggaactg gacatcaatc ggctctccga ctacgacgtg    2520
gatcatatcg tgccccagtc ttttctcaaa gatgattcta ttgataataa agtgttgaca    2580
agatccgata aaaatagagg gaagagtgat aacgtcccct cagaagaagt tgtcaagaaa    2640
atgaaaaatt attggcggca gctgctgaac gccaaactga tcacacaacg gaagttcgat    2700
aatctgacta aggctgaacg aggtggcctg tctgagttgg ataaagccgg cttcatcaaa    2760
aggcagcttg ttgagacacg ccagatcacc aagcacgtgg cccaaaattct cgattcacgc    2820 atgaacacca gtacgatga aaatgacaaa ctgattcgag aggtgaaagt tattactctg     2880
aagtctaagc tggtctcaga tttcagaaag gactttcagt tttataaggt gagagagatc    2940
aacaattacc accatgcgca tgatgcctac ctgaatgcag tggtaggcac tgcacttatc    3000
aaaaaatatc ccaagcttga atctgaattt gtttacggag actataaagt gtacgatgtt    3060
aggaaaatga tcgcaaagtc tgagcaggaa ataggcaagg ccaccgctaa gtacttcttt    3120
tacagcaata ttatgaattt tttcaagacc gagattacac tggccaatgg agagattcgg    3180
aagcgaccac ttatcgaaac aaacggagaa acaggagaaa tcgtgtggga caagggtagg    3240
gatttcgcga cagtccggaa ggtcctgtcc atgccgcagg tgaacatcgt taaaaagacc    3300
gaagtacaga ccggaggctt ctccaaggaa agtatcctcc cgaaaaggaa cagcgacaag    3360
ctgatcgcac gcaaaaaaga ttgggacccc aagaaatacg gcggattcga ttctcctaca    3420
gtcgcttaca gtgtactggt tgtggccaaa gtggagaaag ggaagtctaa aaaactcaaa    3480
agcgtcaagg aactgctggg catcacaatc atggagcgat caagcttcga aaaaaacccc    3540
atcgactttc tcgaggcgaa aggatataaa gaggtcaaaa aagacctcat cattaagctt    3600
cccaagtact ctctctttga gcttgaaaac ggccggaaac gaatgctcgc tagtgcgggc    3660
gagctgcaga aaggtaacga gctggcactg ccctctaaat acgttaattt cttgtatctg    3720
gccagccact atgaaaagct caagggtctc cccgaagata atgagcagaa gcagctgttc    3780
```

```
gtggaacaac acaaacacta ccttgatgag atcatcgagc aaataagcga attctccaaa    3840
agagtgatcc tcgccgacgc taacctcgat aaggtgcttt ctgcttacaa taagcacagg    3900
gataagccca tcagggagca ggcagaaaac attatccact tgtttactct gaccaacttg    3960
ggcgcgcctg cagccttcaa gtacttcgac accaccatag acagaaagcg gtacacctct    4020
acaaaggagg tcctggacgc cacactgatt catcagtcaa ttacggggct ctatgaaaca    4080
agaatcgacc tctctcagct cggtggagac agcagggctg accccaagaa gaagaggaag    4140
gtggctagcg agggcagagg aagtcttcta acatgcggtg acgtggagga gaatcccggc    4200
cctggtaccg tgagcaaggg cgaggagctg ttcaccgggg tggtgcccat cctggtcgag    4260
ctggacggcg acgtaaacgg ccacaagttc agcgtgtccg gcgagggcga gggcgatgcc    4320
acctacggca agctgaccct gaagttcatc tgcaccaccg gcaagctgcc cgtgccctgg    4380
cccaccctcg tgaccaccct gacctacggc gtgcagtgct tcagccgcta ccccgaccac    4440
atgaagcagc acgacttctt caagtccgcc atgcccgaag gctacgtcca ggagcgcacc    4500
atcttcttca aggacgacgg caactacaag acccgcgccg aggtgaagtt cgagggcgac    4560
accctggtga accgcatcga gctgaagggc atcgacttca aggaggacgg caacatcctg    4620
gggcacaagc tggagtacaa ctacaacagc cacaacgtct atatcatggc cgacaagcag    4680
aagaacggca tcaaggtgaa cttcaagatc cgccacaaca tcgaggacgg cagcgtgcag    4740
ctcgccgacc actaccagca gaacaccccc atcggcgacg gccccgtgct gctgcccgac    4800
aaccactacc tgagcaccca gtccgccctg agcaaagacc ccaacgagaa gcgcgatcac    4860
atggtcctgc tggagttcgt gaccgccgcc gggatcactc tcggcatgga cgagctgtac    4920
aagaccggtt ag                                                       4932
```

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tcctactcag actgttactc tgg                                          23

<210> SEQ ID NO 151
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
tcctactcac actgttactc agg                                          23

<210> SEQ ID NO 152
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
acctgctcac actgttactc cag                                          23

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
gcattctcaa actgttactc agg                                          23

<210> SEQ ID NO 154
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
ggattctcac actgttactc ggg                                          23

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
acatacttat actgttactc tag                                          23

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tattcctaag actgttactc aag                                            23

<210> SEQ ID NO 157
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
aaggactaag actgttactc ggg                                            23

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
gagctctcat actgttactc tag                                            23

<210> SEQ ID NO 159
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gcaaaatgag actgttactc cag                                            23

<210> SEQ ID NO 160
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
cctcattcag actgttactc aag                                            23

<210> SEQ ID NO 161
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
cattggcttt gatttcccta ggg                                            23

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
aattggcatt gatttcccta gag                                            23

<210> SEQ ID NO 163
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
cattggcttt aatttcccta tag                                          23

<210> SEQ ID NO 164
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
gataggctgt gatttcccta gag                                          23

<210> SEQ ID NO 165
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
gaatagcctt gatttcccta aag                                          23

<210> SEQ ID NO 166
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
aatttgcttt gatttccctg agg                                          23

<210> SEQ ID NO 167
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gatgtgcttt gatttccctt ggg                                          23

<210> SEQ ID NO 168
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
aattggtttt aatttcccta aag                                          23

<210> SEQ ID NO 169
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
aattgggttt gatttccctt tgg                                              23

<210> SEQ ID NO 170
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
gatgggtttt tatttcccta gag                                              23

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
gaatggtttt gatttccctg gag                                              23

<210> SEQ ID NO 172
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
acagttgcct aagaactggt ggg                                              23

<210> SEQ ID NO 173
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
ccagttgtct aagaactggg gag                                              23

<210> SEQ ID NO 174
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
gcagttgcct gtgaactggt agg                                              23

```
<210> SEQ ID NO 175
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
gcagatgcag aagaactggt gag                                          23

<210> SEQ ID NO 176
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gcagttccag aagaactggt gag                                          23

<210> SEQ ID NO 177
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
caacttgcct atgaactggt agg                                          23

<210> SEQ ID NO 178
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
acacctgcct aagaactgga ggg                                          23

<210> SEQ ID NO 179
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
tcaggtggct aagaactggg tgg                                          23

<210> SEQ ID NO 180
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
gaagttggcc aagaactgga gag                                          23

<210> SEQ ID NO 181
```

-continued

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
gctgctgccc aagaactggc agg                                              23

<210> SEQ ID NO 182
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
tcagctggct aagaacgggt aag                                              23

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
agggctccac cctcacgagt ggg                                              23

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gcagctcagc cctcacgagt cag                                              23

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
ggggcttcag catcacgagt gag                                              23

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
ggggctctcc cctcactagt gag                                              23

<210> SEQ ID NO 187
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ggggatccac cttcaccagt cag                                              23

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
agggctggac cctcacaagt aag                                              23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tggtctcctc ccccacgagt ggg                                              23

<210> SEQ ID NO 190
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
agggctccca ccccacgagt gag                                              23

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
gaggctccat actcaccagt gag                                              23

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ggagctgccc cttcacgagt ggg                                              23

<210> SEQ ID NO 193
<211> LENGTH: 23
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 193
atgactccac cctcaagagt aag                                             23

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gccttcttta tccgctatcg agg                                             23

<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gtctgctgtg tccctatcg ggg                                              23

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
cccttctcta tccctgtcg tgg                                              23

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
gccttcttta tccctctct tgg                                              23

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
gcgctctttt tccctatct tag                                              23

<210> SEQ ID NO 199
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 199
gccctctgtc tccctgtcg cag                                              23

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 200
tccatctttg tccctattg agg                                              23

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 201
accttctctc tccctatag agg                                              23

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 202
gttttctttt tccctatgg gag                                              23

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 203
tgcttcttaa tccctatca aag                                              23

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 204
accttcttac tccctatcc ggg                                              23

<210> SEQ ID NO 205
<211> LENGTH: 22
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 205
gagaggttat gtggctttac ca                                              22

<210> SEQ ID NO 206
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 206
aaaaatgctt cccactttgc                                                 20

<210> SEQ ID NO 207
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 207
ctcattctca tgcctggaca                                                 20

<210> SEQ ID NO 208
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 208
gagtttggct caaattgtta ctctt                                           25

<210> SEQ ID NO 209
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 209
gggaaatggt ctaggagagt aaagt                                           25

<210> SEQ ID NO 210
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 210
gtttggctca aattgttact cttca                                           25

<210> SEQ ID NO 211
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 211
gtgagagtaa tgtgtttgct gagag                                            25

<210> SEQ ID NO 212
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 212
cgggcttgga cagaacttac                                                  20

<210> SEQ ID NO 213
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 213
ctgcgtagtg ccaaaacaaa                                                  20

<210> SEQ ID NO 214
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 214
taatttcatt gaagagtggc tgaa                                             24

<210> SEQ ID NO 215
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 215
aagccctgtg tggtagtagt cagt                                             24

<210> SEQ ID NO 216
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 216
tgagtcatgt tggataacca gtct                                             24

<210> SEQ ID NO 217
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 217
gaaggtcagg aacatacaat tcaa						24

<210> SEQ ID NO 218
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 218
gatatgggca tgtcagtttc atag						24

<210> SEQ ID NO 219
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 219
tgctgttgat taatggttga tagg						24

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 220
ttttaaattg ccatgtttgt gtc						23

<210> SEQ ID NO 221
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 221
atgaataacc taatgggcag aaaa						24

<210> SEQ ID NO 222
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 222
tcaagtcgct tcattttgat agac						24

<210> SEQ ID NO 223
<211> LENGTH: 24
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 223
cacaacaaaa catatagcca aagc                                        24

<210> SEQ ID NO 224
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 224
tgctgctaaa ataacacaaa tcagt                                       25

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 225
ctgtgcctat tgtggttatc ctg                                         23

<210> SEQ ID NO 226
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 226
attgatctgc aatacatgtg gagt                                        24

<210> SEQ ID NO 227
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
tttgcctctg ctattacagt atgg                                        24

<210> SEQ ID NO 228
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 228
tgtagggtgg ttggctaaaa taat                                        24

<210> SEQ ID NO 229
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
tttttgcaca gtcaataaca caaa                                              24

<210> SEQ ID NO 230
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
ggctggtctc acaattgtac ttta                                              24

<210> SEQ ID NO 231
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
cattatggac tgaaaatctc agca                                              24

<210> SEQ ID NO 232
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
atcatcctag ccataacaca atga                                              24

<210> SEQ ID NO 233
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
ttcagcttta acgtgatttt ctgt                                              24

<210> SEQ ID NO 234
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 234
ggattcagaa gctgtttacg aagt                                              24

<210> SEQ ID NO 235
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
tttagctgga ttggaaaaac aaat                                          24

<210> SEQ ID NO 236
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 236
aactcacccc attgttggta tatt                                          24

<210> SEQ ID NO 237
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 237
ccttgtccaa ataccgaaat acat                                          24

<210> SEQ ID NO 238
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 238
cacataattc atgaacttgg cttc                                          24

<210> SEQ ID NO 239
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 239
tagtagctgg ggaggaagat acag                                          24

<210> SEQ ID NO 240
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 240
tttttgtttt aattgcgact gtgt                                          24

<210> SEQ ID NO 241
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 241
agaaaagggg ttttcttttg actt                                          24

<210> SEQ ID NO 242
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 242
cattgtgact ggatgagaag aaac                                          24

<210> SEQ ID NO 243
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 243
aacggctgtt attaaagtcc tcag                                          24

<210> SEQ ID NO 244
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 244
caagtcagaa gtcacttgct ttgt                                          24

<210> SEQ ID NO 245
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 245
ttttatgtgc aggaatcagt ctgt                                          24

<210> SEQ ID NO 246
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 246
tggcggcgtt ttcattat                                                 18

<210> SEQ ID NO 247
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 247
ttcgatccgt aatgattgtt ctagcc                                        26

<210> SEQ ID NO 248
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 248
ggtcttccag agtgctgagg                                               20

<210> SEQ ID NO 249
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 249
tgtgtgcttc tgtacacatc atct                                          24

<210> SEQ ID NO 250
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 250
agatttcaac cctcaaaaac tgag                                          24

<210> SEQ ID NO 251
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 251
taaactcttt cttttccgca attc                                          24

<210> SEQ ID NO 252
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 252
caaggtgacc tgctacctaa aaat                                          24

<210> SEQ ID NO 253
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 253
tatgaccaag gctatgtgtt cact                                          24

```
<210> SEQ ID NO 254
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 254
acagcctctc tccagtaaca ttct                                              24

<210> SEQ ID NO 255
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 255
tattcttgca gtggtttcac attt                                              24

<210> SEQ ID NO 256
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 256
atattttaag ccaagaccca acaa                                              24

<210> SEQ ID NO 257
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 257
ctttcaactg tctgtctgat tgct                                              24

<210> SEQ ID NO 258
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 258
aacagcctct cttcattgtt ctct                                              24

<210> SEQ ID NO 259
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 259
ctctggaact tgtctctgtc ttga                                              24

<210> SEQ ID NO 260
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 260
ctttcctgcg ttctcatgtt acta                                            24

<210> SEQ ID NO 261
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 261
ccttatatcc gtatcgctca ctct                                            24

<210> SEQ ID NO 262
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 262
catatctgtc taacttccgc acac                                            24

<210> SEQ ID NO 263
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 263
acaggtgtta tgttgtctgc atct                                            24

<210> SEQ ID NO 264
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 264
actccattcc cagattagtt atgc                                            24

<210> SEQ ID NO 265
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 265
ctgttttctt tgtgagagtg gaga                                            24

<210> SEQ ID NO 266
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 266
tgtaaggtgg tcaaacttgc tcta                                            24

<210> SEQ ID NO 267
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 267
tttttcctag tacccacaga ttttt                                           25

<210> SEQ ID NO 268
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 268
tccctgattc tctcatttgt gtta                                            24

<210> SEQ ID NO 269
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 269
ttgggaacat cagagaaagt atga                                            24

<210> SEQ ID NO 270
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 270
acaaattaca gtctcctggg aaag                                            24

<210> SEQ ID NO 271
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 271
agtagcttac cttggcagag aaaa                                            24

<210> SEQ ID NO 272
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 272
tgacatactg ttaccctttg cagt                                          24

<210> SEQ ID NO 273
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 273
gaaaggctca gtgaatgttt gtt                                           23

<210> SEQ ID NO 274
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 274
cactgcatca tctcattaaa tcaa                                          24

<210> SEQ ID NO 275
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 275
cccatatatt catgattacc caca                                          24

<210> SEQ ID NO 276
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 276
tatcagaacg agcactaaaa gcac                                          24

<210> SEQ ID NO 277
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 277
ttgggaggct gaggtacaag                                               20

<210> SEQ ID NO 278
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 278
gaatgaaaaa caaacagaag gtga                                              24

<210> SEQ ID NO 279
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 279
ctcctcatct gtaccttca atct                                               24

<210> SEQ ID NO 280
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 280
agagtggcat ctagtgtcag tgag                                              24

<210> SEQ ID NO 281
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 281
taccaaaagc ttctcctgtt tacc                                              24

<210> SEQ ID NO 282
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 282
gtaagttgga tggcctattc tttg                                              24

<210> SEQ ID NO 283
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 283
gaaggaaatg caaggataca agat                                              24

<210> SEQ ID NO 284
<211> LENGTH: 24
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 284
tgattgaaag aatcattcca gaaa                                              24

<210> SEQ ID NO 285
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 285
tcagaaggaa aattgaaatt ggtt                                              24

<210> SEQ ID NO 286
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 286
cagatgtgtt cttcatcatt cctc                                              24

<210> SEQ ID NO 287
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 287
ttctctttag ggaaagctct caaa                                              24

<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 288
gggtatagat catatggagg gaag                                              24

<210> SEQ ID NO 289
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 289
agatgatctg cccacctcag                                                   20

<210> SEQ ID NO 290
<211> LENGTH: 24
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 290
ctttcttcct catttagtgg caat                                    24

<210> SEQ ID NO 291
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 291
atgaattgca gattgatggt actg                                    24

<210> SEQ ID NO 292
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 292
tctcaccaag aaccaaattg tcta                                    24

<210> SEQ ID NO 293
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 293
gtaggatacc ttggcaacag tctt                                    24

<210> SEQ ID NO 294
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 294
ttaacgaatt gtgagatttg ctgt                                    24

<210> SEQ ID NO 295
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 295
tcagaaagtc aagtagcaca caca                                    24

<210> SEQ ID NO 296
<211> LENGTH: 23
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 296
agaagcacac actcaggtaa agc                                          23

<210> SEQ ID NO 297
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 297
tctttggggg aataatgact aaaa                                         24

<210> SEQ ID NO 298
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 298
tttggcattt atgggaataa aact                                         24

<210> SEQ ID NO 299
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 299
actaattctg gtcaagccca tca                                          23

<210> SEQ ID NO 300
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 300
ttaagacatc ggatgaacag aaag                                         24

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 301
agaagctttc tgacatgatc tgc                                          23

<210> SEQ ID NO 302
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 302
tcaattgcat taggacttag acca                                              24

<210> SEQ ID NO 303
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 303
gttaaattac ctgtgaagcc cttg                                              24

<210> SEQ ID NO 304
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 304
cggaaaacag atccacttta tgat                                              24

<210> SEQ ID NO 305
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 305
aaatccactg gaaacatctt gagt                                              24

<210> SEQ ID NO 306
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 306
agtctcttca gaatcatgcc ctat                                              24

<210> SEQ ID NO 307
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 307
gcttggtggc acatacctgt ag                                                22

<210> SEQ ID NO 308
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 308
ggtaggtaga tttgcttgct tgtt                                            24

<210> SEQ ID NO 309
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 309
agctctcagc agagtaggga ttta                                            24

<210> SEQ ID NO 310
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 310
gtgagtctac tgcaccccat c                                               21

<210> SEQ ID NO 311
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 311
tgacactgtg aagtcaattc tgtc                                            24

<210> SEQ ID NO 312
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 312
tcaagaactt gacaatgagc aaat                                            24

<210> SEQ ID NO 313
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 313
tatccgatcc actgttgtgt gt                                              22

<210> SEQ ID NO 314
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 314
caggagaccc aaaaccactc tac                                            23

<210> SEQ ID NO 315
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 315
ttgttctaca aatagggctt cctt                                           24

<210> SEQ ID NO 316
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 316
tgttaagttt gggcttatgt tcct                                           24

<210> SEQ ID NO 317
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 317
cacaagtctc actgcacaaa cat                                            23

<210> SEQ ID NO 318
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 318
tgacccatga ttatctctct ttga                                           24

<210> SEQ ID NO 319
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 319
ttcagcttct gattggtttt aatg                                           24

<210> SEQ ID NO 320
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 320
ccaattcctt aatttccct acag                                            24

<210> SEQ ID NO 321
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 321
atctcagacc aggagggaga c                                           21

<210> SEQ ID NO 322
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 322
cctcagggtc agtacatttt tcag                                        24

<210> SEQ ID NO 323
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 323
ttcttaggac attgctccac atac                                        24

<210> SEQ ID NO 324
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 324
gcaaacataa tgcaactcgt aatc                                        24

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 325
gcaagggagt ctgtgtcttt g                                           21

<210> SEQ ID NO 326
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 326
tcatttaagt ggctgttctg tgtt                                        24

<210> SEQ ID NO 327
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 327
acaaaacaga gagaaaaggc agag                                            24

<210> SEQ ID NO 328
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 328
gttttgattt ctggtgccta cag                                             23

<210> SEQ ID NO 329
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 329
actgaagctg aagcccagtc                                                 20

<210> SEQ ID NO 330
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 330
acatgagctc tcaggtttct gac                                             23

<210> SEQ ID NO 331
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 331
tcaaacttag atggttccct atgtt                                           25

<210> SEQ ID NO 332
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 332
gtaccctgaa aatgtagggt gact                                            24

```
<210> SEQ ID NO 333
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333
cacttcccaa gtgaggcaat                                              20

<210> SEQ ID NO 334
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 334
ctatacttgg ggctgacttg ctac                                         24

<210> SEQ ID NO 335
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 335
tcgtataggt tactttggct caca                                         24

<210> SEQ ID NO 336
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 336
agggatcttt actcctcagt gtgt                                         24

<210> SEQ ID NO 337
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 337
tgtagaagtt ggaatatcct gctg                                         24

<210> SEQ ID NO 338
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 338
gtcaacaatt tgatctcagg cttc                                         24

<210> SEQ ID NO 339
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 339
ctcagtacta aagatggacg cttg                                          24

<210> SEQ ID NO 340
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 340
aatcatttca gtcttcccaa caat                                          24

<210> SEQ ID NO 341
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 341
gggaatcaca gtagatgttt gtca                                          24

<210> SEQ ID NO 342
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 342
agaccaggag gtaagaacat tttg                                          24

<210> SEQ ID NO 343
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 343
ccacatagaa agagacttgc agaa                                          24

<210> SEQ ID NO 344
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 344
agagatgcca aaagaacagt caat                                          24

<210> SEQ ID NO 345
<211> LENGTH: 24
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 345
tgtgccttag gctatgtaaa ctgt                                            24

<210> SEQ ID NO 346
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 346
aaacccttgt aaccaaaatt acca                                            24

<210> SEQ ID NO 347
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 347
taactgcatc agaagtcctt gcta                                            24

<210> SEQ ID NO 348
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 348
ggagaccaag ctgctaaagt ca                                              22

<210> SEQ ID NO 349
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 349
gtggtgccgc gggagtttgg ctcaaattgt tactctt                              37

<210> SEQ ID NO 350
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 350
gtggtgccgc gggggaaatg gtctaggaga gtaaagt                              37

<210> SEQ ID NO 351
<211> LENGTH: 34
<212> TYPE: DNA

<213> ORGANISM: Artificial Sequence
<220> FEATURE:
<223> OTHER INFORMATION: Description of Artificial Sequence: Synthetic primer

<400> SEQUENCE: 351
gtggtgccgc gggagaggtt atgtggcttt acca                                    34

<210> SEQ ID NO 352
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 352
gtggtgccgc ggctcattct catgcctgga ca                                      32

<210> SEQ ID NO 353
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 353
gtggtgccgc ggcgggcttg dacagaactt ac                                      32

<210> SEQ ID NO 354
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 354
gtggtgccgc ggctgcgtag tgccaaaaca aa                                      32

<210> SEQ ID NO 355
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 355
gtggtgccgc ggtaatttca ttgaagagtg gctgaa                                  36

<210> SEQ ID NO 356
<211> LENGTH: 36
<212> TYPE: DNA
<213> ORGANISM: Artificial Sequence
<220> FEATURE:
<223> OTHER INFORMATION: Description of Artificial Sequence: Synthetic primer

<400> SEQUENCE: 356
gtggtgccgc ggaagccctg tgtggtagta gtcagt                                  36

<210> SEQ ID NO 357
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 357
gtggtgccgc ggcaagtcag aagtcacttg ctttgt                36

<210> SEQ ID NO 358
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 358
gtggtgccgc ggttttatgt gcaggaatca gtctgt                36

<210> SEQ ID NO 359
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 359
gtggtgccgc ggtgtgtgct tctgtacaca tcatct                36

<210> SEQ ID NO 360
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 360
gtggtgccgc ggagatttca accctcaaaa actgag                36

<210> SEQ ID NO 361
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 361
gtggtgccgc ggttgggaac atcagagaaa gtatga                36

<210> SEQ ID NO 362
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 362
gtggtgccgc ggacaaatta cagtctcctg ggaaag                36

<210> SEQ ID NO 363
<211> LENGTH: 32
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 363
gtggtgccgc ggcacttccc aagtgaggca at                                32

<210> SEQ ID NO 364
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 364
gtggtgccgc ggctatactt ggggctgact tgctac                            36

<210> SEQ ID NO 365
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 365
gtggtgccgc ggttggctct ttagcttgtg tttc                              34

<210> SEQ ID NO 366
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 366
gtggtgccgc ggtgagactc ccaaaggcaa tc                                32

<210> SEQ ID NO 367
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 367
gtggtgccgc ggttggctct ttagcttgtg tttc                              34

<210> SEQ ID NO 368
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 368
gtggtgccgc ggactgaggg gtgatcttgg tg                                32

<210> SEQ ID NO 369
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 369
gtggtgccgc gggcagagaa agccagtcgg ta    32

<210> SEQ ID NO 370
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 370
gtggtgccgc ggtgagactc ccaaaggcaa tc    32

<210> SEQ ID NO 371
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 371
gtggtgccgc gggcagagaa agccagtcgg ta    32

<210> SEQ ID NO 372
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 372
gtggtgccgc ggactgaggg gtgatcttgg tg    32

<210> SEQ ID NO 373
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 373
gtggtgccgc ggccagagtt cctagggcag ag    32

<210> SEQ ID NO 374
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 374
gtggtgccgc ggagctagtc cccacattcc ac    32

<210> SEQ ID NO 375
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 375
gtggtgccgc ggccagagtt cctagggcag ag                                       32

<210> SEQ ID NO 376
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 376
gtggtgccgc ggggtggagg gaaactttag gc                                       32

<210> SEQ ID NO 377
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 377
gtggtgccgc ggctcattct catgcctgga ca                                       32

<210> SEQ ID NO 378
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 378
gtggtgccgc ggagctagtc cccacattcc ac                                       32

<210> SEQ ID NO 379
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 379
gtggtgccgc ggtctcatgc ctggacaagt aact                                     34

<210> SEQ ID NO 380
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 380
gtggtgccgc ggggtggagg gaaactttag gc                                       32

<210> SEQ ID NO 381
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 381
gtggtgccgc ggggcttgga cagaacttac cg                32

<210> SEQ ID NO 382
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 382
gtggtgccgc ggcaccactg tctgcctaag ga                32

<210> SEQ ID NO 383
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 383
gtggtgccgc ggggcttgga cagaacttac cg                32

<210> SEQ ID NO 384
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 384
gtggtgccgc ggggtggagg gaaactttag gc                32

<210> SEQ ID NO 385
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 385
gtggtgccgc ggcgtagtgc caaaacaaac agt                33

<210> SEQ ID NO 386
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 386
gtggtgccgc ggcaccactg tctgcctaag ga                32

<210> SEQ ID NO 387
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 387
gtggtgccgc ggcgtagtgc caaaacaaac agt                                          33

<210> SEQ ID NO 388
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 388
gtggtgccgc ggggtggagg gaaactttag gc                                           32

<210> SEQ ID NO 389
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 389
gtggtgccgc gggcgagggc ctacttgata tg                                           32

<210> SEQ ID NO 390
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 390
gtggtgccgc ggcttcccaa gtgaggcaat gc                                           32

<210> SEQ ID NO 391
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 391
gtggtgccgc ggacgttttg tgctgctgta aca                                          33

<210> SEQ ID NO 392
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 392
gtggtgccgc ggctgcaggc acattctctt cc                                           32

<210> SEQ ID NO 393
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 393

-continued gtggtgccgc gggccctgtg tggtagtagt ca                32

<210> SEQ ID NO 394
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 394
gtggtgccgc ggcttcccaa gtgaggcaat gc                32

<210> SEQ ID NO 395
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 395
gtggtgccgc ggcagtatta aggggtggga gct                33

<210> SEQ ID NO 396
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 396
gtggtgccgc ggtctcttcc tcacacagct ga                32

<210> SEQ ID NO 397
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 397
gtggtgccgc ggggagcttg gagggaagag aa                32

<210> SEQ ID NO 398
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 398
gtggtgccgc ggcttcccaa gtgaggcaat gc                32

<210> SEQ ID NO 399
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 399
gtggtgccgc ggatggatgg ggaagacact gg                32

<210> SEQ ID NO 400
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 400
gtggtgccgc ggctgcaggc acattctctt cc                                    32

<210> SEQ ID NO 401
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 401
gtggtgccgc ggggatgaaa cagggcagga ac                                    32

<210> SEQ ID NO 402
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 402
gtggtgccgc ggttcccaag tgaggcaatg c                                     31

<210> SEQ ID NO 403
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 403
gtggtgccgc ggtttgcaga gccatgatga gg                                    32

<210> SEQ ID NO 404
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 404
gtggtgccgc ggcgacagcc aaaacagccg                                       30

<210> SEQ ID NO 405
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
aaaatatttt agctcctact cagactgtta ctctggtgac acaa                       44

<210> SEQ ID NO 406
<211> LENGTH: 44
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 406
ttgtgtcacc agagtaacag tctgagtagg agctaaaata tttt                44

<210> SEQ ID NO 407
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 407
tagctcctac tcagactgtt actctggtga cacaac                         36

<210> SEQ ID NO 408
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 408
tagctcctac tcagactggt gacccaac                                  28

<210> SEQ ID NO 409
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 409
tagctcctac tctggtgaca caac                                      24

<210> SEQ ID NO 410
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 410
tagctcctac tcagactggt gacacaac                                  28

<210> SEQ ID NO 411
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 411
tagctcctac tcagac                                               16

```
<210> SEQ ID NO 412
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
tagctcctac tcagactgtt acacaac                                            27

<210> SEQ ID NO 413
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 413
tagctcctac tcagactgtg gtgaggtgac                                         30

<210> SEQ ID NO 414
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
tagctcctac tcagactctc tggtgacaca ac                                      32

<210> SEQ ID NO 415
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
tagctcctac tcagacctct ggtgacacaa c                                       31

<210> SEQ ID NO 416
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
tagctcctac tcaggctgtc tggtgacaca ac                                      32

<210> SEQ ID NO 417
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
tagctcctac tcagactact ctggtgacac aac                                     33

<210> SEQ ID NO 418
```

```
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
tagctcctac tcagactgtt gacacaac                                          28

<210> SEQ ID NO 419
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 419
ctggtgacac aac                                                          13

<210> SEQ ID NO 420
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
tagctcctac tcagactgtt agacacaac                                         29

<210> SEQ ID NO 421
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
tagctcctac tcagactgct ctggtgacac aac                                    33

<210> SEQ ID NO 422
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
cagactgtta ctctggtgac                                                   20

<210> SEQ ID NO 423
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
cagaccacct gtggtctcct actggtgac                                         29

<210> SEQ ID NO 424
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
gctttgattt ccctaggg                                                  18

<210> SEQ ID NO 425
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 425
gctttgattt ccagttctta ggcaa                                          25

<210> SEQ ID NO 426
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
gctttgattc ttaggcaa                                                  18

<210> SEQ ID NO 427
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(53)
<223> OTHER INFORMATION: a, c, t, g, unknown or other

<400> SEQUENCE: 427
gctttgattt ccnnnnnnnn nnnnnnnnnn nnnnnnnnnn nnnnnnnnnn nnncttaggc    60
aa                                                                   62

<210> SEQ ID NO 428
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
tcttaaccat taccatag                                                  18

<210> SEQ ID NO 429
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
```
tcttaaccat taccatagag ttcttaggca ac                                        32

<210> SEQ ID NO 430
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430
tcttaaccat taccaaagtt cttaggcaac                                           30

<210> SEQ ID NO 431
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 431
tcttaaccat taccataggt tcttaggcaa c                                         31

<210> SEQ ID NO 432
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
gaaccaaacc cact                                                            14

<210> SEQ ID NO 433
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
gaaccaaacc cacttagggg ataa                                                 24

<210> SEQ ID NO 434
<211> LENGTH: 2328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 434
atgaggtctg actacaaaga ccatgacggt gattataaag atcatgacat cgattacaag           60
gatgacgatg acaagatggc ccccaagaag aagaggaagg tgggcctcga gcccggagaa          120
aaaccgtaca agtgccctga gtgcgggaaa tcattctccg accctggggc gctcgtccgg          180
caccaaagga cgcatacagg ggaaaagccg tataagtgcc ccgagtgtgg aaagagcttc          240
tcgcagagag cccaccttga acgacaccaa agaacacaca ctggtgagaa accctataag          300
tgtccagagt gcggcaaatc gtttagcaga tccgatgact ggtgcgcca ccagcggaca           360 cacacgggtg aaaagcccta caatgcccg gagtgtggga agtcgttttc aaggtcggat           420

| | |
|---|---|
| catctgacta cccatcagcg cacccatacg ggagcggccg cccgcgccct ggtgaagagc | 480 |
| gagctggagg agaagaagtc cgagctgcgg cacaagctga agtacgtgcc ccacgagtac | 540 |
| atcgagctga tcgagatcgc caggaacccc acccaggacc gcatcctgga gatgaaggtg | 600 |
| atggagttct tcatgaaggt gtacggctac aggggagagc acctgggcgg aagcagaaag | 660 |
| cctgacggcg ccatctatac agtgggcagc cccatcgatt acggcgtgat cgtggacaca | 720 |
| aaggcctaca gcggcggcta caatctgcct atcggccagg ccgacgagat gcagagatac | 780 |
| gtgaaggaga accagacccg gaataagcac atcaaccca cgagtggtg aaggtgtac | 840 |
| cctagcagcg tgaccgagtt caagttcctg ttcgtgagcg ccacttcaa gggcaactac | 900 |
| aaggcccagc tgaccaggct gaaccgcaaa accaactgca atggcgccgt gctgagcgtg | 960 |
| gaggagctgc tgatcggcgg cgagatgatc aaagccggca ccctgacact ggaggaggtg | 1020 |
| cggcgcaagt tcaacaacgg cgagatcaac ttcgagggca gaggaagtct tctaacatgc | 1080 |
| ggtgacgtgg aggagaatcc cggccctaga tctgactaca agaccatga cggtgattat | 1140 |
| aaagatcatg acatcgatta caaggatgac gatgacaaga tggcccccaa gaagaagagg | 1200 |
| aaggtgggcc tcgagccggg agagaagccg tacaagtgtc ccgaatgtgg aaagagcttc | 1260 |
| tcacagtcgg gggaccttcg cgccaccag cgcacacata ctggtgaaaa gccgtataag | 1320 |
| tgtccagaat gtggcaaatc attctccaca tcagggagcc tggtcaggca ccagcgaacc | 1380 |
| cacacgggtg agaagcccta aagtgcccc gaatgcggga gtcctttttc gcagagagcc | 1440 |
| cacttggaga ggcaccagag gacccatacg ggggagaaac cttacaagtg ccctgaatgc | 1500 |
| ggaaagtcgt tctcgaccca tctggatctc atcagacatc agagaacgca cactggagag | 1560 |
| aaaccctaca atgtcccga gtgtgggaag tcgtttagcc gaaaggacaa tctcaaaaac | 1620 |
| catcaacgga cacacacggg tgaaaaacca tacaaatgcc cggagtgcgg caaatcgttt | 1680 |
| tcccaacttg cgcacttgcg ggcacaccaa cgcacgcata ctggagcggc cgcccgcgcc | 1740 |
| ctggtgaaga gcgagctgga ggagaagaag tccgagctgc ggcacaagct gaagtacgtg | 1800 |
| ccccacgagt acatcgagct gatcgagatc gccaggaacc ccacccagga ccgcatcctg | 1860 |
| gagatgaagg tgatggagtt cttcatgaag gtgtacggct acaggggaga gcacctgggc | 1920 |
| ggaagcagaa agcctgacgg cgccatctat acagtgggca gccccatcga ttacggcgtg | 1980 |
| atcgtggaca caaaggccta cagcggcggc tacaatctgc ctatcggcca ggccgacgag | 2040 |
| atggagagat acgtggagga gaaccagaca cgggataagc acctcaaccc caacgagtgg | 2100 |
| tggaaggtgt accctagcag cgtgaccgag ttcaagttcc tgttcgtgag cggccacttc | 2160 |
| aagggcaact acaaggccca gctgaccagg ctgaaccaca tcaccaactg caatggcgcc | 2220 |
| gtgctgagcg tggaggagct gctgatcggc ggcgagatga tcaaagccgg caccctgaca | 2280 |
| ctggaggagg tgcggcgcaa gttcaacaac ggcgagatca acttctga | 2328 |

<210> SEQ ID NO 435
<211> LENGTH: 775
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435

```
Met Arg Ser Asp Tyr Lys Asp His Asp Gly Asp Tyr Lys Asp His Asp
1               5                   10                  15

Ile Asp Tyr Lys Asp Asp Asp Asp Lys Met Ala Pro Lys Lys Lys Arg
```

```
                20                  25                  30
Lys Val Gly Leu Glu Pro Gly Glu Lys Pro Tyr Lys Cys Pro Glu Cys
                35                  40                  45

Gly Lys Ser Phe Ser Asp Pro Gly Ala Leu Val Arg His Gln Arg Thr
                50                  55                  60

His Thr Gly Glu Lys Pro Tyr Lys Cys Pro Glu Cys Gly Lys Ser Phe
65                  70                  75                  80

Ser Gln Arg Ala His Leu Glu Arg His Gln Arg Thr His Thr Gly Glu
                    85                  90                  95

Lys Pro Tyr Lys Cys Pro Glu Cys Gly Lys Ser Phe Ser Arg Ser Asp
                100                 105                 110

Asp Leu Val Arg His Gln Arg Thr His Thr Gly Glu Lys Pro Tyr Lys
                115                 120                 125

Cys Pro Glu Cys Gly Lys Ser Phe Ser Arg Ser Asp His Leu Thr Thr
                130                 135                 140

His Gln Arg Thr His Thr Gly Ala Ala Ala Arg Ala Leu Val Lys Ser
145                 150                 155                 160

Glu Leu Glu Glu Lys Lys Ser Glu Leu Arg His Lys Leu Lys Tyr Val
                165                 170                 175

Pro His Glu Tyr Ile Glu Leu Ile Glu Ile Ala Arg Asn Pro Thr Gln
                180                 185                 190

Asp Arg Ile Leu Glu Met Lys Val Met Glu Phe Phe Met Lys Val Tyr
                195                 200                 205

Gly Tyr Arg Gly Glu His Leu Gly Gly Ser Arg Lys Pro Asp Gly Ala
                210                 215                 220

Ile Tyr Thr Val Gly Ser Pro Ile Asp Tyr Gly Val Ile Val Asp Thr
225                 230                 235                 240

Lys Ala Tyr Ser Gly Gly Tyr Asn Leu Pro Ile Gly Gln Ala Asp Glu
                245                 250                 255

Met Gln Arg Tyr Val Lys Glu Asn Gln Thr Arg Asn Lys His Ile Asn
                260                 265                 270

Pro Asn Glu Trp Trp Lys Val Tyr Pro Ser Ser Val Thr Glu Phe Lys
                275                 280                 285

Phe Leu Phe Val Ser Gly His Phe Lys Gly Asn Tyr Lys Ala Gln Leu
                290                 295                 300

Thr Arg Leu Asn Arg Lys Thr Asn Cys Asn Gly Ala Val Leu Ser Val
305                 310                 315                 320

Glu Glu Leu Leu Ile Gly Gly Glu Met Ile Lys Ala Gly Thr Leu Thr
                325                 330                 335

Leu Glu Glu Val Arg Arg Lys Phe Asn Asn Gly Glu Ile Asn Phe Glu
                340                 345                 350

Gly Arg Gly Ser Leu Leu Thr Cys Gly Asp Val Glu Asn Pro Gly
                355                 360                 365

Pro Arg Ser Asp Tyr Lys Asp His Asp Gly Asp Tyr Lys Asp His Asp
                370                 375                 380

Ile Asp Tyr Lys Asp Asp Asp Asp Lys Met Ala Pro Lys Lys Lys Arg
385                 390                 395                 400

Lys Val Gly Leu Glu Pro Gly Glu Lys Pro Tyr Lys Cys Pro Glu Cys
                405                 410                 415

Gly Lys Ser Phe Ser Gln Ser Gly Asp Leu Arg Arg His Gln Arg Thr
                420                 425                 430

His Thr Gly Glu Lys Pro Tyr Lys Cys Pro Glu Cys Gly Lys Ser Phe
                435                 440                 445
```

Ser Thr Ser Gly Ser Leu Val Arg His Gln Arg Thr His Thr Gly Glu
    450                 455                 460

Lys Pro Tyr Lys Cys Pro Glu Cys Gly Lys Ser Phe Ser Gln Arg Ala
465                 470                 475                 480

His Leu Glu Arg His Gln Arg Thr His Thr Gly Glu Lys Pro Tyr Lys
                485                 490                 495

Cys Pro Glu Cys Gly Lys Ser Phe Ser Thr His Leu Asp Leu Ile Arg
            500                 505                 510

His Gln Arg Thr His Thr Gly Glu Lys Pro Tyr Lys Cys Pro Glu Cys
        515                 520                 525

Gly Lys Ser Phe Ser Arg Lys Asp Asn Leu Lys Asn His Gln Arg Thr
    530                 535                 540

His Thr Gly Glu Lys Pro Tyr Lys Cys Pro Glu Cys Gly Lys Ser Phe
545                 550                 555                 560

Ser Gln Leu Ala His Leu Arg Ala His Gln Arg Thr His Thr Gly Ala
                565                 570                 575

Ala Ala Arg Ala Leu Val Lys Ser Glu Leu Glu Glu Lys Lys Ser Glu
            580                 585                 590

Leu Arg His Lys Leu Lys Tyr Val Pro His Glu Tyr Ile Glu Leu Ile
        595                 600                 605

Glu Ile Ala Arg Asn Pro Thr Gln Asp Arg Ile Leu Glu Met Lys Val
    610                 615                 620

Met Glu Phe Phe Met Lys Val Tyr Gly Tyr Arg Gly Glu His Leu Gly
625                 630                 635                 640

Gly Ser Arg Lys Pro Asp Gly Ala Ile Tyr Thr Val Gly Ser Pro Ile
                645                 650                 655

Asp Tyr Gly Val Ile Val Asp Thr Lys Ala Tyr Ser Gly Gly Tyr Asn
            660                 665                 670

Leu Pro Ile Gly Gln Ala Asp Glu Met Glu Arg Tyr Val Glu Glu Asn
        675                 680                 685

Gln Thr Arg Asp Lys His Leu Asn Pro Asn Glu Trp Trp Lys Val Tyr
    690                 695                 700

Pro Ser Ser Val Thr Glu Phe Lys Phe Leu Phe Val Ser Gly His Phe
705                 710                 715                 720

Lys Gly Asn Tyr Lys Ala Gln Leu Thr Arg Leu Asn His Ile Thr Asn
                725                 730                 735

Cys Asn Gly Ala Val Leu Ser Val Glu Glu Leu Leu Ile Gly Gly Glu
            740                 745                 750

Met Ile Lys Ala Gly Thr Leu Thr Leu Glu Glu Val Arg Arg Lys Phe
        755                 760                 765

Asn Asn Gly Glu Ile Asn Phe
    770                 775

<210> SEQ ID NO 436
<211> LENGTH: 4725
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 436
tggccactcc ctctatgcgc actcgctcgc tcggtggggc ctggcgacca aaggtcgcca      60
gacggacgtg ctttgcacgt ccggccccac cgagcgagcg agtgcgcata gagggagtgg     120

| | |
|---|---|
| ccaactccat cactagaggt atggcagtga cgtaacgcga agcgcgcgaa gcgagaccac | 180 |
| gcctaccagc tgcgtcagca gtcaggtgac ccttttgcga cagtttgcga caccacgtgg | 240 |
| ccgctgaggg tatatattct cgagtgagcg aaccaggagc tccattttga ccgcgaaatt | 300 |
| tgaacgagca gcagccatgc cggggttcta cgagattgtc ctgaaggtcc cgagtgacct | 360 |
| ggacgagcac ctgccgggca tttctaactc gtttgttaac tgggtggccg agaaggaatg | 420 |
| ggagctgccg ccggattctg acatggatcc gaatctgatt gagcaggcac ccctgaccgt | 480 |
| ggccgaaaag cttcagcgcg agttcctggt ggagtggcgc cgcgtgagta aggccccgga | 540 |
| ggccctcttt tttgtccagt tcgaaaaggg ggagacctac ttccacctgc acgtgctgat | 600 |
| tgagaccatc ggggtcaaat ccatggtggt cggccgctac gtgagccaga ttaaagagaa | 660 |
| gctggtgacc cgcatctacc gcggggtcga gccgcagctt ccgaactggt cgcggtgac | 720 |
| caaaacgcga atggcgccg ggggcgggaa caaggtggtg gacgactgct acatccccaa | 780 |
| ctacctgctc cccaagaccc agcccgagct ccagtgggcg tggactaaca tggaccagta | 840 |
| tttaagcgcc tgtttgaatc tcgcgagcg taaacgctg gtggcgcagc atctgacgca | 900 |
| cgtgtcgcag acgcaggagc agaacaaaga gaatcagaac cccaattctg acgcgccggt | 960 |
| catcaggtca aaaacctcag ccaggtacat ggagctggtc gggtggctgg tggaccgcgg | 1020 |
| gatcacgtca gaaaagcaat ggattcagga ggaccaggcc tcgtacatct ccttcaacgc | 1080 |
| cgcctccaac tcgcggtccc agatcaaggc cgcgctggac aatgcctcca agatcatgag | 1140 |
| cctgacaaag acggctccgg actacctggt gggcagcaac ccgccggagg acattaccaa | 1200 |
| aaatcggatc taccaaatcc tggagctgaa cgggtacgat ccgcagtacg cggcctccgt | 1260 |
| cttcctgggc tgggcgcaaa agaagttcgg gaagaggaac accatctggc tctttgggcc | 1320 |
| ggccacgacg ggtaaaacca catcgcggga agccatcgcc cacgccgtgc ccttctacgg | 1380 |
| ctgcgtaaac tggaccaatg agaactttcc cttcaacgat tgcgtcgaca agatggtgat | 1440 |
| ctggtgggag gagggcaaga tgacggccaa ggtcgtggag agcgccaagg ccattctggg | 1500 |
| cggaagcaag gtgcgcgtgg accaaaagtg caagtcatcg gcccagatcg aacccactcc | 1560 |
| cgtgatcgtc acctccaaca ccaacatgtg cgccgtgatt gacgggaaca gcaccaccctt | 1620 |
| cgagcatcag cagccgctgc aggaccggat gtttaaattt gaacttaccc gccgtttgga | 1680 |
| ccatgacttt gggaaggtca ccaaacagga agtaaaggac ttttccggt gggcttccga | 1740 |
| tcacgtgact gacgtggctc atgagttcta cgtcagaaag ggtggagcta agaaacgccc | 1800 |
| cgcctccaat gacgcggatg taagcgagcc aaaacggcag tgcacgtcac ttgcgcagcc | 1860 |
| gacaacgtca gacgcggaag caccggcgga ctacgcggac aggtaccaaa acaaatgttc | 1920 |
| tcgtcacgtg ggcatgaatc tgatgctttt tccctgtaaa acatgcgaga gaatgaatca | 1980 |
| aatttccaat gtctgttta cgcatggtca aagagactgt gggaatgct tccctggaat | 2040 |
| gtcagaatct caacccgttt ctgtcgtcaa aaagaagact tatcagaaac tgtgtccaat | 2100 |
| tcatcatatc ctgggaaggg cacccgagat tgcctgttcg gcctgcgatt tggccaatgt | 2160 |
| ggacttggat gactgtgttt ctgagcaata aatgacttaa accaggtatg gctgctgacg | 2220 |
| gttatcttcc agattggctc gaggacaacc tttctgaagg cattcgtgag tggtgggctc | 2280 |
| tgaaacctgg agtccctcaa cccaaagcga accaacaaca ccaggacaac cgtcggggtc | 2340 |
| ttgtgcttcc gggttacaaa tacctcggac ccggtaacgg actcgacaaa ggagagccgg | 2400 |
| tcaacgaggc ggacgcggca gccctcgaac acgacaaagc ttacgaccag cagctcaagg | 2460 |
| ccggtgacaa cccgtacctc aagtacaacc acgccgacgc cgagtttcag gagcgtcttc | 2520 |

```
aagaagatac gtcttttggg ggcaaccttg gcagagcagt cttccaggcc aaaaagagga   2580
tccttgagcc tcttggtctg gttgaggaag cagctaaaac ggctcctgga agaagaggc    2640 ctgtagatca gtctcctcag gaaccggact catcatctgg tgttggcaaa tcgggcaaac   2700
agcctgccag aaaaagacta aatttcggtc agactggcga ctcagagtca gtcccagacc   2760
ctcaacctct cggagaacca ccagcagccc ccacaagttt gggatctaat acaatggctt   2820
caggcggtgg cgcaccaatg gcagacaata acgaggtgc cgatggagtg ggtaattcct    2880
caggaaattg gcattgcgat tcccaatggc tgggcgacag agtcatcacc accagcacca   2940
gaacctgggc cctgcccact acaacaacc atctctacaa gcaaatctcc agcgcttcaa    3000
cgggagcttc aaacgacaac cactactttg gctacagcac ccttggggg tattttgact    3060 ttaacagatt ccactgccac ttctcaccac gtgactggca gcgactcatt aacaacaact   3120
ggggattccg gcccaagaaa ctcagcttca agctcttcaa catccaagtt aaagaggtca   3180
cgcagaacga tggcacgacg actattgcca ataaccttac cagcacggtt caagtgttta   3240
cggactcgga gtatcagctc ccgtacgtgc tcgggtcggc gcaccaaggc tgtctcccgc   3300
cgtttccagc ggacgtcttc atggtccctc agtatggata cctcaccctg aacaacggaa   3360
gtcaagcggt gggacgctca tccttttact gcctggagta cttcccttcg cagatgctaa   3420
ggactggaaa taacttccaa ttcagctata ccttcgagga tgtaccttt cacagcagct    3480 acgctcacag ccagagtttg gatcgcttga tgaatcctct tattgatcag tatctgtact   3540
acctgaacaa aacgcaagga acaacctctg aacaaccaa ccaatcacgg ctgcttttta    3600
gccaggctgg gcctcagtct atgtctttgc aggccagaaa ttggctacct gggccctgct   3660
accggcaaca gagactttca agactgctac acgacaacaa caacagtaac tttccttgga   3720
cagcggccag caaatatcat ctcaatggcc gcgactcgct ggtgaatcca ggaccagcta   3780
tggccagtca caggacgat gaagaaaaat ttttccctat gcacggcaat ctaatatttg    3840
gcaaagaagg gacaacggca gtaacgcag aattagataa tgtaatgatt acggatgaag    3900
aagagattcg taccaccaat cctgtggcaa cagagcagta tggaactgtg gcaaataact   3960
tgcagagctc aaatacagct cccacgacta gaactgtcaa tgatcagggg gccttacctg   4020
gcatggtgtg gcaagatcgt gacgtgtacc ttcaaggacc tatctgggca aagattcctc   4080
acacggatgg acactttcat ccttctcctc tgatgggagg cttttgactg aaacatccgc   4140
ctcctcaaat catgatcaaa aatactccgg taccggcaaa tcctccgacg actttcagcc   4200
cggccaagtt tgcttcattt atcactcagt actccactgg acaggtcagc gtggaaattg   4260
agtgggagct acagaaagaa aacagcaaac gttggaatcc agagattcag tacacttcca   4320
actacaacaa gtctgttaat gtggacttta ctgtagacac taatggtgtt tatagtgaac   4380
ctcgccctat tggaacccgg tatctcacac gaaacttgta atcctggtta atcaataaac   4440
cgtttaattc gtttcagttg aactttggct cttgtgcact tcttatctta tcttgtttcc   4500
atggctactg cgtagataag cagcggcctg cggcgcttgc gcttcgcggt ttacaactgc   4560
tggttaatat ttaactctcg ccataccact agtgatggag ttggccactc cctctatgcg   4620
cactcgctcg ctcggtgggg ccggacgtgc aaagcacgtc cgtctggcga cctttggtcg   4680
ccaggcccca ccgagcgagc gagtgcgcat agagggagtg gccaa               4725
```

<210> SEQ ID NO 437
<211> LENGTH: 737
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 437

| | | | | | | | | | | | | | | |
|---|---|---|---|---|---|---|---|---|---|---|---|---|---|---|
| Met | Ala | Ala | Asp | Gly | Tyr | Leu | Pro | Asp | Trp | Leu | Glu | Asp | Asn | Leu | Ser |
| 1 | | | | 5 | | | | | 10 | | | | | 15 | |
| Glu | Gly | Ile | Arg | Glu | Trp | Trp | Ala | Leu | Lys | Pro | Gly | Val | Pro | Gln | Pro |
| | | | 20 | | | | | 25 | | | | | 30 | | |
| Lys | Ala | Asn | Gln | Gln | His | Gln | Asp | Asn | Arg | Arg | Gly | Leu | Val | Leu | Pro |
| | | 35 | | | | | 40 | | | | | 45 | | | |
| Gly | Tyr | Lys | Tyr | Leu | Gly | Pro | Gly | Asn | Gly | Leu | Asp | Lys | Gly | Glu | Pro |
| | 50 | | | | | 55 | | | | | 60 | | | | |
| Val | Asn | Glu | Ala | Asp | Ala | Ala | Ala | Leu | Glu | His | Asp | Lys | Ala | Tyr | Asp |
| 65 | | | | | 70 | | | | | 75 | | | | | 80 |
| Gln | Gln | Leu | Lys | Ala | Gly | Asp | Asn | Pro | Tyr | Leu | Lys | Tyr | Asn | His | Ala |
| | | | | 85 | | | | | 90 | | | | | 95 | |
| Asp | Ala | Glu | Phe | Gln | Glu | Arg | Leu | Gln | Glu | Asp | Thr | Ser | Phe | Gly | Gly |
| | | | | 100 | | | | | 105 | | | | | 110 | |
| Asn | Leu | Gly | Arg | Ala | Val | Phe | Gln | Ala | Lys | Lys | Arg | Ile | Leu | Glu | Pro |
| | | | | 115 | | | | | 120 | | | | | 125 | |
| Leu | Gly | Leu | Val | Glu | Glu | Ala | Ala | Lys | Thr | Ala | Pro | Gly | Lys | Lys | Arg |
| | | 130 | | | | | 135 | | | | | 140 | | | |
| Pro | Val | Asp | Gln | Ser | Pro | Gln | Glu | Pro | Asp | Ser | Ser | Ser | Gly | Val | Gly |
| 145 | | | | | 150 | | | | | 155 | | | | | 160 |
| Lys | Ser | Gly | Lys | Gln | Pro | Ala | Arg | Lys | Arg | Leu | Asn | Phe | Gly | Gln | Thr |
| | | | | 165 | | | | | 170 | | | | | 175 | |
| Gly | Asp | Ser | Glu | Ser | Val | Pro | Asp | Pro | Gln | Pro | Leu | Gly | Glu | Pro | Pro |
| | | | | 180 | | | | | 185 | | | | | 190 | |
| Ala | Ala | Pro | Thr | Ser | Leu | Gly | Ser | Asn | Thr | Met | Ala | Ser | Gly | Gly | Gly |
| | | | | 195 | | | | | 200 | | | | | 205 | |
| Ala | Pro | Met | Ala | Asp | Asn | Asn | Glu | Gly | Ala | Asp | Gly | Val | Gly | Asn | Ser |
| | 210 | | | | | 215 | | | | | 220 | | | | |
| Ser | Gly | Asn | Trp | His | Cys | Asp | Ser | Gln | Trp | Leu | Gly | Asp | Arg | Val | Ile |
| 225 | | | | | 230 | | | | | 235 | | | | | 240 |
| Thr | Thr | Ser | Thr | Arg | Thr | Trp | Ala | Leu | Pro | Thr | Tyr | Asn | Asn | His | Leu |
| | | | | 245 | | | | | 250 | | | | | 255 | |
| Tyr | Lys | Gln | Ile | Ser | Ser | Ala | Ser | Thr | Gly | Ala | Ser | Asn | Asp | Asn | His |
| | | | | 260 | | | | | 265 | | | | | 270 | |
| Tyr | Phe | Gly | Tyr | Ser | Thr | Pro | Trp | Gly | Tyr | Phe | Asp | Phe | Asn | Arg | Phe |
| | | 275 | | | | | 280 | | | | | 285 | | | |
| His | Cys | His | Phe | Ser | Pro | Arg | Asp | Trp | Gln | Arg | Leu | Ile | Asn | Asn | Asn |
| | 290 | | | | | 295 | | | | | 300 | | | | |
| Trp | Gly | Phe | Arg | Pro | Lys | Lys | Leu | Ser | Phe | Lys | Leu | Phe | Asn | Ile | Gln |
| 305 | | | | | 310 | | | | | 315 | | | | | 320 |
| Val | Lys | Glu | Val | Thr | Gln | Asn | Asp | Gly | Thr | Thr | Thr | Ile | Ala | Asn | Asn |
| | | | | 325 | | | | | 330 | | | | | 335 | |
| Leu | Thr | Ser | Thr | Val | Gln | Val | Phe | Thr | Asp | Ser | Glu | Tyr | Gln | Leu | Pro |
| | | | | 340 | | | | | 345 | | | | | 350 | |
| Tyr | Val | Leu | Gly | Ser | Ala | His | Gln | Gly | Cys | Leu | Pro | Pro | Phe | Pro | Ala |
| | | 355 | | | | | 360 | | | | | 365 | | | |
| Asp | Val | Phe | Met | Val | Pro | Gln | Tyr | Gly | Tyr | Leu | Thr | Leu | Asn | Asn | Gly |
| | 370 | | | | | 375 | | | | | 380 | | | | |

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
            405                 410                 415

Glu Asp Val Pro Phe His Ser Ser Tyr Ala His Ser Gln Ser Leu Asp
        420                 425                 430

Arg Leu Met Asn Pro Leu Ile Asp Gln Tyr Leu Tyr Tyr Leu Asn Arg
    435                 440                 445

Thr Gln Gly Thr Thr Ser Gly Thr Thr Asn Gln Ser Arg Leu Leu Phe
450                 455                 460

Ser Gln Ala Gly Pro Gln Ser Met Ser Leu Gln Ala Arg Asn Trp Leu
465                 470                 475                 480

Pro Gly Pro Cys Tyr Arg Gln Gln Arg Leu Ser Lys Thr Ala Asn Asp
            485                 490                 495

Asn Asn Asn Ser Asn Phe Pro Trp Thr Ala Ala Ser Lys Tyr His Leu
            500                 505                 510

Asn Gly Arg Asp Ser Leu Val Asn Pro Gly Pro Ala Met Ala Ser His
        515                 520                 525

Lys Asp Asp Glu Glu Lys Phe Phe Pro Met His Gly Asn Leu Ile Phe
530                 535                 540

Gly Lys Glu Gly Thr Thr Ala Ser Asn Ala Glu Leu Asp Asn Val Met
545                 550                 555                 560

Ile Thr Asp Glu Glu Glu Ile Arg Thr Thr Asn Pro Val Ala Thr Glu
            565                 570                 575

Gln Tyr Gly Thr Val Ala Asn Asn Leu Gln Ser Ser Asn Thr Ala Pro
        580                 585                 590

Thr Thr Arg Thr Val Asn Asp Gln Gly Ala Leu Pro Gly Met Val Trp
    595                 600                 605

Gln Asp Arg Asp Val Tyr Leu Gln Gly Pro Ile Trp Ala Lys Ile Pro
610                 615                 620

His Thr Asp Gly His Phe His Pro Ser Pro Leu Met Gly Gly Phe Gly
625                 630                 635                 640

Leu Lys His Pro Pro Pro Gln Ile Met Ile Lys Asn Thr Pro Val Pro
            645                 650                 655

Ala Asn Pro Pro Thr Thr Phe Ser Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Asn Lys Ser Val Asn Val Asp Phe Thr Val Asp Thr Asn Gly
705                 710                 715                 720

Val Tyr Ser Glu Pro Arg Pro Ile Gly Thr Arg Tyr Leu Thr Arg Asn
            725                 730                 735

Leu

<210> SEQ ID NO 438
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 438

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Leu Glu Pro Gly Glu Lys Pro Tyr Lys Cys Pro Glu Cys Gly
        35                  40                  45

Lys Ser Phe Ser Arg Lys Asp Ala Leu Arg Gly His Gln Arg Thr His
50                  55                  60

Thr Gly Glu Lys Pro Tyr Lys Cys Pro Glu Cys Gly Lys Ser Phe Ser
65                  70                  75                  80

His Arg Thr Thr Leu Thr Asn His Gln Arg Thr His Thr Gly Glu Lys
            85                  90                  95

Pro Tyr Lys Cys Pro Glu Cys Gly Lys Ser Phe Ser Gln Arg Asn Ala
        100                 105                 110

Leu Ala Gly His Gln Arg Thr His Thr Gly Glu Lys Pro Tyr Lys Cys
            115                 120                 125

Pro Glu Cys Gly Lys Ser Phe Ser His Lys Asn Ala Leu Gln Asn His
    130                 135                 140

Gln Arg Thr His Thr Gly Glu Lys Pro Tyr Lys Cys Pro Glu Cys Gly
145                 150                 155                 160

Lys Ser Phe Ser Asp Pro Gly His Leu Val Arg His Gln Arg Thr His
            165                 170                 175

Thr Gly Glu Lys Pro Tyr Lys Cys Pro Glu Cys Gly Lys Ser Phe Ser
        180                 185                 190

Thr Ser Gly Asn Leu Val Arg His Gln Arg Thr His Thr Gly Ala Ala
        195                 200                 205

Ala Arg Ala Leu Val Lys Ser Glu Leu Glu Glu Lys Lys Ser Glu Leu
    210                 215                 220

Arg His Lys Leu Lys Tyr Val Pro His Glu Tyr Ile Glu Leu Ile Glu
225                 230                 235                 240

Ile Ala Arg Asn Pro Thr Gln Asp Arg Ile Leu Glu Met Lys Val Met
            245                 250                 255

Glu Phe Phe Met Lys Val Tyr Gly Tyr Arg Gly Glu His Leu Gly Gly
        260                 265                 270

Ser Arg Lys Pro Asp Gly Ala Ile Tyr Thr Val Gly Ser Pro Ile Asp
    275                 280                 285

Tyr Gly Val Ile Val Asp Thr Lys Ala Tyr Ser Gly Gly Tyr Asn Leu
    290                 295                 300

Pro Ile Gly Gln Ala Asp Glu Met Glu Arg Tyr Val Glu Glu Asn Gln
305                 310                 315                 320

Thr Arg Asp Lys His Leu Asn Pro Asn Glu Trp Trp Lys Val Tyr Pro
            325                 330                 335

Ser Ser Val Thr Glu Phe Lys Phe Leu Phe Val Ser Gly His Phe Lys
            340                 345                 350

Gly Asn Tyr Lys Ala Gln Leu Thr Arg Leu Asn His Ile Thr Asn Cys
            355                 360                 365

Asn Gly Ala Val Leu Ser Val Glu Glu Leu Leu Ile Gly Gly Glu Met
    370                 375                 380

Ile Lys Ala Gly Thr Leu Thr Leu Glu Glu Val Arg Arg Lys Phe Asn
385                 390                 395                 400

Asn Gly Glu Ile Asn Phe
            405
```

<210> SEQ ID NO 439
<211> LENGTH: 406
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 439

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Leu Glu Pro Gly Glu Lys Pro Tyr Lys Cys Pro Glu Cys Gly
        35                  40                  45

Lys Ser Phe Ser Gln Gln Arg Ser Leu Val Gly His Gln Arg Thr His
    50                  55                  60

Thr Gly Glu Lys Pro Tyr Lys Cys Pro Glu Cys Gly Lys Ser Phe Ser
65                  70                  75                  80

Asp Lys Lys Asp Leu Thr Arg His Gln Arg Thr His Thr Gly Glu Lys
                85                  90                  95

Pro Tyr Lys Cys Pro Glu Cys Gly Lys Ser Phe Ser Thr Ser Gly His
            100                 105                 110

Leu Val Arg His Gln Arg Thr His Thr Gly Glu Lys Pro Tyr Lys Cys
        115                 120                 125

Pro Glu Cys Gly Lys Ser Phe Ser Gln Arg Ala His Leu Glu Arg His
    130                 135                 140

Gln Arg Thr His Thr Gly Glu Lys Pro Tyr Lys Cys Pro Glu Cys Gly
145                 150                 155                 160

Lys Ser Phe Ser Thr Ser Gly Ser Leu Val Arg His Gln Arg Thr His
                165                 170                 175

Thr Gly Glu Lys Pro Tyr Lys Cys Pro Glu Cys Gly Lys Ser Phe Ser
            180                 185                 190

Thr Ser Gly Asn Leu Val Arg His Gln Arg Thr His Thr Gly Ala Ala
        195                 200                 205

Ala Arg Ala Leu Val Lys Ser Glu Leu Glu Glu Lys Lys Ser Glu Leu
    210                 215                 220

Arg His Lys Leu Lys Tyr Val Pro His Glu Tyr Ile Glu Leu Ile Glu
225                 230                 235                 240

Ile Ala Arg Asn Pro Thr Gln Asp Arg Ile Leu Glu Met Lys Val Met
                245                 250                 255

Glu Phe Phe Met Lys Val Tyr Gly Tyr Arg Gly Glu His Leu Gly Gly
            260                 265                 270

Ser Arg Lys Pro Asp Gly Ala Ile Tyr Thr Val Gly Ser Pro Ile Asp
        275                 280                 285

Tyr Gly Val Ile Val Asp Thr Lys Ala Tyr Ser Gly Gly Tyr Asn Leu
    290                 295                 300

Pro Ile Gly Gln Ala Asp Glu Met Gln Arg Tyr Val Lys Glu Asn Gln
305                 310                 315                 320

Thr Arg Asn Lys His Ile Asn Pro Asn Glu Trp Trp Lys Val Tyr Pro
                325                 330                 335

Ser Ser Val Thr Glu Phe Lys Phe Leu Phe Val Ser Gly His Phe Lys
            340                 345                 350

Gly Asn Tyr Lys Ala Gln Leu Thr Arg Leu Asn Arg Lys Thr Asn Cys
        355                 360                 365
```

```
Asn Gly Ala Val Leu Ser Val Glu Glu Leu Leu Ile Gly Gly Glu Met
    370                 375                 380

Ile Lys Ala Gly Thr Leu Thr Leu Glu Glu Val Arg Arg Lys Phe Asn
385                 390                 395                 400

Asn Gly Glu Ile Asn Phe
                405

<210> SEQ ID NO 440
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 440

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Gly Arg Leu Glu Pro Gly Glu Arg Pro Phe Gln Cys Arg Ile Cys Met
            35                  40                  45

Arg Asn Phe Ser Ser Lys Gln Ala Leu Ala Val His Thr Arg Thr His
    50                  55                  60

Thr Gly Glu Lys Pro Phe Gln Cys Arg Ile Cys Met Arg Asn Phe Ser
65                  70                  75                  80

Gln Ser Thr Thr Leu Lys Arg His Leu Arg Thr His Thr Gly Glu Lys
                85                  90                  95

Pro Phe Gln Cys Arg Ile Cys Met Arg Asn Phe Ser Arg Ser Asp His
            100                 105                 110

Leu Ser Leu His Leu Lys Thr His Leu Arg Gly Ser Gln Leu Val Lys
        115                 120                 125

Ser Glu Leu Glu Glu Lys Lys Ser Glu Leu Arg His Lys Leu Lys Tyr
130                 135                 140

Val Pro His Glu Tyr Ile Glu Leu Ile Glu Ile Ala Arg Asn Pro Thr
145                 150                 155                 160

Gln Asp Arg Ile Leu Glu Met Lys Val Met Glu Phe Phe Met Lys Val
                165                 170                 175

Tyr Gly Tyr Arg Gly Glu His Leu Gly Gly Ser Arg Lys Pro Asp Gly
            180                 185                 190

Ala Ile Tyr Thr Val Gly Ser Pro Ile Asp Tyr Gly Val Ile Val Asp
        195                 200                 205

Thr Lys Ala Tyr Ser Gly Gly Tyr Asn Leu Pro Ile Gly Gln Ala Asp
    210                 215                 220

Glu Met Gln Arg Tyr Val Lys Glu Asn Gln Thr Arg Asn Lys His Ile
225                 230                 235                 240

Asn Pro Asn Glu Trp Trp Lys Val Tyr Pro Ser Ser Val Thr Glu Phe
                245                 250                 255

Lys Phe Leu Phe Val Ser Gly His Phe Lys Gly Asn Tyr Lys Ala Gln
            260                 265                 270

Leu Thr Arg Leu Asn Arg Lys Thr Asn Cys Asn Gly Ala Val Leu Ser
        275                 280                 285

Val Glu Glu Leu Leu Ile Gly Gly Glu Met Ile Lys Ala Gly Thr Leu
    290                 295                 300

Thr Leu Glu Glu Val Arg Arg Lys Phe Asn Asn Gly Glu Ile Asn Phe
305                 310                 315                 320
```

<210> SEQ ID NO 441
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Arg Leu Glu Pro Gly Glu Arg Pro Phe Gln Cys Arg Ile Cys Met
            35                  40                  45

Arg Asn Phe Ser Arg Arg Ala His Leu Gln Asn His Thr Arg Thr His
50                  55                  60

Thr Gly Glu Lys Pro Phe Gln Cys Arg Ile Cys Met Arg Asn Phe Ser
65                  70                  75                  80

Gln Ser Thr Thr Leu Lys Arg His Leu Arg Thr His Thr Gly Glu Lys
                85                  90                  95

Pro Phe Gln Cys Arg Ile Cys Met Arg Asn Phe Ser Asp Gly Gly His
            100                 105                 110

Leu Thr Arg His Leu Lys Thr His Leu Arg Gly Ser Gln Leu Val Lys
            115                 120                 125

Ser Glu Leu Glu Glu Lys Lys Ser Glu Leu Arg His Lys Leu Lys Tyr
130                 135                 140

Val Pro His Glu Tyr Ile Glu Leu Ile Glu Ile Ala Arg Asn Pro Thr
145                 150                 155                 160

Gln Asp Arg Ile Leu Glu Met Lys Val Met Glu Phe Phe Met Lys Val
                165                 170                 175

Tyr Gly Tyr Arg Gly Glu His Leu Gly Gly Ser Arg Lys Pro Asp Gly
            180                 185                 190

Ala Ile Tyr Thr Val Gly Ser Pro Ile Asp Tyr Gly Val Ile Val Asp
            195                 200                 205

Thr Lys Ala Tyr Ser Gly Gly Tyr Asn Leu Pro Ile Gly Gln Ala Asp
210                 215                 220

Glu Met Glu Arg Tyr Val Glu Glu Asn Gln Thr Arg Asp Lys His Leu
225                 230                 235                 240

Asn Pro Asn Glu Trp Trp Lys Val Tyr Pro Ser Ser Val Thr Glu Phe
                245                 250                 255

Lys Phe Leu Phe Val Ser Gly His Phe Lys Gly Asn Tyr Lys Ala Gln
            260                 265                 270

Leu Thr Arg Leu Asn His Ile Thr Asn Cys Asn Gly Ala Val Leu Ser
            275                 280                 285

Val Glu Glu Leu Leu Ile Gly Gly Glu Met Ile Lys Ala Gly Thr Leu
            290                 295                 300

Thr Leu Glu Glu Val Arg Arg Lys Phe Asn Asn Gly Glu Ile Asn Phe
305                 310                 315                 320

<210> SEQ ID NO 442
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 442
caaactagaa atgccatctt ccttgatgtt ggaggtacct gc					42

<210> SEQ ID NO 443
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Leu Glu Pro Gly Glu Lys Pro Tyr Lys Cys Pro Glu Cys Gly
        35                  40                  45

Lys Ser Phe Ser Arg Lys Asp Ala Leu Arg Gly His Gln Arg Thr His
    50                  55                  60

Thr Gly Glu Lys Pro Tyr Lys Cys Pro Glu Cys Gly Lys Ser Phe Ser
65                  70                  75                  80

His Arg Thr Thr Leu Thr Asn His Gln Arg Thr His Thr Gly Glu Lys
                85                  90                  95

Pro Tyr Lys Cys Pro Glu Cys Gly Lys Ser Phe Ser Gln Arg Asn Ala
            100                 105                 110

Leu Ala Gly His Gln Arg Thr His Thr Gly Glu Lys Pro Tyr Lys Cys
        115                 120                 125

Pro Glu Cys Gly Lys Ser Phe Ser His Lys Asn Ala Leu Gln Asn His
    130                 135                 140

Gln Arg Thr His Thr Gly Glu Lys Pro Tyr Lys Cys Pro Glu Cys Gly
145                 150                 155                 160

Lys Ser Phe Ser Asp Pro Gly His Leu Val Arg His Gln Arg Thr His
                165                 170                 175

Thr Gly Glu Lys Pro Tyr Lys Cys Pro Glu Cys Gly Lys Ser Phe Ser
            180                 185                 190

Thr Ser Gly Asn Leu Val Arg His Gln Arg Thr His Thr Gly Ala Ala
        195                 200                 205

Ala Arg Ala Leu Val Lys Ser Glu Leu Glu Glu Lys Lys Ser Glu Leu
    210                 215                 220

Arg His Lys Leu Lys Tyr Val Pro His Glu Tyr Ile Glu Leu Ile Glu
225                 230                 235                 240

Ile Ala Arg Asn Pro Thr Gln Asp Arg Ile Leu Glu Met Lys Val Met
                245                 250                 255

Glu Phe Phe Met Lys Val Tyr Gly Tyr Arg Gly Glu His Leu Gly Gly
            260                 265                 270

Ser Arg Lys Pro Asp Gly Ala Ile Tyr Thr Val Gly Ser Pro Ile Asp
        275                 280                 285

Tyr Gly Val Ile Val Asp Thr Lys Ala Tyr Ser Gly Tyr Asn Leu
    290                 295                 300

Pro Ile Gly Gln Ala Asp Glu Met Glu Arg Tyr Val Glu Glu Asn Gln
305                 310                 315                 320

Thr Arg Asp Lys His Leu Asn Pro Asn Glu Trp Trp Lys Val Tyr Pro
                325                 330                 335
```

Ser Ser Val Thr Glu Phe Lys Phe Leu Phe Val Ser Gly His Phe Lys
            340                 345                 350

Gly Asn Tyr Lys Ala Gln Leu Thr Arg Leu Asn His Ile Thr Asn Cys
            355                 360                 365

Asn Gly Ala Val Leu Ser Val Glu Glu Leu Leu Ile Gly Gly Glu Met
370                 375                 380

Ile Lys Ala Gly Thr Leu Thr Leu Glu Glu Val Arg Arg Lys Phe Asn
385                 390                 395                 400

Asn Gly Glu Ile Asn Phe
            405

<210> SEQ ID NO 444
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Leu Glu Pro Gly Glu Pro Tyr Lys Cys Pro Glu Cys Gly
            35                  40                  45

Lys Ser Phe Ser Gln Gln Arg Ser Leu Val Gly His Gln Arg Thr His
50                  55                  60

Thr Gly Glu Lys Pro Tyr Lys Cys Pro Glu Cys Gly Lys Ser Phe Ser
65                  70                  75                  80

Asp Lys Lys Asp Leu Thr Arg His Gln Arg Thr His Thr Gly Glu Lys
            85                  90                  95

Pro Tyr Lys Cys Pro Glu Cys Gly Lys Ser Phe Ser Thr Ser Gly His
            100                 105                 110

Leu Val Arg His Gln Arg Thr His Thr Gly Glu Lys Pro Tyr Lys Cys
            115                 120                 125

Pro Glu Cys Gly Lys Ser Phe Ser Gln Arg Ala His Leu Glu Arg His
            130                 135                 140

Gln Arg Thr His Thr Gly Glu Lys Pro Tyr Lys Cys Pro Glu Cys Gly
145                 150                 155                 160

Lys Ser Phe Ser Thr Ser Gly Ser Leu Val Arg His Gln Arg Thr His
            165                 170                 175

Thr Gly Glu Lys Pro Tyr Lys Cys Pro Glu Cys Gly Lys Ser Phe Ser
            180                 185                 190

Thr Ser Gly Asn Leu Val Arg His Gln Arg Thr His Thr Gly Ala Ala
            195                 200                 205

Ala Arg Ala Leu Val Lys Ser Glu Leu Glu Glu Lys Lys Ser Glu Leu
            210                 215                 220

Arg His Lys Leu Lys Tyr Val Pro His Glu Tyr Ile Glu Leu Ile Glu
225                 230                 235                 240

Ile Ala Arg Asn Pro Thr Gln Asp Arg Ile Leu Glu Met Lys Val Met
            245                 250                 255

Glu Phe Phe Met Lys Val Tyr Gly Tyr Arg Gly Glu His Leu Gly Gly
            260                 265                 270

Ser Arg Lys Pro Asp Gly Ala Ile Tyr Thr Val Gly Ser Pro Ile Asp

```
            275                 280                 285
Tyr Gly Val Ile Val Asp Thr Lys Ala Tyr Ser Gly Gly Tyr Asn Leu
    290                 295                 300

Pro Ile Gly Gln Ala Asp Glu Met Gln Arg Tyr Val Lys Glu Asn Gln
305                 310                 315                 320

Thr Arg Asn Lys His Ile Asn Pro Asn Glu Trp Trp Lys Val Tyr Pro
                325                 330                 335

Ser Ser Val Thr Glu Phe Lys Phe Leu Phe Val Ser Gly His Phe Lys
            340                 345                 350

Gly Asn Tyr Lys Ala Gln Leu Thr Arg Leu Asn Arg Lys Thr Asn Cys
        355                 360                 365

Asn Gly Ala Val Leu Ser Val Glu Glu Leu Leu Ile Gly Gly Glu Met
    370                 375                 380

Ile Lys Ala Gly Thr Leu Thr Leu Glu Glu Val Arg Arg Lys Phe Asn
385                 390                 395                 400

Asn Gly Glu Ile Asn Phe
                405

<210> SEQ ID NO 445
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (25)..(25)
<223> OTHER INFORMATION: May or may not be present

<400> SEQUENCE: 445
tatctgccca tgactggcgc aggga                                           25

<210> SEQ ID NO 446
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Arg Pro Phe Gln Cys Arg Ile Cys Met
        35                  40                  45

Arg Asn Phe Ser Ser Lys Gln Ala Leu Ala Val His Thr Arg Thr His
    50                  55                  60

Thr Gly Glu Lys Pro Phe Gln Cys Arg Ile Cys Met Arg Asn Phe Ser
65                  70                  75                  80

Gln Ser Thr Thr Leu Lys Arg His Leu Arg Thr His Thr Gly Glu Lys
            85                  90                  95

Pro Phe Gln Cys Arg Ile Cys Met Arg Asn Phe Ser Arg Ser Asp His
        100                 105                 110
```

Leu Ser Leu His Leu Lys Thr His Leu Arg Gly Ser Gln Leu Val Lys
            115                 120                 125

Ser Glu Leu Glu Glu Lys Lys Ser Glu Leu Arg His Lys Leu Lys Tyr
130                 135                 140

Val Pro His Glu Tyr Ile Glu Leu Ile Glu Ile Ala Arg Asn Pro Thr
145                 150                 155                 160

Gln Asp Arg Ile Leu Glu Met Lys Val Met Glu Phe Phe Met Lys Val
            165                 170                 175

Tyr Gly Tyr Arg Gly Glu His Leu Gly Gly Ser Arg Lys Pro Asp Gly
            180                 185                 190

Ala Ile Tyr Thr Val Gly Ser Pro Ile Asp Tyr Gly Val Ile Val Asp
            195                 200                 205

Thr Lys Ala Tyr Ser Gly Gly Tyr Asn Leu Pro Ile Gly Gln Ala Asp
210                 215                 220

Glu Met Gln Arg Tyr Val Lys Glu Asn Gln Thr Arg Asn Lys His Ile
225                 230                 235                 240

Asn Pro Asn Glu Trp Trp Lys Val Tyr Pro Ser Ser Val Thr Glu Phe
            245                 250                 255

Lys Phe Leu Phe Val Ser Gly His Phe Lys Gly Asn Tyr Lys Ala Gln
            260                 265                 270

Leu Thr Arg Leu Asn Arg Lys Thr Asn Cys Asn Gly Ala Val Leu Ser
            275                 280                 285

Val Glu Glu Leu Leu Ile Gly Gly Glu Met Ile Lys Ala Gly Thr Leu
            290                 295                 300

Thr Leu Glu Glu Val Arg Arg Lys Phe Asn Asn Gly Glu Ile Asn Phe
305                 310                 315                 320

<210> SEQ ID NO 447
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Leu Glu Pro Gly Glu Arg Pro Phe Gln Cys Arg Ile Cys Met
            35                  40                  45

Arg Asn Phe Ser Arg Arg Ala His Leu Gln Asn His Thr Arg Thr His
50                  55                  60

Thr Gly Glu Lys Pro Phe Gln Cys Arg Ile Cys Met Arg Asn Phe Ser
65                  70                  75                  80

Gln Ser Thr Thr Leu Lys Arg His Leu Arg Thr His Thr Gly Glu Lys
            85                  90                  95

Pro Phe Gln Cys Arg Ile Cys Met Arg Asn Phe Ser Asp Gly Gly His
            100                 105                 110

Leu Thr Arg His Leu Lys Thr His Leu Arg Gly Ser Gln Leu Val Lys
            115                 120                 125

Ser Glu Leu Glu Glu Lys Lys Ser Glu Leu Arg His Lys Leu Lys Tyr
130                 135                 140

Val Pro His Glu Tyr Ile Glu Leu Ile Glu Ile Ala Arg Asn Pro Thr
145                 150                 155                 160

```
Gln Asp Arg Ile Leu Glu Met Lys Val Met Glu Phe Phe Met Lys Val
                165                 170                 175

Tyr Gly Tyr Arg Gly Glu His Leu Gly Gly Ser Arg Lys Pro Asp Gly
            180                 185                 190

Ala Ile Tyr Thr Val Gly Ser Pro Ile Asp Tyr Gly Val Ile Val Asp
        195                 200                 205

Thr Lys Ala Tyr Ser Gly Gly Tyr Asn Leu Pro Ile Gly Gln Ala Asp
    210                 215                 220

Glu Met Glu Arg Tyr Val Glu Asn Gln Thr Arg Asp Lys His Leu
225                 230                 235                 240

Asn Pro Asn Glu Trp Trp Lys Val Tyr Pro Ser Ser Val Thr Glu Phe
                245                 250                 255

Lys Phe Leu Phe Val Ser Gly His Phe Lys Gly Asn Tyr Lys Ala Gln
            260                 265                 270

Leu Thr Arg Leu Asn His Ile Thr Asn Cys Asn Gly Ala Val Leu Ser
        275                 280                 285

Val Glu Glu Leu Leu Ile Gly Gly Glu Met Ile Lys Ala Gly Thr Leu
    290                 295                 300

Thr Leu Glu Glu Val Arg Arg Lys Phe Asn Asn Gly Glu Ile Asn Phe
305                 310                 315                 320

<210> SEQ ID NO 448
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 448
actagaaatg ccatcttcct tgatgttgga ggtacctgct ct                           42

<210> SEQ ID NO 449
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Arg Leu Glu Pro Gly Glu Lys Pro Tyr Lys Cys Pro Glu Cys Gly
            35                  40                  45

Lys Ser Phe Ser His Arg Thr Thr Leu Thr Asn His Gln Arg Thr His
    50                  55                  60

Thr Gly Glu Lys Pro Tyr Lys Cys Pro Glu Cys Gly Lys Ser Phe Ser
65                  70                  75                  80

Gln Arg Asn Ala Leu Ala Gly His Gln Arg Thr His Thr Gly Glu Lys
                85                  90                  95

Pro Tyr Lys Cys Pro Glu Cys Gly Lys Ser Phe Ser His Lys Asn Ala
            100                 105                 110

Leu Gln Asn His Gln Arg Thr His Thr Gly Glu Lys Pro Tyr Lys Cys
        115                 120                 125
```

-continued

Pro Glu Cys Gly Lys Ser Phe Ser Asp Pro Gly His Leu Val Arg His
    130                 135                 140

Gln Arg Thr His Thr Gly Glu Lys Pro Tyr Lys Cys Pro Glu Cys Gly
145                 150                 155                 160

Lys Ser Phe Ser Thr Ser Gly Asn Leu Val Arg His Gln Arg Thr His
                165                 170                 175

Thr Gly Glu Lys Pro Tyr Lys Cys Pro Glu Cys Gly Lys Ser Phe Ser
            180                 185                 190

Gln Ser Ser Asn Leu Val Arg His Gln Arg Thr His Thr Gly Ala Ala
                195                 200                 205

Ala Arg Ala Leu Val Lys Ser Glu Leu Glu Glu Lys Lys Ser Glu Leu
    210                 215                 220

Arg His Lys Leu Lys Tyr Val Pro His Glu Tyr Ile Glu Leu Ile Glu
225                 230                 235                 240

Ile Ala Arg Asn Pro Thr Gln Asp Arg Ile Leu Glu Met Lys Val Met
                245                 250                 255

Glu Phe Phe Met Lys Val Tyr Gly Tyr Arg Gly Glu His Leu Gly Gly
            260                 265                 270

Ser Arg Lys Pro Asp Gly Ala Ile Tyr Thr Val Gly Ser Pro Ile Asp
    275                 280                 285

Tyr Gly Val Ile Val Asp Thr Lys Ala Tyr Ser Gly Gly Tyr Asn Leu
290                 295                 300

Pro Ile Gly Gln Ala Asp Glu Met Glu Arg Tyr Val Glu Glu Asn Gln
305                 310                 315                 320

Thr Arg Asp Lys His Leu Asn Pro Asn Glu Trp Trp Lys Val Tyr Pro
                325                 330                 335

Ser Ser Val Thr Glu Phe Lys Phe Leu Phe Val Ser Gly His Phe Lys
            340                 345                 350

Gly Asn Tyr Lys Ala Gln Leu Thr Arg Leu Asn His Ile Thr Asn Cys
    355                 360                 365

Asn Gly Ala Val Leu Ser Val Glu Glu Leu Leu Ile Gly Gly Glu Met
    370                 375                 380

Ile Lys Ala Gly Thr Leu Thr Leu Glu Glu Val Arg Arg Lys Phe Asn
385                 390                 395                 400

Asn Gly Glu Ile Asn Phe
                405

<210> SEQ ID NO 450
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Leu Glu Pro Gly Glu Lys Pro Tyr Lys Cys Pro Glu Cys Gly
        35                  40                  45

Lys Ser Phe Ser Gln Arg Asn Ala Leu Ala Gly His Gln Arg Thr His
    50                  55                  60

Thr Gly Glu Lys Pro Tyr Lys Cys Pro Glu Cys Gly Lys Ser Phe Ser
65                  70                  75                  80

```
Gln Gln Arg Ser Leu Val Gly His Gln Arg Thr His Thr Gly Glu Lys
                85                  90                  95

Pro Tyr Lys Cys Pro Glu Cys Gly Lys Ser Phe Ser Asp Lys Lys Asp
            100                 105                 110

Leu Thr Arg His Gln Arg Thr His Thr Gly Glu Lys Pro Tyr Lys Cys
        115                 120                 125

Pro Glu Cys Gly Lys Ser Phe Ser Thr Ser Gly His Leu Val Arg His
    130                 135                 140

Gln Arg Thr His Thr Gly Glu Lys Pro Tyr Lys Cys Pro Glu Cys Gly
145                 150                 155                 160

Lys Ser Phe Ser Gln Arg Ala His Leu Glu Arg His Gln Arg Thr His
                165                 170                 175

Thr Gly Glu Lys Pro Tyr Lys Cys Pro Glu Cys Gly Lys Ser Phe Ser
            180                 185                 190

Thr Ser Gly Ser Leu Val Arg His Gln Arg Thr His Thr Gly Ala Ala
        195                 200                 205

Ala Arg Ala Leu Val Lys Ser Glu Leu Glu Glu Lys Lys Ser Glu Leu
    210                 215                 220

Arg His Lys Leu Lys Tyr Val Pro His Glu Tyr Ile Glu Leu Ile Glu
225                 230                 235                 240

Ile Ala Arg Asn Pro Thr Gln Asp Arg Ile Leu Glu Met Lys Val Met
                245                 250                 255

Glu Phe Phe Met Lys Val Tyr Gly Tyr Arg Gly Glu His Leu Gly Gly
            260                 265                 270

Ser Arg Lys Pro Asp Gly Ala Ile Tyr Thr Val Gly Ser Pro Ile Asp
        275                 280                 285

Tyr Gly Val Ile Val Asp Thr Lys Ala Tyr Ser Gly Gly Tyr Asn Leu
    290                 295                 300

Pro Ile Gly Gln Ala Asp Glu Met Gln Arg Tyr Val Lys Glu Asn Gln
305                 310                 315                 320

Thr Arg Asn Lys His Ile Asn Pro Asn Glu Trp Trp Lys Val Tyr Pro
                325                 330                 335

Ser Ser Val Thr Glu Phe Lys Phe Leu Phe Val Ser Gly His Phe Lys
            340                 345                 350

Gly Asn Tyr Lys Ala Gln Leu Thr Arg Leu Asn Arg Lys Thr Asn Cys
        355                 360                 365

Asn Gly Ala Val Leu Ser Val Glu Glu Leu Leu Ile Gly Gly Glu Met
    370                 375                 380

Ile Lys Ala Gly Thr Leu Thr Leu Glu Glu Val Arg Arg Lys Phe Asn
385                 390                 395                 400

Asn Gly Glu Ile Asn Phe
                405

<210> SEQ ID NO 451
<211> LENGTH: 378
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
```

```
            20                  25                  30
Gly Arg Leu Glu Pro Gly Glu Lys Pro Tyr Lys Cys Pro Glu Cys Gly
        35                  40                  45

Lys Ser Phe Ser Gln Arg Asn Ala Leu Ala Gly His Gln Arg Thr His
    50                  55                  60

Thr Gly Glu Lys Pro Tyr Lys Cys Pro Glu Cys Gly Lys Ser Phe Ser
65                  70                  75                  80

His Lys Asn Ala Leu Gln Asn His Gln Arg Thr His Thr Gly Glu Lys
                85                  90                  95

Pro Tyr Lys Cys Pro Glu Cys Gly Lys Ser Phe Ser Asp Pro Gly His
            100                 105                 110

Leu Val Arg His Gln Arg Thr His Thr Gly Glu Lys Pro Tyr Lys Cys
        115                 120                 125

Pro Glu Cys Gly Lys Ser Phe Ser Thr Ser Gly Asn Leu Val Arg His
    130                 135                 140

Gln Arg Thr His Thr Gly Glu Lys Pro Tyr Lys Cys Pro Glu Cys Gly
145                 150                 155                 160

Lys Ser Phe Ser Gln Ser Ser Asn Leu Val Arg His Gln Arg Thr His
                165                 170                 175

Thr Gly Ala Ala Ala Arg Ala Leu Val Lys Ser Glu Leu Glu Glu Lys
            180                 185                 190

Lys Ser Glu Leu Arg His Lys Leu Lys Tyr Val Pro His Glu Tyr Ile
        195                 200                 205

Glu Leu Ile Glu Ile Ala Arg Asn Pro Thr Gln Asp Arg Ile Leu Glu
    210                 215                 220

Met Lys Val Met Glu Phe Phe Met Lys Val Tyr Gly Tyr Arg Gly Glu
225                 230                 235                 240

His Leu Gly Gly Ser Arg Lys Pro Asp Gly Ala Ile Tyr Thr Val Gly
                245                 250                 255

Ser Pro Ile Asp Tyr Gly Val Ile Val Asp Thr Lys Ala Tyr Ser Gly
            260                 265                 270

Gly Tyr Asn Leu Pro Ile Gly Gln Ala Asp Glu Met Glu Arg Tyr Val
        275                 280                 285

Glu Glu Asn Gln Thr Arg Asp Lys His Leu Asn Pro Asn Glu Trp Trp
    290                 295                 300

Lys Val Tyr Pro Ser Ser Val Thr Glu Phe Lys Phe Leu Phe Val Ser
305                 310                 315                 320

Gly His Phe Lys Gly Asn Tyr Lys Ala Gln Leu Thr Arg Leu Asn His
                325                 330                 335

Ile Thr Asn Cys Asn Gly Ala Val Leu Ser Val Glu Glu Leu Leu Ile
            340                 345                 350

Gly Gly Glu Met Ile Lys Ala Gly Thr Leu Thr Leu Glu Glu Val Arg
        355                 360                 365

Arg Lys Phe Asn Asn Gly Glu Ile Asn Phe
    370                 375

<210> SEQ ID NO 452
<211> LENGTH: 378
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452
```

```
Met Asp Tyr Lys Asp His Asp Gly Asp Tyr Lys Asp His Asp Ile Asp
1               5                   10                  15
Tyr Lys Asp Asp Asp Lys Met Ala Pro Lys Lys Arg Lys Val
            20                  25                  30
Gly Arg Leu Glu Pro Gly Glu Lys Pro Tyr Lys Cys Pro Glu Cys Gly
        35                  40                  45
Lys Ser Phe Ser Gln Gln Arg Ser Leu Val Gly His Gln Arg Thr His
    50                  55                  60
Thr Gly Glu Lys Pro Tyr Lys Cys Pro Glu Cys Gly Lys Ser Phe Ser
65                  70                  75                  80
Asp Lys Lys Asp Leu Thr Arg His Gln Arg Thr His Thr Gly Glu Lys
                85                  90                  95
Pro Tyr Lys Cys Pro Glu Cys Gly Lys Ser Phe Ser Thr Ser Gly His
            100                 105                 110
Leu Val Arg His Gln Arg Thr His Thr Gly Glu Lys Pro Tyr Lys Cys
        115                 120                 125
Pro Glu Cys Gly Lys Ser Phe Ser Gln Arg Ala His Leu Glu Arg His
    130                 135                 140
Gln Arg Thr His Thr Gly Glu Lys Pro Tyr Lys Cys Pro Glu Cys Gly
145                 150                 155                 160
Lys Ser Phe Ser Thr Ser Gly Ser Leu Val Arg His Gln Arg Thr His
                165                 170                 175
Thr Gly Ala Ala Ala Arg Ala Leu Val Lys Ser Glu Leu Glu Glu Lys
            180                 185                 190
Lys Ser Glu Leu Arg His Lys Leu Lys Tyr Val Pro His Glu Tyr Ile
        195                 200                 205
Glu Leu Ile Glu Ile Ala Arg Asn Pro Thr Gln Asp Arg Ile Leu Glu
    210                 215                 220
Met Lys Val Met Glu Phe Phe Met Lys Val Tyr Gly Tyr Arg Gly Glu
225                 230                 235                 240
His Leu Gly Gly Ser Arg Lys Pro Asp Gly Ala Ile Tyr Thr Val Gly
                245                 250                 255
Ser Pro Ile Asp Tyr Gly Val Ile Val Asp Thr Lys Ala Tyr Ser Gly
        260                 265                 270
Gly Tyr Asn Leu Pro Ile Gly Gln Ala Asp Glu Met Gln Arg Tyr Val
    275                 280                 285
Lys Glu Asn Gln Thr Arg Asn Lys His Ile Asn Pro Asn Glu Trp Trp
        290                 295                 300
Lys Val Tyr Pro Ser Ser Val Thr Glu Phe Lys Phe Leu Phe Val Ser
305                 310                 315                 320
Gly His Phe Lys Gly Asn Tyr Lys Ala Gln Leu Thr Arg Leu Asn Arg
                325                 330                 335
Lys Thr Asn Cys Asn Gly Ala Val Leu Ser Val Glu Glu Leu Leu Ile
        340                 345                 350
Gly Gly Glu Met Ile Lys Ala Gly Thr Leu Thr Leu Glu Glu Val Arg
    355                 360                 365
Arg Lys Phe Asn Asn Gly Glu Ile Asn Phe
    370                 375

<210> SEQ ID NO 453
<211> LENGTH: 26
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (26)..(26)
<223> OTHER INFORMATION: May or may not be present

<400> SEQUENCE: 453
tgccatcttc cttgatgttg gaggta                                    26

<210> SEQ ID NO 454
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Arg Leu Glu Pro Gly Glu Arg Pro Phe Gln Cys Arg Ile Cys Met
        35                  40                  45

Arg Asn Phe Ser Ser Pro Ser Lys Leu Ala Arg His Thr Arg Thr His
    50                  55                  60

Thr Gly Glu Lys Pro Phe Gln Cys Arg Ile Cys Met Arg Asn Phe Ser
65                  70                  75                  80

Val Arg His Asn Leu Thr Arg His Leu Arg Thr His Thr Gly Glu Lys
                85                  90                  95

Pro Phe Gln Cys Arg Ile Cys Met Arg Asn Phe Ser Gln Arg Asn Asn
            100                 105                 110

Leu Gly Arg His Leu Lys Thr His Thr Gly Ala Ala Ala Arg Ala Leu
        115                 120                 125

Val Lys Ser Glu Leu Glu Glu Lys Lys Ser Glu Leu Arg His Lys Leu
    130                 135                 140

Lys Tyr Val Pro His Glu Tyr Ile Glu Leu Ile Glu Ile Ala Arg Asn
145                 150                 155                 160

Pro Thr Gln Asp Arg Ile Leu Glu Met Lys Val Met Glu Phe Phe Met
                165                 170                 175

Lys Val Tyr Gly Tyr Arg Gly Glu His Leu Gly Gly Ser Arg Lys Pro
            180                 185                 190

Asp Gly Ala Ile Tyr Thr Val Gly Ser Pro Ile Asp Tyr Gly Val Ile
        195                 200                 205

Val Asp Thr Lys Ala Tyr Ser Gly Gly Tyr Asn Leu Pro Ile Gly Gln
    210                 215                 220

Ala Asp Glu Met Gln Arg Tyr Val Lys Glu Asn Gln Thr Arg Asn Lys
225                 230                 235                 240

His Ile Asn Pro Asn Glu Trp Trp Lys Val Tyr Pro Ser Ser Val Thr
                245                 250                 255

Glu Phe Lys Phe Leu Phe Val Ser Gly His Phe Lys Gly Asn Tyr Lys
            260                 265                 270

Ala Gln Leu Thr Arg Leu Asn Arg Lys Thr Asn Cys Asn Gly Ala Val
        275                 280                 285

Leu Ser Val Glu Glu Leu Leu Ile Gly Gly Glu Met Ile Lys Ala Gly
290                 295                 300

Thr Leu Thr Leu Glu Glu Val Arg Arg Lys Phe Asn Asn Gly Glu Ile
305                 310                 315                 320

Asn Phe

<210> SEQ ID NO 455
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Gly Arg Leu Glu Pro Gly Glu Arg Pro Phe Gln Cys Arg Ile Cys Met
            35                  40                  45

Arg Asn Phe Ser Ile Pro Asn His Leu Ala Arg His Thr Arg Thr His
50                  55                  60

Thr Gly Glu Lys Pro Phe Gln Cys Arg Ile Cys Met Arg Asn Phe Ser
65                  70                  75                  80

Gln Ser Ala His Leu Lys Arg His Leu Arg Thr His Thr Gly Glu Lys
                85                  90                  95

Pro Phe Gln Cys Arg Ile Cys Met Arg Asn Phe Ser His His Asn Ser
            100                 105                 110

Leu Thr Arg His Leu Lys Thr His Thr Gly Ala Ala Ala Arg Ala Leu
        115                 120                 125

Val Lys Ser Glu Leu Glu Glu Lys Lys Ser Glu Leu Arg His Lys Leu
130                 135                 140

Lys Tyr Val Pro His Glu Tyr Ile Glu Leu Ile Glu Ile Ala Arg Asn
145                 150                 155                 160

Pro Thr Gln Asp Arg Ile Leu Glu Met Lys Val Met Glu Phe Phe Met
                165                 170                 175

Lys Val Tyr Gly Tyr Arg Gly Glu His Leu Gly Gly Ser Arg Lys Pro
            180                 185                 190

Asp Gly Ala Ile Tyr Thr Val Gly Ser Pro Ile Asp Tyr Gly Val Ile
        195                 200                 205

Val Asp Thr Lys Ala Tyr Ser Gly Gly Tyr Asn Leu Pro Ile Gly Gln
210                 215                 220

Ala Asp Glu Met Glu Arg Tyr Val Glu Glu Asn Gln Thr Arg Asp Lys
225                 230                 235                 240

His Leu Asn Pro Asn Glu Trp Trp Lys Val Tyr Pro Ser Ser Val Thr
                245                 250                 255

Glu Phe Lys Phe Leu Phe Val Ser Gly His Phe Lys Gly Asn Tyr Lys
            260                 265                 270

Ala Gln Leu Thr Arg Leu Asn His Ile Thr Asn Cys Asn Gly Ala Val
        275                 280                 285

Leu Ser Val Glu Glu Leu Leu Ile Gly Gly Glu Met Ile Lys Ala Gly
290                 295                 300

Thr Leu Thr Leu Glu Glu Val Arg Arg Lys Phe Asn Asn Gly Glu Ile
305                 310                 315                 320

Asn Phe

<210> SEQ ID NO 456
<211> LENGTH: 6626
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 456

| | | | | | |
|---|---|---|---|---|---|
| gggggggggg | ggggggggtt | ggccactccc | tctctgcgcg | ctcgctcgct | cactgaggcc | 60 |
| gggcgaccaa | aggtcgcccg | acgcccgggc | tttgcccggg | cggcctcagt | gagcgagcga | 120 |
| gcgcgcagag | agggagtggc | caactccatc | actaggggtt | cctagatctg | aattcggtac | 180 |
| ccgttacata | acttacggta | aatggcccgc | ctggctgacc | gcccaacgac | ccccgcccat | 240 |
| tgacgtcaat | aatgacgtat | gttcccatag | taacgccaat | agggactttc | cattgacgtc | 300 |
| aatgggtgga | gtatttacgg | taaactgccc | acttggcagt | acatcaagtg | tatcatatgc | 360 |
| caagtacgcc | ccctattgac | gtcaatgacg | gtaaatggcc | cgcctggcat | tatgcccagt | 420 |
| acatgacctt | atgggacttt | cctacttggc | agtacatcta | cgtattagtc | atcgctatta | 480 |
| ccatggtgat | gcggttttgg | cagtacatca | atgggcgtgg | atagcggttt | gactcacggg | 540 |
| gatttccaag | tctccacccc | attgacgtca | atgggagttt | gttttggcac | caaaatcaac | 600 |
| gggactttcc | aaaatgtcgt | aacaactccg | ccccattgac | gcaaatgggc | ggtaggcgtg | 660 |
| tacggtggga | ggtctatata | agcagagctc | gtttagtgaa | ccgtcagatc | gcctggagac | 720 |
| gccatccacg | ctgttttgac | ctccatagaa | gacaccggga | ccgatccagc | ctccggactc | 780 |
| tagaggatcc | ggtactcgag | gaactgaaaa | accagaaagt | taactggtaa | gtttagtctt | 840 |
| tttgtctttt | atttcaggtc | ccggatccgg | tggtggtgca | aatcaaagaa | ctgctcctca | 900 |
| gtggatgttg | cctttacttc | taggcctgta | cggaagtgtt | acttctgctc | taaaagctgc | 960 |
| ggaattgtac | ccgcggcccg | ggatccaccg | gtggctagcg | tctataggcc | cacccccttg | 1020 |
| gtggaattcg | ccatgaggtc | tgactacaaa | gaccatgacg | gtgattataa | agatcatgac | 1080 |
| atcgattaca | aggatgacga | tgacaagatg | gcccccaaga | agaagaggaa | ggtgggcctc | 1140 |
| gagcccggag | aaaaaccgta | caagtgccct | gagtgcggga | aatcattctc | cgaccctggg | 1200 |
| gcgctcgtcc | ggcaccaaag | gacgcataca | ggggaaaagc | cgtataagtg | ccccgagtgt | 1260 |
| ggaaagagct | tctcgcagag | agcccacctt | gaacgacacc | aaagaacaca | cactggtgag | 1320 |
| aaaccctata | agtgtccaga | gtgcggcaaa | tcgtttagca | gatccgatga | cttggtgcgc | 1380 |
| caccagcgga | cacacacggg | tgaaaagccc | tacaaatgcc | cggagtgtgg | aagtcgttt | 1440 |
| tcaaggtcgg | atcatctgac | tacccatcag | cgcacccata | cggagcggc | cgcccgcgcc | 1500 |
| ctggtgaaga | gcgagctgga | ggagaagaag | tccgagctgc | ggcacaagct | gaagtacgtg | 1560 |
| ccccacgagt | acatcgagct | gatcgagatc | gccaggaacc | ccacccagga | ccgcatcctg | 1620 |
| gagatgaagg | tgatggagtt | cttcatgaag | gtgtacggct | acaggggaga | gcacctgggc | 1680 |
| ggaagcagaa | agcctgacgg | cgccatctat | acagtgggca | gccccatcga | ttacggcgtg | 1740 |
| atcgtggaca | caaaggccta | cagcggcggc | tacaatctgc | ctatcggcca | ggccgacgag | 1800 |
| atgcagagat | acgtgaagga | gaaccagacc | cggaataagc | acatcaaccc | caacgagtgg | 1860 |
| tggaaggtgt | accctagcag | cgtgaccgag | ttcaagttcc | tgttcgtgag | cggccacttc | 1920 |
| aagggcaact | acaaggccca | gctgaccagg | ctgaaccgca | aaaccaactg | caatggcgcc | 1980 |

```
gtgctgagcg tggaggagct gctgatcggc ggcgagatga tcaaagccgg caccctgaca    2040
ctggaggagg tgcggcgcaa gttcaacaac ggcgagatca acttcgaggg cagaggaagt    2100
cttctaacat gcggtgacgt ggaggagaat cccggcccta gatctgacta caaagaccat    2160
gacggtgatt ataaagatca tgacatcgat tacaaggatg acgatgacaa gatggccccc    2220
aagaagaaga ggaaggtggg cctcgagccg ggagagaagc cgtacaagtg tcccgaatgt    2280
ggaaagagct tctcacagtc gggggacctt cggcgccacc agcgcacaca tactggtgaa    2340
aagccgtata agtgtccaga atgtggcaaa tcattctcca catcagggag cctggtcagg    2400
caccagcgaa cccacacggg tgagaagccc tataagtgcc ccgaatgcgg gaagtccttt    2460
tcgcagagag cccacttgga gaggcaccag aggacccata cggggagaa accttacaag     2520 tgccctgaat gcggaaagtc gttctcgacc catctggatc tcatcagaca tcagagaacg    2580
cacactggag agaaacccta caaatgtccc gagtgtggga agtcgtttag ccgaaaggac    2640
aatctcaaaa accatcaacg gacacacacg ggtgaaaaac catacaaatg cccggagtgc    2700
ggcaaatcgt tttcccaact tgcgcacttg cgggcacacc aacgcacgca tactggagcg    2760
gccgcccgcg ccctggtgaa gagcgagctg gaggagaaga gtccgagct gcggcacaag    2820 ctgaagtacg tgccccacga gtacatcgag ctgatcgaga tcgccaggaa ccccacccag    2880
gaccgcatcc tggagatgaa ggtgatggag ttcttcatga aggtgtacgg ctacagggga    2940
gagcacctgg gcgaagcag aaagcctgac ggcgccatct atacagtggg cagccccatc    3000
gattacggcg tgatcgtgga cacaaaggcc tacagcggcg gctacaatct gcctatcggc    3060
caggccgaca gatggagag atacgtggag gagaaccaga cacgggataa gcacctcaac    3120
cccaacgagt ggtggaaggt gtaccctagc agcgtgaccg agttcaagtt cctgttcgtg    3180
agcggccact tcaagggcaa ctacaaggcc cagctgacca ggctgaacca catcaccaac    3240
tgcaatggcg ccgtgctgag cgtggaggag ctgctgatcg gcggcgagat gatcaaagcc    3300
ggcaccctga cactggagga ggtgcggcgc aagttcaaca acggcgagat caacttctga    3360
ttaattaact aatctagagt cgactagagc tcgctgatca gcctcgactg tgccttctag    3420
ttgccagcca tctgttgttt gcccctcccc cgtgccttcc ttgaccctgg aaggtgccac    3480
tcccactgtc ctttcctaat aaaatgagga aattgcatcg cattgtctga gtaggtgtca    3540
ttctattctg gggggtgggg tgggcagga cagcaagggg gaggattggg aagacaatag    3600
caggcatgct ggggagagat ctaggaaccc ctagtgatgg agttggccac tccctctctg    3660
cgcgctcgct cgctcactga ggccgcccgg gcaaagcccg ggcgtcgggc gacctttggt    3720
cgcccggcct cagtgagcga gcgagcgcgc agagagggag tggccaaccc cccccccccc    3780 cccctgcag cccagctgca ttaatgaatc ggccaacgcg cggggagagg cggtttgcgt    3840
attgggcgct cttccgcttc ctcgctcact gactcgctgc gctcggtcgt tcggctgcgg    3900
cgagcggtat cagctcactc aaaggcggta atacggttat ccacagaatc aggggataac    3960
gcaggaaaga acatgtgagc aaaaggccag caaaaggcca ggaaccgtaa aaaggccgcg    4020
ttgctggcgt ttttccatag gctccgcccc cctgacgagc atcacaaaaa tcgacgctca    4080
agtcagaggt ggcgaaaccc gacaggacta taaagatacc aggcgtttcc ccctggaagc    4140
tccctcgtgc gctctcctgt tccgaccctg ccgcttaccg gatacctgtc cgcctttctc    4200
ccttcgggaa gcgtggcgct ttctcaatgc tcacgctgta ggtatctcag ttcggtgtag    4260
gtcgttcgct ccaagctggg ctgtgtgcac gaaccccccg ttcagcccga ccgctgcgcc    4320
ttatccggta actatcgtct tgagtccaac ccggtaagac acgacttatc gccactggca    4380
```

```
gcagccactg gtaacaggat tagcagagcg aggtatgtag gcggtgctac agagttcttg    4440
aagtggtggc ctaactacgg ctacactaga aggacagtat ttggtatctg cgctctgctg    4500
aagccagtta ccttcggaaa aagagttggt agctcttgat ccggcaaaca aaccaccgct    4560
ggtagcggtg gttttttgt ttgcaagcag cagattacgc gcagaaaaaa aggatctcaa    4620
gaagatcctt tgatcttttc tacggggtct gacgctcagt ggaacgaaaa ctcacgttaa    4680
gggattttgg tcatgagatt atcaaaaagg atcttcacct agatcctttt aaattaaaaa    4740
tgaagtttta aatcaatcta agtatatat gagtaaactt ggtctgacag ttaccaatgc    4800
ttaatcagtg aggcacctat ctcagcgatc tgtctatttc gttcatccat agttgcctga    4860
ctccccgtcg tgtagataac tacgatacgg gagggcttac catctggccc cagtgctgca    4920
atgataccgc gagacccacg ctcaccggct ccagatttat cagcaataaa ccagccagcc    4980
ggaagggccg agcgcagaag tggtcctgca actttatccg cctccatcca gtctattaat    5040
tgttgccggg aagctagagt aagtagttcg ccagttaata gtttgcgcaa cgttgttgcc    5100
attgctacag gcatcgtggt gtcacgctcg tcgtttggta tggcttcatt cagctccggt    5160
tcccaacgat caaggcgagt tacatgatcc cccatgttgt gcaaaaaagc ggttagctcc    5220
ttcggtcctc cgatcgttgt cagaagtaag ttggccgcag tgttatcact catggttatg    5280
gcagcactgc ataattctct tactgtcatg ccatccgtaa gatgcttttc tgtgactggt    5340
gagtactcaa ccaagtcatt ctgagaatag tgtatgcggc gaccgagttg ctcttgcccg    5400
gcgtcaatac gggataatac cgcgccacat agcagaactt taaaagtgct catcattgga    5460
aaacgttctt cggggcgaaa actctcaagg atcttaccgc tgttgagatc cagttcgatg    5520
taacccactc gtgcacccaa ctgatcttca gcatctttta ctttcaccag cgtttctggg    5580
tgagcaaaaa caggaaggca aaatgccgca aaaaagggaa taagggcgac acggaaatgt    5640
tgaatactca tactcttcct ttttcaatat tattgaagca tttatcaggg ttattgtctc    5700
atgagcggat acatatttga atgtatttag aaaaataaac aaatagggt tccgcgcaca    5760 tttccccgaa aagtgccacc tgacgtctaa gaaaccatta ttatcatgac attaacctat    5820 aaaaatagc gtatcacgag gccctttcgt ctcgcgcgtt tcggtgatga cggtgaaaac    5880
ctctgacaca tgcagctccc ggagacggtc acagcttgtc tgtaagcgga tgccgggagc    5940
agacaagccc gtcagggcgc gtcagcgggt gttggcgggt gtcggggctg gcttaactat    6000
gcggcatcag agcagattgt actgagagtg caccatatgc ggtgtgaaat accgcacaga    6060
tgcgtaagga gaaaataccg catcaggaaa ttgtaaacgt taatattttg ttaaaattcg    6120
cgttaaattt ttgttaaatc agctcatttt ttaaccaata ggccgaaatc ggcaaaatcc    6180
cttataaatc aaaagaatag accgagatag ggttgagtgt tgttccagtt tggaacaaga    6240
gtccactatt aaagaacgtg gactccaacg tcaaagggcg aaaaaccgtc tatcagggcg    6300
atggcccact acgtgaacca tcaccctaat caagttttt ggggtcgagg tgccgtaaag    6360
cactaaatcg gaaccctaaa gggagccccc gatttagagc ttgacgggga agccggcga    6420 acgtggcgag aaaggaaggg aagaaagcga aggagcgggc gctagggcg ctggcaagtg    6480 tagcggtcac gctgcgcgta accaccacac ccgccgcgct taatgcgccg ctacagggcg    6540
cgtcgcgcca ttcgccattc aggctacgca actgttggga agggcgatcg gtgcgggcct    6600
cttcgctatt acgccagctg gctgca                                        6626
```

<210> SEQ ID NO 457

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 457
gagaggttat gtggctttac ca                                              22

<210> SEQ ID NO 458
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 458
ctgcgtagtg ccaaaacaaa                                                 20

<210> SEQ ID NO 459
<211> LENGTH: 3252
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 459
atgaaaagga actacattct ggggctggac atcgggatta caagcgtggg gtatgggatt      60
attgactatg aaacaaggga cgtgatcgac gcaggcgtca gactgttcaa ggaggccaac     120
gtggaaaaca atgagggacg gagaagcaag aggggagcca ggcgcctgaa acgacggaga     180
aggcacagaa tccagagggt gaagaaactg ctgttcgatt acaacctgct gaccgaccat     240
tctgagctga gtggaattaa tccttatgaa gccagggtga aaggcctgag tcagaagctg     300
tcagaggaag agttttccgc agctctgctg cacctggcta agcgccgagg agtgcataac     360
gtcaatgagg tggaagagga caccggcaac gagctgtcta caaggaaca  gatctcacgc     420 aatagcaaag ctctggaaga agtatgtc  gcagagctgc agctggaacg gctgaagaaa     480
gatggcgagg tgagagggtc aattaatagg ttcaagacaa gcgactacgt caaagaagcc     540
aagcagctgc tgaaagtgca gaaggcttac caccagctgg atcagagctt catcgatact     600
tatatcgacc tgctggagac tcggagaacc tactatgagg gaccaggaga agggagcccc     660
ttcggatgga agacatcaa  ggaatggtac gagatgctga tgggacattg cacctatttt     720
ccagaagagc tgagaagcgt caagtacgct tataacgcag atctgtacaa cgccctgaat     780
gacctgaaca acctggtcat caccaggga  tgaaaacgaga actggaata ctatgagaag     840 ttccagatca tcgaaaacgt gtttaagcag aagaaaagc ctacactgaa acagattgct     900
aaggagatcc tggtcaacga agaggacatc aagggctacc gggtgacaag cactggaaaa     960
ccagagttca ccaatctgaa agtgtatcac gatattaagg acatcacagc acggaaagaa    1020
atcattgaga cgccgaact  gctggatcag attgctaaga tcctgactat ctaccagagc    1080
tccgaggaca tccaggaaga gctgactaac ctgaacagcg agctgaccca ggaagagatc    1140
gaacagatta gtaatctgaa ggggtacacc ggaacacaca acctgtccct gaaagctatc    1200
aatctgattc tggatgagct gtggcataca aacgacaatc agattgcaat ctttaaccgg    1260
ctgaagctgg tcccaaaaaa ggtggacctg agtcagcaga agagatccc  aaccacactg    1320
```

| | |
|---|---|
| gtggacgatt tcattctgtc acccgtggtc aagcggagct tcatccagag catcaaagtg | 1380 |
| atcaacgcca tcatcaagaa gtacggcctg cccaatgata tcattatcga gctggctagg | 1440 |
| gagaagaaca gcaaggacgc acagaagatg atcaatgaga tgcagaaacg aaaccggcag | 1500 |
| accaatgaac gcattgaaga gattatccga actaccggga agagaacgc aaagtacctg | 1560 |
| attgaaaaaa tcaagctgca cgatatgcag gagggaaagt gtctgtattc tctggaggcc | 1620 |
| atcccctgg aggacctgct gaacaatcca ttcaactacg aggtcgatca tattatcccc | 1680 |
| agaagcgtgt ccttcgacaa ttcctttaac aacaaggtgc tggtcaagca ggaagagaac | 1740 |
| tctaaaaagg gcaataggac tccttttccag tacctgtcta gttcagattc caagatctct | 1800 |
| tacgaaacct ttaaaaagca cattctgaat ctggccaaag gaaagggccg catcagcaag | 1860 |
| accaaaaagg agtacctgct ggaagagcgg gacatcaaca gattctccgt ccagaaggat | 1920 |
| tttattaacc ggaatctggt ggacacaaga tacgctactc gcggcctgat gaatctgctg | 1980 |
| cgatcctatt tccgggtgaa caatctggat gtgaaagtca gtccatcaa cggcgggttc | 2040 |
| acatctttc tgaggcgcaa atggaagttt aaaaaggagc gcaacaaagg gtacaagcac | 2100 |
| catgccgaag atgctctgat tatcgcaaat gccgacttca tctttaagga gtggaaaaag | 2160 |
| ctggacaaag ccaagaaagt gatggagaac cagatgttcg aagagaagca ggccgaatct | 2220 |
| atgcccgaaa tcgagacaga acaggagtac aaggagattt tcatcactcc tcaccagatc | 2280 |
| aagcatatca aggatttcaa ggactacaag tactctcacc gggtggataa aaagcccaac | 2340 |
| agagagctga tcaatgacac cctgtatagt acaagaaaag acgataaggg gaataccctg | 2400 |
| attgtgaaca atctgaacgg actgtacgac aaagataatg acaagctgaa aaagctgatc | 2460 |
| aacaaaagtc ccgagaagct gctgatgtac caccatgatc ctcagacata tcagaaactg | 2520 |
| aagctgatta tggagcagta cggcgacgag aagaacccac tgtataagta ctatgaagag | 2580 |
| actgggaact acctgaccaa gtatagcaaa aaggataatg cccccgtgat caagaagatc | 2640 |
| aagtactatg gaacaagct gaatgcccat ctggacatca cagacgatta ccctaacagt | 2700 |
| cgcaacaagg tggtcaagct gtcactgaag ccatacagat tcgatgtcta tctggacaac | 2760 |
| ggcgtgtata aatttgtgac tgtcaagaat ctggatgtca tcaaaaagga gaactactat | 2820 |
| gaagtgaata gcaagtgcta cgaagaggct aaaaagctga aaaagattag caaccaggca | 2880 |
| gagttcatcg cctccttta caacaacgac ctgattaaga tcaatggcga actgtatagg | 2940 |
| gtcatcgggg tgaacaatga tctgctgaac cgcattgaag tgaatatgat tgacatcact | 3000 |
| taccgagagt atctggaaaa catgaatgat aagcgccccc ctcgaattat caaaacaatt | 3060 |
| gcctctaaga ctcagagtat caaaaagtac tcaaccgaca ttctgggaaa cctgtatgag | 3120 |
| gtgaagagca aaaagcaccc tcagattatc aaaaagggca gcggaggcaa gcgtcctgct | 3180 |
| gctactaaga agctggtca gctaagaaa agaaaggat cctacccata cgatgttcca | 3240 |
| gattacgctt aa | 3252 |

<210> SEQ ID NO 460
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 460
gttttagtac tctggaaaca gaatctacta aaacaaggca aaatgccgtg tttatctcgt      60
caacttgttg gcgagatttt ttt                                            83

<210> SEQ ID NO 461
<211> LENGTH: 3333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 461

```
atggtgccta agaagaagag aaaggtggct gccttcaaac ctaattcaat caactacatc      60
ctcggcctcg atatcggcat cgcatccgtc ggctgggcga tggtagaaat tgacgaagaa     120
gaaaacccca tccgcctgat tgatttgggc gtgcgcgtat ttgagcgtgc cgaagtaccg     180
aaaacaggcg actcccttgc catggcaagg cgtttggcgc gcagtgttcg ccgcctgacc     240
cgccgtcgcg cccaccgcct gcttcggacc cgccgcctat tgaaacgcga aggcgtatta     300
caagccgcca attttgacga aaacggcttg attaaatcct taccgaatac accatggcaa     360
cttcgcgcag ccgcattaga ccgcaaactg acgcctttag agtggtcggc agtcttgttg     420
catttaatca acatcgcgg ctatttatcg caacggaaaa acgagggcga aactgccgat     480
aaggagcttg gcgctttgct taaaggcgta gccggcaatg cccatgcctt acagacaggc     540
gatttccgca caccggccga attggcttta aataaatttg agaaagaaag cggccatatc     600
cgcaatcagc gcagcgatta ttcgcatacg ttcagccgca agatttaca ggcggagctg      660
attttgctgt ttgaaaaaca aaaagaattt ggcaatccgc atgtttcagg cggccttaaa     720
gaaggtattg aaaccctact gatgacgcaa cgccctgccc tgtccggcga tgccgttcaa     780
aaaatgttgg gcattgcac cttcgaaccg gcagagccga agccgctaa aaacacctac      840
acagccgaac gtttcatctg gctgaccaag ctgaacaacc tgcgtatttt agagcaaggc     900
agcgagcggc cattgaccga taccgaacgc gccacgctta tggacgagcc atacagaaaa     960
tccaaactga cttacgcaca agcccgtaag ctgctgggtt tagaagatac cgccttttc    1020
aaaggcttgc gctatggtaa agacaatgcc gaagcctcaa cattgatgga atgaaggcc    1080
taccatgcca tcagccgtgc actggaaaaa gaaggattga agacaaaaa atccccatta    1140
aacctttctc ccgaattaca agacgaaatc ggcacggcat tctccctgtt caaaaccgat    1200
gaagacatta caggccgtct gaaagaccgt atacagcccg aaatcttaga agcgctgttg    1260
aaacacatca gcttcgataa gttcgtccaa atttccttga agcattgcg ccgaattgtg    1320
cctctaatgg aacaaggcaa acgttacgat gaagcctgcg ccgaaatcta cggagaccat    1380
tacggcaaga gaatacgga agaaaagatt tatctgccgc cgattccgc cgacgaaatc    1440
cgcaaccccg tcgtcttgcg cgccttatct caagcacgta aggtcattaa cggcgtggta    1500
cgccgttacg gctccccagc tcgtatccat attgaaactg caagggaagt aggtaaatcg    1560
tttaaagacc gcaaagaaat tgagaaacgc aagaagaaa accgcaaaga ccgggaaaaa    1620
gccgccgcca aattccgaga gtatttcccc aattttgtcg agaacccaa atccaaagat    1680
attctgaaac tgcgcctgta cgagcaacaa cacggcaaat gcctgtattc gggcaaagaa    1740
atcaacttag gccgtctgaa cgaaaaaggc tatgtcgaaa tcgaccatgc cctgccgttc    1800
tcgcgcacat gggacgacag tttcaacaat aaagtactgg tattgggcag cgaaaaccaa    1860
aacaaaggca atcaaacccc ttacgaatac ttcaacggca agacaacag ccgcgaatgg    1920
caggaattta agcgcgtgt cgaaaccagc cgtttcccgc gcagtaaaaa acaacggatt    1980
```

```
ctgctgcaaa aattcgatga agacggcttt aaagaacgca atctgaacga cacgcgctac    2040
gtcaaccgtt tcctgtgtca atttgttgcc gaccgtatgc ggctgacagg taaaggcaag    2100
aaacgtgtct ttgcatccaa cggacaaatt accaatctgt tgcgcggctt ttggggattg    2160
cgcaaagtgc gtgcggaaaa cgaccgccat cacgccttgg acgccgtcgt cgttgcctgc    2220
tcgaccgttg ccatgcagca gaaaattacc cgttttgtac gctataaaga gatgaacgcg    2280
tttgacggta aaaccataga caaagaaaca ggagaagtgc tgcatcaaaa aacacacttc    2340
ccacaacctt gggaatttt cgcacaagaa gtcatgattc gcgtcttcgg caaaccggac    2400
ggcaaacccg aattcgaaga agccgatacc ctagaaaaac tgcgcacgtt gcttgccgaa    2460
aaattatcat ctcgccccga agccgtacac gaatacgtta cgccactgtt tgtttcacgc    2520
gcgcccaatc ggaagatgag cgggcaaggg catatggaga ccgtcaaatc cgccaaacga    2580
ctggacgaag gcgtcagcgt gttgcgcgta ccgctgacac agttaaaact gaaagacttg    2640
gaaaaaatgg tcaatcggga gcgcgaacct aagctatacg aagcactgaa agcacggctg    2700
gaagcacata aagacgatcc tgccaaagcc tttgccgagc cgttttacaa atacgataaa    2760
gcaggcaacc gcacccaaca ggtaaaagcc gtacgcgtag agcaagtaca gaaaaccggc    2820
gtatgggtgc gcaaccataa cggtattgcc gacaacgcaa ccatggtgcg cgtagatgtg    2880
tttgagaaag gcgacaagta ttatctggta ccgatttaca gttggcaggt agcgaaaggg    2940
attttgccgg ataggggctgt tgtacaagga aaagatgaag aagattggca acttattgat    3000
gatagtttca actttaaatt ctcattacac cctaatgatt tagtcgaggt tataacaaaa    3060
aaagctagaa tgtttggtta ctttgccagc tgccatcgag gcacaggtaa tatcaatata    3120
cgcattcatg atcttgatca taaaattggc aaaaatggaa tactggaagg tatcggcgtc    3180
aaaaccgccc tttcattcca aaaataccaa attgacgaac tgggcaaaga aatcagacca    3240
tgccgtctga aaaacgccc gcctgtccgt tacccatacg atgttccaga ttacgctgca    3300
gctccagcag cgaagaaaaa gaagctggat taa                                 3333
```

<210> SEQ ID NO 462
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 462

```
gttgtagctc cctttctcat ttcggaaacg aaatgagaac cgttgctaca ataaggccgt     60
ctgaaaagat gtgccgcaac gctctgcccc ttaaagcttc tgctttaagg ggcttttttt    120
```

<210> SEQ ID NO 463
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 463

```
gttgtagctc cctttctcat ttcgcagtgc tacaatgaaa attgtcgcac tgcgaaatga     60
gaaccgttgc tacaataagg ccgtctgaaa agatgtgccg caacgctctg cccttaaag    120 cttctgcttt aaggggcttt tttt                                           144
```

```
<210> SEQ ID NO 464
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 464
tcgggtttat tacagggaca gcag                                              24

<210> SEQ ID NO 465
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 465
tctaaggccg agtcttatga gcag                                              24

<210> SEQ ID NO 466
<211> LENGTH: 4564
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 466
atggactaca aagaccatga cggtgattat aaagatcatg acatcgatta caaggatgac      60
gatgacaaga tggcccccaa gaagaagagg aaggtgggcc gcggaatgga caagaagtac     120
tccattgggc tcgccatcgg cacaaacagc gtcggctggg ccgtcattac ggacgagtac     180
aaggtgccga gcaaaaaatt caaagttctg ggcaataccg atcgccacag cataaagaag     240
aacctcattg gcgccctcct gttcgactcc ggggaaaccg ccgaagccac gcggctcaaa     300
agaacagcac ggcgcagata tacccgcaga aagaatcgga tctgctacct gcaggagatc     360
tttagtaatg agatggctaa ggtggatgac tctttcttcc ataggctgga ggagtccttt     420
ttggtggagg aggataaaaa gcacgagcgc cacccaatct ttggcaatat cgtggacgag     480
gtggcgtacc atgaaaagta cccaaccata tatcatctga ggaagaagct tgtagacagt     540
actgataagg ctgacttgcg gttgatctat ctcgcgctgg cgcatatgat caaatttcgg     600
ggacacttcc tcatcgaggg ggacctgaac ccagacaaca gcgatgtcga caaactcttt     660
atccaactgg ttcagactta caatcagctt ttcgaagaga cccgatcaa cgcatccgga     720 gttgacgcca agcaatcct gagcgctagg ctgtccaaat cccggcggct cgaaaacctc     780
atcgcacagc tccctgggga agaagaac ggcctgtttg gtaatcttat cgccctgtca     840
ctcgggctga cccccaactt taaatctaac ttcgacctgg ccgaagatgc caagcttcaa     900
ctgagcaaag acacctacga tgatgatctc gacaatctgc tggcccagat cggcgaccag     960
tacgcagacc ttttttggc ggcaaagaac ctgtcagacg ccattctgct gagtgatatt    1020
ctgcgagtga acacggagat caccaaagct ccgctgagcg ctagtatgat caagcgctat    1080
gatgagcacc accaagactt gactttgctg aaggcccttg tcagacagca actgcctgag    1140
aagtacaagg aaattttctt cgatcagtct aaaaatggct acgccggata cattgacggc    1200
ggagcaagcc aggaggaatt ttacaaattt attaagccca tcttggaaaa aatggacggc    1260
accgaggagc tgctggtaaa gcttaacaga gaagatctgt tgcgcaaaca gcgcactttc    1320
```

-continued

```
gacaatggaa gcatccccca ccagattcac ctgggcgaac tgcacgctat cctcaggcgg    1380
caagaggatt tctaccccct tttgaaagat aacaggaaa  agattgagaa aatcctcaca    1440
tttcggatac cctactatgt aggccccctc gcccggggaa attccagatt cgcgtggatg    1500
actcgcaaat cagaagagac catcactccc tggaacttcg aggaagtcgt ggataagggg    1560
gcctctgccc agtccttcat cgaaaggatg actaactttg ataaaaatct gcctaacgaa    1620
aaggtgcttc ctaaacactc tctgctgtac gagtacttca cagtttataa cgagctcacc    1680
aaggtcaaat acgtcacaga agggatgaga aagccagcat tcctgtctgg agagcagaag    1740
aaagctatcg tggacctcct cttcaagacg aaccggaaag ttaccgtgaa acagctcaaa    1800
gaagactatt tcaaaaagat tgaatgtttc gactctgttg aaatcagcgg agtggaggat    1860
cgcttcaacg catccctggg aacgtatcac gatctcctga aaatcattaa agacaaggac    1920
ttcctggaca atgaggagaa cgaggacatt cttgaggaca ttgtcctcac ccttacgttg    1980
tttgaagata gggagatgat tgaagaacgc ttgaaaactt acgctcatct cttcgacgac    2040
aaagtcatga acagctcaa  gaggcgccga tatacaggat gggggcggct gtcaagaaaa    2100
ctgatcaatg ggatccgaga caagcagagt ggaaagacaa tcctggattt tcttaagtcc    2160
gatggatttg ccaaccggaa cttcatgcag ttgatccatg atgactctct cacctttaag    2220
gaggacatcc agaaagcaca agtttctggc caggggaca  gtcttcacga gcacatcgct    2280
aatcttgcag gtagcccagc tatcaaaaag gaatactgc  agaccgttaa ggtcgtggat    2340
gaactcgtca agtaatggg  aaggcataag cccgagaata tcgttatcga gatggcccga    2400
gagaaccaaa ctacccagaa gggacagaag aacagtaggg aaaggatgaa gaggattgaa    2460
gagggtataa aagaactggg gtcccaaatc cttaaggaac acccagttga aaacacccag    2520
cttcagaatg agaagctcta cctgtactac ctgcagaacg gcagggacat gtacgtggat    2580
caggaactgg acatcaatcg gctctccgac tacgacgtgg atgccatcgt gccccagtct    2640
tttctcaaag atgattctat tgataataaa gtgttgacaa gatccgataa aaatagaggg    2700
aagagtgata acgtcccctc agaagaagtt gtcaagaaaa tgaaaaatta ttggcggcag    2760
ctgctgaacg ccaaactgat cacacaacgg aagttcgata tctgactaa  ggctgaacga    2820 ggtggcctgt ctgagttgga taaagccggc ttcatcaaaa ggcagcttgt tgagacacgc    2880
cagatcacca agcacgtggc ccaaattctc gattcacgca tgaacaccaa gtacgatgaa    2940
aatgacaaac tgattcgaga ggtgaaagtt attactctga agtctaagct ggtctcagat    3000
ttcagaaagg acttcagtt  ttataaggtg agagagatca acaattacca ccatgcgcat    3060
gatgcctacc tgaatgcagt ggtaggcact gcacttatca aaaatatcc  caagcttgaa    3120 tctgaatttg tttacggaga ctataaagtg tacgatgtta ggaaatgat  cgcaaagtct    3180 gagcaggaaa taggcaaggc caccgctaag tacttctttt acagcaatat tatgaatttt    3240
ttcaagaccg agattacact ggccaatgga gagattcgga agcgaccact tatcgaaaca    3300
aacggagaaa caggagaaat cgtgtgggac aagggtaggg atttcgcgac agtccggaag    3360
gtcctgtcca tgccgcaggt gaacatcgtt aaaaagaccg aagtacagac cggaggcttc    3420
tccaaggaaa gtatcctccc gaaaaggaac agcgacaagc tgatcgcacg caaaaaagat    3480
tgggacccca agaaatacgg cggattcgat tctcctacag tcgcttacag tgtactggtt    3540
gtggccaaag tggagaaagg gaagtctaaa aaactcaaaa gcgtcaagga actgctgggc    3600
atcacaatca tggagcgatc aagcttcgaa aaaaacccca tcgactttct cgaggcgaaa    3660
```

```
ggatataaag aggtcaaaaa agacctcatc attaagcttc ccaagtactc tctctttgag    3720
cttgaaaacg gccggaaacg aatgctcgct agtgcgggcg agctgcagaa aggtaacgag    3780
ctggcactgc cctctaaata cgttaatttc ttgtatctgg ccagccacta tgaaaagctc    3840
aaagggtctc ccgaagataa tgagcagaag cagctgttcg tggaacaaca caaacactac    3900
cttgatgaga tcatcgagca aataagcgaa ttctccaaaa gagtgatcct cgccgacgct    3960
aacctcgata aggtgctttc tgcttacaat aagcacaggg ataagcccat cagggagcag    4020
gcagaaaaca ttatccactt gtttactctg accaacttgg gcgcgcctgc agccttcaag    4080
tacttcgaca ccaccataga cagaaagcgg tacacctcta caaggaggt cctggacgcc     4140 acactgattc atcagtcaat tacggggctc tatgaaacaa gaatcgacct ctctcagctc    4200
ggtggagaca gcagggctga ccccaagaag aagaggaagg tggctagcga tgctaagtca    4260
ctgactgcct ggtcccggac actggtgacc ttcaaggatg tgtttgtgga cttcaccagg    4320
gaggagtgga agctgctgga cactgctcag cagatcctgt acagaaatgt gatgctggag    4380
aactataaga acctggtttc cttgggttat cagcttacta agccagatgt gatcctccgg    4440
ttggagaagg gagaagagcc ctggctggtg gagagagaaa ttcaccaaga gacccatcct    4500
gattcagaga ctgcatttga aatcaaatca tcagttccga aaaagaaacg caaagttgct    4560
agcg                                                                 4564

<210> SEQ ID NO 467
<211> LENGTH: 388
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 467
taagcttcag tttttcctta gttcctgtta catttctgtg tgtctccatt agtgacctcc      60
catagtccaa gcatgagcag ttctggccag gcccctgtcg gggtcagtgc cccacccccg     120
ccttctggtt ctgtgtaacc ttctaagcaa accttctggc tcaagcacag caatgctgag     180
tcatgatgag tcatgctgag gcttagggtg tgtgcccaga tgttctcagc ctagagtgat     240
gactcctatc tgggtcccca gcaggatgct tacagggcag atggcaaaaa aaggagaag      300 ctgaccacct gactaaaact ccacctcaaa cggcatcata agaaaatgg atgcctgaga      360 cagaatgtga catattctag aatatatt                                        388

<210> SEQ ID NO 468
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
cagccgctcg ctgcagcag                                                   19

<210> SEQ ID NO 469
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 469
ctgctgcagc gagcggctg                                                19

<210> SEQ ID NO 470
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 470
gctgggtgtc ccattgaaa                                                19

<210> SEQ ID NO 471
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
tttcaatggg acacccagc                                                19

<210> SEQ ID NO 472
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
gtttattcag ccgggagtc                                                19

<210> SEQ ID NO 473
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
gactcccggc tgaataaac                                                19

<210> SEQ ID NO 474
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 474
tggagagttt gcaaggagc                                                19

<210> SEQ ID NO 475
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
gctccttgca aactctcca                               19

<210> SEQ ID NO 476
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
ccctccagac tttccacct                               19

<210> SEQ ID NO 477
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
aggtggaaag tctggaggg                               19

<210> SEQ ID NO 478
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 478
aattttcttc caagttctc                               19

<210> SEQ ID NO 479
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 479
gagaacttgg aagaaaatt                               19

<210> SEQ ID NO 480
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 480
ctgcggagag aagaaaggg                               19

<210> SEQ ID NO 481
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 481

```
cccttcttc tctccgcag                                                 19
```

<210> SEQ ID NO 482
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 482

```
agagccaccc cctggctcc                                                19
```

<210> SEQ ID NO 483
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 483

```
ggagccaggg ggtggctct                                                19
```

<210> SEQ ID NO 484
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 484

```
cgaagccaac cgcggcggg                                                19
```

<210> SEQ ID NO 485
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 485

```
cccgccgcgg ttggcttcg                                                19
```

<210> SEQ ID NO 486
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 486

```
agagggaaga cgatcgccc                                                19
```

<210> SEQ ID NO 487
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 487

```
gggcgatcgt cttccctct                                                19
```

<210> SEQ ID NO 488
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 488 ccccttttaac tttcctccg                                              19

<210> SEQ ID NO 489
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 489
cggaggaaag ttaaagggg                                               19

<210> SEQ ID NO 490
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 490
gcagccccgc ttccttcaa                                               19

<210> SEQ ID NO 491
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 491
ttgaaggaag cggggctgc                                               19

<210> SEQ ID NO 492
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 492
caccgcagcc gctcgctgca gcag                                         24

<210> SEQ ID NO 493
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 493
aaacctgctg cagcgagcgg ctgc                                         24

<210> SEQ ID NO 494
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 494
caccggctgg gtgtcccatt gaaa                                          24

<210> SEQ ID NO 495
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 495
aaactttcaa tgggacaccc agcc                                          24

<210> SEQ ID NO 496
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 496
caccggttta ttcagccggg agtc                                          24

<210> SEQ ID NO 497
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 497
aaacgactcc cggctgaata aacc                                          24

<210> SEQ ID NO 498
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 498
caccgtggag agtttgcaag gagc                                          24

<210> SEQ ID NO 499
<211> LENGTH: 24
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 499
aaacgctcct tgcaaactct ccac                                          24

```
<210> SEQ ID NO 500
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 500
caccgccctc cagactttcc acct                                              24

<210> SEQ ID NO 501
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 501
aaacaggtgg aaagtctgga gggc                                              24

<210> SEQ ID NO 502
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 502
caccgaattt tcttccaagt tctc                                              24

<210> SEQ ID NO 503
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 503
aaacgagaac ttggaagaaa attc                                              24

<210> SEQ ID NO 504
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 504
caccgctgcg gagagaagaa aggg                                              24

<210> SEQ ID NO 505
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 505 aaacccctt cttctctccg cagc                                               24

<210> SEQ ID NO 506
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 506
caccgagagc caccccctgg ctcc                                              24

<210> SEQ ID NO 507
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 507
aaacggagcc aggggtggc tctc                                               24

<210> SEQ ID NO 508
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 508
caccgcgaag ccaaccgcgg cggg                                              24

<210> SEQ ID NO 509
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 509
aaaccccgcc gcggttggct tcgc                                              24

<210> SEQ ID NO 510
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 510
caccgagagg gaagacgatc gccc                                              24

<210> SEQ ID NO 511
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 511
aaacgggcga tcgtcttccc tctc                                              24

<210> SEQ ID NO 512
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 512
caccgcccct taactttcc tccg                                           24

<210> SEQ ID NO 513
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 513
aaaccggagg aaagttaaag gggc                                          24

<210> SEQ ID NO 514
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 514
caccggcagc cccgcttcct tcaa                                          24

<210> SEQ ID NO 515
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 515
aaacttgaag gaagcgggc tgcc                                           24

<210> SEQ ID NO 516
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 516
cgagagcgag aggagggag                                                19

<210> SEQ ID NO 517
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 517
ctccctcctc tcgctctcg                                                19

<210> SEQ ID NO 518
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 518
gagagagctt gagagcgcg                                                19

<210> SEQ ID NO 519
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 519
cgcgctctca agctctctc                                                19

<210> SEQ ID NO 520
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 520
ggtggagggg gcggggccc                                                19

<210> SEQ ID NO 521
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 521
gggccccgcc ccctccacc                                                19

<210> SEQ ID NO 522
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 522
ggtatccacg taaatcaaa                                                19

<210> SEQ ID NO 523
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 523
tttgatttac gtggatacc                                                19

<210> SEQ ID NO 524
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 524
ccaatcactg gctccggtc                                                    19

<210> SEQ ID NO 525
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 525
gaccggagcc agtgattgg                                                    19

<210> SEQ ID NO 526
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 526
ggcgcccgag ggaagaaga                                                    19

<210> SEQ ID NO 527
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 527
tcttcttccc tcgggcgcc                                                    19

<210> SEQ ID NO 528
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 528
gggtgggggt accagagga                                                    19

<210> SEQ ID NO 529
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 529
tcctctggta cccccaccc                                                    19

<210> SEQ ID NO 530
<211> LENGTH: 19
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 530
ccggggacag aagagaggg                                                    19

<210> SEQ ID NO 531
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 531
ccctctcttc tgtccccgg                                                    19

<210> SEQ ID NO 532
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 532
gagagagagt gggagaagc                                                    19

<210> SEQ ID NO 533
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 533
gcttctccca ctctctctc                                                    19

<210> SEQ ID NO 534
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 534
aaagtaactg tcaaatgcg                                                    19

<210> SEQ ID NO 535
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 535
cgcatttgac agttacttt                                                    19

<210> SEQ ID NO 536
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 536
ttaaccagag cgcccagtc                                              19

<210> SEQ ID NO 537
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 537
gactgggcgc tctggttaa                                              19

<210> SEQ ID NO 538
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 538
cgtcggagct gcccgctag                                              19

<210> SEQ ID NO 539
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
ctagcgggca gctccgacg                                              19

<210> SEQ ID NO 540
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
caccgcgaga gcgagaggag ggag                                        24

<210> SEQ ID NO 541
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
aaacctccct cctctcgctc tcgc                                        24

<210> SEQ ID NO 542
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
caccggagag agcttgagag cgcg					24

<210> SEQ ID NO 543
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
aaaccgcgct ctcaagctct ctcc					24

<210> SEQ ID NO 544
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 544
caccgggtgg aggggggcggg gccc					24

<210> SEQ ID NO 545
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 545
aaacgggccc cgcccccctcc accc					24

<210> SEQ ID NO 546
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 546
caccgggtat ccacgtaaat caaa					24

<210> SEQ ID NO 547
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 547
aaactttgat ttacgtggat accc					24

<210> SEQ ID NO 548
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 548
caccgccaat cactggctcc ggtc                                          24

<210> SEQ ID NO 549
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 549
aaacgaccgg agccagtgat tggc                                          24

<210> SEQ ID NO 550
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 550
caccgggcgc ccgagggaag aaga                                          24

<210> SEQ ID NO 551
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 551
aaactcttct tccctcgggc gccc                                          24

<210> SEQ ID NO 552
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 552
caccggggtg ggggtaccag agga                                          24

<210> SEQ ID NO 553
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 553
aaactcctct ggtacccccca cccc                                         24

<210> SEQ ID NO 554
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
```
caccgccggg gacagaagag aggg                                              24

<210> SEQ ID NO 555
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
aaacccctct cttctgtccc cggc                                              24

<210> SEQ ID NO 556
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
caccggagag agagtgggag aagc                                              24

<210> SEQ ID NO 557
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557
aaacgcttct cccactctct ctcc                                              24

<210> SEQ ID NO 558
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
caccgaaagt aactgtcaaa tgcg                                              24

<210> SEQ ID NO 559
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
aaaccgcatt tgacagttac tttc                                              24

<210> SEQ ID NO 560
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560

```
caccgttaac cagagcgccc agtc                                          24

<210> SEQ ID NO 561
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
aaacgactgg gcgctctggt taac                                          24

<210> SEQ ID NO 562
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
caccgcgtcg gagctgcccg ctag                                          24

<210> SEQ ID NO 563
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
aaacctagcg ggcagctccg acgc                                          24

<210> SEQ ID NO 564
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 564
gagacacaca gaaatgtaac                                               20

<210> SEQ ID NO 565
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 565
ggtggggcac tgaccccgac                                               20

<210> SEQ ID NO 566
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 566
ctagagtgat gactcctatc                                               20
```

<210> SEQ ID NO 567
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 567
gactaaaact ccacctcaaa                                              20

<210> SEQ ID NO 568
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 568
aatatgtcac attctgtctc                                              20

<210> SEQ ID NO 569
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 569
ggactatggg aggtcactaa                                              20

<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 570
gctcatgctt ggactatggg                                              20

<210> SEQ ID NO 571
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 571
gttctggcca ggcccctgtc                                              20

<210> SEQ ID NO 572
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 572
agtgccccac ccccgccttc                                              20

<210> SEQ ID NO 573
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 573
gtggggcact gaccccgaca                                                20

<210> SEQ ID NO 574
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
aaccttctaa gcaaaccttc                                                20

<210> SEQ ID NO 575
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
gttacacaga accagaaggc                                                20

<210> SEQ ID NO 576
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
gaaggttaca cagaaccaga                                                20

<210> SEQ ID NO 577
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 577
agtcatgatg agtcatgctg                                                20

<210> SEQ ID NO 578
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 578
gatgagtcat gctgaggctt                                                20

<210> SEQ ID NO 579
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 579
actctaggct gagaacatct                                           20

<210> SEQ ID NO 580
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 580
gtccccagca ggatgcttac                                           20

<210> SEQ ID NO 581
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 581
gccctgtaag catcctgctg                                           20

<210> SEQ ID NO 582
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 582
cagggcagat ggcaaaaaaa                                           20

<210> SEQ ID NO 583
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 583
gaggtggagt tttagtcagg                                           20

<210> SEQ ID NO 584
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 584
aaacggcatc ataaagaaaa                                           20

<210> SEQ ID NO 585

```
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 585
gagacacaca gaaatgtaac gttttagagc tagaaatagc aagttaaaat aaggctagtc    60
cgttatcaac ttgaaaaagt ggcaccgagt cggtgctttt tttcc                  105

<210> SEQ ID NO 586
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 586
ggtggggcac tgaccccgac gttttagagc tagaaatagc aagttaaaat aaggctagtc    60
cgttatcaac ttgaaaaagt ggcaccgagt cggtgctttt tttcc                  105

<210> SEQ ID NO 587
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 587
ctagagtgat gactcctatc gttttagagc tagaaatagc aagttaaaat aaggctagtc    60
cgttatcaac ttgaaaaagt ggcaccgagt cggtgctttt tttcc                  105

<210> SEQ ID NO 588
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 588
gactaaaact ccacctcaaa gttttagagc tagaaatagc aagttaaaat aaggctagtc    60
cgttatcaac ttgaaaaagt ggcaccgagt cggtgctttt tttcc                  105

<210> SEQ ID NO 589
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 589
aatatgtcac attctgtctc gttttagagc tagaaatagc aagttaaaat aaggctagtc    60
cgttatcaac ttgaaaaagt ggcaccgagt cggtgctttt tttcc                  105

<210> SEQ ID NO 590
<211> LENGTH: 105
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 590
ggactatggg aggtcactaa gttttagagc tagaaatagc aagttaaaat aaggctagtc    60
cgttatcaac ttgaaaaagt ggcaccgagt cggtgctttt tttcc                   105

<210> SEQ ID NO 591
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 591
gctcatgctt ggactatggg gttttagagc tagaaatagc aagttaaaat aaggctagtc    60
cgttatcaac ttgaaaaagt ggcaccgagt cggtgctttt tttcc                   105

<210> SEQ ID NO 592
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 592
gttctggcca ggcccctgtc gttttagagc tagaaatagc aagttaaaat aaggctagtc    60
cgttatcaac ttgaaaaagt ggcaccgagt cggtgctttt tttcc                   105

<210> SEQ ID NO 593
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 593
agtgccccac ccccgccttc gttttagagc tagaaatagc aagttaaaat aaggctagtc    60
cgttatcaac ttgaaaaagt ggcaccgagt cggtgctttt tttcc                   105

<210> SEQ ID NO 594
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 594
gtggggcact gacccgaca gttttagagc tagaaatagc aagttaaaat aaggctagtc    60
cgttatcaac ttgaaaaagt ggcaccgagt cggtgctttt tttcc                   105

<210> SEQ ID NO 595
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 595
aaccttctaa gcaaaccttc gttttagagc tagaaatagc aagttaaaat aaggctagtc    60
cgttatcaac ttgaaaaagt ggcaccgagt cggtgctttt tttcc                    105

<210> SEQ ID NO 596
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 596
gttacacaga accagaaggc gttttagagc tagaaatagc aagttaaaat aaggctagtc    60
cgttatcaac ttgaaaaagt ggcaccgagt cggtgctttt tttcc                    105

<210> SEQ ID NO 597
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 597
gaaggttaca cagaaccaga gttttagagc tagaaatagc aagttaaaat aaggctagtc    60
cgttatcaac ttgaaaaagt ggcaccgagt cggtgctttt tttcc                    105

<210> SEQ ID NO 598
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 598
agtcatgatg agtcatgctg gttttagagc tagaaatagc aagttaaaat aaggctagtc    60
cgttatcaac ttgaaaaagt ggcaccgagt cggtgctttt tttcc                    105

<210> SEQ ID NO 599
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 599
gatgagtcat gctgaggctt gttttagagc tagaaatagc aagttaaaat aaggctagtc    60
cgttatcaac ttgaaaaagt ggcaccgagt cggtgctttt tttcc                    105

<210> SEQ ID NO 600
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 600
actctaggct gagaacatct gttttagagc tagaaatagc aagttaaaat aaggctagtc    60
cgttatcaac ttgaaaaagt ggcaccgagt cggtgctttt tttcc                    105

<210> SEQ ID NO 601
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 601
gtccccagca ggatgcttac gttttagagc tagaaatagc aagttaaaat aaggctagtc     60
cgttatcaac ttgaaaaagt ggcaccgagt cggtgctttt tttcc                    105

<210> SEQ ID NO 602
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 602
gccctgtaag catcctgctg gttttagagc tagaaatagc aagttaaaat aaggctagtc     60
cgttatcaac ttgaaaaagt ggcaccgagt cggtgctttt tttcc                    105

<210> SEQ ID NO 603
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 603
cagggcagat ggcaaaaaaa gttttagagc tagaaatagc aagttaaaat aaggctagtc     60
cgttatcaac ttgaaaaagt ggcaccgagt cggtgctttt tttcc                    105

<210> SEQ ID NO 604
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 604
gaggtggagt tttagtcagg gttttagagc tagaaatagc aagttaaaat aaggctagtc     60
cgttatcaac ttgaaaaagt ggcaccgagt cggtgctttt tttcc                    105

<210> SEQ ID NO 605
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 605
aaacggcatc ataagaaaa gttttagagc tagaaatagc aagttaaaat aaggctagtc      60
cgttatcaac ttgaaaaagt ggcaccgagt cggtgctttt tttcc                    105

<210> SEQ ID NO 606
<211> LENGTH: 19

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
tgtactctct gaggtgctc                                                   19

<210> SEQ ID NO 607
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
acgcagataa gaaccagtt                                                   19

<210> SEQ ID NO 608
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 608
catcaagtca gccatcagc                                                   19

<210> SEQ ID NO 609
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 609
gagtcaccct cctggaaac                                                   19

<210> SEQ ID NO 610
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 610
cctgggctcc ggggcgttt                                                   19

<210> SEQ ID NO 611
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 611
ggcccctgcg gccaccccg                                                   19

<210> SEQ ID NO 612
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 612
ctccctccct gcccggtag                                                    19

<210> SEQ ID NO 613
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
aggtttggaa agggcgtgc                                                    19

<210> SEQ ID NO 614
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
actccactgc actccagtct                                                   20

<210> SEQ ID NO 615
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615 tctgtgggggg acctgcactg                                                  20

<210> SEQ ID NO 616
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
ggggcgccag ttgtgtctcc                                                   20

<210> SEQ ID NO 617
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 617
acaccattgc caccaccatt                                                   20

<210> SEQ ID NO 618
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 618
caatgacccc ttcattgacc                                              20

<210> SEQ ID NO 619
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 619
ttgattttgg agggatctcg                                              20

<210> SEQ ID NO 620
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 620
ggaatccatg gagggaagat                                              20

<210> SEQ ID NO 621
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 621
tgttctcgct caggtcagtg                                              20

<210> SEQ ID NO 622
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 622
ctctctgctc ctttgccaca                                              20

<210> SEQ ID NO 623
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 623
gtgctcttcg ggtttcagga                                              20

<210> SEQ ID NO 624
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 624
cgaaagagaa agcgaaccag tatcgagaac                                          30

<210> SEQ ID NO 625
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 625
cgttgtgcat agtcgctgct tgatcgc                                             27

<210> SEQ ID NO 626
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 626
gagtttggct caaattgtta ctctt                                               25

<210> SEQ ID NO 627
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 627
gggaaatggt ctaggagagt aaagt                                               25

<210> SEQ ID NO 628
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 628
gattggcttt gatttcccta ggg                                                 23

<210> SEQ ID NO 629
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 629
gcctactcag actgttactc tgg                                                 23

<210> SEQ ID NO 630
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 630
gcagttgcct aagaactggt ggg                                           23

<210> SEQ ID NO 631
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 631
ggggctccac cctcacgagt ggg                                           23

<210> SEQ ID NO 632
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 632
gccttcttta tccctatcg agg                                            23

<210> SEQ ID NO 633
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 633
gaaggaccat ttgacgttca gctcctactc agactgttac tctggtga                48

<210> SEQ ID NO 634
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 634

Glu Gly Pro Phe Asp Val Gln Leu Leu Leu Arg Leu Leu Leu Trp
1               5                   10                  15

<210> SEQ ID NO 635
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 635
gaaggaccat ttgacgttca gctcctactc agactgtctc tggtga                  46

<210> SEQ ID NO 636
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 636

Glu Gly Pro Phe Asp Val Gln Leu Leu Leu Arg Leu Ser Leu Val
1               5                   10                  15

<210> SEQ ID NO 637
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 637
gccuacucag acuguuacuc                                           20

<210> SEQ ID NO 638
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 638
cccaccagtt cttaggcaa                                            19

<210> SEQ ID NO 639
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 639
cccaccagtt cttaggcaac                                           20

<210> SEQ ID NO 640
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
tttgatttcc agttcttagg                                           20

<210> SEQ ID NO 641
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
attaccatag agttcttag                                            19

<210> SEQ ID NO 642
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 642
gtggataaag gcaacaatg                                                     19

<210> SEQ ID NO 643
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
cctcgatagg ggataa                                                        16

<210> SEQ ID NO 644
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
accaaaccca cttaggggat aaa                                                23

<210> SEQ ID NO 645
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
ggtatcttaa ggacctccaa g                                                  21

<210> SEQ ID NO 646
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
taggaagtaa attaatttga agcttgccaa ttaatccaaa tcttacc                      47

<210> SEQ ID NO 647
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 647 tttcctttt gcaaaaccca aaatatttta gctcctactc agactgttag agtaggagga          60
gaaggagggc tgtggctctt gtg                                                83

<210> SEQ ID NO 648
<211> LENGTH: 83
<212> TYPE: DNA
<213> ORGANISM: Artificial Sequence
<220> FEATURE:

```
<223> OTHER INFORMATION: Description of Artificial Sequence: Synthetic
      primer
<220> FEATURE:
<221> NAME/KEY: modified_base
<222> LOCATION: (20)..(20)
<223> OTHER INFORMATION: a, c, t, g, unknown or other
<220> FEATURE:
<221> NAME/KEY: modified_base
<222> LOCATION: (31)..(31)
<223> OTHER INFORMATION: a, c, t, g, unknown or other
<220> FEATURE:
<221> NAME/KEY: modified_base
<222> LOCATION: (69)..(69)
<223> OTHER INFORMATION: a, c, t, g, unknown or other

<400> SEQUENCE: 648
aaaaccccca aaccctcccn cttttcctc ntactctaac agtgtgagta ggaggccaca      60
cttagctgng gctctagtaa gtc                                            83

<210> SEQ ID NO 649
<211> LENGTH: 94
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (50)..(50)
<223> OTHER INFORMATION: a, c, t, g, unknown or other

<400> SEQUENCE: 649 cttcttttt ccttttgca aaaacccaaa atatttagc tcctactcan accgttttcg       60
gggggtattt tgtatttgga tgaaacactt gatg                                94

<210> SEQ ID NO 650
<211> LENGTH: 93
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 650
tcttcttttt tccttcccgc aaaaacccaa aatattttcg ctcctactca ggacctggtc    60
gtggggtatt ttgtatttgg atgaaacact tga                                 93

<210> SEQ ID NO 651
<211> LENGTH: 104
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(22)
<223> OTHER INFORMATION: a, c, t, g, unknown or other

<400> SEQUENCE: 651
tcaaggaaga tggcatttct nntttggaga tggcagtttc cttagtaacc acaggttgtg    60
tcaccatggc cagtaagaag gatgccacac ttgtgtgtgt cgct                    104

<210> SEQ ID NO 652
<211> LENGTH: 86
<212> TYPE: DNA
<213> ORGANISM: Artificial Sequence
```

<220> FEATURE:
<223> OTHER INFORMATION: Description of Artificial Sequence: Synthetic
      primer
<220> FEATURE:
<221> NAME/KEY: modified_base
<222> LOCATION: (35)..(36)
<223> OTHER INFORMATION: a, c, t, g, unknown or other
<220> FEATURE:
<221> NAME/KEY: modified_base
<222> LOCATION: (42)..(44)
<223> OTHER INFORMATION: a, c, t, g, unknown or other

<400> SEQUENCE: 652
ttggagatag cagtttcctt ggtaagtaca ggttnntcac cnnnacagtg tgagtaggag    60
gccacactta gctgtggctc tagtaa                                        86

<210> SEQ ID NO 653
<211> LENGTH: 71
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (54)..(54)
<223> OTHER INFORMATION: a, c, t, g, unknown or other
<220> FEATURE:
<221> NAME/KEY: modified_base
<222> LOCATION: (61)..(63)
<223> OTHER INFORMATION: a, c, t, g, unknown or other
<220> FEATURE:
<221> NAME/KEY: modified_base
<222> LOCATION: (69)..(69)
<223> OTHER INFORMATION: a, c, t, g, unknown or other

<400> SEQUENCE: 653
tttctagttt ggagatggca gtttccttag taaccacagg ttgtgtcacc aggnctcgag    60
nnntggttnt g                                                        71

<210> SEQ ID NO 654
<211> LENGTH: 87
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 654
cagttgccat agtcttcact aaccgcgtca ccagagctca ggacctggtc gtggggtatt    60
ttgtatttgg atgaaacact tgatggt                                       87

<210> SEQ ID NO 655
<211> LENGTH: 92
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (52)..(52)
<223> OTHER INFORMATION: a, c, t, g, unknown or other
<220> FEATURE:
<221> NAME/KEY: modified_base
<222> LOCATION: (59)..(59)
<223> OTHER INFORMATION: a, c, t, g, unknown or other
<220> FEATURE:
<221> NAME/KEY: modified_base
<222> LOCATION: (78)..(78)

<223> OTHER INFORMATION: a, c, t, g, unknown or other

<400> SEQUENCE: 655
tattgtatct tggtttttct tcactgctgg ccagtttact aacaatctga antaagccna    60
ttaatccaaa tcttaccnga cgaaaaatca aa    92

<210> SEQ ID NO 656
<211> LENGTH: 89
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (6)..(6)
<223> OTHER INFORMATION: a, c, t, g, unknown or other
<220> FEATURE:
<221> NAME/KEY: modified_base
<222> LOCATION: (10)..(10)
<223> OTHER INFORMATION: a, c, t, g, unknown or other
<220> FEATURE:
<221> NAME/KEY: modified_base
<222> LOCATION: (19)..(19)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (57)..(57)
<223> OTHER INFORMATION: a, c, t, g, unknown or other

<400> SEQUENCE: 656
atggtntttn gtcattgcng gccagttttn taacaatgtg atcaatgcca attaatncaa    60
atcttaccag aggaaaaatc aagccacag    89

<210> SEQ ID NO 657
<211> LENGTH: 94
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (93)..(94)
<223> OTHER INFORMATION: a, c, t, g, unknown or other

<400> SEQUENCE: 657
aataaaaaga aaaaaatatg ataaactgct cccagtataa aatacagagc taagacaaga    60
acgtttcatt ggctgttaaa agtcggaaat cgnn    94

<210> SEQ ID NO 658
<211> LENGTH: 94
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 658
ttctgattta aaattcccctt gaataggaag taaattaatt tgaagcttgc caattaatcc    60
aaatcttacc agaggaaaaa tcaagccaca gata    94

<210> SEQ ID NO 659

```
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 659
caaaacaaga tgggataaaa tcttctttct gatttaaaat tcccttgaat aggaagtaaa    60
ttactagagc tgttcaaggc ctgaactcta                                     90

<210> SEQ ID NO 660
<211> LENGTH: 96
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (49)..(49)
<223> OTHER INFORMATION: a, c, t, g, unknown or other
<220> FEATURE:
<221> NAME/KEY: modified_base
<222> LOCATION: (51)..(52)
<223> OTHER INFORMATION: a, c, t, g, unknown or other
<220> FEATURE:
<221> NAME/KEY: modified_base
<222> LOCATION: (54)..(54)
<223> OTHER INFORMATION: a, c, t, g, unknown or other

<400> SEQUENCE: 660
ctgatttaaa attcccttga ataggaagta aattactaga gctgttcang nncngaactc    60
taggctagca tttccagccc aaaacaaaca cagttc                              96

<210> SEQ ID NO 661
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(26)
<223> OTHER INFORMATION: a, c, t, g, unknown or other

<400> SEQUENCE: 661
ttgtttgnnn nnnnnnnnn nnnnnn                                          26

<210> SEQ ID NO 662
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(24)
<223> OTHER INFORMATION: a, c, t, g, unknown or other

<400> SEQUENCE: 662
caccgnnnnn nnnnnnnnnn nnnn                                           24

<210> SEQ ID NO 663
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(24)
<223> OTHER INFORMATION: a, c, t, g, unknown or other

<400> SEQUENCE: 663
tcccannnnn nnnnnnnnnn nnnn                                            24

<210> SEQ ID NO 664
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(24)
<223> OTHER INFORMATION: a, c, t, g, unknown or other

<400> SEQUENCE: 664
cctcgnnnnn nnnnnnnnnn nnnn                                            24

<210> SEQ ID NO 665
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(23)
<223> OTHER INFORMATION: a, c, t, g, unknown or other

<400> SEQUENCE: 665
aaacnnnnnn nnnnnnnnnn nnncaa                                          26

<210> SEQ ID NO 666
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(23)
<223> OTHER INFORMATION: a, c, t, g, unknown or other

<400> SEQUENCE: 666
aaacnnnnnn nnnnnnnnnn nnnc                                            24

<210> SEQ ID NO 667
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(23)
<223> OTHER INFORMATION: a, c, t, g, unknown or other

<400> SEQUENCE: 667
aaacnnnnnn nnnnnnnnnn nnnt                                            24
```

<210> SEQ ID NO 668
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(23)
<223> OTHER INFORMATION: a, c, t, g, unknown or other

<400> SEQUENCE: 668
aaacnnnnnn nnnnnnnnnn nnnc                                          24

<210> SEQ ID NO 669
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 669
ttgtttgtct tcgagaagac ctgttt                                        26

<210> SEQ ID NO 670
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
caccgggtct tcgagaagac ctgttt                                        26

<210> SEQ ID NO 671
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
tcccaggtct tcgagaagac ctgttt                                        26

<210> SEQ ID NO 672
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
cctcgggtct tcgagaagac ctgttt                                        26

<210> SEQ ID NO 673
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 673
ggcctaccgc taaggctagc ctagt                                         25

<210> SEQ ID NO 674
<211> LENGTH: 1411
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 674

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
                20                  25                  30

Gly Arg Gly Met Asp Lys Lys Tyr Ser Ile Gly Leu Ala Ile Gly Thr
            35                  40                  45

Asn Ser Val Gly Trp Ala Val Ile Thr Asp Glu Tyr Lys Val Pro Ser
        50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Arg Tyr Thr Arg Arg Lys Asn
            100                 105                 110

Arg Ile Cys Tyr Leu Gln Glu Ile Phe Ser Asn Glu Met Ala Lys Val
        115                 120                 125

Asp Asp Ser Phe Phe His Arg Leu Glu Glu Ser Phe Leu Val Glu Glu
    130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
            180                 185                 190

Leu Ala His Met Ile Lys Phe Arg Gly His Phe Leu Ile Glu Gly Asp
        195                 200                 205

Leu Asn Pro Asp Asn Ser Asp Val Asp Lys Leu Phe Ile Gln Leu Val
    210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
            260                 265                 270

Phe Gly Asn Leu Ile Ala Leu Ser Leu Gly Leu Thr Pro Asn Phe Lys
        275                 280                 285

Ser Asn Phe Asp Leu Ala Glu Asp Ala Lys Leu Gln Leu Ser Lys Asp
    290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu

-continued

```
                340                 345                 350
Ser Ala Ser Met Ile Lys Arg Tyr Asp Glu His His Gln Asp Leu Thr
            355                 360                 365
Leu Leu Lys Ala Leu Val Arg Gln Gln Leu Pro Glu Lys Tyr Lys Glu
        370                 375                 380
Ile Phe Phe Asp Gln Ser Lys Asn Gly Tyr Ala Gly Tyr Ile Asp Gly
385                 390                 395                 400
Gly Ala Ser Gln Glu Glu Phe Tyr Lys Phe Ile Lys Pro Ile Leu Glu
                405                 410                 415
Lys Met Asp Gly Thr Glu Glu Leu Leu Val Lys Leu Asn Arg Glu Asp
            420                 425                 430
Leu Leu Arg Lys Gln Arg Thr Phe Asp Asn Gly Ser Ile Pro His Gln
        435                 440                 445
Ile His Leu Gly Glu Leu His Ala Ile Leu Arg Arg Gln Glu Asp Phe
    450                 455                 460
Tyr Pro Phe Leu Lys Asp Asn Arg Glu Lys Ile Glu Lys Ile Leu Thr
465                 470                 475                 480
Phe Arg Ile Pro Tyr Tyr Val Gly Pro Leu Ala Arg Gly Asn Ser Arg
                485                 490                 495
Phe Ala Trp Met Thr Arg Lys Ser Glu Glu Thr Ile Thr Pro Trp Asn
            500                 505                 510
Phe Glu Glu Val Val Asp Lys Gly Ala Ser Ala Gln Ser Phe Ile Glu
        515                 520                 525
Arg Met Thr Asn Phe Asp Lys Asn Leu Pro Asn Glu Lys Val Leu Pro
    530                 535                 540
Lys His Ser Leu Leu Tyr Glu Tyr Phe Thr Val Tyr Asn Glu Leu Thr
545                 550                 555                 560
Lys Val Lys Tyr Val Thr Glu Gly Met Arg Lys Pro Ala Phe Leu Ser
                565                 570                 575
Gly Glu Gln Lys Lys Ala Ile Val Asp Leu Leu Phe Lys Thr Asn Arg
            580                 585                 590
Lys Val Thr Val Lys Gln Leu Lys Glu Asp Tyr Phe Lys Lys Ile Glu
        595                 600                 605
Cys Phe Asp Ser Val Glu Ile Ser Gly Val Glu Asp Arg Phe Asn Ala
    610                 615                 620
Ser Leu Gly Thr Tyr His Asp Leu Leu Lys Ile Ile Lys Asp Lys Asp
625                 630                 635                 640
Phe Leu Asp Asn Glu Glu Asn Glu Asp Ile Leu Glu Asp Ile Val Leu
                645                 650                 655
Thr Leu Thr Leu Phe Glu Asp Arg Glu Met Ile Glu Glu Arg Leu Lys
            660                 665                 670
Thr Tyr Ala His Leu Phe Asp Asp Lys Val Met Lys Gln Leu Lys Arg
        675                 680                 685
Arg Arg Tyr Thr Gly Trp Gly Arg Leu Ser Arg Lys Leu Ile Asn Gly
    690                 695                 700
Ile Arg Asp Lys Gln Ser Gly Lys Thr Ile Leu Asp Phe Leu Lys Ser
705                 710                 715                 720
Asp Gly Phe Ala Asn Arg Asn Phe Met Gln Leu Ile His Asp Asp Ser
                725                 730                 735
Leu Thr Phe Lys Glu Asp Ile Gln Lys Ala Gln Val Ser Gly Gln Gly
            740                 745                 750
Asp Ser Leu His Glu His Ile Ala Asn Leu Ala Gly Ser Pro Ala Ile
        755                 760                 765
```

Lys Lys Gly Ile Leu Gln Thr Val Lys Val Val Asp Glu Leu Val Lys
    770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
        835                 840                 845

Tyr Tyr Leu Gln Asn Gly Arg Asp Met Tyr Val Asp Gln Glu Leu Asp
    850                 855                 860

Ile Asn Arg Leu Ser Asp Tyr Asp Val Asp His Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
            900                 905                 910

Lys Met Lys Asn Tyr Trp Arg Gln Leu Leu Asn Ala Lys Leu Ile Thr
        915                 920                 925

Gln Arg Lys Phe Asp Asn Leu Thr Lys Ala Glu Arg Gly Gly Leu Ser
    930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
                965                 970                 975

Lys Tyr Asp Glu Asn Asp Lys Leu Ile Arg Glu Val Lys Val Ile Thr
            980                 985                 990

Leu Lys Ser Lys Leu Val Ser Asp Phe Arg Lys Asp Phe Gln Phe Tyr
        995                 1000                1005

Lys Val Arg Glu Ile Asn Asn Tyr His His Ala His Asp Ala Tyr
    1010                1015                1020

Leu Asn Ala Val Val Gly Thr Ala Leu Ile Lys Lys Tyr Pro Lys
    1025                1030                1035

Leu Glu Ser Glu Phe Val Tyr Gly Asp Tyr Lys Val Tyr Asp Val
    1040                1045                1050

Arg Lys Met Ile Ala Lys Ser Glu Gln Glu Ile Gly Lys Ala Thr
    1055                1060                1065

Ala Lys Tyr Phe Phe Tyr Ser Asn Ile Met Asn Phe Phe Lys Thr
    1070                1075                1080

Glu Ile Thr Leu Ala Asn Gly Glu Ile Arg Lys Arg Pro Leu Ile
    1085                1090                1095

Glu Thr Asn Gly Glu Thr Gly Glu Ile Val Trp Asp Lys Gly Arg
    1100                1105                1110

Asp Phe Ala Thr Val Arg Lys Val Leu Ser Met Pro Gln Val Asn
    1115                1120                1125

Ile Val Lys Lys Thr Glu Val Gln Thr Gly Gly Phe Ser Lys Glu
    1130                1135                1140

Ser Ile Leu Pro Lys Arg Asn Ser Asp Lys Leu Ile Ala Arg Lys
    1145                1150                1155

Lys Asp Trp Asp Pro Lys Lys Tyr Gly Gly Phe Asp Ser Pro Thr
    1160                1165                1170

-continued

```
Val Ala Tyr Ser Val Leu Val Val Ala Lys Val Glu Lys Gly Lys
    1175                1180                1185

Ser Lys Lys Leu Lys Ser Val Lys Glu Leu Leu Gly Ile Thr Ile
    1190                1195                1200

Met Glu Arg Ser Ser Phe Glu Lys Asn Pro Ile Asp Phe Leu Glu
    1205                1210                1215

Ala Lys Gly Tyr Lys Glu Val Lys Lys Asp Leu Ile Ile Lys Leu
    1220                1225                1230

Pro Lys Tyr Ser Leu Phe Glu Leu Glu Asn Gly Arg Lys Arg Met
    1235                1240                1245

Leu Ala Ser Ala Gly Glu Leu Gln Lys Gly Asn Glu Leu Ala Leu
    1250                1255                1260

Pro Ser Lys Tyr Val Asn Phe Leu Tyr Leu Ala Ser His Tyr Glu
    1265                1270                1275

Lys Leu Lys Gly Ser Pro Glu Asp Asn Glu Gln Lys Gln Leu Phe
    1280                1285                1290

Val Glu Gln His Lys His Tyr Leu Asp Glu Ile Ile Glu Gln Ile
    1295                1300                1305

Ser Glu Phe Ser Lys Arg Val Ile Leu Ala Asp Ala Asn Leu Asp
    1310                1315                1320

Lys Val Leu Ser Ala Tyr Asn Lys His Arg Asp Lys Pro Ile Arg
    1325                1330                1335

Glu Gln Ala Glu Asn Ile Ile His Leu Phe Thr Leu Thr Asn Leu
    1340                1345                1350

Gly Ala Pro Ala Ala Phe Lys Tyr Phe Asp Thr Thr Ile Asp Arg
    1355                1360                1365

Lys Arg Tyr Thr Ser Thr Lys Glu Val Leu Asp Ala Thr Leu Ile
    1370                1375                1380

His Gln Ser Ile Thr Gly Leu Tyr Glu Thr Arg Ile Asp Leu Ser
    1385                1390                1395

Gln Leu Gly Gly Asp Pro Lys Lys Lys Arg Lys Val Gly
    1400                1405                1410

<210> SEQ ID NO 675
<211> LENGTH: 1483
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 675

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Arg Gly Met Asp Lys Lys Tyr Ser Ile Gly Leu Ala Ile Gly Thr
        35                  40                  45

Asn Ser Val Gly Trp Ala Val Ile Thr Asp Glu Tyr Lys Val Pro Ser
    50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Arg Tyr Thr Arg Arg Lys Asn
            100                 105                 110
```

```
Arg Ile Cys Tyr Leu Gln Glu Ile Phe Ser Asn Glu Met Ala Lys Val
    115                 120                 125

Asp Asp Ser Phe Phe His Arg Leu Glu Glu Ser Phe Leu Val Glu Glu
130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
            180                 185                 190

Leu Ala His Met Ile Lys Phe Arg Gly His Phe Leu Ile Glu Gly Asp
            195                 200                 205

Leu Asn Pro Asp Asn Ser Asp Val Asp Lys Leu Phe Ile Gln Leu Val
        210                 215                 220

Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
        260                 265                 270

Phe Gly Asn Leu Ile Ala Leu Ser Leu Gly Leu Thr Pro Asn Phe Lys
        275                 280                 285

Ser Asn Phe Asp Leu Ala Glu Asp Ala Lys Leu Gln Leu Ser Lys Asp
        290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
            340                 345                 350

Ser Ala Ser Met Ile Lys Arg Tyr Asp Glu His His Gln Asp Leu Thr
            355                 360                 365

Leu Leu Lys Ala Leu Val Arg Gln Gln Leu Pro Glu Lys Tyr Lys Glu
        370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
            420                 425                 430

Leu Leu Arg Lys Gln Arg Thr Phe Asp Asn Gly Ser Ile Pro His Gln
        435                 440                 445

Ile His Leu Gly Glu Leu His Ala Ile Leu Arg Arg Gln Glu Asp Phe
    450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
            500                 505                 510

Phe Glu Glu Val Val Asp Lys Gly Ala Ser Ala Gln Ser Phe Ile Glu
        515                 520                 525
```

```
Arg Met Thr Asn Phe Asp Lys Asn Leu Pro Asn Glu Lys Val Leu Pro
    530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
            580                 585                 590

Lys Val Thr Val Lys Gln Leu Lys Glu Asp Tyr Phe Lys Lys Ile Glu
            595                 600                 605

Cys Phe Asp Ser Val Glu Ile Ser Gly Val Glu Asp Arg Phe Asn Ala
610                 615                 620

Ser Leu Gly Thr Tyr His Asp Leu Leu Lys Ile Ile Lys Asp Lys Asp
625                 630                 635                 640

Phe Leu Asp Asn Glu Glu Asn Glu Asp Ile Leu Glu Asp Ile Val Leu
                645                 650                 655

Thr Leu Thr Leu Phe Glu Asp Arg Glu Met Ile Glu Glu Arg Leu Lys
            660                 665                 670

Thr Tyr Ala His Leu Phe Asp Asp Lys Val Met Lys Gln Leu Lys Arg
            675                 680                 685

Arg Arg Tyr Thr Gly Trp Gly Arg Leu Ser Arg Lys Leu Ile Asn Gly
690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
                725                 730                 735

Leu Thr Phe Lys Glu Asp Ile Gln Lys Ala Gln Val Ser Gly Gln Gly
            740                 745                 750

Asp Ser Leu His Glu His Ile Ala Asn Leu Ala Gly Ser Pro Ala Ile
            755                 760                 765

Lys Lys Gly Ile Leu Gln Thr Val Lys Val Val Asp Glu Leu Val Lys
770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
                805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
            835                 840                 845

Tyr Tyr Leu Gln Asn Gly Arg Asp Met Tyr Val Asp Gln Glu Leu Asp
850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
                885                 890                 895

Lys Asn Arg Gly Lys Ser Asp Asn Val Pro Ser Glu Glu Val Val Lys
            900                 905                 910

Lys Met Lys Asn Tyr Trp Arg Gln Leu Leu Asn Ala Lys Leu Ile Thr
            915                 920                 925

Gln Arg Lys Phe Asp Asn Leu Thr Lys Ala Glu Arg Gly Gly Leu Ser
930                 935                 940

Glu Leu Asp Lys Ala Gly Phe Ile Lys Arg Gln Leu Val Glu Thr Arg
```

-continued

```
945                 950                 955                 960
Gln Ile Thr Lys His Val Ala Gln Ile Leu Asp Ser Arg Met Asn Thr
                965                 970                 975
Lys Tyr Asp Glu Asn Asp Lys Leu Ile Arg Glu Val Lys Val Ile Thr
                980                 985                 990
Leu Lys Ser Lys Leu Val Ser Asp Phe Arg Lys Asp Phe Gln Phe Tyr
                995                1000                1005
Lys Val Arg Glu Ile Asn Asn Tyr His His Ala His Asp Ala Tyr
    1010                1015                1020
Leu Asn Ala Val Val Gly Thr Ala Leu Ile Lys Lys Tyr Pro Lys
    1025                1030                1035
Leu Glu Ser Glu Phe Val Tyr Gly Asp Tyr Lys Val Tyr Asp Val
    1040                1045                1050
Arg Lys Met Ile Ala Lys Ser Glu Gln Glu Ile Gly Lys Ala Thr
    1055                1060                1065
Ala Lys Tyr Phe Phe Tyr Ser Asn Ile Met Asn Phe Phe Lys Thr
    1070                1075                1080
Glu Ile Thr Leu Ala Asn Gly Glu Ile Arg Lys Arg Pro Leu Ile
    1085                1090                1095
Glu Thr Asn Gly Glu Thr Gly Glu Ile Val Trp Asp Lys Gly Arg
    1100                1105                1110
Asp Phe Ala Thr Val Arg Lys Val Leu Ser Met Pro Gln Val Asn
    1115                1120                1125
Ile Val Lys Lys Thr Glu Val Gln Thr Gly Gly Phe Ser Lys Glu
    1130                1135                1140
Ser Ile Leu Pro Lys Arg Asn Ser Asp Lys Leu Ile Ala Arg Lys
    1145                1150                1155
Lys Asp Trp Asp Pro Lys Lys Tyr Gly Gly Phe Asp Ser Pro Thr
    1160                1165                1170
Val Ala Tyr Ser Val Leu Val Val Ala Lys Val Glu Lys Gly Lys
    1175                1180                1185
Ser Lys Lys Leu Lys Ser Val Lys Glu Leu Leu Gly Ile Thr Ile
    1190                1195                1200
Met Glu Arg Ser Ser Phe Glu Lys Asn Pro Ile Asp Phe Leu Glu
    1205                1210                1215
Ala Lys Gly Tyr Lys Glu Val Lys Lys Asp Leu Ile Ile Lys Leu
    1220                1225                1230
Pro Lys Tyr Ser Leu Phe Glu Leu Glu Asn Gly Arg Lys Arg Met
    1235                1240                1245
Leu Ala Ser Ala Gly Glu Leu Gln Lys Gly Asn Glu Leu Ala Leu
    1250                1255                1260
Pro Ser Lys Tyr Val Asn Phe Leu Tyr Leu Ala Ser His Tyr Glu
    1265                1270                1275
Lys Leu Lys Gly Ser Pro Glu Asp Asn Glu Gln Lys Gln Leu Phe
    1280                1285                1290
Val Glu Gln His Lys His Tyr Leu Asp Glu Ile Ile Glu Gln Ile
    1295                1300                1305
Ser Glu Phe Ser Lys Arg Val Ile Leu Ala Asp Ala Asn Leu Asp
    1310                1315                1320
Lys Val Leu Ser Ala Tyr Asn Lys His Arg Asp Lys Pro Ile Arg
    1325                1330                1335
Glu Gln Ala Glu Asn Ile Ile His Leu Phe Thr Leu Thr Asn Leu
    1340                1345                1350
```

```
Gly Ala Pro Ala Ala Phe Lys Tyr Phe Asp Thr Thr Ile Asp Arg
    1355                1360                1365

Lys Arg Tyr Thr Ser Thr Lys Glu Val Leu Asp Ala Thr Leu Ile
    1370                1375                1380

His Gln Ser Ile Thr Gly Leu Tyr Glu Thr Arg Ile Asp Leu Ser
    1385                1390                1395

Gln Leu Gly Gly Asp Pro Ile Ala Gly Ser Lys Ala Ser Pro Lys
    1400                1405                1410

Lys Lys Arg Lys Val Gly Arg Ala Asp Ala Leu Asp Asp Phe Asp
    1415                1420                1425

Leu Asp Met Leu Gly Ser Asp Ala Leu Asp Asp Phe Asp Leu Asp
    1430                1435                1440

Met Leu Gly Ser Asp Ala Leu Asp Asp Phe Asp Leu Asp Met Leu
    1445                1450                1455

Gly Ser Asp Ala Leu Asp Asp Phe Asp Leu Asp Met Leu Ile Asn
    1460                1465                1470

Tyr Pro Tyr Asp Val Pro Asp Tyr Ala Ser
    1475                1480

<210> SEQ ID NO 676
<211> LENGTH: 2048
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 676

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Gly Arg Gly Met Asp Lys Lys Tyr Ser Ile Gly Leu Ala Ile Gly Thr
                35                  40                  45

Asn Ser Val Gly Trp Ala Val Ile Thr Asp Glu Tyr Lys Val Pro Ser
50                  55                  60

Lys Lys Phe Lys Val Leu Gly Asn Thr Asp Arg His Ser Ile Lys Lys
65                  70                  75                  80

Asn Leu Ile Gly Ala Leu Leu Phe Asp Ser Gly Glu Thr Ala Glu Ala
                85                  90                  95

Thr Arg Leu Lys Arg Thr Ala Arg Arg Arg Tyr Thr Arg Arg Lys Asn
                100                 105                 110

Arg Ile Cys Tyr Leu Gln Glu Ile Phe Ser Asn Glu Met Ala Lys Val
                115                 120                 125

Asp Asp Ser Phe Phe His Arg Leu Glu Glu Ser Phe Leu Val Glu Glu
                130                 135                 140

Asp Lys Lys His Glu Arg His Pro Ile Phe Gly Asn Ile Val Asp Glu
145                 150                 155                 160

Val Ala Tyr His Glu Lys Tyr Pro Thr Ile Tyr His Leu Arg Lys Lys
                165                 170                 175

Leu Val Asp Ser Thr Asp Lys Ala Asp Leu Arg Leu Ile Tyr Leu Ala
                180                 185                 190

Leu Ala His Met Ile Lys Phe Arg Gly His Phe Leu Ile Glu Gly Asp
                195                 200                 205

Leu Asn Pro Asp Asn Ser Asp Val Asp Lys Leu Phe Ile Gln Leu Val
```

```
               210                 215                 220
Gln Thr Tyr Asn Gln Leu Phe Glu Glu Asn Pro Ile Asn Ala Ser Gly
225                 230                 235                 240

Val Asp Ala Lys Ala Ile Leu Ser Ala Arg Leu Ser Lys Ser Arg Arg
                245                 250                 255

Leu Glu Asn Leu Ile Ala Gln Leu Pro Gly Glu Lys Lys Asn Gly Leu
                260                 265                 270

Phe Gly Asn Leu Ile Ala Leu Ser Leu Gly Leu Thr Pro Asn Phe Lys
                275                 280                 285

Ser Asn Phe Asp Leu Ala Glu Asp Ala Lys Leu Gln Leu Ser Lys Asp
                290                 295                 300

Thr Tyr Asp Asp Asp Leu Asp Asn Leu Leu Ala Gln Ile Gly Asp Gln
305                 310                 315                 320

Tyr Ala Asp Leu Phe Leu Ala Ala Lys Asn Leu Ser Asp Ala Ile Leu
                325                 330                 335

Leu Ser Asp Ile Leu Arg Val Asn Thr Glu Ile Thr Lys Ala Pro Leu
                340                 345                 350

Ser Ala Ser Met Ile Lys Arg Tyr Asp Glu His His Gln Asp Leu Thr
                355                 360                 365

Leu Leu Lys Ala Leu Val Arg Gln Gln Leu Pro Glu Lys Tyr Lys Glu
                370                 375                 380

Ile Phe Phe Asp Gln Ser Lys Asn Gly Tyr Ala Gly Tyr Ile Asp Gly
385                 390                 395                 400

Gly Ala Ser Gln Glu Glu Phe Tyr Lys Phe Ile Lys Pro Ile Leu Glu
                405                 410                 415

Lys Met Asp Gly Thr Glu Glu Leu Leu Val Lys Leu Asn Arg Glu Asp
                420                 425                 430

Leu Leu Arg Lys Gln Arg Thr Phe Asp Asn Gly Ser Ile Pro His Gln
                435                 440                 445

Ile His Leu Gly Glu Leu His Ala Ile Leu Arg Arg Gln Glu Asp Phe
                450                 455                 460

Tyr Pro Phe Leu Lys Asp Asn Arg Glu Lys Ile Glu Lys Ile Leu Thr
465                 470                 475                 480

Phe Arg Ile Pro Tyr Tyr Val Gly Pro Leu Ala Arg Gly Asn Ser Arg
                485                 490                 495

Phe Ala Trp Met Thr Arg Lys Ser Glu Glu Thr Ile Thr Pro Trp Asn
                500                 505                 510

Phe Glu Glu Val Val Asp Lys Gly Ala Ser Ala Gln Ser Phe Ile Glu
                515                 520                 525

Arg Met Thr Asn Phe Asp Lys Asn Leu Pro Asn Glu Lys Val Leu Pro
530                 535                 540

Lys His Ser Leu Leu Tyr Glu Tyr Phe Thr Val Tyr Asn Glu Leu Thr
545                 550                 555                 560

Lys Val Lys Tyr Val Thr Glu Gly Met Arg Lys Pro Ala Phe Leu Ser
                565                 570                 575

Gly Glu Gln Lys Lys Ala Ile Val Asp Leu Leu Phe Lys Thr Asn Arg
                580                 585                 590

Lys Val Thr Val Lys Gln Leu Lys Glu Asp Tyr Phe Lys Lys Ile Glu
                595                 600                 605

Cys Phe Asp Ser Val Glu Ile Ser Gly Val Glu Asp Arg Phe Asn Ala
                610                 615                 620

Ser Leu Gly Thr Tyr His Asp Leu Leu Lys Ile Ile Lys Asp Lys Asp
625                 630                 635                 640
```

```
Phe Leu Asp Asn Glu Glu Asn Glu Asp Ile Leu Glu Asp Ile Val Leu
            645                 650                 655

Thr Leu Thr Leu Phe Glu Asp Arg Glu Met Ile Glu Glu Arg Leu Lys
            660                 665                 670

Thr Tyr Ala His Leu Phe Asp Asp Lys Val Met Lys Gln Leu Lys Arg
            675                 680                 685

Arg Arg Tyr Thr Gly Trp Gly Arg Leu Ser Arg Lys Leu Ile Asn Gly
        690                 695                 700

Ile Arg Asp Lys Gln Ser Gly Lys Thr Ile Leu Asp Phe Leu Lys Ser
705                 710                 715                 720

Asp Gly Phe Ala Asn Arg Asn Phe Met Gln Leu Ile His Asp Asp Ser
            725                 730                 735

Leu Thr Phe Lys Glu Asp Ile Gln Lys Ala Gln Val Ser Gly Gln Gly
            740                 745                 750

Asp Ser Leu His Glu His Ile Ala Asn Leu Ala Gly Ser Pro Ala Ile
            755                 760                 765

Lys Lys Gly Ile Leu Gln Thr Val Lys Val Val Asp Glu Leu Val Lys
770                 775                 780

Val Met Gly Arg His Lys Pro Glu Asn Ile Val Ile Glu Met Ala Arg
785                 790                 795                 800

Glu Asn Gln Thr Thr Gln Lys Gly Gln Lys Asn Ser Arg Glu Arg Met
            805                 810                 815

Lys Arg Ile Glu Glu Gly Ile Lys Glu Leu Gly Ser Gln Ile Leu Lys
            820                 825                 830

Glu His Pro Val Glu Asn Thr Gln Leu Gln Asn Glu Lys Leu Tyr Leu
            835                 840                 845

Tyr Tyr Leu Gln Asn Gly Arg Asp Met Tyr Val Asp Gln Glu Leu Asp
        850                 855                 860

Ile Asn Arg Leu Ser Asp Tyr Asp Val Asp Ala Ile Val Pro Gln Ser
865                 870                 875                 880

Phe Leu Lys Asp Asp Ser Ile Asp Asn Lys Val Leu Thr Arg Ser Asp
            885                 890                 895

Lys Asn Arg Gly Lys Ser Asp Asn Val Pro Ser Glu Glu Val Val Lys
            900                 905                 910

Lys Met Lys Asn Tyr Trp Arg Gln Leu Leu Asn Ala Lys Leu Ile Thr
            915                 920                 925

Gln Arg Lys Phe Asp Asn Leu Thr Lys Ala Glu Arg Gly Gly Leu Ser
        930                 935                 940

Glu Leu Asp Lys Ala Gly Phe Ile Lys Arg Gln Leu Val Glu Thr Arg
945                 950                 955                 960

Gln Ile Thr Lys His Val Ala Gln Ile Leu Asp Ser Arg Met Asn Thr
            965                 970                 975

Lys Tyr Asp Glu Asn Asp Lys Leu Ile Arg Glu Val Lys Val Ile Thr
            980                 985                 990

Leu Lys Ser Lys Leu Val Ser Asp Phe Arg Lys Asp Phe Gln Phe Tyr
            995                 1000                1005

Lys Val Arg Glu Ile Asn Asn Tyr His His Ala His Asp Ala Tyr
            1010                1015                1020

Leu Asn Ala Val Val Gly Thr Ala Leu Ile Lys Lys Tyr Pro Lys
            1025                1030                1035

Leu Glu Ser Glu Phe Val Tyr Gly Asp Tyr Lys Val Tyr Asp Val
            1040                1045                1050
```

-continued

```
Arg Lys Met Ile Ala Lys Ser Glu Gln Glu Ile Gly Lys Ala Thr
1055                1060                1065

Ala Lys Tyr Phe Phe Tyr Ser Asn Ile Met Asn Phe Phe Lys Thr
    1070                1075                1080

Glu Ile Thr Leu Ala Asn Gly Glu Ile Arg Lys Arg Pro Leu Ile
1085                1090                1095

Glu Thr Asn Gly Glu Thr Gly Glu Ile Val Trp Asp Lys Gly Arg
    1100                1105                1110

Asp Phe Ala Thr Val Arg Lys Val Leu Ser Met Pro Gln Val Asn
1115                1120                1125

Ile Val Lys Lys Thr Glu Val Gln Thr Gly Gly Phe Ser Lys Glu
    1130                1135                1140

Ser Ile Leu Pro Lys Arg Asn Ser Asp Lys Leu Ile Ala Arg Lys
1145                1150                1155

Lys Asp Trp Asp Pro Lys Lys Tyr Gly Gly Phe Asp Ser Pro Thr
    1160                1165                1170

Val Ala Tyr Ser Val Leu Val Val Ala Lys Val Glu Lys Gly Lys
1175                1180                1185

Ser Lys Lys Leu Lys Ser Val Lys Glu Leu Leu Gly Ile Thr Ile
    1190                1195                1200

Met Glu Arg Ser Ser Phe Glu Lys Asn Pro Ile Asp Phe Leu Glu
1205                1210                1215

Ala Lys Gly Tyr Lys Glu Val Lys Lys Asp Leu Ile Ile Lys Leu
    1220                1225                1230

Pro Lys Tyr Ser Leu Phe Glu Leu Glu Asn Gly Arg Lys Arg Met
1235                1240                1245

Leu Ala Ser Ala Gly Glu Leu Gln Lys Gly Asn Glu Leu Ala Leu
    1250                1255                1260

Pro Ser Lys Tyr Val Asn Phe Leu Tyr Leu Ala Ser His Tyr Glu
1265                1270                1275

Lys Leu Lys Gly Ser Pro Glu Asp Asn Glu Gln Lys Gln Leu Phe
    1280                1285                1290

Val Glu Gln His Lys His Tyr Leu Asp Glu Ile Ile Glu Gln Ile
1295                1300                1305

Ser Glu Phe Ser Lys Arg Val Ile Leu Ala Asp Ala Asn Leu Asp
    1310                1315                1320

Lys Val Leu Ser Ala Tyr Asn Lys His Arg Asp Lys Pro Ile Arg
1325                1330                1335

Glu Gln Ala Glu Asn Ile Ile His Leu Phe Thr Leu Thr Asn Leu
    1340                1345                1350

Gly Ala Pro Ala Ala Phe Lys Tyr Phe Asp Thr Thr Ile Asp Arg
1355                1360                1365

Lys Arg Tyr Thr Ser Thr Lys Glu Val Leu Asp Ala Thr Leu Ile
    1370                1375                1380

His Gln Ser Ile Thr Gly Leu Tyr Glu Thr Arg Ile Asp Leu Ser
1385                1390                1395

Gln Leu Gly Gly Asp Pro Ile Ala Gly Ser Lys Ala Ser Pro Lys
    1400                1405                1410

Lys Lys Arg Lys Val Gly Arg Ala Ile Phe Lys Pro Glu Glu Leu
1415                1420                1425

Arg Gln Ala Leu Met Pro Thr Leu Glu Ala Leu Tyr Arg Gln Asp
    1430                1435                1440

Pro Glu Ser Leu Pro Phe Arg Gln Pro Val Asp Pro Gln Leu Leu
```

-continued

```
              1445                1450                1455
Gly Ile Pro Asp Tyr Phe Asp Ile Val Lys Ser Pro Met Asp Leu
          1460                1465                1470
Ser Thr Ile Lys Arg Lys Leu Asp Thr Gly Gln Tyr Gln Glu Pro
      1475                1480                1485
Trp Gln Tyr Val Asp Asp Ile Trp Leu Met Phe Asn Asn Ala Trp
  1490                1495                1500
Leu Tyr Asn Arg Lys Thr Ser Arg Val Tyr Lys Tyr Cys Ser Lys
      1505                1510                1515
Leu Ser Glu Val Phe Glu Gln Glu Ile Asp Pro Val Met Gln Ser
      1520                1525                1530
Leu Gly Tyr Cys Cys Gly Arg Lys Leu Glu Phe Ser Pro Gln Thr
      1535                1540                1545
Leu Cys Cys Tyr Gly Lys Gln Leu Cys Thr Ile Pro Arg Asp Ala
      1550                1555                1560
Thr Tyr Tyr Ser Tyr Gln Asn Arg Tyr His Phe Cys Glu Lys Cys
      1565                1570                1575
Phe Asn Glu Ile Gln Gly Glu Ser Val Ser Leu Gly Asp Asp Pro
      1580                1585                1590
Ser Gln Pro Gln Thr Thr Ile Asn Lys Glu Gln Phe Ser Lys Arg
      1595                1600                1605
Lys Asn Asp Thr Leu Asp Pro Glu Leu Phe Val Glu Cys Thr Glu
      1610                1615                1620
Cys Gly Arg Lys Met His Gln Ile Cys Val Leu His His Glu Ile
      1625                1630                1635
Ile Trp Pro Ala Gly Phe Val Cys Asp Gly Cys Leu Lys Lys Ser
      1640                1645                1650
Ala Arg Thr Arg Lys Glu Asn Lys Phe Ser Ala Lys Arg Leu Pro
      1655                1660                1665
Ser Thr Arg Leu Gly Thr Phe Leu Glu Asn Arg Val Asn Asp Phe
      1670                1675                1680
Leu Arg Arg Gln Asn His Pro Glu Ser Gly Glu Val Thr Val Arg
      1685                1690                1695
Val Val His Ala Ser Asp Lys Thr Val Glu Val Lys Pro Gly Met
      1700                1705                1710
Lys Ala Arg Phe Val Asp Ser Gly Glu Met Ala Glu Ser Phe Pro
      1715                1720                1725
Tyr Arg Thr Lys Ala Leu Phe Ala Phe Glu Glu Ile Asp Gly Val
      1730                1735                1740
Asp Leu Cys Phe Phe Gly Met His Val Gln Glu Tyr Gly Ser Asp
      1745                1750                1755
Cys Pro Pro Pro Asn Gln Arg Arg Val Tyr Ile Ser Tyr Leu Asp
      1760                1765                1770
Ser Val His Phe Phe Arg Pro Lys Cys Leu Arg Thr Ala Val Tyr
      1775                1780                1785
His Glu Ile Leu Ile Gly Tyr Leu Glu Tyr Val Lys Lys Leu Gly
      1790                1795                1800
Tyr Thr Thr Gly His Ile Trp Ala Cys Pro Pro Ser Glu Gly Asp
      1805                1810                1815
Asp Tyr Ile Phe His Cys His Pro Pro Asp Gln Lys Ile Pro Lys
      1820                1825                1830
Pro Lys Arg Leu Gln Glu Trp Tyr Lys Lys Met Leu Asp Lys Ala
      1835                1840                1845
```

Val Ser Glu Arg Ile Val His Asp Tyr Lys Asp Ile Phe Lys Gln
    1850                1855                1860

Ala Thr Glu Asp Arg Leu Thr Ser Ala Lys Glu Leu Pro Tyr Phe
    1865                1870                1875

Glu Gly Asp Phe Trp Pro Asn Val Leu Glu Glu Ser Ile Lys Glu
    1880                1885                1890

Leu Glu Gln Glu Glu Glu Arg Lys Arg Glu Glu Asn Thr Ser
    1895                1900                1905

Asn Glu Ser Thr Asp Val Thr Lys Gly Asp Ser Lys Asn Ala Lys
    1910                1915                1920

Lys Lys Asn Asn Lys Lys Thr Ser Lys Asn Lys Ser Ser Leu Ser
    1925                1930                1935

Arg Gly Asn Lys Lys Lys Pro Gly Met Pro Asn Val Ser Asn Asp
    1940                1945                1950

Leu Ser Gln Lys Leu Tyr Ala Thr Met Glu Lys His Lys Glu Val
    1955                1960                1965

Phe Phe Val Ile Arg Leu Ile Ala Gly Pro Ala Ala Asn Ser Leu
    1970                1975                1980

Pro Pro Ile Val Asp Pro Asp Pro Leu Ile Pro Cys Asp Leu Met
    1985                1990                1995

Asp Gly Arg Asp Ala Phe Leu Thr Leu Ala Arg Asp Lys His Leu
    2000                2005                2010

Glu Phe Ser Ser Leu Arg Arg Ala Gln Trp Ser Thr Met Cys Met
    2015                2020                2025

Leu Val Glu Leu His Thr Gln Ser Gln Asp Tyr Pro Tyr Asp Val
    2030                2035                2040

Pro Asp Tyr Ala Ser
    2045

<210> SEQ ID NO 677
<211> LENGTH: 23
<212> TYPE: DNA
<213> ORGANISM: Artificial Sequence
<220> FEATURE:
<223> OTHER INFORMATION: Description of Artificial Sequence: Dystrophin
      gene reference sequence
<220> FEATURE:
<221> NAME/KEY: modified_base
<222> LOCATION: (1)..(21)
<223> OTHER INFORMATION: a, c, t, g, unknown or other

<400> SEQUENCE: 677
nnnnnnnnnn nnnnnnnnnn ngg                                              23

<210> SEQ ID NO 678
<211> LENGTH: 23
<212> TYPE: DNA
<213> ORGANISM: Artificial Sequence
<220> FEATURE:
<223> OTHER INFORMATION: Description of Artificial Sequence: Dystrophin
      gene reference sequence
<220> FEATURE:
<221> NAME/KEY: modified_base
<222> LOCATION: (2)..(21)
<223> OTHER INFORMATION: a, c, t, g, unknown or other

<400> SEQUENCE: 678
gnnnnnnnnn nnnnnnnnnn ngg                                              23

<210> SEQ ID NO 679

<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 679
gtgtagagta agtcagccta                                           20

<210> SEQ ID NO 680
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 680
gttggacaga acttaccgac                                           20

<210> SEQ ID NO 681
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 681
gtttgcttcg ctataaaacg                                           20

<210> SEQ ID NO 682
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 682
gtctgaggat ggggccgcaa                                           20

<210> SEQ ID NO 683
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 683
ggatctgtca aatcgcctgc                                           20

<210> SEQ ID NO 684
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 684
gccaggatgg cattgggcag                                           20

<210> SEQ ID NO 685
<211> LENGTH: 20

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 685
gctgaatctg cggtggcagg                                            20

<210> SEQ ID NO 686
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 686
gttcttttgt tcttctagcc                                            20

<210> SEQ ID NO 687
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 687
ggaaaagctt gagcaagtca                                            20

<210> SEQ ID NO 688
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 688
ggaagagttg cccctgcgcc                                            20

<210> SEQ ID NO 689
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 689
gacaaatctc cagtggataa                                            20

<210> SEQ ID NO 690
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 690
gtgtttctca ggtaaagctc                                            20

<210> SEQ ID NO 691
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 691
ggaaggacca tttgacgtta                                              20

<210> SEQ ID NO 692
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 692
gaactgctat ttcagtttcc                                              20

<210> SEQ ID NO 693
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
gccagccact cagccagtga                                              20

<210> SEQ ID NO 694
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 694
ggtatgcttt tctgttaaag                                              20

<210> SEQ ID NO 695
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 695
gctcctggac tgaccactat                                              20

<210> SEQ ID NO 696
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 696
ggaacagagg cgtccccagt tgg                                          23

<210> SEQ ID NO 697
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 697
ggaggctaga acaatcatta                                                     20

<210> SEQ ID NO 698
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 698
gacaagaaca ccttcagaac                                                     20

<210> SEQ ID NO 699
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 699
gggtttctgt gattttcttt                                                     20

<210> SEQ ID NO 700
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 700
gggccaaaga cctccgccag                                                     20

<210> SEQ ID NO 701
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
gttggagaag cattcataaa                                                     20

<210> SEQ ID NO 702
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
gtcgctcact caccctgcaa                                                     20

<210> SEQ ID NO 703
<211> LENGTH: 20
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 703
gaaaagagct gatgaaacaa                                                  20

<210> SEQ ID NO 704
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 704
gtacactttt caaaatgctt                                                  20

<210> SEQ ID NO 705
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
ggagatgatc atcaagcaga                                                  20

<210> SEQ ID NO 706
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706
gctttgaaag agcaataaaa                                                  20

<210> SEQ ID NO 707
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
gcacaaaagt caaatcggaa                                                  20

<210> SEQ ID NO 708
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
gatttcaata taagattcgg                                                  20

<210> SEQ ID NO 709
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 709
gcttaagcaa tcccgaactc                                              20

<210> SEQ ID NO 710
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 710
gaggccaaac ctcggcttac                                              20

<210> SEQ ID NO 711
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 711
gttcgaaaat ttcaggtaag                                              20

<210> SEQ ID NO 712
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 712
ggcagaacag gagataacag                                              20

<210> SEQ ID NO 713
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 713
ggcggccctc gcccttctct                                              20

<210> SEQ ID NO 714
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 714
gtagtgatcg tggatacgag                                              20

<210> SEQ ID NO 715
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 715
gtacagccct cggtgtatat                                              20

<210> SEQ ID NO 716
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 716
gggaaggaat taagcccgaa                                              20

<210> SEQ ID NO 717
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 717
gggaacagct ttcgtagttg                                              20

<210> SEQ ID NO 718
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 718
gataaagtcc agtgtcgatc                                              20

<210> SEQ ID NO 719
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 719
gaaaaccaga gcttcggtca                                              20

<210> SEQ ID NO 720
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 720
ggagtcttct gggcaggctt aaaggctaac c                                 31

<210> SEQ ID NO 721
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 721
gtcgggtgag catgtcttta atctacctcg a                                      31

<210> SEQ ID NO 722
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 722
ggtgtcacca gagtaacagt                                                   20

<210> SEQ ID NO 723
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 723
gtgatcatca agcagaaggt                                                   20

<210> SEQ ID NO 724
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 724
gaacttcgaa aatttcaggt a                                                 21

<210> SEQ ID NO 725
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 725
ggaaactcat caaatatgcg t                                                 21

<210> SEQ ID NO 726
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 726
gtcatttaca ctaacacgca t                                                 21

<210> SEQ ID NO 727
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 727
ggaatgaaac tcatcaaata t                                              21

<210> SEQ ID NO 728
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 728
gtcatcaata tctttgaagg a                                              21

<210> SEQ ID NO 729
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 729
gtgttttcat aggaaaaata g                                              21

<210> SEQ ID NO 730
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
gaattggaaa atgtgatggg a                                              21

<210> SEQ ID NO 731
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
gatgatcatc aagcagaagg t                                              21

<210> SEQ ID NO 732
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 732
gagatgatca tcaagcagaa g                                              21

<210> SEQ ID NO 733
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 733
gcattttttc tcataccttc t         21

<210> SEQ ID NO 734
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 734
gtcctactca gactgttact c         21

<210> SEQ ID NO 735
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 735
gacaggttgt gtcaccagag t         21

<210> SEQ ID NO 736
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 736
gttatcattt tttctcatac c         21

<210> SEQ ID NO 737
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 737
gttgcctaag aactggtggg a         21

<210> SEQ ID NO 738
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 738
gaaacagttg cctaagaact g         21

<210> SEQ ID NO 739
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 739
gtttcccacc agttcttagg c         21

<210> SEQ ID NO 740
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 740
gtggctttga tttccctagg g                                         21

<210> SEQ ID NO 741
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 741
gtagggaaat caaagccaat g                                         21

<210> SEQ ID NO 742
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
ggaccctagg gaaatcaaag c                                         21

<210> SEQ ID NO 743
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 743
gtgagggctc caccctcacg a                                         21

<210> SEQ ID NO 744
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 744
gaaggattga gggctccacc c                                         21

<210> SEQ ID NO 745
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 745
ggctccaccc tcacgagtgg g                                         21

```
<210> SEQ ID NO 746
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 746 gtatcccta tcgaggaaac c                                                21

<210> SEQ ID NO 747
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
ggataaagaa ggcctatttc a                                               21

<210> SEQ ID NO 748
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 748
gaggccttct ttatcccta t                                                21

<210> SEQ ID NO 749
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 749
gtgagggctc caccctcacg a                                               21

<210> SEQ ID NO 750
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 750
ggataaagaa ggcctatttc a                                               21
```

What is claimed is:

1. A DNA targeting system that binds to a human gamma globin gene comprising at least one guide RNA (gRNA) that binds and targets a polynucleotide sequence selected from SEQ ID NO: 33, 34, 35, or 36, or variant thereof.

2. The DNA targeting system of claim 1, further comprising a fusion protein comprising two heterologous polypeptide domains, wherein the first polypeptide domain comprises a Clustered Regularly Interspaced Short Palindromic Repeats associated (Cas) protein and the second polypeptide domain has an activity selected from the group consisting of transcription activation activity, transcription repression activity, transcription release factor activity, histone modification activity, nuclease activity, nucleic acid association activity, methylase activity, and demethylase activity, and wherein the fusion protein comprises an amino acid sequence selected from SEQ ID NOs: 1 and 674-676.

3. A DNA targeting system that binds to a human gamma globin gene comprising at least one guide RNA (gRNA) and a fusion protein comprising two heterologous polypeptide domains, wherein the first polypeptide domain comprises a Clustered Regularly Interspaced Short Palindromic Repeats associated (Cas) protein and the second polypeptide domain has an activity selected from the group consisting of transcription activation activity, transcription repression activity, transcription release factor activity, histone modification activity, nuclease activity, nucleic acid association activity, methylase activity, and demethylase activity, wherein the at least one guide RNA (gRNA) binds and targets a polynucleotide sequence selected from SEQ ID NO: 33, 34, 35, or 36, or variant thereof, and wherein the fusion protein comprises an amino acid sequence selected from SEQ ID NOs: 1 and 674-676.

4. The DNA targeting system claim 2, wherein the Cas protein comprises a Cas9, wherein the Cas9 comprises at least one amino acid mutation which knocks out nuclease activity of Cas9.

5. The DNA targeting system of claim 4, wherein the at least one amino acid mutation is at least one of D10A and H840A.

6. The DNA targeting system of claim 5, wherein the Cas protein comprises iCas9 (amino acids 36-1403 of SEQ ID NO: 1).

7. The DNA targeting system of claim 2, wherein the second polypeptide domain of the fusion protein comprises at least one VP16 transcription activation domain repeat or a KRAB domain.

8. The DNA targeting system of claim 7, wherein the second polypeptide domain of the fusion protein comprises a VP16 tetramer ("VP64") or a p65 activation domain.

9. The DNA targeting system of claim 2, wherein the fusion protein further comprises a linker connecting the first polypeptide domain to the second polypeptide domain.

10. An isolated polynucleotide encoding the DNA targeting system of claim 1.

11. A vector comprising the isolated polynucleotide of claim 10.

12. A cell comprising the isolated polynucleotide of claim 10.

13. A method of modulating mammalian gene expression in a cell, the method comprising contacting the cell with the DNA targeting system of claim 1.

14. A composition for inducing gene expression in a subject, the composition comprising the DNA targeting system of claim 1.

15. A modified lentiviral vector comprising an isolated polynucleotide encoding the DNA targeting system of claim 2, the isolated polynucleotide comprising a first polynucleotide sequence encoding the fusion protein and a second polynucleotide sequence encoding the at least one gRNA.

16. A method of activating endogenous gene expression in a subject, the method comprising contacting a cell with the modified lentiviral vector of claim 15.

17. The method of claim 16, wherein the subject is suffering from sickle cell disease or thalassaemia.

* * * * *